(12) United States Patent
Goldwasser et al.

(10) Patent No.: US 10,814,131 B2
(45) Date of Patent: *Oct. 27, 2020

(54) APPARATUSES AND METHODS FOR NEUROMODULATION

(71) Applicant: Thync Global, Inc., Los Gatos, CA (US)

(72) Inventors: Isy Goldwasser, Los Gatos, CA (US); William J. Tyler, Newton, MA (US); Jonathan Charlesworth, Menlo Park, CA (US); Sumon K. Pal, Boston, MA (US); Daniel Z. Wetmore, Brooklyn, NY (US); Douglas Jeffery, San Jose, CA (US); Wing Law, Cupertino, CA (US); Jason Egnal, Menlo Park, CA (US); Anil Thakur, Fremont, CA (US); Remi Demers, Saint-Nicolas (CA); Jay Frederick Hamlin, Santa Cruz, CA (US); Rafal Piersiak, Los Gatos, CA (US)

(73) Assignee: Thync Global, Inc., Los Gatos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/264,224

(22) Filed: Sep. 13, 2016

(65) Prior Publication Data
US 2017/0224990 A1    Aug. 10, 2017

Related U.S. Application Data

(63) Continuation-in-part of application No. 14/558,604, filed on Dec. 2, 2014, now Pat. No. 9,440,070, which
(Continued)

(51) Int. Cl.
*A61N 1/04* (2006.01)
*A61N 1/36* (2006.01)

(52) U.S. Cl.
CPC ....... *A61N 1/36025* (2013.01); *A61N 1/0456* (2013.01); *A61N 1/0476* (2013.01); *A61N 1/0492* (2013.01); *A61N 1/36014* (2013.01)

(58) Field of Classification Search
CPC ...... A61N 1/04; A61N 1/0404; A61N 1/0456; A61N 1/0476; A61N 1/048; A61N 1/32;
(Continued)

(56) References Cited

U.S. PATENT DOCUMENTS

| 3,255,753 A | 6/1966 | Wing |
| 3,388,699 A | 6/1968 | Webb et al. |

(Continued)

FOREIGN PATENT DOCUMENTS

| CN | 1204268 A | 1/1999 |
| CN | 1607970 A | 4/2005 |

(Continued)

OTHER PUBLICATIONS

Pal et al.; U.S. Appl. No. 14/956,193 entitled "Transdermal electrical stimulation devices for modifying or inducing cognitive state," filed Dec. 1, 2015.
(Continued)

*Primary Examiner* — Allen Porter
(74) *Attorney, Agent, or Firm* — Shay Glenn LLP

(57) ABSTRACT

Apparatuses (e.g., devices, systems), and methods for transdermal electrical stimulation (TES). Apparatuses described herein can be self-contained, lightweight, and wearable. The apparatuses and methods described herein be configured to apply an ensemble current waveform between the two or more electrodes, wherein the ensemble current waveform comprises a series of component waveforms that are sequentially applied, and wherein each component waveform is different from a component waveform immediately before it and wherein transitions between the component waveforms
(Continued)

temporally correlates with transitions in the sensory experience. Also described are neurostimulators for application of transdermal electrical stimulation (TES) and methods of using them for comfortably inducing a cognitive effect. Also described are Methods and apparatuses for amplitude modulation of all or a portion of an ensemble waveform to modify a user's cognitive state by transdermal electrical stimulation (TES).

15 Claims, 198 Drawing Sheets

Related U.S. Application Data is a continuation-in-part of application No. 14/091,121, filed on Nov. 26, 2013, now Pat. No. 8,903,494, application No. 15/264,224, filed on Sep. 13, 2016, which is a continuation-in-part of application No. 15/170,878, filed on Jun. 1, 2016, now Pat. No. 10,485,972, application No. 15/264,224, which is a continuation-in-part of application No. 14/715,470, filed on May 18, 2015, now Pat. No. 9,474,891, application No. 15/264,224, which is a continuation-in-part of application No. 14/715,476, filed on May 18, 2015, now Pat. No. 9,517,351, application No. 15/264,224, which is a continuation of application No. 15/169,445, filed on May 31, 2016.

(60) Provisional application No. 61/729,851, filed on Nov. 26, 2012, provisional application No. 61/765,795, filed on Feb. 17, 2013, provisional application No. 61/767,945, filed on Feb. 22, 2013, provisional application No. 61/770,479, filed on Feb. 28, 2013, provisional application No. 61/841,308, filed on Jun. 29, 2013, provisional application No. 61/845,845, filed on Jul. 12, 2013, provisional application No. 61/875,424, filed on Sep. 9, 2013, provisional application No. 61/900,880, filed on Nov. 6, 2013, provisional application No. 61/875,891, filed on Sep. 10, 2013, provisional application No. 61/888,910, filed on Oct. 9, 2013, provisional application No. 61/907,394, filed on Nov. 22, 2013, provisional application No. 62/076,459, filed on Nov. 6, 2014, provisional application No. 62/169,522, filed on Jun. 1, 2015, provisional application No. 62/169,523, filed on Jun. 1, 2015, provisional application No. 62/170,111, filed on Jun. 2, 2015, provisional application No. 62/268,084, filed on Dec. 16, 2015, provisional application No. 62/002,910, filed on May 25, 2014, provisional application No. 62/076,459, filed on Nov. 6, 2014, provisional application No. 62/099,950, filed on Jan. 5, 2015, provisional application No. 62/075,896, filed on Nov. 6, 2014, provisional application No. 62/099,960, filed on Jan. 5, 2015, provisional application No. 62/100,022, filed on Jan. 5, 2015, provisional application No. 61/994,860, filed on May 17, 2014, provisional application No. 62/100,029, filed on Jan. 5, 2015, provisional application No. 62/168,615, filed on May 29, 2015, provisional application No. 62/190,211, filed on Jul. 8, 2015, provisional application No. 62/200,256, filed on Aug. 3, 2015, provisional application No. 62/213,949, filed on Sep. 3, 2015.

(58) Field of Classification Search
CPC ... A61N 1/36; A61N 1/36014; A61N 1/36025
See application file for complete search history.

(56) References Cited

U.S. PATENT DOCUMENTS

| | | |
|---|---|---|
| 3,620,219 A | 11/1971 | Barker |
| 3,648,708 A | 3/1972 | Haeri |
| 3,762,396 A | 10/1973 | Ballentine et al. |
| 4,418,687 A | 12/1983 | Matsumoto et al. |
| 4,431,000 A | 2/1984 | Butler et al. |
| 4,646,744 A | 3/1987 | Capel |
| 4,664,117 A | 5/1987 | Beck |
| 4,865,048 A | 9/1989 | Eckerson |
| 5,144,952 A | 9/1992 | Frachet et al. |
| 5,183,041 A | 2/1993 | Toriu et al. |
| 5,335,657 A | 8/1994 | Terry et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,540,736 A | 7/1996 | Haimovich et al. |
| 5,573,552 A | 11/1996 | Hansjurgens |
| 5,578,065 A | 11/1996 | Hattori et al. |
| 5,593,427 A | 1/1997 | Gliner et al. |
| 5,738,647 A | 4/1998 | Bernhard et al. |
| 5,792,067 A | 8/1998 | Karell |
| 6,066,163 A | 5/2000 | John |
| 6,280,454 B1 | 8/2001 | Wang |
| 6,324,432 B1 | 11/2001 | Rigaux et al. |
| 6,445,955 B1 | 9/2002 | Michelson et al. |
| 6,463,328 B1 | 10/2002 | John |
| 6,516,227 B1* | 2/2003 | Meadows ............ A61N 1/0553 607/117 |
| 6,526,318 B1 | 2/2003 | Ansarinia |
| 6,567,702 B1 | 5/2003 | Nekhendzy et al. |
| 6,731,987 B1 | 5/2004 | McAdams et al. |
| 6,983,184 B2 | 1/2006 | Price |
| 7,120,499 B2 | 10/2006 | Thrope et al. |
| 7,146,217 B2 | 12/2006 | Firlik et al. |
| 7,263,501 B2 | 8/2007 | Tirinato et al. |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 | 2/2010 | Castel et al. |
| 7,801,600 B1 | 9/2010 | Carbunaru et al. |
| 7,891,615 B2 | 2/2011 | Bevirt |
| 7,949,403 B2 | 5/2011 | Palermo et al. |
| 8,029,431 B2 | 10/2011 | Tononi |
| 8,034,294 B1 | 10/2011 | Goldberg |
| 8,086,318 B2 | 12/2011 | Strother et al. |
| 8,097,926 B2 | 1/2012 | De Graff et al. |
| 8,116,875 B2 | 2/2012 | Osypka et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,197,276 B2 | 6/2012 | Egioff et al. |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 8,346,337 B2 | 1/2013 | Heller et al. |
| 8,380,315 B2 | 2/2013 | DeGiorgio et al. |
| 8,428,738 B2 | 4/2013 | Valencia |
| 8,463,383 B2 | 6/2013 | Sakai et al. |
| 8,494,625 B2 | 7/2013 | Hargrove |
| 8,494,627 B2 | 7/2013 | Bikson et al. |
| 8,506,469 B2 | 8/2013 | Dietrich et al. |
| 8,532,758 B2 | 9/2013 | Silverstone |
| 8,560,075 B2 | 10/2013 | Covalin |
| 8,571,651 B2 | 10/2013 | Ben-Ezra et al. |
| 8,583,238 B1 | 11/2013 | Heldman et al. |
| 8,583,256 B2 | 11/2013 | Tracey et al. |
| 8,612,005 B2 | 12/2013 | Rezai et al. |
| 8,639,343 B2 | 1/2014 | De Vos |

(56) References Cited

U.S. PATENT DOCUMENTS

| | | |
|---|---|---|
| 8,660,644 B2 | 2/2014 | Jaax et al. |
| 8,688,239 B2 | 4/2014 | Hartlep et al. |
| 8,843,210 B2 | 9/2014 | Simon et al. |
| 8,874,219 B2 | 10/2014 | Trier et al. |
| 8,903,494 B2 | 12/2014 | Goldwasser et al. |
| 8,983,621 B2 | 3/2015 | Hou et al. |
| 9,002,458 B2 | 4/2015 | Pal et al. |
| 9,014,811 B2 | 4/2015 | Pal et al. |
| 9,067,054 B2 | 6/2015 | Simon et al. |
| 9,168,374 B2 | 10/2015 | Su |
| 9,205,258 B2 | 12/2015 | Simon et al. |
| 9,233,244 B2 | 1/2016 | Pal et al. |
| 9,248,292 B2 | 2/2016 | Trier et al. |
| 9,333,334 B2 | 5/2016 | Jeffery et al. |
| 9,364,674 B2 | 6/2016 | Cook et al. |
| 9,393,401 B2 | 7/2016 | Goldwasser et al. |
| 9,393,430 B2 | 7/2016 | Demers et al. |
| 9,399,126 B2 | 7/2016 | Pal et al. |
| 9,415,219 B2 | 8/2016 | Simon et al. |
| 9,440,070 B2 | 9/2016 | Goldwasser et al. |
| 9,446,242 B2 | 9/2016 | Griffith |
| 9,474,891 B2 | 10/2016 | Demers et al. |
| 9,474,905 B2 | 10/2016 | Doan et al. |
| 9,655,772 B2 | 5/2017 | Smith et al. |
| 9,656,076 B2 | 5/2017 | Trier et al. |
| 9,700,725 B2 | 7/2017 | Zhu |
| 9,731,116 B2 | 8/2017 | Chen |
| 9,744,347 B2 | 8/2017 | Chen et al. |
| 9,764,133 B2 | 9/2017 | Thomas et al. |
| 9,782,587 B2 | 10/2017 | Trier et al. |
| 2001/0000187 A1* | 4/2001 | Peckham ............ A61N 1/36003 607/48 |
| 2002/0116036 A1 | 8/2002 | Daignault et al. |
| 2003/0088279 A1* | 5/2003 | Rissmann ............ A61N 1/3931 607/5 |
| 2003/0134545 A1 | 7/2003 | McAdams et al. |
| 2003/0171685 A1* | 9/2003 | Lesser ...................... A61F 7/12 600/509 |
| 2003/0225323 A1 | 12/2003 | Kiani et al. |
| 2004/0019370 A1 | 1/2004 | Gliner et al. |
| 2004/0098065 A1 | 5/2004 | Hagglof et al. |
| 2004/0158305 A1 | 8/2004 | Axelgaard |
| 2004/0267333 A1 | 12/2004 | Kronberg |
| 2005/0165460 A1 | 7/2005 | Erfan |
| 2005/0267388 A1 | 12/2005 | Hanna |
| 2005/0283259 A1 | 12/2005 | Wolpow |
| 2006/0047215 A1 | 3/2006 | Newman et al. |
| 2006/0064139 A1 | 3/2006 | Chung et al. |
| 2006/0149119 A1 | 7/2006 | Wang |
| 2006/0190057 A1 | 8/2006 | Reese |
| 2006/0195159 A1* | 8/2006 | Bradley ............. A61N 1/36132 607/48 |
| 2006/0206163 A1 | 9/2006 | Wahlstrand et al. |
| 2006/0247985 A1 | 11/2006 | Liamos et al. |
| 2007/0053466 A1* | 3/2007 | Klostermann ...... H04L 27/2331 375/316 |
| 2007/0088419 A1 | 4/2007 | Fiorina et al. |
| 2007/0097593 A1 | 5/2007 | Armstrong |
| 2007/0100275 A1 | 5/2007 | Fischer et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2008/0015641 A1* | 1/2008 | Armstrong ................ A61N 1/08 607/2 |
| 2008/0045882 A1 | 2/2008 | Finsterwald |
| 2008/0071626 A1 | 3/2008 | Hill |
| 2008/0097564 A1 | 4/2008 | Lathrop |
| 2008/0132974 A1 | 6/2008 | Strother et al. |
| 2008/0207985 A1 | 8/2008 | Farone |
| 2008/0208266 A1 | 8/2008 | Lesser et al. |
| 2008/0215113 A1 | 9/2008 | Pawlowicz |
| 2008/0275293 A1 | 11/2008 | Lattner et al. |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0054952 A1 | 2/2009 | Glukhovsky et al. |
| 2009/0099623 A1 | 4/2009 | Bentwich |
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0076533 A1 | 3/2010 | Dar et al. |
| 2010/0094375 A1 | 4/2010 | Donders et al. |
| 2010/0145399 A1 | 6/2010 | Johari et al. |
| 2010/0145428 A1 | 6/2010 | Cameron et al. |
| 2010/0152817 A1 | 6/2010 | Gillbe |
| 2010/0222734 A1 | 9/2010 | Jayes et al. |
| 2010/0256436 A1 | 10/2010 | Partsch et al. |
| 2010/0318168 A1 | 12/2010 | Bignetti |
| 2011/0029045 A1 | 2/2011 | Cevette et al. |
| 2011/0034756 A1 | 2/2011 | Hacking et al. |
| 2011/0077660 A1* | 3/2011 | Janik .................... A61N 1/0553 606/129 |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0178441 A1 | 7/2011 | Tyler |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brooke |
| 2011/0301683 A1 | 12/2011 | Axelgaard |
| 2011/0307029 A1 | 12/2011 | Hargrove |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0182924 A1 | 7/2012 | Gaines et al. |
| 2012/0184801 A1 | 7/2012 | Simon et al. |
| 2012/0185020 A1 | 7/2012 | Simon et al. |
| 2012/0209340 A1 | 8/2012 | Escribano |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0296390 A1 | 11/2012 | Nakashima et al. |
| 2012/0302912 A1 | 11/2012 | Moffitt et al. |
| 2012/0306628 A1 | 12/2012 | Singhal |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0096641 A1 | 4/2013 | Strother et al. |
| 2013/0131551 A1 | 5/2013 | Raghunathan et al. |
| 2013/0158627 A1 | 6/2013 | Gozani et al. |
| 2013/0184779 A1 | 7/2013 | Bikson et al. |
| 2013/0204315 A1 | 8/2013 | Wongsarnpigoon et al. |
| 2013/0226275 A1 | 8/2013 | Duncan |
| 2013/0253613 A1 | 9/2013 | Salahovic et al. |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle et al. |
| 2013/0333094 A1 | 12/2013 | Rogers et al. |
| 2014/0031895 A1 | 1/2014 | Rahimi et al. |
| 2014/0128939 A1 | 5/2014 | Embrey et al. |

(56) References Cited

U.S. PATENT DOCUMENTS

| | | |
|---|---|---|
| 2014/0128944 A1 | 5/2014 | Stern et al. |
| 2014/0163645 A1 | 6/2014 | Dinsmoor et al. |
| 2014/0182350 A1 | 7/2014 | Bhavaraju et al. |
| 2014/0186807 A1 | 7/2014 | Rastatter et al. |
| 2014/0222102 A1 | 8/2014 | Lemus et al. |
| 2014/0257449 A1 | 9/2014 | Helmer |
| 2014/0275933 A1 | 9/2014 | Meyer et al. |
| 2014/0277324 A1 | 9/2014 | DiUbaldi et al. |
| 2014/0309709 A1 | 10/2014 | Gozani et al. |
| 2014/0336728 A1 | 11/2014 | Franke et al. |
| 2014/0371814 A1 | 12/2014 | Spizzirri et al. |
| 2015/0066104 A1 | 3/2015 | Wingeier et al. |
| 2015/0224310 A1 | 8/2015 | Sharma et al. |
| 2015/0230863 A1 | 8/2015 | Youngquist et al. |
| 2015/0257970 A1 | 9/2015 | Mucke et al. |
| 2015/0328461 A1 | 11/2015 | Charlesworth et al. |
| 2015/0335877 A1 | 11/2015 | Jeffery et al. |
| 2016/0008632 A1 | 1/2016 | Wetmore et al. |
| 2016/0074657 A1 | 3/2016 | Kwan et al. |
| 2016/0279435 A1 | 9/2016 | Hyde et al. |
| 2017/0252562 A1 | 9/2017 | Goldwasser et al. |
| 2018/0036533 A1 | 2/2018 | Yoo et al. |
| 2018/0272118 A1 | 9/2018 | Goldwasser et al. |
| 2019/0336765 A1 | 11/2019 | Charlesworth et al. |

FOREIGN PATENT DOCUMENTS

| | | |
|---|---|---|
| CN | 1704131 A | 12/2005 |
| CN | 1842356 A | 10/2006 |
| CN | 101234233 A | 8/2008 |
| CN | 101244314 A | 8/2008 |
| CN | 201353374 Y | 12/2009 |
| CN | 102245253 A | 11/2011 |
| CN | 102725021 A | 10/2012 |
| CN | 102906752 A | 1/2013 |
| CN | 103517732 A | 1/2014 |
| EP | 502919 B1 | 11/1993 |
| EP | 801957 A1 | 10/1997 |
| EP | 09965358 A2 | 12/1999 |
| EP | 1529550 A1 | 5/2005 |
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49-061984 A | 6/1974 |
| JP | 5-31197 A | 2/1993 |
| JP | 06339531 A | 12/1994 |
| JP | 10-108913 A | 4/1998 |
| JP | 2001129100 A | 5/2001 |
| JP | 2001293097 A | 10/2001 |
| JP | 2002-306604 A | 10/2002 |
| JP | 2003-10230 A | 1/2003 |
| JP | 2006-192302 A | 7/2006 |
| JP | 3129187 U | 1/2007 |
| JP | 2007535372 A | 12/2007 |
| JP | 2009-85901 A | 4/2009 |
| JP | 2009513248 A | 4/2009 |
| JP | 2011-118293 A | 6/2011 |
| JP | 2011519654 A | 7/2011 |
| JP | 2013512076 A | 4/2013 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/08071 A1 | 2/2001 |
| WO | WO01/78834 A1 | 10/2001 |
| WO | WO03/018120 A1 | 3/2003 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2010/120823 A2 | 10/2010 |
| WO | WO2011/044176 A1 | 4/2011 |
| WO | WO2011/057028 A1 | 5/2011 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/107624 A1 | 7/2014 |
| WO | WO2014/195516 A1 | 12/2014 |
| WO | WO2015/036420 A1 | 3/2015 |
| WO | WO2015/061663 A1 | 4/2015 |
| WO | WO2015/143053 A1 | 9/2015 |
| WO | WO2017/201525 A1 | 11/2017 |

OTHER PUBLICATIONS

Tyler et al.; U.S. Appl. No. 15/536,148 entitled "Methods and apparatuses for transdermal stimulation of the outer ear," filed Jun. 15, 2017.

Tyler et al.; U.S. Appl. No. 15/536,151 entitled "Systems and methods for transdermal electrical stimulation to improve sleep," filed Jun. 15, 2017.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Chaieb et al.; Transcranial alternating current stimulation in the low kHz range increases motor cortex excitability; Restor Neurol Neurosci; 29(3); pp. 167-175; Mar. 2011.

Coutinho et al.; Musical emotions: predicting second-by-second subjective feelings of emotion from low-level psychoacoustic features and physiological measurements; Emotion; 11(4); pp. 921-937; Aug. 2011.

DaSilva et al.; Electrode positioning and montage in transcranial direct current stimulation; J Vis Exp; 51; e2744; 11 pgs.; May 2011.

Digitimer Ltd.; DS2 and DS3 Isolated Stimulator (product information); 2 pgs.; downloaded from http://www.digitimer.com/research/stimulators/index.htm on Feb. 10, 2014.

Electozyme; Company and Product Information; 3 pgs.; printed Feb. 11, 2014 from http://electrozyme.com/applications/.

Feurra et al.; Frequency specific modulation of human somatosensory cortex; Front Psychol; 2(13); 6 pgs.; Feb. 2011.

GoFLOW; tDCS Kit; product information; 9 pgs..; printed Feb. 10, 2014 (http://flowstateengaged.com/).

Gracenote; Timeline-metadata-api; 3 pages; retrieved from the Internet Jul. 7, 2015; (https://github.com/gracenote/timeline-metadata-api/blob/master/README.md).

Grindhouse Wetware; Thinking Cap; product information; 1 pg.; printed Feb. 10, 2014 (http://www.grindhousewetware.com/thinkingcap.html).

Kanai et al.; Frequency-dependent electrical stimulatioin of the visual cortex; Curr. Biol.; 18(23); pp. 1839-1843; Dec. 9, 2008.

Paulus, W.; Transcranial electrical stimulation (tES-tDCS; tRNS, tACS) methods; Neuropsychol Rehabil.; 21(5); pp. 602-617; Oct. 2011.

Prausnitz; The effects of electric current applied to skin: a review for transdermal drug delivery; Advanced Drug Delivery Reviews; vol. 18; pp. 395-425; Feb. 8, 1996.

Saiote et al.; High-frequency TRNS reduces BOLD activity during visuomotor learning; PLOS one; 8(3); e59669; 8 pgs.; Mar. 2013.

(56) References Cited

OTHER PUBLICATIONS

Schutter et al.; Brain oscillations and frequency-dependent modulation of cortical excitability; Brain Stimulation; 4(2); pp. 97-103; Apr. 2011.
STD Pharmaceutical Products; Idrostar intophoresis machine (product and use information); 9 pgs.; Dec. 2011 (printed Feb. 11, 2014 from http://www.iontophoresis.info/instructions/).
Terney et al.; Increasing human brain excitability by transcranial high-frequency random noise stimulation; The Journal of Neuroscience; 28(52); pp. 14127-14155; Dec. 2008.
Turi et al.; Both the cutaneous sensation and phosphene perception are modulated in a frequency-specific manner during transcranial alternating current stimulation; Restor. Neurol. Neurosci.; 31(3); pp. 275-285; 2013 (year of pub. sufficiently earlier than effective US filed and any foreign priority date).
Tyler et al.; U.S. Appl. No. 61/550,334 entitled "Improvement of Direct of Communication," filed Oct. 21, 2011.
Tyler et al.; U.S. Appl. No. 61/663,409 entitled "Device and Methods for Noninvasive Neuromodulation Using Targeted Transcranial Electrical Stimulation," filed Jun. 22, 2012.
Jeffery et al.; U.S. Appl. No. 15/169,445 entitled "Methods and apparatuses for transdermal electrical stimulation," filed May 31, 2016.
Pal et al.; U.S. Appl. No. 15/170,878 entitled "Apparatuses and methods for neuromodulation," filed Jun. 1, 2016.
Pal et al.; U.S. Appl. No. 15/210,742 entitled "Methods for user control of neurostimulation to modify a cognitive state," filed Jul. 14, 2016.
Egnal et al.; U.S. Appl. No. 15/265,633 entitled "Apparatuses and methods for auto-replenishment of electrodes for transdermal electrical stimulation," filed Sep. 14, 2016.
Aston-Jones et al.; An integrative theory of locus coeruleus-norepinephrine function: adaptive gain and optimal performance; Annu. Rev. Neurosci.; 28: pp. 403-450; Jul. 21, 2005.
Aston-Jones et al.; Role of locus coeruleus in attention and behavioral flexibility; Biological Psychiatry; 46(9); pp. 1309-1320; Nov. 1, 1999.
Backhaus et al.; Sleep disturbances are correlated with decreased morning awakening salivary cortisol; Psychoneuroendocrinology; 29(9): pp. 1184-1191; Oct. 31, 2004.
Basta et al.; Chronic insomnia and the Stress System; Sleep Medicine Clinics; 2(2): pp. 279-291; (Author Manuscript, 20 pages); Jun. 30, 2007.
Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.
Berridge et al.; The locus coeruleus-noradrenergic system: modulation of behavioral state and state-dependent cognitive processes; Brain Research Reviews; 42(1); pp. 33-84; Apr. 30, 2003.
Brown et al.; Control of sleep and wakefulness; Physiological reviews; 92(3); pp. 1087-1187; Jul. 1, 2012.
Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.
Buchanan et al.; Salivary alpha-amylase levels as a biomarker of experienced fear; Communicative and Integrative Biology; 3(6); pp. 525-527; Nov. 1, 2010.
Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90(5); pp. 3106-3114; May 1, 2005.
Buysse et al.; The Pittsburgh Sleep Quality Index: a new instrument for psychiatric practice and research; Psychiatric Research; 28(2); pp. 193-213; May 31, 1989.
Carter et al.; Tuning arousal with optogenetic modulation of locus coeruleus neurons; Nature Neuroscience; 13(12); pp. 1526-1533; Dec. 1, 2010.
Cook et al.; Trigeminal nerve stimulation in major depressive disorder: acute outcomes in an open pilot study; Epilepsy and Behavior; 28(2): pp. 221-226; Aug. 31, 2013.
Degiorgio et al., Trigeminal nerve stimulation for epilepsy: long-term feasibility and efficacy; Neurology; 72(10): pp. 936-938; Mar. 10, 2009.
Degiorgio et al.; Randomized controlled trial of trigeminal nerve stimulation for drug-resistant epilepsy; Neurology; 80(9); pp. 786-791; Feb. 26, 2013.
Elder et al.; The cortisol awakening response-applications and implications for sleep medicine; Sleep Medicine Reviews; 18(3): pp. 215-224; Jun. 30, 2014.
Eschenko et al.; Noradrenergic neurons of the locus coeruleus are phase locked to cortical up-down states during sleep; Cerebral Cortex; 22(2); pp. 426-435; Feb. 1, 2012.
Franowicz et al.; Treatment with the noradrenergic alpha-2 agonist clonidine, but not diazepam, improves spatial working memory in normal young rhesus monkeys; Neuropsychopharmacology; 21(5); pp. 611-621; Nov. 1, 1999.
Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.
Golestanirad et al; Analysis of fractal electrodes for efficient neural stimulation; Frontiers in Neurengineering; 6(3); 10 pages; Jul. 2013.
Granger et al.; Salivary alpha-amylase in biobehavioral research: recent developments and applications; Annals of the New York Academy of Sciences; 1098(1); pp. 122-144; Mar. 1, 2007.
Gummadavelli et al.; Neurostimulation to improve level of consciousness in patients with epilepsy. Neurosurgical Focus; 38(6); pp. E10; (manuscript version,14 pages); Jun. 2015.
Hajos et al.; Norepinephrine but not serotonin reuptake inhibitors enhance theta and gamma activity of the septo-hippocampal system; Neuropsychopharmacology; 28(5); pp. 857-864; May 1, 2003.
Hass et al.; Waking with the hypothalamus. Pflugers Arch R Eur. J. Physiol.; 463(1): pp. 31-42; Jan. 1, 2012.
Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.
Hirotsu et al.; Interactions between sleep, stress, and metabolism; From physiological to pathological conditions; Sleep Science; 8(3); pp. 143-152; Nov. 2015.
Horvath et al.; Evidence that transcranial direct current stimulation (tDCS) generates little-to-no reliable neurophysiologic effect beyond MEP amplitude modulation in healthy human subjects: A systematic review; Neuropsychologia; 66: pp. 213-236; Jan. 31, 2015.
Just et al.; Bold responses to trigeminal nerve stimulation; Magnetic Resonance Imaging; 28(8): pp. 1143-1151; Oct. 31, 2010.
Kubota et al.; Role of the brain stem in cardiovascular changes induced by stimulation of the trigeminal nerve; Anesthesia Progress; 36(4-5); pp. 236-237; Jul. 1989.
Lee et al.; Neuromodulation of Brain States; Neuron; 76(1): pp. 209-222. Oct. 4, 2012.
Leproult et al.; Sleep loss results in an elevation of cortisol levels the next evening; Sleep; 20(10): pp. 865-870; Oct. 1997.
Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.
Lu et al.; A putative flip-flop switch for control of REM sleep; Nature; 441 (7093): pp. 589-594; Jun. 1, 2006.
Magis et al.; Safety and patients' satisfaction of transcutaneous supraorbital neurostimulation (tSNS) with the Cefaly(R) device in headache treatment; a survey of 2,313 headache sufferers in the general population; The Journal of Headache and Pain, 14(1); pp. 95; (manuscript version, 8 pages) Dec. 1, 2013.
McGough et al.; An eight-week, open-trial, pilot feasibility study of trigeminal nerve stimulation in youth with attention-deficit/hyperactivity disorder; Brain Stimulation; 8(2); pp. 299-304; Apr. 30, 2015.

(56) References Cited

OTHER PUBLICATIONS

Meltzer et al; Direct comparison of two new actigraphs and polysomnography in children and adolescents; Sleep; 35(1); pp. 159-166; Jan. 1, 2012.
Nash et al.; Differential activation of the human trigeminal nuclear complex by noxious and non-noxious orofacial stimulation; Human Brain Mapping; 30(11); pp. 3772-3782; Nov. 1, 2009.
Nieuwenhuis et al.; Decision making, the P3, and the locus coeruleus-norepinephrine system; Psychological Bulletin; 131(4); pp. 510-532; Jul. 2005.
Parvizi et al.; Consciousness and the brainstem; Cognition; 79(1): pp. 135-60; Apr. 30, 2001.
Penzel et al.; Dynamics of Heart Rate and Sleep Stages in Normals and Patients with Sleep Apnea; Neuropsychopharmacology; 28(S1); pp. S48-S53; Jul. 1, 2003.
Piquet et al.; Supraorbital transcutaneous neurostimulation has sedative effects in healthy subjects; BMC Neurology; 11(1); p. 135; (manual transcript, 8 pages); Oct. 28, 2011.
Plewnia et al.; Enhancement of human cortico-motoneuronal excitability by the selective norepinephrine reuptake inhibitor reboxetine; Neuroscience Letters; 330(3); pp. 231-234; Sep. 27, 2002.
Pusch et al.; Electrical stimulation of the vestibular system prevents postoperative nausea and vomiting; Acta Annesthesiol Scand.; 44(9); pp. 1145-1148; Oct. 2000.
Riemann et al.; The hyperarousal model of insomnia: A review of the concept and its evidence; Sleep Medicine Reviews; 14(1); pp. 19-31; Feb. 28, 2010.
Rill et al.; Pedunculopontine arousal system physiology—implications for insomnia; Sleep Science; 8(2); pp. 92-99; Jun. 30, 2015.
Rohleder et al.; Psychosocial stress-induced activation of salivary alpha-amylase: an indicator of sympathetic activity; Annals of the New York Academy of Sciences; 1032(1); pp. 258-263; Dec. 1, 2004.
Sara; The locus coeruleus and noradrenergic modulation of cognition; Nature Reviews Neuroscience; 10(3): pp. 211-223. Mar. 1, 2009.
Schmidt et al.; Adrenaline rush: the role of adrenergic receptors in stimulant-induced behaviors; Molecular Pharmacology; 85(4): pp. 640-650; Apr. 1, 2014.
Seugnet et al.; Identification of a biomarker for sleep drive in flies and humans; Proceedings of the National Academy of Sciences; 103(52); pp. 19913-19918; Dec. 26, 2006.
Shiozawa et al.; Transcutaneous vagus and trigeminal nerve stimulation for neuropsychiatric disorders: a systematic review; Arquivos de neuro-psiquiatria; 72(7): pp. 542-547; Jul. 2014.
Siegel; Brain mechanisms that control sleep and waking. Naturwissenschaften; 91(8); pp. 355-365; Aug. 1, 2004.
Somana et al.; Cerebellar afferents from the trigeminal sensory nuclei in the cat. Brain Res.; 38(1); pp. 57-64; Jan. 1980.
Strassman et al; Response of brainstem trigeminal neurons to electrical stimulation of the dura; Brain Research; 379(2): pp. 242-250; Aug. 6, 1986.
Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.
Thoma et al.; Acute stress responses in salivary alpha-amylase predict increases of plasma norepinephrine; Biological Psychology; 91(3): pp. 342-348; Dec. 31, 2012.
Tremblay et al.; Uncertain Outcome of Prefrontal tDCS; Brain Stimulation; 7 (6): pp. 773-783; Dec. 31, 2014.
Trevizol et al.; Trigeminal Nerve Stimulation (TNS) for Generalized Anxiety Disorder: A Case Study; Brain Stimulation; 8(3): pp. 659-660; Jan. 1, 2015.
Trevizol et al.; Trigeminal Nerve Stimulation (TNS) for Post-traumatic Stress Disorder: A Case Study; Brain Stimulation; 8(3): pp. 676-678; Jan. 1, 2015.
Tyler et al.; Transdermal neuromodulation of noradrenergic activity suppresses psychophysiological and biochemical stress responses in humans; Scientific Reports; 5; (manual transcript, 22 pages); Feb. 8, 2015.
Tyler et al.; U.S. Appl. No. 62/166,674 entitled "Systems and Methods for Suppression of Stress Responses by Transdermal Electrical Neuromodulation," filed May 26, 2015.
Upadhyay et al.; Noninvasive mapping of human trigeminal brainstem pathways; Magnetic Resonance in Medicine; 60(5): pp. 1037-1046; Nov. 1, 2008.
Van Stegeren et al.; Salivary alpha amylase as marker for adrenergic activity during stress: effect of betablockade; Psychoneuroendocrinology; 31(1); pp. 137-141; Jan. 31, 2006.
Voisin et al.; Nociceptive stimulation activates locus coeruleus neurones projecting to the somatosensory thalamus in the rat; The Journal of Physiology; 566( 3); pp. 929-937; Aug. 1, 2005.
Voss et al.; Induction of self awareness in dreams through frontal low current stimulation of gamma activity; Nature Neuroscience; 17(6); pp. 810-812; Jun. 1, 2014.
Watson et al.; Development and validation of brief measures of positive and negative affect: the PANAS scales; Jouranl of Personality and Social Psychology; 54(6); pp. 1063-1070; Jun. 1988.
Weiss et al; Validity of Activity-Based Devices to Estimate Sleep; Journal of Clinical Sleep Medicine : 6(4); pp. 336-342; Aug. 2010.
Charlesworth et al.; U.S. Appl. No. 15/384,249 entitled "Apparatuses and methods for transdermal electrical stimulation of nerves to modify or induce a cognitive state," filed Dec. 19, 2017.
Jeffery; U.S. Appl. No. 15/380,028 entitled "Electrodes having surface exclusions," filed Dec. 15, 2017.
Tyler et al.; U.S. Appl. No. 15/460,138 entitled "Systems and methods for transdermal electrical stimulation to improve sleep," filed Mar. 15, 2017.
Law et al.; U.S. Appl. No. 16/393,590 entitled "Streamlined and pre-set neuromodulators," filed Apr. 24, 2019.

\* cited by examiner

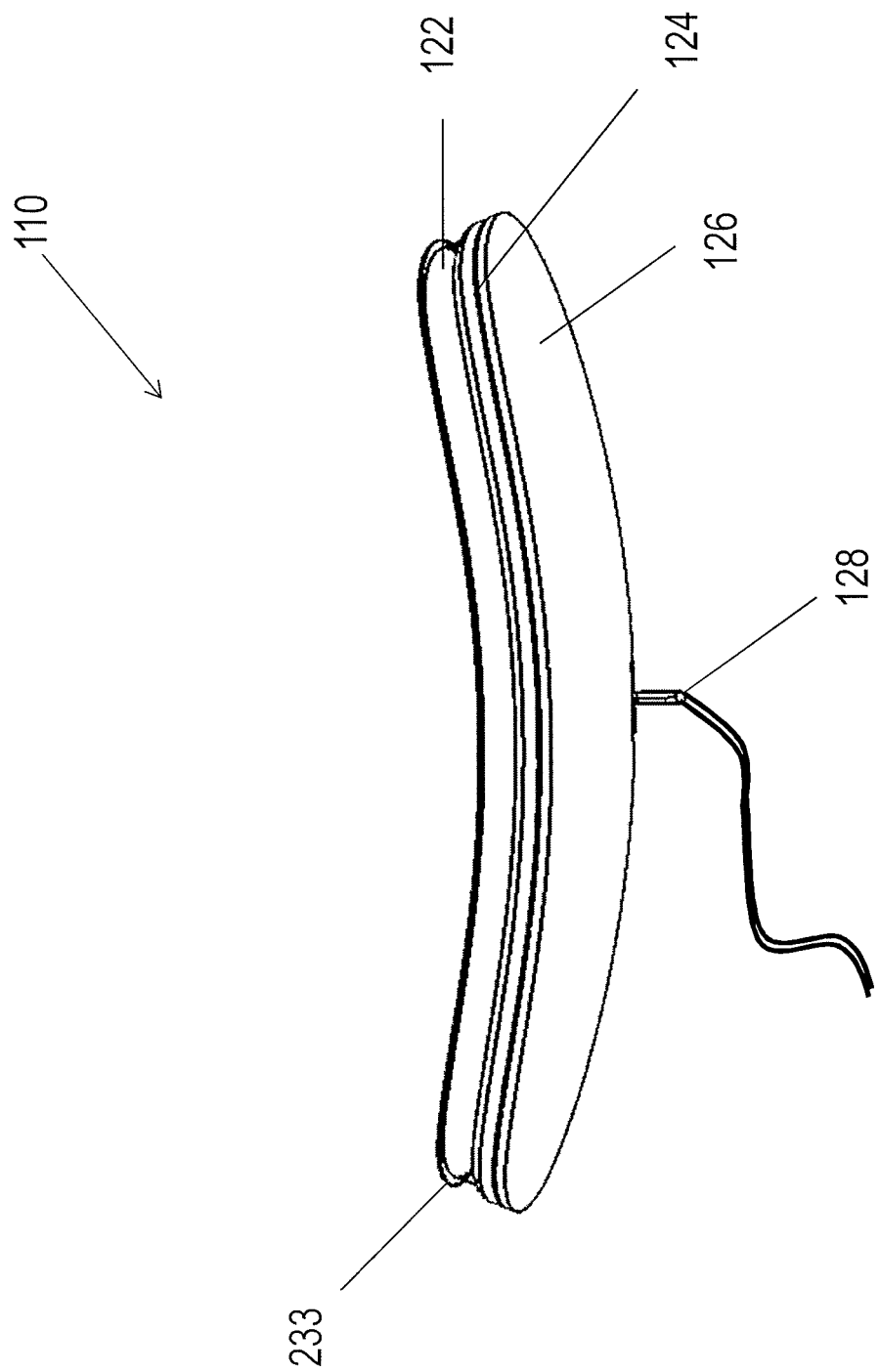

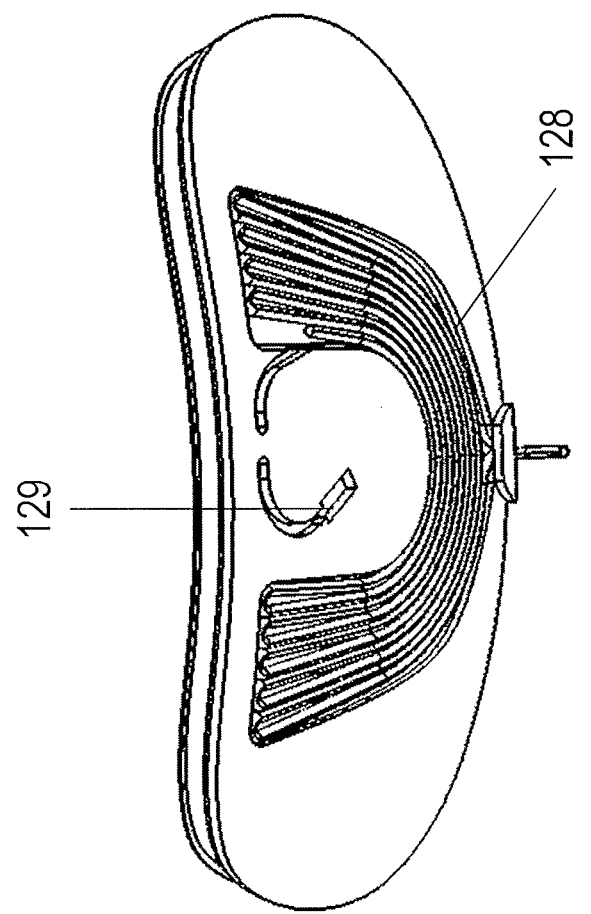

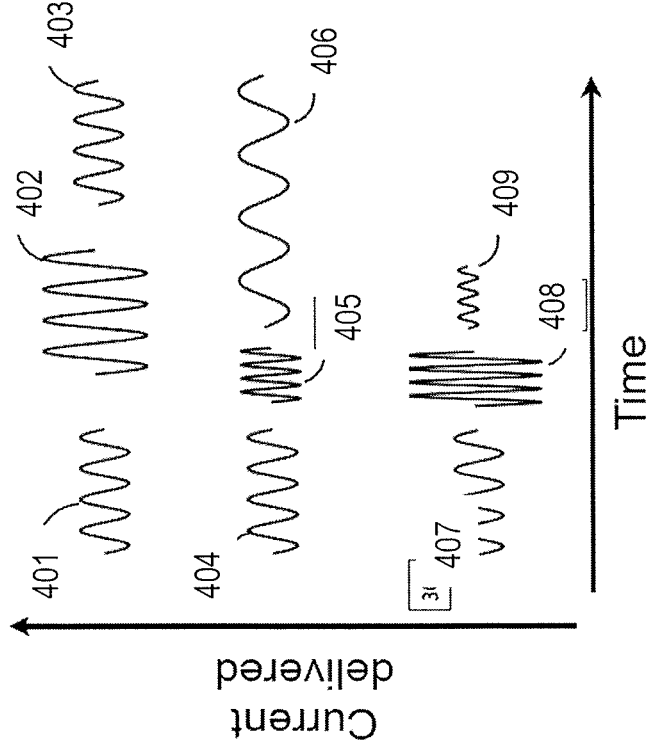
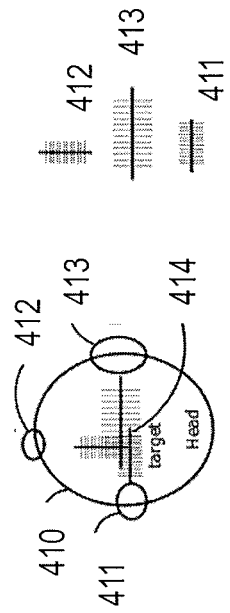
FIG. 8C
FIG. 8B
FIG. 8A

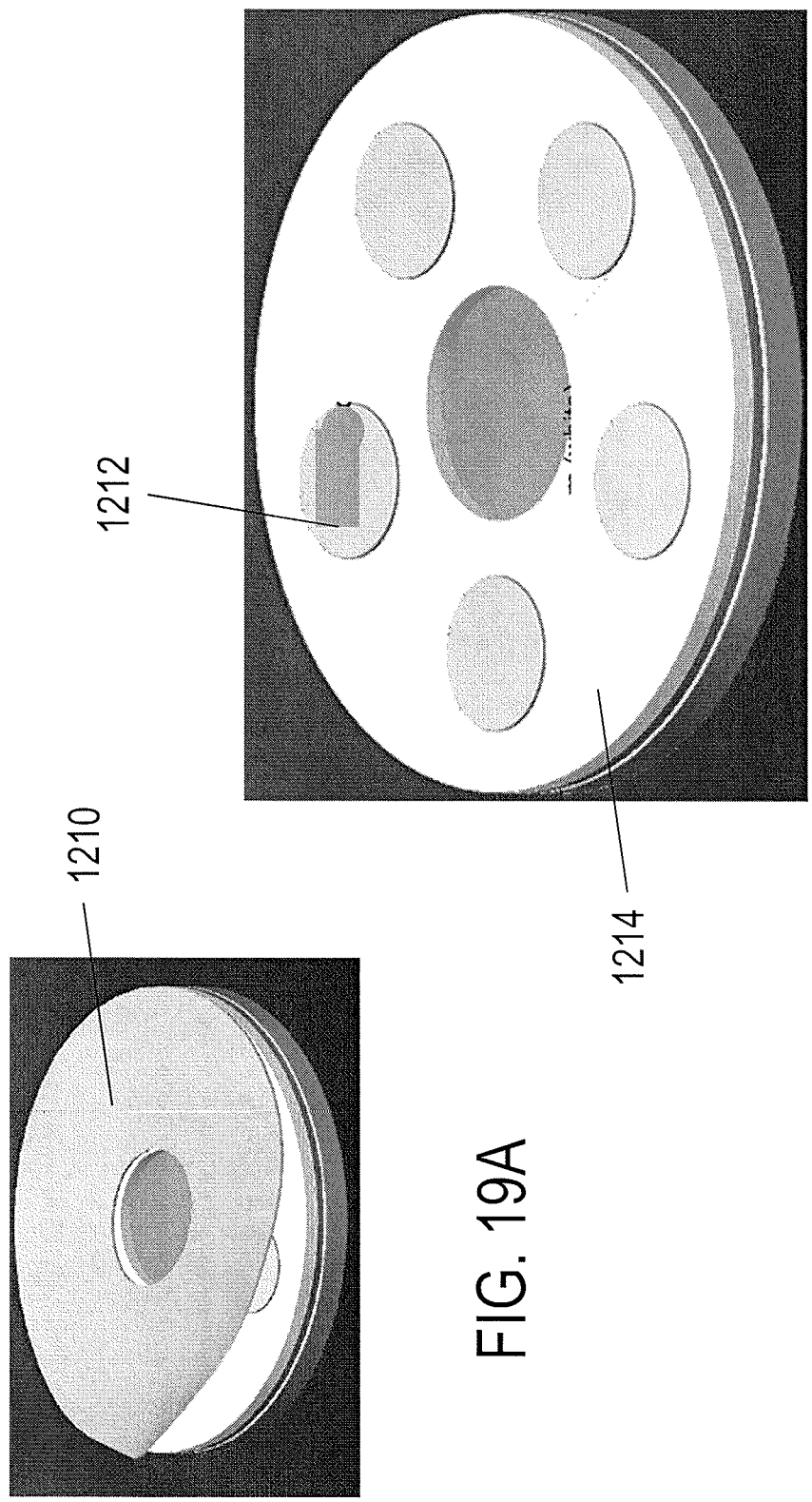

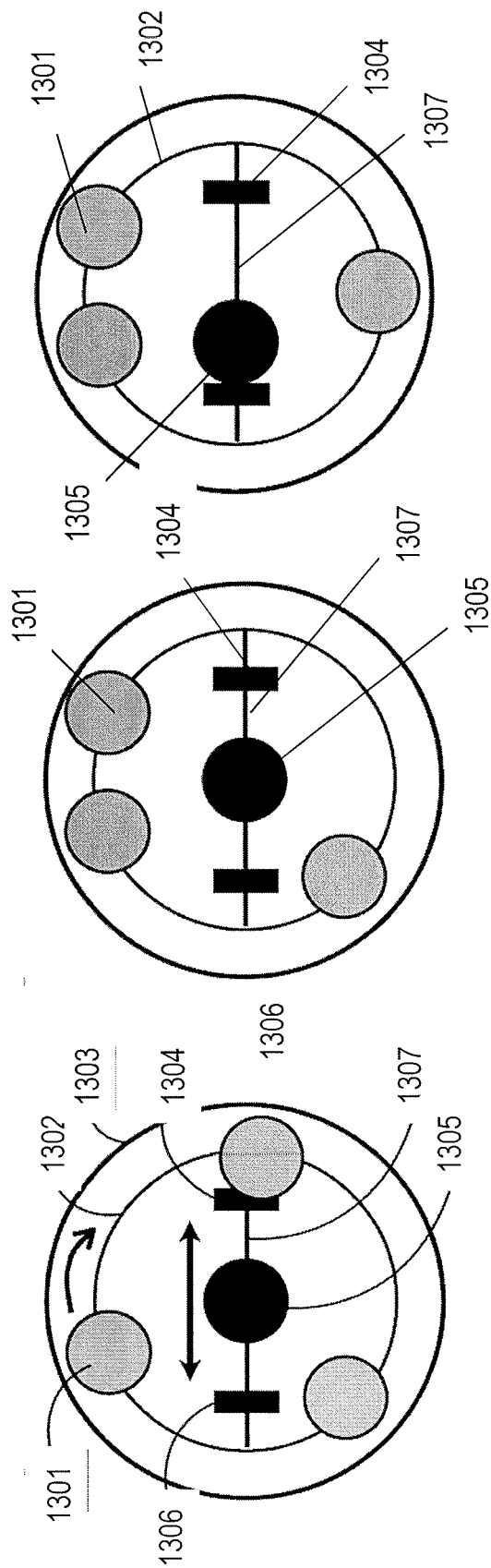

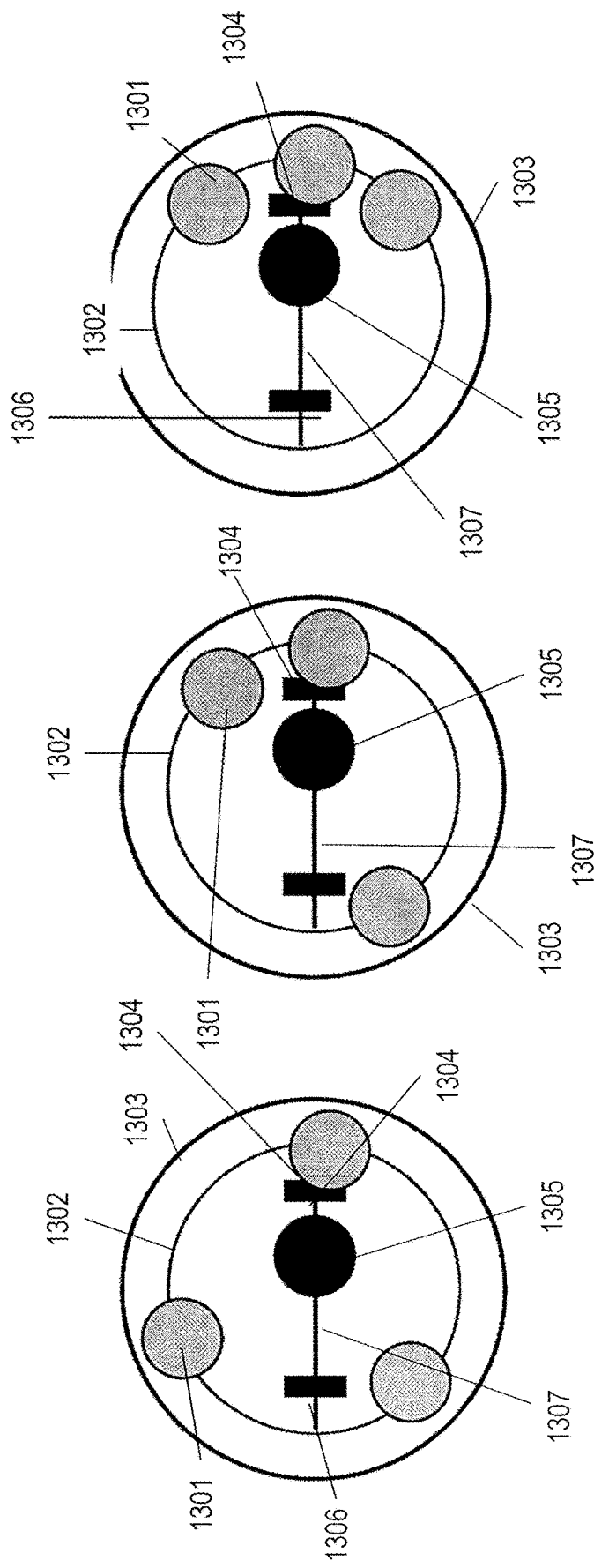

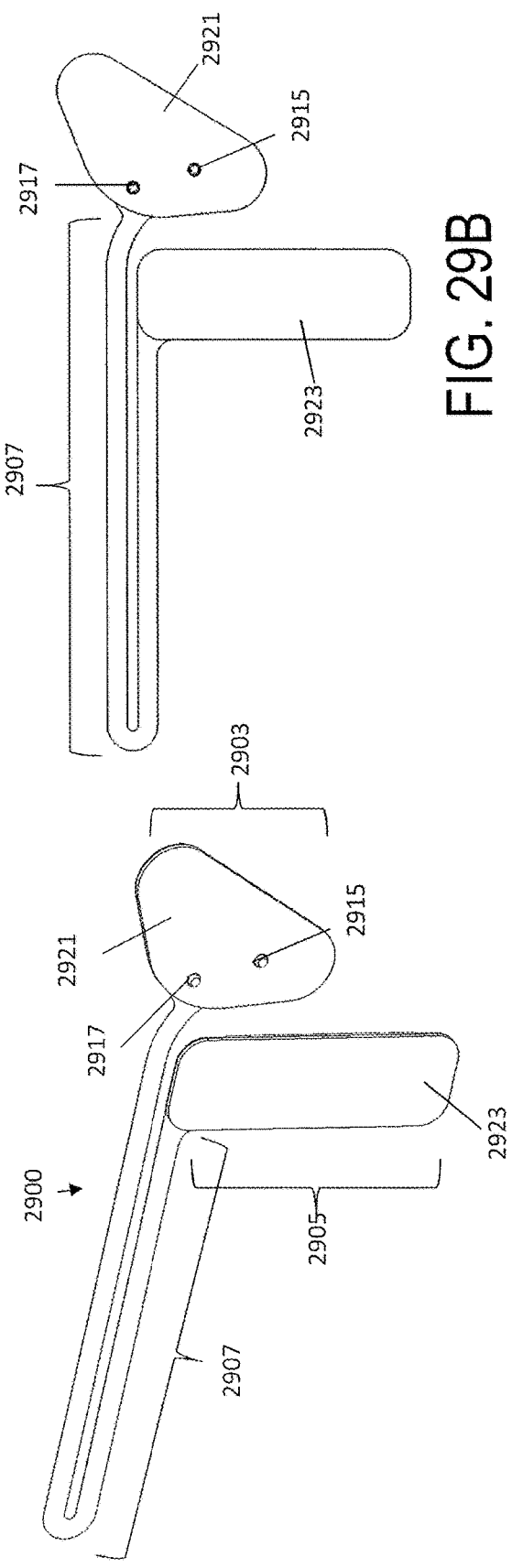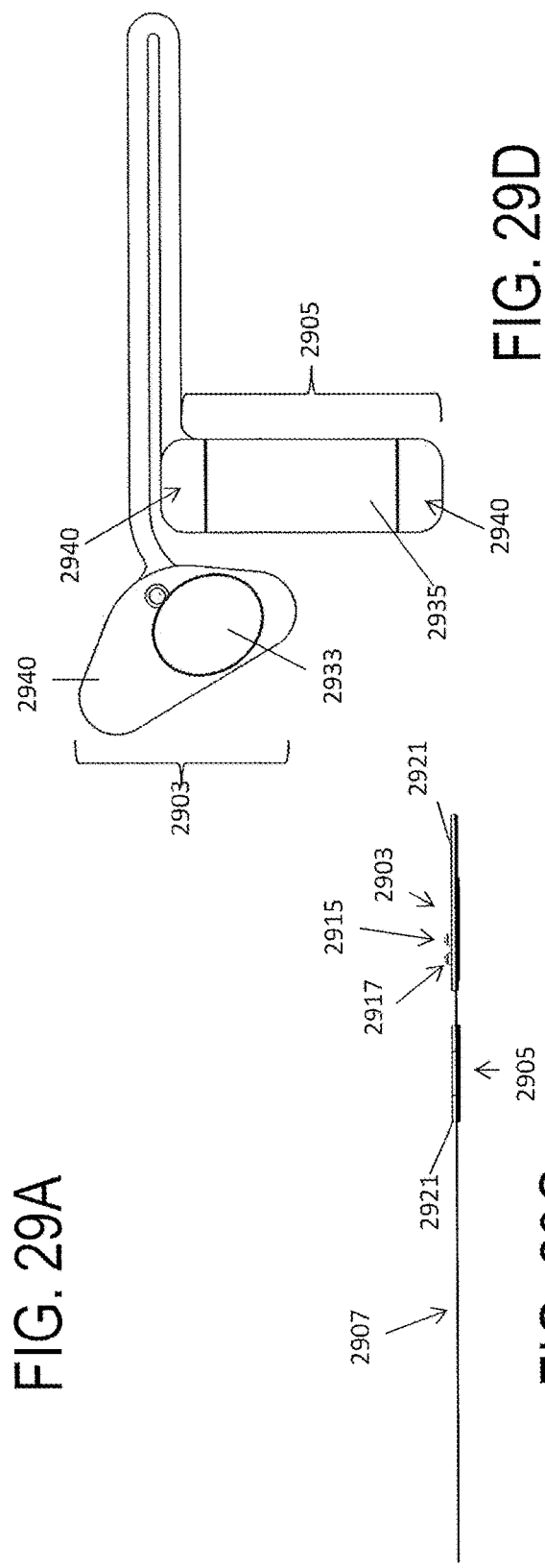

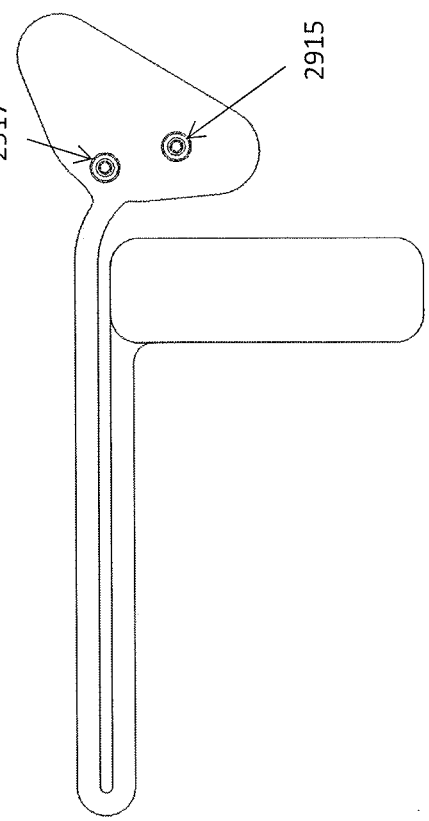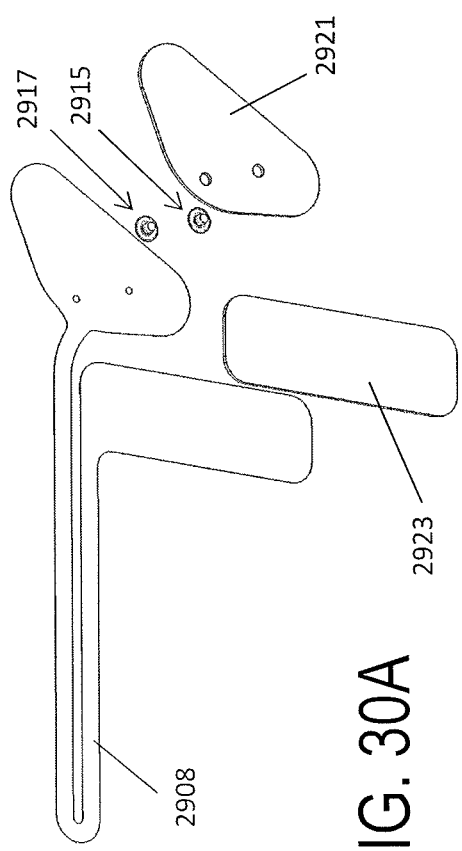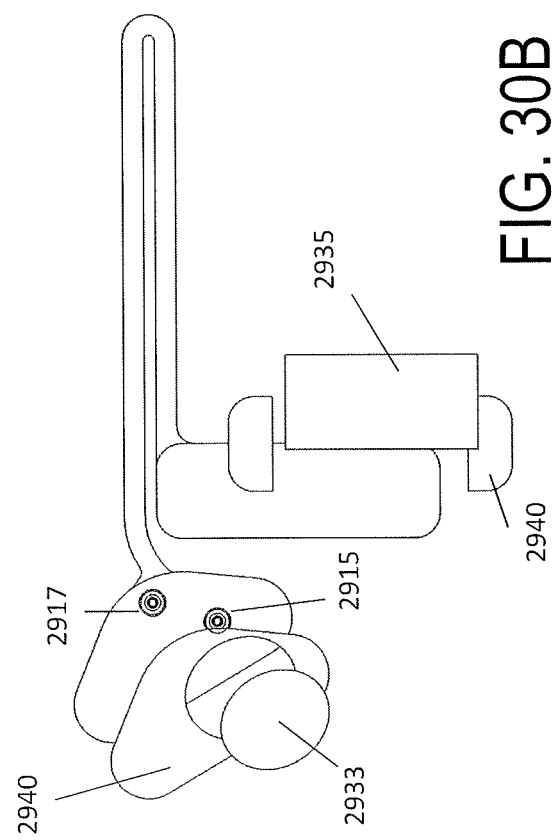
FIG. 30A
FIG. 30B
FIG. 31

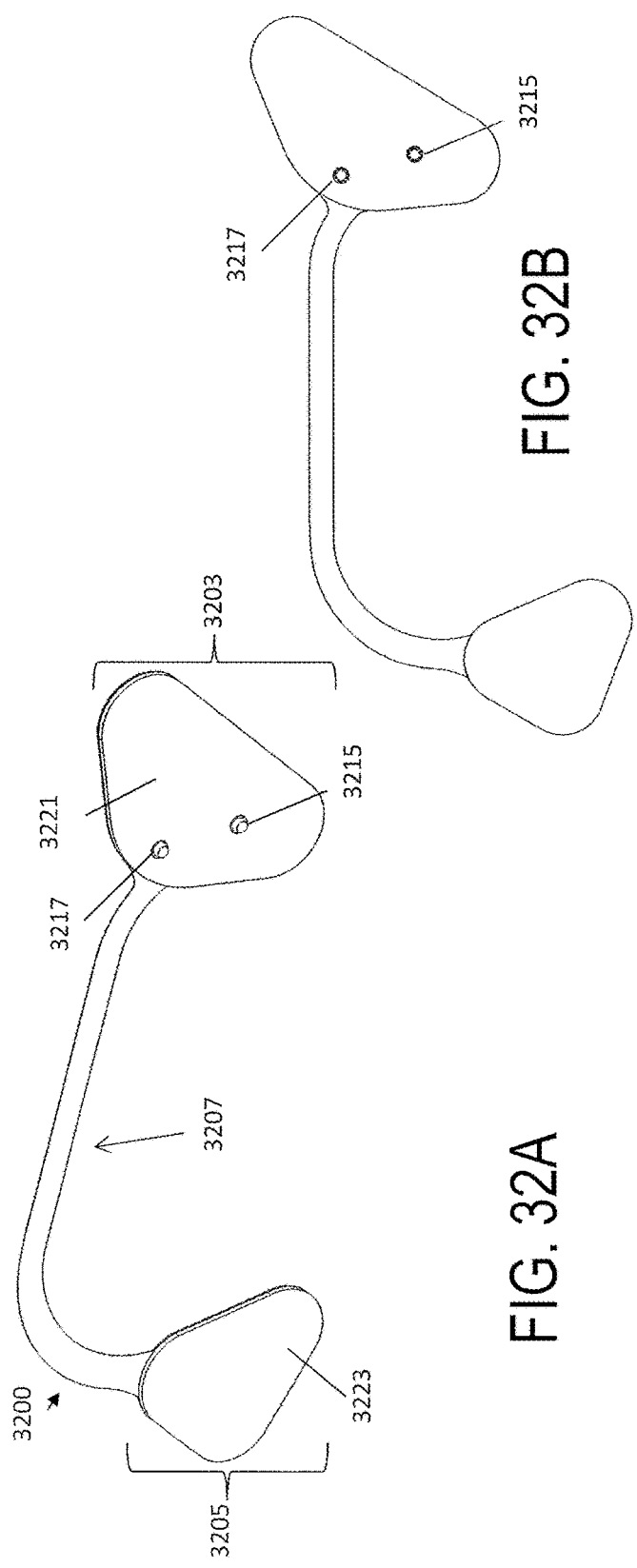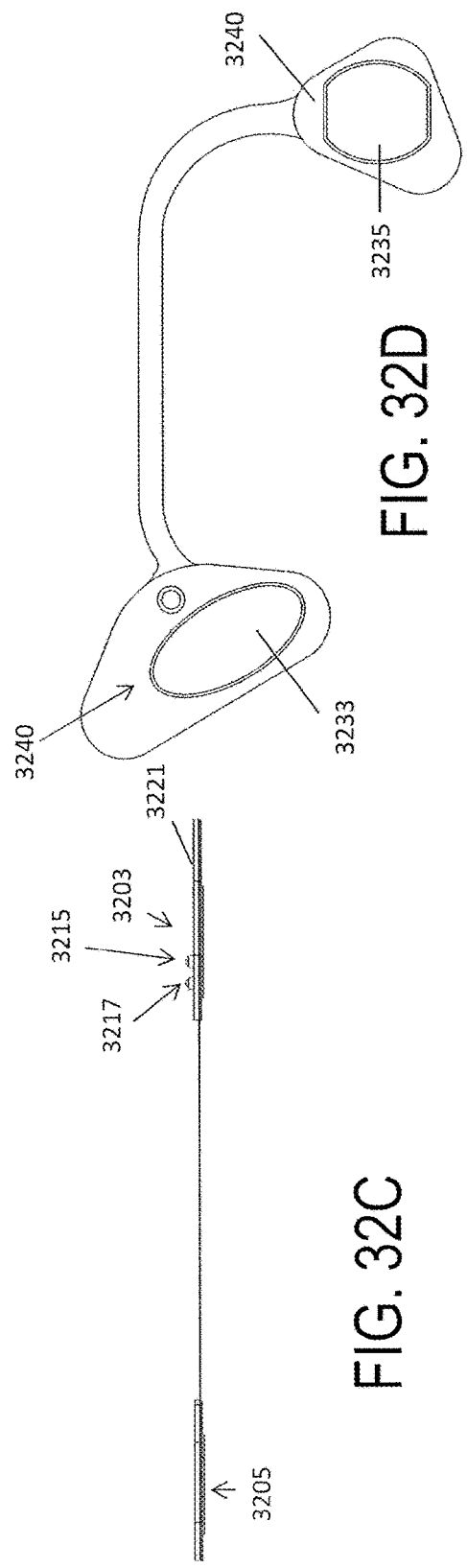
FIG. 32A
FIG. 32B
FIG. 32C
FIG. 32D

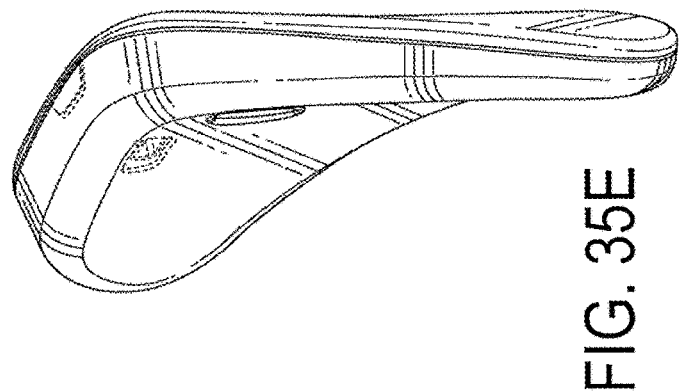
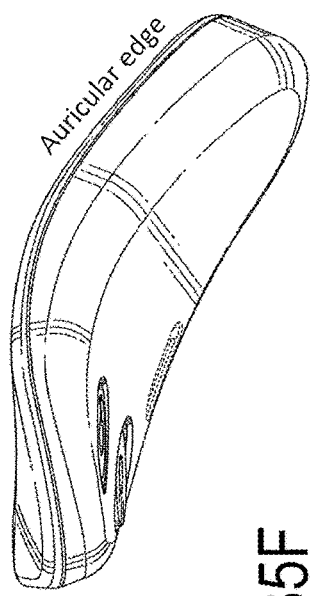
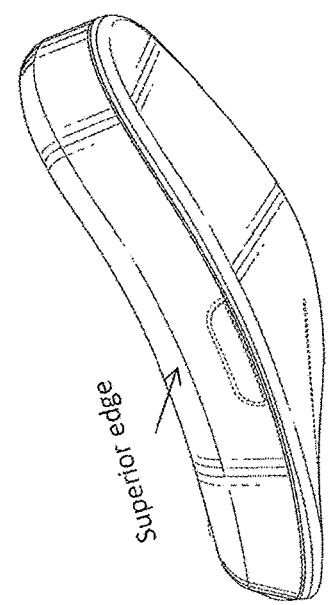
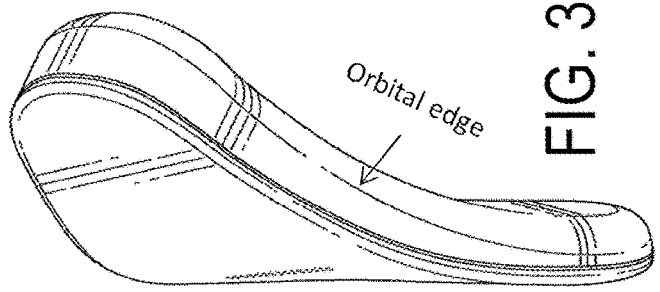
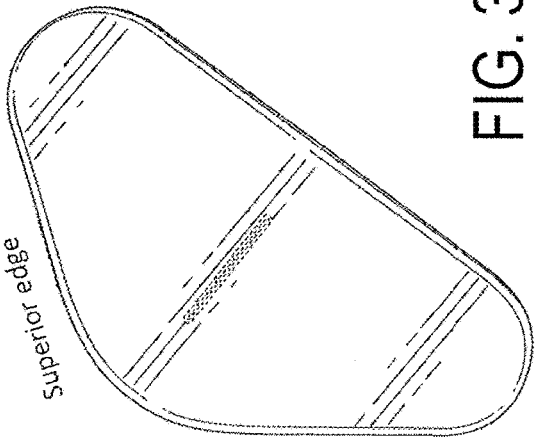
FIG. 35A, FIG. 35B, FIG. 35C, FIG. 35D, FIG. 35E, FIG. 35F

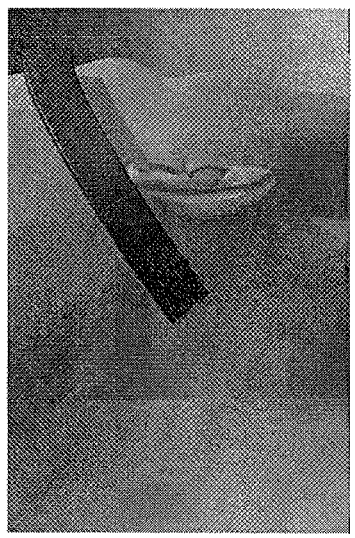
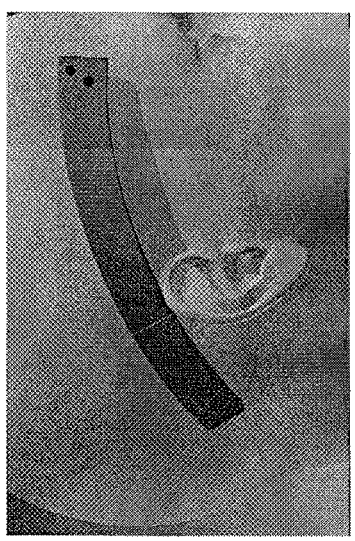
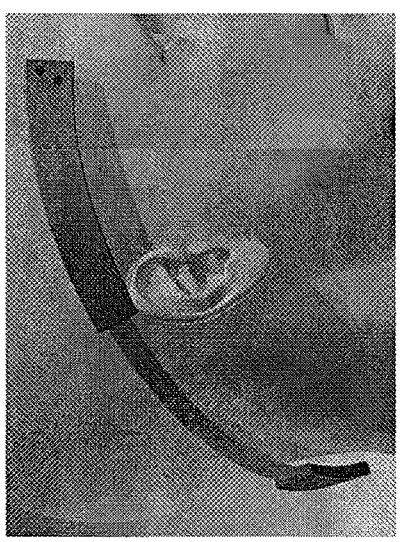
FIG. 37A  FIG. 37B  FIG. 37C
FIG. 38A  FIG. 38B  FIG. 38C

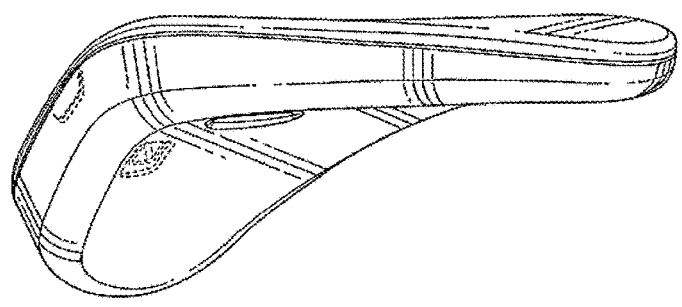
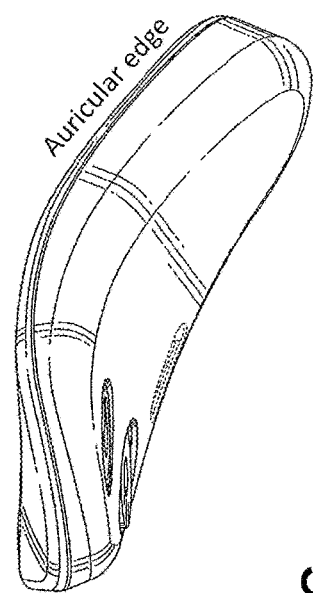
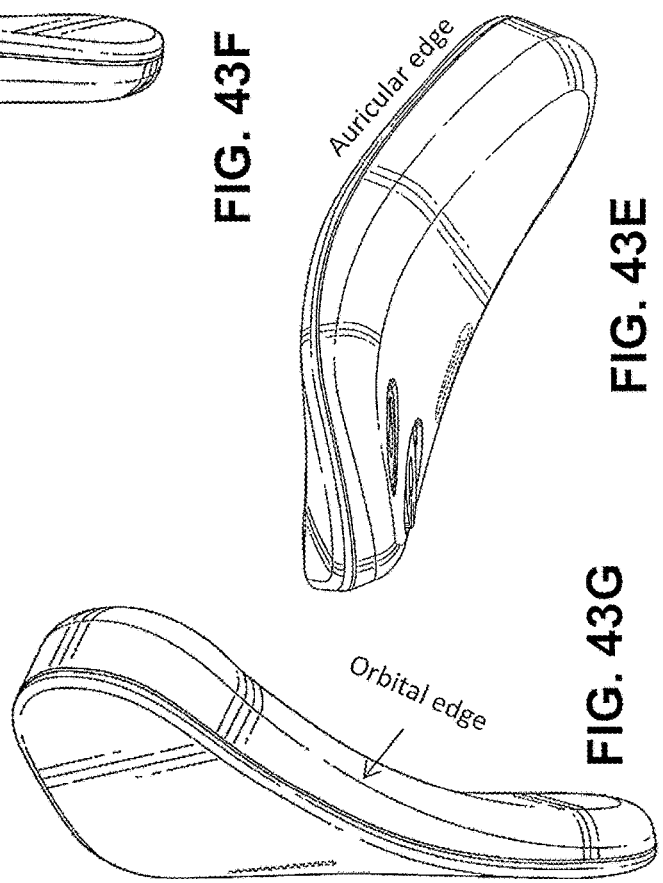
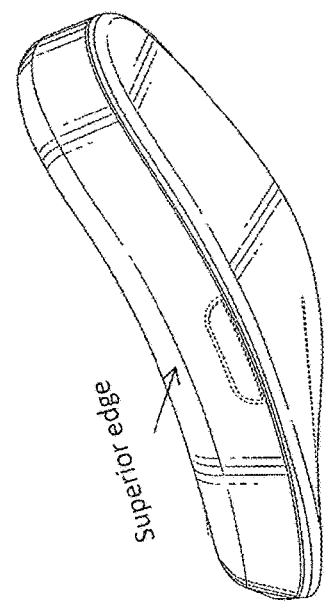
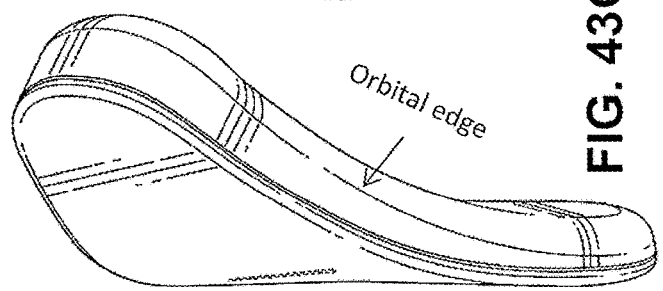
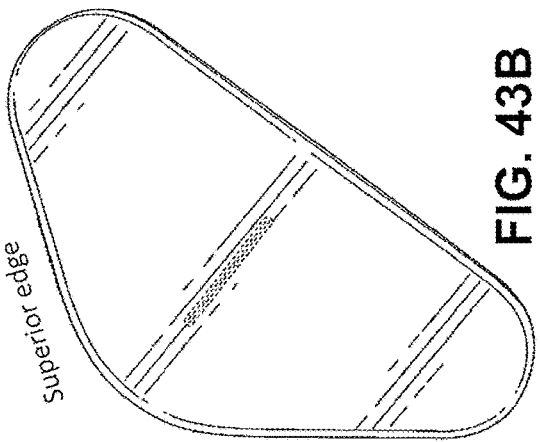
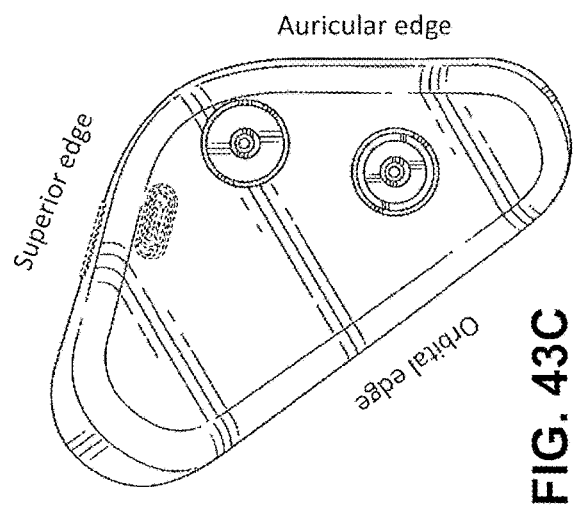

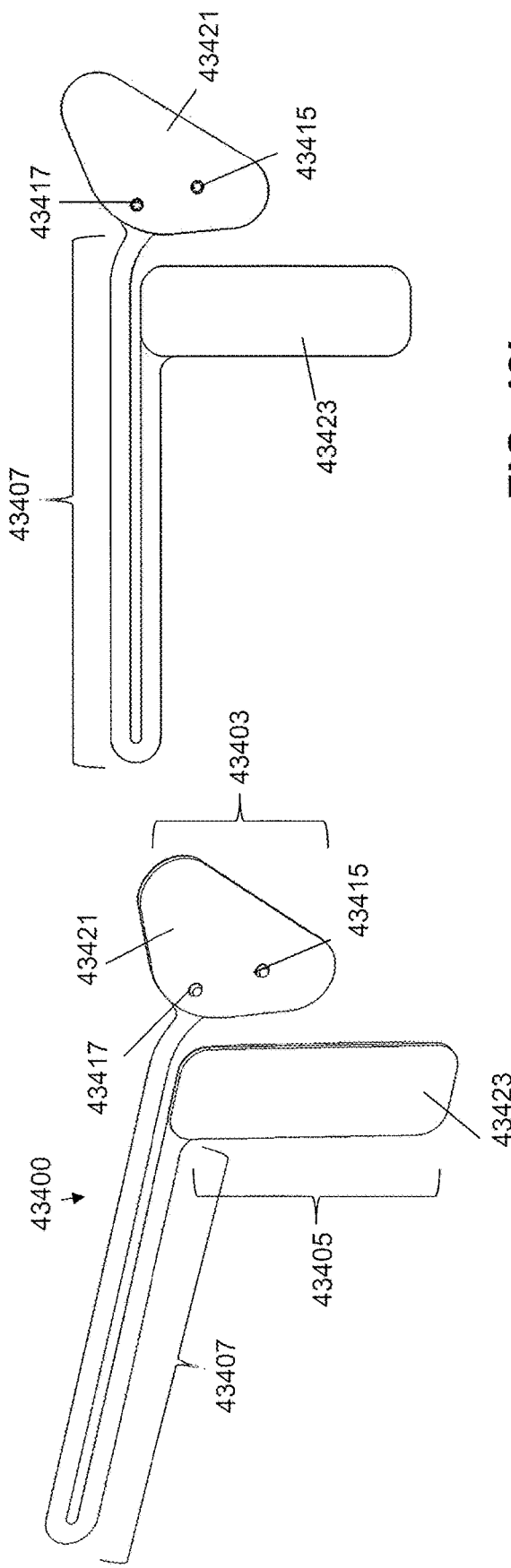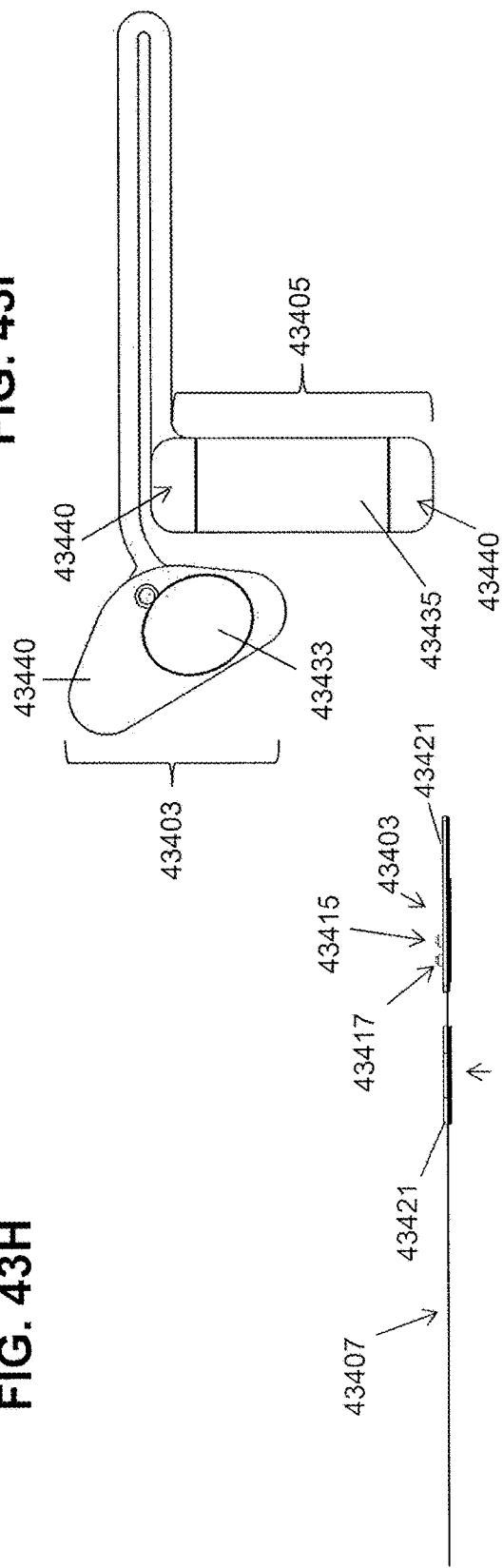

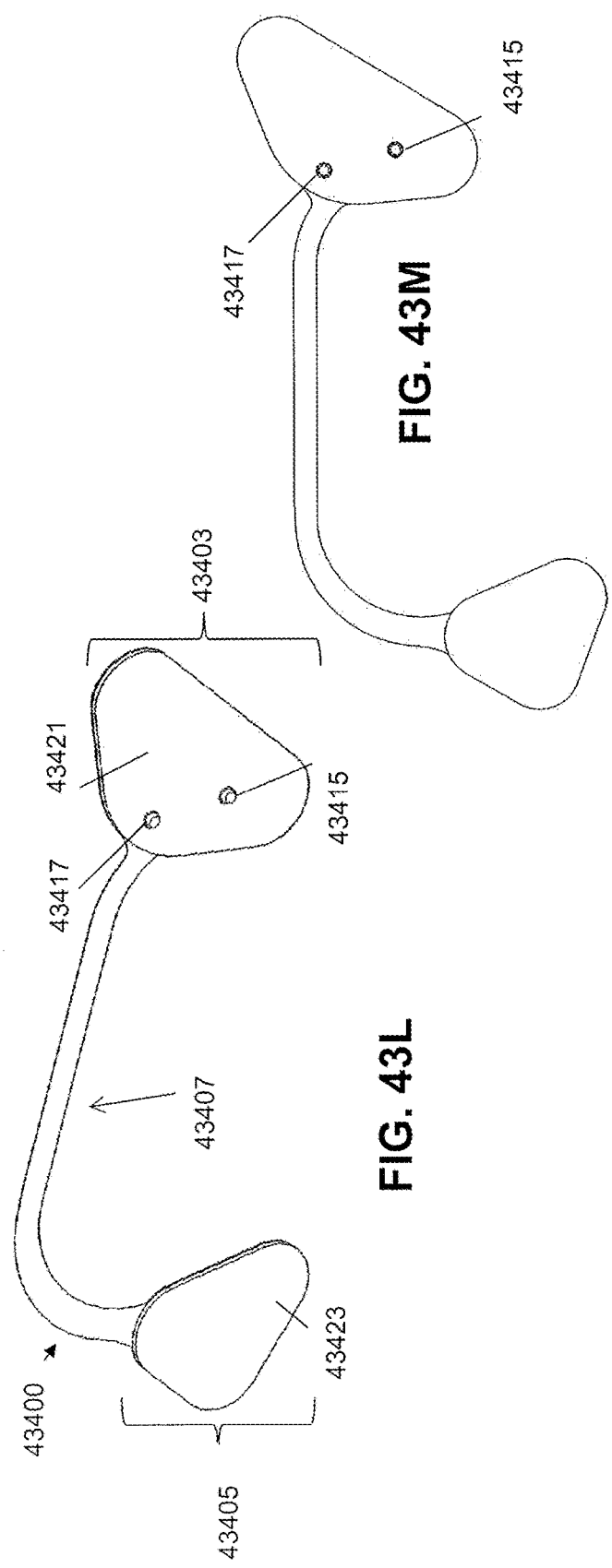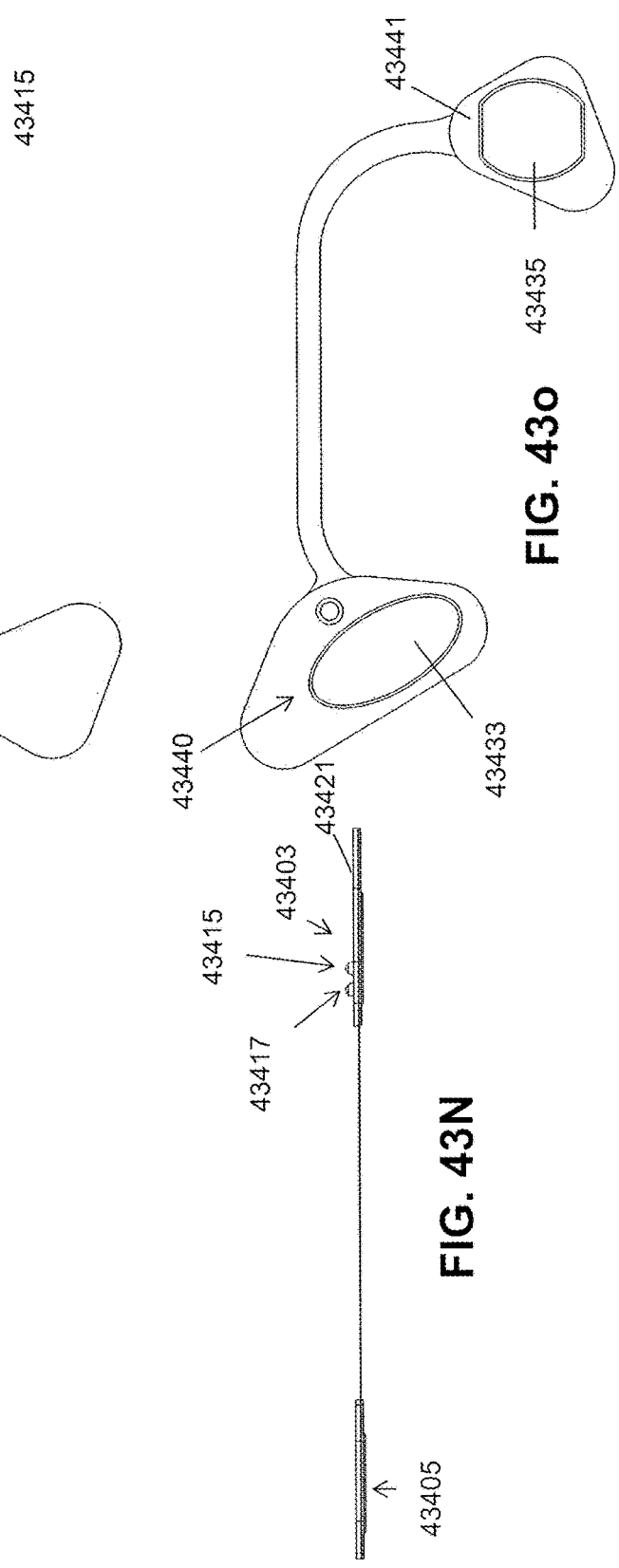

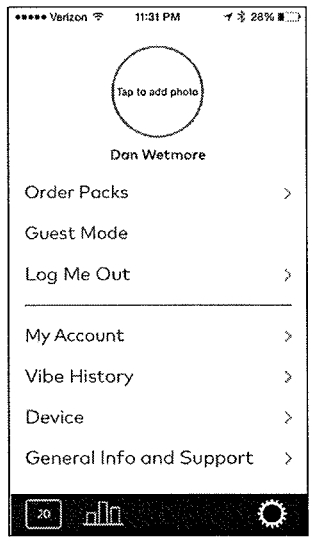
FIG. 53A
FIG. 53B
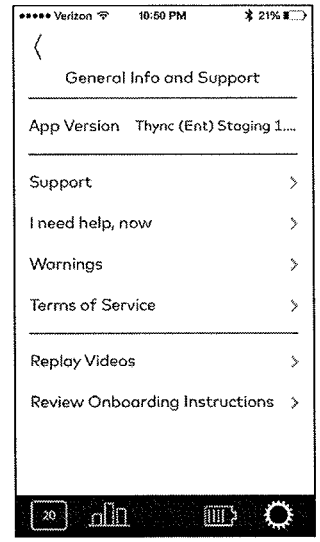
FIG. 53C
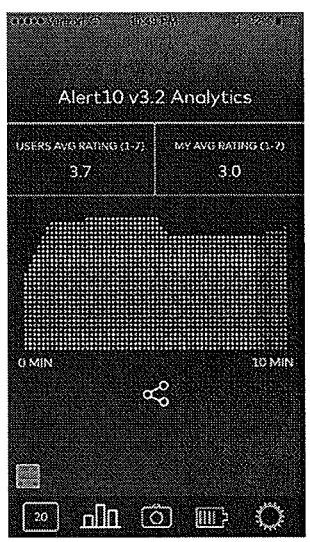
FIG. 53D
FIG. 53E

Before You Get Started, Please Read the Following Warnings

Do not use this device if you have a cardiac pacemaker, implanted defibrillator, or other implanted metallic or electronic device. Doing so could cause electric shock, burns, electrical interference or death.

Do not use during pregnancy or if you are breastfeeding. If you are in the care of a physician, consult your physician before using this device.

Do not use this device if you have epilepsy or a history of seizures.

Do not use this device if you have a Temporomandibular Joint Disorder, Bell's Palsy, impaired cranial nerve function, or facial pain.

Do not place Thync Strips on body in locations other than those directed.

Do not use this device while driving, operating machinery, or during any activity in which electrical stimulation can put you at risk for injury.

Do not use the device while in a shower, bath, pool, or other body of water.

Do not place Thync Strips over open wounds, sores or rashes, or over swollen, red, infected, or inflamed areas or skin eruptions. If you experience an adverse reaction, discontinue use.

Do not use device if the housing has been damaged.

Do not use device in the presence of strong electromagnetic fields.

Do not use this device on children under the age of 18.

Do not place this device across your chest. The introduction of an electrical current to the chest may cause rhythm disturbances to your heart, which could be lethal.

Do not place device over the carotid sinus nerves, the front of the neck, or around the mouth.

For more information and assistance with the contents of this document or the use of your Thync module, please contact: Support@Thync.com. Additional precautions and warnings are listed on page 38.

2 / Stick
Placement and Fit
Calm

Module Placement
Position the Thync Module on your right temple/forehead area above your right eyebrow as shown.

Press firmly for several seconds to STICK the Module on your forehead. Please ENSURE that the Thync Strip and module fit FLUSH where applied. Poor points of contact can lead to discomfort during Vibes.

Calm Strip Placement
Position the backend of the Calm Strip horizontally and centered on the back of your neck just below your hairline.

Press firmly for several seconds to STICK the B end of the Thync Calm Strip in the specified position to ensure a good connection.

Note: Thync Module and Strips may not adhere properly if excessive oils, lotions, makeup or sunscreens are used, resulting in less effective results and possible discomfort.

FIG. 54N

Important Information

Usage

The intended use of the Thync System is to deliver pulsed neurostimulation waveforms to modulate psychophysiological arousal for lifestyle or wellness applications.

The Thync System is not intended to treat or diagnose any disease or medical condition. For detailed usage instructions and warnings, please consult: Thync.com

Disclaimer

Thync does not approve or endorse any changes or modifications to this system, which may alter its performance characteristics. Any such changes void warranty and authority for use.

Adverse Reactions

If you experience adverse reactions, stop using the system and consult with your physician. Users with sensitive skin may experience skin irritation in the area where the Thync Strip is applied. You may experience a headache and other painful sensations during or following the application of electrical stimulation.

32

Precautions

Use caution if Thync Strip is placed over areas of skin that lack normal sensation.

Clean and dry the area of skin to which the Thync Strip will be applied before applying it.

Use of accessories not approved by the manufacturer may cause harm or injury.

Do not disassemble the Module.

Thync Strips should only be applied to normal, intact, healthy skin over locations as directed.

Keep dry. Clean by wiping with dry cloth. Do not immerse.

Operation in close proximity to short wave or microwave therapy equipment may produce instability in the Module output.

Keep this system out of reach of children.

FIG. 54Q

What's in the box

- Thync Module
- 10 Calm Strips
- 10 Energy Strips
- Calm & Energy Vibes
- Charging Cable
- User Guide

Order

Technology Requirements iPhone 4s, 5, 5s, 6 and 6 plus
iOS 8 and Higher

Technology Specs

Dimensions, weight, and other details.

MORE

Warnings

Before using the Thync System, please review these warnings, precautions and adverse reactions.

MORE

FIG. 56G

Intended Use

The intended use of the Thync System is to deliver pulsed neurostimulation waveforms to modulate psychophysiological arousal for lifestyle or wellness applications. The Thync System is not intended to treat or diagnose any disease or medical condition.

FIG. 56H

How do Vibes feel?

It's similar to the relaxing sensation of a massage or the invigoration of splashing cold water on your face - only more focused.

How does it feel to relax and get a good night's sleep? What is it like to feel motivated and make it to the gym every day? That's how good feels. That's what Vibes do for you.

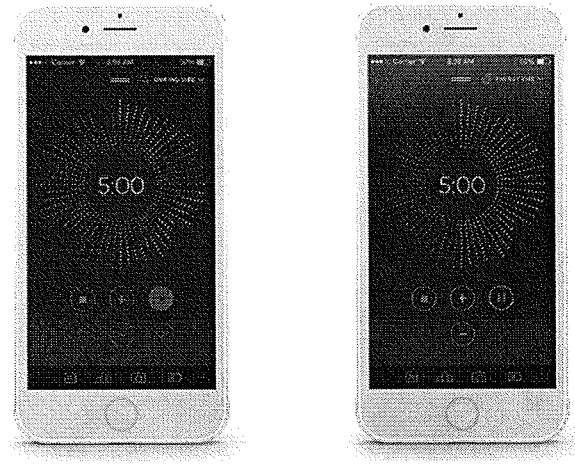

FIG. 57C

How to Vibe

Vibing is easy.
Just 3 steps - Snap, Stick, Shift.

For some users, Vibe effects are immediate and obvious. Others may require multiple Vibes or need to try various placement and tuner settings to experience the desired effects.

FIG. 57D

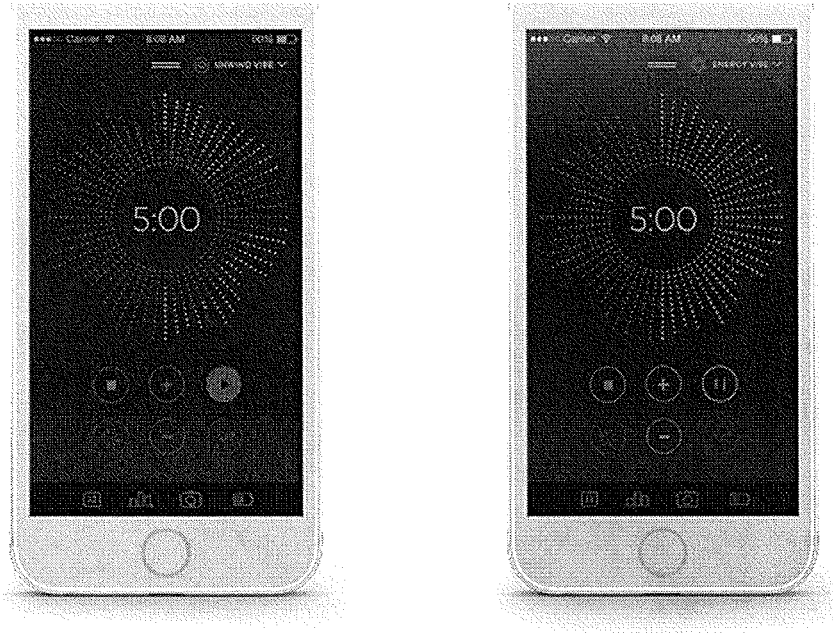

Calm Vibe users feel
Physically relaxed, more centered
More aware of breathing and heart rate
Detached from stressful thoughts
Less likely to react emotionally
Mild euphoria in some cases Thync Science Energy Vibe users feel
Mental alertness, focused
Burst of physical energy, excited
Motivation to be active
Need to accomplish something
Warm feeling in their chest Order Now

FIG. 57E

The Thync Approach

A soothing neck massage. A splash of cold water. A kiss from someone you love. Each action influences peripheral nerves in your head and face, signaling brain regions to change the way you feel. Thync works using the same pathways by delivering low-level electrical pulses to these nerves.

Every day, your body balances the activity between your sympathetic and parasympathetic nervous systems. The sympathetic system is associated with a "fight or flight" response to help regulate your reaction to stress. The parasympathetic system counteracts stress to help you enter a relaxed "rest and digest" mode.

Thync uses neurosignaling to activate specific cranial and peripheral nerves to influence this balance and shift you to a state of calm or give you a boost of energy in minutes.

Thync is a new category of wearable technology that acts in synergy with your mind and body.

FIG. 58A

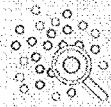

Neurosignaling: The Science

Neurosignaling is the coupling of an energy waveform to a neural structure (receptor, nerve or brain tissue) to modulate its activity.

Neurosignaling waveforms or Vibes consist of precise algorithms that bias activity of the sympathetic and parasympathetic nervous systems, so that you can enjoy a shift into a more energetic or relaxed state.

Neurosignaling builds upon the best features of long-standing tDCS and TENS techniques by using pulsed currents with lower-intensity and higher-frequency outputs delivered through bio-compatible materials for greater safety and comfort.

At Thync, we have developed proprietary neurosignaling technology that delivers signals to the brain through three neural pathways:

FIG. 58B

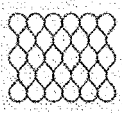

Safety

Thync is the result of years of research and development by Thync neuroscientists and engineers. Thync Vibes were safely tested on several thousand individuals under a variety of conditions to optimize their performance and comfort.

The Thync System builds upon more than 40 years of extensive research, documentation and consumer use that supports the safety and tolerability of our limited output neurosignaling approach.

The Thync System is a low-risk transdermal neurostimulation device intended for lifestyle use at home, work, or in wellness applications to temporarily induce mental relaxation or calmness or to temporarily increase energy, awareness, and alertness. The Thync system is a safe and low-risk device. It is not intended to treat or diagnose any disease or medical condition.

Based on intended use and output characteristics, the FDA notified Thync that its device is not subject to medical device regulations requiring pre-market clearance or approval.

Safety Study – PDF

FIG. 58E

Testing

Thync Vibes are the culmination of testing on thousands of subjects conducted internally by our scientists, externally through our university collaborators, and by our early adopters in the real world. We capture, record, and analyze data such as heart rate, heart rate variability, galvanic skin response, pupil diameter, and EEG to quantify how Vibes influence the parasympathetic and sympathetic nervous systems. We monitor biometric signals, assay psychophysiological variables, and conduct psychometric evaluations.

We have developed a technology that can consistently, and in a statistically reliable manner, beat the placebo effect. Our studies incorporate the use of placebo controls in blind tests under a variety of experimental conditions. All studies are performed using IRB-approved protocols and procedures.

Neurosignaling Study – PDF

FIG. 58F

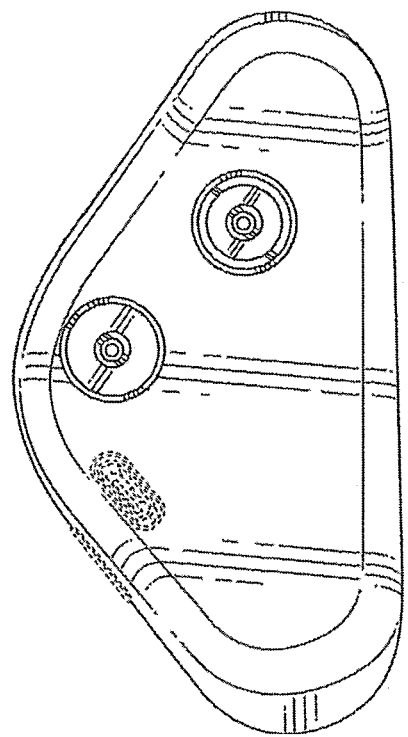
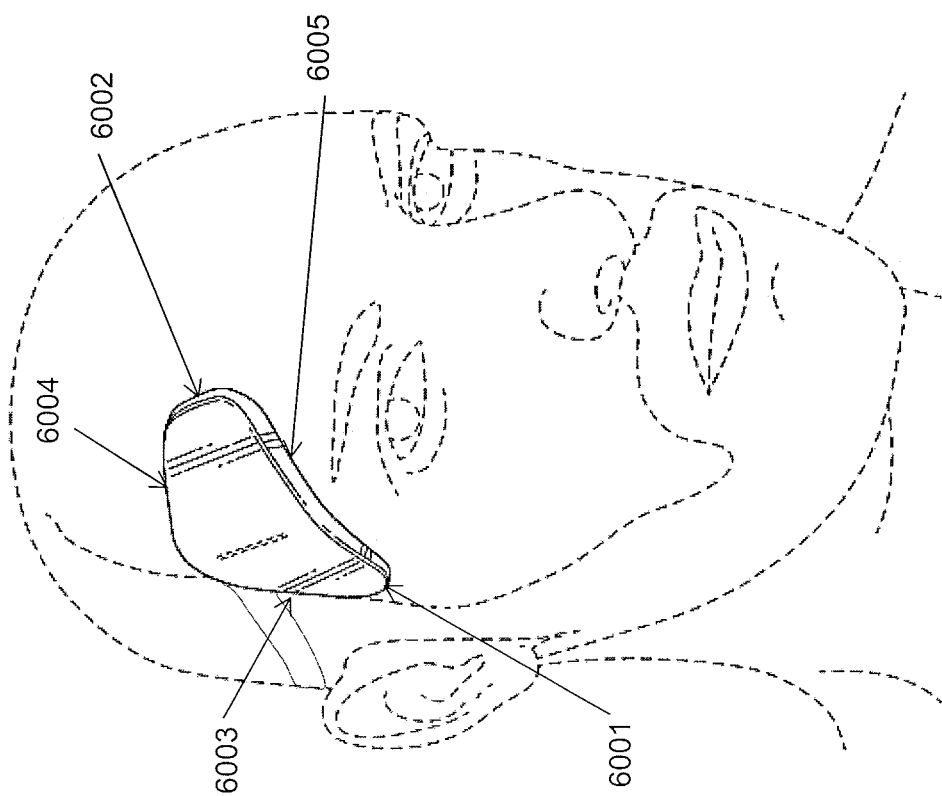
FIG. 60B
FIG. 60A

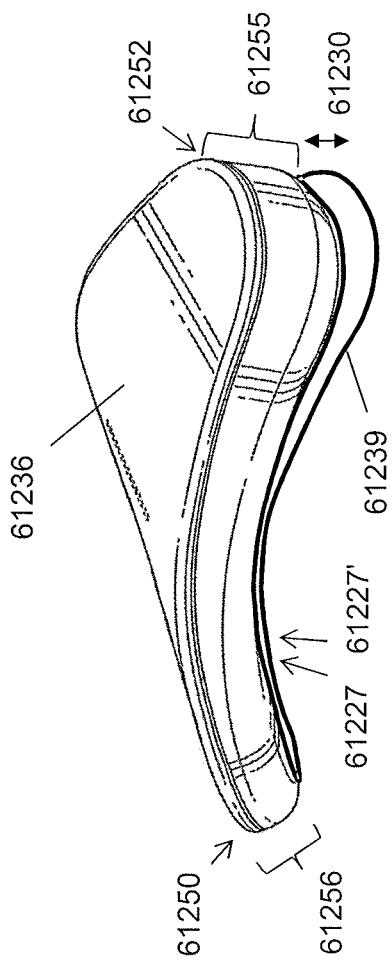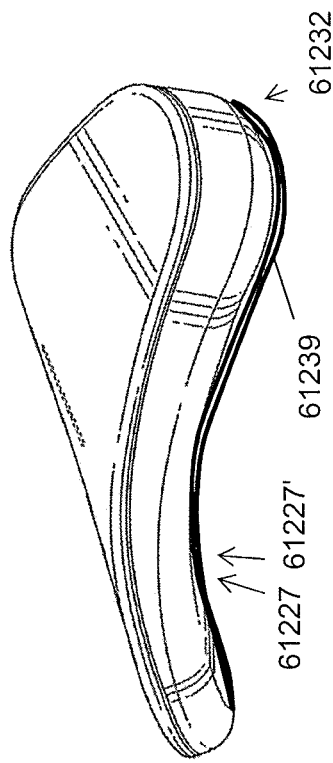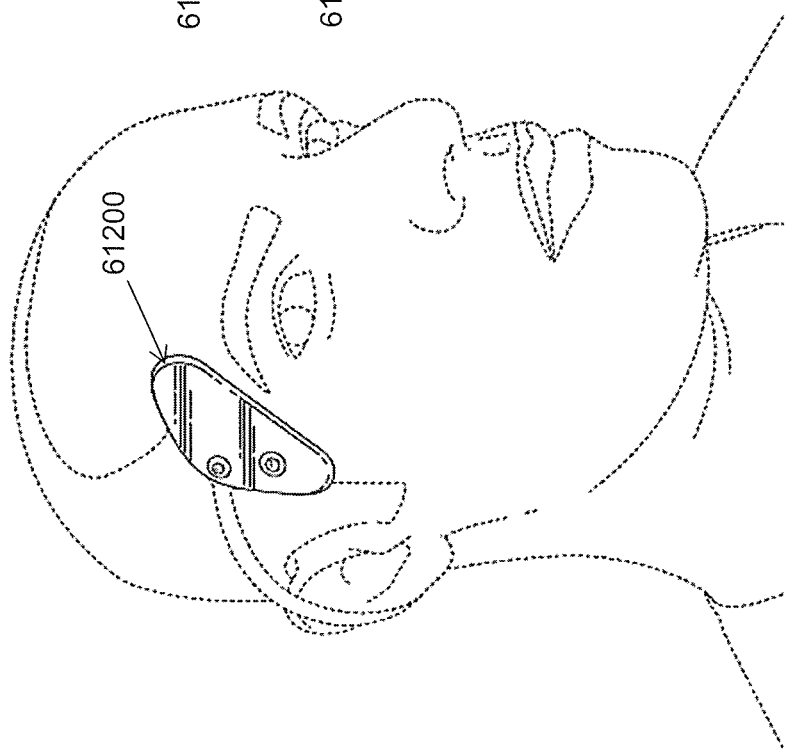
FIG. 61B
FIG. 61C
FIG. 61A

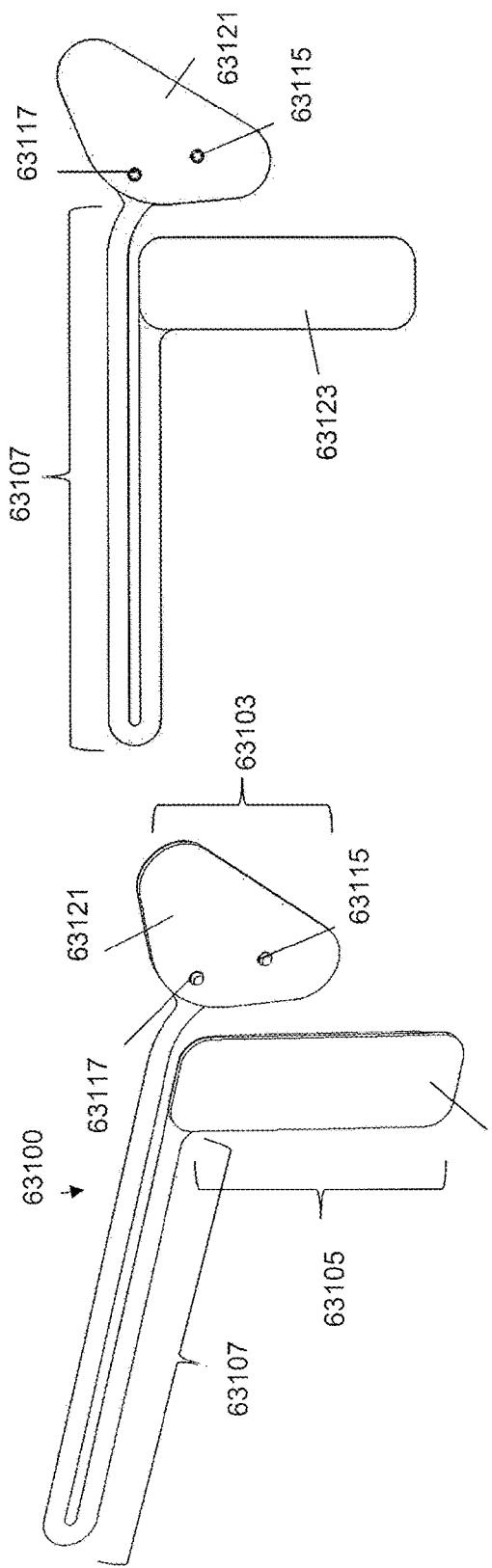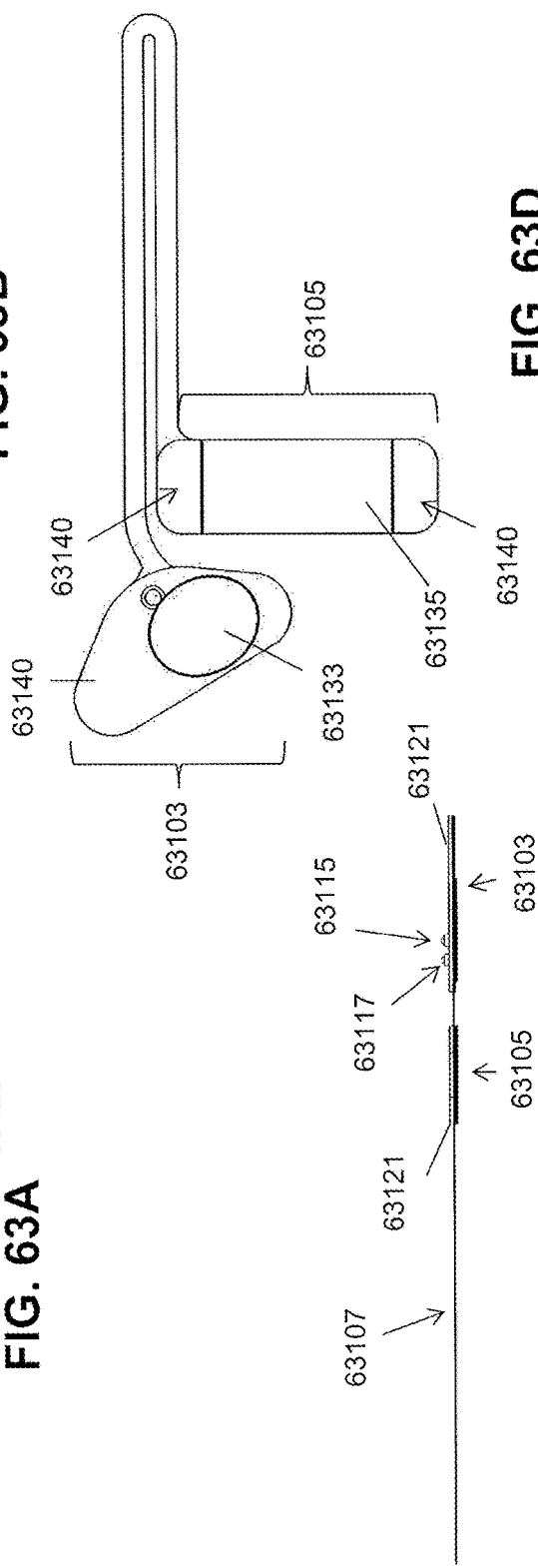

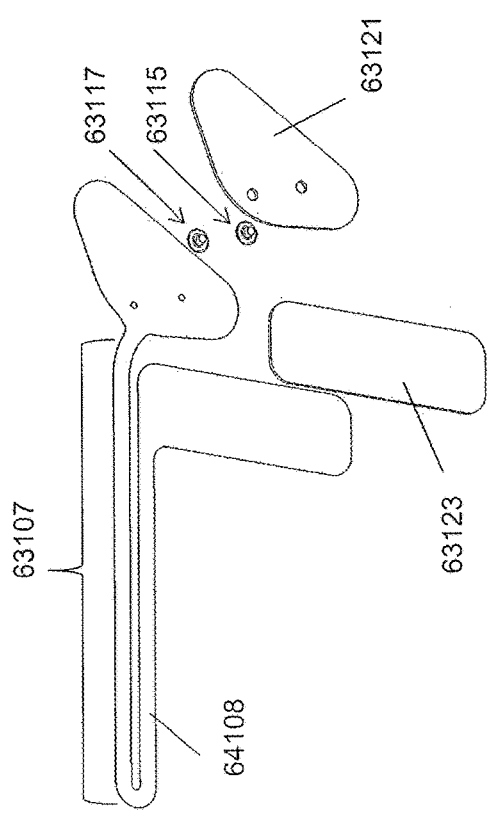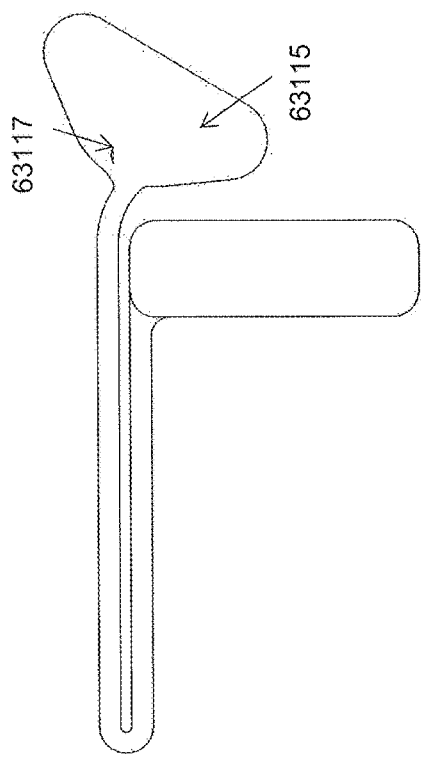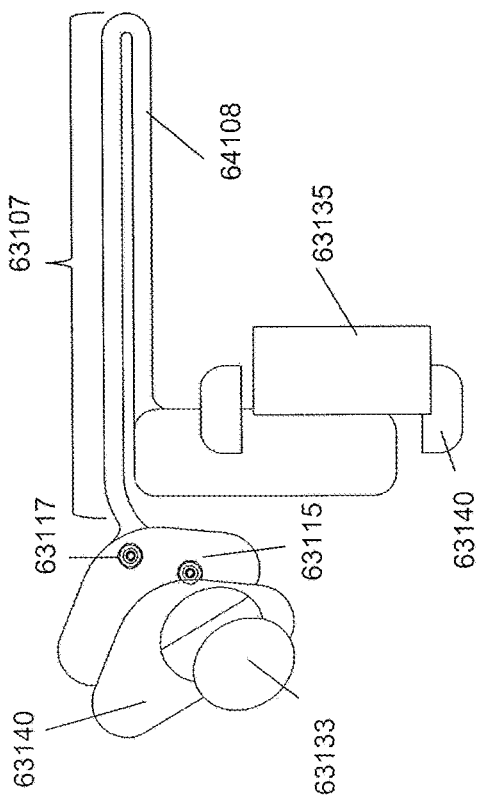

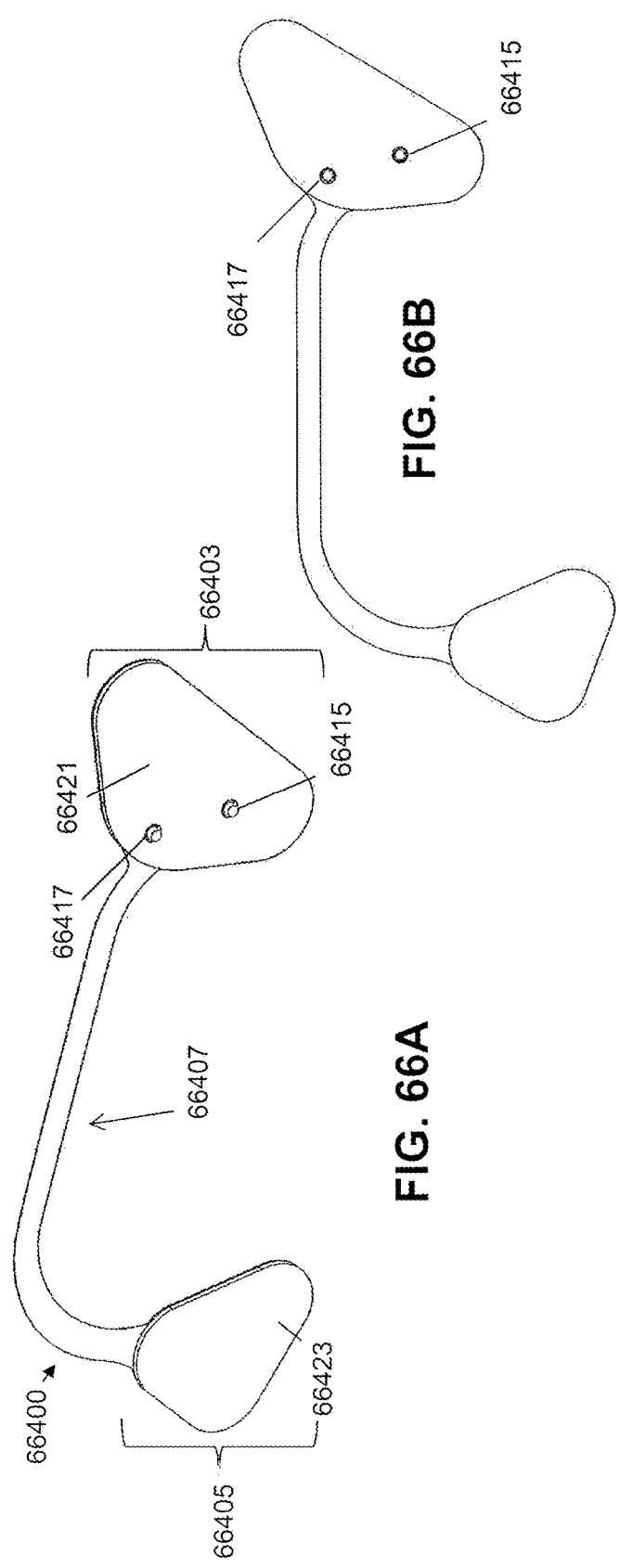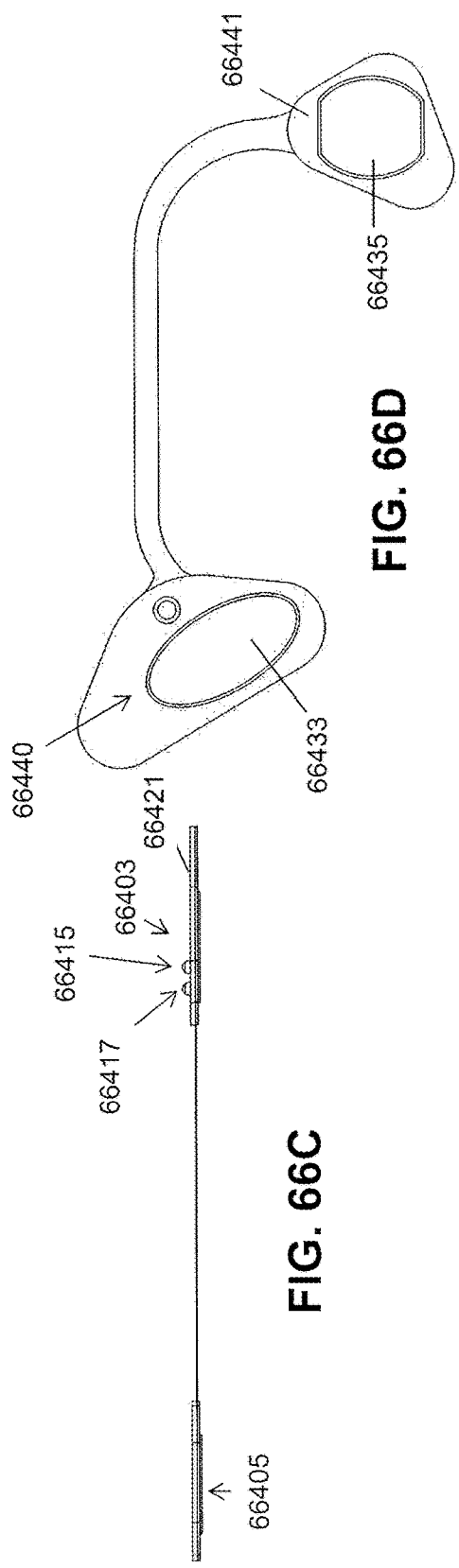

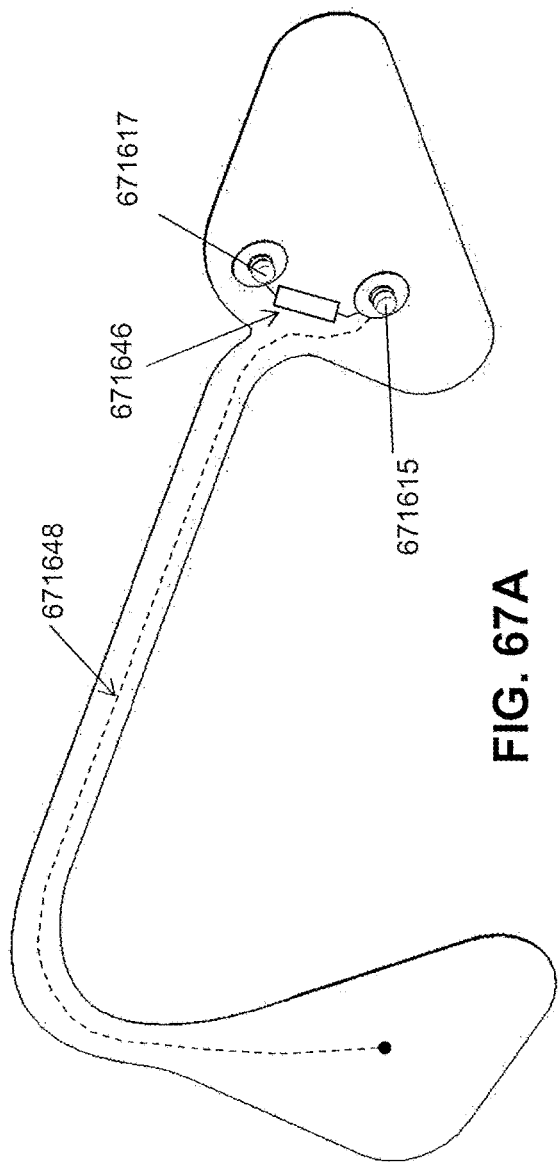
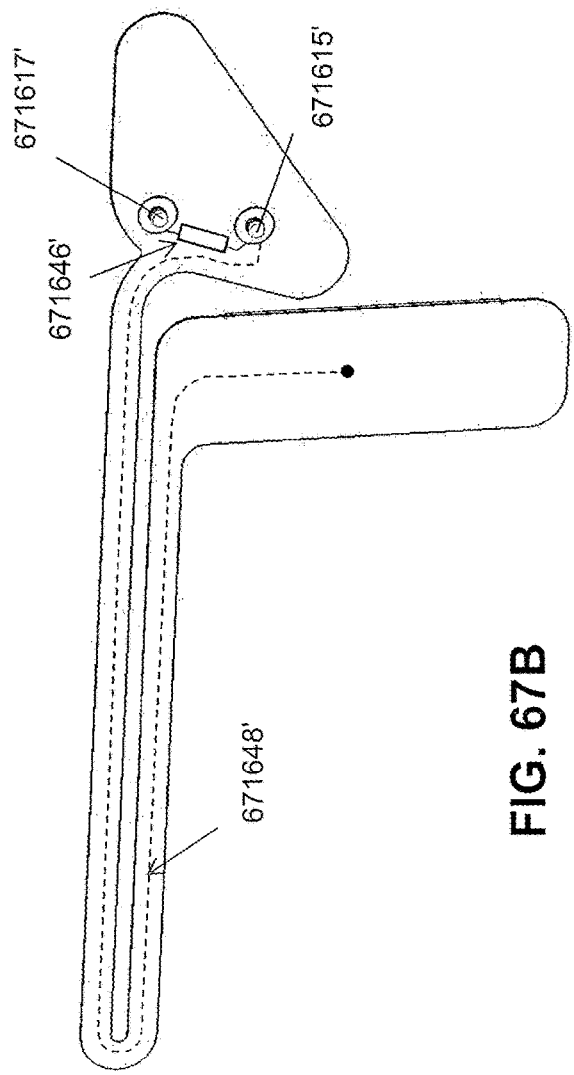
FIG. 67A
FIG. 67B $t_n$, time spent at negative peak current
$t_p$, time spent at positive peak current
$t_c$, time for one period of cycle duty cycle = $(t_p + t_n)/t_c$

% direct current = $(t_p - t_n)/(t_p + t_n)$

| Test # | No sticker | Sticker, No Cap. | Sticker w/ 180 pF | Sticker w/ 680 pF |
|---|---|---|---|---|
| 1 | 12000 | 22 | 264 | 408 |
| 2 | 12000 | 13 | 281 | 431 |
| 3 | 12000 | 5 | 281 | 431 |
| 4 | 12000 | 0 | 257 | 413 |
| 5 | 12000 | 6 | 260 | 424 |
| 6 | 12000 | 0 | 253 | 420 |
| 7 | 12000 | 13 | 262 | 415 |
| 8 | 12000 | 0 | 262 | 424 |
| 9 | 12000 | 18 | 261 | 416 |
| 10 | 12000 | 5 | 261 | 415 |
FIG. 79
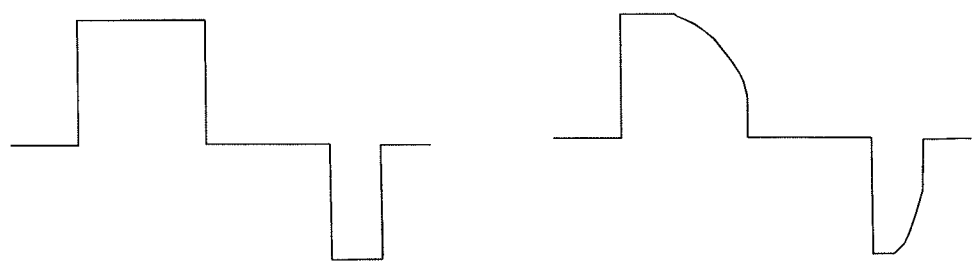
FIG. 80A
FIG. 80B
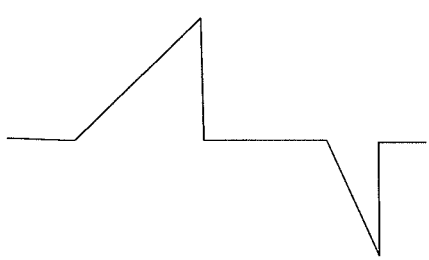
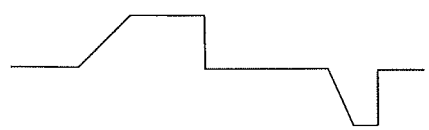
FIG. 80C
FIG. 80D

| CURRENT | | | Vs saturation | |
|---|---|---|---|---|
| | | Modulate current per waveform | Reduce current | No change |
| Overheat limit | | Reduce current | Reduce current | |
| | | | Max Vs reached | |

| VOLTAGE | | | Vs saturation | |
|---|---|---|---|---|
| | | Adjust Vs | No change | Adjust Vs |
| Overheat limit | | Adjust Vs | No change | |
| | | | Max Vs reached | |

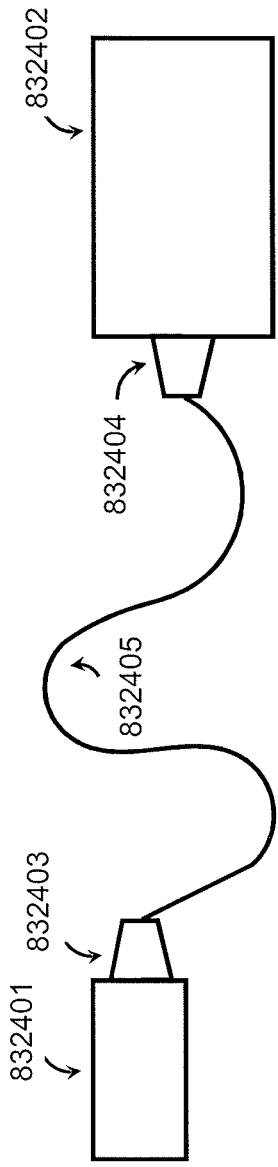
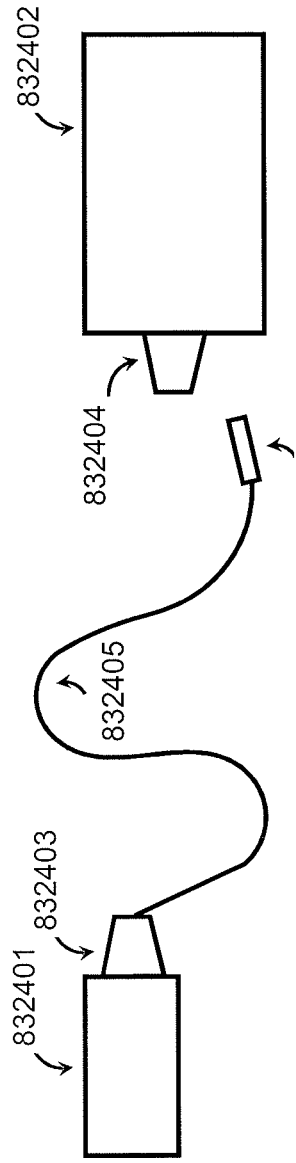
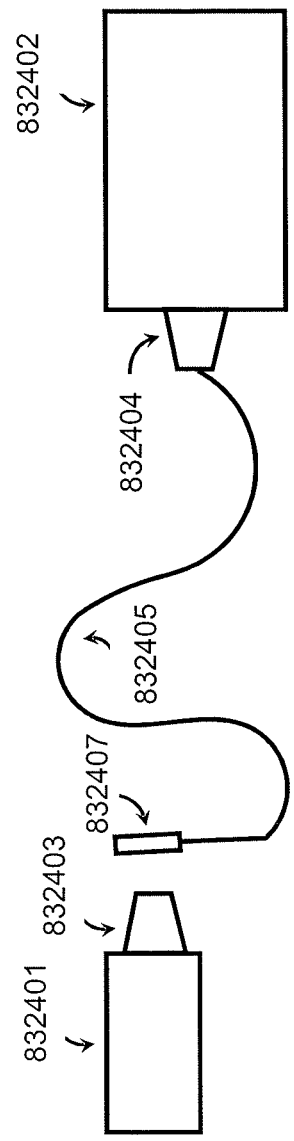
FIG. 83A
FIG. 83B
FIG. 83C

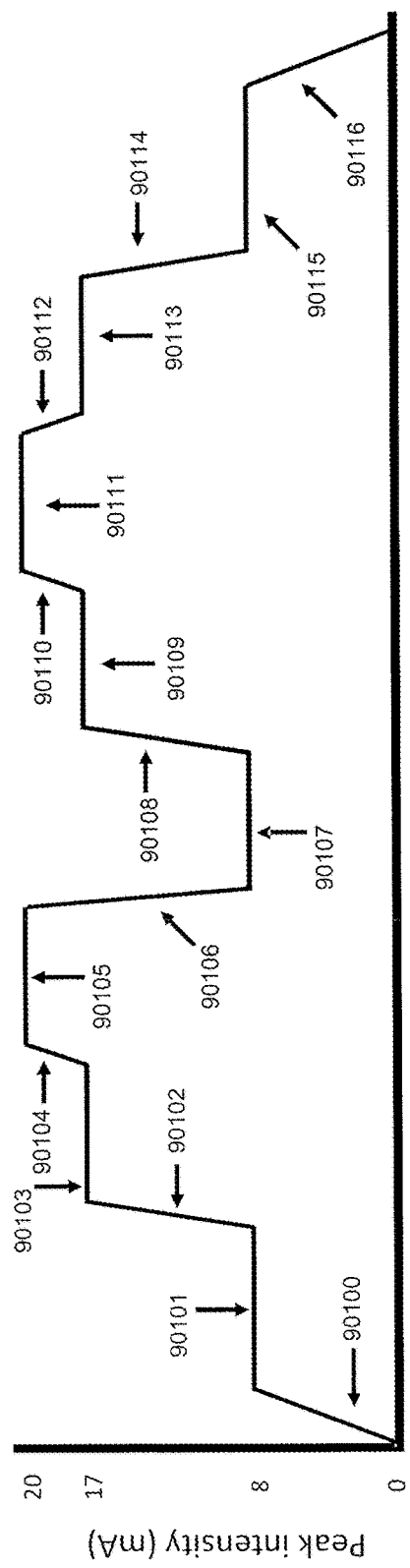
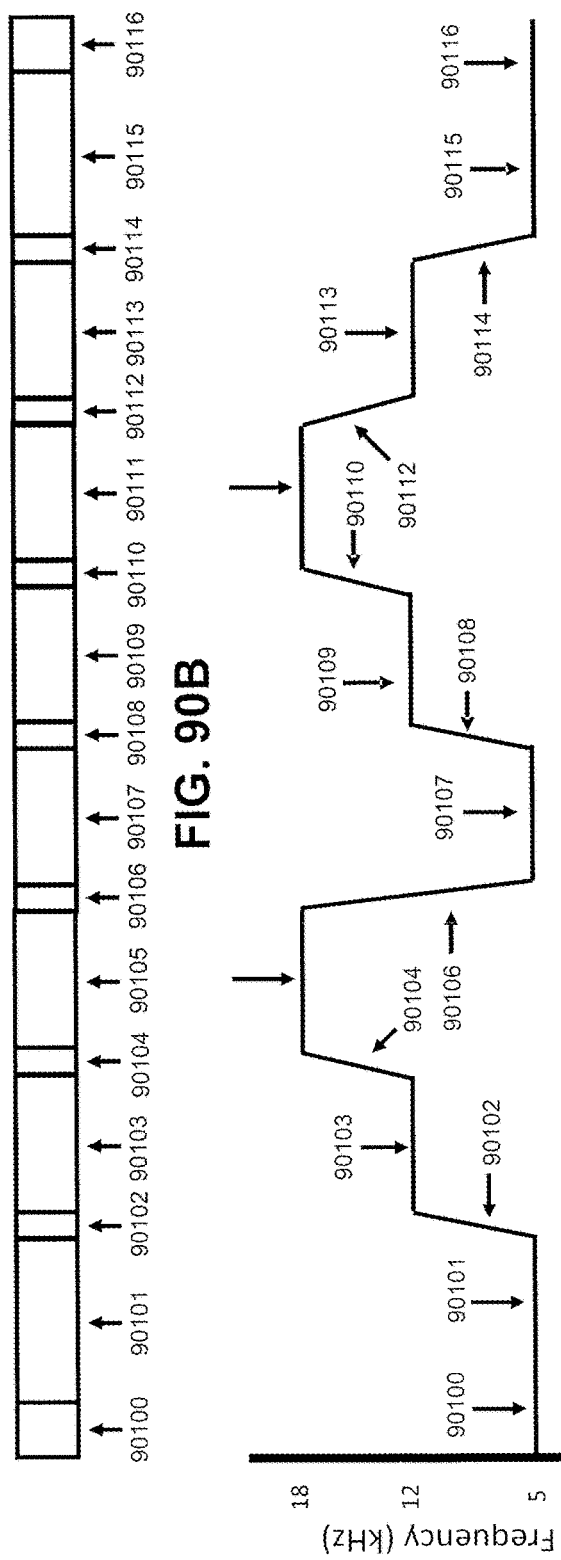
FIG. 90A
FIG. 90B
FIG. 90C

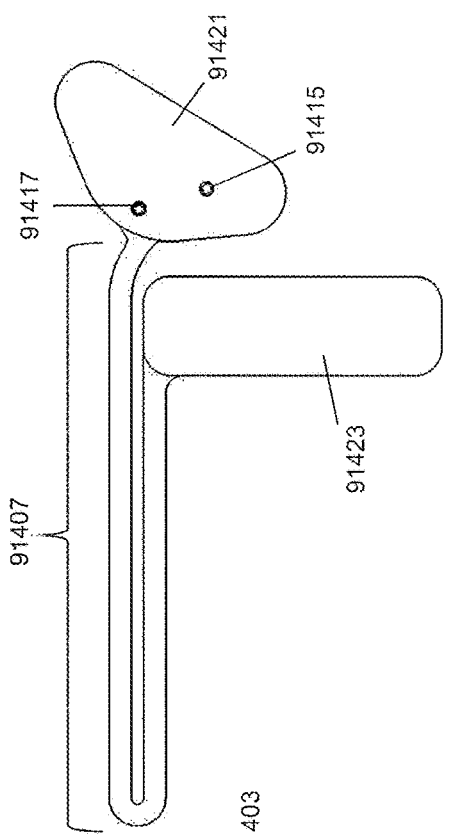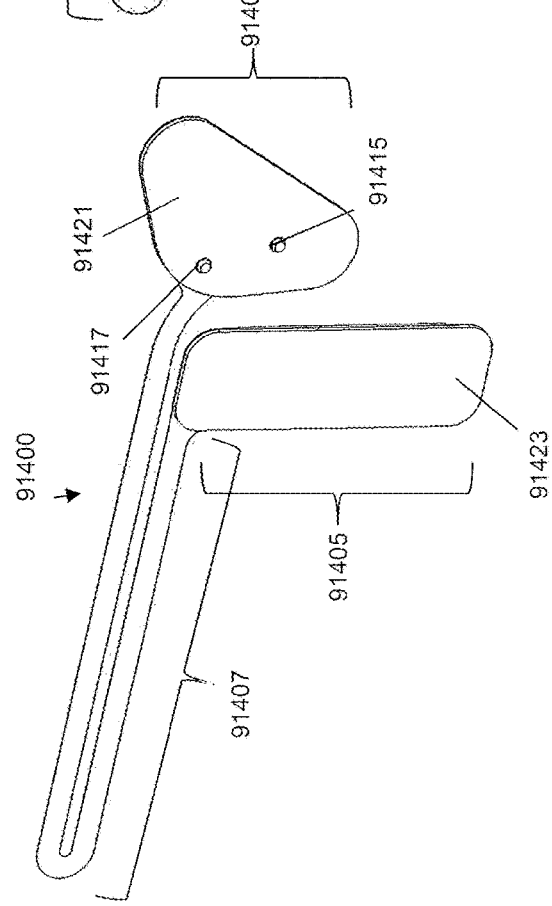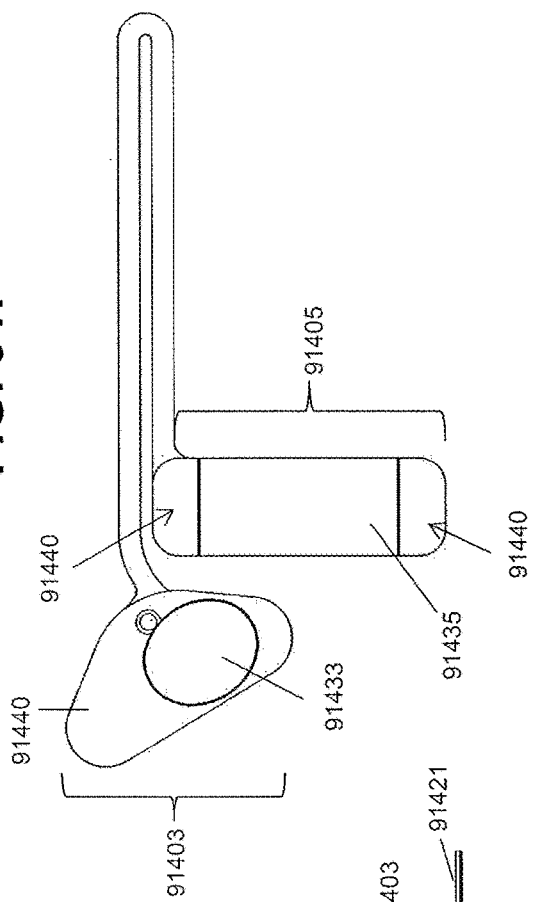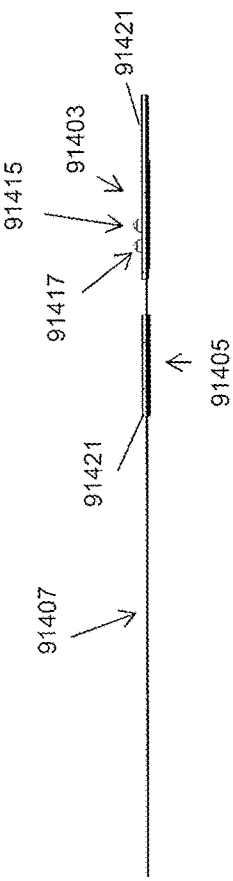
FIG. 91i
FIG. 91K
FIG. 91H
FIG. 91J

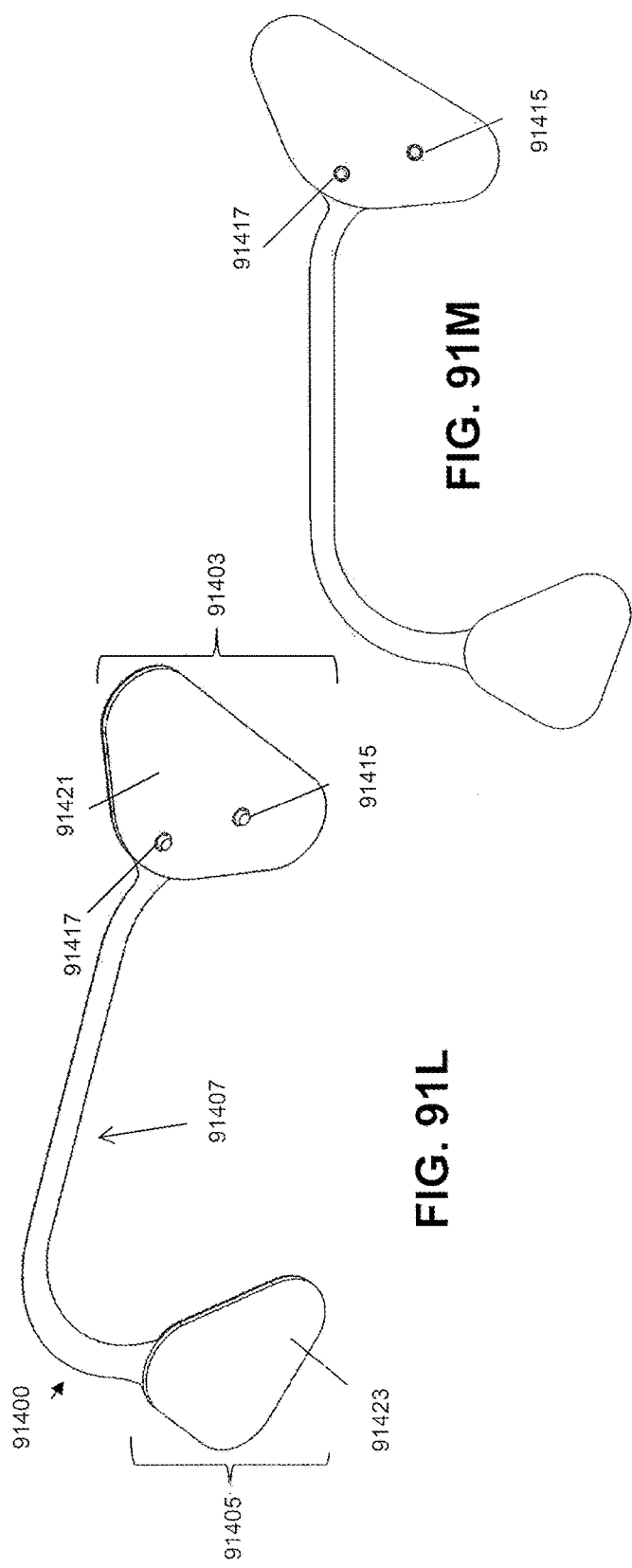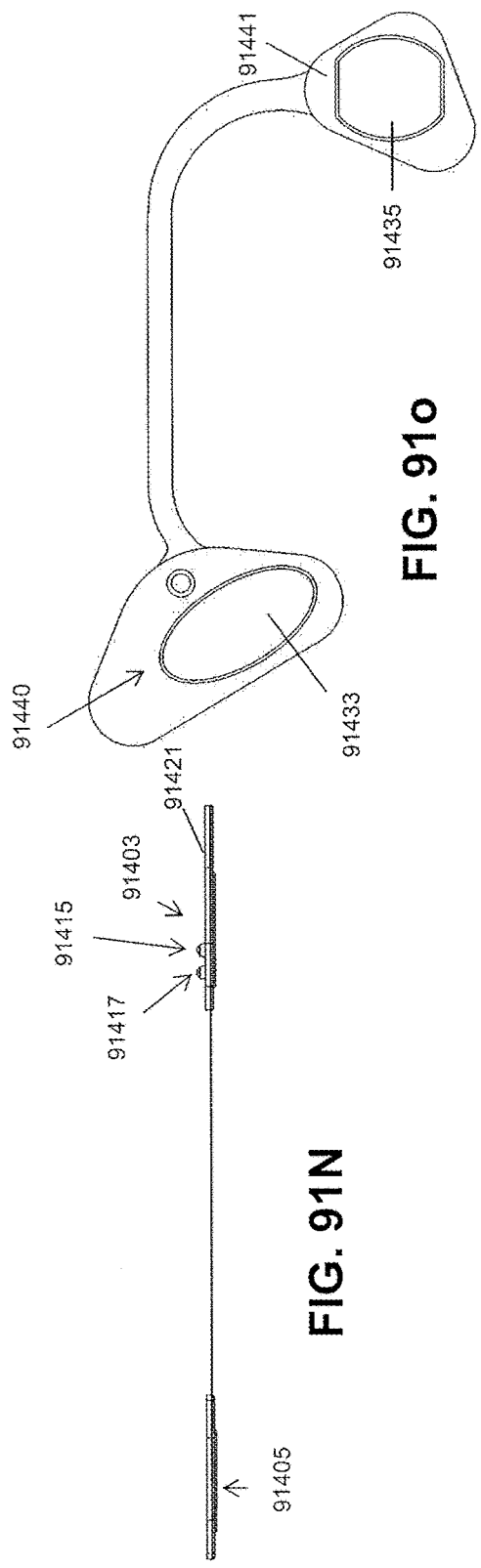

FIG. 92A

| Component Waveform # | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Duration (sec) | 3 | 27 | 60 | 60 | 2 | 3 | 63 | 2 | 30 | 58 | 2 | 18 | 28 | 10 | 60 | 60 | 5 |
| Frequency (Hz) | 11000 | 11000 | 11000 | 11000 | 11000 | 11000 | 11000 | 11000 | 11000 | 11000 | 11000 | 11000 | 11000 | 7500 | 6700 | 6700 | 6700 |
| Current (mA) | 0 | 16 | 18 | 18 | 11 | 18 | 18 | 11 | 18 | 18 | 11 | 18 | 18 | 11 | 11 | 0 | 0 |
| Percent charge imbalance | 85 | 85 | 85 | 85 | 85 | 85 | 85 | 85 | 85 | 85 | 85 | 85 | 85 | 100 | 100 | 0 | 0 |
| Percent Duty Cycle | 41 | 41 | 41 | 41 | 41 | 41 | 41 | 41 | 41 | 41 | 41 | 41 | 41 | 38 | 38 | 0 | 0 |
| End time | 3 | 30 | 90 | 150 | 152 | 155 | 218 | 220 | 250 | 308 | 310 | 328 | 356 | 366 | 426 | 431 | |

FIG. 92B

| Component Waveform # | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Duration | 2 | 28 | 30 | 60 | 1 | 4 | 65 | 1 | 1 | 20 | 69 | 1 | 20 | 59 | 1 | 20 | 59 |
| Freq. (Hz) | 11000 | 11000 | 11000 | 11000 | 11000 | 11000 | 11000 | 11000 | 11000 | 11000 | 11000 | 11000 | 11000 | 11000 | 11000 | 11000 | 11000 |
| Current (mA) | 1 | 16 | 19 | 19 | 12 | 19 | 19 | 11 | 11 | 19 | 19 | 12 | 19 | 19 | 12 | 19 | 19 |
| % Charge imb. | 85 | 85 | 85 | 85 | 85 | 85 | 85 | 85 | 85 | 85 | 85 | 85 | 85 | 85 | 85 | 85 | 85 |
| % Duty Cycle | 39 | 41 | 41 | 41 | 41 | 41 | 41 | 41 | 41 | 41 | 41 | 41 | 41 | 41 | 41 | 41 | 41 |
| End time | 2 | 30 | 60 | 120 | 121 | 125 | 190 | 191 | 211 | 280 | 281 | 301 | 360 | 361 | 381 | 440 | |

| Component Waveform # | 18 | 19 | 20 | 21 | 22 | 23 | 24 | 25 | 26 | 27 |
|---|---|---|---|---|---|---|---|---|---|---|
| Duration | 30 | 30 | 60 | 0.4 | 59.6 | 0.4 | 59.6 | 0.4 | 39.6 | 5 |
| Freq. (Hz) | 7500 | 7500 | 6800 | 7500 | 6700 | 7500 | 6700 | 7500 | 6800 | 6800 |
| Current (mA) | 0 | 12 | 12 | 12 | 12 | 12 | 12 | 12 | 12 | 0 |
| % Charge imb. | 100 | 100 | 100 | 100 | 100 | 100 | 100 | 100 | 100 | 100 |
| % Duty Cycle | 38 | 38 | 38 | 38 | 38 | 38 | 38 | 38 | 38 | 38 |
| End time | 470 | 500 | 560 | 560.4 | 620 | 620.4 | 680 | 680.4 | 720 | 725 |

| Component Waveform # | 1 | 2 | 3 | 4 | 5 | 6 | 7 | 8 | 10 | 11 | 12 | 13 | 14 | 15 | 16 | 17 |
|---|---|---|---|---|---|---|---|---|---|---|---|---|---|---|---|---|
| Duration | 2 | 28 | 60 | 60 | 4 | 6 | 60 | 4 | 26 | 60 | 4 | 26 | 60 | 4 | 26 | 30 |
| Freq. (Hz) | 11000 | 11000 | 11000 | 10600 | 11000 | 11000 | 10600 | 11000 | 11000 | 10600 | 11000 | 11000 | 10600 | 11000 | 11000 | 7500 |
| Current (mA) | 1 | 16 | 19 | 19 | 11 | 16 | 19 | 11 | 19 | 19 | 11 | 19 | 19 | 11 | 19 | 1 |
| % Charge imb. | 90 | 90 | 90 | 90 | 90 | 90 | 90 | 85 | 90 | 90 | 85 | 90 | 90 | 85 | 90 | 100 |
| % Duty Cycle | 41 | 41 | 41 | 41 | 41 | 41 | 41 | 41 | 41 | 41 | 41 | 41 | 41 | 41 | 41 | 41 |
| End time | 2 | 30 | 90 | 150 | 154 | 160 | 220 | 224 | 250 | 310 | 314 | 340 | 400 | 404 | 430 | 460 |

| Component Waveform # | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|
| Duration | 40 | 60 | 2 | 58 | 2 | 58 | 2 | 58 | 10 | 30 | 30 | 30 | 4 | 16 | 80 | 5 |
| Freq. (Hz) | 7500 | 6700 | 7500 | 6700 | 7600 | 6700 | 7500 | 6700 | 11000 | 11000 | 11000 | 10500 | 11000 | 11000 | 10500 | 10800 |
| Current (mA) | 11 | 11 | 11 | 11 | 11 | 11 | 11 | 100 | 1 | 16 | 19 | 19 | 11 | 19 | 19 | 0 |
| % Charge imb. | 100 | 100 | 100 | 100 | 100 | 100 | 100 | 100 | 85 | 90 | 90 | 90 | 85 | 90 | 90 | 85 |
| % Duty Cycle | 39 | 39 | 39 | 39 | 39 | 39 | 39 | 39 | 39 | 41 | 41 | 41 | 43 | 41 | 41 | 41 |
| End time | 500 | 560 | 562 | 620 | 622 | 680 | 682 | 740 | 750 | 780 | 810 | 840 | 844 | 860 | 940 | 945 |

FIG. 92C

| Component Waveform # | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Duration | 1 | 30 | 105 | 15 | 105 | 15 | 105 | 15 | 105 | 15 | 105 | 15 | 30 | 105 | 15 |
| Freq. (Hz) | 9000 | 5000 | 5000 | 12000 | 12000 | 18000 | 18000 | 18000 | 18000 | 5000 | 5000 | 5000 | 5000 | 5000 | 12000 |
| Current (mA) | 0 | 8 | 8.2 | 17.3 | 17.7 | 17.7 | 18.1 | 18.1 | 18.5 | 8.8 | 9 | 0 | 9.1 | 9.2 | 19.8 |
| % Charge imb. | 0 | 40 | 40 | 40 | 40 | 40 | 40 | 40 | 40 | 40 | 40 | 40 | 40 | 40 | 40 |
| % Duty Cycle | 40 | 40 | 40 | 45 | 45 | 60 | 60 | 45 | 45 | 40 | 40 | 40 | 40 | 40 | 45 |
| End time | 1 | 31 | 136 | 151 | 256 | 271 | 376 | 391 | 496 | 511 | 616 | 631 | 661 | 766 | 886 |

| Component Waveform # | 16 | 17 | 18 | 19 | 20 | 21 |
|---|---|---|---|---|---|---|
| Duration | 15 | 105 | 15 | 105 | 15 | 105 |
| Freq. (Hz) | 18000 | 18000 | 12000 | 12000 | 5000 | 5000 |
| Current (mA) | 19.8 | 20.2 | 20.2 | 20.6 | 9.8 | 10 |
| % Charge imb. | 40 | 40 | 40 | 40 | 40 | 40 |
| % Duty Cycle | 60 | 60 | 45 | 45 | 40 | 40 |
| End time | 901 | 1006 | 1021 | 1126 | 1141 | 1246 |

FIG. 93A

| Component Waveform # | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Duration | 1 | 59 | 75 | 30 | 90 | 30 | 120 | 30 | 90 | 30 | 30 | 60 | 30 | 90 | 30 | 120 |
| Freq. (Hz) | 9000 | 9000 | 9000 | 750 | 750 | 3600 | 3600 | 750 | 750 | 9000 | 9000 | 9000 | 750 | 750 | 3600 | 3600 |
| Current (mA) | 0 | 9.1 | 10.9 | 3 | 3.1 | 8 | 9.3 | 3.2 | 3.3 | 3 | 9.5 | 11.4 | 3.3 | 3.4 | 8.5 | 9.8 |
| % Charge imb. | 30 | 30 | 30 | 30 | 35 | 40 | 40 | 35 | 35 | 30 | 30 | 30 | 30 | 35 | 40 | 40 |
| % Duty Cycle | 50 | 50 | 50 | 35 | 40 | 40 | 40 | 35 | 40 | 50 | 50 | 50 | 35 | 40 | 40 | 40 |
| End time | 1 | 60 | 135 | 165 | 255 | 285 | 405 | 435 | 525 | 555 | 585 | 645 | 675 | 765 | 795 | 915 |

| Component Waveform # | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|
| Duration | 30 | 90 | 60 | 0.4 | 1.2 | 0.4 | 2 | 0.4 | 1.2 | 0.4 | 2 | 0.4 | 1.2 | 0.4 | 20 | 0.4 |
| Freq. (Hz) | 750 | 750 | 750 | 1300 | 1300 | 750 | 750 | 1600 | 1600 | 750 | 750 | 1800 | 1800 | 750 | 750 | 2000 |
| Current (mA) | 3.4 | 3.5 | 4 | 4 | 4 | 4 | 4 | 4 | 4 | 4 | 4 | 4 | 4 | 4 | 4 | 4 |
| % Charge imb. | 35 | 35 | 35 | 35 | 35 | 35 | 35 | 35 | 35 | 35 | 35 | 35 | 35 | 35 | 35 | 35 |
| % Duty Cycle | 35 | 40 | 40 | 40 | 40 | 40 | 40 | 40 | 40 | 40 | 40 | 40 | 40 | 40 | 40 | 40 |
| End time | 945 | 1035 | 1095 | 1095.4 | 1096.6 | 1097 | 1099 | 1099.4 | 1100.6 | 1101 | 1103 | 1103 | 1104.6 | 1105 | 1125 | 1125 |

| Component Waveform # | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|
| Duration | 1.2 | 0.4 | 2 | 0.4 | 1.2 | 0.4 | 2 | 0.4 | 1.2 | 0.4 | 2 | 0.4 | 1.2 | 0.4 | 101 |
| Freq. (Hz) | 2000 | 750 | 750 | 2000 | 2000 | 750 | 750 | 2000 | 2000 | 750 | 750 | 2000 | 2000 | 750 | 750 |
| Current (mA) | 4 | 4 | 4 | 4 | 4 | 4 | 4 | 4 | 4 | 4 | 4 | 4 | 4 | 4 | 4 |
| % Charge imb. | 35 | 35 | 35 | 35 | 35 | 35 | 35 | 35 | 35 | 35 | 35 | 35 | 35 | 35 | 35 |
| % Duty Cycle | 40 | 40 | 40 | 40 | 40 | 40 | 40 | 40 | 40 | 40 | 40 | 40 | 40 | 40 | 45 |
| End time | 1127 | 1127 | 1129 | 1129.4 | 1130.6 | 1131 | 1133 | 1133.4 | 1134.6 | 1135 | 1137 | 1137 | 1138.6 | 1139 | 1240 |

FIG. 93B

Add-in example

| Component Waveform # | 1 | 2 | 3 | 4 | 5 | 6 |
|---|---|---|---|---|---|---|
| Duration (s) | 0.8 | 0.8 | 0.8 | 0.8 | 4 | 2 |
| Intensity Factor (%) | 80 | 60 | 40 | 20 | 0 | 100 |
| End time (s) | 0.8 | 1.6 | 2.4 | 3.2 | 7.2 | 9.2 |

FIG. 94

| Component Waveform # | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Duration (s) | 5 | 25 | 30 | 30 | 30 | 2 | 28 | 30 | 30 | 30 | 60 | 30 | 30 | 30 | 30 | 5 | 75 | 30 | 30 | 40 |
| Freq. (kHz) | 11 | 11 | 11 | 11 | 11 | 11 | 11 | 11 | 11 | 11 | 11 | 7.5 | 7.5 | 7.5 | 7.5 | 11 | 11 | 10.6 | 11 | 11 |
| Current (mA) | 1 | 18 | 18 | 18 | 18 | 11 | 19 | 19 | 19 | 19 | 19 | 14 | 14 | 14 | 14 | 5 | 18 | 18 | 18 | 18 |
| % Charge imb. | 90 | 90 | 90 | 90 | 90 | 90 | 90 | 90 | 90 | 90 | 90 | 90 | 90 | 90 | 90 | 90 | 90 | 90 | 90 | 90 |
| % Duty cycle | 37 | 37 | 37 | 37 | 37 | 37 | 37 | 37 | 37 | 37 | 37 | 37 | 37 | 37 | 37 | 37 | 37 | 37 | 37 | 37 |
| AM Freq. (Hz) | 800 | 800 | 800 | 800 | 500 | 500 | 500 | 800 | 500 | 800 | 500 | 800 | 500 | 500 | 800 | 800 | 700 | 700 | 500 | 500 |
| AM % duty cycle | 80 | 80 | 80 | 45 | 45 | 45 | 80 | 80 | 45 | 80 | 45 | 80 | 45 | 70 | 70 | 70 | 80 | 40 | 40 | 80 |
| End time (s) | 5 | 30 | 60 | 90 | 120 | 122 | 150 | 180 | 210 | 240 | 300 | 330 | 360 | 390 | 420 | 425 | 500 | 530 | 560 | 600 |

FIG. 95

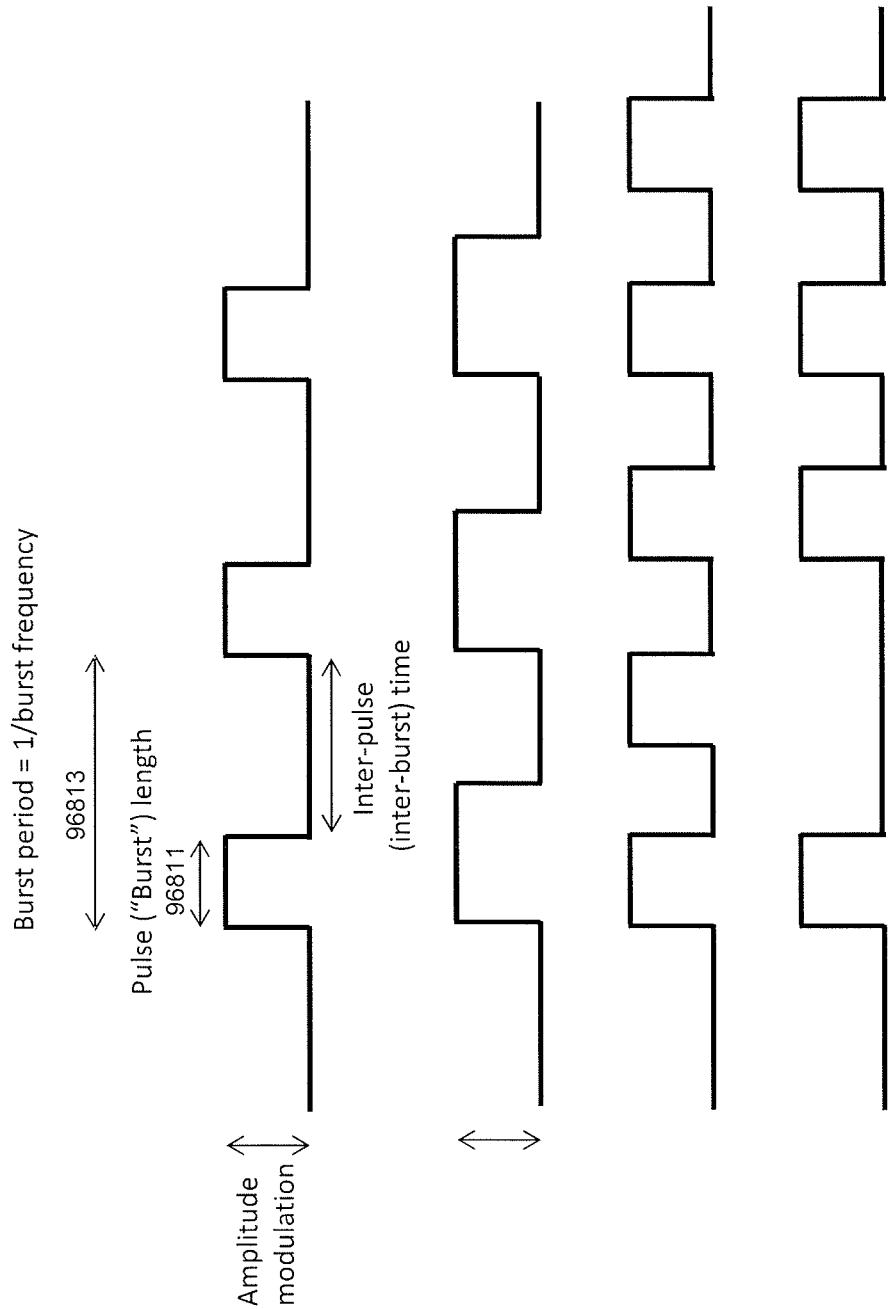

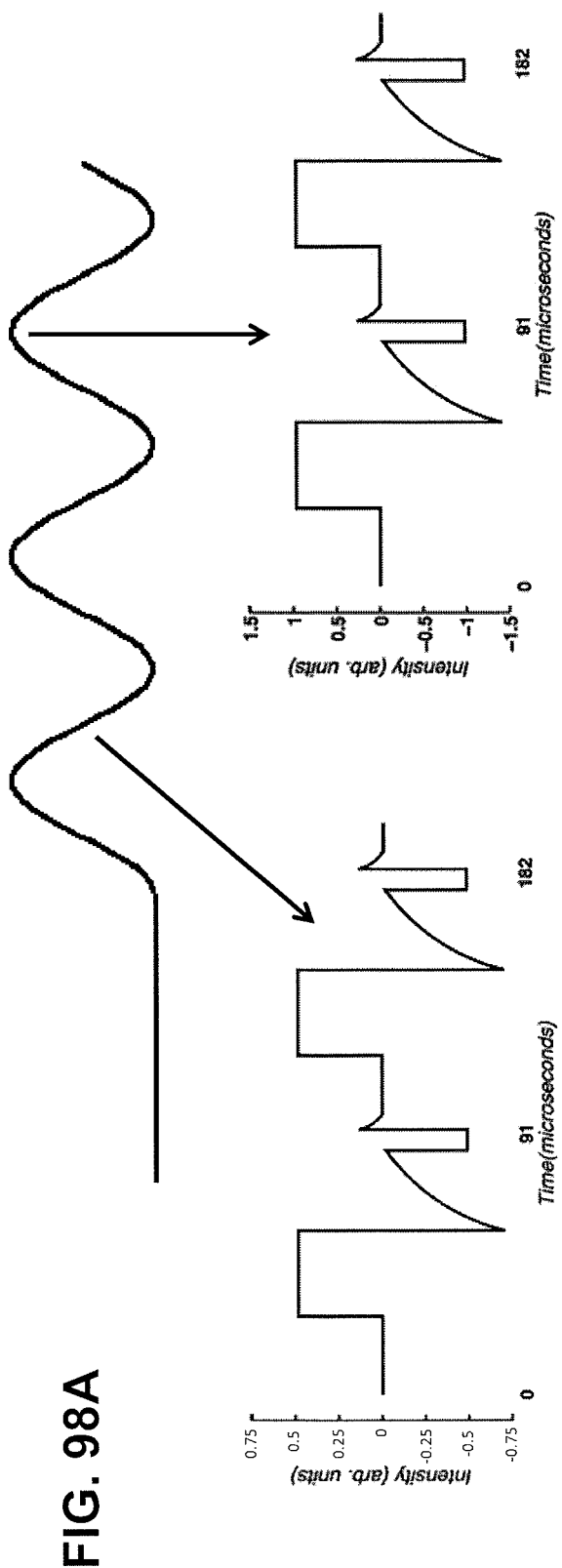
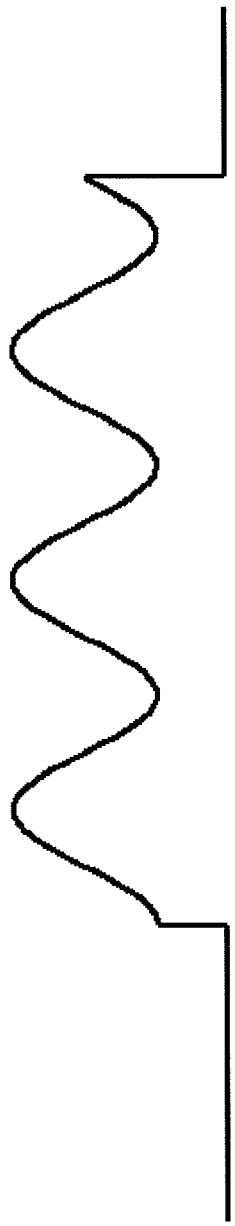
FIG. 98A
FIG. 98B
FIG. 98C
FIG. 98D

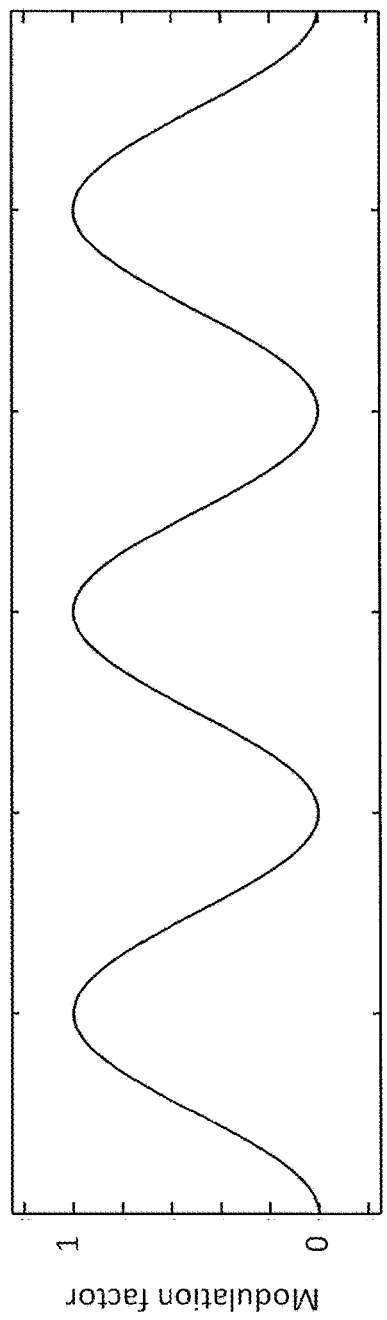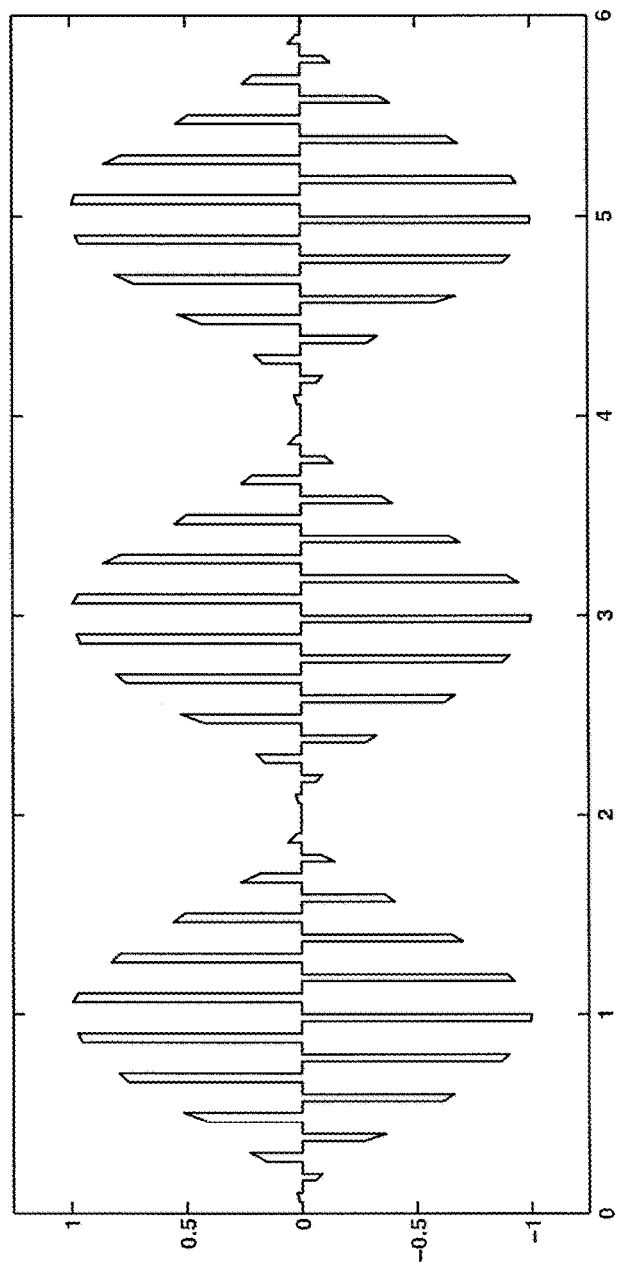

FIG. 101

| Component waveform # | 1 | 2 | 3 |
|---|---|---|---|
| Duration | 1 | 59 | 540 |
| End Time | 1 | 60 | 600 |
| Frequency(Hz) | 7000 | 7000 | 7000 |
| Current(ma) | 1 | 11 | 11 |
| Percentage DC | 85 | 85 | 85 |
| Duty Cycle % | 49 | 49 | 70 |
| AM Frequency (Hz) | 70 | 70 | 70 |
| AM Duty Cycle % | 35 | 35 | 35 |

FIG. 102

| | 1 | 2 | 3 | 4 | 5 | 6 | 7 | 8 | 9 | 10 | 11 |
|---|---|---|---|---|---|---|---|---|---|---|---|
| Duration | 5 | 55 | 30 | 30 | 30 | 30 | 30 | 30 | 60 | 30 | 30 |
| End Time | 5 | 60 | 90 | 120 | 150 | 180 | 210 | 240 | 300 | 330 | 360 |
| Frequency(Hz) | 11000 | 11000 | 11000 | 11000 | 11300 | 11000 | 11000 | 11300 | 11000 | 11300 | 11000 |
| Current(ma) | 1 | 19 | 19 | 19 | 19 | 19 | 19 | 19 | 19 | 19 | 19 |
| Percentage DC | 90 | 90 | 90 | 90 | 90 | 90 | 90 | 90 | 90 | 90 | 90 |
| Duty Cycle % | 39 | 39 | 39 | 39 | 39 | 39 | 39 | 39 | 39 | 39 | 39 |
| AM Freq. (Hz) | 800 | 800 | 800 | 350 | 350 | 750 | 350 | 750 | 350 | 750 | 350 |
| AM Duty Cycle % | 90 | 90 | 45 | 45 | 90 | 90 | 45 | 90 | 45 | 90 | 45 |

| | 1 | 2 | 3 | 4 | 5 | 6 | 7 | 8 | 9 | 10 |
|---|---|---|---|---|---|---|---|---|---|---|
| Duration | 5 | 25 | 30 | 30 | 30 | 2 | 28 | 30 | 30 | 30 |
| End Time | 5 | 30 | 60 | 90 | 120 | 122 | 150 | 180 | 210 | 240 |
| Freq. (Hz) | 11000 | 11000 | 11000 | 11000 | 11000 | 11000 | 11000 | 11000 | 11000 | 11000 |
| Current(ma) | 1 | 18 | 18 | 18 | 18 | 11 | 19 | 19 | 19 | 19 |
| Percentage DC | 90 | 90 | 90 | 90 | 90 | 90 | 90 | 90 | 90 | 90 |
| Duty Cycle % | 37 | 37 | 37 | 37 | 37 | 37 | 37 | 37 | 37 | 37 |
| AM Freq. (Hz) | 800 | 800 | 800 | 800 | 500 | 500 | 500 | 800 | 500 | 800 |
| AM Duty Cycle % | 80 | 80 | 80 | 45 | 45 | 45 | 80 | 80 | 45 | 80 |

| | 11 | 12 | 13 | 14 | 15 | 16 | 17 | 18 | 19 | 20 |
|---|---|---|---|---|---|---|---|---|---|---|
| Duration | 60 | 30 | 30 | 30 | 30 | 5 | 75 | 30 | 30 | 40 |
| End Time | 300 | 330 | 360 | 390 | 420 | 425 | 500 | 530 | 560 | 600 |
| Freq. (Hz) | 11000 | 7500 | 7500 | 7500 | 7500 | 11000 | 11000 | 10600 | 11000 | 11000 |
| Current(ma) | 19 | 14 | 14 | 14 | 14 | 5 | 18 | 18 | 18 | 18 |
| Percentage DC | 90 | 90 | 90 | 90 | 90 | 90 | 90 | 90 | 90 | 90 |
| Duty Cycle % | 37 | 37 | 37 | 37 | 37 | 37 | 37 | 37 | 37 | 37 |
| AM Freq. (Hz) | 500 | 800 | 500 | 500 | 800 | 800 | 700 | 700 | 500 | 500 |
| AM Duty Cycle % | 45 | 80 | 45 | 70 | 70 | 70 | 80 | 40 | 40 | 80 |

FIG. 103

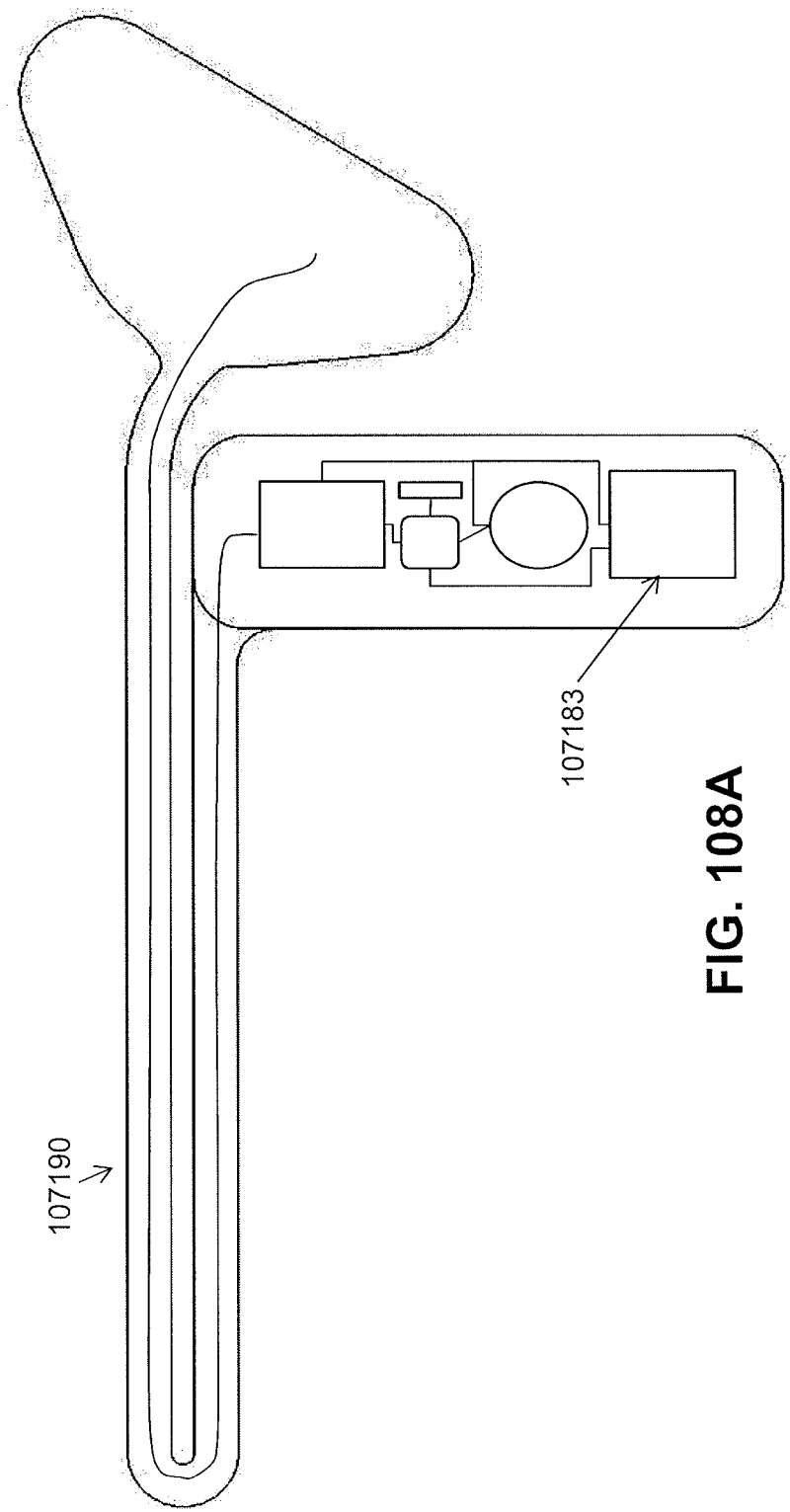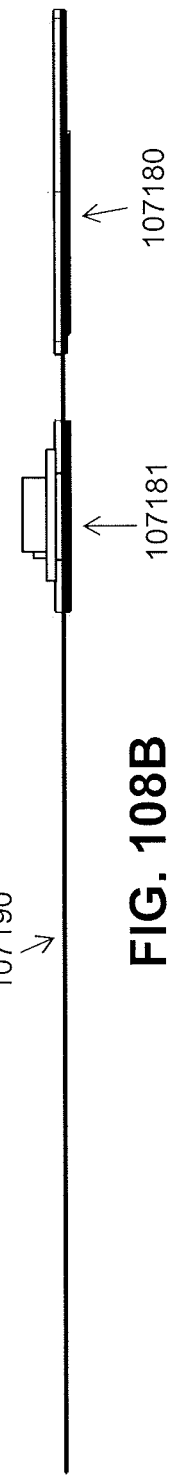
FIG. 108A
FIG. 108B

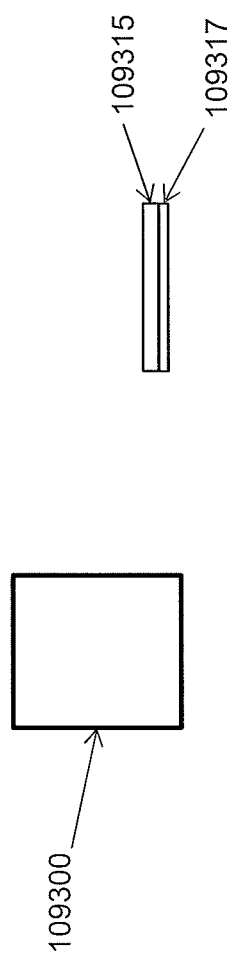

FIG. 109A  FIG. 109B  FIG. 109C

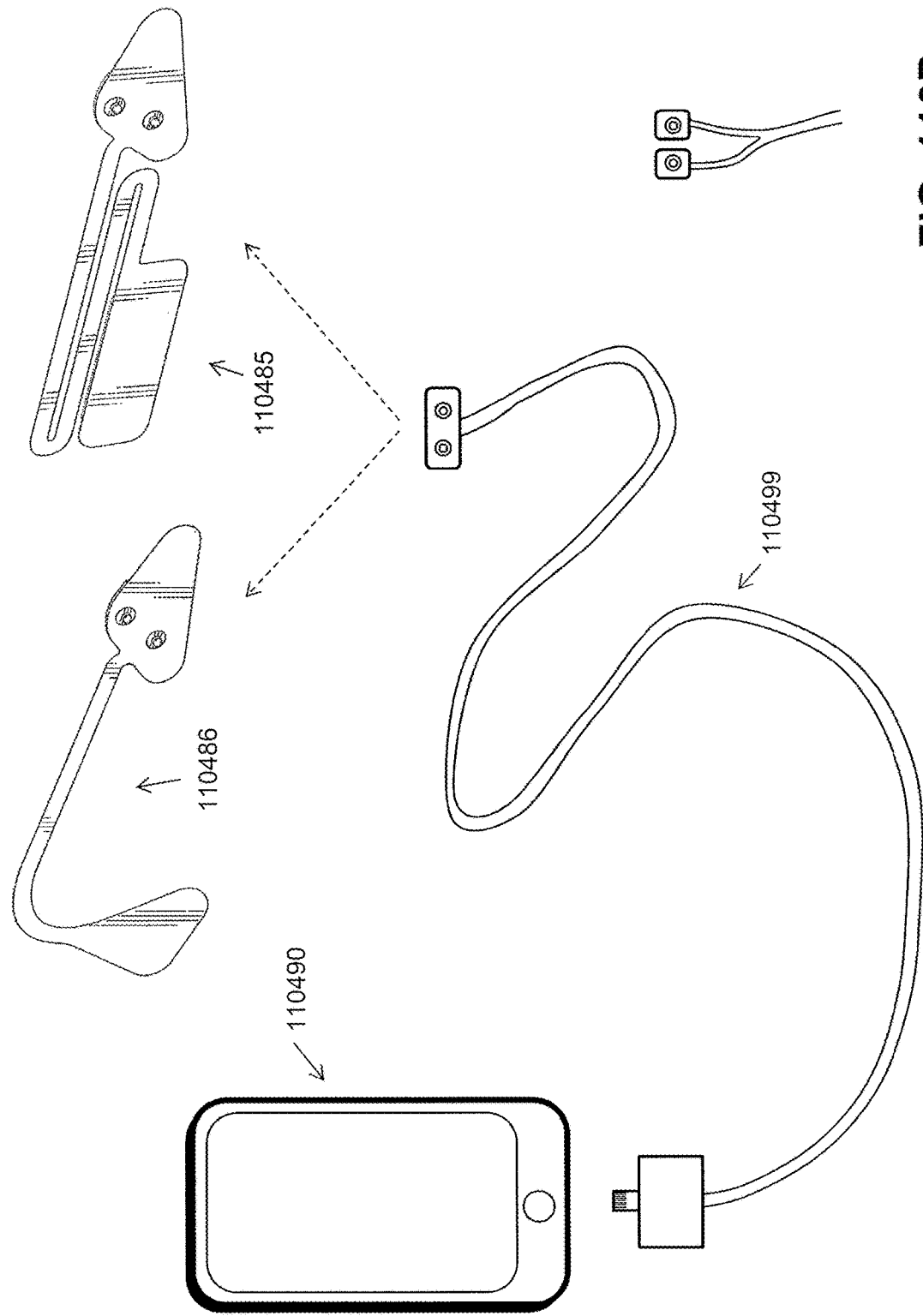

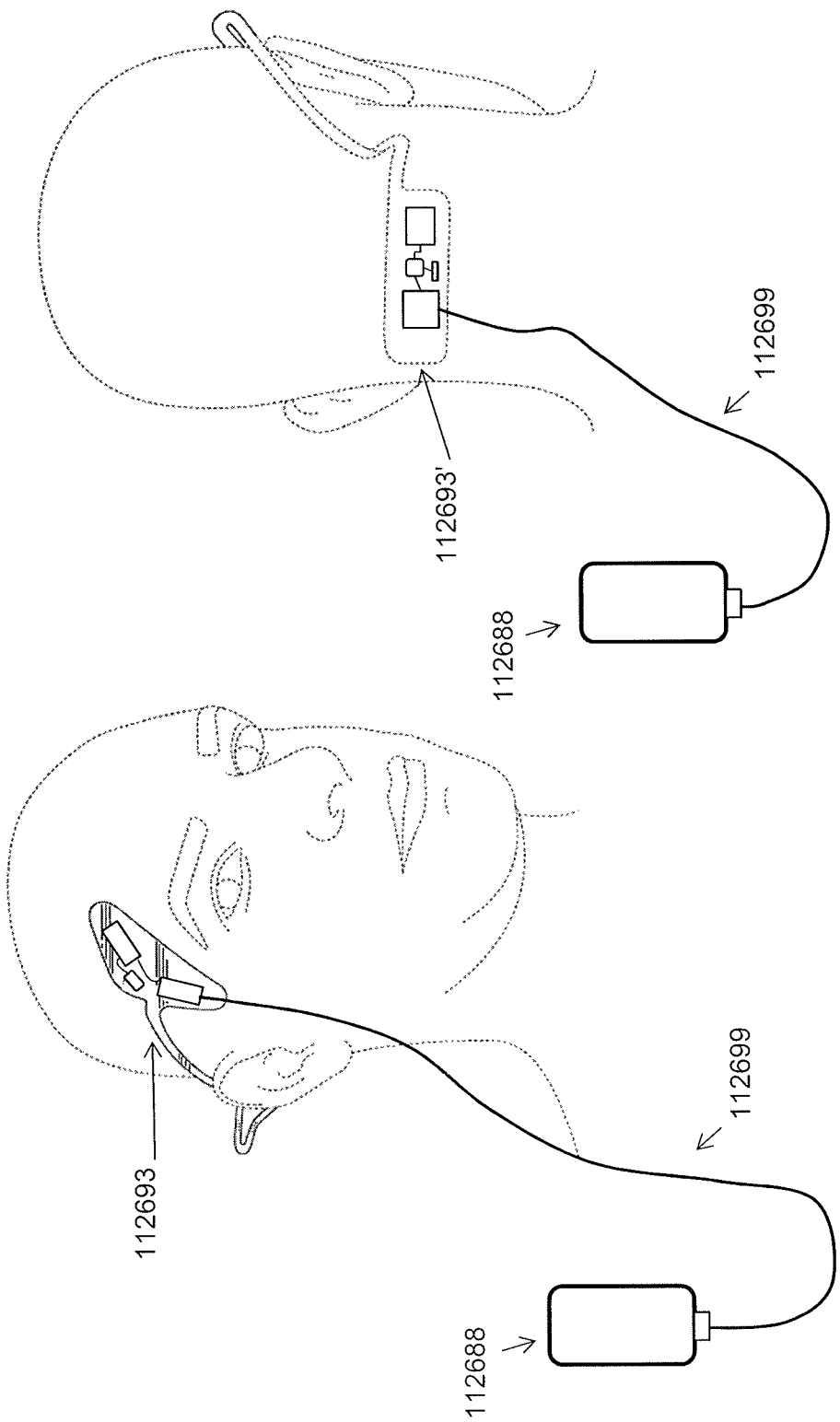

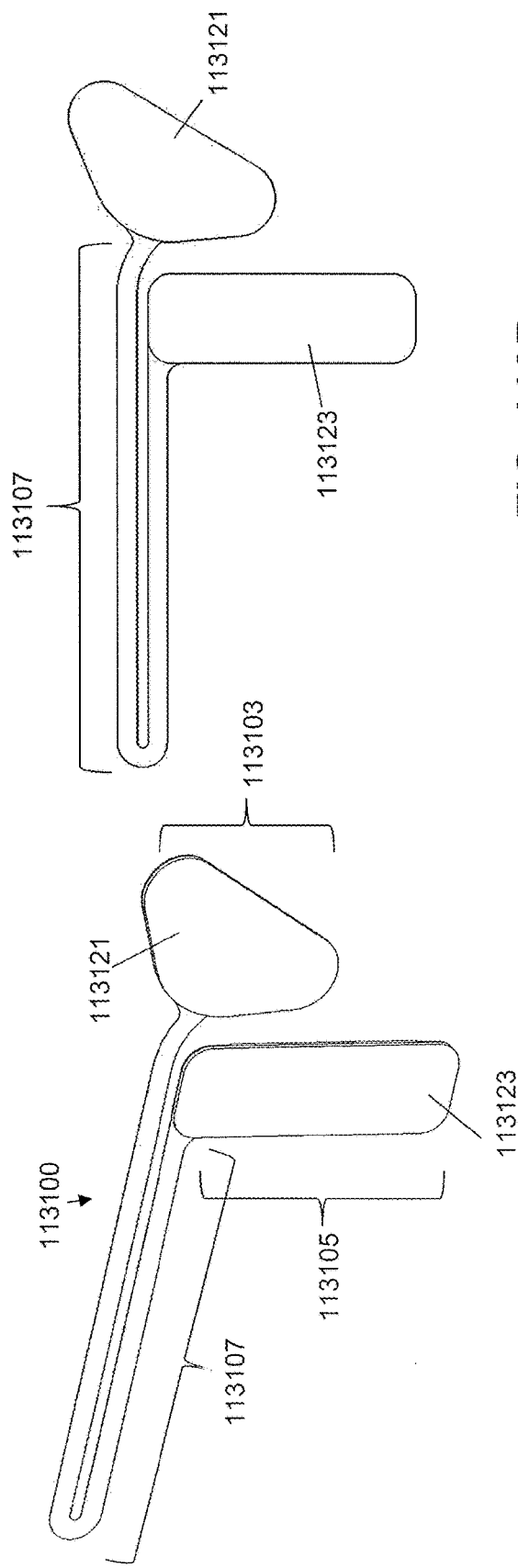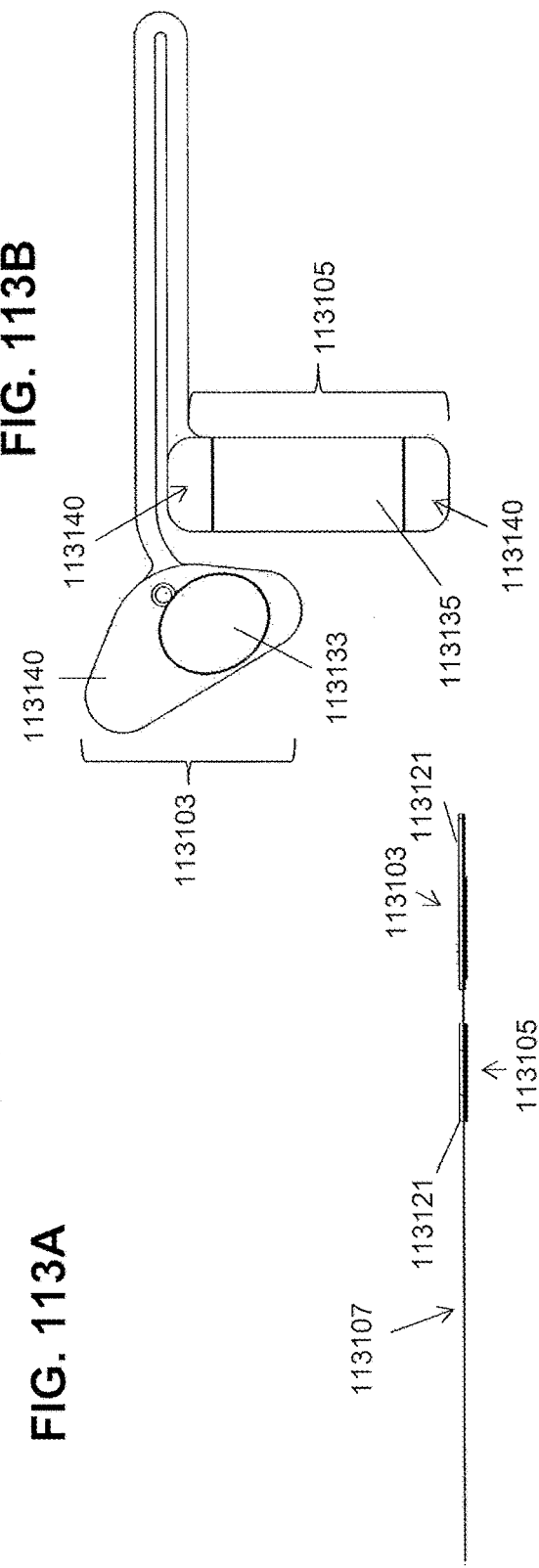
FIG. 113A
FIG. 113B
FIG. 113C
FIG. 113D

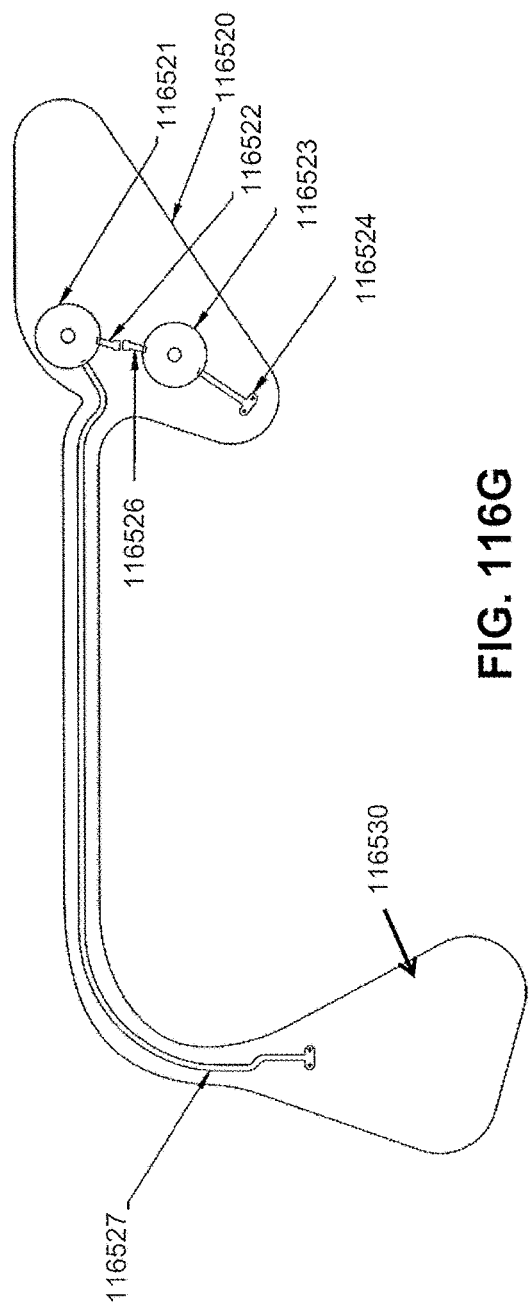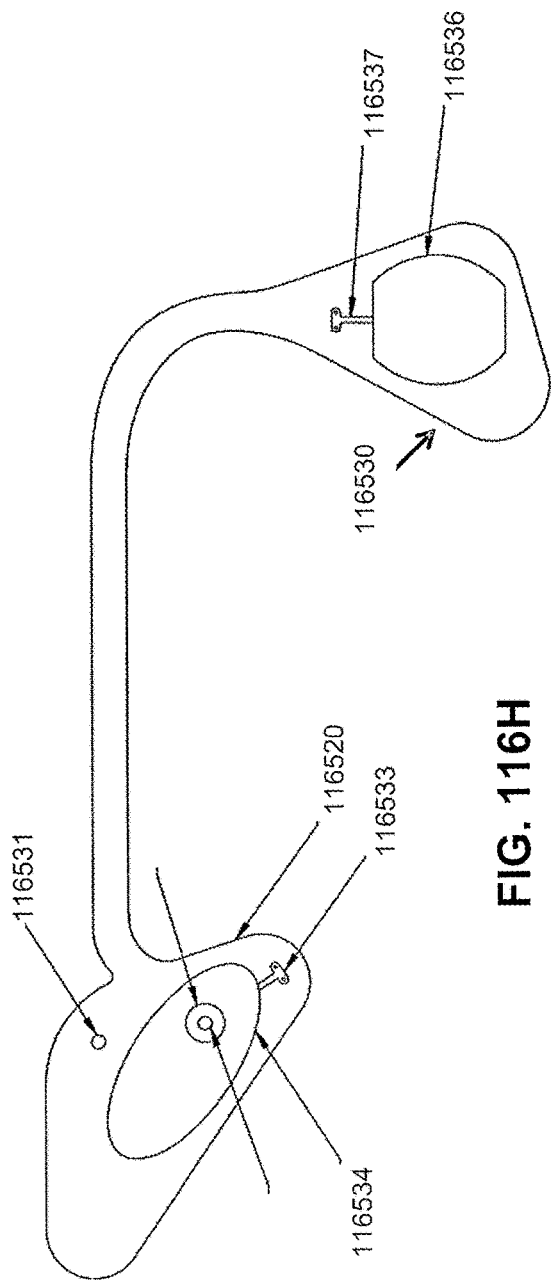
FIG. 116G
FIG. 116H

118901

1181001

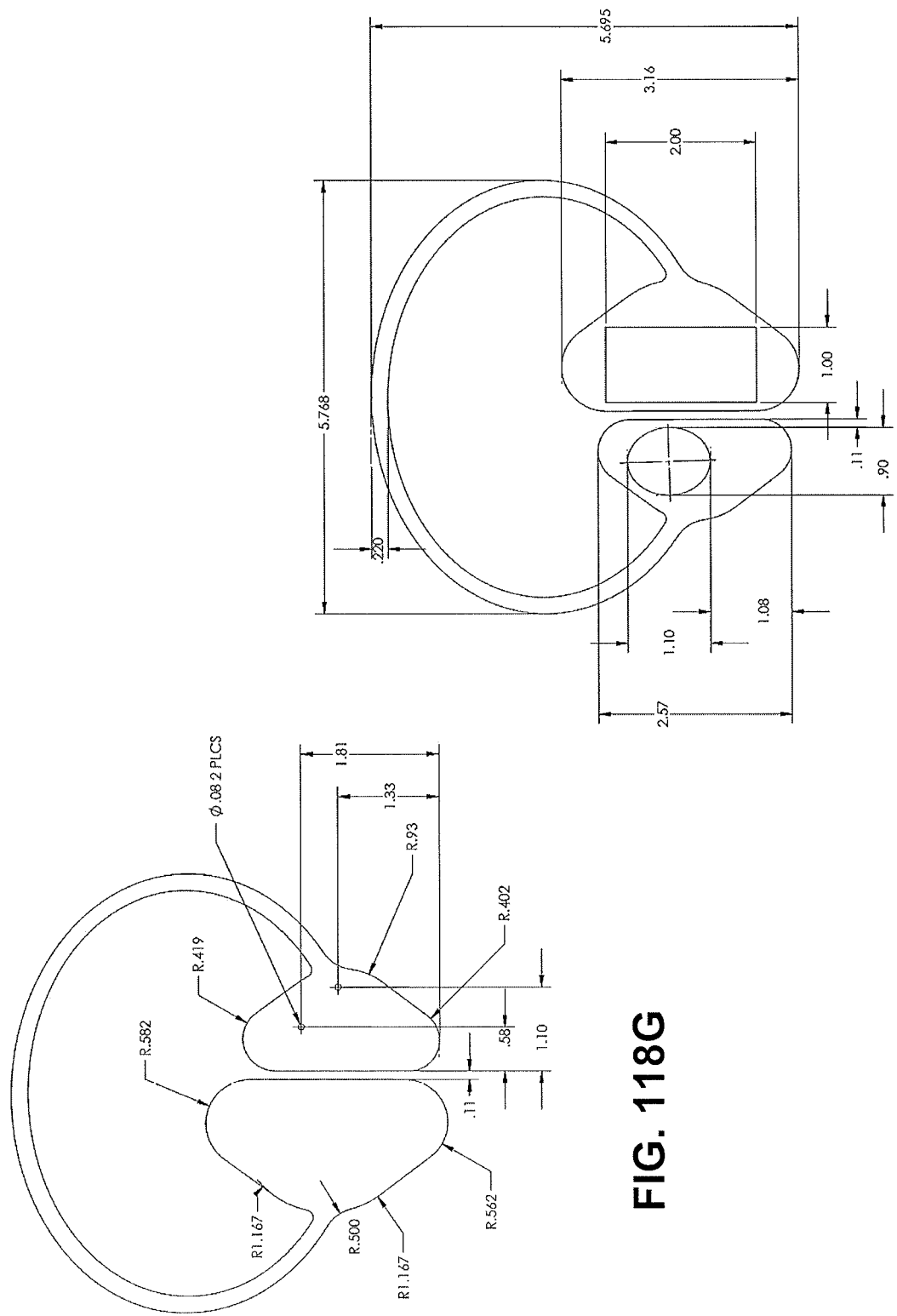

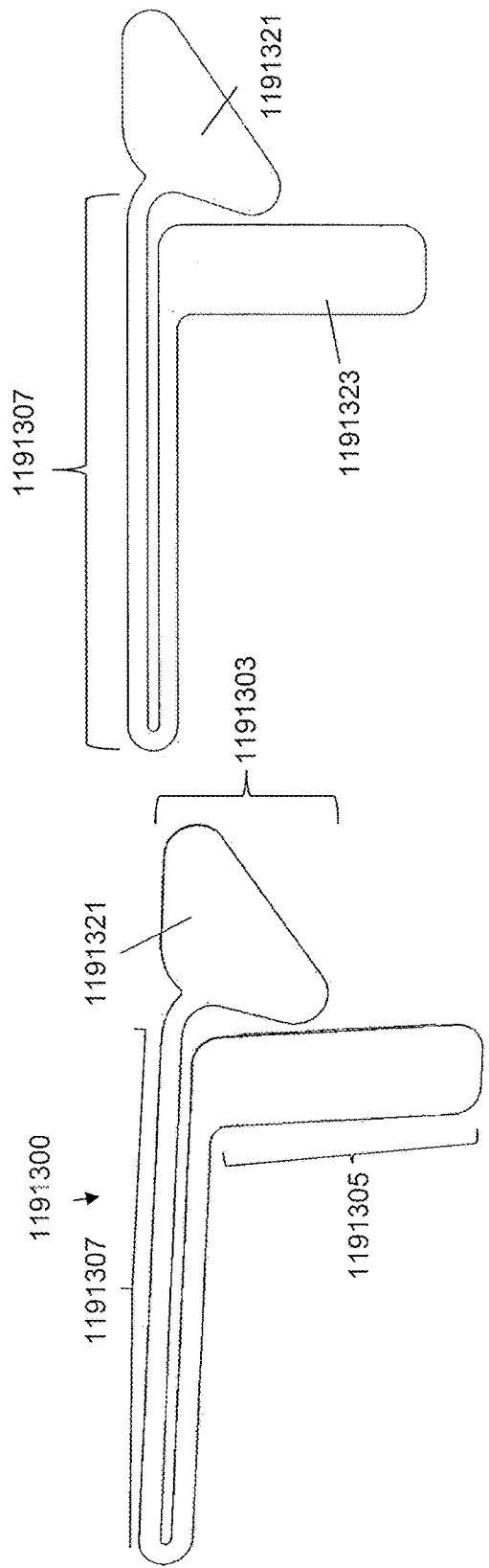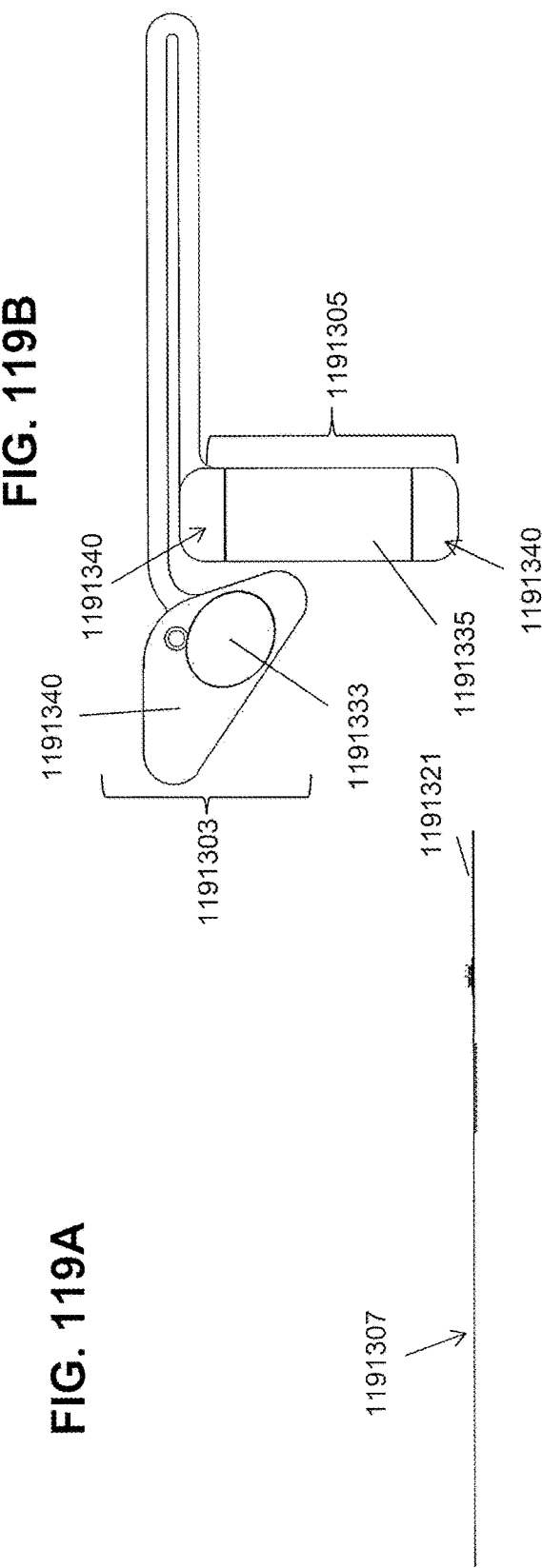
FIG. 119A
FIG. 119B
FIG. 119C
FIG. 119D

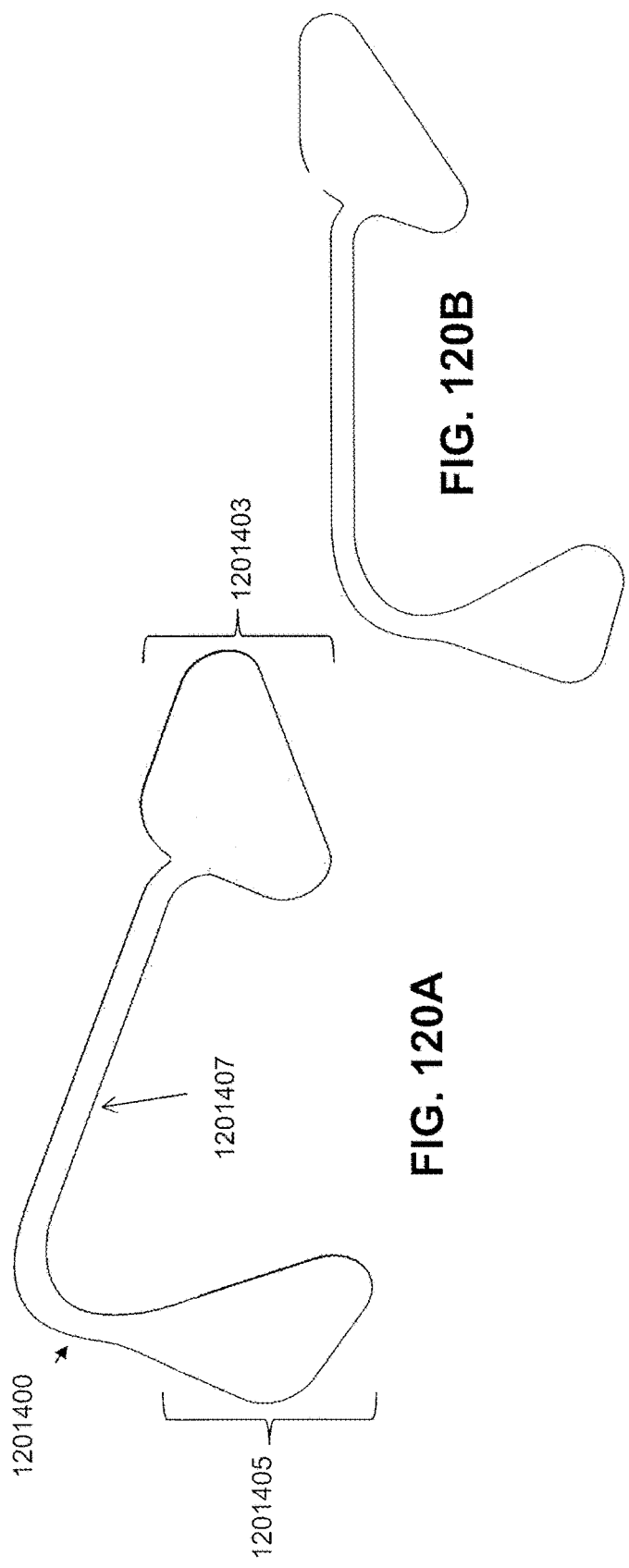
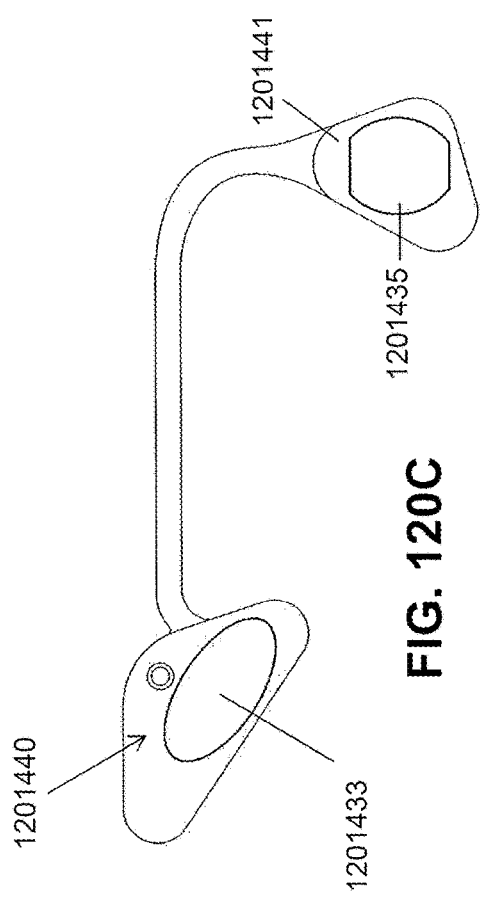
FIG. 120A
FIG. 120B
FIG. 120C

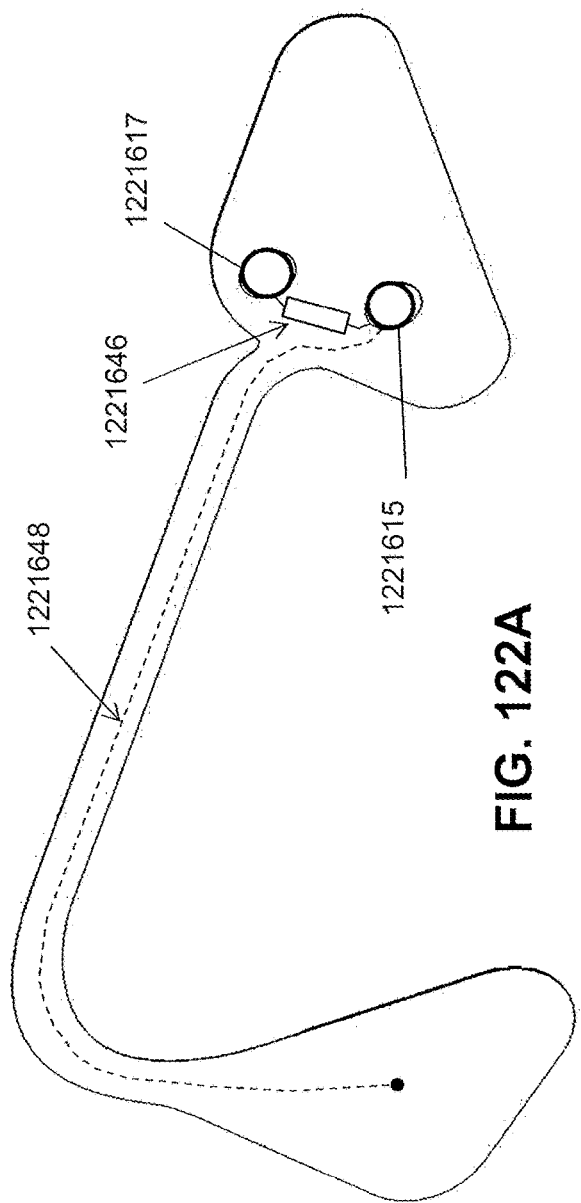
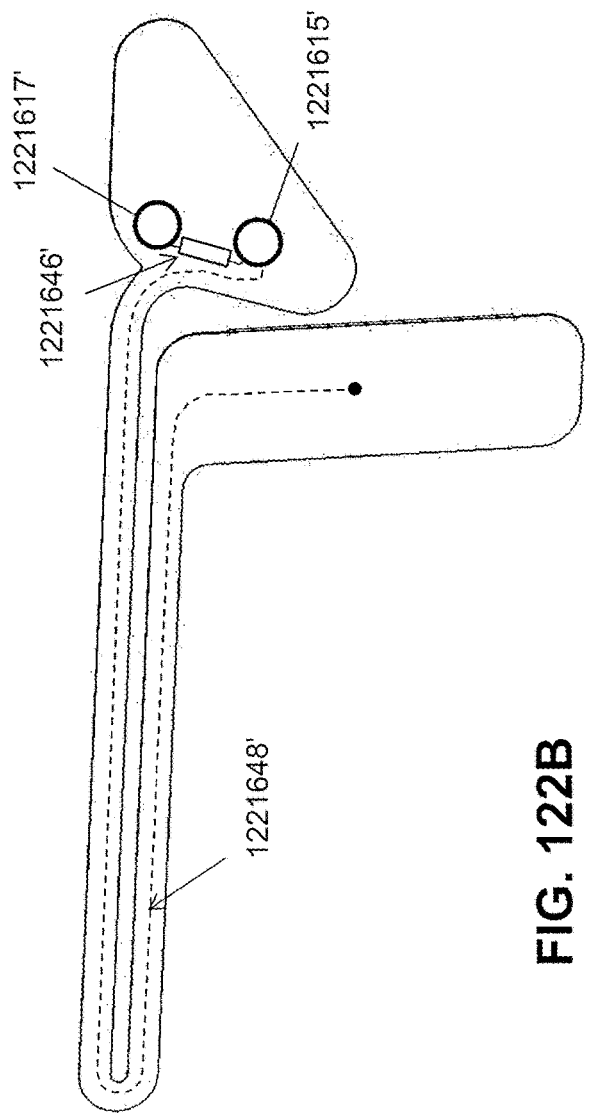
FIG. 122A
FIG. 122B

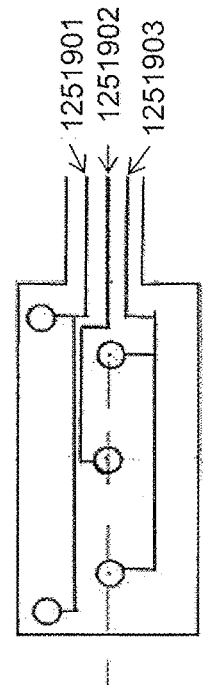
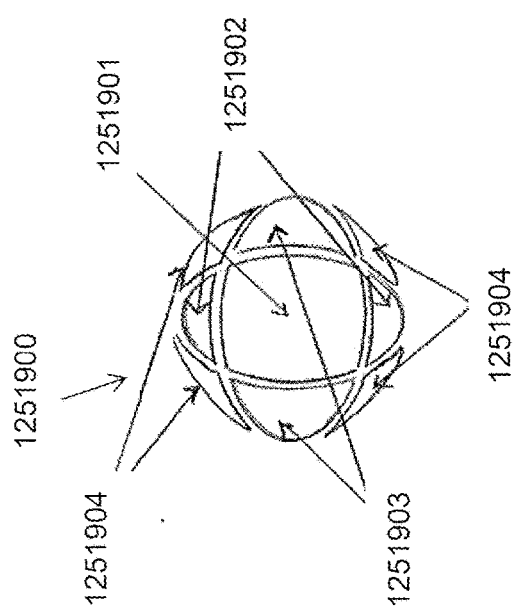
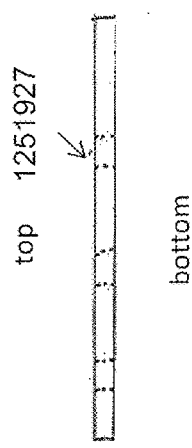
FIG. 125D
FIG. 125A
FIG. 125B

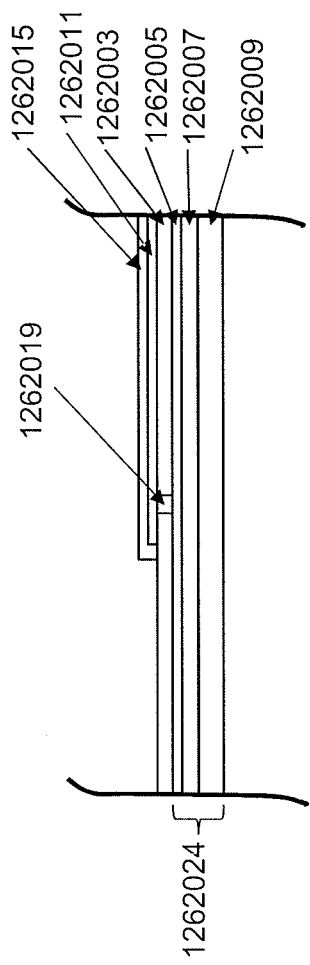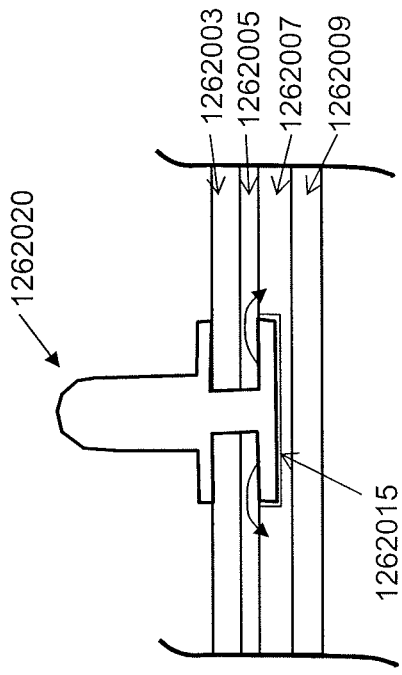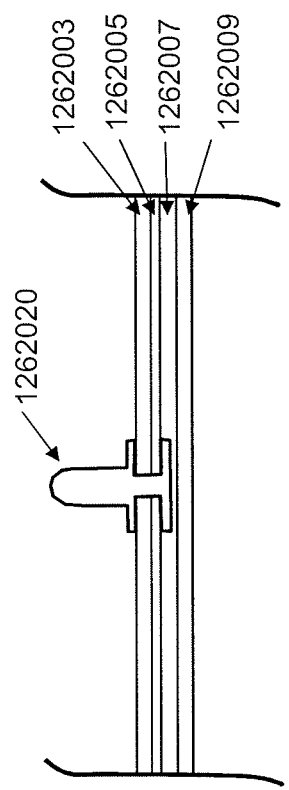
FIG. 126A
FIG. 126B
FIG. 126C

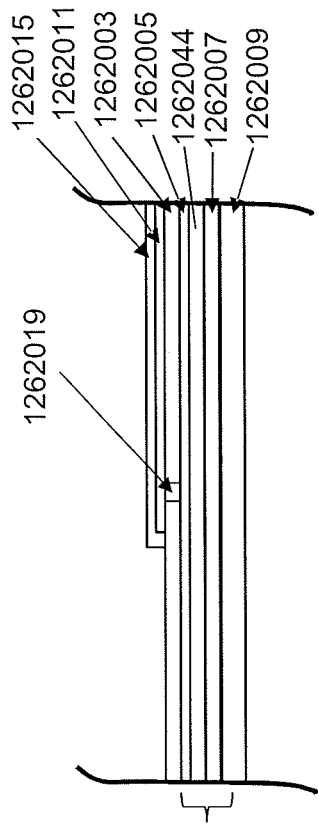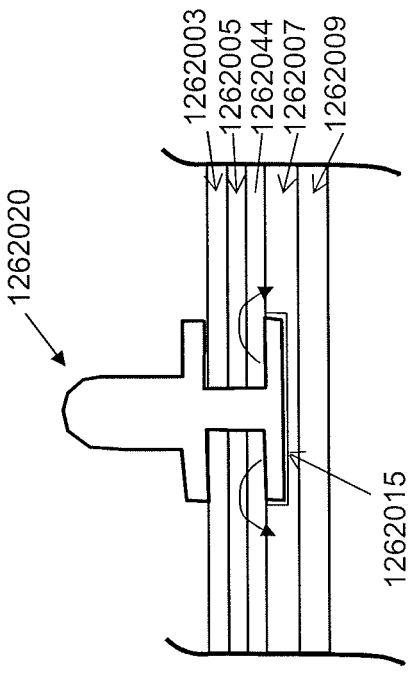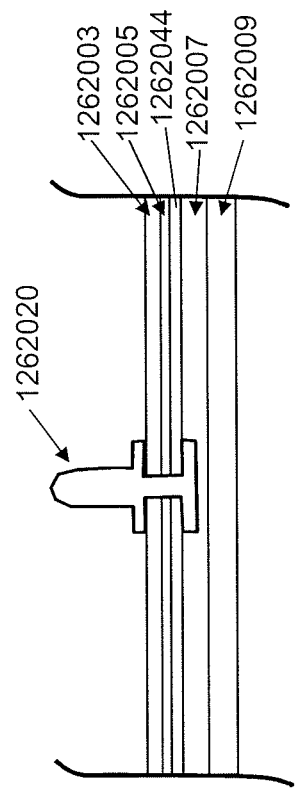
FIG. 126D
FIG. 126E
FIG. 126F

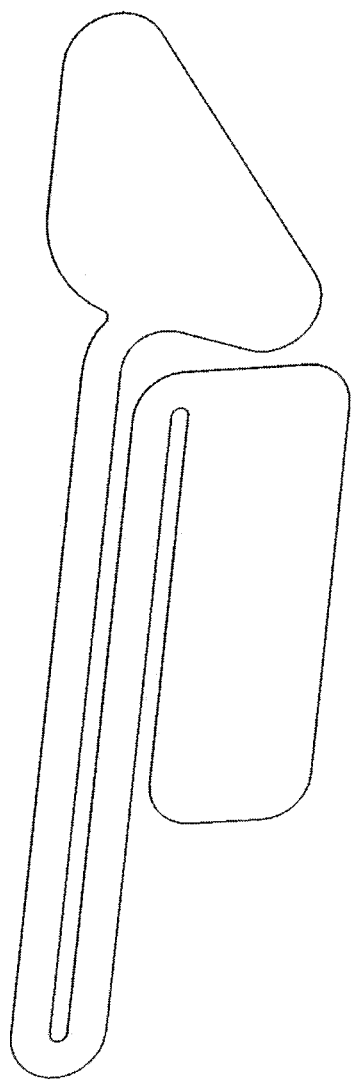
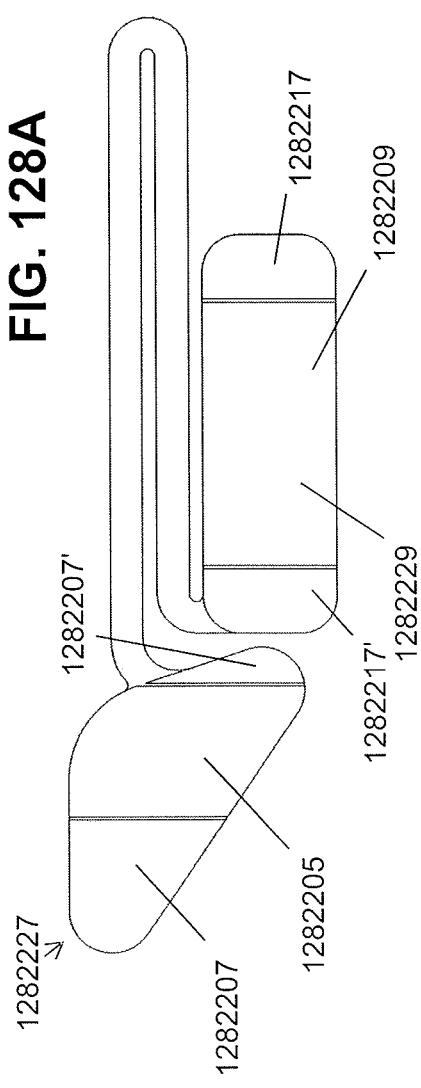
FIG. 128A
FIG. 128B

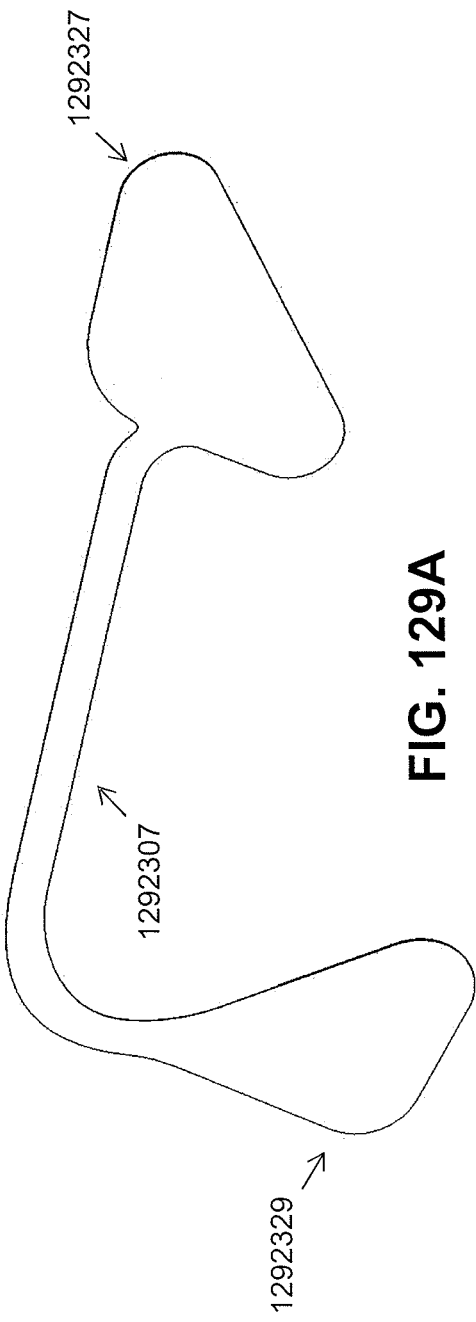
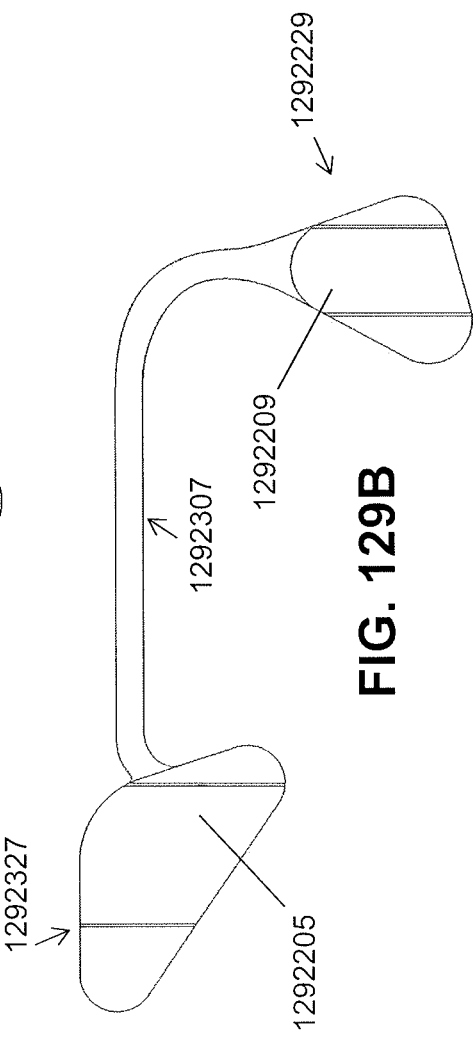
FIG. 129A
FIG. 129B

APPARATUSES AND METHODS FOR NEUROMODULATION

CROSS REFERENCE TO RELATED APPLICATIONS

This application is a continuation-in-part of U.S. patent application Ser. No. 14/558,604, filed Dec. 2, 2014, titled "WEARABLE TRANSDERMAL ELECTRICAL STIMULATION DEVICES AND METHODS OF USING THEM," Publication No. US-2015-0088224-A1, which is a continuation-in-part of U.S. patent application Ser. No. 14/091,121, filed Nov. 26, 2013, titled "WEARABLE TRANSDERMAL ELECTRICAL STIMULATION DEVICES AND METHODS OF USING THEM," now U.S. Pat. No. 8,903,494, which claimed the benefit of U.S. Provisional Patent Application No. 61/729,851, filed Nov. 26, 2012, titled "DISPOSABLE AND SEMI-DISPOSABLE TRANSCRANIAL ELECTRICAL STIMULATION SYSTEMS;" U.S. Provisional Patent Application No. 61/765,795, filed Feb. 17, 2013, titled "TRANSCRANIAL ELECTRICAL STIMULATION SYSTEMS;" U.S. Provisional Patent Application No. 61/767,945, filed Feb. 22, 2013, titled "TRANSCRANIAL NEUROMODULATION SYSTEMS;" U.S. Provisional Patent Application No. 61/770,479, filed Feb. 28, 2013, titled "TRANSCRANIAL NEUROMODULATION CONTROLLER AND DELIVERY SYSTEMS;" U.S. Provisional Patent Application No. 61/841,308, filed Jun. 29, 2013, titled "TRANSCRANIAL ELECTRICAL STIMULATIONS SYSTEMS;" U.S. Provisional Patent Application No. 61/845,845, filed Jul. 12, 2013, titled "TRANSCRANIAL ELECTRICAL STIMULATION SYSTEMS AND METHODS;" U.S. Provisional Patent Application No. 61/875,424, filed Sep. 9, 2013, titled "TRANSCRANIAL ELECTRICAL STIMULATION SYSTEMS AND METHODS;" U.S. Provisional Patent Application No. 61/900,880, filed Nov. 6, 2013, titled "NEUROMODULATION CONTROL AND USER INTERFACE SYSTEMS;" U.S. Provisional Patent Application No. 61/875,891, filed Sep. 10, 2013, titled "SYSTEMS AND METHODS FOR TRANSCRANIAL ELECTRICAL STIMULATION DURING A PERFORMANCE OR GROUP INVENT;" U.S. Provisional Patent Application No. 61/888,910, filed Oct. 9, 2013, titled "TRANSCRANIAL ELECTRICAL STIMULATION SYSTEMS AND METHODS;" U.S. Provisional Patent Application No. 61/907,394, filed Nov. 22, 2013, titled "TRANSCRANIAL ELECTRICAL STIMULATION SYSTEMS AND METHODS." Each of these applications is herein incorporated by reference in its entirety.

U.S. patent application Ser. No. 14/558,604 also claims the benefit of U.S. Provisional Patent Application No. 62/076,459, filed Nov. 6, 2014, titled "CANTILEVER ELECTRODES FOR TRANSDERMAL AND TRANSCRANIAL STIMULATION," which is herein incorporated by reference in its entirety.

This application is a continuation-in-part of U.S. patent application Ser. No. 15/170,878, filed Jun. 1, 2016, titled "APPARATUSES AND METHODS FOR NEUROMODULATION," which claims priority to each of the following: U.S. Provisional Patent Application No. 62/169,522, filed Jun. 1, 2015, titled "SYSTEMS AND METHODS FOR NEUROMODULATION TO TRANSFORM CONCURRENT SENSORY EXPERIENCES;" U.S. Provisional Patent Application No. 62/169,523, filed Jun. 1, 2015, titled "APPARATUSES AND METHODS FOR NEUROMODULATION;" U.S. Provisional Patent Application No. 62/170,111, filed Jun. 2, 2015, titled "SYSTEMS AND METHODS FOR NEUROMODULATION WITH FACIAL AND MASTOID ELECTRODES;" and U.S. Provisional Patent Application No. 62/268,084, filed Dec. 16, 2015, titled "SYSTEMS AND METHODS FOR NEUROMODULATION WITH FACIAL AND MASTOID ELECTRODES". Each of these applications is herein incorporated by reference in its entirety.

This application is a continuation-in-part of U.S. patent application Ser. No. 14/715,470, filed May 18, 2015, titled "TRANSDERMAL NEUROSTIMULATOR ADAPTED TO REDUCE CAPACITIVE BUILD-UP," Publication No. US-2015-0335888-A1, which claims priority to U.S. Provisional Patent Application No. 62/002,910, filed May 25, 2014, titled "TRANSDERMAL ELECTRICAL STIMULATION ELECTRODE DEGRADATION DETECTION SYSTEMS AND METHODS OF USING THEM;" U.S. Provisional Patent Application No. 62/076,459, filed Nov. 6, 2014, titled "CANTILEVER ELECTRODES FOR TRANSDERMAL AND TRANSCRANIAL STIMULATION;" U.S. Provisional Patent Application No. 62/099,950, filed Jan. 5, 2015, titled "CANTILEVER ELECTRODES FOR TRANSDERMAL AND TRANSCRANIAL STIMULATION;" U.S. Provisional Patent Application No. 62/075,896, filed Nov. 6, 2014, titled "SYSTEMS AND METHODS FOR NEUROMODULATION;" U.S. Provisional Patent Application No. 62/099,960, filed Jan. 5, 2015, titled "METHODS AND APPARATUSES FOR USER CONTROL OF NEUROSTIMULATION;" U.S. Provisional Patent Application No. 62/100,022, filed Jan. 5, 2015, titled "WEARABLE TRANSDERMAL NEUROSTIMULATOR." Each of these applications is herein incorporated by reference in its entirety.

This application is a continuation-in-part of U.S. patent application Ser. No. 14/715,476, filed May 18, 2015, titled "METHODS AND APPARATUSES FOR AMPLITUDE-MODULATED ENSEMBLE WAVEFORMS FOR NEUROSTIMULATION," Publication No. US-2015-0328461-A1, which claims priority to the following provisional patent applications: U.S. Provisional Patent Application No. 61/994,860, filed May 17, 2014, titled "SYSTEMS, DEVICES, AND METHODS FOR TRANSDERMAL ELECTRICAL STIMULATION WAVEFORM DESIGN AND USE" and U.S. Provisional Patent Application No. 62/100,029, filed Jan. 5, 2015, titled "METHODS AND APPARATUSES FOR DELIVERY OF ENSEMBLE WAVEFORMS." Each of these applications is herein incorporated by reference in its entirety.

This application is a continuation-in-part of U.S. patent application Ser. No. 15/169,445, filed May 31, 2016, titled "METHODS AND APPARATUSES FOR TRANSDERMAL ELECTRICAL STIMULATION," which claims priority to each of the following: U.S. Provisional Patent Application No. 62/168,615, filed May 29, 2015, titled "METHODS AND APPARATUSES FOR TRANSDERMAL ELECTRICAL STIMULATION;" U.S. Provisional Patent Application No. 62/190,211, filed Jul. 8, 2015, titled "METHODS AND APPARATUSES FOR TRANSDERMAL ELECTRICAL STIMULATION;" U.S. Provisional Patent Application No. 62/200,256, filed Aug. 3, 2015, titled "METHODS AND APPARATUSES FOR TRANSDERMAL ELECTRICAL STIMULATION;" U.S. Provisional Patent Application No. 62/213,949, filed Sep. 3, 2015, titled "METHODS AND APPARATUSES FOR TRANSDERMAL ELECTRICAL STIMULATION." Each of these applications is herein incorporated by reference in its entirety.

This application may also be related to U.S. patent application Ser. No. 14/320,443, filed Jun. 30, 2014, titled "TRANSDERMAL ELECTRICAL STIMULATION METHODS FOR MODIFYING OR INDUCING COGNITIVE STATE," now U.S. Pat. No. 9,014,811 and U.S. patent application Ser. No. 14/320,461, filed Jun. 30, 2014, titled "TRANSDERMAL ELECTRICAL STIMULATION DEVICES FOR MODIFYING OR INDUCING COGNITIVE STATE," now U.S. Pat. No. 9,002,458. Each of these applications is herein incorporated by reference in its entirety.

This application may also be related to one or more of: U.S. patent application Ser. No. 14/639,015, filed Mar. 4, 2015, titled "TRANSDERMAL ELECTRICAL STIMULATION DEVICES FOR MODIFYING OR INDUCING COGNITIVE STATE," now U.S. Pat. No. 9,233,244; U.S. patent application Ser. No. 14/634,551, filed Feb. 27, 2015, titled "METHODS FOR USER CONTROL OF NEUROSTIMULATION TO MODIFY A COGNITIVE STATE," now U.S. Pat. No. 9,399,126. Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present application relates to apparatuses (e.g., systems and devices) and methods for noninvasive neuromodulation to elicit a cognitive effect using transdermal electrical stimulation.

The methods and apparatuses described herein may relate to transdermal electrical neuromodulation. In particular described herein are wearable neurostimulator apparatuses configured to deliver electrical stimulation waveforms for inducing a change in cognitive state, delivered concurrently with other sensory experiences so that the cognitive effects of the sensory experience (primary sensory effects, as well as secondary and higher order sensory-driven cognitive effects, including emotion, arousal, mood, etc.) are enhanced, mitigated, or otherwise modulated by the sensory and cognitive effects of electrical stimulation.

The methods and apparatuses described herein relate to transdermal electrical neuromodulation. In particular described herein are wearable neurostimulator apparatuses configured to deliver electrical stimulation waveforms for inducing a change in cognitive state using two or more electrodes placed on the face and/or mastoid(s).

Alternatively or additionally, the present application may relate to apparatuses (e.g., systems and devices) and methods for noninvasive neuromodulation to elicit a cognitive effect using transdermal electrical stimulation. In particular, described herein are wearable transdermal neurostimulators that may be used (and connected to) a separate electrode assembly.

Alternatively or additionally, this invention may relate generally to methods and apparatuses for noninvasive neuromodulation, and more specifically to transdermal electrical stimulation systems using complex waveform compositions adapted to evoke a particular cognitive effect and control systems for controlling these systems so that they can deliver these complex waveform compositions.

Also described herein are non-invasive neuromodulation apparatuses, including devices and systems, and methods of their use.

BACKGROUND

The brain is composed of neurons and other cell types in connected networks that process sensory input, generate motor commands, and control other behavioral and cognitive functions. Neurons communicate primarily through electrochemical pulses that transmit signals between connected cells within and between brain areas. Stimulation technologies that affect electric fields and electrochemical signaling in neurons can modulate the pattern of neural activity and cause altered behavior, cognitive states, perception, and motor output.

Electrical stimulation applied to the head and neck area, such as transcranial electric stimulation (TES) through scalp electrodes, has been used to affect brain function in the form of transcranial alternating current stimulation (tACS), transcranial direct current stimulation (tDCS), and transcranial random noise stimulation (tRNS). Relative to tDCS, tACS and tRNS offer the advantage of reductions in pain, tingling, and other side effects on the scalp. Another strategy to reduce side effects is to use a high-density-tDCS (HD-tDCS) system with smaller electrode pads, such as ones sold by Soterix Medical. tACS also has the advantage of being inherently temporal in nature and thus capable of affecting, inducing, or destructively interfering with endogenous brain rhythms.

TES is advantageous for modulating brain activity and cognitive function in man. TES has been shown to improve motor control and motor learning, improve memory consolidation during slow-wave sleep, regulate decision-making and risk assessment, affect sensory perception, and cause movements. Systems and methods for TES have been disclosed (see for example, U.S. Pat. No. 4,646,744 to Capel; U.S. Pat. No. 5,540,736 to Haimovich et al.; U.S. Pat. No. 8,190,248 to Besio et al.; U.S. Pat. No. 8,239,030 to Hagedorn and Thompson; U.S. Patent Application Publication No. 2011/0144716 to Bikson et al.; and U.S. Patent Application Publication No. 2009/0177243 to Lebedev et al.). Many such TES systems described in the prior art require surgical implantation of components for electrical stimulation on the head of a user (see for example U.S. Pat. No. 8,121,695 to Gilner and U.S. Pat. No. 8,150,537 to Tanaka and Nakanishi). Although tDCS systems with numerous electrodes and a high level of configurability have been disclosed (see, for example, U.S. Patent Application Publication Nos. 2012/0209346, 2012/0265261, and 2012/0245653 to Bikson et al.), as have portable TES systems for auto-stimulation (U.S. Patent Application Publication No. 2011/0288610 to Brocke), such prior art TES systems are complicated, and would be difficult for an end-user (e.g., a patient or subject wearing the device) to apply and operate.

The simplest form of TES is tDCS. Several open source tDCS projects have released designs for inexpensive TES systems, including the 'Thinking Cap' from Grindhouse Wetware and the Go Flow. In such examples, the electronic circuitry requires a voltage supply (generally 9 V or 12 V); a current regulator to supply constant current as the impedance between an electrode and a subject's head changes slightly (e.g. due to movement, sweating, etc.); and some circuitry to ensure that spikes of current do not pass into the subject. Additional components can be added to select the current delivered, limit the time of stimulation, and provide visual or other indicators of stimulation.

tACS requires additional hardware to deliver alternating currents to the electrodes at an appropriate frequency. An oscillator, microcontroller, or timing circuit can be used to deliver a desired time-varying stimulation. In some designs, a digital-to-analog converter is used.

tRNS additionally requires a microcontroller or other processor configured to provide random values with appropriate structure that are then converted to an analog signal and used to gate current at a the desired intensity (e.g. at a desired amplitude, frequency, and/or duration) through appropriate circuitry.

For each form of TES, one or more pairs of electrodes coupled to a subject's head or body are used to deliver the desired energy to the subject's brain or nervous system. A battery or AC power supply is used to supply power. For example, hardware and software systems for TES typically include: a battery or power supply safely isolated from mains power by magnetic, optic, or other techniques; control hardware and/or software for triggering a TES event and controlling the waveform, duration, intensity, and other parameters of stimulation of each electrode; and one or more pairs of electrodes with gel, saline, or another material for electrical coupling to the scalp. Such prior art apparatuses are typically cumbersome, and can be heavy and difficult to operate and apply.

Historically, stimulation electrodes used in TES have been relatively large, on the order of about more than 2 cm by 2 cm. The motivation for large electrode pads has been to reduce the tingling, itchy, or painful sensation created at the edge of the electrodes from the generated electric field. For instance, Feurra and colleagues used a 3 cm×4 cm electrode and a 5 cm×7 cm electrode for stimulating somatosensory cortex (Feurra et al., 2011a). Bikson and co-inventors have proposed a 'high density' electrode system with multiple smaller electrodes arranged in groups and improved coupling of the electrical fields to the scalp in order to reduce discomfort (U.S. patent application Ser. No. 12/937,950, titled "APPARATUS AND METHOD FOR NEUROCRANIAL ELECTROSTIMULATION" by inventors Marom Bikson, Abhishek Datta, Fortunato Battaglia, Maged Elwassif).

Similarly, Schutter (Schutter and Hortensius, 2011) used conductive-rubber electrodes placed in wet sponges saturated with Parker Spectra 360 electrode gel (Parker Laboratories, Fairfield, USA). Other skin surface mounted electrodes known to be employed in TES include adhesive stimulation electrodes that maintain positioning by adhering to the scalp. In other embodiments, a band, helmet, or other head-mounted assembly maintains the positioning of the stimulation electrodes. In general, these prior art systems all include electrodes that may be attached to the subject and are connected, typically by a wire or other connector, to a base unit that is remotely located from the electrodes and the subject's head. These base units may include the stimulator/controller for applying the waveforms.

Various commercial and custom systems for triggering a specified stimulus waveform using one or more pairs of TES electrodes have been described and are well known to one skilled in the art of brain recording or TES, e.g. DS2 or DS3 Isolated Stimulator (Digitimer Ltd., Welwyn Garden City, Hertfordshire, U.K.). Such systems are not typically portable or wearable, at least in part because of subject safety concerns; in order to provide sufficient power (current, voltage) to a subject to produce an effect, many systems require bulky and durable signal conditioning and electrical isolation, and therefore physically isolate these control units from the subject (and particularly the subject's head).

Described herein are apparatuses (devices, systems, etc.) that may provide effective stimulation (e.g., TES) to produce a cognitive effect in a subject, yet be intuitive and easy to apply and operate and may be lightweight, durable and self-contained, so that the entire apparatus (electrodes and stimulator) can be applied and worn on the subject's (patient's) head. Some or all of the control functions for the apparatus may be remotely controlled, e.g., using non-transient control logic executable on a remote processing device (e.g., smartphone, pad, computer, etc.). The apparatuses and methods of making and using them, described herein may address many of the shortcomings and may dramatically improve upon prior art TES apparatuses and methods.

Also described herein are exemplary brain stimulation techniques that are known in the art can also be combined with (and improved upon by) TES to create advantageous forms of neuromodulation. For example, transcranial ultrasound neuromodulation employs ultrasound for stimulating neural tissue rather than for imaging, see, for example, U.S. Patent Application Publication No. 2011/0178441 and International Patent Application No. PCT/US2010/055527 (Publication No. WO 2011/057028). Such parallel or additional techniques may include transcranial magnetic stimulation, optogenetic stimulation, and electrocorticography.

Transcranial magnetic stimulation (TMS) induces electric fields in the brain by generating a strong (generally pulsed) magnetic field with a coiled electromagnet at or near the head. The magnetic field is transmitted painlessly and efficiently through the skin and skull to the underlying neural tissue. Deep brain stimulation (DBS) requires implantation of electrodes targeted to a brain area of interest, generally one at some depth from the brain surface. A long thin electrode assembly, generally with several conductive leads near the tip delivers electrical stimulation to a tissue of interest. DBS is an effective strategy for treating Parkinson's disease in subjects unresponsive to drugs.

Optogenetic stimulation uses light of a specified wavelength to activate an engineered protein expressed in neurons or other cell types that modifies the electrical and/or biochemical activity of a targeted cell. For deep brain applications, light is generally introduced via an implanted optical fiber.

Electrocorticography (ECoG) arrays are electrodes implanted on the surface of the brain or dura. ECoG arrays can be used to record electrical potentials and/or stimulate underlying cortical tissue, for instance to map the focal point of a seizure.

Noninvasive neuromodulation technologies that affect neuronal activity can modulate neural activity and potentially alter behavior, cognitive states, perception, and motor output without requiring an invasive procedure. The induced neuromodulation occurs in the context of a subject's ongoing sensory experiences and endogenous cognitive state, yet, to date, noninvasive neuromodulation technologies have not been configured to integrate or coordinate with the subject's sensory experiences and cognitive state to create new and more effective forms of neuromodulation.

For example, transcranial/transdermal electric stimulation ("TES") using scalp electrodes has been used to affect brain function in humans in the form of transcranial alternating current stimulation (hereinafter "tACS"), transcranial direct current stimulation (hereinafter "tDCS"), cranial electrotherapy stimulation (hereinafter "CES"), and transcranial random noise stimulation (hereinafter "tRNS").

TES devices have historically been used therapeutically in clinical applications, including treatment of pain, depression, epilepsy, and tinnitus. "Lifestyle" applications of neuromodulation have been proposed, including those for affecting states of calmness and energy, but these neuromodulation systems and methods are lacking in at least some instances because they are not well integrated and coordinated with the cognitive effects induced by other sensory experiences such as music, film or video, and other olfactory, gustatory, vestibular, and somatosensory sensory experiences and related cognitive effects. Thus, the cognitive effects induced by TES are limited and lacking in at least some instances.

Despite the research to date on noninvasive neuromodulation, existing systems and methods for noninvasive neuromodulation, including TES, are lacking in at least some cases for enhancing the experience of a musical event or other individual or group experience by inducing a cognitive state that modifies the experience of the event or other experience in a positive or beneficial manner. Systems and methods for integrating noninvasive neuromodulation such as (but not limited to) TES with a musical event (e.g. concert or DJ set at a club), musical track (e.g. listened to by oneself), or other sensory experiences (e.g. video or film) would be advantageous.

Despite advances in the creation and management of multi-sensory experiences associated with performances and other forms of produced art (i.e. a recorded audio track or video), methods to modulate the subjective experience of an audience are lacking in at least some instances for enhancing the experience of a musical event or other individual or group experience by inducing a cognitive state that modifies the experience of the event or other individual or group experience in a positive or beneficial manner. Moreover, systems and methods for integrating TES with a musical event (e.g. concert or DJ set at a club) or other group experience would be advantageous.

To date, the majority of transdermal non-invasive neuromodulatory devices apply electrical energy to a subject's skin using one or more electrodes that typically attach to the neurostimulator via a cord or cable, which can be long and awkward to wear, particularly in a non-clinical or non-research setting.

TES has been used therapeutically in various clinical applications, including treatment of pain, depression, epilepsy, and tinnitus. Despite the research to date on TES neuromodulation, existing systems and methods for delivering TES are lacking. In particular, neurostimulators that are effective, comfortable and easy-to-use, e.g., easy to apply and remove, particularly in a non-clinical (e.g., home) setting, have been lacking.

Although a handful of small, lightweight and presumably wearable neuromodulation devices have been described, none of these systems are adapted for use with electrodes (e.g., disposable electrode assemblies) for applying energy to a user's head. In particular, none of these systems may be secured to a separate electrode assembly so that the neurostimulator may be well-secured to the user's head (or other body region) for a variety of sizes of users. For example, previously described neurostimulators either attach directly to the user (e.g., adhesively, and must therefore rest directly against the user's body) or they are secured to an electrode which is secured to the body but requires additional support (e.g., from a strap or additional adhesive on the neurostimulator) to be worn by the subject.

Thus, there is a need for lightweight, wearable neuromodulation devices (e.g., neurostimulators) that may be securely worn by the user by attachment through a separate electrode assembly. Furthermore, there is a need for lightweight neurostimulators that mechanically and electrically secure to an electrode assembly in a manner that fits a variety of body shapes and sizes. In particular, there is a need for wearable neurostimulators that are configured to be comfortably wearable and will not fall off when a user is moving around, or even when a user is wearing additional clothing or glasses. Described herein are methods and apparatuses (e.g., devices and systems, and methods of operating such apparatuses) that may address at least the needs identified above.

In addition, the cognitive effects induced by existing TES are also limited and lacking in at least some instances in terms of the effects induced and the simplicity and possibilities for miniaturization of a wearable TES neurostimulator system with electrodes targeting the face and/or mastoid(s).

Noninvasive neuromodulation technologies that affect neuronal activity can modulate neural activity and potentially alter behavior, cognitive states, perception, and motor output without requiring an invasive procedure. To date, the majority of transdermal non-invasive neuromodulatory devices apply electrical energy to a subject's skin using one or more electrodes that typically attach to the neurostimulator via a cord or cable, which can be long and awkward to wear, particularly in a non-clinical or non-research setting.

For example, transcranial/transdermal electric stimulation ("TES") using scalp electrodes has been used to affect brain function in humans in the form of transcranial alternating current stimulation ("tACS"), transcranial direct current stimulation ("tDCS"), cranial electrotherapy stimulation ("CES"), and transcranial random noise stimulation ("tRNS").

Thus, there is a need for lightweight, wearable neuromodulation devices (e.g., neurostimulators) that may be securely worn by the user by attachment through a separate electrode assembly. Furthermore, there is a need for lightweight neurostimulators that mechanically and electrically secure to an electrode assembly in a manner that fits a variety of body shapes and sizes. In particular, there is a need for wearable neurostimulators that are configured to be comfortably wearable and will not fall off when a user is moving around, or even when a user is wearing additional clothing or glasses.

Moreover, during a TES session, capacitance might be built up between the electrodes, which might cause pain and discomfort. The user might be distracted, thus the cognitive effects of the TES might be reduced. Alternatively, the user might be sufficiently uncomfortable from the skin sensations of electrical stimulation that the subjective experience of pain overwhelms another cognitive, subjective, or physiological effect. Therefore, there is a need for a neurostimulator to include stimulation circuits that may reduce discomfort. For example, described herein are neurostimulators that include a "short-circuiting" feature that is configured to reduce discomfort and accordingly increase the cognitive effects induced by TES (due to one or both of: reducing the distraction of discomfort so that other cognitive effects can be experienced by a subject and permitting higher peak current intensities to be delivered that induce more significant cognitive effects).

In addition, there is a need for neurostimulator devices (and indeed, generally for electrical stimulation devices) that are both energy efficient and effective. In particular, there is a need for electrical stimulation devices (such as neurostimulators) that include a relatively high-voltage power source, yet that are capable of dynamically adjusting the power supplied to the electronics of the device so that power is conserved (and heat dissipation is minimized), while maintaining the functionality of the device.

Described herein are methods and apparatuses (e.g., devices and systems, and methods of operating such apparatuses) that may address at least the needs identified above.

For example, U.S. Pat. No. 8,554,324 to Brocke discloses a mobile system for TES auto-stimulation by a user. Brocke further describes an embodiment wherein a wired or wireless remote control is used to control an electrical stimulation generator, as well as the use of smartphones, cellular telephones, or PDAs as a remote control. However, the systems and methods described by Brocke are lacking in at least some instances for defining, acquiring, and/or delivering effective TES waveforms to a user.

Indeed most TES systems are described with only rudimentary waveforms, and typically apply the same stimulation (or repeated versions of the same basic stimulation set), including simple ramps up and down. Such stimulation is not specific to a particular effect (e.g., cognitive effect such as calming or energizing a subject) and may not be universally effective. What is needed are detailed waveform patterns that are effective to modify a subject's cognitive state across a variety of subjects.

Thus, systems, devices, and methods for applying such complex waveforms by a wearable TES system would be advantageous. Described herein are methods and apparatuses (including devices and systems) for neurostimulation to apply waveforms, which may be referred to as ensemble waveforms, that include numerous sequential sub-components in which a subset of waveform parameters found by the inventors to be important for effective neuromodulation may be altered alone or in combinations at different portions of the delivered waveform to achieve high levels of efficacy and comfort in modulating a subject's (user's) cognitive state.

Also described herein are systems, devices, and methods for transmitting waveform parameters of an ensemble waveform to a neurostimulator controller that achieve robust, efficient, and reliable control of the neurostimulator with regard to transmitting various waveform parameters of an ensemble TES waveform.

Most electrical stimulation systems targeting the nervous system incorporate a tabletop or handheld hardware comprising a user interface, electrical control circuitry, a power supply (e.g. battery), wires leading to electrodes affixed to a user, and predetermined and/or preconfigured electrical stimulation protocols. Conventional systems are limited regarding the comfort, design, and use of electrodes to deliver TES waveforms. For example, they may use uncomfortable and inflexible electrodes, such that the electrodes do not conform to the body of the user, resulting in uneven impedance, increased irritation during stimulation, and reduced cognitive effects. Further, most prior art electrodes are not able to act as substrates for electronic circuits and are not well suited to attach to a wearable neurostimulator so that the neurostimulator is held to the body by the electrode.

Although other designs of neuromodulation devices included small, wearable devices, it would be desirable to have a neuromodulation device that was not only more cost-effective to produce but also possessing an even more discrete profile. Further, it would be useful to provide an integrated neuromodulation unit and electrode assembly. There is a need for integrated, lightweight, low-profile, wearable neuromodulation systems, that integrate the electrodes and neuromodulation components such that there is no concern for maintaining the connection between the electrodes and neuromodulation components when contact is between two or more widely separated regions of the wearer's body, including the head or head and neck. Integrating electrodes with a neuromodulation unit is beneficial for reducing weight and improving the ease of wearing the system adhesively on the skin.

In most related designs, neurostimulators were separate units from the electrode apparatuses that could be coupled together to provide electrical stimulation to the wearer. For example, existing TES systems generally provide a separate neurostimulation module and dermally-adhesive electrode apparatus, as described (for example) in PCT applications by some of the named inventors of this application: PCT/US2015/031,966 titled "CANTILEVER ELECTRODES FOR TRANSDERMAL AND TRANSCRANIAL STIMULATION" and PCT/US2015/031,424 titled "WEARABLE TRANSDERMAL NEUROSTIMULATORS". A new, simpler, and easier to use system requires no connecting of separate units by designing the electrodes and the neuromodulation components integrated into a unified system on a flexible circuit backing. Similar to prior device designs, the present integrated neuromodulation device may include a pH regulating consumptive layer that is flexible and can make reliable electrical contact with the user's skin. An integrated neuromodulation device can be designed to include a variety of electrode configurations. Finally, it would remain useful to provide electrode assemblies that are capable of making reliable and durable electrical contact with the user at various locations on the user's head and neck regions.

To date, TES systems, including wearable TES systems, generally require a microprocessor and power source (e.g. battery). New TES system that remove the need for either or both of a microprocessor and power source (e.g. battery) by connecting directly to a smartphone, tablet, or other user computing device would permit TES systems to be smaller, lighter weight, less expensive, simpler to operate, and better for the environment (i.e. due to the elimination or size reduction of a battery contained on the TES system).

The apparatuses (e.g., devices and systems), and methods described herein may address at least the needs identified above.

SUMMARY OF THE DISCLOSURE

In general, described herein are lightweight and wearable transdermal electrical stimulation apparatuses for inducing a cognitive effect in a subject. In particular, described herein are lightweight and wearable transdermal electrical stimulation apparatuses that are self-contained. The apparatus may include all of the elements necessary and sufficient to drive stimulation and achieve a predetermined cognitive effect. The apparatus may be untethered from any component that is not worn or wearable with the rest of the apparatus; for example, the entire apparatus may be attached and worn on the head and/or neck of the subject. Although the apparatus may be self-contained, it may be configured to receive instructions from one or more remote systems (and may transmit signals to the same or a different remote system), including instructions that select or modify stimulation parameters.

For example, described herein are lightweight and wearable transdermal electrical stimulation apparatuses for inducing a cognitive effect in a subject that include a durable portion that couples with a disposable or replaceable portion (e.g., an electrode portion or electrode apparatus) to form the lightweight and wearable transdermal electrical stimulation apparatus. The durable or reusable portion may include a processor and/or controller, power source, and one or more connectors for connecting to two or more electrodes in the disposable portion to drive stimulation between the electrodes to induce a cognitive effect in a subject wearing the apparatus. As used herein, a disposable element may refer to a limited-use item (e.g., single-use or limited multiple-use, including 2-3 uses, 2-5 uses, 2-7 uses, 2-10 uses, or less than 5 uses, less than 10 uses, etc.). A disposable element may be used once (or 2-3 times, etc.) and then removed from the apparatus and replaced with a new element. In particular, the electrodes described herein may be disposable elements that include a conductive material (e.g., conductive gel, conductive adhesive, etc.) and/or adhesive that is only reliably useful a limited number of times before needing to be replaced or refurbished.

The apparatuses described herein include devices and systems which may include multiple connected or connectable elements. These apparatuses may be used or worn by a subject. The subject wearing or using the device may be referred to as a subject or operator. The apparatuses described herein may be configured to provide one or more cognitive effects. In general, a cognitive effect may include any induced cognitive effect that is perceived subjectively by the recipient as a sensory perception, movement, concept, instruction, other symbolic communication, or modifies the recipient's cognitive, emotional, physiological, attentional, or other cognitive state. For example, an effect of electrical stimulation is one or more of inhibition, excitation, or modulation of neuronal activity. Specific examples of cognitive effects may include relaxation, enhanced attention, mood elevation, increased energy (e.g., physiological arousal, increased subjective feelings of energy), or the like. Cognitive effects may be stereotypical across a population (though with individual variation and degree) and may be demonstrated by any appropriate means, including by subject reporting, objective testing, imaging, physiological recording, etc. Particular cognitive effects evoked may depend upon the position of the electrodes of the apparatus with respect to the subject, and/or the stimulation parameters described herein. The apparatuses described herein may be optimized to achieve a specific cognitive effect.

A cognitive effect of neuromodulation may cause a change in a user's level of energy, fatigue, sleepiness, alertness, wakefulness, anxiety, stress, sensory experience, motor performance, formation of ideas and thoughts, sexual arousal, creativity, relaxation, empathy, and/or connectedness that is detectable by an objective measurement (e.g. behavioral assay) and/or subjective report by the user.

For example, a cognitive effect of neuromodulation may cause a change in an emotional state of the user where the change is detectable by an objective measurement (e.g. behavioral assay) and/or subjective report by the user and an emotion affected is selected from the list including but not limited to: affection, anger, angst, anguish, annoyance, anxiety, apathy, arousal, awe, boredom, confidence, contempt, contentment, courage, curiosity, depression, desire, despair, disappointment, disgust, distrust, dread, ecstasy, embarrassment, envy, euphoria, excitement, fear, frustration, gratitude, grief, guilt, happiness, hatred, hope, horror, hostility, hurt, hysteria, indifference, interest, jealousy, joy, loathing, loneliness, love, lust, outrage, panic, passion, pity, pleasure, pride, rage, regret, relief, remorse, sadness, satisfaction, self-confidence, shame, shock, shyness, sorrow, suffering, surprise, terror, trust, wonder, worry, zeal, and zest.

In some variations, the cognitive effects evoked by the apparatuses described herein may be positive cognitive effects; positive cognitive effects refers to cognitive effects resulting in an increase in alertness, an increase in relaxation, a decrease in fatigue, and a decrease in anxiety, an enhancement in motor performance, an increase in recall, and an increase in empathy.

A cognitive effect of neuromodulation may cause a change in brain activity measured by one or a plurality of: electroencephalography (EEG), magnetoencephalography (MEG), functional magnetic resonance imaging (fMRI), functional near-infrared spectroscopy (fNIRS), positron emission tomography (PET), single-photon emission computed tomography (SPECT), computed tomography (CT), functional tissue pulsatility imaging (fTPI), xenon 133 imaging, or other techniques for measuring brain activity known to one skilled in the art.

A cognitive effect of neuromodulation may be detectable by a physiological measurement of a subject, including but not limited to measurements of the following: brain activity, body temperature, electromyogram (EMG), galvanic skin response (GSR), heart rate, blood pressure, respiration rate, pulse oximetry, pupil dilation, eye movement, and gaze direction.

A cognitive effect of neuromodulation may be detectable by a cognitive assessment that takes the form of one or more of: a test of motor control, a test of cognitive state, a test of cognitive ability, a sensory processing task, an event related potential assessment, a reaction time task, a motor coordination task, a language assessment, a test of attention, a test of emotional state, a behavioral assessment, an assessment of emotional state, an assessment of obsessive compulsive behavior, a test of social behavior, an assessment of risk-taking behavior, an assessment of addictive behavior, a standardized cognitive task, an assessment of "cognitive flexibility" such as the Stroop task, a working memory task (such as the n-back task), tests that measure learning rate, or a customized cognitive task.

In particular, the lightweight and wearable apparatuses described herein may include a pair of electrodes arranged so that one electrode is coupled closely and/or directly to a controller/processor controlling stimulation and a second electrode that is tethered to the first electrode and/or the controller/processor by a connecting region (e.g., a cable, cord, wire, ribbon, flex circuit, etc.) to permit independent positioning of the first and second electrodes on the subject's head and/or neck. The connecting region between the first and second electrodes is typically configured to pass current to the electrode for stimulation and may be of an appropriate length (e.g., less than about 18 inches, less than about 17 inches, less than about 16 inches, less than about 15 inches, less than about 14 inches, less than about 13 inches, less than about 12 inches, less than about 11 inches, less than about 10 inches, less than about 9 inches, less than about 8 inches, less than about 7 inches, less than about 6 inches, between about 3-4 inches, between about 3-6 inches, between about 3-10 inches, between about 3-12 inches, etc.). The electrodes may be skin-contact electrodes and may be configured to include an adhesive which may be an electrically conductive adhesive to hold the electrodes and/or apparatus to the subject's head/neck.

For example, disclosed herein are lightweight and wearable transdermal electrical stimulation (TES) systems for inducing a cognitive effect in a subject that include a durable primary unit (e.g., electrical stimulator) and a removable/replaceable, e.g., disposable) electrode portion (e.g., electrode assembly). The system may include: a disposable electrode portion, the disposable electrode portion including: a first electrode on a first base region, a second electrode on a second base region, a connecting region extending between the first and second electrodes, wherein the connecting region is between 3 and 12 inches long, and a first connector on the first base region, wherein the connector is in electrical communication with the first electrode; and a durable low-profile primary unit having a maximum thickness of 30 mm, the primary unit including: a housing having a first outer surface that is curved inward, a power supply within the housing; a controller within the housing, the controller including a current source configured to provide a current at a frequency of greater than 640 Hz to the receiver, and a receiver at the first outer surface, the receiver configured to electrically connect the first connector to the controller, wherein the first base region of the electrode portion is configured to connect to the first outer surface of the primary unit so that the first connector connects to the receiver, and wherein when the first electrode is attached to a first position on the subject's head and the second electrode is attached to a second position on the subject's head or neck, the controller is configured to apply stimulation at greater than 640 Hz between the first and second electrodes to induce a cognitive effect in the subject.

The base regions (e.g., the first and second base regions) may also be referred to as substrates, and may be any material, in particular, thin (e.g., less than 2 mm, less than 1 mm, less than 0.5 mm, between 0.5 and 0.01 mm, etc.) and flexible materials. For example, the material may be a plastic/polymeric material. In some variations the material is a flex circuit material. The connecting region between the first and second base regions may be part of the same sheet of material, or it may be a separate material that is connected to the first and second base regions. In some variations the first and second base regions and the connecting region comprises a flex circuit material. In some variations the connecting region comprises a cable. In some variations just the connecting region comprises a flex circuit.

In general, the first and second electrodes may both be connected to the durable primary unit through a single connector (the first connector) or through two separate connectors. In particular, the first and second electrodes may be connected to the primary unit (electrical stimulator) through a first set of snap connectors that extend from the first base region of the electrode assembly. For example, the electrode portion may include a second connector on the first base region that is in electrical connection with the second electrode. The second connector, like the first connector, may be just an electrical connector and/or it may be a mechanical connector. The second connector, like the first connector, may be a snap connector extending proud from a back side of the first base region. For example, the first connector on the first base region may comprises a snap connector extending proud of the first base region.

Any of the electrode portions (electrode assemblies) may be configured to adhesively secure the electrodes to different regions of the patient's body. In particular, these electrodes may include an adhesive (including a conductive adhesive, e.g., conductive gel adhesive) to secure the electrode to the subject's head and/or neck. In some variations the primary unit is attached to the subject wearing the device through the electrode portion, and in particular, through attachment of the first electrode (the first base region) to the subject. Thus, the first and second electrodes may be configured to adhesively attach to the subject, and the primary unit may attach to the back of the first base region. The primary unit may be attached by the first connector and/or it may be adhesively or otherwise mechanically attached to the electrode portion. For example, the first base may be configured to adhesively attach to the first outer surface of the primary unit.

In general, as mentioned above, the apparatus is wearable, which may mean that is small and lightweight. For example, in some variations the maximum diameter of the housing is less than about 10 cm (e.g., less than about 9 cm, 8 cm, 7 cm, 6 cm, 5 cm, 4 cm, 3 cm, etc., between about 10 cm and about 2 cm, etc.)

For example, described herein are lightweight and wearable transdermal electrical stimulation (TES) system for inducing a cognitive effect in a subject, the system comprising: a disposable electrode portion, the disposable electrode portion including: a first electrode on a front side of a first base region, a second electrode on a front side of a second base region, a connecting region extending between the first and second electrodes, wherein the connecting region is between 3 and 12 inches long, and a first connector comprising a snap connector extending proud from a back side of the first base region, wherein the first connector is in electrical communication with the first electrode; and a second connector on the first base region that is in electrical connection with the second electrode; and a durable, low-profile primary unit having a maximum thickness of 30 mm, the primary unit including: a housing having a first outer surface that is curved inward to conform to the subject's head, a first receiver at the first outer surface, the first receiver configured to electrically and mechanically connect to the first connector, a second receiver at the first outer surface, the first receiver configured to electrically and mechanically connect to the second connector, and a controller within the housing, the controller including a current source configured to provide a current at a frequency of greater than 640 Hz between the first and second receivers, wherein the first base region is configured to releasably connect to the first outer surface so that the first connector connects to the first receiver and the second connector connects to the second receiver, wherein the primary unit will be worn on a first position on the subject's head when the first electrode is attached to the subject's head at the first position, and wherein the second electrode is configured to attach to a second position on the subject's head or neck.

A lightweight and wearable transdermal electrical stimulation (TES) system for inducing a cognitive effect in a subject may include: a disposable electrode portion, the disposable electrode portion including: a first electrode on a front side of a first base region, an adhesive configured to secure the first electrode to a subject's head, a second electrode on a front side of a second base region, an adhesive configured to secure the second electrode to a subject's head or neck, a flexible connecting base region extending between 3 and 12 inches between the first and second electrodes, further wherein the first base region, second base region and connecting base region all comprise regions of a substrate, and a first connector comprising a snap connector extending proud from a back side of the first base region, wherein the first connector is in electrical communication with the first electrode; and a second connector comprising a snap connector extending proud from the back side of the first base region, wherein the second connector is in electrical connection with the second electrode through an electrical connection on the connecting base region; and a durable, low-profile primary unit having a maximum thickness of 30 mm and a weigh of less than 5 ounces, the primary unit including: a housing having a first outer surface that is curved inward to conform to the subject's head, a first receiver at the first outer surface, the first receiver configured to electrically and mechanically connect to the first connector, a second receiver at the first outer surface, the first receiver configured to electrically and mechanically connect to the second connector, a power supply within the housing, and a controller within the housing, the controller including a current source configured to provide a current at a frequency of greater than 640 Hz between the first and second receivers, wherein the first base region is configured to releasably connect to the first outer surface so that the first connector connects to the first receiver and the second connector connects to the second receiver, wherein the primary unit will be worn on a first position on the subject's head when the first electrode is attached to the subject's head at the first position, and wherein the second electrode is configured to attach to a second position on the subject's head or neck.

Thus, in general, described herein are wearable neuromodulation devices configured to be worn on a subject's head or on the subject's head and neck. Also described herein are electrode portions for use with the wearable neuromodulation devices. These electrode portions may also be referred to as electrode apparatuses or as cantilevered electrodes. A cantilevered electrode (cantilevered electrode apparatus) may be considered a particular subset of the electrode portions described herein.

The electrode portions (e.g., cantilevered electrodes) described herein may be configured to mate with the wearable neuromodulation devices to form a neuromodulation system as just discussed. The neuromodulation systems described herein may also be referred to as primary units, neurostimulation systems, neurostimluator systems, neuromodulator systems, applicator systems, neuromodulation applicator systems, or the like.

The wearable neuromodulation devices described herein are small, lightweight and specifically adapted to be conforming to the subject so that they can be worn while the subject goes about their daily activities. In particular, these devices are adapted to be worn on the subject's head (e.g., at the temple region) comfortably even while wearing headgear such as hats, glasses, hoods, scarves, or the like. These devices typically have a first surface (subject-facing surface) that has a curved and twisted shape so that an electrode on the surface conforms to a subject's temple region. The thickness of the device (measured from the first surface) is typically thinner at one end and thicker at the other end. The thinner end may be configured to be oriented relative to the subject's eye, with the thicker region worn higher on the subject's head. The neuromodulation devices described herein are also configured to include attachments to the cantilevered electrodes on the underside (e.g., the first surface), providing electrical connection to at least two electrodes on the cantilevered electrode assembly. In these neuromodulation devices may also be referred to as neurostimulation devices, neurostimulators, neuromodulators, applicators, neuromodulation applicators, electrical stimulators, or the like.

A cantilevered electrodes may also be referred to as electrode pads, electrode systems, or electrode apparatuses, may be durable or disposable, and are generally configured to connect to the neuromodulation device and apply energy (e.g., current) from the neuromodulation device to the subject's skin to modulate a subject's mental state (e.g., mood).

For example, described herein are electrode apparatuses for use with an electrical stimulator to be worn on a subject's head. In general, these electrode apparatuses include two electrical connections on one end (which may be mechanical connectors such as snap connectors or the like) for connecting to the electrical stimulator. The position of these electrical connectors may be between about 0.6 and 0.9 inches from center-to-center. This distance has been found to be sufficient to both allow electrical isolation when connecting to different active regions of the electrode apparatus, while also providing sufficient mechanical support and/or tolerance to the cantilevered electrode when it is connected to the electrical stimulator and then worn by a subject.

The cantilevered electrode apparatuses described herein are generally elongated, thin bodies that include a first active region for applying electrical energy to a subject's skin at or near one end, and a second active region for applying electrical energy to another region of a subject's skin at or near a second end. The electrical connectors to connect to the electrical stimulator are typically both at or near one end of the elongate body. The first and second active regions on the body may be connected by an elongated portion that is typically greater than 2 inches long. In some variations the elongate body is stiff or relatively rigid (though it may be ductile or include a ductile region that can be bent to set a shape). In some variations the elongate body has a limited flexibility, e.g., so that it is flexible in a first axis (e.g., an x-axis) but is not flexible in a second axis (e.g., y-axis), and may be rotated. For example, the elongate body of the electrode apparatus may be formed of a sheet of material such as a flex circuit material.

For example, an electrode apparatus may include: a first electrode portion having a front side and a back side; a first active region on the front side that is configured to deliver energy to the subject's skin; a first connector extending proud from the back side, wherein the first connector is in electrical communication with the first active region; a second connector extending proud from the back side, wherein the first and second connector are separated by between about 0.7 and about 0.8 inches from center to center; a second electrode portion separated from the first electrode portion by an elongate body region extending at least two inches between the first electrode portion and the second electrode portion; and a second active region on a front side of second electrode portion that is in electrical communication with the second connector and is configured to deliver energy to the subject's skin.

As mentioned, the first and second conductors are typically configured to electrically connect the apparatus to the electrical stimulator. For example, the first and second connectors may be snap connectors. The connectors may provide mechanical as well as electrical connection to the electrical stimulator. The connectors may hold (or assist in holding) the cantilevered electrode apparatus to the electrical applicator. Alternatively or additionally, the electrode apparatus may include a mechanical fastener configured to secure the electrode apparatus to the electrical stimulator. In some variations the connectors are sufficient to secure the electrode apparatus to the electrical stimulator. In some variations an adhesive may be used between the electrode apparatus and the electrical applicator (e.g., neurostimulator) to secure the cantilevered electrode apparatus to the electrical applicator. For example, the apparatus may include an adhesive on the back side of the first flat electrode portion configured to hold the electrode apparatus to the electrical stimulator. In general, the first and second connectors are configured to electrically connect the electrode apparatus to the electrical stimulator.

As mentioned above, the elongate body region between the first and second electrode portions (and the first and second active regions) may be flexible in a first direction but not flexible in a direction normal to the first direction. For example, the elongate body region may be formed of a strip of material such as a flex circuit material. Examples of flex circuit materials are well known, including, for example, polymers such as polyester (PET), polyimide (PI), polyethylene napthalate (PEN), Polyetherimide (PEI), various fluropolymers (FEP) and copolymers.

In general, the electrode apparatus may be substantially flat. For example, the thickness of the electrode apparatus may have an overall thickness (e.g., thickens of the substrate) that is less than 5 mm, less than 3 mm, less than 1 mm, less than 0.9 mm, less than 0.8 mm, less than 0.7 mm, less than 0.6 mm, etc., and extend in a plane (that may be bent or curved). The connectors may extend proud of this thickness. In addition, the electrode portions may extend above/below this overall thickness.

In any of the variations described herein the electrode apparatus may include an electrically conductive gel over the first active region and/or the second active region. The conductive gel may be adhesive and/or it may be surrounded by an additional adhesive for securing the active region to the patient's skin. For example, the electrode apparatus may include an adhesive on the front side of the first electrode portion and/or on the front side of the second electrode portion.

In some variations the electrode apparatus include a foam region. For example, the apparatus may include a foam on the first electrode portion. The foam may help comfortably seat the first active region against the subject's skin, and may also provide spacing between the apparatus and the subject's skin.

Both the first and second connectors are typically adjacent to each other on the back side of the first electrode portion, though separated by a distance sufficient to allow tolerance and support, as mentioned above. In some variations the first connector is behind the first active region and the second connector is not behind the first active region.

The first active region of the first electrode portion may be positioned off-center on the first electrode portion.

The apparatus may generally include a thin (e.g., flat) and flexible elongate body having a front side and a back side, wherein the first electrode portion is at a first end region of the flexible elongate body and wherein the second flat electrode portion is at a second end region of the flexible elongate body and the elongate body region extends between the first and second active regions. The elongate body may be greater than two inches long (e.g., greater than 3 inches long, greater than 4 inches long, etc.). In some variations the elongate body is curved or bent (when not flexed). For example, the elongate body may extend have a bend in it.

In some variations the elongate body region may include an electrical trace printed on a flexible elongate substrate. The electrical trace may provide the electrical connection between the second connector and the second active region of the second electrode portion.

An electrode apparatus for use with an electrical stimulator to be worn on a subject's head may include: a flat and flexible elongate body having a front side and a back side; a first electrode portion at a first end of the elongate body; a first active region on the front side of the first electrode portion, wherein the first active region is configured to deliver energy to the subject's skin; a first connector extending proud from behind the back side of the first electrode portion, wherein the first connector is in electrical communication with the first active region; a second connector extending proud from the back side of the first electrode portion; a second electrode portion at a second end of the elongate body that is separated from the first electrode portion by at least two inches; and a second active region on the front side of second electrode portion that is in electrical communication with the second connector and is configured to deliver energy to the subject's skin; wherein the first and second connectors are configured to electrically connect the apparatus to the electrical stimulator.

As mentioned, the first and second connectors are configured to electrically connect the apparatus to the electrical stimulator, and may be, for example, snap connectors.

As mentioned above, the electrode apparatus may include an electrically conductive gel (e.g., over the first active region and/or the second active region), an adhesive on the front side of the first electrode portion and on the front side of the second electrode portion, a foam on the first flat electrode portion, or the like. In any of the electrode apparatuses described herein the first and second connectors may be separated by between about 0.6 to about 0.9 inches (e.g., about 0.7 and about 0.8 inches, about 0.72 inches, etc.).

A flexibly connected electrode apparatus for use with an electrical stimulator to be worn on a subject's head may include: a flat and flexible elongate body having a front side and a back side; a first electrode portion at a first end of the elongate body; a first active region on the front side of the first electrode portion, wherein the first active region is configured to deliver energy to the subject's skin; a first connector extending proud from behind the back side of the first active region, wherein the first connector is in electrical communication with the first active region; a second connector extending proud from behind the back side of the first active region, wherein the first and second connectors are separated by between about 0.7 and about 0.8 inches; a second electrode portion at a second end of the elongate body; and a second active region on the front side of second electrode portion that is in electrical communication with the second connector and is configured to deliver energy to the subject's skin; wherein the first and second snap connectors are configured to electrically connect the apparatus to the electrical stimulator.

Also described herein are methods of applying the electrode apparatuses to a subject, and methods of applying electrical stimulation to a subject using any of these electrode apparatuses. For example, a method of applying electrical stimulation to a subject's head (or head and neck) using a flat elongate electrode apparatus coupled to a wearable electrical stimulator may include: connecting a first and second electrical connector of the electrode apparatus to the wearable electrical stimulator by inserting the first electrical connector into a first receptacle on an underside of the wearable electrical simulator and a second electrical connector of the electrode apparatus into a second receptacle on the underside of the wearable electrical stimulator, wherein the first and second electrical connectors extend proud of a back side of a first active region of the electrode apparatus; adhesively securing the electrode apparatus coupled to the electrical stimulator to the subject's head so that the first active region on a front side of the electrode apparatus is in electrical contact with the subject's head; and adhesively securing a second active region on the front side of the electrode apparatus at a second location on the subject's head or neck wherein the second active region is connected to the first active region through a flat and flexible elongate body so that the second active region is electrically connected to the second electrical connector. The method may also include adhesively securing the back side of the first active region to the underside of the wearable electrical stimulator.

The method may also include applying energy from the wearable electrical stimulator between the first and second active regions. For example, the method may include applying current from the wearable electrical simulator having a peak current of about 3 mA peak, a frequency above 640 Hz, and a duty cycle of greater than about 10%.

Adhesively securing the electrode apparatus coupled to the electrical stimulator may comprise securing the first active region and the wearable electrical stimulator to the subject's temple. For example, with the active region lateral and/or slightly above the subject's eye. In some variations, adhesively securing the second active region comprises securing the second active region to the subject's neck or a region behind the subject's ear (e.g., in the mastoid region, e.g., on or near the mastoid). Connecting the first and second electrical connectors may comprises connecting the first and second electrical connectors wherein the first electrical connector is between about 0.7 and 0.8 inches from the second first electrical connector.

In general, adhesively securing a second active region comprises bending the flat and flexible elongate body around the subject's head to position the second active region on the subject's head or neck (e.g., on the back of the subject's neck or behind the subject's ear on or near the mastoid region).

A methods of wearing an electrode apparatuses may include: connecting a first and second electrical connector of the electrode apparatus to a wearable electrical stimulator by inserting the first electrical connector into a first receptacle on an underside of the wearable electrical simulator and a second electrical connector of the electrode apparatus into a second receptacle on the underside of the wearable electrical stimulator, wherein the first and second electrical connectors extend proud of a back side of a first active region of the electrode apparatus; adhesively securing the electrode apparatus coupled to the electrical stimulator to the subject's head so that the first active region on a front side of the electrode apparatus is in electrical contact with the subject's head; and adhesively securing a second active region on the front side of the electrode apparatus at a second location on the subject's head or neck wherein the second active region is connected to the first active region through a flat and flexible elongate body so that the second active region is electrically connected to the second electrical connector. The method may also include adhesively securing the back side of the first active region to the underside of the wearable electrical stimulator.

For example, a lightweight and wearable transdermal electrical stimulation device for inducing a cognitive effect in a subject may include a primary unit and a secondary unit. The primary unit may include a power source, a controller, and a first transdermal electrode. The secondary unit may be electrically connected to the primary unit by a cable extending from the primary unit and may include a second transdermal electrode. One or both of the primary unit and the secondary unit may be configured to be worn on the subject's head or neck and the secondary unit may be configured to be independently positioned on the subject relative to the primary unit, so that the controller can drive stimulation between the first and second electrodes to induce a cognitive effect in the subject.

In general, the primary unit may include (or may be) a durable component that may be reused with different disposable components. The primary unit may include a controller to control stimulation across the electrodes of the apparatus, a lightweight power source (e.g., battery, capacitive power source, etc.), and an electrode or connector to an electrode. The controller may be configured to apply one or more pre-determined stimulation protocols when driving stimulation between the first and second electrodes to induce a cognitive effect. The secondary unit may correspond to a disposable portion, and may include one more (e.g., 2, 3, 4, or all) electrodes and/or the connector (cable, cord, wire, ribbon, etc.) between the second electrode and the primary unit. The primary and secondary units may be referred to as master and slave components/units. The primary and second units may be configured to couple together before being applied to the subject. For example, the secondary unit may be configured to be detachably coupled to the primary unit before applying the primary and secondary units to the subject.

In general, the primary unit may be configured to be adhesively attached to the subject's head or neck.

As mentioned, any of the variations described herein may be adapted to be lightweight and wearable. For example, the combined weight of a primary unit and secondary unit together may be less than about 8 ounces (e.g., less than about 6 ounces, less than about 5 ounces, less than about 4 ounces, less than about 3 ounces, less than about 2 ounces, less than about 1.5 ounces, less than about 1 ounce, less than about 0.5 ounces, less than about 0.25 ounces, etc.). Generally, an apparatus having an overall weight of less than about 3 ounces is particular helpful. Further, the device may be adapted for wearability by limiting the dimensions (height) of the device above the surface of the subject's skin. For example, the apparatus may have a maximum thickness of the primary unit (and/or the secondary unit) that is less than about 30 mm (e.g., less than about 25 mm, less than about 20 mm, less than about 15 mm, less than about 10 mm, less than 5 mm, etc.). The thickness (which may also refer to as height) of the device may refer to the maximum amount that the applicator extends from the skin when worn.

The apparatuses described herein may be configured as TES apparatus (transcranial electrical stimulator; however, it should be understood that in some variation the cognitive effect may arise from one or a combination of stimulation effects, including stimulation of nerves (e.g., cranial nerves) and/or brain cells. Any appropriate electrical stimulation may be applied by the apparatus to provoke the desired cognitive effect. For example, a controller may be configured to cause alternating current, direct current, or a combination of alternating and direct current between the first and second electrodes.

In general, the apparatus may be formed into an assembly in which the secondary unit, which includes the second electrode, is tethered by a cable making electrical communication with the primary unit and the primary and secondary units are engaged with each other to form the apparatus; before being applied to the subject, the secondary unit may be separated from the primary unit while remaining coupled via the cable to the primary unit, and independently applied to the head, neck, or shoulder of the subject. Both the primary and secondary unit may be positioned on the subject's head and/or neck.

The apparatus may include one or more indicators on the primary and/or secondary units to indicate function or control of the apparatus. For example, the apparatus may include a visual indicator on an outer surface of the primary unit. The apparatus may include an input control on an outer surface of the primary unit.

As mentioned, the first and second electrode may be configured to be disposable and replaceably detachably attached to the device. Thus, in some variations the primary unit includes a connector to a disposable (primary) electrode and is also configured to connect to the secondary electrode, e.g., through the cable. For example, the first electrode may be part of a replaceable cartridge configured to be releasably detachably coupled to the primary unit. The first electrode and the secondary unit may be part of a replaceable cartridge configured to be releasably detachably coupled to the primary unit.

Any of the variations described herein may be configured so that the controller regulates the applied energy (e.g., current) by adjusting the applied current based on a detected resistance/impedance between the electrodes. For example, the controller may be configured to adjust current across the first and second electrodes based on a detected impedance.

The primary unit further may comprise a wireless communications module in communication with the controller and configured to provide stimulation instructions to the controller. Thus, although the apparatus may operate independently (e.g., without a connection either remote or local) to a separate processor providing control/feedback, in some variations the apparatus may include a connection to a remote processor that provides control and/or feedback on operation of the device. For example, the remote processor may select and/or instruct the apparatus what parameters to apply to provide a particular cognitive effect, and/or to coordinate the application of the stimulation parameters.

As mentioned, the apparatus may be configured to apply any appropriate stimulation protocol to provoke the desired cognitive effect. For example, a device may be configured to apply pulsed electrical stimulation.

In general, the apparatuses described herein may be configured to be positioned on the head and/or neck of the subject in positions adapted to invoke a particular cognitive effect when stimulation is applied. For example, the second electrode may be configured to be positioned on a neck or head of a subject.

Also described herein are methods of operating such devices, including methods of inducing a cognitive effect in a subject. For example, a method of inducing a cognitive effect may include attaching a primary unit of a lightweight, wearable, and self-contained transdermal electrical stimulation device to a first location so that a first electrode of the primary unit contacts the subject's skin. The method may further comprise attaching a secondary unit comprising a second electrode to a second location on the subject, wherein the secondary unit is electrically connected to the primary unit by a cable. One or both of the first location and second location is on the subject's head or neck. The method may also include driving stimulation between the first and second electrodes to induce a cognitive effect in the subject, wherein a controller in the primary unit drives stimulation.

In any of the variations described herein, the method may also include separating the primary unit from the secondary unit before driving stimulation between the first and second electrodes. This separation may be performed after connecting any disposable elements to the reusable elements. Separation may involve removing the secondary unit from the primary unit so that the cable extends between the two; the cable may be contained within (e.g., between) the primary and secondary unit, and may extended to allow independent positioning of the primary and secondary units on the subject. For example, the secondary unit may be separated from the primary unit by unwinding the cable to increase the distance between the two units.

Either or both the primary and secondary units may be adhesively attached directly to the subject. For example, attaching the primary unit may comprise adhesively attaching the primary unit to the subject's head or neck at the first location. Attaching the secondary unit may comprise adhesively attaching the secondary unit to the subject. Attaching the secondary unit may comprise attaching the secondary unit to the subject's neck or head. The primary and secondary units may include a biocompatible adhesive; the adhesive may extend over the electrodes in the primary and secondary unit, or it may be separated from the electrodes. Adhesive over the electrodes may be a conductive adhesive.

In some variations, the methods may include selecting which stimulation parameter(s) to operate the apparatus when driving stimulation. The apparatus may include one or more controls on the device to allow selection of the driving stimulation (e.g., selection based on the desired cognitive effect(s), power levels, power on/off, etc.). In some variations the method includes manually selecting the stimulation parameters (e.g., by the user directly). In some variations, the method of operation may also or alternatively include wirelessly transmitting stimulation parameters (e.g., from a mobile communications device, etc.) to the controller in the primary unit.

Any appropriate stimulation parameters may be used, but effective stimulation parameters may include driving stimulation between the first and second electrodes to induce the cognitive effect in the subject may comprises supplying a maximum current of at least 2 mA during stimulation. Driving stimulation between the first and second electrodes to induce the cognitive effect in the subject may comprise supplying current at a frequency of about 400 Hz-20 kHz (e.g., between about 500 Hz-10 kHz, or specifically, between 650 Hz-10 kHz, or greater than 640 Hz).

In some variations of the methods of operating the devices described herein, the methods may include attaching a cartridge including the first electrode to the primary unit before attaching the primary unit to the subject's head or neck.

As mentioned above, any of the lightweight and wearable apparatuses described herein may be self-contained and configured to wirelessly receive controlling instructions from a remote site. For example, a lightweight and wearable transdermal electrical stimulation device for inducing a cognitive effect in a subject may include a primary unit and a secondary unit. The primary unit may include a power source, a wireless communications module, a controller configured to receive instructions from a remotely located processor via the wireless communications module, and a first transdermal electrode. The secondary unit may include a second transdermal electrode and is electrically connected to the primary unit by a cable extending from the primary unit. Either or both the primary unit and the secondary unit may be configured to be worn on the subject's head or neck, and the secondary unit is configured to be independently positioned at a second location on the subject relative to the primary unit so that the controller can drive stimulation between the first and second electrodes to induce a cognitive effect in the subject.

The secondary unit may be configured to be detachably coupled to the primary unit before driving stimulation between the first and second electrodes, and may be configured to be separated from the primary unit before being applied.

As mentioned above, any of the apparatuses described herein may be worn on the head and/or neck. For example, the primary unit may be adhesively attached to the subject's head or neck. In some variations the primary unit is secured to the subject by a strap (e.g., headband, etc.) or other item (e.g. wearable support structure) instead of or in addition to an adhesive attachment. For example, the primary unit may be clipped onto a set of glasses or worn over the subject's ear(s), etc.

As also mentioned above, any of the apparatuses described herein may include an indicator, such as a visual indicator on the apparatus (e.g., on the primary and/or secondary units). For example, the apparatus may include a visual indicator on an outer surface of the primary unit, such as an LED. The visual indicator may indicate communication status (e.g., receiving instructions, sending data, etc.), power status (on/off), stimulation protocol (e.g., target cognitive state, etc.), or the like.

Any of the apparatuses described herein may also include one or more manual inputs and/or controls. For example, a device may include an input control on an outer surface of the primary unit and/or secondary unit. The input may be a button, dial, switch, etc. For example, an input may be a button for controlling the power on/off state.

Any of the apparatuses described herein may include one or more inputs and/or controls to allow selection of the stimulation parameters. In general the stimulation parameters may be selected based on a predetermined menu of parameter values (e.g., selecting the stimulation protocol based on the desired cognitive effect, and/or pre-customized stimulation parameters for a particular user or class of users, etc.). For example, the apparatus may receive controlling stimulation instructions that control one or more of: current amplitude, current frequency, pulse width, pulse duration, pulse frequency, pulse waveform, burst duration, burst frequency, off-time, burst waveform, positive duty cycle, negative duty cycle, and on/off.

Also described herein are non-transitory computer-readable storage mediums storing a set of instructions capable of being executed by a remote processor (and particularly a smartphone or the like), that when executed by the smartphone causes the smartphone to allow a subject to select one or more (or a set) of control parameters for controlling the lightweight, wearable apparatuses described herein. The set of instructions may include confirming a communication link with one or more lightweight, wearable apparatuses, presenting a list and/or menu of pre-selected control values (e.g., for one or more of current amplitude, current frequency, pulse width, pulse duration, pulse frequency, pulse waveform, burst duration, burst frequency, off-time, burst waveform, positive duty cycle, negative duty cycle, and on/off, etc.), or for allowing modification of one or more of these control values separately. The set of instructions may also permit transmission of the control values to the apparatus or an index to select from a list of possible predetermined profiles of such control values in the apparatus. The set of instructions may also allow the subject to turn the device on/off.

The set of instructions may also include instructions and/or guidance for applying the device (e.g., both primary and secondary units) to the proper positions on the body. For example the set of instructions executable on the remote processor may include displaying one or more diagrams indicating where on the subject to position the first and second electrodes of the primary and secondary device components.

The lightweight, wearable apparatus may be configured for wirelessly communication with the remote processor by any appropriate wireless technique, including (but not limited to) electromagnetic (e.g., RF, UWB, etc.), ultrasound, or the like. For example, the wireless communications module of the lightweight, wearable apparatus may comprise a Bluetooth transmitter.

A lightweight, wearable and self-contained transdermal electrical stimulation device for inducing a cognitive effect in a subject may also or alternatively include a primary unit having a housing and a secondary unit electrically connected to the primary unit by a cable extending from the housing. The housing of the primary unit may at least partially enclose a power source; a wireless communications module; a current generator connected to the power source; a controller configured to receive stimulation instructions from a remotely located processor via the wireless communications module; and a replaceable cartridge including a first transdermal electrode. The secondary unit may include a second transdermal electrode. Either or both the primary unit and the secondary unit may be configured to be worn on the subject's head or neck and the secondary unit may be configured to be independently attached to a second location on the subject independently of the primary unit (though tethered to the primary unit) so that the controller controls the current generator to drive stimulation between the first and second electrodes based on stimulation instructions received from the remotely located processor to induce a cognitive effect in the subject.

A method of inducing a cognitive effect in a subject may include wireless communication control instructions to the apparatus from a remote processor. For example, a method of inducing a cognitive effect may include attaching a primary unit of a lightweight and wearable transdermal electrical stimulation device to a first location on the subject so that a first electrode of the primary unit contacts the subject's skin. The method may further comprise attaching a secondary unit comprising a second electrode to a second location on the subject, wherein the secondary unit is electrically connected to the primary unit by a cable. Either or both the first location and the second location may be on the subject's head or neck. The method may include wirelessly receiving stimulation information in the primary unit and driving stimulation between the first and second electrodes to induce a cognitive effect in the subject.

As mentioned, wirelessly receiving may include wirelessly receiving stimulation parameters from a remote processor, wherein the stimulation parameters include at least one of current amplitude, current frequency, pulse width, pulse duration, pulse frequency, pulse waveform, burst duration, burst frequency, off-time, and burst waveform, positive duty cycle, negative duty cycle, and on/off. In some variations the remote processor transmits an index value that corresponds to a choice from a menu of preset stimulation parameters in the apparatus. Transmitted control instructions may include both an index value and one or more modification of the stimulation parameters such as current amplitude, current frequency, pulse width, pulse duration, pulse frequency, pulse waveform, burst duration, burst frequency, off-time, and burst waveform, positive duty cycle, negative duty cycle, and on/off.

A method of inducing a cognitive effect in a subject may comprise adhesively securing a primary unit of a lightweight and wearable transdermal electrical stimulation device to a first location on the subject's head or neck so that a first electrode of the primary unit contacts the subject's skin. The method may also include attaching a secondary unit comprising a second electrode to a second location on the subject's head or neck, wherein the secondary unit is electrically connected to the primary unit by a cable. Stimulation control information may be wirelessly transmitted to the primary unit from a remote processor. The method may include applying the stimulation control information to drive stimulation between the first and second electrodes to induce a cognitive effect in the subject.

As mentioned, any of the apparatuses described herein may be configured so that they include a durable (reusable) portion and a disposable (e.g., limited-use, single-use, non-durable, etc.) component. In general, the electrodes and/or cable connecting the second electrode to the primary unit may be disposable, while the processor/controller is durable. The non-durable or disposable components may be formed as a cartridge that couples to the durable components. The disposable components may also be referred to as removable and/or replaceable components, as they may be swapped out between uses.

For example a lightweight and wearable transdermal electrical stimulation apparatus for inducing a cognitive effect in a subject is provided. The apparatus comprises a primary unit configured to be worn on the subject (including on the subject's head and/or neck) and including a power source, a controller and an electrode connector. The apparatus further comprises a disposable first electrode configured to detachably connect to the primary unit via the electrode connector. The apparatus comprises a disposable second electrode configured to detachably electrically connect to the controller via a cable extending from either the primary unit or the first electrode. Either the primary or secondary units or both the primary and secondary units are positioned on the subject's head and/or neck. The second electrode is configured to be independently positioned at a second location on the subject relative to the first electrode of the primary unit (although flexibly tethered to the primary unit by the cable) so that the controller can drive stimulation between the first electrode and the second electrode to induce a cognitive effect in the subject.

In another aspect, a method of inducing a cognitive effect in a subject is provided. The method comprises coupling a disposable first electrode and disposable second electrode to a reusable primary unit of a lightweight and wearable transdermal electrical stimulation apparatus, wherein the disposable first electrode is coupled to the primary unit via an electrode connector on the primary unit so that the first electrode is attached to the primary unit and in electrical communication with a controller in the primary unit, and wherein the second electrode is electrically connected to the controller via a cable. The method further comprises attaching the primary unit to a first location (e.g., on the subject's head or neck) so that the first electrode contacts the subject's skin. The method comprises independently attaching the second electrode to a second location on the subject (e.g., on the subject's head or neck) so that the second electrode contacts the subject's skin. The method comprises activating the controller to drive stimulation between the first and second electrodes to induce a cognitive effect in the subject.

Also described herein are methods and apparatuses for pairing and coordinating one or more non-invasive transdermal stimulation with an audiovisual (e.g., musical, video, etc.) composition. Any appropriate modality of non-invasive transdermal (and/or transcranial) stimulation may be used, particularly those that apply energy to one or more brain regions to induce a cognitive state by actively or passively stimulating and/or inhibiting activity (e.g., neuronal activity). Examples of such transdermal stimulation modalities include transdermal electrical stimulation (TES, TDCS, etc.), ultrasound (e.g., transcranial ultrasound stimulation), transcranial magnetic stimulation (TMS), and transcranial phototherapy (transcranial phototransduction, etc.), or combinations and variations thereof. Although the examples provided herein are focused on and exemplify transdermal electrical stimulation (TES) methods and apparatuses, the principles describe herein may be applied to any of these other energy modalities as well.

For example, embodiments of the present invention provide improved systems and methods for transdermal electrical stimulation (hereinafter "TES," and including transdermal electrical stimulation) and other modalities of noninvasive energy delivery to the brain in order to induce neuromodulation and overcome at least some of the deficiencies of prior systems and methods. The systems and methods described herein include systems for associating music, video, and/or other sensory experiences with neuromodulation. By appropriately pairing a neuromodulation stimulation regime with appropriate music, video, and/or other temporally structured sensory experiences, a more significant cognitive effect can be induced in a subject than by either neuromodulation or sensory experience (e.g. music) alone.

Embodiments of the present invention provide improved systems and methods for transdermal electrical stimulation to induce neuromodulation and overcome at least some of the deficiencies of prior systems and methods. The systems and methods described herein include systems for inducing cognitive effects using electrodes that are closely spaced on the face or low profile (small and hidden) on the mastoid behind the ear, unilaterally or bilaterally. The new form factors of TES neurostimulator systems (and electrode assemblies associated with a TES neurostimulator system) represent advances on the state of the art for wearable, portable, and, optionally, disposable systems for TES.

Described herein are methods of applying transdermal electrical stimulation (TES) to a subject to enhance a concurrent sensory experience. The sensory experience may be auditory (e.g., heard, including music, spoken word, etc.), visual (e.g., seen, including cinematic, animated, discrete images, etc.), audiovisual (movies, live performances, 3D or virtual reality, etc.), tactile (e.g., felt, including amusement rides, etc.). Changes in the sensory experience may be correlated with changes in the applied TES waveforms, as described herein. For example, a transitions in the music (e.g., changes in tempo, key, pitch, timbre, instrumentation, musical key, loudness, sharpness, changes to different musical pieces, etc.), may be correlated with a change in the applied TES waveform parameter (e.g., current amplitude, frequency, DC offset, percent duty cycle, percent charge imbalance, amplitude modulation (on/off, change in amplitude modulation frequency, envelope, etc.). The sensory experience (e.g., performance) may be prerecorded and may include markers to trigger changes in the TES waveform parameters, or the apparatus (e.g., TES applicator or a controller associated with one or more TES applicators) may analyze the performance to detect changes in the sensor experience and select the change in the TES waveform applied. The type of change in the TES waveform may correlate with the type of change in the sensory experience. For example, an increase in tempo, pitch, etc. may increase the intensity of the TES signal (current and/or frequency), particularly when applying waveforms using an "energy" configuration that enhances alertness, etc. Although musical performance are described, other sensory performance, such as audiovisual performances that include visual transitions (e.g., changes in lighting, rate of motion of object's being visualized, etc.) may also or alternatively be correlated with TES waveform parameters. Similarly, a tactile experience such an amusement park ride or VR experience may also include features (lighting, rate of motion, vibration, etc.) that may be correlated with TES waveform parameters.

For example, methods of applying transdermal electrical stimulation (TES) to a subject to enhance a concurrent sensory experience, by applying the TES to the subject (including but not limited to the subject's head or head and neck from two or more electrodes that are coupled to a neurostimulator) may include: applying an ensemble current waveform between the two or more electrodes, wherein the ensemble current waveform comprises a series of component waveforms that are sequentially applied, wherein each component waveform comprises a duration between about 100 milliseconds and about 600 seconds, a current amplitude, a frequency, a percent charge imbalance, and a percent duty cycle, and wherein each component waveform is different from a component waveform immediately before it and/or immediately after it in the series by one or more waveform descriptor; further wherein transitions between the component waveforms temporally correlates with transitions in the sensory experience.

The one or more waveform descriptor may be selected from the group consisting of: current amplitude, frequency, percent charge imbalance or percent duty cycle, capacitive discharge pulsing, amplitude modulation, etc.

The method may generally be remotely triggered (e.g., by a server or processor that is remote to the user but communicating with the TES applicator) or by the TES applicator being worn by the subject. The sensory experience may be prerecorded (e.g., music, video, etc.) and may include markers that are detected by the TES applicator and/or a remote server (processor) communicating with the TES applicator to trigger the change in one or more of the waveform descriptors mentioned. The markers may be generic (e.g., 'change to next sub-waveform in an ensemble waveform having one or more different waveform descriptors/characteristics) or specific (indicating which waveform characteristic/descriptor to change, such as current amplitude, frequency, etc.).

In general, these methods may include synchronizing the delivery of the sensory experience and the TES stimulation. In some variations the TES applicator and/or a remote server/processor may synchronize the two; in some variations the sensory experience (e.g., music, video, VR, etc.) is displayed to the user by the TES applicator or by a system integrating the TES applicator. For example, the method may include playing the sensory experience from the neurostimulator.

In general, the transitions between the component waveforms may temporally correlate with transitions in a musical element of the sensory experience. Thus a change in the TES waveform may be simultaneous with the transition in the sensory experience (including musical transitions), or within a few seconds or partial seconds (+/−0.1 sec, 0.2 sec, 0.3 sec, 0.4 sec, 0.5 sec, 1 sec, etc.). For example, the transition between the component waveforms may temporally correlates with transitions in one or more of: tempo, theme, genre, timbre, instrumentation, musical key, loudness, pitch level, and sharpness.

Applying the ensemble current waveform may comprise applying component waveforms that are biphasic, and may include applying a series of greater than 5 component waveforms (e.g., 5 immediacy consecutive waveforms having one or more different waveform properties). Applying the ensemble current waveform may comprise applying the series of component waveforms wherein a component waveform in the series differs from another component waveform immediately before and/or immediately after the component waveform in the series by two or more of: the current amplitude, the frequency, the percent charge imbalance, and the percent duty cycle. The TES waveform applied may transition to other waveform parameters (descriptors) at other times that are not correlated with transitions in the sensory experience and/or may only occur when correlated.

Applying the ensemble current waveform may comprise sequentially applying component waveforms in the series for their duration and, during the duration of each component waveform, ramping one or more of the current amplitude, the frequency, the percent charge imbalance, and the percent duty cycle from a previous current amplitude, frequency, percent charge imbalance, and percent duty cycle to the current amplitude, the frequency, the percent charge imbalance, and the percent duty cycle of the component waveform.

These methods may also include placing a first electrode of a portable TES applicator on the subject's skin on a temple or forehead region, and/or on a subject's temple/forehead region and on the back of the subject's neck and/or on a subject's temple/forehead region and behind the subject's ear(s). In general, the electrodes may be placed in any appropriate location on the subject ("user"). For example, placing a first electrode of a portable TES applicator on the subject's skin on a temple or forehead and placing a second electrode on the subject's skin on either the subject's mastoid region or on the subject's neck.

Applying an ensemble current waveform may comprise sequentially applying the series of component waveforms wherein the absolute value of the peak current amplitude of the component waveforms is between about 3 mA and 25 mA, wherein the frequency of the component waveforms is between about 250 Hz and 30 kHz, and/or wherein the duty cycle of the component waveforms is between about 20 and 80%. Applying an ensemble current waveform may comprises sequentially applying the series of component waveforms wherein the percent charge imbalance of component waveforms is between about 10% and 100%.

In general, a user may modify the intensity (e.g., to avoid pain and discomfort) at any time during the application of the TES. For example, a method may include modifying the ensemble waveform during application by a user intensity adjustment factor.

For example, a method of applying transdermal electrical stimulation (TES) to a subject to enhance a concurrent audio or audiovisual experience, by applying the TES to the subject's head or head and neck from two or more electrodes that are coupled to a neurostimulator, may include: synchronizing the audio or audiovisual experience with an ensemble waveform; applying the ensemble current waveform between the two or more electrodes, wherein the ensemble current waveform comprises a series of component waveforms that are sequentially applied, wherein each component waveform comprises a duration between about 100 milliseconds and about 600 seconds, a current amplitude, a frequency, a percent charge imbalance, and a percent duty cycle, and wherein each component waveform is different from a component waveform immediately before it and/or immediately after it in the series by one or more of the current amplitude, the frequency, the percent charge imbalance or the percent duty cycle; further wherein transitions between the component waveforms temporally correlates with transitions in the audio or audiovisual experience.

A method of applying transdermal electrical stimulation (TES) to a subject to enhance a concurrent musical performance, by applying the TES to the subject's head or head and neck from two or more electrodes that are coupled to a neurostimulator, may include: synchronizing the musical performance with an ensemble waveform; applying the ensemble current waveform between the two or more electrodes, wherein the ensemble current waveform comprises a series of component waveforms that are sequentially applied, wherein each component waveform comprises a duration between about 100 milliseconds and about 600 seconds, a current amplitude, a frequency, a percent charge imbalance, and a percent duty cycle, and wherein each component waveform is different from a component waveform immediately before it and/or immediately after it in the series by one or more of the current amplitude, the frequency, the percent charge imbalance or the percent duty cycle; further wherein transitions between the component waveforms temporally correlates with transitions in a musical element of the performance, wherein the musical element is one or more of: loudness, tempo, pitch level, sharpness, and key.

Also described herein are method of applying stimulation to evoke a cognitive effect (e.g., relaxation, energy) by applying TES to the subject's temple and a region in front of the subject's ear, and electrode apparatuses configured to apply TES in these locations.

For example, a method of applying transdermal electrical stimulation to a user to modulate the user's cognitive state using an electrode apparatus formed of a flat substrate extending in a plane having a first electrode portion and a second electrode portion, a first active region on a back of the substrate in the first electrode portion, and a second active region on the back of the substrate in the second electrode portion, wherein the first and second electrode portions are connected by a connecting region of the substrate that extends in a path that is 1.5 inches or longer, may include: adhesively securing the first active region of the electrode apparatus to the user's temple; bending the connecting region out of the plane; adhesively securing the second active region of the electrode apparatus to the user's cheek in front of the user's ear; and coupling a wearable electrical stimulator to a first and second connector extending proud from the first electrode portion so that the wearable electrical stimulator is worn on the user in the first location.

Although this electrode configuration and these TES applicator devices (including electrode pads/patches) may be used with the methods and apparatuses for enhancing a concurrent sensory experience, they may be used in other TES methods and with other TES applicator devices as well, and are not limited to this application.

Coupling the wearable electrical stimulator to the first and second connector extending proud from the first electrode portion may comprises snapping the wearable electrical stimulator onto the first and second connectors wherein the first and second connectors are separated from each other by a predetermined amount (e.g., between 0.5 and 1.5 inches, between 0.5 and 1.2 inches, between 0.5 and 1 inches, between 0.5 and 0.8 inches, between about 0.7 and 0.8 inches, etc.).

Coupling the wearable electrical stimulator to the first and second connector may comprise snapping the wearable electrical stimulator onto the first and second connectors. Adhesively securing the first active region may comprise attaching a hydrogel on the first active region against the user's head in the first location.

Coupling the wearable electrical stimulator may comprise connecting an underside of the wearable electrical stimulator to the first and second connectors to make an electrical contact with the wearable electrical stimulator and the first and second active regions.

Any of these methods may include applying TES waveforms to evoke a state of energy in the user.

Also described herein are methods of using this configuration. For example, a method of applying transdermal electrical stimulation to a user to modulate the user's cognitive state using an electrode apparatus formed of a flat substrate extending in a plane having a first electrode portion and a second electrode portion, a first active region on a back of the substrate in the first electrode portion, and a second active region on the back of the substrate in the second electrode portion, wherein the first and second electrode portions are connected by a connecting region of the substrate that extends in a path that is 1.5 inches or longer, may include: adhesively securing the first active region of the electrode apparatus to the user's cheek in front of the user's first ear; bending the connecting region out of the plane; adhesively securing the second active region of the electrode apparatus to the user's cheek in front of the user's second ear; and coupling a wearable electrical stimulator to a first and second connector extending proud from the first electrode portion so that the wearable electrical stimulator is worn on the user in the first location.

Coupling the wearable electrical stimulator to the first and second connector extending proud from the first electrode portion may comprise snapping the wearable electrical stimulator onto the first and second connectors wherein the first and second connectors are separated from each other by between a predetermined amount (e.g., between about 0.7 and 0.8 inches, etc.). Coupling the wearable electrical stimulator to the first and second connectors may comprise snapping the wearable electrical stimulator onto the first and second connectors.

Adhesively securing the first active region may comprise attaching a hydrogel on the first active region against the user's head in the first location. Coupling the wearable electrical stimulator may comprise connecting an underside of the wearable electrical stimulator to the first and second connectors to make an electrical contact with the wearable electrical stimulator and the first and second active regions. Any of these methods may be used to evoke a desired cognitive state, for example any of these methods may include applying TES waveforms to evoke a state of energy in the user.

Also described herein are neurostimulator apparatuses and methods of using them to modulate a subject's cognitive state.

In general, described herein are lightweight, wearable neurostimulator apparatuses that may be operated with an electrode assembly so that the neurostimulator apparatus may be comfortably and securely held to the user's body (e.g., head, neck, etc.) by attachment to the electrode assembly. These apparatuses may typically include one or more (e.g., two) connectors, such as mechanical and electrical connectors for releasably but securely connecting to an electrode assembly that is adapted to be worn on the user's body. The mechanical and electrical connectors may be arranged so that the device may cantilever from the electrical connector (which may therefore be referred to as a cantilevered electrode assembly) and therefore the subject's body, allowing the device to be worn by a variety of body shapes and/or sizes while still ensuring conformability of an electrode apparatus. The electrical contacts are configured to connect with electrodes. Any of these apparatuses may also include control circuitry, which may include wireless communication circuitry, current generator circuitry, one or more timers, memory, a power supply (which may be adjustable and/or rechargeable), and safety circuits. The circuitry may be programmable, dedicated, or some combination of programmable (re-programmable) and dedicated. In some variations the circuitry includes capacitive discharge circuitry that is configured to controllably apply current to one or more electrical contacts (and therefore the electrodes they are connected to) to prevent or eliminate capacitive charge. Additional circuitry may also include circuitry for regulating the power supply to prevent heat/overheating, and to prevent saturation of the power supply while meeting the power demands of an applied target neurostimulation waveform (or ensemble waveform).

The disclosure that follows describes a variety of features and embodiments, which may be described separately, including in separate sections, or jointly. One of skill in the art should understand any of the features or elements described herein may be combined with any of the other features or elements described herein. Further, although the majority of the examples described herein are specific to wearable neurostimulators, it should be understood that these features and elements may be used with any other type of stimulator, including, e.g., TENS stimulators generally, electrical stimulators generally, muscle stimulators, nerve stimulators, implantable stimulators, magnetic stimulators, ultrasound stimulators, and the like.

Also described herein are stimulators (e.g., neurostimulators) that may be worn by a user in conjunction with an electrode assembly. For example, described herein are stimulators configured to securely fit a variety of different subjects' temple regions. In some variations, these apparatuses may be configured as neurostimulators that are specifically adapted to be worn in a particular location on a subject's temple. Thus any of the variations described herein may include a user-facing surface that has a flat, twisted shape specifically configured to advantageously conform to a subject's temple.

For example, a wearable transdermal neurostimulator for inducing a cognitive effect that is configured to be comfortably worn on a subject's temple may include: a housing enclosing control circuitry, a current source comprising a power supply; a first, user-facing, surface on the housing, wherein the first surface is twisted along a twist axis wherein the first surface twists between 2 degrees and 45 degrees per 3 cm along a length of the axis of twist; and an electrode on the first surface or a connector on the first surface that is configured to connect to an electrode; wherein the neurostimulator weighs less than 5 ounces.

The electrode on the first surface or connector on the first surface may comprise one or more connectors at an edge region of the first surface, wherein the one or more connectors are configured to make an electrical and mechanical connection with a mating surface of an electrode apparatus comprising one or more electrodes.

In general, the apparatuses described herein may be lightweight. For example, the neurostimulator may weigh less than 7 ounces (e.g., less than 7 ounces, 6 ounces, 5 ounces, 4 ounces, 3 ounces, 2 ounces).

The neurostimulator housing may be less than 30 mm thick, and may have a non-uniform thickness. For example, the neurostimulator housing may comprise an outward-facing surface opposite from the first surface, and wherein the thickness of the housing between the outward-facing surface and first surface is more than 15% greater (more than 20%, more than 25%, more than 30%, more than 35%, etc.) at one end of the neurostimulator than at an opposite end of the neurostimulator.

These apparatuses may generally connect to one or more electrode apparatuses (e.g., an adhesive electrode) through one or more connectors on the apparatus that may connect (mechanically and/or electrically) with one or more complimentary connectors on the electrode assembly. The connectors on the apparatus may be on the body of the apparatus and may comprise a pair of mechanical and electrical connectors. The one or more connectors may comprise a pair of sockets configured to receive posts, snaps, projections, etc., from the electrode assembly, or the electrode assembly may have sockets configured to couple to connectors on/projecting proud of the apparatus which may be snaps, posts, projections, etc.

As will be described in greater detail below, apparatuses having two connectors (e.g., sockets, etc.) for connecting to an electrode apparatus may be particularly useful. In particular, described herein are apparatuses having a pair of connectors positioned at a predetermined location relative to each other (and off-center on a user-facing surface of the apparatus). The positioning and/or spacing may be optimized for securing the apparatus to the electrode assembly, maintaining a secure attachment, while allowing the apparatus to fit to a variety of body shapes and sizes, and in some cases, allowing the apparatus to cantilever relative to the electrode assembly worn against the user's body (and therefore to cantilever relative to the user's body). For example, an apparatus may include a pair of connectors separated from each other by between about 0.5 inches and 1.0 inches (more optimally, between 0.6 and 0.9, between 0.7 and 0.8, etc.). This separation may be center-to-center or nearest-edge to nearest-edge.

In general, any of the housings described herein may be approximately triangular in shape. Approximately triangular shapes include trianguloid shapes, which may have three edges (which may be curved or straight) and may generally have three corner regions, which may be sharp or curved (e.g., rounded edges).

The housing may include a lower user-facing surface (which may typically but not necessarily include the one or more connectors). The housing may also include an upper surface, approximately opposite (or generally opposite) from the lower surface. The distance between the upper and lower surfaces may be the thickness of the apparatus. In general, the thickness may be constant or may vary across the apparatus.

As mentioned, the lower (user-facing) surface may be concave and/or twisted along a twist axis wherein the first surface twists between 2 degrees and 45 degrees per 3 cm along a length of the axis of twist (e.g., between 1 degree and 45 degrees, between 2 degrees and 40 degrees, between any of a lower boundary selected from: 2°, 3°, 4°, 5°, 6°, 7°, 8°, 9°, 10° and any of an upper boundary selected from: 10°, 15°, 20°, 25°, 30°, 35°, 40°, 45°, where the lower boundary is always less than the upper boundary). This may also be expressed as between about 0.07 degrees/1 nm and about 1.5 degrees/mm).

Functionally, any of the neurostimulator apparatuses described herein may be configured to deliver a transdermal electrical stimulus. In particular, the apparatuses may include control circuitry including a current source that may include a power supply and a waveform generator, configured to deliver a biphasic current of up to 35 mA between about 750 Hz and 30 kHz that is asymmetric. The neurostimulator current source may generally comprise a high-voltage power supply configured to supply a voltage between about 10 and 100 V. This power supply may be adjustable so that the available voltage (voltage source) provided by the power supply may be adjusted by voltage control circuitry which may receive feedback from the electrical connectors connected to the electrodes and/or directly from the electrodes.

Also described herein are methods of modulating a subject's cognitive state with a wearable transdermal neurostimulator (including any of the neurostimulators described herein). For example, a neurostimulator having a housing comprising a first concave user-facing surface, a second outward-facing surface opposite the user-facing surface and thickness there between, wherein the housing is bounded between the first and second surfaces by a superior edge, an auricular edge and an orbital edge, and wherein the thickness of a region of the housing near an intersection of the auricular edge and the orbital edge is less than 2 cm thick, may be used to modulate a subject's cognitive state. A method of modulating a cognitive state using such an apparatus may include: attaching the neurostimulator to the subject's temple region with the orbital edge extending facing the subject's eye orbit region and the auricular edge facing the subject's ear and the superior edge facing a top of the subject's head (and/or temple region).

For example, a method of modulating a subject's cognitive state with a wearable transdermal neurostimulator, wherein the neurostimulator has a housing comprising a first concave user-facing surface that is approximately triangular, a second outward-facing surface opposite the user-facing surface and thickness there between, wherein the housing is bounded between the first and second surfaces by a superior edge, an auricular edge and an orbital edge, and wherein the thickness of a region of the housing near an intersection of the auricular edge and the orbital edge is at least 15% thinner than the thickness of a region of the housing near an intersection of the superior edge and the orbital edge, may include: attaching the neurostimulator to the subject's temple region with the orbital edge extending facing the subject's eye orbit region and the auricular edge facing the subject's ear and the superior edge facing a top of the subject's head.

In any of these variations, the method may include attaching an electrode assembly to the subject's temple and coupling the user-facing surface of the neurostimulator to an outward-facing surface of the electrode assembly. The method may include adhesively attaching an electrode assembly to the subject's temple and coupling the user-facing surface of the neurostimulator to an outward-facing surface of the electrode assembly by at least one electrical and mechanical attachment.

Any of these methods may include attaching a first electrode portion of an electrode assembly to the subject's temple and a second electrode portion of an electrode assembly to a second region on the subject's head or neck and coupling the user-facing surface of the neurostimulator to an outward-facing surface opposite from the first electrode portion of the electrode assembly so that the neurostimulator is in electrical contact with both the first and second electrode portions of the electrode assembly.

Any of these methods may include wearing glasses or other jewelry or garments over at least a portion of the neurostimulator.

Also described herein are neurostimulators that include capacitive discharge during some or all of the delivered pulses forming the waveforms (e.g., ensemble waveforms). For example, a wearable transdermal neurostimulator for inducing a cognitive in a subject, the neurostimulator may include: a housing enclosing a controller, a wireless communication sub-system connected to the controller, and a high-voltage power supply; a first, user-facing, surface on the housing; a first connector configured to connect with a first electrode an a second connector configured to connect with a second electrode; and wherein the controller comprises a waveform generator configured to deliver a biphasic electrical signal between the first electrode and the second electrode, and a capacitive discharge circuit, wherein the controller is configured to trigger the capacitive discharge circuit to discharge a capacitance on the first electrode and the second electrode during the delivery of the biphasic electrical stimulation signal. In any of the apparatuses and methods described herein, the discharge circuit may be configured so that a capacitive discharge current may be applied in a single direction (e.g., to one or the other electrodes), separately or individually, including without applying a capacitive discharge current in both directions (e.g., to both electrodes, anode and cathode).

Examples of capacitive discharge circuits are provided herein, but in some variations may include a double H-Bridge circuit. The neurostimulator controller may include a switch configured to turn off the current source when the capacitive discharge circuit is triggered. The neurostimulator capacitive discharge circuit may be configured to discharge a capacitance for a duration between 0 and 100 microseconds. The neurostimulator controller may include an amplifier configured to measure a voltage delivered to the first electrode and the second electrode during an electrical stimulation pulse.

The neurostimulator controller may be configured to adjust the voltage provided by the high-voltage power supply to the waveform generator based on a historical demand of the applied voltage estimated from a plurality of earlier cycles.

Also described are neurostimulators that are configured to detect (using detection circuitry or capacitive detection circuitry) the connection to an electrode assembly having a capacitive element between the electrodes (e.g., between the connectors to the electrodes); the capacitive element may act as a high-frequency (high pass) filter, which is only detectable at frequencies above a threshold (e.g., above 50 kHz) but otherwise acts as an open circuit. These neurostimulators may also detect a resonance of the capacitive element which may be used to both confirm connection and to identify the type or class of electrode assembly attached. For example, a wearable transdermal neurostimulator for inducing a cognitive effect in a subject, wherein the neurostimulator is configured to couple with an electrode assembly worn by the subject, may include: a housing enclosing a controller, a wireless communication sub-system connected to the controller, and a high-voltage power supply; a first, user-facing, surface on the housing; a first connector configured to connect with a first electrode and a second connector configured to connect with a second electrode; and wherein the controller comprises a waveform generator configured to deliver a biphasic electrical signal between the first electrode and the second electrode, and a capacitive sensing circuit, wherein the controller is configured to detect a capacitance signal between the first and second electrodes indicating that the electrodes have been connected, and further configured to detect a characteristic resonance.

Any of the neurostimulator apparatuses described herein may be configured to cantilever, e.g., to be securely connected at one region of the user-facing surface, but free to float relative to the user and/or electrode apparatus attached/attachable to the subject at an opposite end. This may generally be achieved by positioning two (or potentially more) mechanical and/or electrical connector(s) between the adhesive electrode apparatus and the neurostimulator apparatus off-center, with a predetermined spacing between the two. For example, a transdermal neurostimulator that is connectable to a subject via attachment with an electrode apparatus may include: a housing enclosing a controller and a current source, wherein the housing comprises a concave user-facing surface and a top surface opposite the user-facing surface; a first edge region and a second edge region between the user-facing concave surface and the top surface, wherein the first edge region is thinner than the second edge region; a first and second connector on the user-facing concave surface and off-center relative to the user-facing concave surface, wherein the first and second connectors are each configured to make an electrical and mechanical connection with a connector mate on an electrode apparatus, further wherein the first and second connectors are separated by between 0.7 and 0.8 inches.

A wearable transdermal neurostimulator that is connectable to a subject via a cantilevered attachment with an electrode apparatus may include: a housing enclosing control circuitry and a current source; a user-facing first surface on the housing, wherein the first surface is concave and twisted; and one or more connectors on the first surface and off-center relative to the first surface, wherein the one or more connectors is configured to make an electrical and mechanical connection with a connector mate on a mating surface of the electrode apparatus; wherein the neurostimulator weighs less than 5 ounces.

Any of the stimulation devices described herein (e.g., neurostimulators) may include two connectors (e.g., the one or more connectors comprise a first and a second connector). As used herein, a connector may be an electrical and mechanical connector that may both make electrical contact and may mechanically secure the stimulation device to the electrode apparatus (e.g., an electrode assembly). A connector may be a male (protruding) connector that inserts into a female (receiver) connector, a female connector (receiver) that receives a male (protruding) connector, a grasping (clamping) connector that mates with a graspable connector (knob, etc.), or any other type of connector. For example, connectors may be snaps, clasps, plugs, magnets, or the like. A stimulation device may include a pair of (or more) connectors that are both the same type (e.g., snaps or snap receivers) or different types (e.g., snaps and snap receivers). For example, in a variation having a first and second connectors on the neurostimulator apparatus (e.g., on a user-facing surface of the neurostimulator apparatus), the connectors may comprise snap receivers (e.g., configured to receive a male snap post).

Any of the neurostimulator apparatuses described herein may be configured as cantilevered attachments, so that the connectors on the apparatus (e.g., first and second connectors) secure an edge region of the user-facing concave surface to the electrode apparatus (electrode assembly) while permitting an end of the user-facing concave surface opposite from the edge region to move relative to the electrode apparatus. The separation between the connectors on the neurostimulator apparatuses (e.g., with between about 0.7 and 0.8 inches between the two) is particularly well suited to this configuration, and especially when the apparatus is less than 5 inches in diameter and/or less than 0.5 inches thick, on average), although this arrangement may work with neurostimulator apparatuses having different dimensions as well.

For example, in some variations, the first and second connectors are separated by between about 0.7 and 0.75 inches, or between about 0.72 and about 0.74 inches, etc.

In some variations, an adaptor unit may couple to the first and second connectors and provide a second set of electrode connectors with a larger separation between them than the inter-connector distance on the neurostimulator unit (e.g. greater than 0.8 inches, greater than 1 inch, etc.).

As mentioned, in general these devices are lightweight, and in particular, the apparatus may weigh less than 5 ounces. The weight may be non-uniformly distributed within the apparatus; in particular in neurostimulator apparatuses configured to cantilever off of an electrode apparatus, the weight (and/or thickness) of the neurostimulator apparatus may be greater at or near the end of the neurostimulator apparatus above the connectors, so that the lighter end (which may also be thinner) is opposite this end/edge region. Counterintuitively, in some variations this may be reversed, so that the thicker and/or heavier end/edge region of the neurostimulator apparatus is positioned opposite from the region of electrical and mechanical attachment by the connectors; this configuration may be unexpectedly advantageous in allowing the device to conform to the subject's head while remaining securely attached to the electrode apparatus. This configuration may also allow separation between the connectors (e.g., snap receivers) and internal electrical circuitry and/or power storage (e.g., battery) components.

Any of the devices described herein may be generally fairly thin. For example, the housing of any of the neurostimulator apparatuses described herein may be less than 30 mm thick (e.g., less than 20 mm thick, less than 15 mm thick, less than 14 mm thick, less than 13 mm thick, less than 12 mm thick, less than 11 mm thick, less than 10 mm thick, less than 9 mm thick, less than 8 mm thick, less than 7 mm thick, less than 6 mm thick, less than 5 mm thick, etc.). This may refer to average or absolute (maximum) thickness of the housing. In general, these devices may have a uniform or non-uniform thickness, as mentioned above. As mentioned above, in any of these variations, the housing of any of these wearable electrical stimulators may have a top surface opposite from the first (e.g., user-facing or electrode assembly-facing) surface that is more than 10% (or 15%, or 20%, or 25% or 30%, or 35%, or 40% or 45% or 50%, or 60%, or 70%, or 80%, or 90%, or 100%, or 110%, etc.) greater at one end region of the neurostimulator than at an opposite end of the neurostimulator.

In some variations, the housing of the neurostimulator apparatuses is trianguloid. As mentioned above, this may refer to the roughly three-sided shape (looking down on the neurostimulator apparatuses housing) of the housing when the device is attached to an electrode assembly. The sides may be curved or straight, as may the corners of the trianguloid outer perimeter.

The user-facing surface may be flat, or in some variations it may be twisted and/or concave. As described above, the user-facing surface may be concave and twisted along a twist axis wherein the first surface twists between 2 degrees and 45 degrees per 3 cm along a length of the twist axis.

Any of the neurostimulator apparatuses described herein may be adapted for use to deliver TES through the attached (or in some variations, integrated) electrode apparatuses to modify a subject's cognitive state. For example, any of these devices may be specifically configured to provide stimulation through the connectors to a pair of electrodes to apply electrical stimulation as described in U.S. patent application Ser. No. 14/639,015, titled "TRANSDERMAL ELECTRICAL STIMULATION DEVICES FOR MODIFYING OR INDUCING COGNITIVE STATE," filed Mar. 4, 2015 (which claims priority to U.S. Pat. No. 9,002,458). In some variations, the neurostimulator includes a controller within the housing that is configured to deliver pulsed, asymmetric, biphasic current greater than 3 mA between about 750 Hz and 30 kHz between the connectors so that this energy may be applied through connected (or integrated) electrodes.

In particular, the neurostimulator apparatuses described herein may include hardware and/or software and/or firmware (e.g., circuitry, programmable processors, memory, etc.) that enable the relatively high-current, high-frequency stimulation that is particularly effective for modifying a cognitive state when applied in the proper location on a user's head and/or neck. Thus, the housing may enclose (partially or completely) one or more processors, circuit boards, circuitry (including any of the circuits or sub-systems described herein), comparators, amplifiers (e.g., op-amps, etc.), capacitors, resistors, transformers, inductive coils, LEDs, batteries, or the like. In particular, any of the neurostimulator apparatuses described herein may include a current source (e.g., current supply circuitry) and/or may include a high-voltage power supply configured to supply a voltage between about 10 and 100 V, which may be particularly helpful for achieving the target stimulation parameters for modulating a cognitive state by TES.

Any of the neurostimulator apparatuses described herein may also be generally configured for wireless communication, e.g., with a remote or local device providing instructions (including waveforms to be delivered from the neurostimulator apparatuses), and thus any of these apparatuses may include a wireless sub-system (e.g., Bluetooth chipset and antenna, etc.) within the housing and connected to the controller.

Also described herein are methods of modulating a subject's cognitive state with a wearable transdermal neurostimulator. For example in some variations the method may include using any of the neurostimulator apparatuses described herein. For example, a method may include: making an electrical and mechanical connection between a first and second connector on a first surface of a housing of the wearable transdermal neurostimulator and a first and second connector mate on an electrode apparatus, wherein the first and second connectors are separated by between 0.7 and 0.8 inches and wherein the housing comprises the first surface and a second surface opposite the first surface, and a first edge region and a second edge region between the first surface and the second surface, wherein the first edge region is thinner than the second edge region; securing the electrode apparatus to the subject's temple or forehead; and applying electrical stimulation from the electrode apparatus by delivering pulsed, asymmetric, biphasic current. Applying electrical stimulation may include delivering pulsed, asymmetric, biphasic current of greater than 3 mA that is between about 750 Hz and 30 kHz.

Another example of a method of modulating a subject's cognitive state with a wearable transdermal neurostimulator includes: making an electrical and mechanical connection between one or more connectors on a first surface of the wearable transdermal neurostimulator and one or more connector mates on an electrode apparatus, wherein the first surface is concave and twisted along a twist axis so that the first surface twists between 2 degrees and 45 degrees per 3 cm along a length of the twist axis and wherein the one or more connectors are located off-center relative to a first surface; attaching the electrode apparatus to the subject's temple or forehead; and applying electrical stimulation from the electrode apparatus by delivering pulsed, asymmetric, biphasic current.

In general, making electrical and mechanical connection comprises snapping the first connector mate into the first connector and the second connector mate into the second connector. Making the electrical and mechanical connection may include connecting the first and second connector on the first surface of the housing to the first and second connector mates on the electrode apparatus; the first surface may be concave.

Securing the electrode apparatus to the subject's temple or forehead may include adhesively securing the electrode apparatus to the subject's temple or forehead.

Any of these methods may also include making the electrical and mechanical connection between the electrode apparatus and the neurostimulator before attaching the neurostimulator to the subject's temple or forehead. For example, the method may include connecting a portion of the electrode apparatus to the subject's neck or mastoid region, and another portion (to which the neuromodulation apparatus may connect) to the subject's temple and/or forehead region.

As mentioned above, the apparatuses described herein may be worn with garments, jewelry and/or prosthetics, including, e.g., glasses, hearing aids, hats, etc., typically without interfering with the comfort, position, and function of these garments, jewelry and/or prosthetics. For example, a method of applying, using or wearing the apparatuses described herein may include wearing glasses over at least a portion of the neurostimulator.

Application of the apparatuses described herein may include initially determining where to apply the apparatus (e.g., the combined neuromodulation apparatus and the electrode assembly, which may be first connected together using the connectors as described herein). For example, any of these methods may include 'testing' the position of the apparatus and electrode assembly on the head before adhesively securing the device onto the head and/or neck. For example, a method of modulating a subject's cognitive state with a wearable transdermal neurostimulator device may include: positioning a concave surface of the neurostimulator device over a subject's forehead or temple region in a first position; removing a backing layer from an adhesive on the concave surface of the neurostimulator device; and repositioning the concave surface of the neurostimulator device in approximately the first position to adhesively secure the neurostimulator device to the subject's forehead or temple region.

Any of the methods described herein may include applying electrical stimulation from the electrode apparatus by delivering pulsed, asymmetric, biphasic current of between about 3 mA to 25 mA that is between about 750 Hz and 30 kHz.

In general, any of these methods may include removing the neurostimulator device from the user's head in a 'testing' position before removing the backing layer, e.g. to expose the adhesive so that it can be applied in the desired location. A mirror or an application (e.g., smartphone, tablet, etc. application/software) that can display a real-time image of the user via a front-facing camera may be used when applying the apparatus to confirm the location of the apparatus. For example, the method may include displaying a mirror image of the subject's head and/or comprising capturing an image of the subject's head after positioning the concave surface of the neurostimulator device and displaying the image while repositioning the neurostimulator device. In some variations an actual mirror may be used to display the user's image; in some variations a front-facing camera may be used, as described above.

A neurostimulator apparatus may be connected to (and may include a step of connecting) an electrode assembly having an adhesive covered by the backing layer. In some variations the electrode assembly and neurostimulator apparatus are coupled together before adhesively applying the device to the user. In some variations, the electrode assembly may be attached to the user's body first partially or completely, before coupling the neurostimulator apparatus to the electrode assembly.

In methods in which the neurostimulator apparatus and electrode apparatus are applied on the users head and/or neck, positioning the concave surface may include shifting the neurostimulator device to identify a conformable position of the shape to the subject's forehead or temple region (e.g., before adhesively securing the two to the user's head). Positioning the concave surface may include shifting the neurostimulator device relative to one or more of the subject's: eyebrow, eye, hairline, or midline of forehead.

As mentioned above, any of the apparatuses described herein may include a high-voltage power supply; these power supplies may be adjustable by the apparatus during operation, so that the available voltage supplied by the power supply (supply voltage, $V_s$) is controlled and variable. As mentioned above, this adjustment may allow the apparatus to prevent overheating and conserve power, as well as prevent the circuitry (e.g., the current source) from saturating during an electrical stimulation pulse. This adjustment may be dynamic. For example, also described herein are transdermal neurostimulator apparatuses (e.g., devices) that include: a housing enclosing a high-voltage power supply having a maximum voltage of greater than 10V and further configured to provide a supply voltage of less than the maximum voltage, wherein the supply voltage is adjustable; a first connector configured to electrically connect with a first electrode and a second connector configured to electrically connect with a second electrode; and a controller within the housing, the controller comprising: a waveform generator configured to deliver a pulsed, asymmetric, biphasic electrical signal between the first and the second connectors, wherein the waveform generator receives the supply voltage from the high-voltage power supply, and wherein the controller is configured to compare a difference between the supply voltage and an applied voltage between the first and second connectors to a target voltage offset, and further wherein the controller is configured to adjust the supply voltage based on the comparison.

In any of these variations of transdermal neurostimulator apparatuses described herein, the apparatus may include: a housing enclosing a high-voltage power supply having maximum voltage of greater than 10V and further configured to provide a supply voltage of less than the maximum voltage, wherein the supply voltage is adjustable; a first connector configured to electrically connect with a first electrode and a second connector configured to electrically connect with a second electrode; and a controller within the housing, the controller comprising: a waveform generator configured to deliver a pulsed, asymmetric, biphasic electrical signal between the first and the second connectors, wherein the waveform generator receives the supply voltage from the high-voltage power supply, and a sensing circuit configured to detect an applied voltage between the first and second connectors, wherein the controller is configured to compare a difference between the supply voltage and the applied voltage with a target voltage offset, and to adjust the supply voltage by decreasing the supply voltage if the difference between the supply voltage and the applied voltage is greater than the target voltage offset and to adjust the supply voltage by increasing the supply voltage if the difference between the supply voltage and the applied voltage is less than the target voltage offset.

In any of these examples, the high-voltage power supply may be configured to provide supply voltages between a generally high-voltage range (e.g., greater than 20 V, between 10V and 120V, between 20V and 100V, etc.).

The target voltage offset may generally be a threshold value (e.g., 2V, 3V, 4V, 5V, 6V, 7V, etc.) or a voltage range (e.g., between about 2V-10V, between about 3V-9V, between about 4V-8V, between about 5V-7V, between about 4V-10V, between any one of about 1V, 2V, 3V, 4V, 5V, 6V, etc., and about 8V, 9V, 10V, 11V, 12V, etc.).

The adjustment of the voltage may be regulated by a regulator and/or controller (e.g., control/regulator circuitry or sub-system) that may be generally configured to decrease the supply voltage if the difference between the supply voltage and the applied voltage is above the target voltage offset and to increase the supply voltage if the difference between the supply voltage and the applied voltage is below the target voltage offset. The controller may be configured to adjust the supply voltage as a function of the difference between the supply voltage and the applied voltage.

In general, the apparatus may include a sensing circuit. The sensing circuit may include an amplifier connected to one or both of the first and second connectors (e.g., to measure the voltage difference between the two, $V_{applied}$, which may be applied to the user).

The controller may be configured to determine if the device is in an overheating state based on an applied current and the difference between the supply voltage and the applied voltage. In some variations, the controller is configured to determine if the apparatus is in a saturation state (e.g., if the currently supply sub-system/circuitry is saturated). In general, the regulator circuitry or sub-system may also include a temperature sensor (e.g. thermistor) for determining the overheating condition.

Also described herein are methods of operating a neurostimulation device to dynamically adjust the available voltage supplied by a power supply. For example, a method of regulating the power of a wearable transdermal neurostimulator device may include: delivering a biphasic electrical signal between a first electrode and a second electrode of the transdermal neurostimulator device, wherein the transdermal neurostimulator device comprises a high-voltage power supply providing an adjustable supply voltage and a waveform generator receiving the supply voltage; detecting an applied voltage between the first electrode and the second electrode; and comparing a difference between the supply voltage and the applied voltage to a target voltage offset, and adjusting the supply voltage by: increasing the supply voltage if the difference between the supply voltage and the applied voltage is below the target voltage offset, or decreasing the supply voltage if the difference between the supply voltage and the applied voltage is above the target voltage offset.

Detecting the applied voltage may include detecting the applied voltage at a first connector connected to the first electrode and a second connector connected to the second electrode. In general, detecting the applied voltage may occur during one or more pulses of a TES waveform and may avoid measurements of applied voltage between pulses (open circuit condition) or during periods of a TES waveform when a capacitive discharge occurs. Measuring during a pulsing period of a TES waveform may include detecting a gating or other digital or analog signal generated by a controller of the neurostimulation device that identifies active pulse periods distinct from open circuit and capacitive discharge periods.

The target voltage offset may be a range of voltages (e.g., between about 2 V and 10 V, between about 3 V and 9 V, between about 4 V and about 8 V, between 6 V and 7 V, etc.).

Any of the neurostimulator apparatuses described herein may be configured as cantilevered devices for use with an electrode assembly, as described above. For example, a neurostimulator apparatus may be a wearable transdermal neurostimulator that is connectable to a subject with an electrode apparatus and may include: a housing enclosing a controller and a current source; a concave user-facing surface on the housing; and a first and second connector on the user-facing concave surface and off-center relative to the user-facing concave surface, wherein the first and second connectors are each configured to make an electrical and mechanical connection with a connector mate on an electrode apparatus, further wherein the first and second connectors are separated by between 0.7 and 0.8 inches.

The first and second connectors may secure a first edge region of the user-facing surface to the electrode apparatus while permitting a second edge region of the user-facing surface that is opposite from the first edge region to float relative to the electrode apparatus. As discussed above, the first and second connectors may comprise snap receivers. The first and second connectors may be separated by any appropriate length, typically between 0.5 and 1 inch, but particularly 0.6 and 0.9 inches and more particularly 0.7 and 0.8 inches (e.g., between about 0.7 and 0.75 inches). As described above, such cantilevered apparatuses may be lightweight (e.g., may weigh less than 5 ounces), and may be relatively thin (e.g., the housing may be less than 30 mm thick, less than 20 mm thick, less than 15 mm thick, less than 11 mm thick, etc.).

The housing may include a top surface opposite from the user-facing surface, and the thickness of the housing between the outward-facing surface and first surface may be more than 15% greater at one end of the neurostimulator than at an opposite end of the neurostimulator. The user-facing surface may be concave and/or twisted. For example, the user-facing surface may be concave and twisted along a twist axis wherein the user-facing surface twists between 2 degrees and 45 degrees per 3 cm along a length of the twist axis.

The controller may be configured to deliver pulsed, asymmetric, biphasic current greater than 3 mA between about 750 Hz and 30 kHz.

A wearable transdermal neurostimulator that is connectable to a subject with an electrode apparatus may include: a housing enclosing a controller and a current source; a user-facing first surface on the housing, wherein the first surface is concave; and a first and second connector on the first surface and off-center relative to the first surface, wherein the first and second connectors are configured to make an electrical and mechanical connection with a connector mate on a mating surface of the electrode apparatus when the electrode apparatus is attached to a subject's head with the mating surface facing away from the subject's head so that the first and second connectors secure one side of the first surface to the mating surface of the electrode apparatus while permitting an opposite side of the first surface to float relative to the mating surface. The first and second connectors are separated from each other by between about 0.7 inches and 0.8 inches.

In any of the apparatuses described herein, the first and second connectors may comprise a pair of sockets configured to receive snaps from the electrode assembly. The neurostimulator may weigh less than 5 ounces. The housing may include an outward-facing surface opposite from the first surface, wherein the thickness of the housing between the outward-facing surface and first surface may be more than 15% greater at one end of the neurostimulator than at an opposite end of the neurostimulator. The first surface may be concave and twisted along a twist axis wherein the first surface twists between 2 degrees and 45 degrees per 3 cm along a length of the twist axis.

The controller may be configured to deliver pulsed, asymmetric, biphasic current greater than 3 mA between about 750 Hz and 30 kHz.

Also described herein are methods of attaching a neurostimulation apparatus to a user so that one end is cantilevered relative to an electrode assembly (and thus the user's body), such as methods of modulating a subject's cognitive state with a wearable transdermal neurostimulator. Any of these methods may include: making an electrical and mechanical connection between a first and second connector located off-center on a first surface of a housing of the wearable transdermal neurostimulator with a first and second connector mate on an electrode apparatus, wherein the first and second connectors are separated from each other on the first surface by between 0.7 and 0.8 inches; securing the electrode apparatus to the subject's temple or forehead; and applying electrical stimulation from the electrode apparatus by delivering an asymmetric, pulsed, biphasic current.

For example, applying electrical stimulation may include delivering pulsed, asymmetric, biphasic current of greater than 3 mA that is between about 750 Hz and 30 kHz. Making the electrical and mechanical connection may comprise snapping the first connector of the electrode apparatus into the first connector mate of the neurostimulator and the second connector of the electrode apparatus into the second connector mate of the neurostimulator.

Securing the electrode apparatus to the subject's temple or forehead may comprise adhesively securing the electrode apparatus to the subject's temple and/or forehead so that an end of the neurostimulator is cantilevered relative to the electrode apparatus, and/or adhesively securing a first region of the electrode apparatus to the subject's temple or forehead, and adhesively securing a second portion of the electrode apparatus to another portion of the subject's head or neck. In some variations, securing the electrode apparatus to the subject's temple or forehead comprises adhesively securing a first portion of the electrode apparatus adjacent to the first surface of the neurostimulator to the subject's temple or forehead and a second portion of the neurostimulator to another portion of the subject's neck or mastoid region.

A method of modulating a subject's cognitive state with a wearable transdermal neurostimulator may include: making an electrical and mechanical connection between a first surface of the wearable transdermal neurostimulator and an electrode apparatus by coupling a first and second connector located off-center on the first surface with a first and second connector mate on the electrode apparatus, so that the electrical and mechanical connection holds a first side region of the first surface to the electrode apparatus while permitting an opposite side region of the first surface to float relative to the electrode apparatus; attaching the electrode apparatus to the subject's temple or forehead; and applying electrical stimulation from the electrode apparatus by delivering pulsed, asymmetric, biphasic current of between about 3 mA to 25 mA that is between about 750 Hz and 30 kHz.

Making the electrical and mechanical connection may include snapping the first connector of the electrode apparatus into the first connector mate of the neurostimulator and the second connector of the electrode apparatus into the second connector mate of the neurostimulator. Making the electrical and mechanical connection may comprise making the electrical and mechanical connection between the first and second connectors on the first surface, wherein the first and second connectors are separated from each other on the first surface by between 0.7 and 0.8 inches, and the first and second connector mates on the electrode apparatus are separated from each other by between 0.7 and 0.8 inches, to provide a connection between a first side region of the neurostimulator and a first region of the electrode apparatus while allowing a second side region of the neurostimulator to float relative to a second region of the electrode apparatus.

Attaching the electrode apparatus to the subject's temple or forehead may include adhesively securing a first region of the electrode apparatus to the subject's temple or forehead, and adhesively securing a second portion of the electrode apparatus to another portion of the subject's head or neck. In some variations, attaching the electrode apparatus to the subject's temple or forehead comprises adhesively securing a first region of the electrode apparatus to the subject's temple or forehead and adhesively securing a second portion of the electrode apparatus to another portion of the subject's neck or mastoid region Any of the electrical stimulation (e.g., neurostimulator apparatuses, including systems and devices) described herein may be configured to controllably and reliably apply a current that is directed to oppose the capacitive charge build-up that may otherwise form on the electrodes, particularly when stimulating in the manner as described herein. This capacitive discharge signal may be included as part of the waveform(s) used by the apparatuses described herein to modulate a user's cognitive state. In general, the capacitive discharge signal is controlled, and opposes the charge build-up on the electrodes. The apparatus may include circuitry (capacitive discharge circuitry) included in the housing.

For example, a transdermal neurostimulator apparatus may include: a housing having a first surface; a first connector and a second connector, wherein the first connector is configured to electrically connect with a first electrode and the second connector is configured to electrically connect with a second electrode; and a controller within the housing, the controller comprising: a waveform generator configured to deliver a pulsed, asymmetric, biphasic current between the first and second connectors, and a capacitive discharge circuit triggered by the controller and connected to one or both of the first and second connectors and configured to deliver a gradual capacitive discharging current pulse during a portion of a cycle of the biphasic electrical stimulation signal to either or both the first electrode and the second electrode. The capacitive discharge circuit may include a double H-Bridge circuit configured to generate the gradual capacitive discharging pulse.

Gradual (in the context of the gradual discharging pulse) may generally include any period of time that is greater than 1 microsecond ($\mu s$) (e.g., greater than 1 $\mu s$, greater than 2 $\mu s$, greater than 5 $\mu s$, greater than 10 $\mu s$, greater than 15 $\mu s$, greater than 20 $\mu s$, greater than 30 $\mu s$, greater than 40 $\mu s$, greater than 50 $\mu s$, greater than 100 $\mu s$, greater than 150 $\mu s$, greater than 200 $\mu s$, greater than 300 $\mu s$, greater than 400 $\mu s$, greater than 500 $\mu s$, etc.). More specifically, the capacitive discharge pulse is not instantaneous, and is not the result of shorting ("short circuiting") one or both electrodes, but is instead the application of a current so that capacitive charge on the electrodes connected to the apparatus is opposed and reduced or removed. For example, in some variations, the maximum current of capacitive discharge (e.g., 10 s of mA, generally in the 50 mA or greater range) is either on or off during a portion of a waveform used to modulate the user's cognitive state.

In general, the controller may be configured to trigger the capacitive discharge circuit multiple times within each cycle of the pulsed, asymmetric, biphasic electrical stimulation signal. The capacitive discharge circuit may be configured to generate the gradual capacitive discharging pulse so that it lasts between about 1 microsecond and 1 ms. The controller may be further configured to discharge capacitance built up on the first electrode and the second electrode at different time points of an electrical stimulation waveform, wherein the direction of capacitive discharge (i.e. capacitance on which electrode is discharged) may be determined by history of stimulation pulses (i.e. their cumulative history of charge imbalance since a previous capacitive discharge) or may be determined by the neurostimulator controller enabling capacitive discharge in one direction (i.e. from first electrode) but not in the other direction (i.e. from the second electrode).

The controller may be configured to turn off the current source when the capacitive discharge circuit is triggered.

As mentioned above, any of the apparatuses described herein may include wireless communication sub-systems within the housing and connected to the controller.

In any of the electrical stimulator (e.g., neurostimulator) apparatuses described herein, the controller may be configured to trigger the capacitive discharge circuit to deliver the gradual capacitive discharging pulse at a start or an end of a positive-going portion of the biphasic electrical signal. The controller may be configured to activate the capacitive discharge circuit to deliver the gradual capacitive discharging pulse at a start or an end of a negative-going portion of the biphasic electrical signal. The controller may be configured to activate the capacitive discharge circuit at a phase offset from a positive-going or negative-going portion of the biphasic electrical signal (i.e. not at the start or end of a positive-going or negative-going pulse).

For example, a transdermal neurostimulator apparatus may include: a housing enclosing a current source; a first surface on the housing; a first connector and a second connector, wherein the first connector is configured to electrically connect with a first electrode of an electrode apparatus and the second connector is configured to electrically connect with a second electrode; and a controller within the housing, the controller comprising: a waveform generator configured to deliver a pulsed, asymmetric, biphasic current between the first and second connectors, and a capacitive discharge circuit triggered by the controller and connected to one or both of the first and second connectors and configured to deliver a gradual capacitive discharging current pulse during a portion of a cycle of the biphasic electrical stimulation signal, the capacitive discharging current pulse delivering either or both: a first charge to counter a first capacitive charge on the first electrode, and a second charge to counter a second capacitive charge on the second electrode. The countering of capacitive charge on the electrode(s) by the capacitive discharge (and the capacitive discharge circuit) may be partial or complete. For example, the applied capacitive discharge current may not completely eliminate the capacitive charge on the electrode or electrodes. Thus, as used herein "countering" the capacitive charge on the electrode(s) does not require completely eliminating the charge.

As mentioned, the capacitive discharge circuit may include any appropriate circuitry for applying a current to reduce or eliminate any capacitive charge on the electrode(s). For example, a capacitive discharge circuit may include a double H-Bridge circuit configured to generate the gradual capacitive discharging pulse.

The capacitive discharge (e.g., the application of the capacitive discharge current) may be triggered at any point during the application of a waveform. The triggering of the capacitive discharge may be controlled by the controller. For example, the apparatus may include a controller that is configured to trigger the capacitive discharge circuit multiple times within each cycle of the pulsed, asymmetric, biphasic electrical stimulation signal. The controller may be configured to trigger the capacitive discharge circuit to deliver the gradual capacitive discharging pulse at a start or an end of a positive-going portion of the biphasic electrical signal. The controller may be configured to activate the capacitive discharge circuit to deliver the gradual capacitive discharging pulse at a start or an end of a negative-going portion of the biphasic electrical signal.

The capacitive discharge signal (pulse) may be of any duration, but is typically between a few microseconds and a few hundred microseconds (though it could be longer if desired). For example, the capacitive discharge circuit may be configured to generate the gradual capacitive discharging pulse so that it lasts between about 1 microsecond and 1 ms. In general, the duration of a capacitive discharge signal (pulse) may be controlled by limiting or defining the maximum discharge current.

Any of the apparatuses (e.g., devices or methods) described herein, including those with a capacitive discharge circuit, may include electrodes coupled or coupleable to the connectors. For example, the apparatus may include a first electrode connected to the first connector and a second electrode connected to the second connector.

Also described herein are methods of modulating a subject's cognitive state with a transdermal neurostimulator that may include applying a capacitive discharging current pulse during the electrical stimulation, which may allow the use of relatively stronger stimulation (e.g., higher intensity current) than would otherwise be possible. For example, a method of modulating a subject's cognitive state with a transdermal neurostimulator may include: delivering a pulsed, asymmetric, biphasic current between a pair of electrodes of a transdermal neurostimulator attached to subject, wherein the neurostimulator comprises a first connector configured to electrically connect with a first electrode of the pair of electrodes and a second connector configured to electrically connect with a second electrode of the pair of electrodes, and a housing enclosing a controller having a waveform generator and a capacitive discharge circuit; and applying a capacitive discharging current pulse during a portion of a cycle of the biphasic electrical stimulation signal, the capacitive discharging current pulse delivering either or both: a first charge that counters a first capacitive charge on the first electrode, and a second charge that counters a second capacitive charge on the second electrode.

In any of the methods described herein, the method may include delivering a pulsed, asymmetric, biphasic current comprising delivering a pulsed, asymmetric, biphasic current between the pair of electrodes wherein the first electrode is attached to the subject's temple or forehead. For example, delivering a pulsed, asymmetric, biphasic current may include delivering a pulsed, asymmetric, biphasic current between the pair of electrodes wherein the first electrode is attached to the subject's temple or forehead and the second electrode is attached to the subject's neck or mastoid region. Delivering the pulsed, asymmetric biphasic current may comprise delivering a pulsed, asymmetric, biphasic current of between about 3 mA to 25 mA that is between about 750 Hz and 30 kHz.

In general, in any of the apparatuses and methods described herein, the electrodes (and particularly the second electrode) may be configured for placement in any appropriate region of the body, and are not limited to the mastoid and neck regions described in these examples. Other locations include other face regions (e.g., central forehead, etc.), scalp regions, the body below the neck, etc.

As mentioned above, applying a capacitive discharging current pulse may include a controller triggering the capacitive discharging current pulse during a cycle of the pulsed, asymmetric, biphasic current. Applying the capacitive discharging current pulse may include activating the capacitive discharge circuit to deliver the capacitive discharging current pulse before or after a positive-going pulse within the cycle of the pulsed, asymmetric, biphasic current. Applying the capacitive discharging current pulse may comprise activating the capacitive discharge circuit to deliver the capacitive discharging current pulse before or after a negative-going pulse within the cycle of the pulsed, asymmetric, biphasic current. In some variations, applying the capacitive discharging current pulse comprises activating the capacitive discharge circuit to deliver the capacitive discharging current pulse multiple times during one or more cycles of the pulsed, asymmetric, biphasic current.

For example, a method of modulating a subject's cognitive state with a transdermal neurostimulator may include: delivering a pulsed, asymmetric, biphasic current of between about 3 mA to 25 mA that is between about 750 Hz and 30 kHz between a pair of electrodes of a transdermal neurostimulator attached to subject's head, neck, or head and neck, wherein the neurostimulator comprises a first connector configured to electrically connect with a first electrode of the pair of electrodes and a second connector configured to electrically connect with a second electrode of the pair of electrodes, and a housing enclosing a controller having a waveform generator and a capacitive discharge circuit; and applying a capacitive discharging current pulse during a portion of a cycle of the biphasic electrical stimulation signal, the capacitive discharging current pulse delivering either or both: a first charge that counters a first capacitive charge on the first electrode, and a second charge that counters a second capacitive charge on the second electrode.

Also described herein are methods and apparatuses for delivering neurostimulation using ensemble waveforms. In general, an ensemble waveform typically includes a series or ordered set of waveform parameters, where the set of waveform parameters may specify peak current amplitude (also referred to as peak current intensity, and which in general may refer to the peak positive-going current intensity and/or the peak negative-going current intensity), frequency, duty cycle, percent charge imbalance, and optionally, capacitive discharge state. Each set may also include a time specifying the duration that these waveform parameters are valid, and in some variations, a ramping value indicating the value that the parameter is ramped over and, optionally, the pattern of ramping (i.e., linear, step-wise linear, exponential, etc.). The set of these waveform parameters, duration, and ramping values may together define a stimulation protocol having a plurality of different waveform parameters that are arranged sequentially. For example, an ensemble waveform may include a series of 3 or more (e.g., 4 or more, 5 or more, 6 or more, 7 or more, 8 or more, 9 or more, 10 or more, etc.) component waveforms, wherein component waveforms are typically biphasic and each has a duration and a predefined set of waveform parameters including a frequency, an intensity, a duty cycle and a percent charge imbalance, wherein at least one of the waveform parameters of each component waveform is different from the waveform parameters of a component waveform preceding it, following it, or preceding and following it in the series. Each component waveform may also include a ramping time or ramping indicator, indicating that any waveform parameter that changes from a preceding component waveform parameter is to be ramped to the new value over the duration of the component waveform (or over the duration of the ramping time in some variations). Functionally, a waveform ensemble may be created to evoke a particular cognitive effect, such as relaxation, calmness, energy, etc. A waveform ensemble may also be created to be comfortable and effective with a particular neurostimulator device and electrodes. Examples of waveform ensembles are described herein.

In general, also described herein are methods of modifying a subject's cognitive state by transdermal electrical stimulation (TES) using an ensemble waveform. For example, the methods described herein may be methods of modifying a subject's cognitive state by TES of an ensemble waveform comprising a series of (e.g., five or more) component waveforms, wherein each component waveform has a duration of between about 100 ms and 10 min, and wherein each component waveform has a predetermined ramping time between 0 sec and the duration of the component waveform and a predetermined set of waveform properties comprising an intensity, a frequency, a duty cycle, and a percent charge imbalance, and wherein each component waveform except a first component waveform differs from a component waveform that immediately precedes it in the series by one or more of the ramping time or waveform properties. Any of these methods may include delivering a current between a pair of electrodes configured to be placed on the subject's head or head and neck, wherein the delivered current is based on the ensemble waveform.

A method of modulating a subject's cognitive state by transdermal electrical stimulation (TES) may include: delivering a current based on an ensemble waveform between a pair of electrodes on the subject's head or head and neck, wherein the ensemble waveform comprises a series of 5 or more component waveforms, wherein each component waveform may be biphasic and each has a duration and a predefined set of waveform parameters including a frequency, an intensity, a duty cycle, and a percent charge imbalance, wherein at least one of the waveform parameters of each component waveform is different from the waveform parameters of a component waveform preceding it, following it, or preceding and following it in the series. In some variations, some of the component waveforms may be unipolar, rather than biphasic (e.g., may include very brief unipolar pulses, or even periods of direct current (non-pulsed) stimulation). However in general the component waveforms described herein are biphasic.

Methods of modulating a subject's cognitive state by transdermal electrical stimulation (TES) based on an ensemble waveform may generally include sequentially delivering the linked string of component waveforms forming the ensemble waveform. For example, an ensemble waveform may comprise a series of 5 or more component waveforms, wherein each component waveform is biphasic and has a duration and a predefined set of waveform parameters including a frequency, an intensity, a duty cycle and a percent charge imbalance, wherein at least one of the waveform parameters of each component waveform is different from the waveform parameters of a component waveform preceding it, following it, or preceding and following it in the series. For example, a method of modulating a subject's cognitive state by transdermal electrical stimulation (TES) based on an ensemble waveform may include: delivering a current with delivered current waveform parameters comprising a frequency, an intensity, a duty cycle, and a percent charge imbalance, wherein delivering comprises: during a first time period that is equal to the duration of the first component waveform, setting the delivered current waveform parameters to the first waveform parameters, wherein one or more of the waveform parameters of the delivered current waveform parameters are scalable by a user adjustment; and during a set of subsequent and sequential time periods that are equal to the subsequent and sequential durations of the series of component waveforms, sequentially adjusting the delivered current waveform parameters to the waveform parameters of each component waveform of the series of component waveforms during each time period in the set of time periods corresponding to the duration of the component waveform, wherein one or more of the delivered current waveform parameters are scaled by a user adjustment.

As described herein an ensemble waveform may include three or more component waveforms (e.g., four or more, five or more, six or more, seven or more, eight or more, nine or more, etc.). Five or more component waveforms may be used, for example, in instances in which there are a minimum of component waveforms for ramping up at beginning of the neurostimulation, ramping down at end of the neurostimulation; and at least two transitions within the main waveform, such as a either a quick change in intensity, frequency etc., and then back to the previous value, or a shift between three waveform parameter sets.

As used herein the term ramping may refer to the transition between a previous predetermined set of waveform properties (including transitioning from or to no waveform properties or zero-value properties at the start and end of a neurostimulation, respectively), and a new predetermined set of waveform properties that occurs over time (ramping time). In some variations only a single property from the set of waveform properties is ramped during a component waveform (e.g., one of: current amplitude/intensity, frequency, duty cycle, percent charge imbalance). In some variations, ramping may transition between two or more properties (e.g., two or more of: current amplitude/intensity, frequency, duty cycle, percent charge imbalance). Ramping may be linear (e.g., constant change in the waveform property or properties being changed over time), or there may be a ramping profile, including smooth (e.g., exponential, etc.) or discrete (e.g., step-wise linear, etc.), or other more complex patterns that may include a stochastic (i.e., random, not pre-determined) feature, as well as a particular ramping time over which the ramping profile is applied. For variations in which the ramping time is zero, no ramping may occur, and instead the value may be stepped to the new value in the waveform parameters being applied for that period of time, although the transition to the new value may not be fully instantaneous, depending on the transitioning capabilities of the devices (e.g., the clock period, circuit capacitance, etc.). For example, for a ramping time of 0 sec, the change in waveform properties happens as soon as possible using the device, e.g., immediately (or in a brief period of time limited, for example, by the communication in the system and/or speed of processor on the neurostimulator device).

In general, sequential waveform components may differ from a preceding or following waveform by one or more property values of the component waveform, but may not necessarily differ from all previous waveform components that are not adjacent to it in the sequence forming the ensemble waveform (i.e. some waveform component sets may be repeated as non-sequential elements of an ensemble waveform).

Although the methods and apparatuses described herein are generally directed to methods and apparatuses for delivery to a subject's head or head and neck, any of the methods and apparatuses described herein may also be useful for other regions of the body. For example, the methods and apparatuses may be used with other electrode locations, including electrode locations that are only on the body below the neck (e.g., arms, legs, torso, etc.). In particular, the ensemble waveforms described herein may generally be useful when electrically stimulating regions of the body other than the head and neck. In addition the ensemble waveforms described herein for neurostimulation to change cognitive states may be used for other electrical stimulation methods (such as TENS, etc.).

In general, the methods and systems described herein may be used in a method or apparatus in which the user may self-adjust the perceived intensity of the applied waveform. As used herein perceived intensity refers to the perceived experience evoked by the applied waveform, including the cognitive effect (e.g., a state of calmness, a state of increased energy, etc.) and/or the physical effects of stimulation that may be localized to the region at and/or around the electrode contact site (e.g., tingling, stinging, burning, shocking, prickling, itching, etc.). A user may adjust the perceived intensity by adjusting a control (dial, knob, slider, button, etc.) that increases or decreases one or more of the waveform parameters (frequency, peak current, percent charge imbalance, duty cycle) either directly or indirectly. The control may adjust a percentage between, e.g., 0 and 100% or any sub-range thereof, of the applied waveform parameters. The adjustment may adjust multiple waveform parameters using a relationship between different waveform parameters. As one non-limiting example, increasing the perceived intensity may increase the current amplitude (e.g., from 5 mA to 18 mA), while simultaneously increasing the frequency (e.g., from 7 kHz to 15 kHz). Thus, the user-selected modification of the perceived intensity may adjust one or more of the waveform parameters by applying a scaling formula. In some variations, the scaling may be based on the range, e.g., adjusting one or more parameters (or differently scaling them) over different ranges of the perceived intensity adjustment. For example, the current amplitude when adjusting the perceived intensity to be between 0% and 25% of the peak or target waveform parameter values, adjusting the frequency when adjusting between 25% and 50% of the peak or target waveform parameter values, adjusting the duty cycle when adjusting between 50% and 75% of the peak or target waveform parameter values, and adjusting the current amplitude and frequency when adjusting between 75% and 100% of the peak or target waveform parameter values.

In general, in systems and methods in which the user is permitted to adjust the perceived intensity (which may result in a multiplier/percent/modifier of the applied waveform parameters), as the ensemble waveform is being applied and transitioning from one component waveform to the next, the same user adjustment to the perceived intensity may be applied to the new parameters. For example, if the user adjustment to the perceived intensity is 50% of the applied perceived intensity during a first period (e.g., when applying one or more composite waveforms), the same 50% adjustment (e.g., to one or more of: current amplitude, frequency, duty cycle, percent charge imbalance) will be made to the next composite waveform, until and unless the user again adjusts the perceived intensity. For example, a user adjustment during a preceding component waveform time period may automatically be applied to the waveform parameters (frequency, peak current amplitude, or frequency and peak current amplitude, etc.) of subsequent time periods. In some variations the system or device may be configured to initially set the value of the adjustment to perceived intensity as 50% (e.g., half of the maximum perceived intensity set by the waveform parameters of the ensemble waveform). In other variations, the system or device may be configured to initially set the value of perceived intensity to a custom value for a particular user based on their control of perceived intensity during previous TES sessions.

Any of the methods and apparatuses described herein, e.g., ensemble waveforms, may also be used with systems and methods that do not permit the user to adjust the perceived intensity.

In particular, the methods describe herein may be useful for delivering neurostimulation to modify a subject's cognitive state by applying electrodes in predetermined locations effective for inducing a perception of enhanced energy or a perception of increased calmness. For example, any of these methods may include placing a first electrode of a portable TES applicator on the subject's skin on a temple and/or forehead and a second electrode of a portable TES applicator on a second region (e.g., for calm, at the subject's neck and, for energy, behind the subject's ear over the mastoid region), e.g., placing a first electrode of a portable TES applicator on the subject's skin on a temple and/or forehead and placing a second electrode on the subject's skin on either the subject's mastoid region or on the subject's neck.

In general, each component waveform of a waveform ensemble may have a duration of between about 100 ms and 10 min. The component waveforms may include a ramping (or ramp) time of the values of the waveform parameters defining the component waveform (current amplitude, frequency, duty cycle, percent charge imbalance). In some variation, the ramp time is a ramp register, which may be 0 (if not ramped) or 1 if ramped (e.g., linearly to step-wise linearly) over the entire duration of the waveform. For example, the ramping time may be either 0 seconds or the duration of the component waveform. In other examples, a component waveform may maintain static values for each waveform parameter and thus not include any ramping. In any of the methods and apparatuses described herein, the waveform parameters may include start and stop values for each class of waveform parameter (e.g., current amplitude, frequency, duty cycle, percent charge imbalance, etc.) where, if the start and stop values are different, a system may ramp between them using a predefined ramping parameter.

In some variations, the set of waveform parameters (or waveform properties) may generally comprises a peak intensity of between about 5 mA and 25 mA, a frequency between about 500 Hz and 30 kHz (e.g., having a lower bound of greater than 550, 600, 650, 700, 750, etc. Hz), a duty cycle of between about 20 and 80%, and a percent charge imbalance of between about 10% and 100%.

As mentioned, in any of these variations, the method (or an apparatus configured to perform or apply the method) may include receiving a user adjustment to the delivered current (e.g., adjusting the perceived intensity). For example, the method may include receiving a user adjustment to the delivered current, and delivering the current may include adjusting the frequency, intensity, duty cycle, percent charge imbalance, or more than one of these parameters based on the user adjustment.

The ensemble current waveforms (e.g., ensemble waveforms), methods of applying them to treat a user, and methods of controlling neurostimulator devices described herein may be used for virtually any type of stimulation, but are particularly helpful in preventing or reducing habituation which may otherwise occur with TES neurostimulation/neuromodulation, as will be described in greater detail below.

For example, a method of modifying a subject's cognitive state by transdermal electrical stimulation (TES) to a subject's head or head and neck from two or more electrodes that are coupled to a neurostimulator may include: applying an ensemble current waveform between the two or more electrodes, wherein the ensemble current waveform comprises a series of component waveforms that are sequentially applied, wherein each component waveform comprises a duration (e.g., between about 100 milliseconds and about 600 seconds, between about 100 milliseconds and about 300 seconds, between about 100 milliseconds and about 150 seconds, or any range between a lower value of about: 100, 125, 150, 175, 200, 225, 250, 275, 300, 350, 400, 450, 500, 1000, 1500, 2000, 2500, etc. msec, and an upper value of about: 600, 450, 300, 250, 200, 150, 100, 75, 50, 25, 20, 15, 14, 13, 12, 11, 10, 9, 8, 7, 6, 5 etc. seconds), a current amplitude, a frequency, a percent charge imbalance, and a percent duty cycle; further wherein each component waveform in the series differs from a component waveform immediately before it and/or immediately after it in the series by one or more of: the current amplitude, the frequency, the percent charge imbalance, and the percent duty cycle, and during the application of each component waveform, the neurostimulator applies current at the current amplitude, the frequency, the percent charge imbalance, and the percent duty cycle.

A method of modifying a subject's cognitive state by transdermal electrical stimulation (TES) may include applying TES to a subject's head or head and neck from two or more electrodes that are coupled to a neurostimulator. Such methods may include: attaching the first electrode to the user's temple and/or forehead region; attaching the second electrode to a second location on the user's head and/or neck; applying an ensemble current waveform between the two or more electrodes, wherein the ensemble current waveform comprises a series of component waveforms that are sequentially applied, wherein each component waveform comprises a duration between about 100 milliseconds and about 600 seconds, a current amplitude between about 3 mA and 25 mA, a frequency between about 700 Hz and 30 kHz, a percent charge imbalance between about 10% and 100%, and a percent duty cycle between about 20 and 80%; further wherein each component waveform in the series differs from a component waveform immediately before it and/or immediately after it in the series by one or more of: the current amplitude, the frequency, the percent charge imbalance, and the percent duty cycle, and during the application of each component waveform, the neurostimulator applies current at the current amplitude, the frequency, the percent charge imbalance, and the percent duty cycle.

Applying the ensemble current waveform may include applying component waveforms that are biphasic. For example, applying the ensemble current waveform may comprise applying a series of greater than 5 component waveforms. Applying the ensemble current waveform may comprise applying the series of component waveforms wherein a component waveform in the series differs from another component waveform immediately before and/or immediately after the component waveform in the series by two or more of: the current amplitude, the frequency, the percent charge imbalance, and the percent duty cycle. Applying the ensemble current waveform may comprise sequentially applying component waveforms in the series for their duration and, during the duration of each component waveform, ramping one or more of the current amplitude, the frequency, the percent charge imbalance, and the percent duty cycle from a previous current amplitude, frequency, percent charge imbalance, and percent duty cycle to the current amplitude, the frequency, the percent charge imbalance, and the percent duty cycle of the component waveform.

Any of the methods described herein may include placing a first electrode of a portable TES applicator on the subject's skin on a temple or forehead, for example, and placing a second electrode on the subject's skin on either the subject's mastoid region or on the subject's neck.

Applying an ensemble current waveform may include sequentially applying the series of component waveforms wherein the absolute value of the peak current amplitude of the component waveforms is between about 3 mA and 30 mA (e.g., between about 4 mA and 30 mA, between about 3 mA and 25 mA, between about 5 mA and 30 mA, etc., including any range between a lower limit of about 2, 3, 4, 5, 6, 7, etc. mA and an upper range of about 15, 20, 22, 23, 24, 25, 26, 27, 28, 29, 30, 31, 32, 33, 34, 35, etc. mA). Applying an ensemble current waveform may comprise sequentially applying the series of component waveforms wherein the frequency of the component waveforms is between about 700 Hz and 30 kHz (e.g., between about 550 Hz and about 50 kHz, between about 600 Hz and about 40 kHz, between about 650 Hz and about 35 kHz, etc., including any range between a lower limit of about 500, 550, 575, 600, 625, 650, 675, 700, 725, 750, 775, 800, 825, 850, 875, 900, etc. Hz, and an upper limit of about 10 kHz, 15 kHz, 20 kHz, 25 kHz, 30 kHz, 35 kHz, 40 kHz, 45 kHz, 50 kHz, etc.). Applying an ensemble current waveform may include sequentially applying the series of component waveforms wherein the duty cycle of the component waveforms is between about 20 and 80% (e.g., any range between a lower limit of about 20, 25, 30, 35, 40, 45, 50, etc., percent, and an upper limit of about 50, 55, 60, 65, 70, 75, 80, 85, etc., percent, where the lower limit is always less than the upper limit). Applying an ensemble current waveform may include sequentially applying the series of component waveforms wherein the percent charge imbalance of component waveforms is between about 10% and 100% (or any sub-range between a lower limit of about 5, 10, 15, 20, 25, 30, 35, 40, 45, 50, etc., percent, and an upper limit of about 50, 55, 60, 65, 70, 75, 80, 85, 90, 95, etc., percent, where the lower limit is always less than the upper limit, and the upper limit may be 100%, in which case the pulsed signal is all positive-going or all negative going, as described below).

In any of the variations described herein, applying an ensemble current waveform may comprise modifying the ensemble waveform during application by a user intensity adjustment factor. For example, a user (operating a control device) may manually, and dynamically, adjust the perceived intensity by moving a control to adjust the applied energy; the output of the control may be transmitted to the neurostimulator and used to adjust the intensity of the actual applied signal, by adjusting (e.g., scaling) one or more of peak current, percent duty cycle, and/or frequency. For example, any of the methods described herein may include receiving a user intensity adjustment factor in the neurostimulator (i.e. via a user interface such as a touchscreen or button) and adjusting the ensemble waveform delivered by the user intensity adjustment factor; any of the methods described herein may also include receiving a user intensity adjustment factor in the neurostimulator and adjusting the ensemble waveform delivered by the user intensity adjustment factor by scaling one or more of the frequency, duty cycle, and intensity of the applied ensemble current.

Any of the methods described herein may be performed by a device (e.g., a dedicated device) that includes one or more structures to perform the recited methods. For example, a transdermal electrical stimulation (TES) applicator apparatus for modifying a subject's cognitive state, may include: a body; a first connector configured to connect to a first electrode; a second connector configured to connect to a second electrode; and a TES controller at least partially within the body configured to apply an ensemble current waveform between the two electrode connectors, wherein the ensemble current waveform comprises a series of component waveforms that are sequentially applied, wherein each ensemble waveform comprises a duration between about 100 milliseconds and about 600 seconds, a current amplitude, a frequency, a percent charge imbalance, and a percent duty cycle; further wherein each component waveform in the series differs from a component waveform immediately before it and/or immediately after it in the series by one or more of: the current amplitude, the frequency, the percent charge imbalance, and the percent duty cycle, and during the application of each component waveform, the neurostimulator applies current at the current amplitude, the frequency, the percent charge imbalance, and the percent duty cycle.

In any of these variations, the TES controller may be configured to apply an ensemble current waveform comprising biphasic pulses. In any variation of these controllers, the TES controller may be configured to apply the series, wherein the series comprises 5 or more (e.g., more than 4, 5, 6, 7, 8, 9, 10, 11, 12, 13, 14, 15, 16, 17, 18, 19, 20, 25, 30, 35, 40, 45, 50, etc.) ensemble current waveforms.

In any of the variations described herein, the TES controller may be configured to apply the series of component waveforms wherein a component waveform in the series differs from another component waveform immediately before and/or immediately after the component waveform in the series by two or more of: the current amplitude, the frequency, the percent charge imbalance, and the percent duty cycle.

The TES controller may be configured to sequentially apply component waveforms in the series for their duration and, during that duration, ramp one or more of the current amplitude, the frequency, the percent charge imbalance, and the percent duty cycle from a previous current amplitude, frequency, percent charge imbalance, and percent duty cycle to the current amplitude, the frequency, the percent charge imbalance, and the percent duty cycle of the component waveform.

As suggested above, the TES controller may be configured to apply an ensemble current waveform by sequentially applying the series of component waveforms wherein the current amplitude of the component waveforms is between about 3 mA and 25 mA (or the current amplitude is within the ranges discussed above, which may refer to peak current amplitude during the duration of the component waveform). The TES controller may be configured to apply an ensemble current waveform by sequentially applying the series of component waveforms wherein the frequency of the component waveforms is between about 700 Hz and 30 kHz (or any of the frequency ranges discussed above). The TES controller may be configured to apply an ensemble current waveform by sequentially applying the series of component waveforms wherein the duty cycle of the component waveforms is between about 20% and 80% (or any of the percent duty cycle ranges described above). The TES controller may be configured to apply an ensemble current waveform by sequentially applying the series of component waveforms wherein the percent charge imbalance of component waveforms is between about 10% and 100%.

In any of the variations described herein, the TES controller may be configured to apply an ensemble current waveform by sequentially applying the series of component waveforms wherein applying an ensemble current waveform comprises modifying the ensemble waveform during application by a user intensity adjustment factor. Any of the apparatuses described herein may include a wireless receiver circuit, the wireless receiver circuit configured to receive an intensity adjustment factor and further wherein the TES controller is configured to adjust the ensemble waveform delivered by the user intensity adjustment factor.

Further, any of these apparatuses may include a wireless receiver circuit, the wireless receiver circuit configured to receive an intensity adjustment factor, wherein the TES controller is configured to adjust the ensemble waveform delivered by the user intensity adjustment factor by scaling one or more of the frequency, percent duty cycle, and intensity of the applied ensemble current.

Also described herein are methods of and systems for separately modulating any of the ensemble waveforms described herein, including applying an envelope or scaling signal (which may be herein referred to as an amplitude modulation) to all or, in some variations, one or more portions (e.g., one or more component waveforms) of the ensemble waveform. The envelope is typically a lower frequency (e.g., 1 Hz to 900 Hz, 1 Hz to 300 Hz, 1 Hz to 400 Hz, 1 Hz to 500 Hz, 1 Hz to 600 Hz, 1 Hz to 700 Hz, 1 Hz to 800 Hz, 1 Hz to 1 kHz, etc., and is typically lower than the frequency of the component waveforms that it is modulating) pulsed scaling waveform. The low-frequency pulsed signal (envelope signal or amplitude modulation signal, also referred to as a burst signal) may be a square wave, saw tooth wave, etc., and may have a value of between 1 and 0 (or −1 and 1) so that the resulting signal includes bursts and/or modulated intensities of the higher-frequency component waveforms forming the ensemble waveform. As described in greater detail below, applying this amplitude modulation over even one or a few of the component waveforms forming the ensemble waveform may provide a tremendous advantage both in power efficiency for the system and efficacy for inducing a cognitive and/or physiological effect while potentially reducing or eliminating pain or discomfort associated with stimulation.

In general, any of the ensemble waveforms described herein may be fully or partially amplitude modulated. In particular, to reduce the potential for pain (e.g., from capacitive build-up, pH changes in the skin, and the like), the methods and apparatuses described herein that include amplitude modulation as described herein may also be adapted so that the amplitude modulation prevents truncation of the fundamental pulses being applied during a component waveform. The modulation frequency may be set and/or adjusted to prevent truncating the pulses (signals). One method to prevent truncating the (fundamental or unit) pulses of the ensemble waveform, which may be biphasic (see, e.g., FIG. 89A, described in greater detail below) is to set the amplitude modulation period (duration) so that it is a multiple of the time for one period of a component waveform to which the modulation is being applied, for example by setting the amplitude modulation duration to be a multiple of an inverse of the component waveform frequency. For example, when the amplitude modulation frequency is set (e.g., by a user) without necessarily avoiding truncating pulses of the component waveforms, it may be adjusted (e.g., either in the neurostimulator apparatus or before the parameters are transmitted to the neurostimulator) so that, for example, the amplitude modulation (AM) frequency is adjusted by subtracting time equivalent to the duration of the truncation that would occur if not adjusted For example, the number of fundamental pulses that occur per second of the component waveforms (the frequency of the component waveform being modulated) times the duration of the original/unadjusted modulation envelope (the inverse of the frequency of the original, or target, not yet adjusted, amplitude modulation frequency) gives the number of pulses within the duration of the original modulation envelope, which is a whole number plus the remaining fraction; the modulation frequency may be adjusted by multiplying this fraction by the duration of each fundamental pulse (the time for one period of a cycle, $t_c$) of the component waveform, and subtracting this time from the original/uncorrected duration of the amplitude modulation envelope (the period of the amplitude modulation pulse, which is the inverse of the amplitude modulation frequency), to give the adjusted/corrected duration of the modulation envelope. The adjusted or corrected amplitude modulation envelope frequency for this particular component waveform to avoid truncation is the inverse of the adjusted/corrected duration of the amplitude modulation envelope, and will be slightly shifted relative to the target, original (uncorrected) AM frequency. In another example adjustment to ensure fundamental pulses of a burst are not truncated, the amplitude modulation duty cycle (i.e. the proportion of the amplitude modulation period during which the fundamental pulses are delivered) is adjusted by adding or subtracting duty cycle percentage for rounding to a non-truncated fundamental pulse cycle.

Similarly, the duration of the non-zero portion of the envelope pulse (e.g., in a square pulse envelope, the duration of the "on" portion of the pulse within each period, may be set or adjusted to be a multiple of the duration of the period of the fundamental pulse ($t_c$) for the component waveform being amplitude modulated. When both the period of the envelope of the amplitude modulation and the pulse duration (the time spent above zero within each a pulse of the amplitude modulated envelope) are multiples of the time for the period of one cycle of the component waveform, the pulses of the component waveform will not be truncated.

For example, a method of modulating a user's cognitive state by transdermal electrical stimulation may include: delivering an ensemble current waveform for application between two or more electrodes, wherein the ensemble current waveform comprises a series of component waveforms that are sequentially delivered, wherein the component waveforms comprise biphasic pulses and wherein each component waveform in the series is different from a component waveform immediately before it and/or immediately after it in the series by one or more of: a duration, a current amplitude, a frequency, a percent charge imbalance, and a percent duty cycle; wherein, prior to delivery, one or more of the component waveforms of the ensemble current waveform is modulated (e.g., amplitude modulated) by setting the current amplitude to zero at a modulation frequency for a modulation duration that does not result in truncated pulses in the delivered waveform.

Thus, in any of the methods and apparatuses described herein, amplitude modulation may be applied to one or more of the component waveforms, and the duration of the envelope applied for amplitude modulation (e.g., the modulation duration, which may also be referred to as the modulation duty cycle) may be a multiple of an inverse of the component waveform frequency. In some variations, and particularly but not exclusively amplitude modulation square waveforms, the duration of the non-zero portion of the pulse (also referred to herein as burst length) is also set or adjusted to be a multiple of an inverse of the component waveform frequency. The inverse of the component waveform frequency is the duration of each cycle of the component waveform. For example, the duration of the modulation pulse is the time for one period of a cycle of the modulation pulse and may also be referred to equivalently as the burst period (or bursting period) of amplitude modulation, and/or the time for one period of the amplitude modulation envelope may be set to or may otherwise equal a multiple of the time for one period of a cycle (one fundamental pulse) of the component waveform.

For example, the modulation duration is generally the inverse of the modulation frequency, and in some examples may comprises a bursting duty cycle divided by the modulation frequency, further wherein the modulation duration is adjusted to prevent truncation of pulses in the delivered waveform. The modulation duration may comprise a bursting duty cycle divided by the modulation frequency, further wherein the modulation duration is adjusted to prevent truncation of pulses in the delivered waveform.

Amplitude modulation may be applied (and devices for delivering current to a user may be adapted to include amplitude modulation) to any ensemble waveform as described herein, including ensemble waveforms having more than 2 component waveforms, e.g., more than 3 component waveforms, more than 4 component waveforms, more than 5 component waveforms, more than 6 component waveforms, more than 7 component waveforms, more than 8 component waveforms, more than 9 component waveforms, more than 10 component waveforms, etc. Each component waveform may be longer than 100 ms as discussed above.

The ensemble current waveform may be modulated by turning off the current for a portion of the amplitude modulation envelope. For example, when applying a square wave envelope for amplitude modulation, the component waveform to which this bursting (amplitude modulation) is applied may be zeroed when the pulse is low (or zero) and it may be multiplied by 1 (passed) when the pulse is high. Alternatively, in some variations, the burst may be modified by scaling, e.g., when using saw tooth, sinusoidal, or other amplitude modulation pulses.

In general, any of the methods described herein may include applying the ensemble current waveform to a user wearing the two or more electrodes, e.g., applying the ensemble current waveform to a user wearing a first electrode of the two or more electrodes on the user's temple and/or forehead region and a second electrode of the two or more electrodes on the neck or mastoid region.

Also in general, the ensemble waveforms may include a plurality (e.g., 2 or more, 3 or more, 4 or more, 5 or more, 6 or more, etc.) component waveforms each having a defined amplitude, frequency, percent duty cycle, and percent charge imbalance. Each component waveform may also have amplitude modulation (e.g., AM on/off) including an amplitude duty cycle frequency (which may be referred to herein as an amplitude modulation frequency, AM frequency). In some variations the amplitude modulation may also include an amplitude modulation duty cycle (AM % duty cycle), which may indicate the percentage of time that the amplitude modulation pulse is "on" during the period of a single amplitude modulation pulse, and may be between 0% (signal totally suppressed, or set to 0) and 100% (all of the signal passed). The amplitude modulation percent duty cycle may be set and/or adjusted to adjust as mentioned above to prevent truncation of the pulses of the component waveform (of the ensemble waveform) being amplitude modulated. For example, percent duty cycle may be adjusted by increasing or decreasing the duration of the non-zero pulse (within the amplitude modulation envelope waveform) so that it is a multiple of the duration of the time for one period of a cycle (e.g., the inverse of the frequency of stimulation) of the component waveform.

Thus, each component waveform may be specified by: current amplitude (typically in mA), frequency (e.g., of the fundamental pulses, typically biphasic), percent duty cycle (e.g., the time spent in the negative peak current plus the time spent in the positive peak current, divided by the time for one period of a cycle of a fundamental pulse), and the percent charge imbalance (e.g., the difference between the time spent in the positive peak current and the time spent in the negative peak current, divided by the sum of the time spent in the positive and negative peak current of a fundamental pulse). The percent charge imbalance may also be referred to as the "percent DC" (or percent direct current). Each component waveform may also specific if capacitive discharging current is to be applied (capacitive discharge "on" or "off") and/or how the capacitive discharge is to be applied (e.g., where in the cycle it is to be discharge, and/or for how long). In addition or alternatively, any of the component waveforms may also include an indicator indicating if amplitude modulation is on and/or the frequency for amplitude modulation and/or the amplitude modulation percent duty cycle (e.g., the duration of a, e.g., square wave, pulse within a single period of the amplitude modulation cycle divided by the total time for the single period of the amplitude modulation cycle (e.g., 1/frequency of the amplitude modulation)). Thus, the apparatuses described herein may be configured to operate with all or some of these parameters specifying each component waveform of the ensemble waveform.

In any of the methods and apparatuses described herein, the ensemble waveform is delivered by sequentially delivering the sequence of component waveforms forming the ensemble waveforms. In general, the duration of each component waveform is between about 100 milliseconds and 600 seconds. Delivering may include sequentially delivering the component waveforms wherein the amplitude of each component waveform is between about 3 mA and about 25 mA. Delivering may include sequentially delivering the component waveforms, wherein the frequency of each, some or any of the component waveform is between about 700 Hz and about 30 kHz. Delivering may comprise sequentially delivering the component waveforms wherein the percent charge imbalance of each component waveform is between about 10% and 100%. Delivering may comprise sequentially delivering the component waveforms wherein the percent duty cycle of each component waveform is between about 20% and 80%.

Methods of modulating a user's cognitive state that include the use of amplitude modulation are also described. For example, a method of modulating a user's cognitive state by transdermal electrical stimulation (TES) to a subject's head or head and neck from two or more electrodes that are coupled to a neurostimulator may include: applying an ensemble current waveform between the two or more electrodes, wherein the ensemble current waveform comprises a series of component waveforms that are sequentially applied, wherein the component waveforms comprise biphasic pulses and wherein each component waveform in the series is different from a component waveform immediately before it and/or immediately after it in the series by one or more of: a duration, wherein the duration is between about 100 milliseconds and about 600 seconds, a current amplitude, a frequency, a percent charge imbalance, and a percent duty cycle; wherein, prior to application, one or more of the component waveforms of the ensemble current waveform is modulated by setting the current amplitude to zero at a modulation frequency for a modulation duration that is a multiple of an inverse of the component waveform frequency.

A method of modulating a user's cognitive state by transdermal electrical stimulation may include: delivering an ensemble current waveform for application between two or more electrodes, wherein the ensemble current waveform comprises a series of component waveforms that are sequentially delivered, wherein the component waveforms comprise biphasic pulses and wherein each component waveform in the series is different from a component waveform immediately before it and/or immediately after it in the series by one or more of: a duration, a current amplitude, a frequency, a percent charge imbalance, and a percent duty cycle; wherein, prior to delivery, one or more of the component waveforms of the ensemble current waveform is modulated by setting the current amplitude to zero at a modulation frequency for a modulation duration.

Any of the methods described herein may be performed by apparatuses, including hardware, software and firmware, for performing all or some of the steps described. For example a method of modulating a subject's cognitive state using TES as described, and particularly for applying an ensemble waveform and separately (and in some cases independently) amplitude modulating one or more component waveforms forming the ensemble waveform may be performed using a wearable transdermal electrical stimulation (TES) apparatus with control circuitry (e.g. controller) that is adapted for the application of the ensemble waveforms described herein.

For example, a transdermal electrical stimulation (TES) applicator apparatus for modifying a subject's cognitive state may include: a body; a first connector configured to connect to a first electrode; a second connector configured to connect to a second electrode; and a TES controller at least partially within the body and comprising a processor, a timer and a waveform generator, wherein the TES controller is adapted to deliver an ensemble current waveform for application between the first and second connectors, wherein the ensemble current waveform comprises a series of component waveforms that are sequentially delivered, wherein the component waveforms comprise biphasic pulses and wherein each component waveform in the series is different from a component waveform immediately before it and/or immediately after it in the series by one or more of: a duration, a current amplitude, a frequency, a percent charge imbalance, and a percent duty cycle; further wherein, prior to delivery, the controller is configured to modulate one or more of the component waveforms of the ensemble current waveform by setting the current amplitude to zero at a modulation frequency for a modulation duration that does not result in truncated biphasic pluses in the delivered waveform.

The controller may be configured to modulate one or more of the component waveforms of the ensemble current waveform by setting the current amplitude to zero at a modulation frequency for the modulation duration, wherein the modulation duration is a multiple of an inverse of the component waveform frequency. The controller may be configured to modulate one or more of the component waveforms of the ensemble current waveform by setting the current amplitude to zero at a modulation frequency for the modulation duration, wherein the modulation duration comprises a bursting duty cycle divided by the modulation frequency, further wherein the modulation duration is adjusted to prevent truncation of biphasic pulses in the delivered waveform.

The TES controller may be adapted to deliver the ensemble current waveform for application between the first and second connectors, wherein the ensemble current waveform comprises a series of five or more component waveforms. The TES controller may generally be adapted to deliver an ensemble current waveform by sequentially delivering the component waveforms wherein the amplitude of each, some or any of the component waveforms is between about 3 mA and about 25 mA, wherein the frequency of each component waveform is between about 700 Hz and about 30 kHz, wherein the percent charge imbalance of each component waveform is between about 10% and 100%, and/or wherein the percent duty cycle of each component waveform is between about 20% and 80%.

Any of the apparatuses described herein may include a wireless receiver circuit, the wireless receiver circuit configured to receive an intensity adjustment factor, wherein the TES controller is configured to adjust the ensemble current waveform delivered by the user intensity adjustment factor by scaling one or more of the frequency, percent duty cycle and intensity of the applied ensemble current.

Also described herein are methods and apparatuses for controlling a wearable neurostimulator (or other wearable electrical stimulators) by transmitting control information instructing the wearable neurostimulator to deliver an ensemble waveform having any of the properties described herein. In particular, described herein are methods and apparatuses for transmitting from a controller to a processor of a wearable neurostimulator to cause the neurostimulator to deliver an ensemble waveform. This may generally be achieved by transmitting a series of predefined messages from a controller to the processor of the wearable neurostimulator, where the series of messages includes a first message telling the processor to prepare to receive a number of segments that specify the component waveform properties described above (e.g., segment number, current amplitude, duration, and a state code that defines the direction and/or type of current applied, e.g., positive, negative, capacitive discharge, zero (ground) current, etc.).

The controller may be remote from the wearable neurostimulator, e.g., it may be held by the user or included as part of personal computing device (e.g., smartphone, tablet, smartwatch, wearable electronics, desktop, laptop, etc.), or it may be integrated into the wearable apparatus. For example, a remote controller may communicate wirelessly with the wearable device (e.g., by Bluetooth, UWB, ultrasound, WiFi, near-field electrical communication, or any other wireless modality); the apparatus may be configured for this type of communication and may be paired or otherwise connected to the device. The wearable neurostimulator may be configured to monitor and/or receive transmissions. For example, when wireless transmission is used, the wearable neurostimulator may be adapted to receive and process the transmitted information, and may therefore include wireless transmission circuitry and/or memory for storing this information.

In some variations, the controller is not remote to the processor, but may be part of the same device, and/or connected by one or more transmission lines, e.g., electrical traces, wires, etc. For example, the controller may be part of an integrated electrode assembly and neurostimulator that can be worn by the user. When the controller is remotely located and wirelessly communicates with the neurostimulator apparatus, the communication between the remotely located controller and the processor of the neurostimulator may be one way (e.g., from the remotely located controller to the neurostimulator) or two-way. In general, communication between the two may be specifically encoded (and in some cases may be encrypted), to optimize the speed, power usage and efficiency of the communication between the controller and the processor of the neurostimulator apparatus, to allow the quick and accurate transfer of instructions for stimulation between a controller and a neurostimulator. Although there are numerous ways that these instructions may be encoded and/or processed, described herein are particularly advantageous methods and apparatuses embodying these methods.

For example, a method of controlling a wearable neurostimulator from a control apparatus (either remote or local to the processor of the wearable neurostimulator apparatus) may include: transmitting a first message from the control apparatus instructing the wearable neurostimulator to prepare to receive a new set of waveform parameters or a modification of a stored set of waveform parameters; and transmitting one or more segment messages from the control apparatus, the segment messages defining segments of the new waveform parameters or the modification to the stored waveform parameters, the segment messages each comprising a message encoding: a segment index number, a segment duration, a current amplitude, and a state code, wherein the state code indicates one of: positive current, negative current, capacitive discharge, and open circuit.

In any of these variations, the first message may typically include a message identification code identifying the first message as containing instructions instructing the wearable neurostimulator to prepare to receive the new set of waveform parameters or the modification of the stored waveform parameters. The one or more segment messages may comprise a message identification code identifying them as segment messages.

Transmission of the first message may include transmitting the first message comprising a four byte message. The segment messages may each comprise a seven byte message.

In any of the variations described herein, transmitting the first message and the one or more segment messages may include wirelessly transmitting from the control apparatus to the wearable neurostimulator. Alternatively, transmitting from the first message and the one or more segment messages may include transmitting through a physical connection between the control apparatus and the wearable neurostimulator.

In any of these methods described herein, the method may include pairing or synchronizing the wearable neurostimulator and the remote control apparatus.

In general, in any of these methods, the first message may include one or more of: a code indicating transmission of a new waveform or transmission of a modification of a stored waveform, a number of segments to expect, and an indication that the waveform will be burst modulated.

The control apparatus may transmit at regular intervals, which may be matched with receiving intervals at the neurostimulator. For example, a neurostimulator may transmit the first message and/or the one or more segment messages about every 400 milliseconds. In any of the methods and apparatuses described, a message may not be sent (or a null message sent, or messages not specific to the control of the waveform) at each communication interval (e.g., 400 msec intervals, etc.).

As mentioned above, any appropriate communication protocol may be used; for example, the control apparatus may transmit the first message and the one or more segment messages by Bluetooth.

A method of controlling a wearable neurostimulator from a control apparatus may include: transmitting a first message from the control apparatus instructing the wearable neurostimulator to prepare to receive a new set of waveform parameters or a modification of a stored set of waveform parameters, the first message comprising a four byte message, wherein the first message includes: a code indicating transmission of a new waveform or transmission of a modification of a stored waveform, a number of segments to expect, and an indication whether the waveform will be burst modulated; and transmitting one or more segment messages from the control apparatus, the segment messages defining segments of the new waveform parameters or the modification to the stored waveform parameters, the segment messages each comprising a seven byte message encoding: a segment index number, a segment duration, a current amplitude, and a state code, wherein the state code indicates one of: positive current, negative current, capacitive discharge, and open circuit (zero).

As mentioned above, the first message may include a message identification code identifying the first message as containing instructions instructing the wearable neurostimulator to prepare to receive the new set of waveform parameters or the modification of the stored waveform parameters. The one or more segment messages comprise a message identification code identifying them as segment messages.

Also described herein are apparatuses configured to control a wearable neurostimulator. These apparatuses may include software, firmware or the like for communicating with a wearable neurostimulator. For example, a control may comprise a smartphone, watch, or wearable electronic (glasses, etc.) that can wirelessly communicate with a wearable neurostimulator, and is adapted to run control logic (e.g., software, firmware, etc.) for structuring and controlling communication with a neurostimulator. For example, a control apparatus for controlling a wearable neurostimulator may include a processor, the processor configured to: transmit a first message instructing the wearable neurostimulator to prepare to receive a new set of waveform parameters or a modification of a stored set of waveform parameters, the first message comprising: a code indicating transmission of a new waveform or transmission of a modification of a stored waveform, a number of segments to expect, and an indication whether the waveform will be burst modulated; and transmit one or more segment messages from the control apparatus, the segment messages defining segments of the new waveform parameters or the modification to the stored waveform parameters, the segment messages each encoding: a segment index number, a segment duration, a current amplitude, and a state code, wherein the state code indicates one of: positive current, negative current, capacitive discharge, and open circuit.

As mentioned, the processor may be configured to transmit the first message as a four byte message (message payload), e.g., a first message alerting the neurostimulator processor to prepare to receive and/or modify a component waveform. The four bytes message payload typically including: a code indicating transmission of a new waveform or transmission of a modification of a stored waveform, a number of segments to expect, and an indication whether the waveform will be burst modulated. The message may include additional bytes indicating, for example, the message ID (e.g., a code specifying the type of message), the routing information (destination, source, etc.), The processor may be configured to transmit the one or more segment messages including a seven byte message payload (segment payload). The processor may be configured to transmit the first message to include a message identification code identifying the first message as containing instructions instructing the wearable neurostimulator to prepare to receive the new set of waveform parameters or the modification of the stored waveform parameters. The processor may be configured to transmit the one or more segment messages to each include a message identification code identifying them as segment messages. The processor may be configured to wirelessly transmit the first message and the one or more segment messages on a wireless circuit. The processor may be connected via a physical connection to the wearable neurostimulator, and/or may be integrated into the wearable neurostimulator, so that the processor transmits the first message and the one or more segment messages through the physical connection between the control apparatus and the wearable neurostimulator.

The processor may be configured to wirelessly transmit the first message and the one or more segment messages from the control apparatus. The control apparatus may be configured to transmit the first message and/or the one or more segment messages about every 400 msec or multiples of 400 msec.

Also described herein are single-use or limited-use TES neuromodulation apparatuses including integrated electrodes and neuromodulation components that can be worn, e.g., on a user's head and/or neck region (although they may be adapted for other body regions) for electrical stimulation to modulate the user's cognitive state. These apparatuses may be referred to as TES patches or neurostimulation patches, and may be formed of a flex-circuit material. Also described herein are waveform selectors, which may be applied to these apparatuses to select and/or program the limited-use TES neurostimulator in order to apply a predetermined waveform or set of waveforms, or to adjust a waveform, to evoke a cognitive effect. A waveform selector may be a near-field communication component (e.g., RFID, other inductive mechanisms) that communicates with the TES neurostimulator (TES patch) via an NFC antenna contained thereon.

Also described herein are TES neuromodulation apparatuses including connecting cables having circuitry configured to communicate between a portable personal electronics device (e.g., smartphone, tablet, smartwatch, or other wearable electronics) and an electrode apparatus including connectors, such as the electrode apparatuses described in U.S. patent application Ser. No. 14/634,664, titled "CANTILEVER ELECTRODES FOR TRANSDERMAL AND TRANSCRANIAL STIMULATION" and filed Feb. 27, 2015, herein incorporated by reference in its entirety. The personal electronic device may include software, firmware, and/or hardware that controls the application of TES waveforms, and the cable (which may be referred to herein as a smart cable or a TES cable neurostimulator) may include circuitry to amplify or otherwise modify (i.e. by incorporating a capacitive discharge) the waveforms. In some variations the TES cable neurostimulator may include circuitry including any of: current generator circuitry (e.g., waveform generators), safety circuitry, user interface (e.g. buttons, touch interface), controller, memory, processor, digital-to-analog and/or analog-to-digital converters, or the like. The TES cable neurostimulator may be configured to connect to a port (e.g., a USB port (i.e. a micro USB port), a Lightning Connector™, audio jack, etc.) of the portable electronic device. In general, the TES cable neurostimulator may include any of the components (and their functions) of the wearable TES neurostimulator devices described, for example, in U.S. patent application Ser. No. 14/715,470, titled "TRANSDERMAL NEUROSTIMULATOR ADAPTED TO REDUCE CAPACITIVE BUILD-UP" and filed May 18, 2015, which is herein incorporated by reference in its entirety.

The TES neurostimulator functionality may be shared between the TES cable neurostimulator and the portable electronic device (e.g., smartphone). For example, in some variations a smartphone is configured to generate a TES waveform (including any of the TES ensemble waveforms such as those described in U.S. patent application Ser. No. 14/639,015, titled "TRANSDERMAL ELECTRICAL STIMULATION DEVICES FOR MODIFYING OR INDUCING COGNITIVE STATE" and filed Mar. 4, 2015 and U.S. patent application Ser. No. 14/715,476, titled "METHODS AND APPARATUSES FOR AMPLITUDE-MODULATED ENSEMBLE WAVEFORMS FOR NEUROSTIMULATION," and filed May 18, 2015, each of which is herein incorporated by reference in its entirety) and then deliver it to the TES cable neurostimulator that is connected to an electrode assembly; the TES cable neurostimulator amplifies (and, if necessary, interprets, modifies, and/or parses) the signal from the portable personal electronics device, and applies it between the electrodes of the electrode assembly for delivery to the subject. The TES cable neurostimulator may include circuitry configured to confirm that the cable is connected to an electrode assembly, and/or that the electrode assembly is attached to the user's head; alternatively, this functionality may be performed by the personal electronics device (e.g., smartphone) to which the TES cable neurostimulator is connected. In some variations, the TES cable neurostimulator includes a waveform generator and/or a current generator but receives control information from the personal electronics device (e.g. to determine the parameters of a waveform to deliver to the electrode assembly; to start or stop a waveform; to modulate a parameter of an ongoing waveform; etc.).

Also described herein are intermediate embodiments between the completely integrated "patch" TES neurostimulator devices described (which may be limited-use or single-use) and typically include their own power supply, and the TES cable neurostimulator devices, which connect to an electrode apparatus that does not include a power supply or neurostimulator circuitry (though they may include other circuitry, such as electrode-identification circuitry or physiological recording circuitry). For example, an intermediate embodiment may include a cable that is configured to provide power and/or communication from a portable electronic device (e.g., smartphone) and a partially-integrated electrode assembly onto which TES neurostimulator circuitry is included. For example, a partially-integrated TES neurostimulator patch may include all of the neurostimulator circuitry, but may not have an independent power supply (e.g., battery); alternatively, as with the TES cable neurostimulator embodiment, an intermediate apparatus may share the neurostimulator functions and/or components with the personal computing device, and may use the processor of the personal computing device to control the selection and formation of the waveforms to be applied by the patch portion.

In general, described herein are wearable neuromodulation devices configured to be worn on a subject's head or on the subject's head and neck (though in some variations, the electrodes may be configured to connect to a portion of a subject's body other than the head or neck). The neuromodulation systems described herein may be referred to as neurostimulation systems, neurostimulator systems, neuromodulator systems, applicator systems, neuromodulation applicator systems, or the like. Some of the neuromodulation devices described herein integrate the electrode assembly and the neuromodulation components into one device or onto one flexible substrate (also referred to as a strip) or strip-like assembly.

The wearable neuromodulation devices described herein are small, lightweight and specifically adapted to be conforming to the subject so that they can be worn while the subject goes about their daily activities. In particular, these devices are adapted to be worn on the subject's head (e.g., at the temple region) comfortably even while wearing headgear such as hats, glasses, hoods, scarves, or the like. These devices typically have a first surface (subject-facing surface) that has a curved and twisted shape so that an electrode on the surface conforms to a subject's temple region. In some examples, the thickness of the overall device is approximately the same throughout. In other examples, there may be curves on the first surface of the neuromodulation device such that the neuromodulation device can better conform to the subject's temple and neck regions. In yet other examples, the thickness of the device (measured from the first surface) is typically thinner at one end and thicker at the other end. The thinner end region may be configured to be oriented relative to the subject's eye, with the thicker region worn higher on the subject's head, toward the center of the subject's forehead. These devices may also be adapted to conform to other body areas, including the neck. These neuromodulation devices may also be referred to as neurostimulation devices, neurostimulators, neuromodulators, applicators, neuromodulation applicators, electrical stimulators, or the like.

The electrode may also be referred to as an electrode assembly, electrode pad, electrode system, strip, electrode strip, or electrode apparatus, and may be durable or disposable. In reference to the electrode assemblies described herein, the electrode assemblies may have a relatively long, flat body (e.g., an elongate body) and may have a length that is greater than a few inches long (e.g., greater than 2 inches, greater than 3 inches, greater than 4 inches, greater than 5 inches, e.g., from a first region of electrical contact to the next nearest region of electrical contact). In some variations, the two electrodes of the apparatus are near each other in order to target a more spatially restricted area.

Described herein are electrode apparatuses for use with an electrical stimulator to be worn on a subject's head. The electrode apparatuses described herein are generally elongated, thin bodies that include a first active region for applying electrical energy to a subject's skin at or near one end region, and a second active region for applying electrical energy to another region of a subject's skin at or near a second end region. The first and second active regions on the body may be connected by an elongated portion that is typically greater than two inches long. In some variations the elongate body is stiff or relatively rigid (though it may be ductile or include a ductile region that can be bent to set a shape). In some variations the elongate body has a limited flexibility, e.g., so that it is flexible in a first axis (e.g., an x-axis) but is not flexible in a second axis (e.g., y-axis), and may be rotated. For example, the elongate body of the electrode apparatus may be formed of a sheet of material such as a flex circuit material.

As used herein, when a component is described as being at an end region of another component, it should be understood that the first component is not limited to being at the extreme end of other component, but may be adjacent to or near the absolute end or edge of the other component. For example, the first component may be within 20% or less of the total length of the other component from an edge or absolute end of the other component. In contrast, when a component is described as being at the end or edge of another component, the first component may be at or immediately adjacent to the absolute end or edge of the other component.

For example, an electrode apparatus may include: a first electrode portion having a front side and a back side; a first active region on the front side that is configured to deliver energy to the subject's skin; a second electrode portion separated from the first electrode portion by an elongate body region extending at least two inches between the first electrode portion and the second electrode portion; and a second active region on a front side of the second electrode portion that is in electrical communication with the second connector and is configured to deliver energy to the subject's skin. Although the integrated electrode strips described herein that include TES control circuitry integrated with the flexible electrode strip may not include connectors to connect to additional TES control devices, in some variations additional connectors are included. For example, an electrode device may include a first connector extending proud from the back side, wherein the first connector is in electrical communication with the first active region; a second connector extending proud from the back side, wherein the first and second connectors are separated by a predetermined (or in some variations, adjustable) distance, e.g., between about 0.7 and about 0.8 inches from center to center.

As used herein, an electrode portion may refer to a region of the electrode assembly that includes, on one surface, an electrically active region that is, for example, configured as a cathodic or anodic region, and may also include surrounding non-electrically active regions including, for example, adhesive for holding the electrically active region to the skin of the user. The electrically active region may include multiple sub-regions that may be electrically activated together or as sub-sets, as described in detail below. An electrode portion may also include a surface that is opposite from the surface with the electrically active region. Other electrode portions may not include contacts, but may be connected (e.g., by electrical trace(s)) to contacts that are present at other locations on the electrode assembly. An electrode portion may be a sub-region of the substrate forming the electrode assembly, for example, at an end region of the substrate. In some variations the electrode portion is a discrete region of the electrode assembly (which may include two or more such electrode portions). The first active region of the first electrode portion may be positioned off-center on the first electrode portion.

As mentioned above, the elongate body region between the first and second electrode portions (and the first and second active regions) may be flexible in a first direction but not flexible in a direction normal to the first direction. For example, the elongate body region may be formed of a flex circuit material. Examples of flex circuit materials are well known, including, for example, polymers such as polyester (PET), polyimide (PI), polyethylene napthalate (PEN), Polyetherimide (PEI), various fluropolymers (FEP) and copolymers.

In general, the electrode apparatus may be substantially flat. For example, the thickness of the electrode apparatus may have an overall thickness (e.g., thickness of the substrate, and layers printed, silk-screened, soldered, or otherwise adhered onto the substrate) that is less than 5 mm, less than 4 mm, less than 3 mm, less than 1 mm, less than 0.9 mm, less than 0.8 mm, less than 0.7 mm, less than 0.6 mm, etc., and extend in a plane (that may be bent or curved). The connectors may extend proud of this overall thickness. In addition, the electrode portions may extend above/below this overall thickness.

In any of the variations described herein the electrode apparatus may include an electrically conductive gel over the first active region and/or the second active region. The conductive gel may be adhesive and/or it may be surrounded by an additional adhesive for securing the active region to the subject's skin. For example, the electrode apparatus may include an adhesive on the front side of the first electrode portion and/or on the front side of the second electrode portion.

In some variations the electrode apparatus includes a foam region. For example, the apparatus may include a foam on the first electrode portion.

Further disclosed herein are components for controlling and outputting selected waveform sessions incorporated into the neuromodulation device. The integration of the neuromodulation device with the electrode assembly has the advantage of being less bulky and lower in profile relative to having a separate electrode assembly and neurostimulator device that connects to the electrode assembly. Having a lower profile enables the neuromodulation device to be more easily worn under eyeglasses, sunglasses, hats, and other headwear.

In this example, the neuromodulation device can contain pre-loaded waveform sessions. Having preloaded waveform sessions eliminates the need for having software and applications that are used to define or control the waveform output externally. Similarly, eliminating external control requirements for the neuromodulation device also eliminates the need for the neuromodulation device to contain a wireless (or wired, e.g. via a TES cable neurostimulator) connection.

In another example, the neuromodulation device can include a detachable tether. The tether can be a cord or a wire having a tether first end and a tether second end. The tether may contain all the neuromodulation components within its body. The tether first end can electrically connect to the neuromodulation device body, which in this example only contains the electrodes. The tether second end can connect to a telecommunication device that is able to control the waveform outputs. The tether (cord) may include current control circuitry for preparing the TES waveform to be applied by the device; optionally, the tether (as part of the current control circuitry or separate therefrom) can also include a current or power amplifier for supplying additional power when delivering the waveform stimuli to a subject and/or other electronic components (analog-to-digital converter, microprocessor, memory, digital-to-analog converter, etc.).

In yet other examples, the neuromodulation components are only partially contained within the neuromodulation device body and the remaining neuromodulation components can be placed within the tether or a component connected to a tether that connects the neuromodulation device to a telecommunication device for controlling the waveform output. Then, similar to the previous example, the tether can also include current control circuitry (e.g., an amplifier and/or other components) for providing the waveform output with appropriate intensity and other parameters.

The apparatus may generally include a thin (e.g., flat) and flexible elongate body having a front side and a back side, wherein the first electrode portion is at or near a first end region of the flexible elongate body and wherein the second flat electrode portion is at or near a second end region of the flexible elongate body and the elongate body region extends between the first and second active regions. The elongate body may be greater than two inches long (e.g., greater than 3 inches long, greater than 4 inches long, etc.). In some variations the elongate body is curved or bent (when not flexed). For example, the elongate body may have a bend in it or other out-of-plane structure or rigidity.

In some variations the elongate body region may include an electrical trace on a flexible elongate substrate. The electrical trace may be printed or otherwise applied onto (or embedded in) the substrate. For example, the trace may be flexographically printed, silk screened, or laser printed using conductive ink. The electrical trace may provide the electrical connection between the second connector and the second active region of the second electrode portion.

An electrode apparatus for use with an electrical stimulator to be worn on a subject's head may include: a flat and flexible elongate body having a front side and a back side; a first electrode portion at or near a first end region of the elongate body; a first active region on the front side of the first electrode portion, wherein the first active region is configured to deliver energy to the subject's skin; a second electrode portion at or near a second end region of the elongate body that is separated from the first electrode portion by at least two inches; and a second active region on the front side of the second electrode portion that is in electrical communication with the second connector and is configured to deliver energy to the subject's skin; wherein the first and second connectors are configured to electrically connect the apparatus to the electrical stimulator.

As mentioned above, the neuromodulation device may include an electrically conductive gel (e.g., over the first active region and/or the second active region), an adhesive on the front side of the first electrode portion and on the front side of the second electrode portion, a foam on the first flat electrode portion, or the like. In any of the electrode apparatuses described herein the first and second connectors may be separated by between about 0.6 to about 0.9 inches (e.g., about 0.7 to about 0.8 inches, about 0.72 inches, etc.).

The neuromodulation device to be worn on a subject's head may include: a flat and flexible elongate body having a front side and a back side; a first electrode portion at a first end region of the elongate body; a first active region on the front side of the first electrode portion, wherein the first active region is configured to deliver energy to the subject's skin; neuromodulation components contained within the body of the neuromodulation device; controls on the back side of the neuromodulation device (e.g., for turning on and off the neuromodulation device), controls for selecting the waveform sessions and intensity, and an indicator, such as a display or LED(s), for showing the user the status of neurostimulation by the neuromodulation device.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 8A-8C illustrate embodiments of example waveforms and electrode configurations.

FIG. 10B shows the distribution of electric potential on the scalp from this arrangement, FIG. 10C shows the distribution of electric potential in the brain, and FIG. 10D shows the absolute magnitude of the electric field in the brain.

11B shows the electric potential on the scalp, and FIG. 11C shows the resulting distribution of electric potential in the brain. FIG. 11D shows the resulting absolute magnitude of the electric field in the brain.

FIG. 12B shows the resulting electric potential on the scalp, and FIG. 12C shows the resulting electric potential in the brain. FIG. 12D shows the resulting absolute magnitude of electric fields in the brain.

FIG. 16B illustrates the disposable portion positioned within a blister pack.

FIG. 19A shows an optional backer on one side of a disposable portion of the apparatus (covering one or more electrodes and an adhesive).

FIG. 19B shows the disposable portion including the electrodes.

In FIG. 23A the battery door is open, while in FIG. 23B the battery door is closed.

FIGS. 24A-24F shows a variation of a lightweight and wearable apparatus for transdermal stimulation (e.g., TES) having a four electrode configuration that is configurable with additional or fewer electrodes in various positions. FIG. 24A shows the electrodes at equidistant positions on a track. FIG. 24B shows the electrodes and holder (primary unit) of FIG. 24A with the electrodes arranged asymmetrically. FIG. 24C shows another arrangement of the electrodes and holder (primary unit) of FIG. 24A. FIG. 24D shows another arrangement of the electrodes and holder (primary unit) of FIG. 24A. FIG. 24E shows another arrangement of the electrodes and holder (primary unit) of FIG. 24A with the electrodes arranged asymmetrically. FIG. 24F shows another arrangement of the electrodes and holder (primary unit) of FIG. 24A.

In FIG. 25A electrodes are arranged concentrically and various concentric rings may be connected together to form the cathode or the anode. FIG. 25B shows a similar configurable system for focusing electric fields using a triangle configuration. FIG. 25C shows another variation having a pie configuration of electrodes.

FIG. 27A shows a workflow for configuring, actuating, and ending a TES session. FIG. 27B shows components of a portable, wired TES system (e.g., lightweight, wearable, and self-contained apparatus for TES to induce a cognitive effect). FIG. 27C shows components of a TES system that connects wirelessly to a remote control unit having a microprocessor. FIG. 27D is a schematic of control logic that causes a remote processor (e.g., of the computer, smartphone, etc.) to wirelessly transmit control instructions to a lightweight, wearable, and self-contained electrical stimulation apparatus

FIG. 29A is a perspective view of a first variation of an electrode apparatus as described herein.

FIGS. 29B, 29C and 29D show front, top and back views, respectively of the cantilever electrode apparatus of FIG. 29A.

FIG. 30A is an exploded view of the front of the cantilever electrode apparatus similar to that shown in FIG. 29B.

FIG. 30B is an exploded view of the back of the cantilever electrode apparatus similar to that shown in FIG. 29D.

FIG. 31 is an alternative front view of a cantilever electrode apparatus similar to the apparatus shown in FIG. 29B, in which a foam pad is not included over the front of the first electrode region.

FIG. 32A is a perspective view of a variation of an electrode apparatus as described herein.

FIGS. 32B, 32C and 32D show front, top and back views, respectively of the cantilever electrode apparatus of FIG. 32A.

FIGS. 35A-35F illustrate front, back, left side, right side, top and bottom perspective views, respectively of a variation of a neurostimulation device (electrical stimulator) that may be used with any of the cantilever electrode apparatuses described herein.

FIGS. 37A-37C show three views illustrating another variation of a cantilever electrode apparatus having a rigid body.

FIGS. 38A-38C show three views illustrating another variation of a cantilever electrode apparatus.

FIGS. 43B-43G illustrate another example of a neurostimulator as described herein.

FIGS. 43H-43K illustrates a first example of one variation of an electrode assembly, configured as a "calm" electrode assembly.

FIGS. 43L-43o illustrate a second example of one variation of an electrode assembly, configured as an "energy" electrode assembly.

FIGS. 53A-53E show screens of an app for controlling a neurostimulator for TES that display a settings menu; provide information and controls about a TES neurostimulator; display general information and access to support; and show analytics data about current, recent, and historical TES sessions.

FIG. 54C shows a warnings page of a user guide for a TES system.

FIGS. 54L-54N show pages of a user guide for a TES system with instructions for properly positioning a wearable TES neurostimulator (i.e. 'Module') and variations of electrode assemblies (i.e. 'Energy Strip' and 'Calm Strip').

FIGS. 54o-54Q show pages of a user guide for a TES system with instructions for controlling a wearable TES neurostimulator with the smartphone app.

FIGS. 56G and 56H show resources (e.g. websites) describing the components of a wearable TES system and its intended use.

FIGS. 57A-57E show resources (e.g. websites) describing TES waveforms to be delivered through a neurostimulator (also referred to as 'Vibes'), including categories of Vibes (i.e. Calm Vibes and Energy Vibes), suggested contexts for use, expected skin sensations, common cognitive effects, and basic instructions for use.

FIGS. 58A-58F show resources (e.g. websites) describing the science and technology of a TES system (i.e. a 'Thync system').

FIG. 60A illustrates a lightweight and wearable electrical stimulation apparatus worn on a subject in accordance with some embodiments of the disclosure.

FIG. 60B illustrates a back perspective view of a wearable electrical stimulation apparatus in accordance with some embodiments of the disclosure.

FIG. 61A illustrates a cantilever electrode apparatus on a subject's head.

FIGS. 61B and 61C illustrate the cantilever effect of the attachment mechanism on the skin-facing surface of the neurostimulator housing. In FIG. 61B the neurostimulator has a rigid housing that is coupled at only one end by a pair of connectors 61227, 61227' (e.g., snaps) to the electrode assembly (flexible pad 61239 that is configured to adhesively stick to the subject's temple). The opposite end of the neurostimulator 61236 is free to float, as shown by the different separations between FIGS. 61B 61230 and 2C 61232.

FIG. 63A is a perspective view of a first variation of an electrode apparatus as described herein.

FIGS. 63B, 63C and 63D show front, top and back views, respectively, of the cantilever electrode apparatus of FIG. 63A.

FIG. 64A is an exploded view of the front of the cantilever electrode apparatus similar to that shown in FIG. 63B.

FIG. 64B is an exploded view of the back of the cantilever electrode apparatus similar to that shown in FIG. 63D.

FIG. 65 is an alternative front view of a cantilever electrode apparatus similar to the apparatus shown in FIG. 63B, in which a foam pad is not included over the front of the first electrode region.

FIG. 66A is a perspective view of a variation of an electrode apparatus as described herein.

FIGS. 66B, 66C and 66D show front, top and back views, respectively of the cantilever electrode apparatus of FIG. 66A.

FIG. 67A is an example of a perspective view of a variation of a cantilever electrode apparatus having a capacitive element between the first and second electrodes that can be sensed by a neurostimulator.

FIG. 67B is another example of a perspective view of a cantilever electrode apparatus having a capacitive element between the first and second electrodes that can be sensed by a neurostimulator.

FIG. 68A is one embodiment of a detection circuit that may be used to detect connection and/or the type or identity of an electrode apparatus; the detection circuit may be included on a neurostimulator to detect some variations of the electrode apparatuses described herein.

FIG. 68B is another embodiment of a detection circuit on a neurostimulator that may be used to detect connection and/or the type or identity of an electrode apparatus.

FIG. 68C is yet another embodiment of a detection circuit that may be used to detect connection and/or the type or identity of an electrode apparatus.

Figure 69:
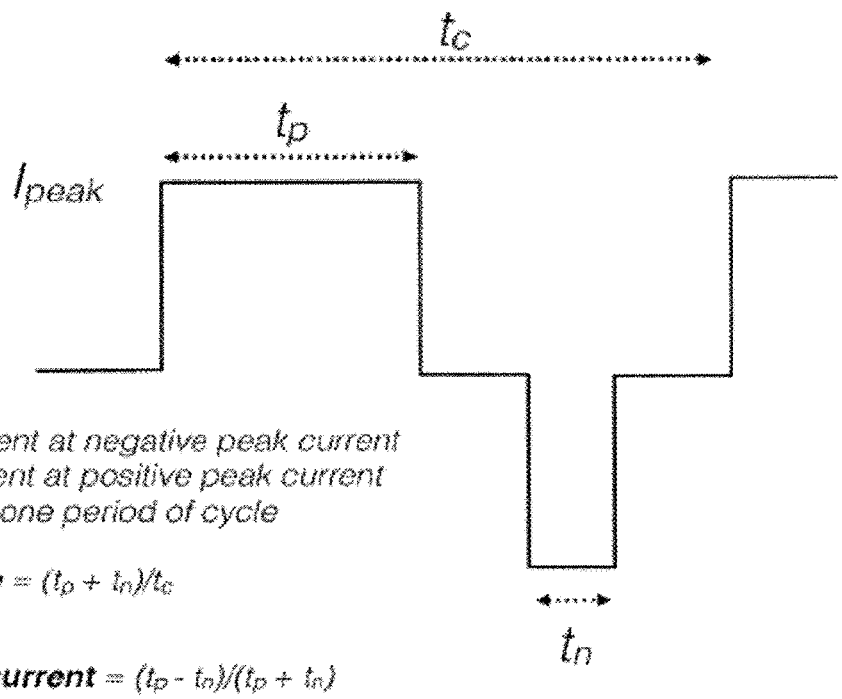

FIG. 69 schematically illustrates a TES waveform according to some embodiments of the disclosure.

Figure 70A:
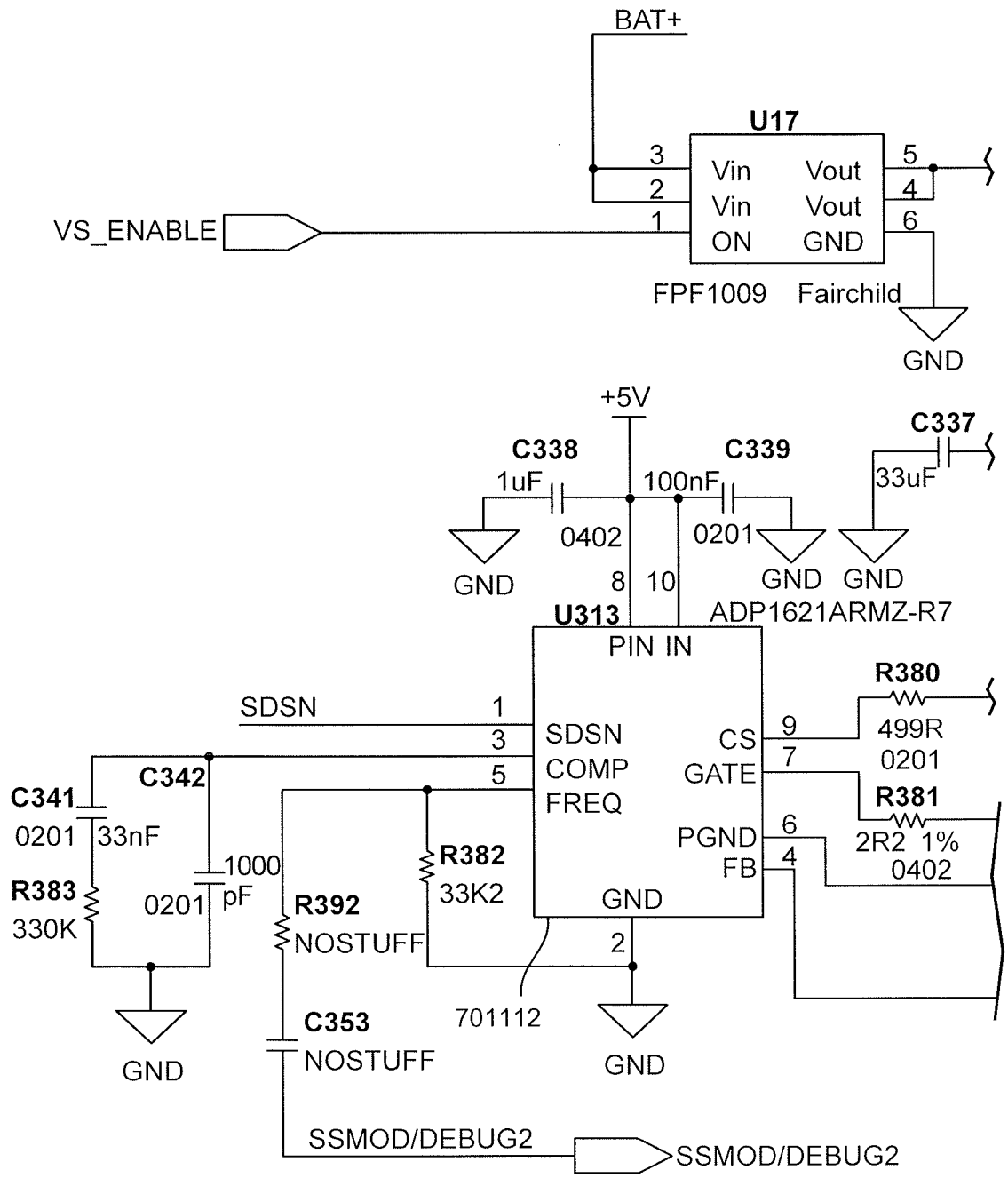
Figure 70A:
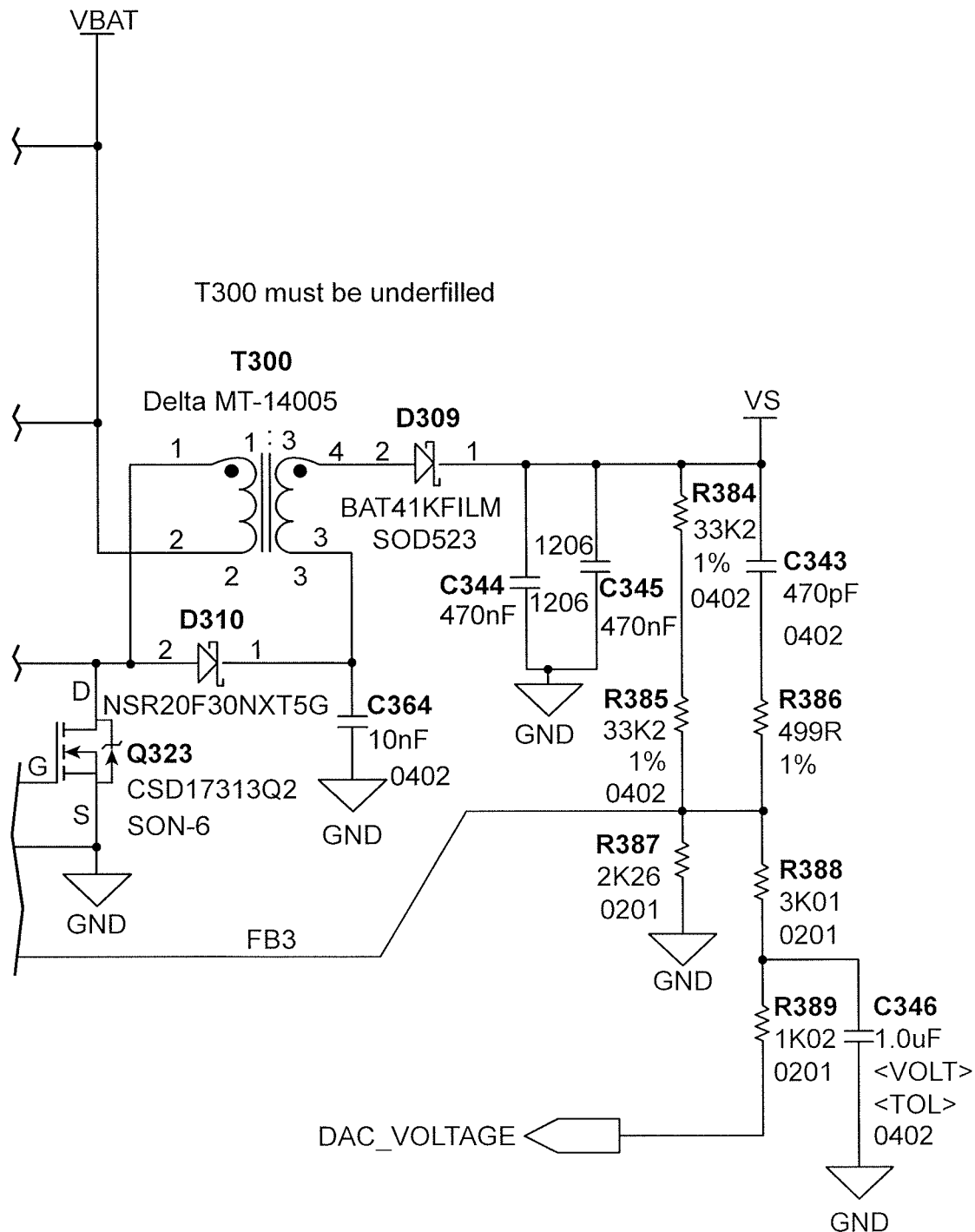

FIG. 70A illustrates a portion of an example of a circuit of a controller of a neurostimulator.

Figures 1, 70B:
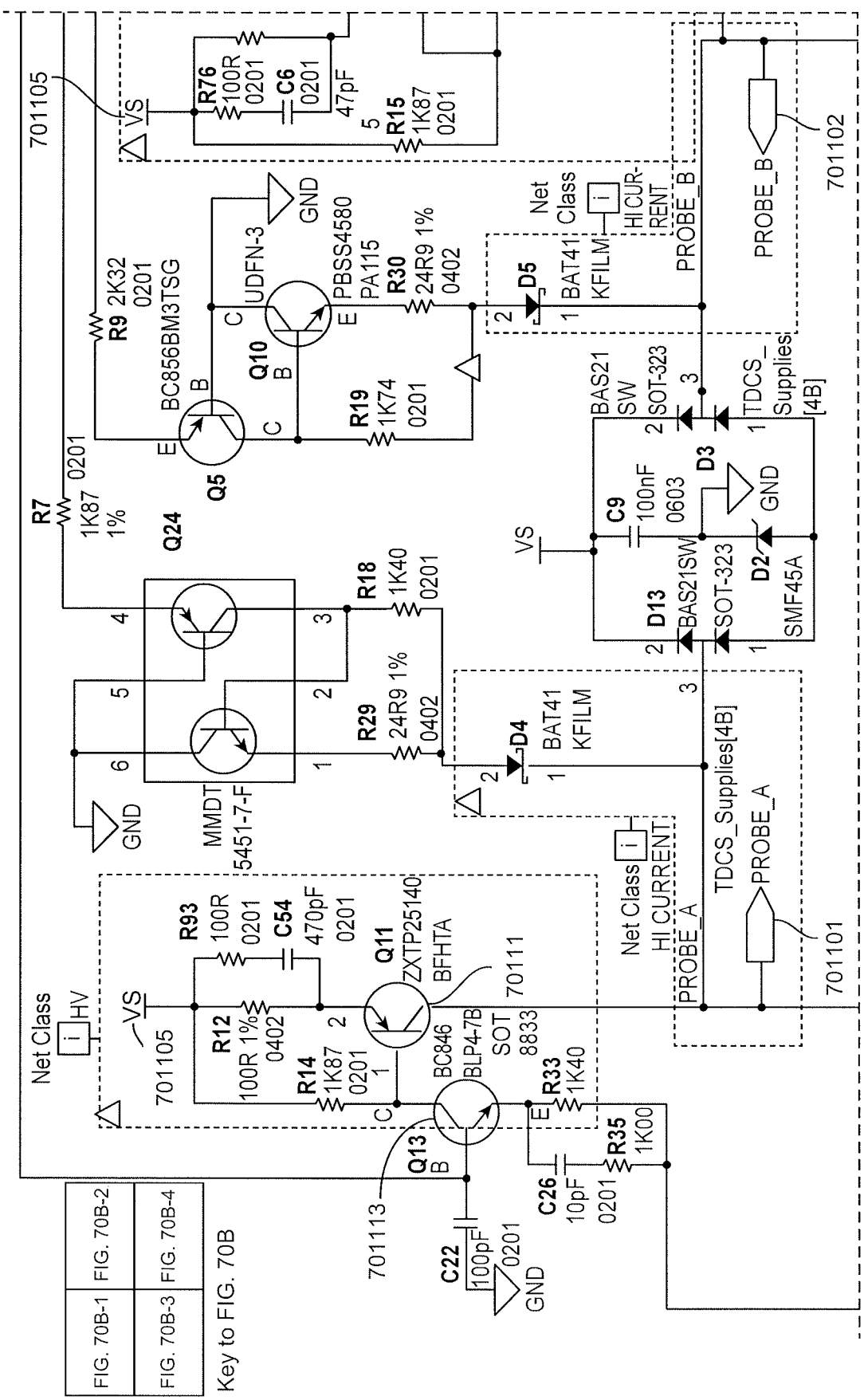
Figures 2, 70B:
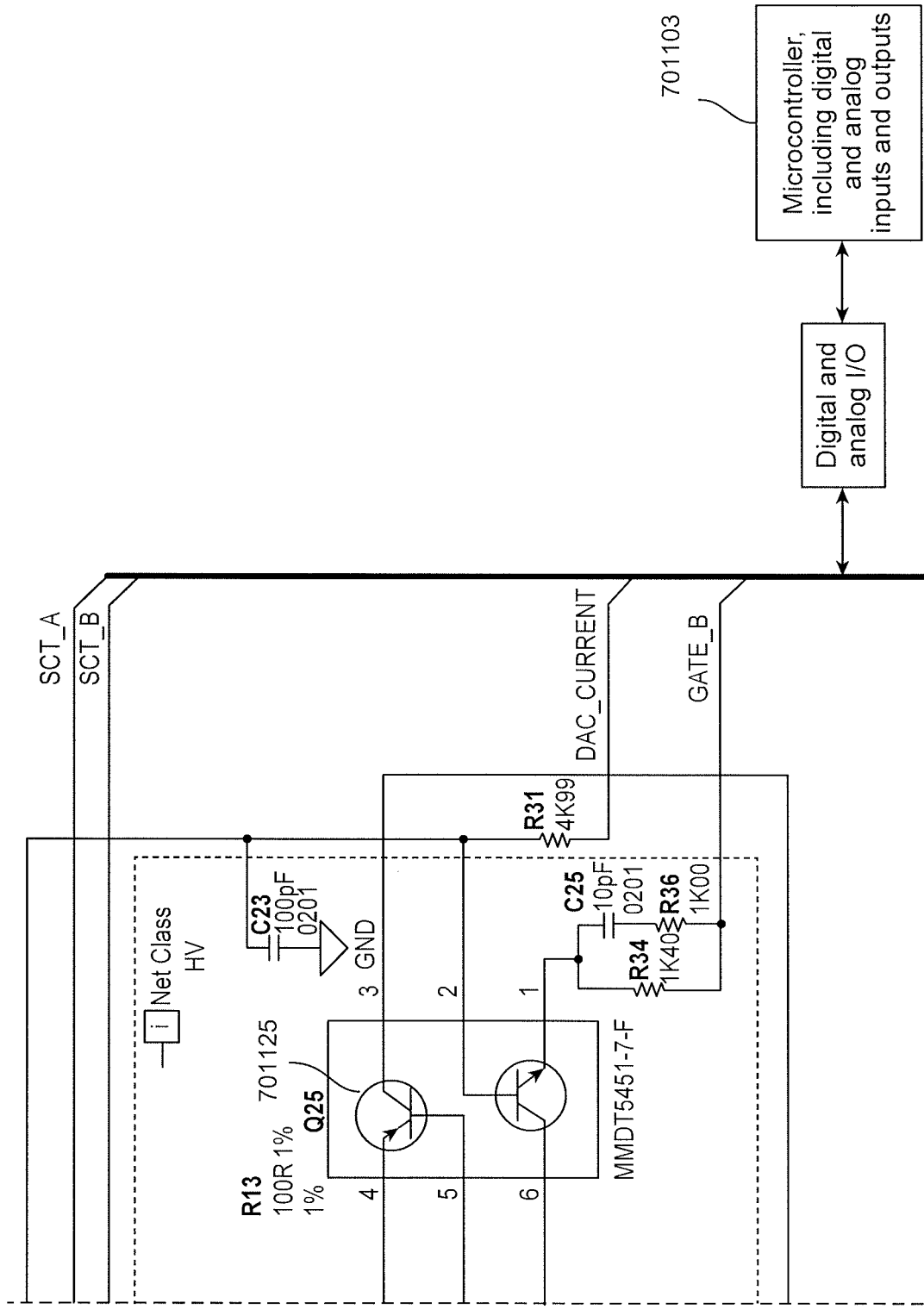

FIG. 70B illustrates another portion of an example of a circuit of a controller of a neurostimulator.

Figure 71B:
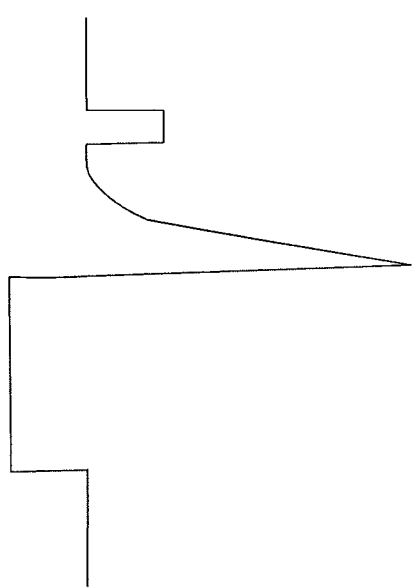
Figure 71D:
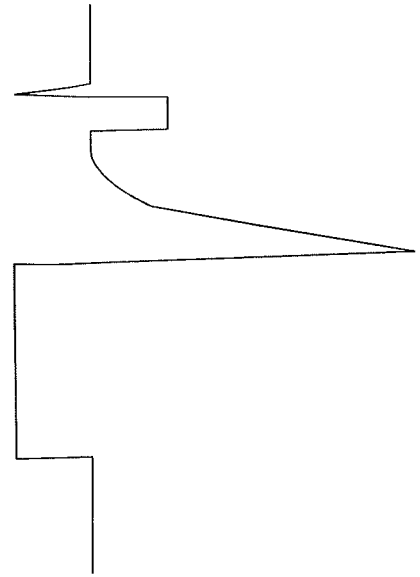
Figure 71A:
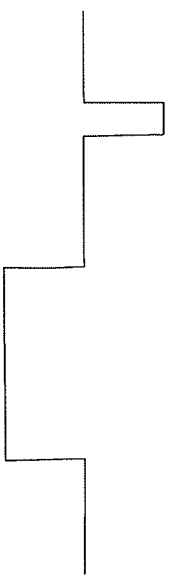

FIG. 71A schematically illustrates a biphasic electrical stimulation waveform with a positive pulse and a negative pulse in one cycle.

FIG. 71B schematically illustrates a capacitive discharge pulse triggered immediately after the positive pulse.

Figure 71C:
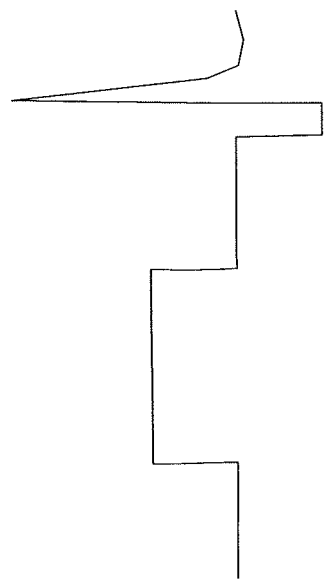

FIG. 71C schematically illustrates a capacitive discharge pulse triggered immediately after the negative pulse.

FIG. 71D schematically illustrates capacitive discharge pulses triggered immediately after the positive pulse and the negative pulse.

Figure 71E:
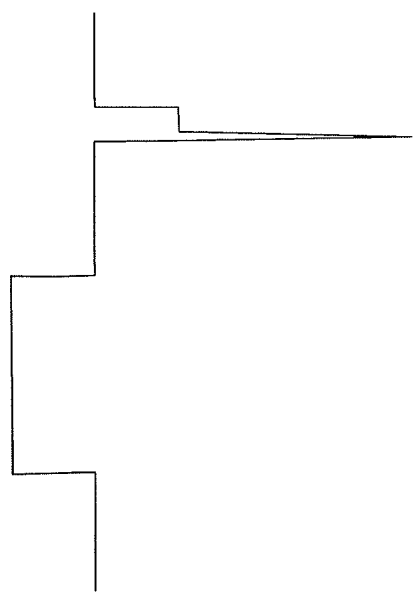

FIG. 71E schematically illustrates a capacitive discharging pulse in the negative going direction occurs at the onset of each negative going pulse.

Figure 72:
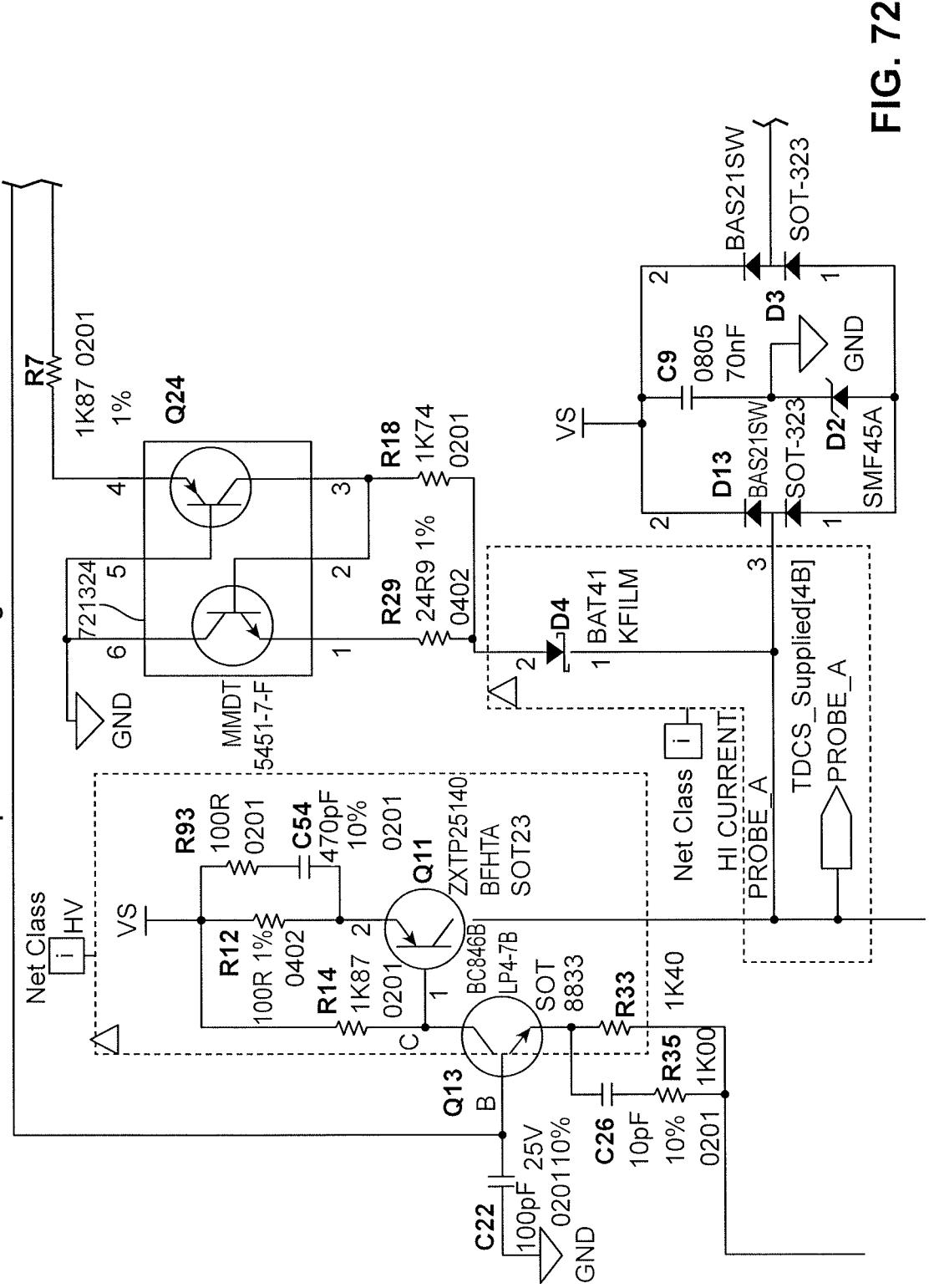
Figure 72:
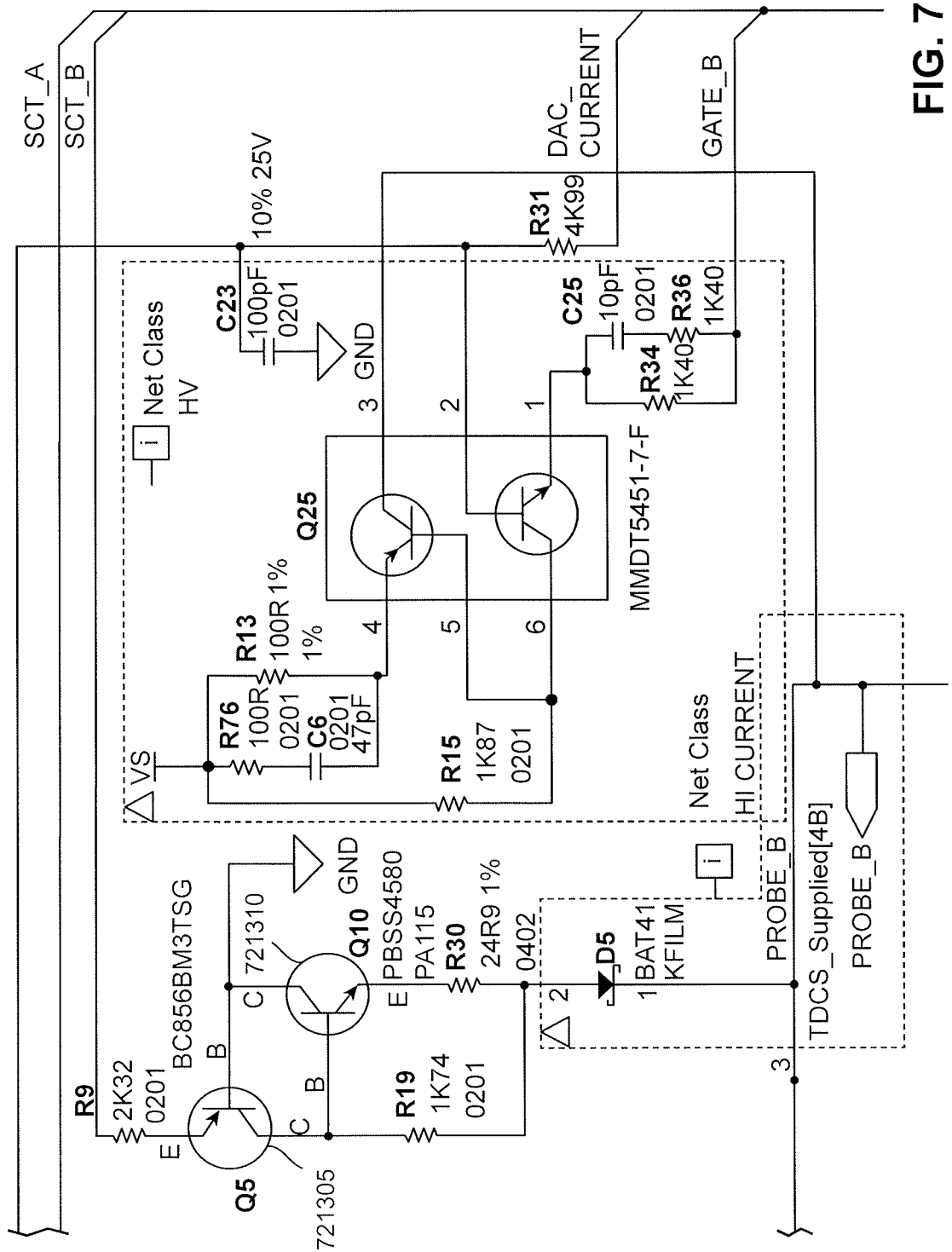

FIG. 72 schematically illustrates an example of a capacitive discharge circuit including a double H-bridge according to some embodiments of the disclosure.

Figure 73A:
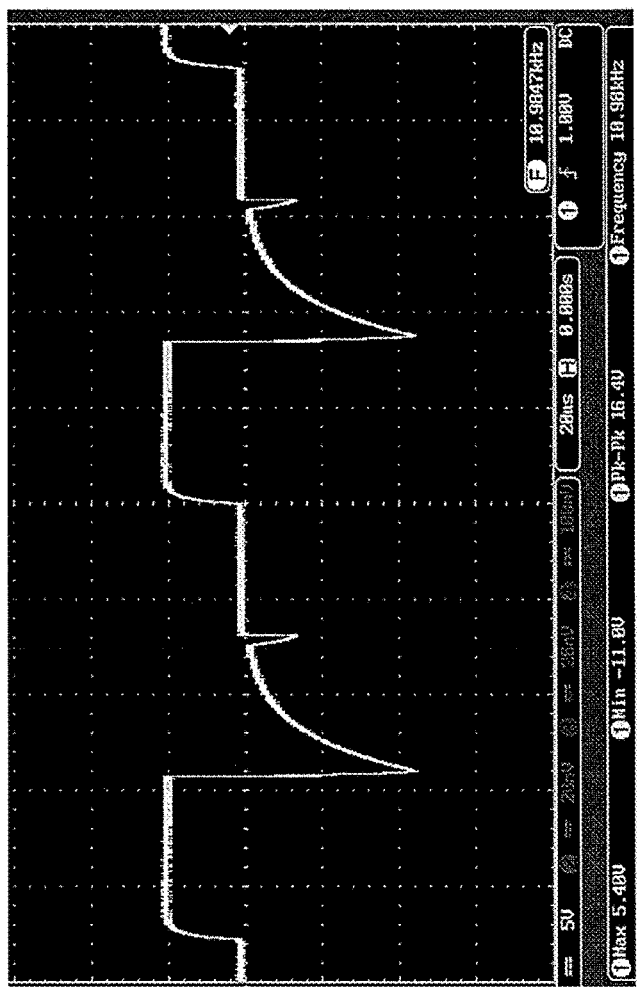

FIG. 73A illustrates an example of capacitive discharging pulses from the double H-bridge capacitive discharge circuit.

Figure 73B:
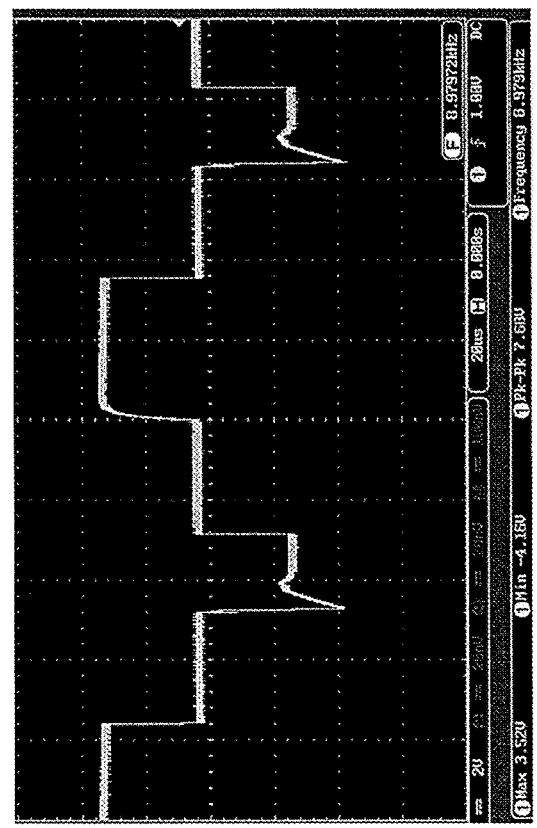

FIG. 73B illustrates another example of capacitive discharging pulses from the capacitive discharge circuit with the double H-bridge.

Figure 74:
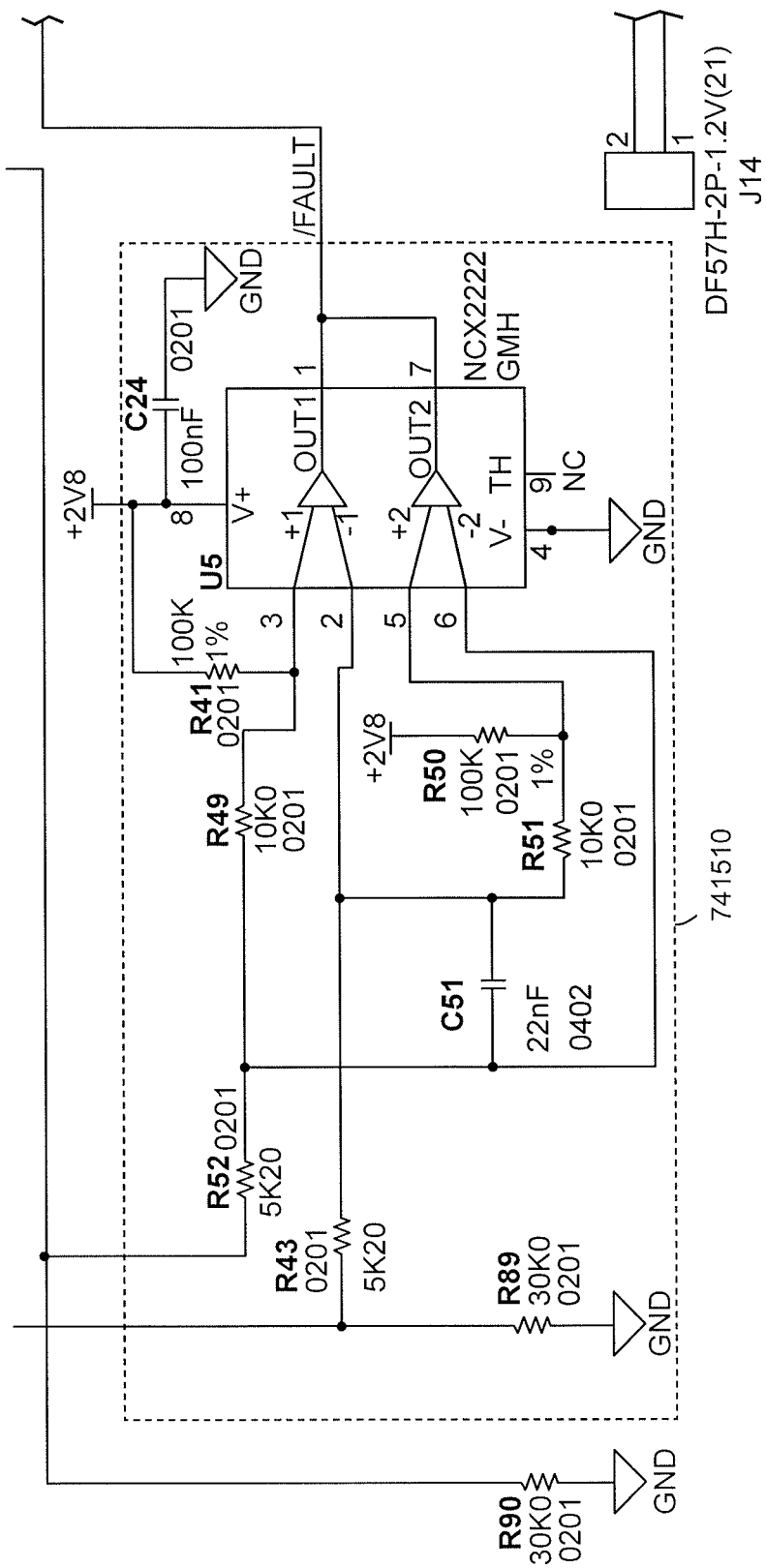
Figure 74:
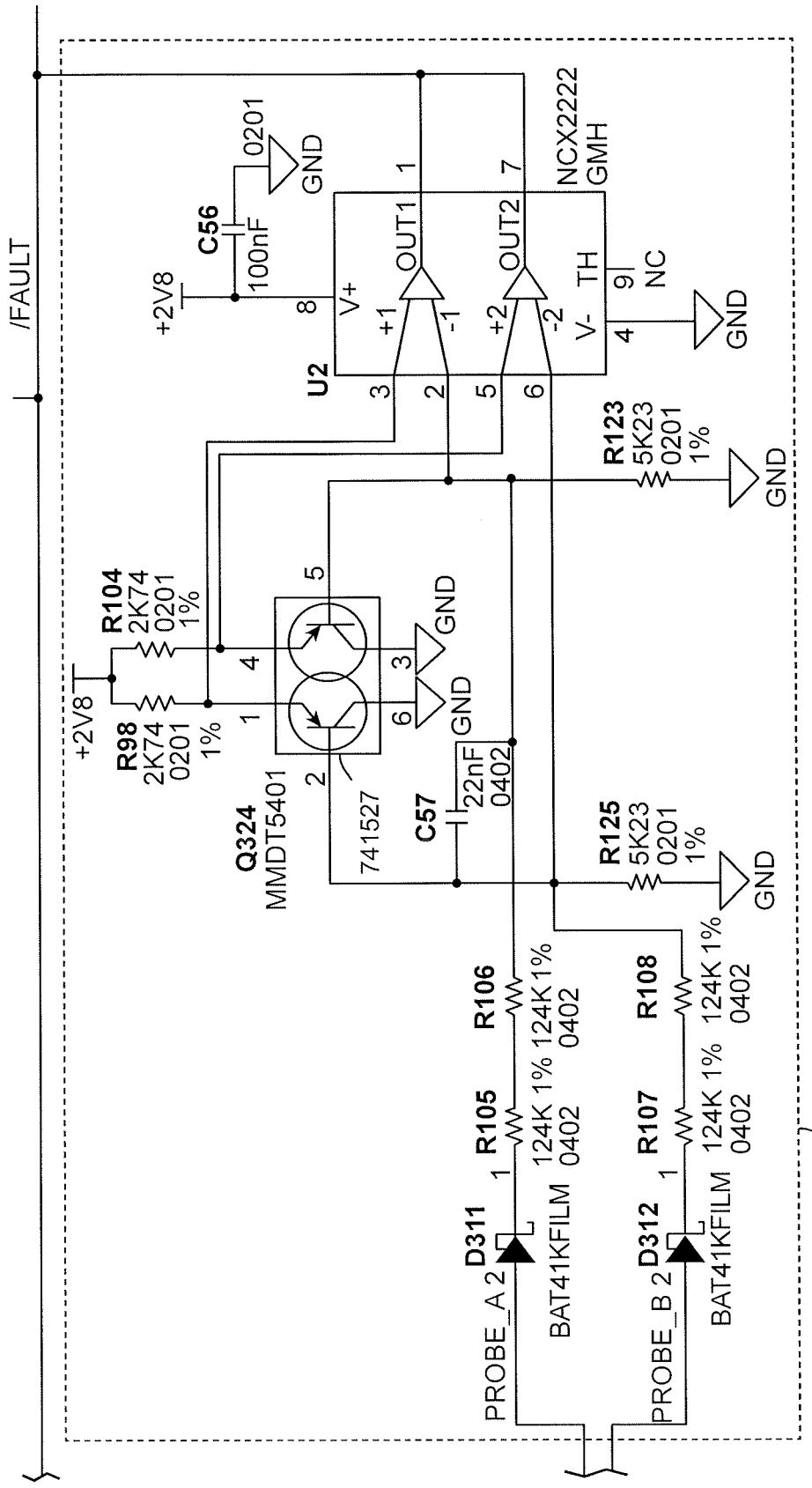

FIG. 74 schematically illustrates an example of a safety comparison circuit according to some embodiments of the disclosure.

Figure 75A:
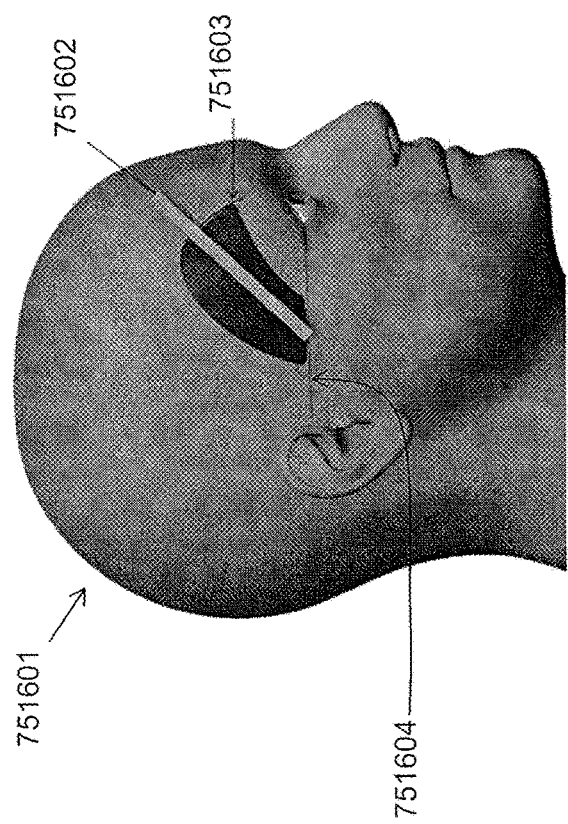

FIG. 75A illustrates one example of placement of a neurostimulator apparatus (TES apparatus) on a user's temple/forehead region.

Figure 75B:
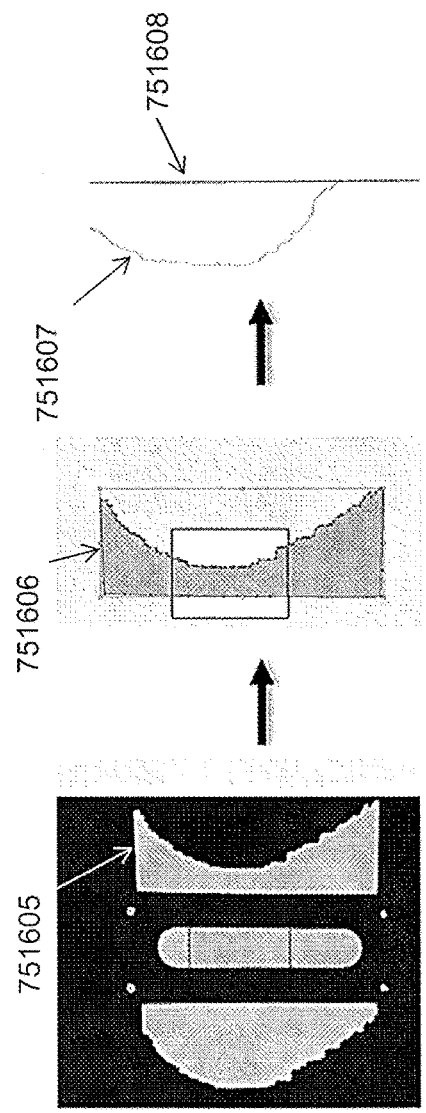

FIG. 75B illustrates one method of determining the curvature of a user's temple/forehead region.

Figure 75C:
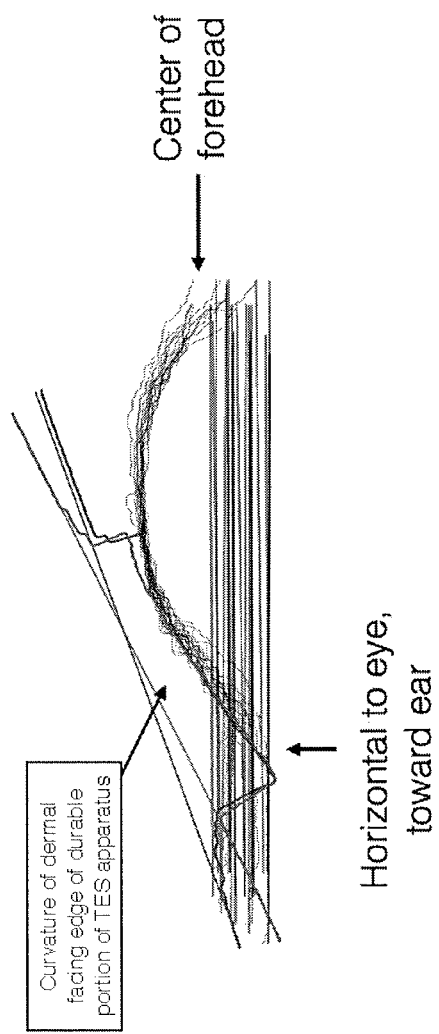

FIG. 75C shows exemplary curvature measurements taken from a sample of users (N=20), showing a generic curvature in one axis.

Figure 76A:
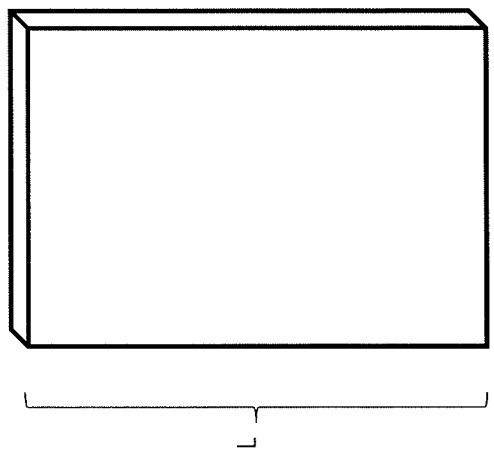
Figure 76B:
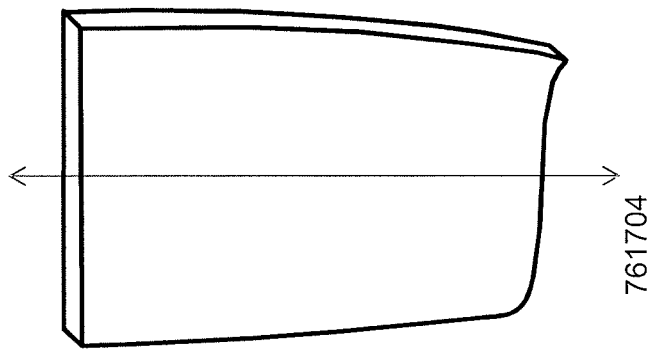
Figure 76C:
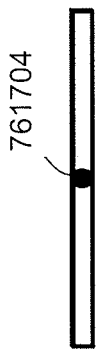
Figure 76D:
Figure 76E:
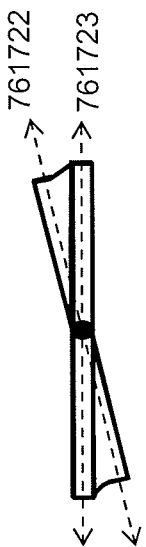
Figure 76F:
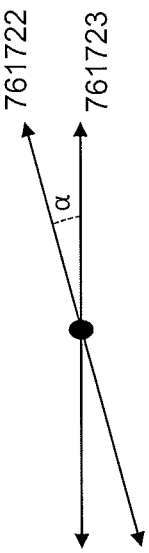

FIGS. 76A-76F illustrate twist (along an axis of twist) for an exemplary body (shown here as a sheet or rectangular body). FIGS. 76A and 76B show front perspective views of a sheet before (FIG. 76A) and after (FIG. 76B) twisting along an axis of twist. FIGS. 76C and 76D show top views, looking down, on the bodies shown in FIGS. 76A and 76B, respectively. FIGS. 76E and 76F illustrate the angle of twist (alpha, α).

Figures 77A, 77B, 77C:
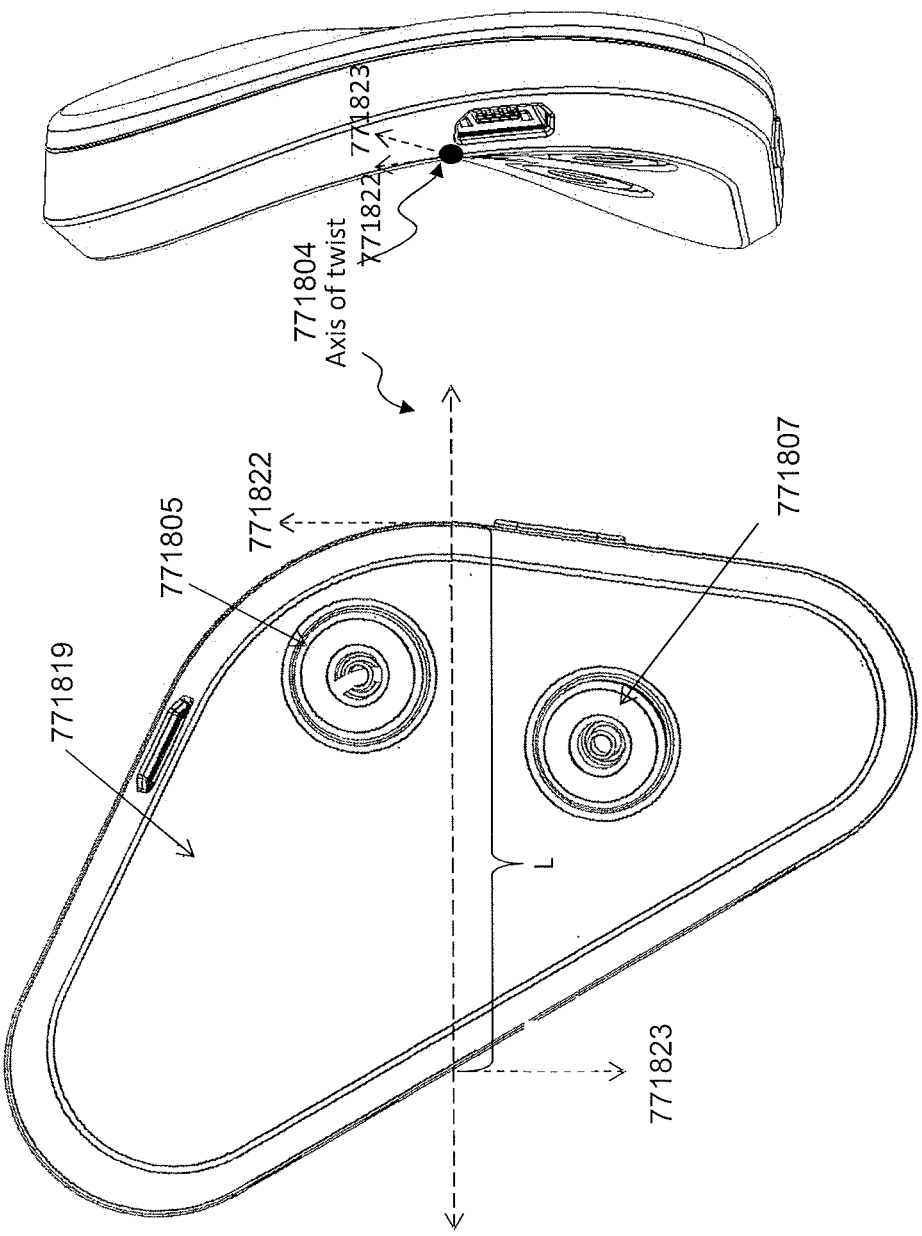

FIGS. 77A and 77B show back perspective and side perspective views, respectively, of a neurostimulator apparatus as described herein having a curved and twisted (along an axis of twist) back, user-facing surface, as well as a pair of connectors separated by approximately 0.72 inches.

FIG. 77C illustrates the angle of twisting of the back surfaces of the apparatus of FIGS. 77A and 77B.

Figure 78A:
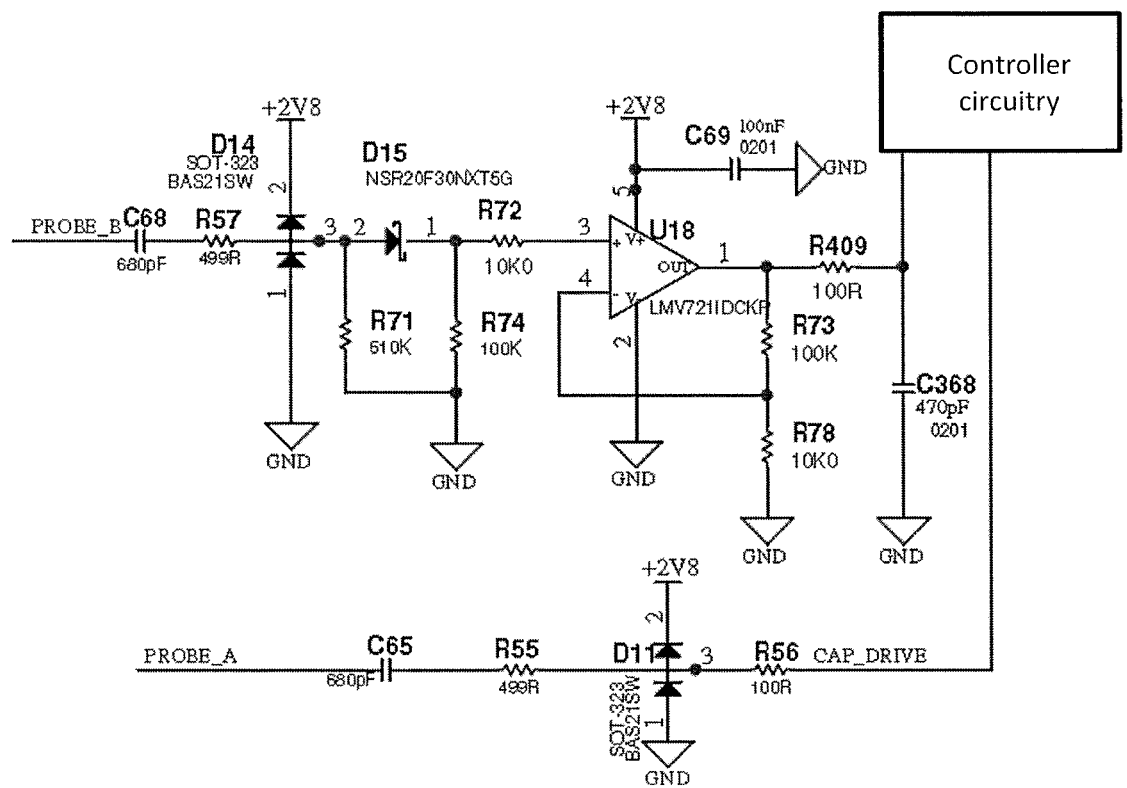

FIG. 78A is another example of a capacitance detection circuit to identify different electrode apparatuses connected to the neurostimulator apparatus.

Figure 78B:
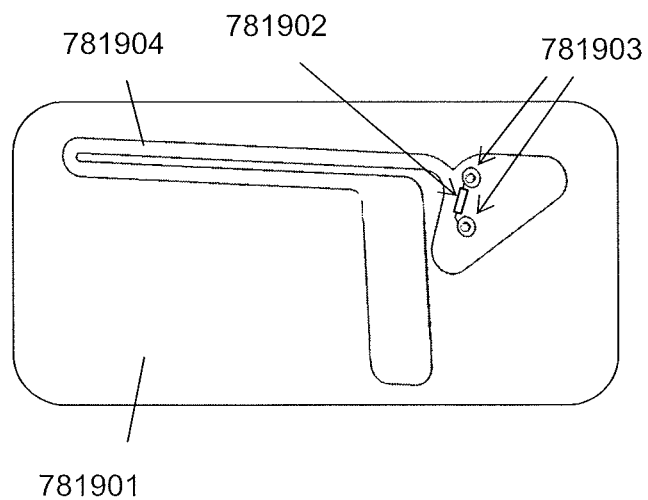

FIG. 78B is an example of an electrode assembly including a capacitor between the connectors to each of the two electrodes of the electrode assembly. In FIG. 78B, the electrode assembly is shown on support backing ('liner') that it may be peeled off of (and replaced onto).

Figure 78C:
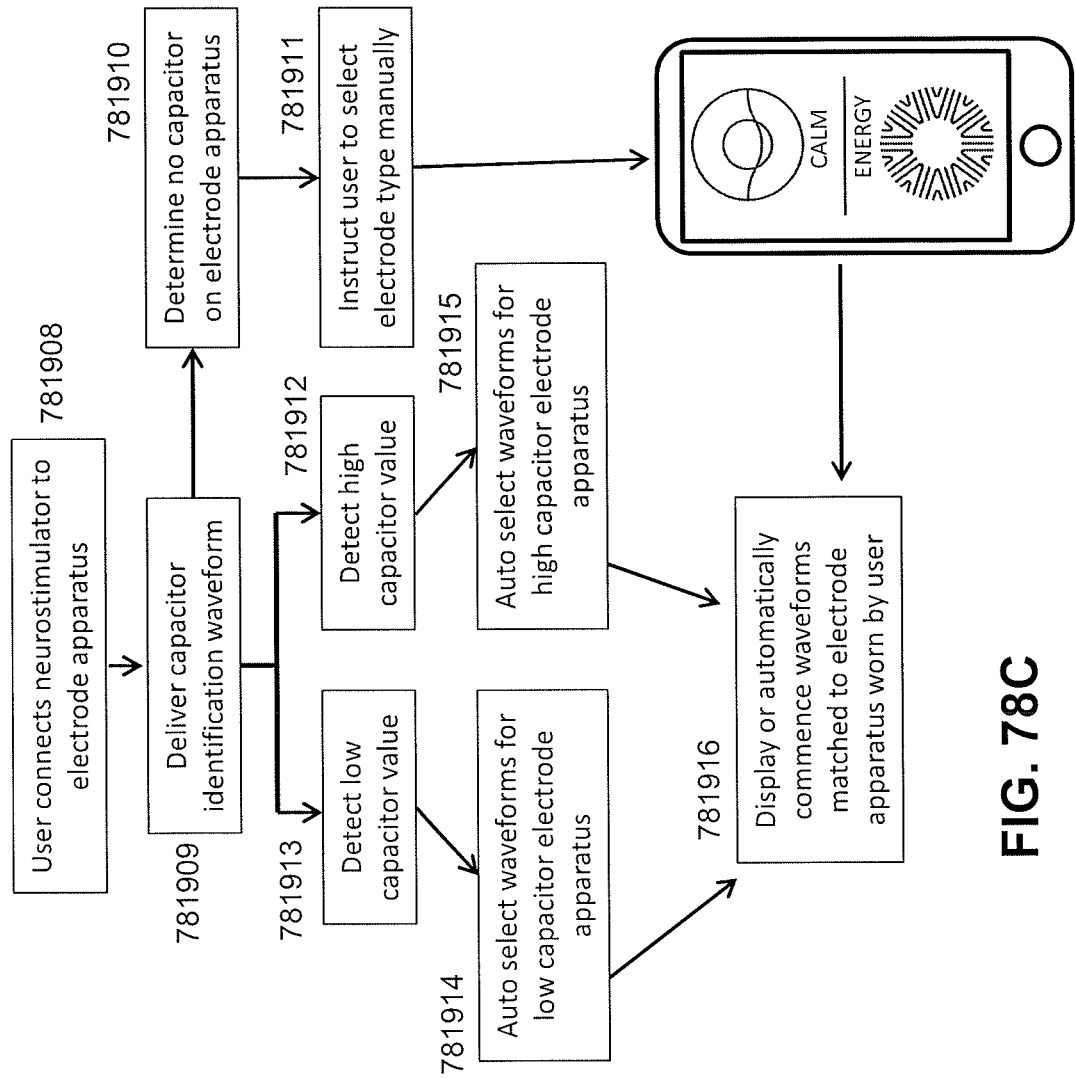

FIG. 78C is a flow diagram illustrating a method of determining the identity of different types of electrode apparatuses to which an electrical stimulator (e.g., neurostimulator) is attached.

FIG. 79 is a table illustrating the detection of three types of electrode assemblies using the capacitance detection circuit of FIG. 78A.

FIGS. 80A and 80B illustrate an example of an undistorted (FIG. 80A) and a distorted (FIG. 80B) current delivered across a pair of dermal electrodes.

FIGS. 80C and 80D illustrate the corresponding electrode voltage for the undistorted and distorted currents of FIGS. 80C and 80D, respectively.

Figures 81, 82A, 82B:
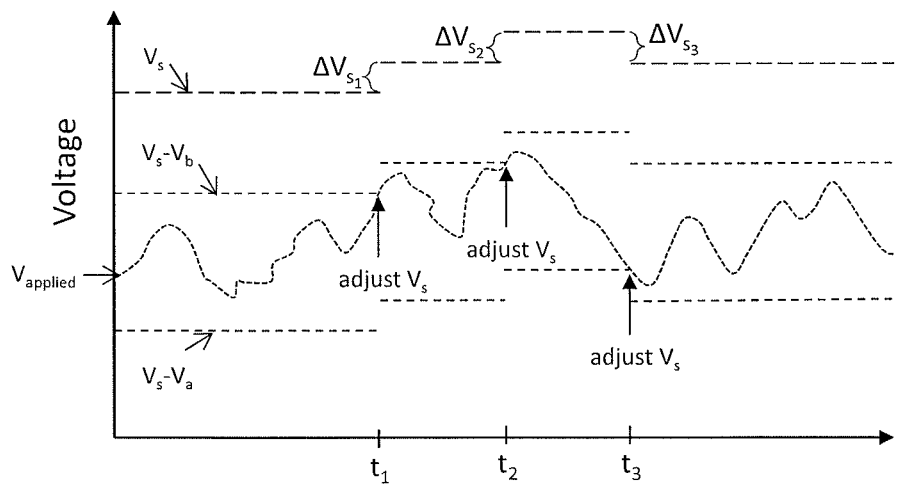

FIG. 81 graphically illustrates one variation of a method for adjusting the supply voltage ($V_s$) based on a comparison (e.g., difference) between the applied voltage and a predefined target voltage offset.

FIGS. 82A and 82B are an example of a control loop for regulating the supply voltage $V_s$ (FIG. 82B) as well as the applied current (FIG. 82A).

FIGS. 83A-83C show schematic representations of a TES apparatus having two modules connected by a durable cable that can be disconnected.

Figure 84:
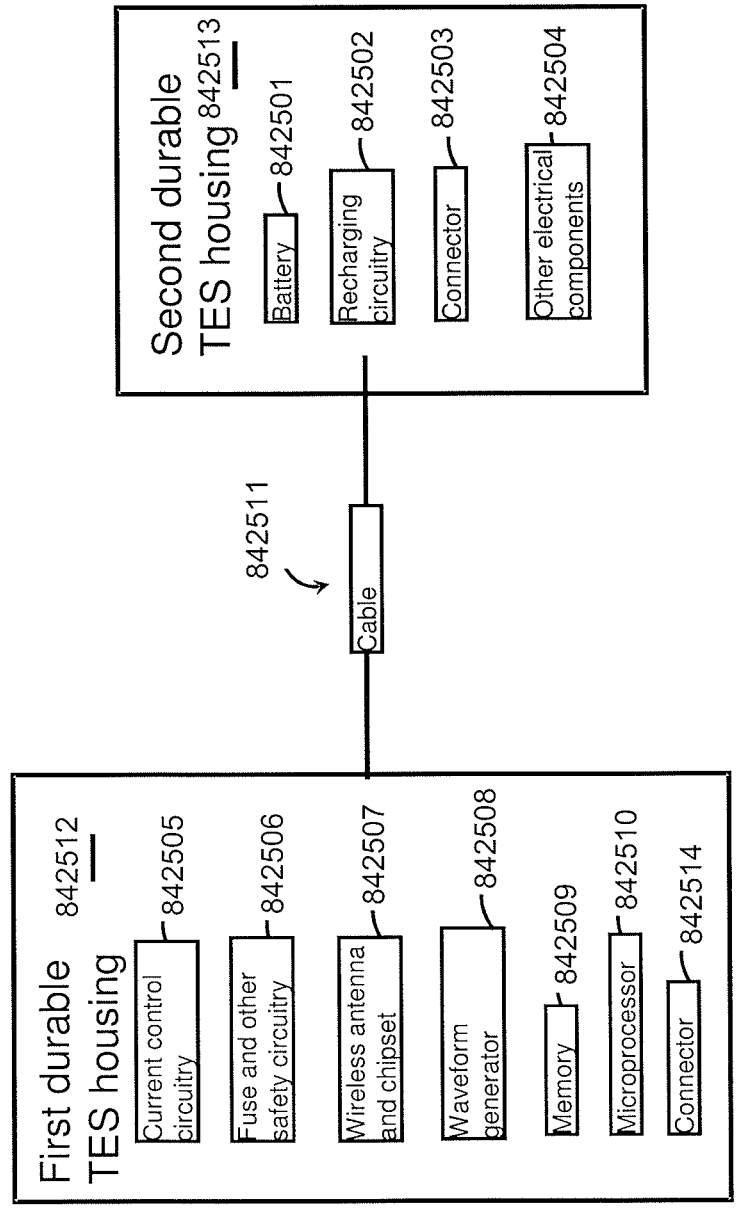

FIG. 84 shows the hardware features in a first durable TES housing and a second durable TES housing connected by a cable.

Figure 85:
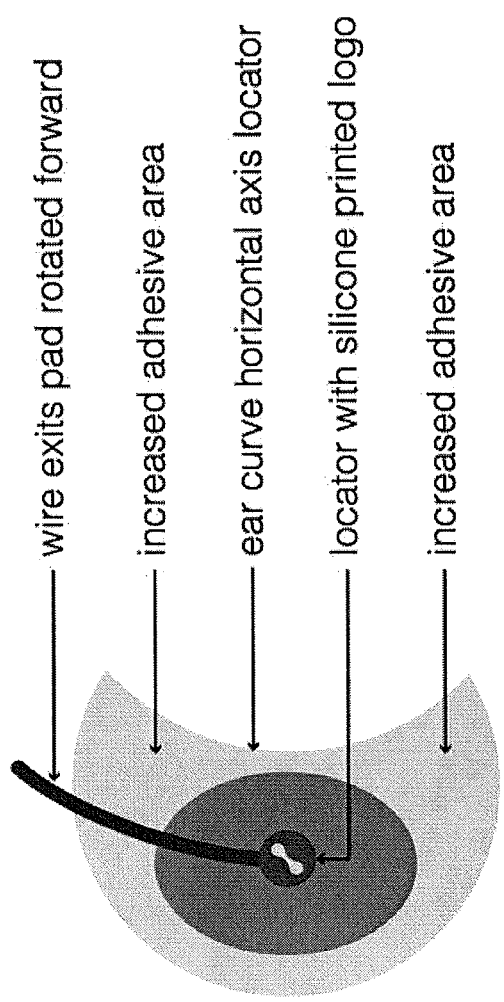

FIG. 85 shows a schematic of an adherent electrode assembly to be placed on the mastoid behind the right ear.

Figure 86:
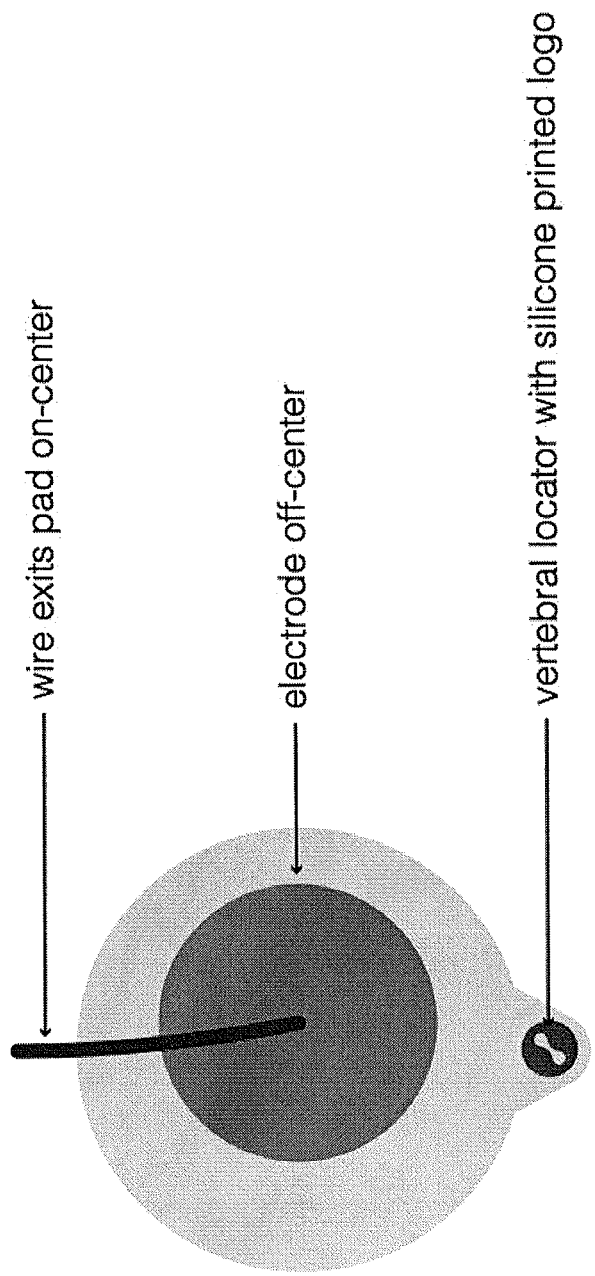

FIG. 86 shows a schematic of an adherent electrode assembly to be placed on the neck, slightly to the right of the midline.

Figure 87:
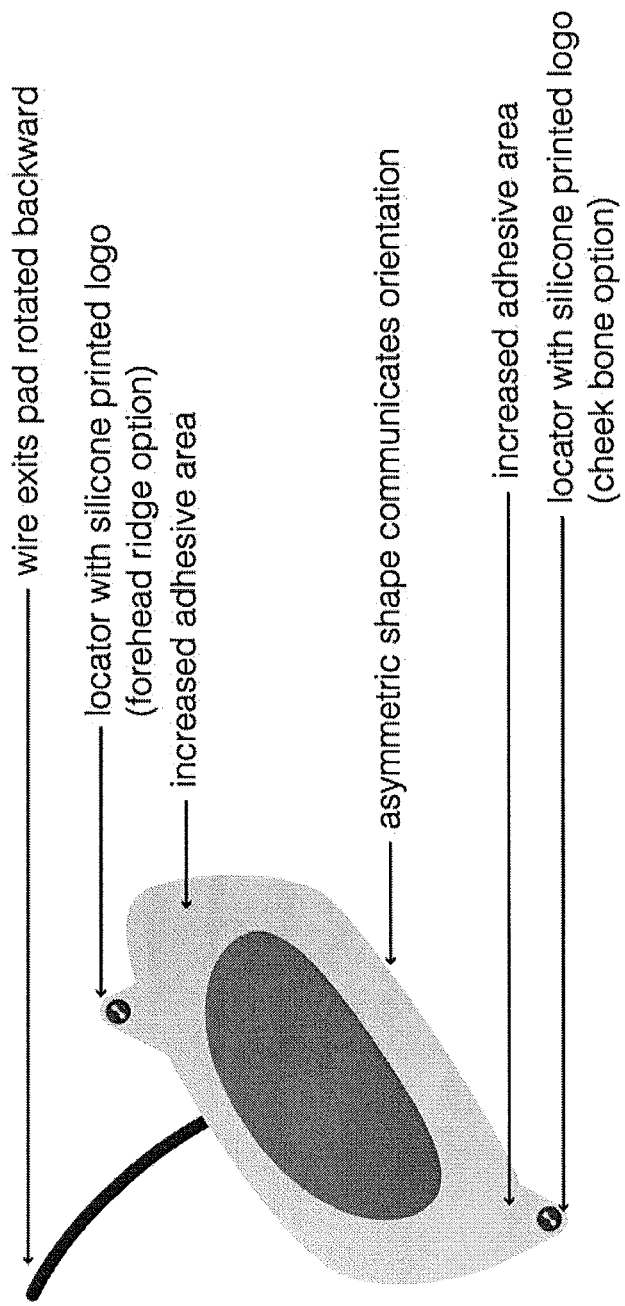

FIG. 87 shows a schematic of an adherent electrode assembly to be placed on the right temple area.

Figure 88C:
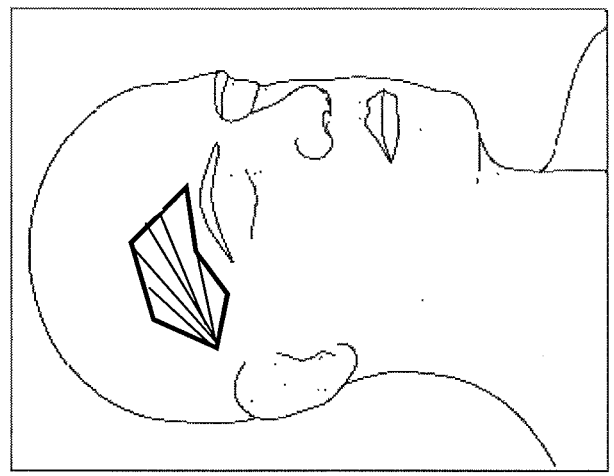
Figure 88B:
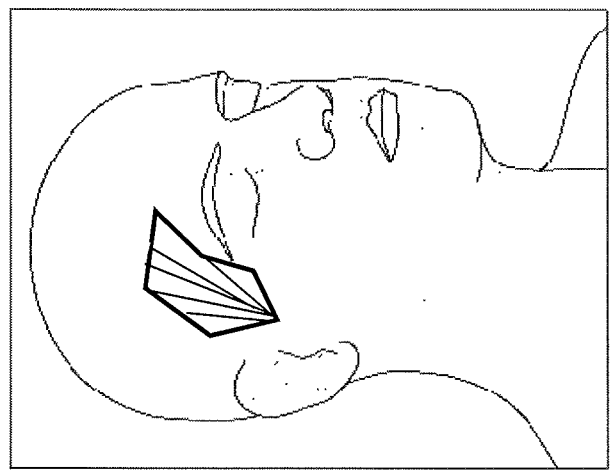
Figure 88A:
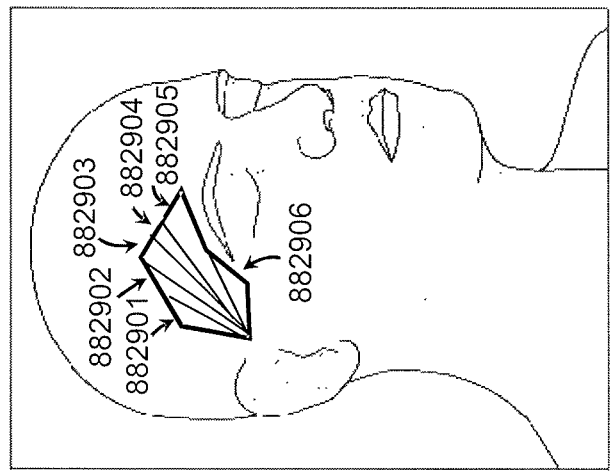

FIGS. 88A-88C show an electrode assembly for use with a neurostimulator having an array of electrodes contained within the electrode assembly that can be used to improve anatomical positioning by activating a subset of electrodes overlying targeted regions of the user.

Figure 89A:
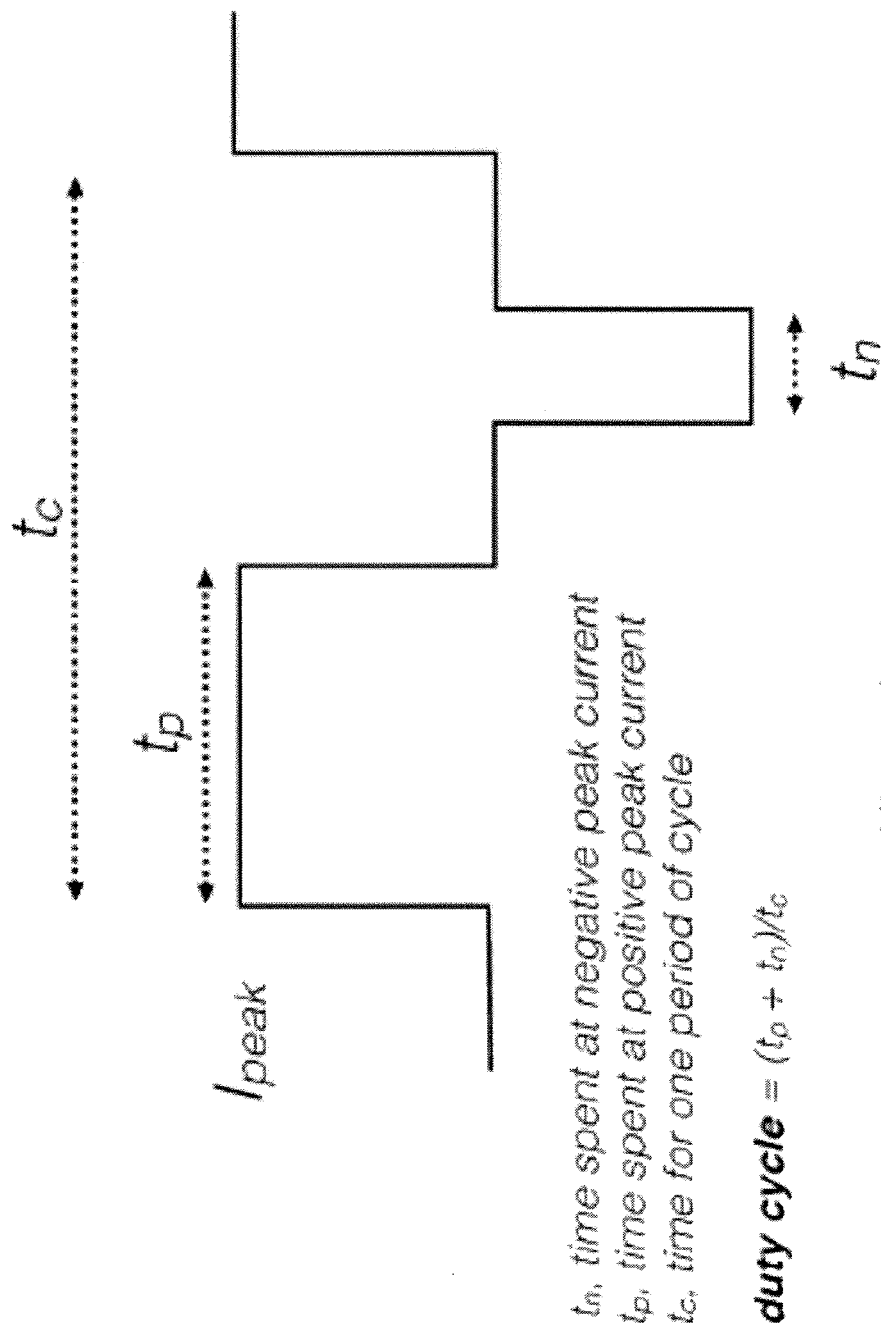

FIG. 89A schematically illustrates a base waveform which may be repeated and modified according to waveform parameters to form component waveforms which may be combined to form ensemble waveforms, as described herein.

Figure 89B:
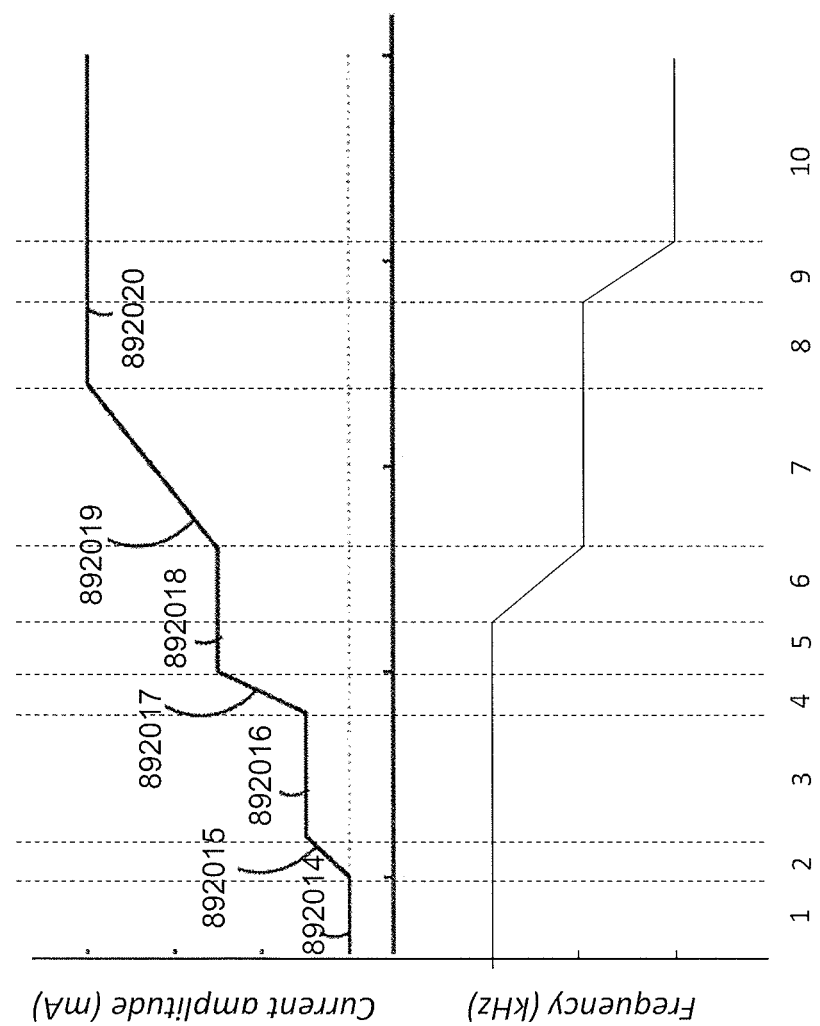

FIG. 89B illustrates one variation of an ensemble waveform, graphically depicted to show the current amplitude and frequency waveform components (but not percent charge imbalance or duty cycle).

Figure 89C:
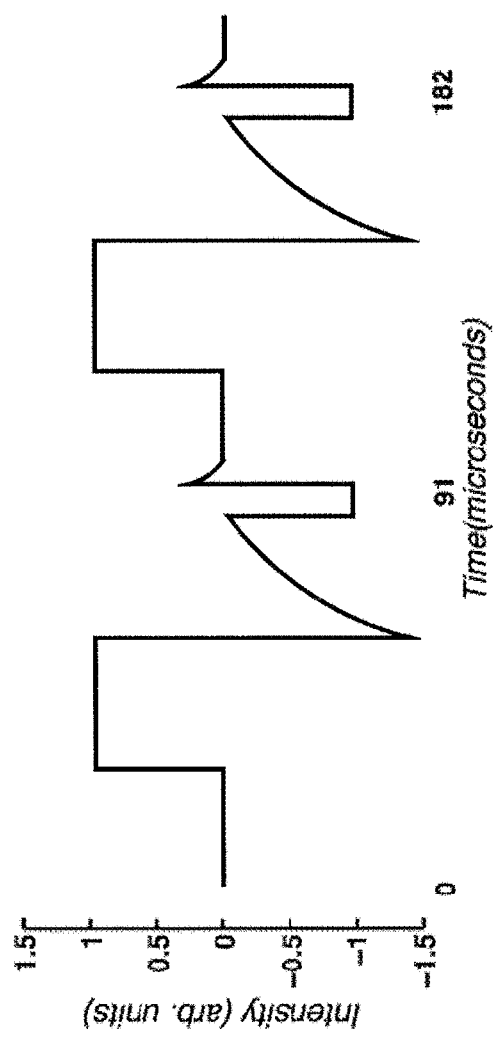

FIG. 89C illustrates one variation of a pair of base waveforms including a first variation of a capacitive discharge.

Figure 89D:
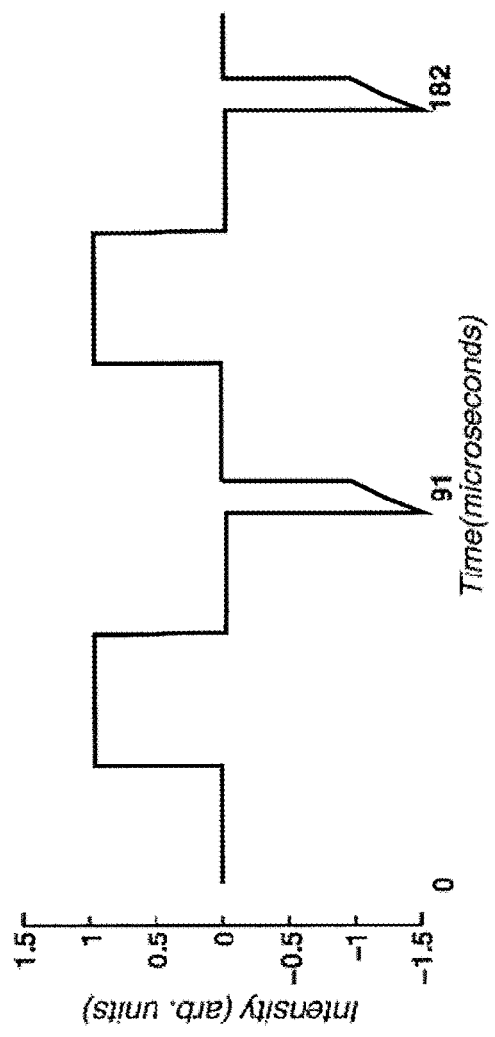

FIG. 89D illustrates a second variation of a pair of base waveforms including a second variation of capacitive discharge.

FIGS. 90A, 90B and 90C schematically illustrate another example of an ensemble waveform (configured as an 'energy' ensemble waveform) as described herein. FIG. 90A illustrates the current parameter of the ensemble waveform. FIG. 90B schematically indicates the durations of the component waveforms forming the ensemble waveform. FIG. 90C illustrates the frequency parameter of the ensemble waveform.

Figure 90D:
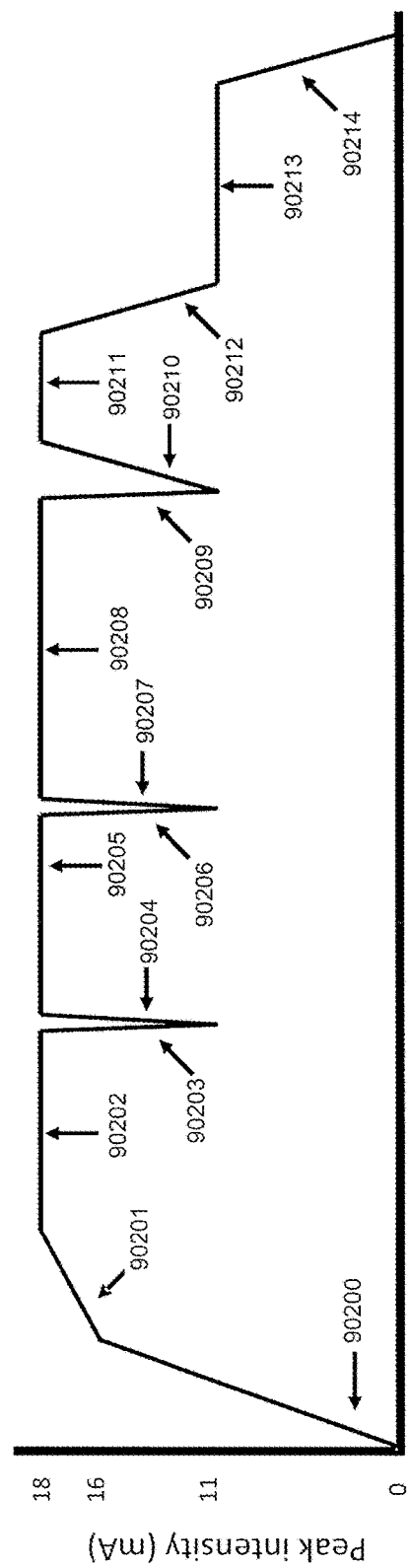
Figure 90E:
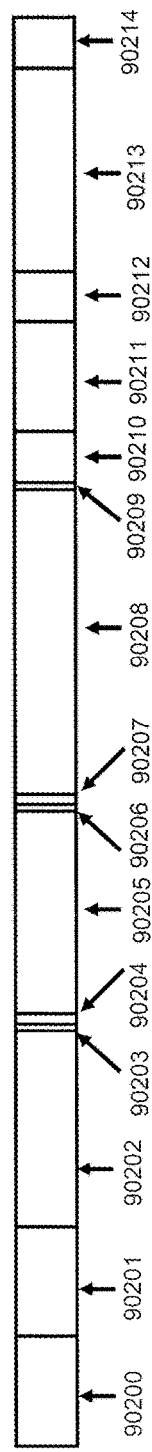
Figure 90F:
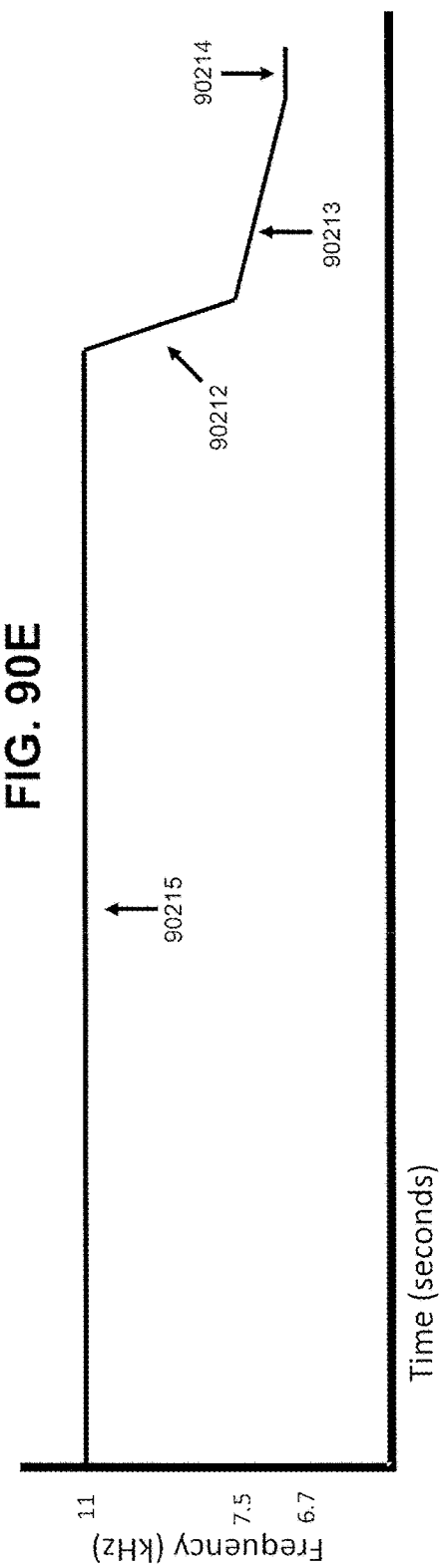

FIGS. 90D, 90E and 90F schematically illustrate another example of an ensemble waveform (configured as a 'calm' ensemble waveform) as described herein. FIG. 90D illustrates the current parameter of the ensemble waveform. FIG. 90E schematically indicates the durations of the component waveforms forming the ensemble waveform. FIG. 90F illustrates the frequency parameter of the ensemble waveform.

Figure 91A:
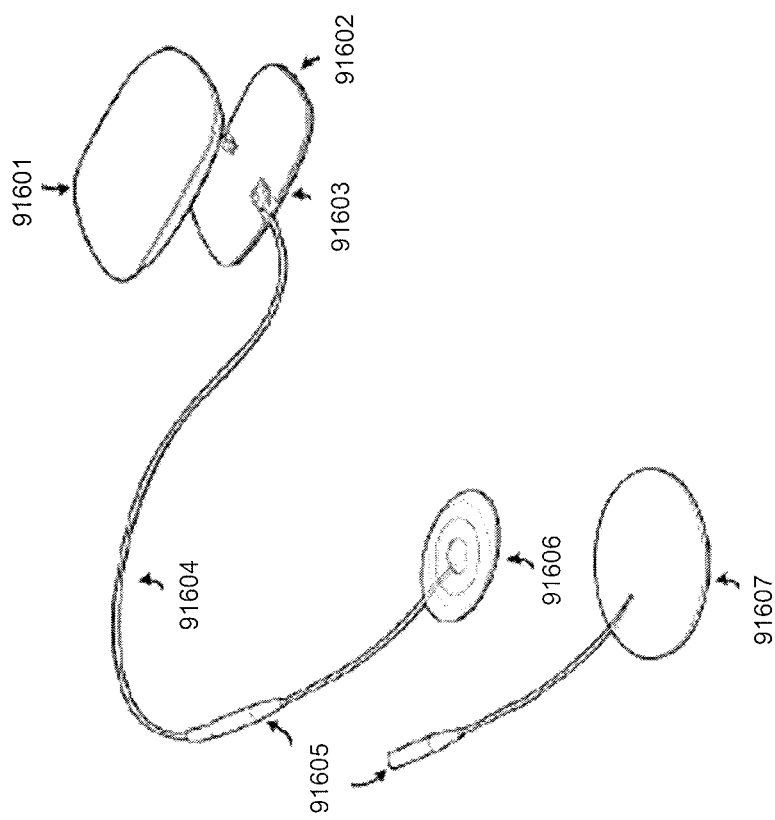
Figure 91F:
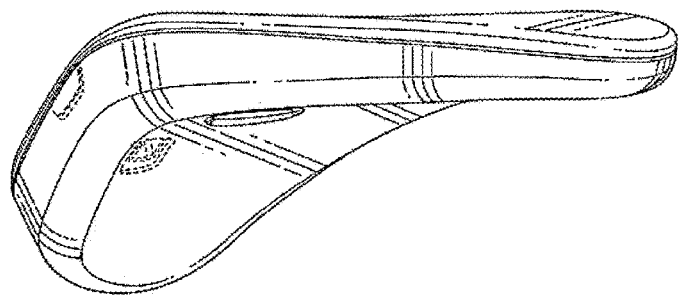
Figure 91D:
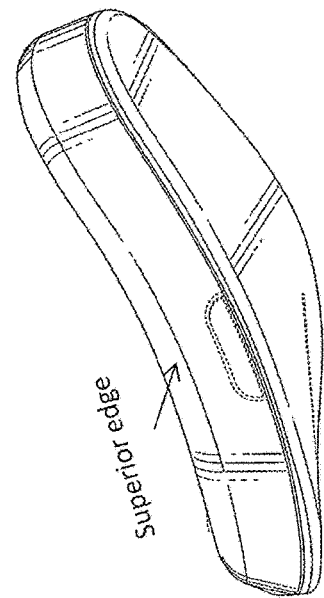
Figure 91E:
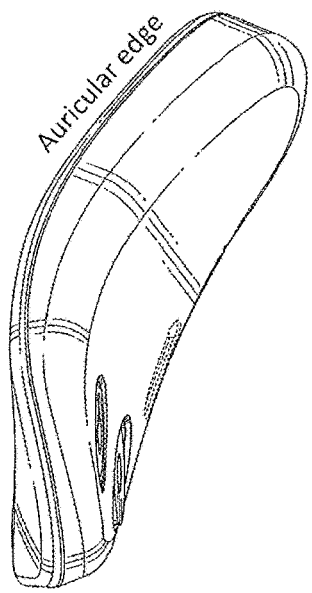
Figure 91G:
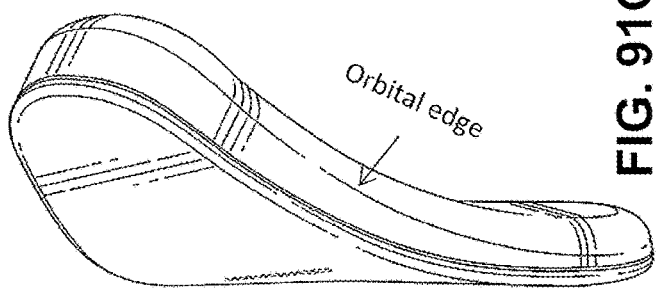
Figure 91B:
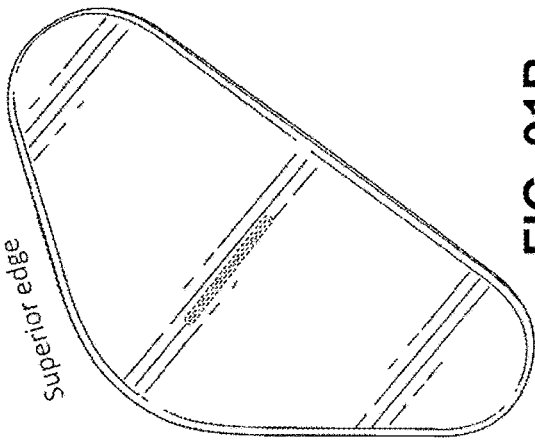
Figure 91C:
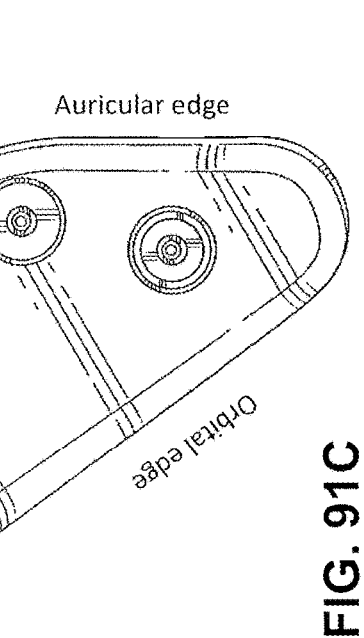

FIG. 91A illustrates one example of a neurostimulator that may be configured for use with (and may deliver) the ensemble waveforms described herein.

FIGS. 91B-91G illustrate another example of a neurostimulator as described herein.

FIGS. 91H-91K illustrates a first example of one variation of an electrode assembly, configured as a "calm" electrode assembly.

FIGS. 91L-91o illustrate a second example of one variation of an electrode assembly, configured as an "energy" electrode assembly.

Figure 91Q:
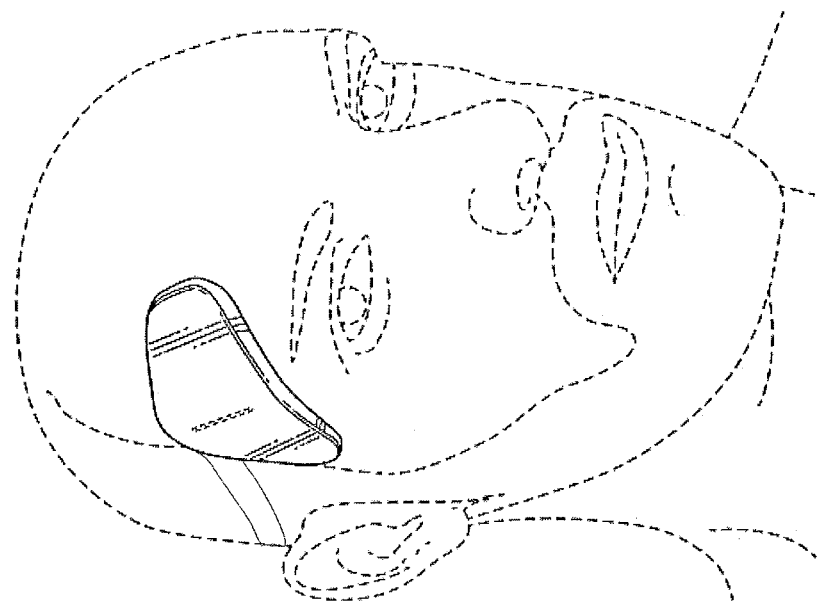
Figure 91P:
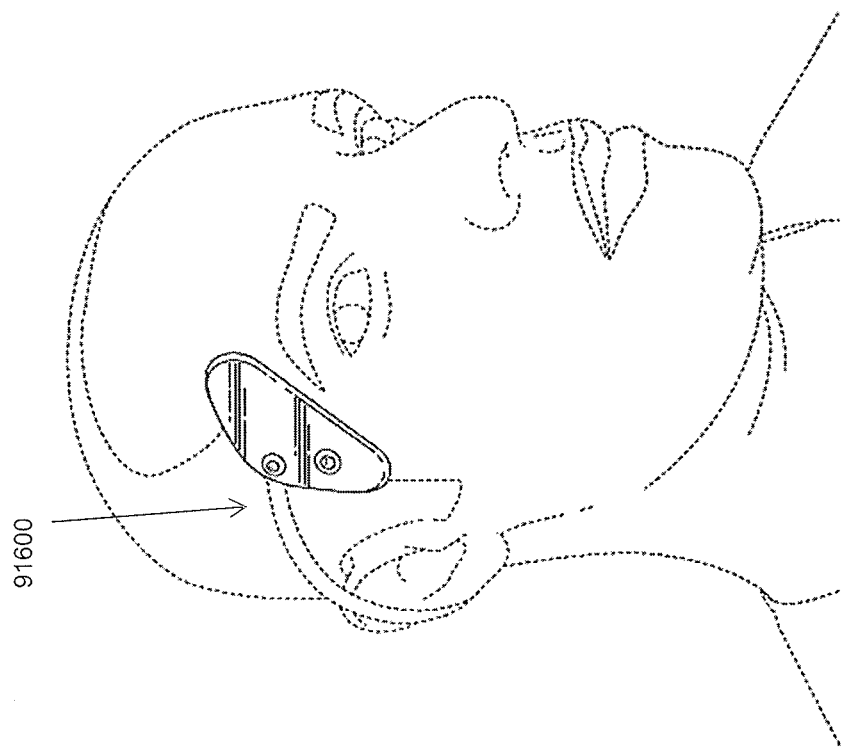

FIG. 91P illustrates the application of an electrode assembly that may be worn on the subject's head, and/or head and neck to induce a cognitive effect.

FIG. 91Q illustrates the neurostimulator device worn on the subject's head.

FIG. 92A is a table with waveform parameters of another example of a calm ensemble waveform.

FIG. 92B is a table with another variation of a calm ensemble waveform.

FIG. 92C is a table with another variation of a calm ensemble waveform.

FIG. 93A is a table listing waveform parameters of another example of an energy ensemble waveform.

FIG. 93B is a table listing waveform parameters of another example of an energy ensemble waveform.

FIG. 94 is a table describing one example of an "add-in" waveform, which may be selected by the user to evoke a predetermined effect, such as enhancing the cognitive effect. In this example, the add-in parameters modify the parameters of the ensemble waveform, for example by adjusting the intensity for a predetermined duration (having 6 component epochs or regions of the add-in, spanning 9.2 seconds). This example adjusts the stimulation intensity down gradually (over 7 seconds or so), then rapidly steps up back to its previous value.

FIG. 95 is a table showing values for one variation of an ensemble waveform that may be used for evoking a calming cognitive effect. This variation is a 10 minute compound or ensemble waveform having 20 component waveforms, where all of the component waveforms are amplitude modulated (e.g., using a square waveform) and each component waveform may be amplitude modulated with different AM frequencies and/or duty cycles.

FIGS. 96A-96D illustrate examples of the amplitude modulation (AM) waveforms that may be applied onto the ensemble waveforms (or component waveforms of the ensemble waveforms described herein). In FIGS. 96A-96D, amplitude modulation square pulses are used as the amplitude modulating waveform (typically having an amplitude of zero or 1, and an instantaneous or near-instantaneous rise/fall time).

FIGS. 97A-97D show examples of various amplitude modulation waveform shapes that may be used to provide a repeating and time-varying scaling factor of waveform intensity.

FIGS. 98A-98C illustrate an example of amplitude modulation using a sinusoid waveform as the amplitude modulating waveform; FIGS. 98B and 98C illustrate expanded time scale views of the amplitude modulated component waveforms (note the different peak intensities).

FIG. 98D illustrates another example of a sinusoidal amplitude modulation signal that has a non-zero minimum, so that the ensemble (or component waveforms of the ensemble waveform) are dampened to a non-zero level.

Figure 99:
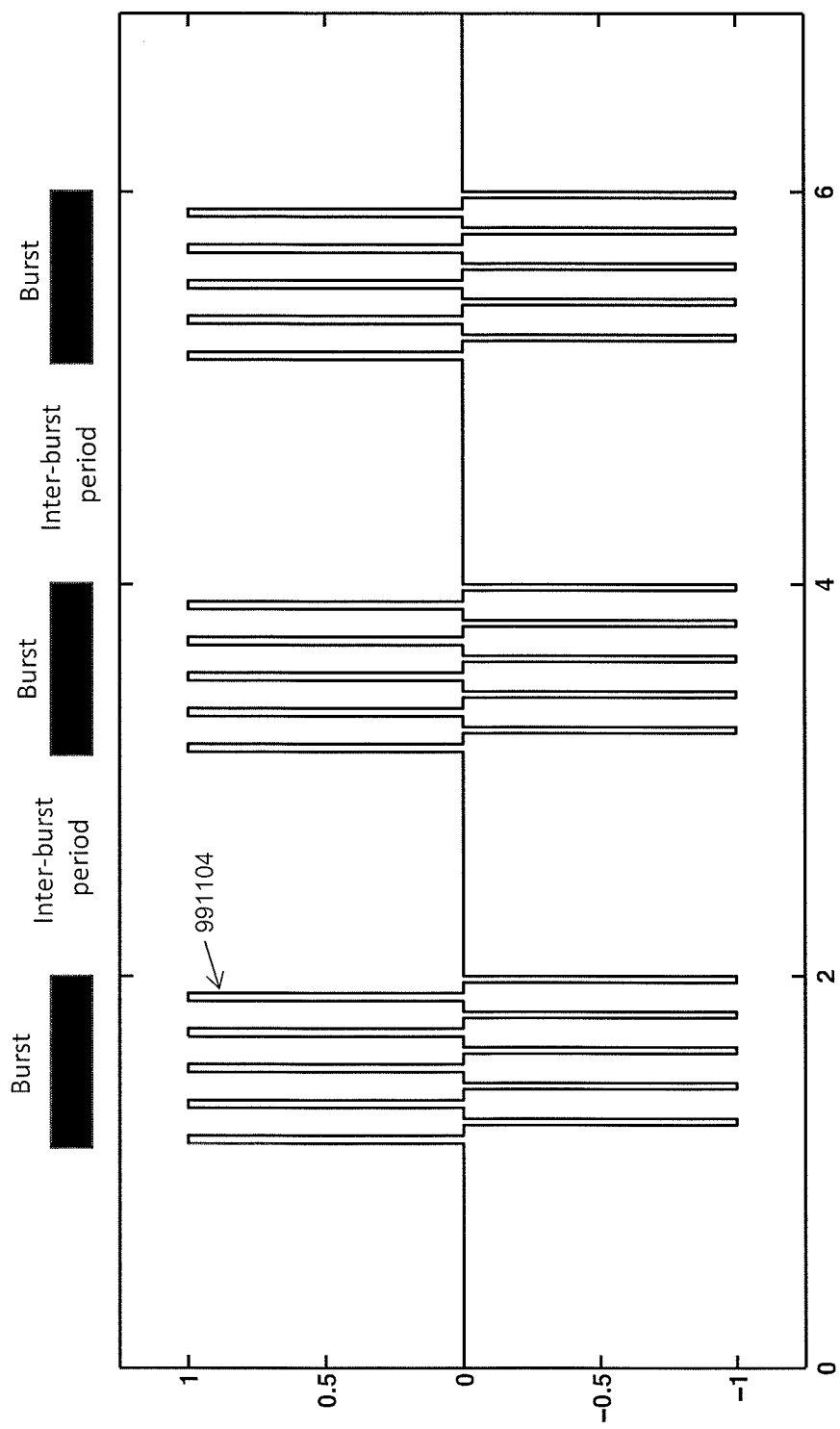

FIG. 99 graphically depicts the use of amplitude modulation (AM) with a square pulse AM modulating waveform.

FIGS. 100A and 100B graphically illustrate the use of amplitude modulation (where the modulating waveform is a sinusoid as shown in FIG. 100A) to modulate a component (or ensemble) waveform as shown.

FIG. 101 is a table showing one example of the component waveform parameters configured to evoke a calm cognitive state, having a five minute duration. This example is amplitude modulated (at a constant level across all 3 component waveforms). The waveform shape of the AM may be square, sinusoidal, etc.

FIG. 102 is a table showing an example of the component waveform parameters for an ensemble waveform configured to evoke a calm cognitive state, having a six minute duration. In this example the ensemble waveform is amplitude modulated and the amplitude modulation changes (e.g., at each component waveform beginning after the second component waveform).

FIG. 103 is a table showing an example of the component waveform parameters for an ensemble waveform configure to evoke a calm cognitive state, having a ten minute duration. In this example, the amplitude modulation also changes between some of the different component waveforms (e.g., changing AM frequency and/or percent duty cycle).

Figures 104A, 104B, 104C, 104D, 104E:
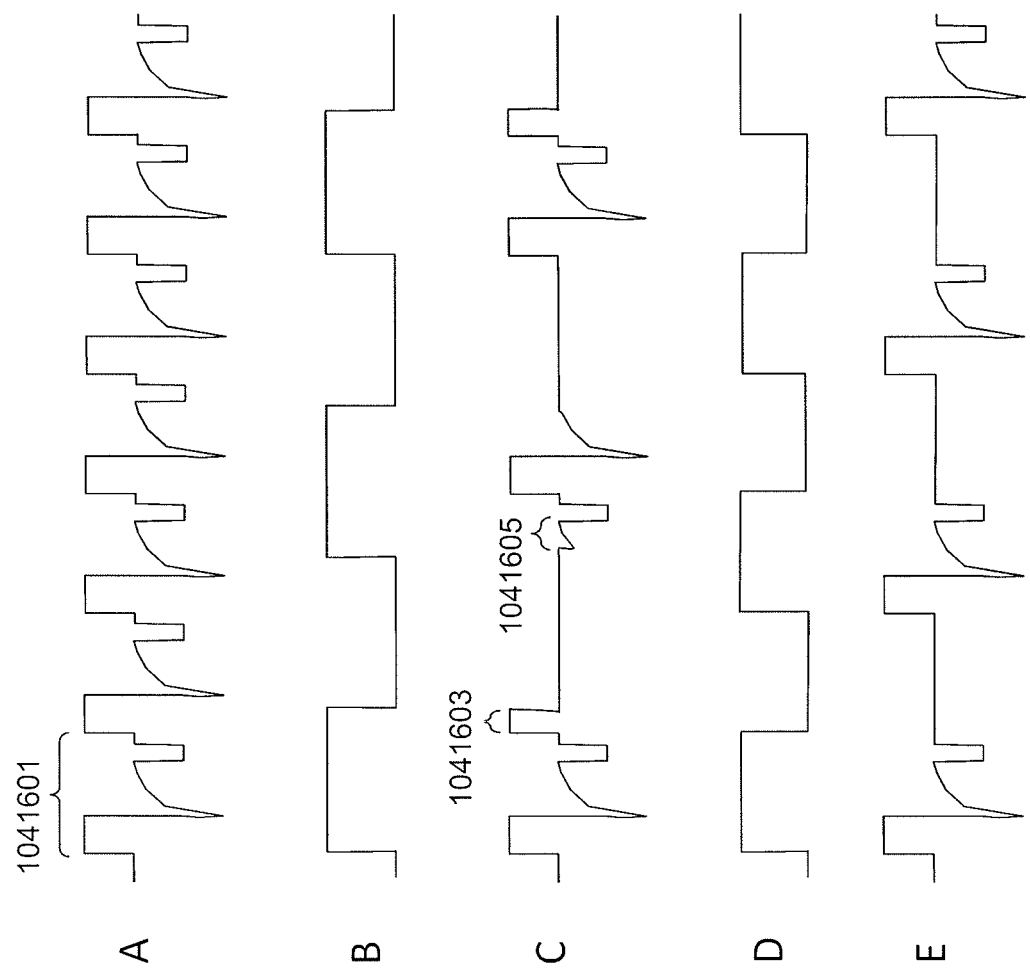

FIGS. 104A-104E illustrate the principle of correction, adjustment and/or selection of an amplitude modulation signal (e.g., frequency and/or percent duty cycle, also referred to as burst frequency and burst length) for an amplitude modulated component waveform, in order to prevent truncation of component waveforms. FIG. 104A illustrates one example of a component waveform. FIG. 104B illustrates one example of an amplitude modulation envelope waveform. FIG. 104C illustrates truncation of signals from the exemplary component waveform shown in FIG. 104A when amplitude modulated by the AM envelope shown in FIG. 104B. FIG. 104D illustrates a corrected AM envelope in which the AM frequency (the inverse of the amplitude modulation duration) of the envelope signal has been modified to prevent truncation of the component waveform signals, as shown in FIG. 104E.

Figure 105B:
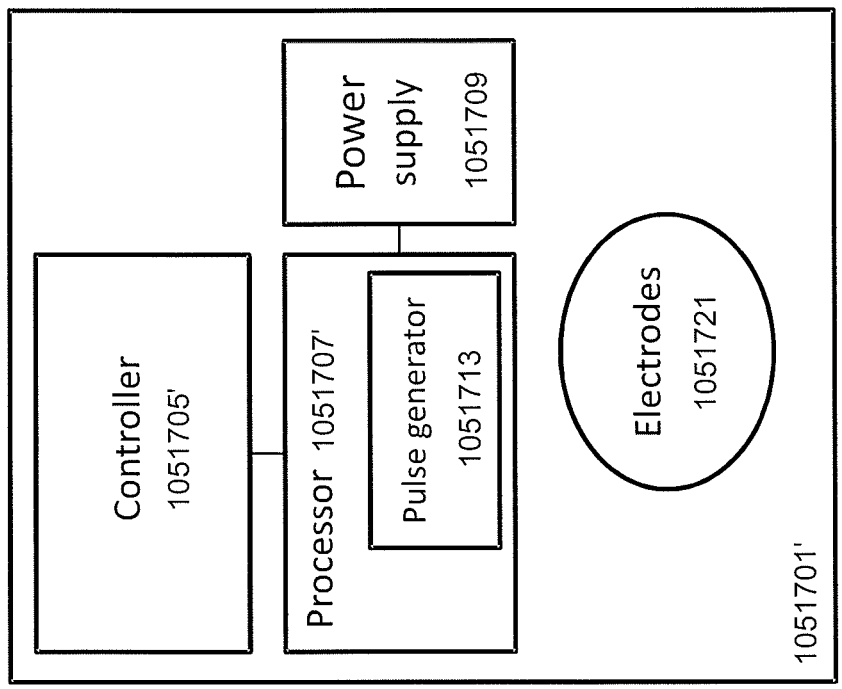
Figure 105A:
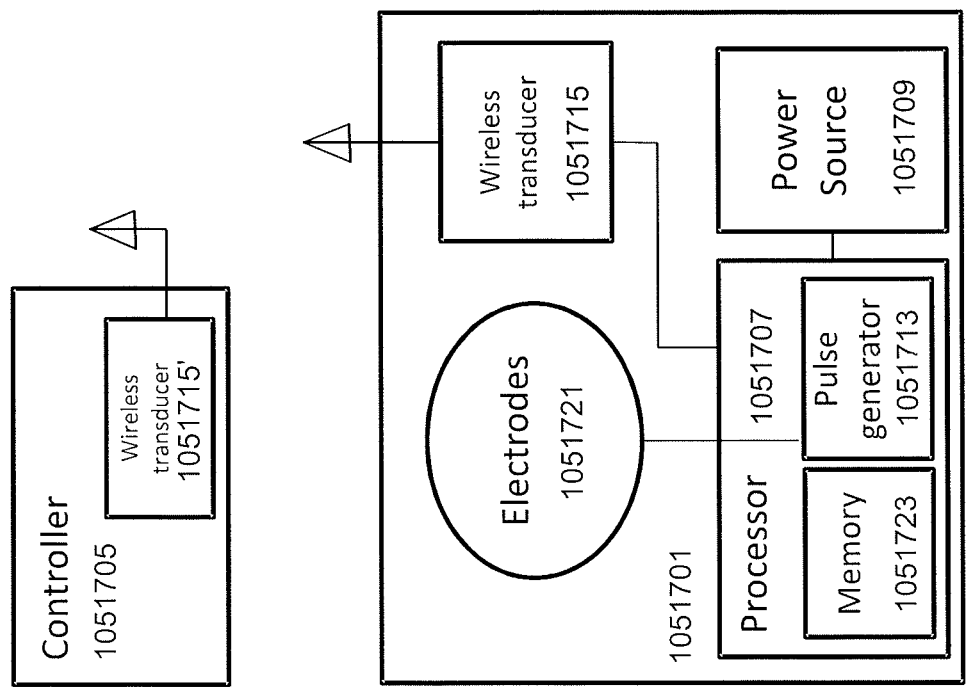

FIG. 105A is a schematic illustration of one example of an apparatus (e.g., system) including a wireless controller that sends command instructions, including ensemble waveform information, to a wearable neurostimulator having a processor adapted to receive and interpret this information, which may be sent in an abbreviated and efficient message encoding system.

FIG. 105B is a schematic illustration of another example of a system in which the controller and processor are directly connected, rather than wirelessly connected.

Figure 106A:
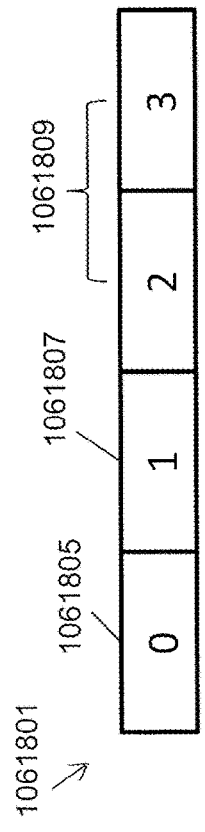

FIG. 106A schematically illustrates a generic message (e.g., a message format having a size, in this example, of 20 bytes) configured for transmission between the controller and the processor of the neurostimulator.

Figure 106B:
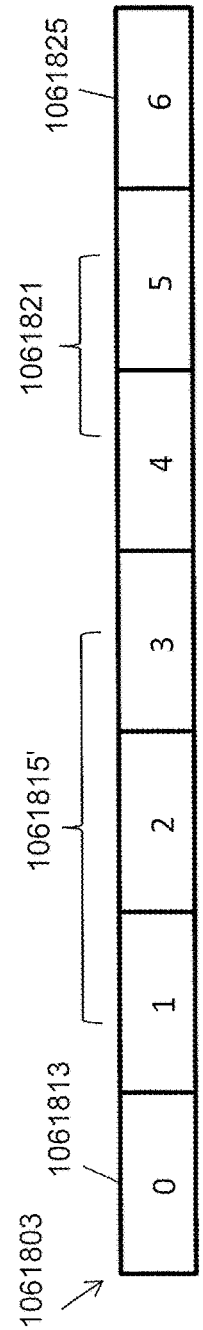

FIG. 106B illustrates one example of a first control signal (e.g., the message payload of the first control signal) that may be sent by a remote controller to a processor of a wearable neurostimulation device in order to prepare the device (e.g., prepare space in the processors memory) to start a new waveform (new component waveform of an ensemble waveform) or modify an existing component waveform. The neurostimulator apparatus may be configured to receive this signal.

Figure 106C:
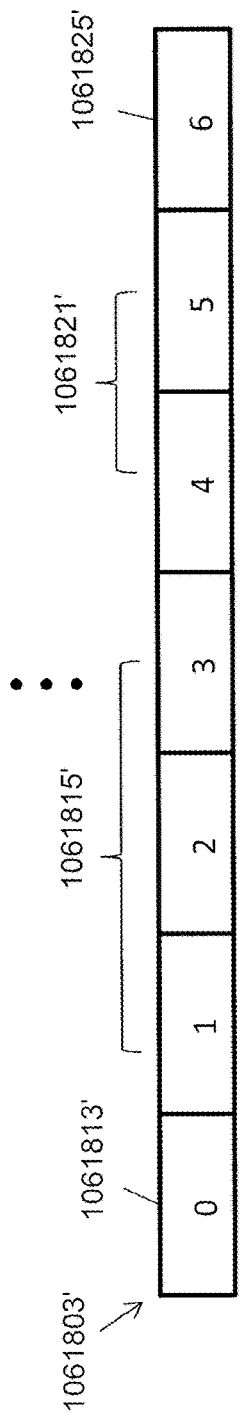

FIG. 106C illustrates one example of a second (and additional, e.g., n) control signal in a series of segments (segment message payloads) encoding information sufficient to allow the neurostimulator to drive the component (and therefore ensemble) waveform signals. A total of n different segment control messages (including message payloads as shown here) may be sent and received as illustrated to efficiently and effectively guide the controller (e.g., a smartphone or other apparatus) in applying effective neurostimulation.

Figure 107A:
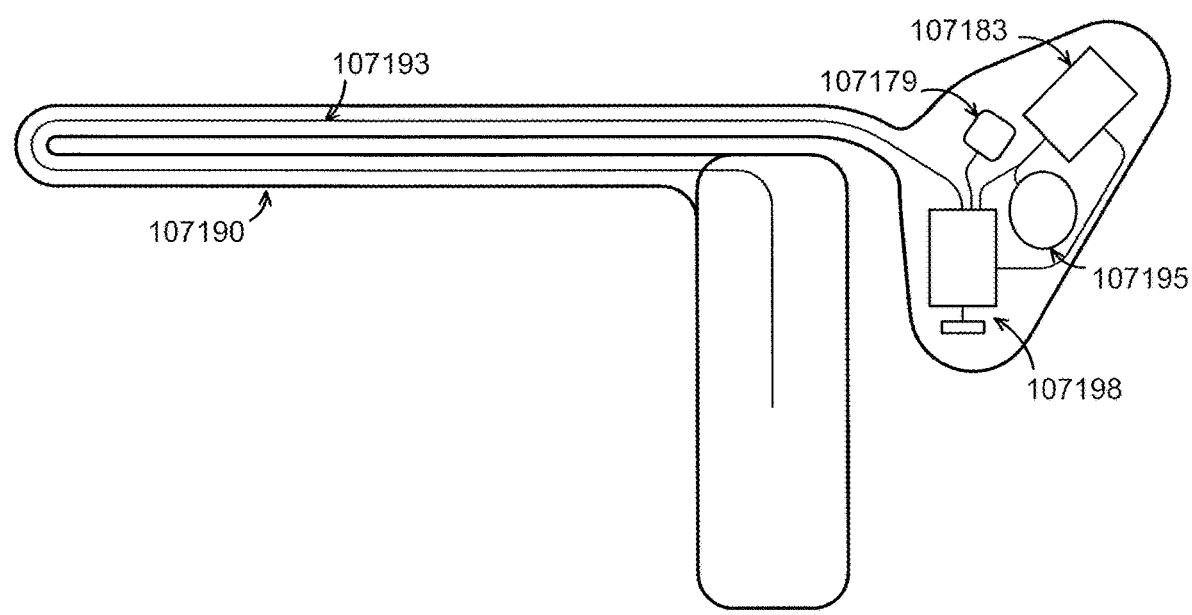

FIG. 107A is an example of a TES patch neurostimulator apparatus configured to be worn on a subject's head. The apparatus includes a pair of electrodes connected through flexible circuit body to neurostimulator circuitry (including a power source).

Figure 107B:
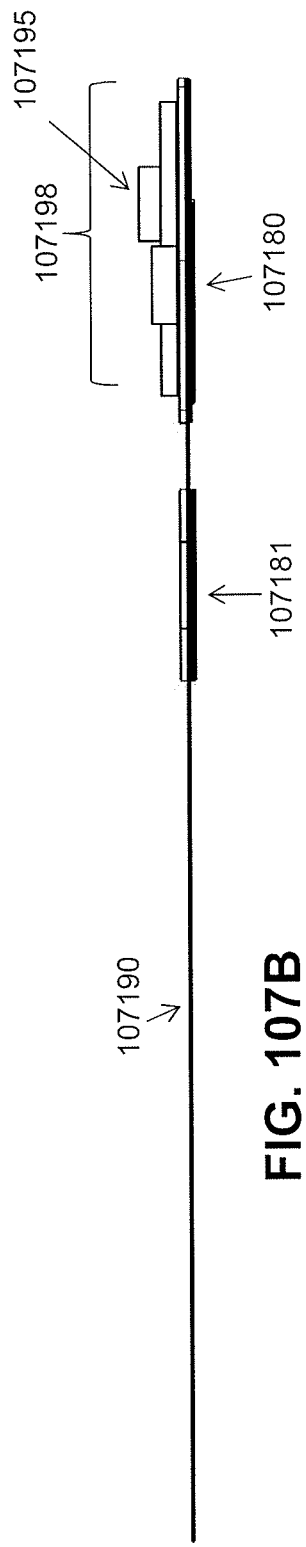

FIG. 107B is a side view (end on) of the apparatus of FIG. 107A.

Figure 107D:
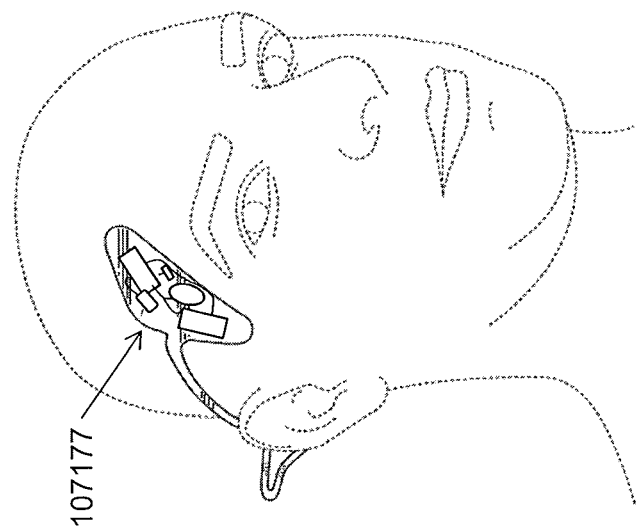
Figure 107C:
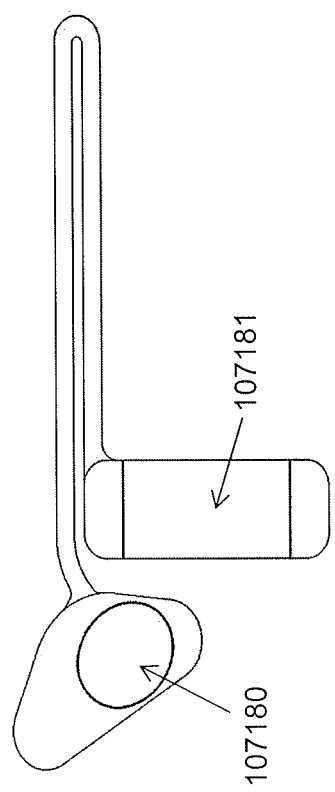

FIG. 107C is a back view of the apparatus of FIG. 107A, showing the electrode regions.

FIG. 107D is a perspective view of the TES patch neurostimulator worn on a user's head.

FIG. 108A is another example of a TES patch neurostimulator similar to the variation shown in FIG. 107A, but with the majority of the neurostimulator circuitry on a portion of the flex circuit body to be worn on the back of the user's neck, rather than the temple/forehead region.

FIG. 108B shows a side view of the apparatus of FIG. 108A.

FIG. 109A is an example of near-field communication selector to be used with a TES patch neurostimulator apparatus such as those shown in FIGS. 107A and 108A. This near-field communication selector may include waveform parameters (e.g., ensemble waveform parameters and/or instructions for selecting an ensemble waveform parameter) and other control information (e.g. a waveform intensity or frequency) to be used for operation of the TES patch neurostimulator.

FIG. 109B is a side view of the near-field communication selector of FIG. 109A.

FIG. 109C illustrates the application of the near-field communications selector onto a TES patch neurostimulator to provide control information for operating the apparatus. In this example, the near-field communication selector is adhesively secured to the TES patch neurotransmitter, enabling the function of the apparatus.

FIG. 110A is an example of a smart cable (TES cable neurostimulator) for use with an electrode assembly to be worn on a subject. The TES cable neurostimulator may connect (and receive power and control instructions) to a portable computing device such as a smartphone, and also connect directly to the connectors (e.g., snap connectors are shown) of an electrode assembly. The cable may be reused with multiple disposable (single-use or limited-use) electrode assemblies.

FIG. 110B illustrates another example of distal end of a TES cable neurostimulator having a pair of connectors that may be independently connected to an electrode assembly.

Figure 110C:
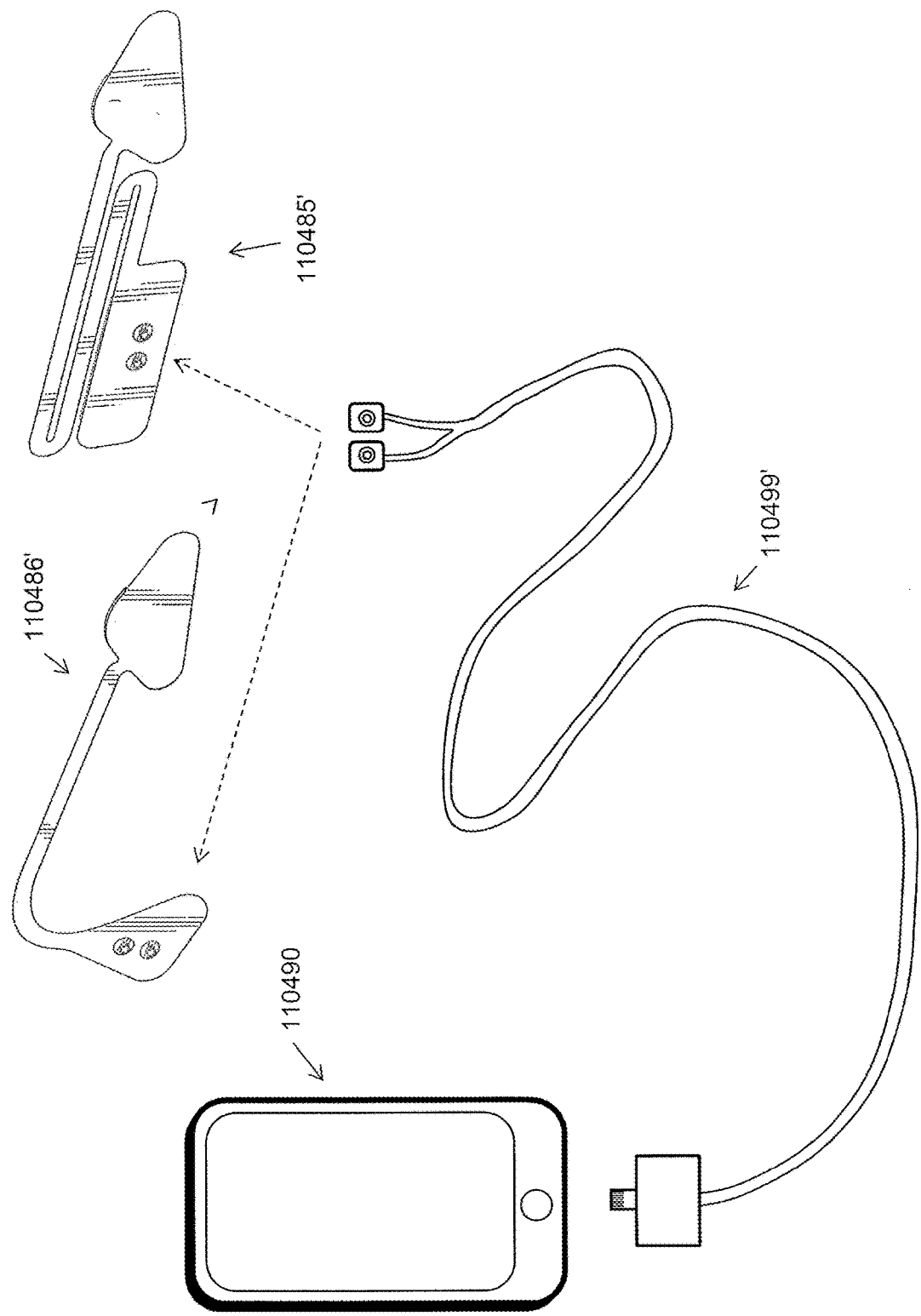

FIG. 110C illustrates another example of a TES cable neurostimulator connecting to another pair of electrode assemblies having connectors on a region of the electrode assembly that is configured to be worn on the back of the user's head, e.g., on the neck or mastoid region, rather than the temple/forehead region as in FIG. 110A.

Figure 111B:
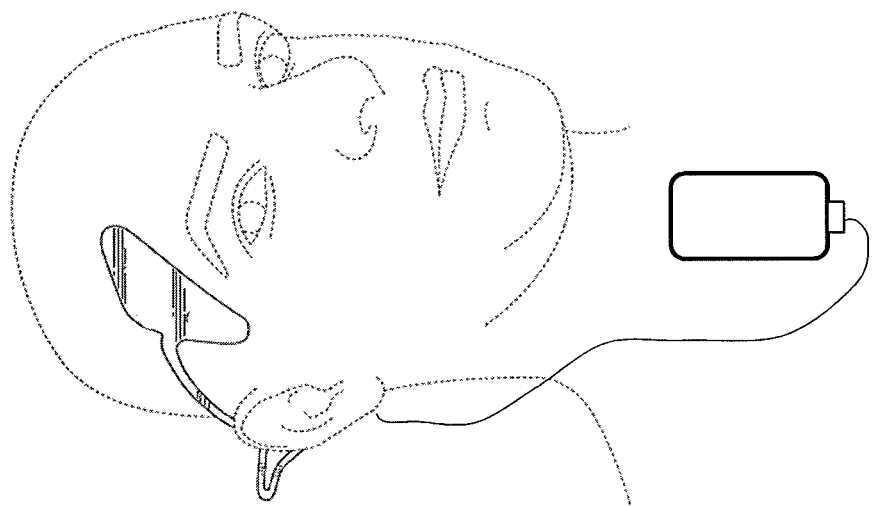
Figure 111A:
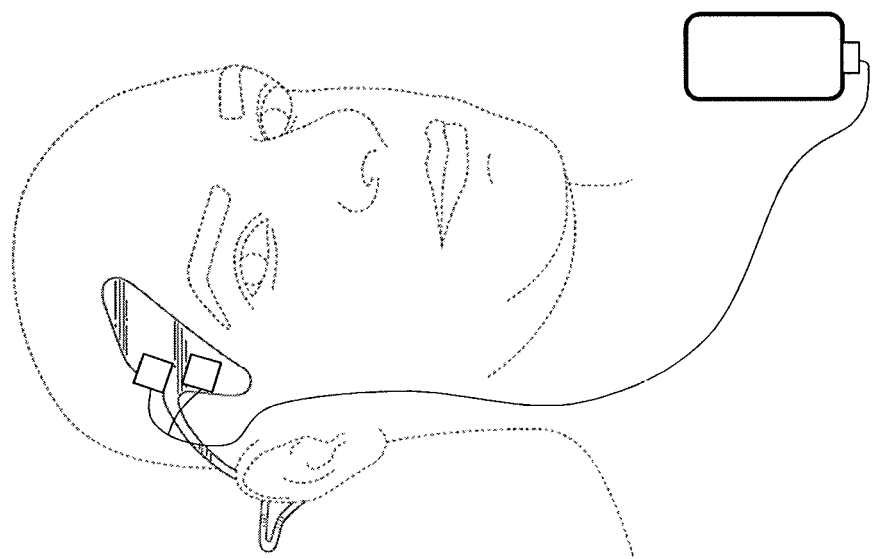

FIG. 111A illustrates connection of a TES cable neurostimulator to both a smartphone and an electrode assembly on a user, similar to the variation shown in FIG. 110A.

FIG. 111B illustrates connection of a TES cable neurostimulator to a smartphone and an electrode assembly similar to that shown in FIG. 110C.

FIG. 112A illustrates an intermediate apparatus (system) including a TES neurostimulator cable and TES neurostimulator patch, in which the neurostimulator patch is somewhat simplified compared to the variation shown in FIGS. 107A-109C, and the cable provides power (and/or control information) to the patch.

FIG. 112B illustrates another variation of an intermediate apparatus similar to that shown in FIG. 112A, but with the cable connecting to circuitry on a region of the electrode assembly configured to be worn on the back of the user's head.

FIG. 113A is a perspective view of a first variation of an electrode apparatus as described herein.

FIGS. 113B, 113C and 113D show front, top and back views, respectively of the electrode assembly of FIG. 113A.

Figure 114A:
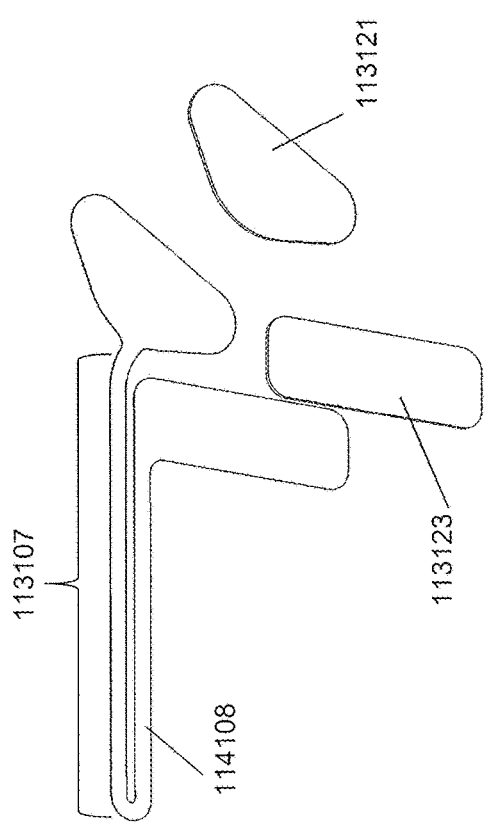

FIG. 114A is an exploded view of the front of the electrode assembly similar to that shown in FIG. 113B.

Figure 114B:
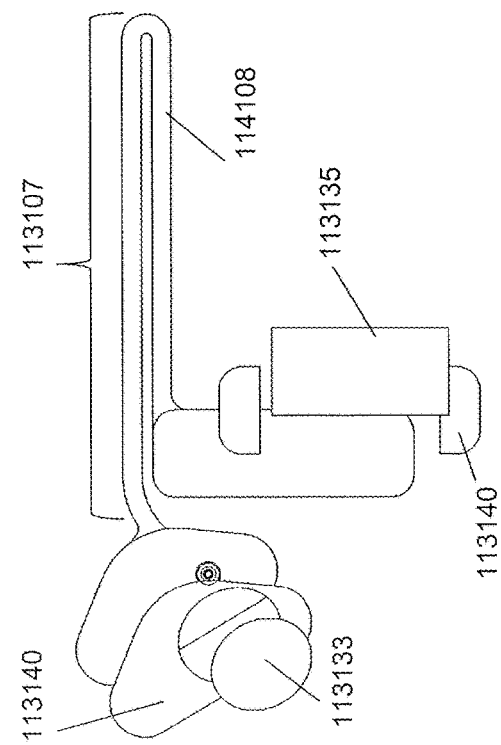

FIG. 114B is an exploded view of the back of the electrode assembly similar to that shown in FIG. 113D.

Figure 115:
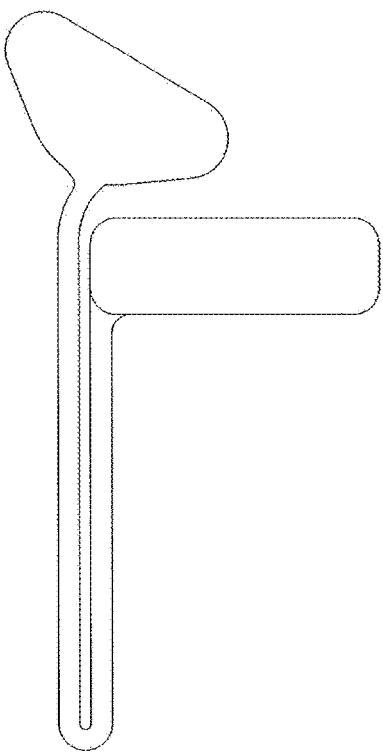

FIG. 115 is an alternative front view of an electrode assembly similar to the apparatus shown in FIG. 113B, in which a foam pad is not included over the front of the first electrode region.

Figure 116A:
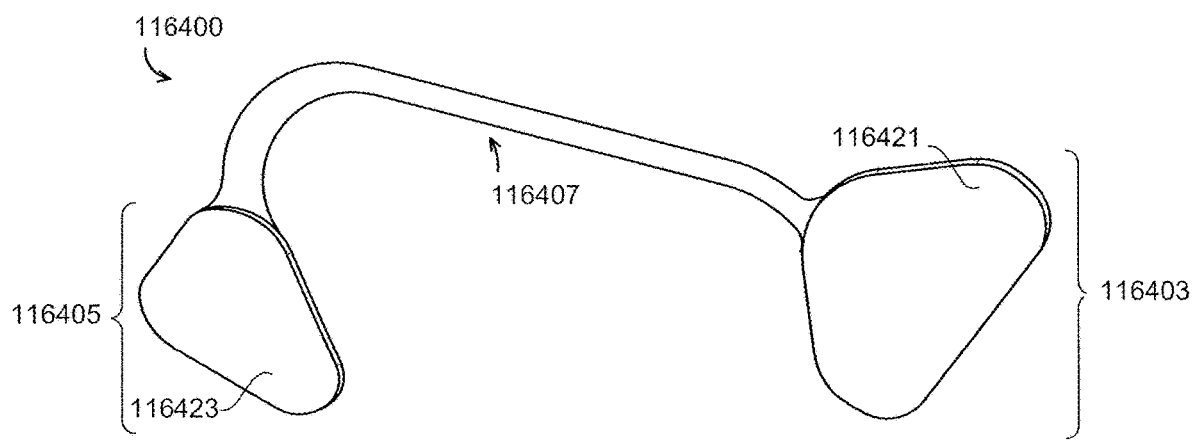

FIG. 116A is a perspective view of a variation of an electrode apparatus as described herein.

Figure 116B:
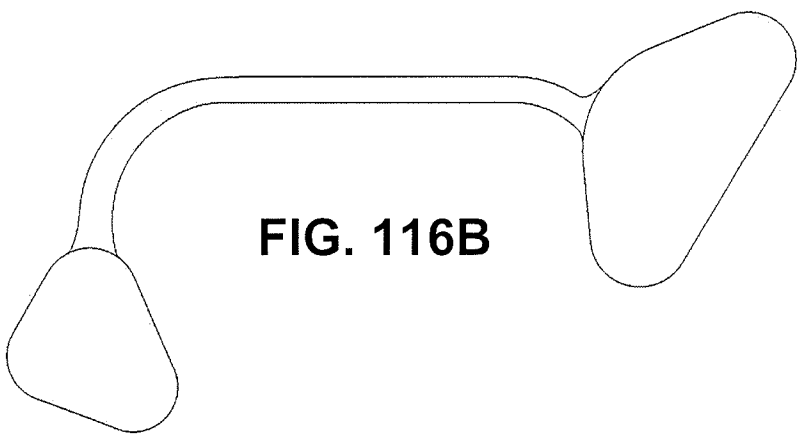
Figure 116C:
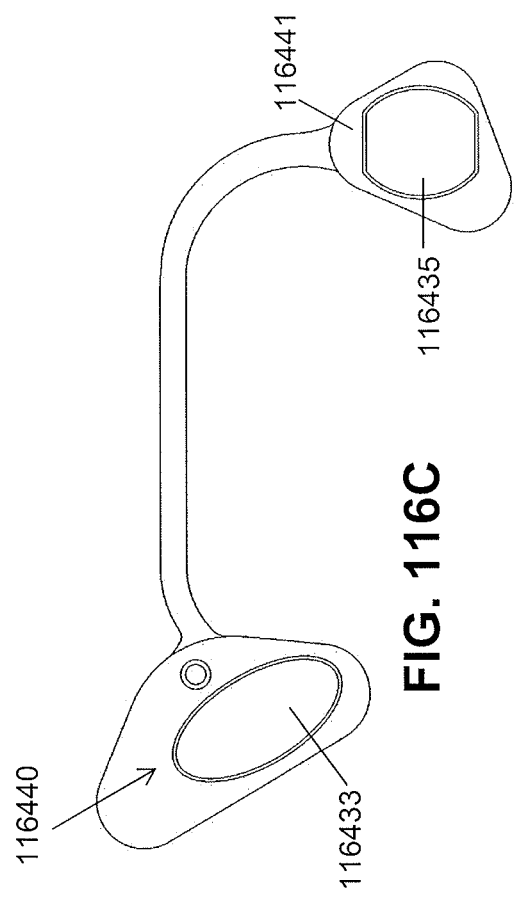

FIGS. 116B and 116C show front and back views, respectively of the electrode assembly of FIG. 116A.

Figure 116E:
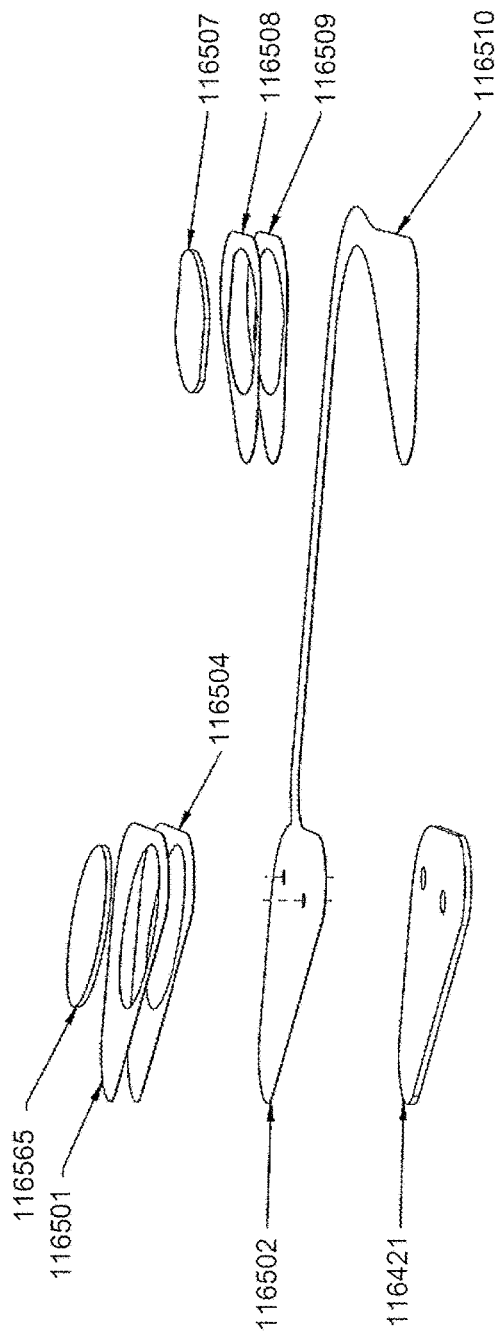
Figure 116F:
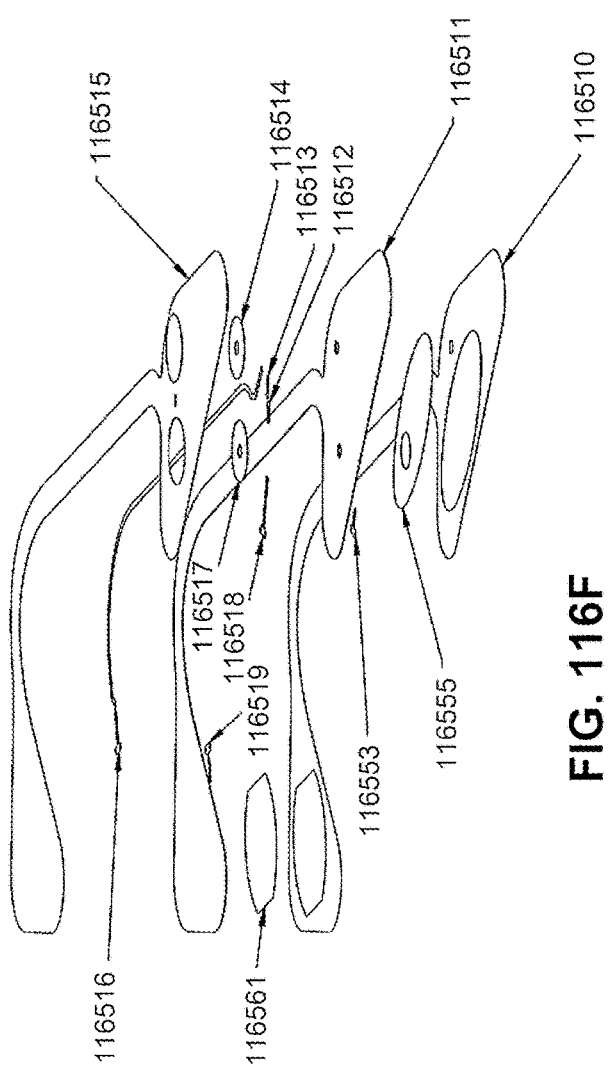
Figures 116D, 116I:
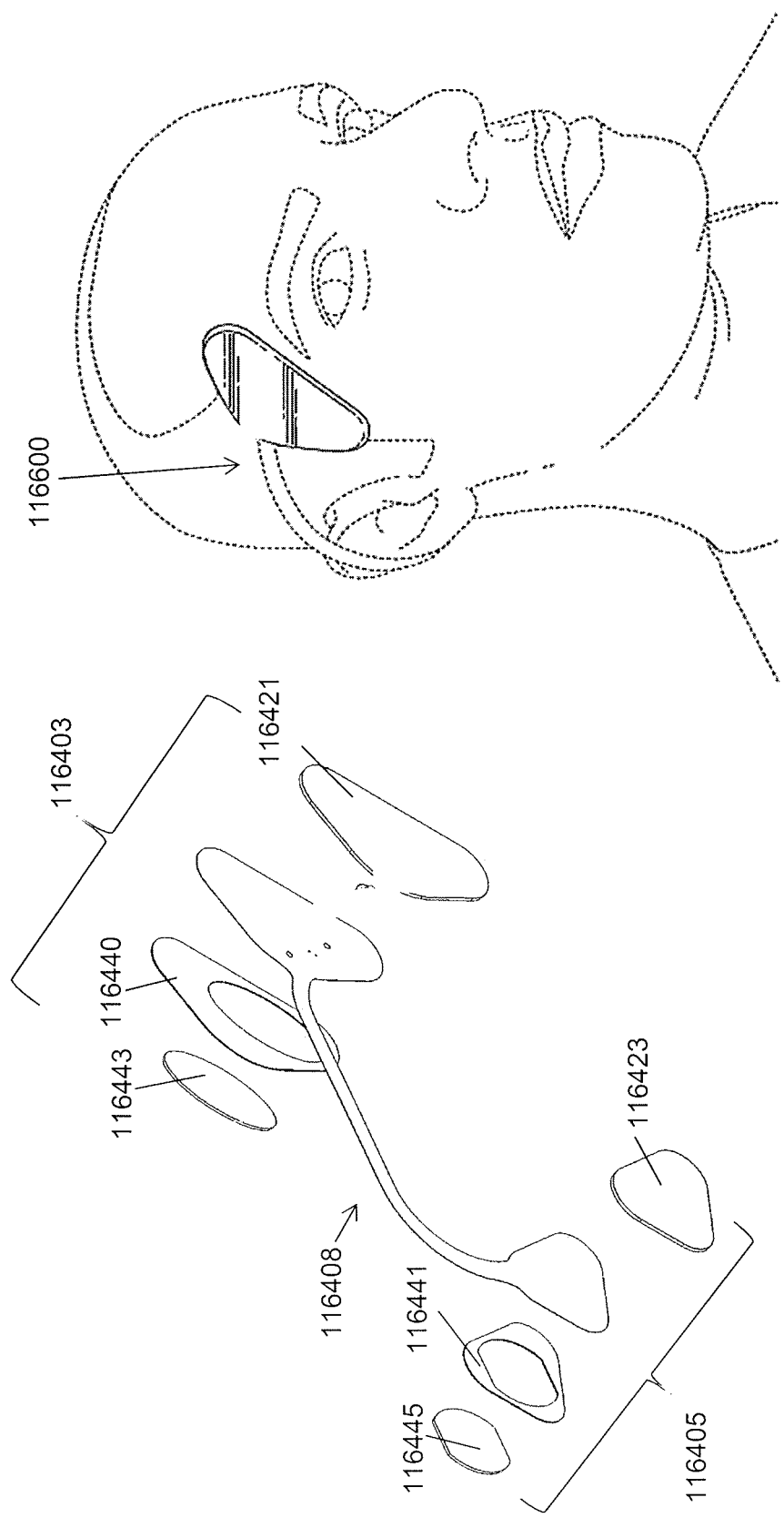

FIG. 116D is an exploded view of the electrode apparatus of FIG. 116A.

FIG. 116E is another variation of an electrode assembly similar to the variation shown in FIG. 116A, shown in an exploded bottom perspective view.

FIG. 116F is another variation of an electrode apparatus, shown in an exploded view.

FIG. 116G is a front view of the variation shown in FIG. 116F that may be worn so that a first electrode active region is positioned on a user's temple region on a first (e.g., right or left) side of the body while a second electrode active region is positioned on the user's mastoid region.

FIG. 116H is a back view of the electrode assembly of FIG. 116G.

FIG. 116i illustrates an electrode assembly (similar to those shown in FIGS. 113A and 116A) worn on a subject's head.

Figure 117A:
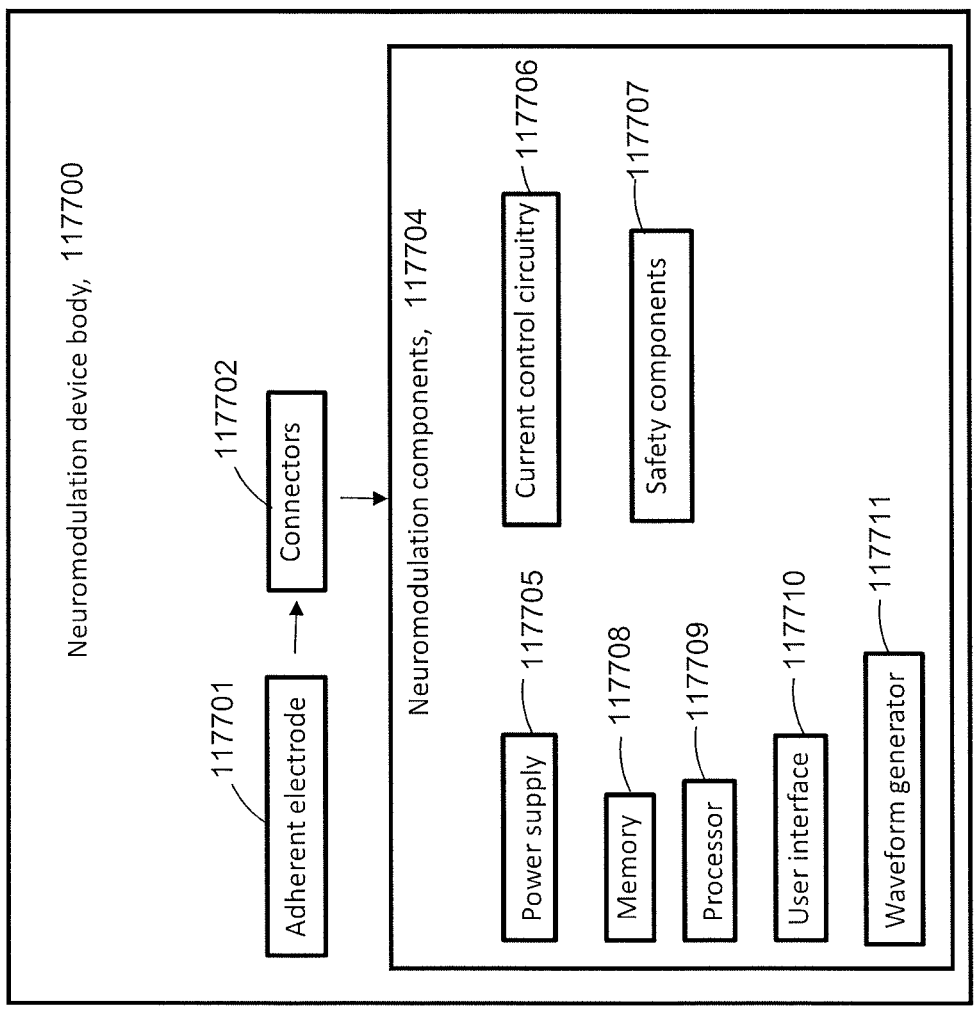

FIG. 117A is a diagram showing the overall configuration of the integrated neuromodulation device.

Figure 117B:
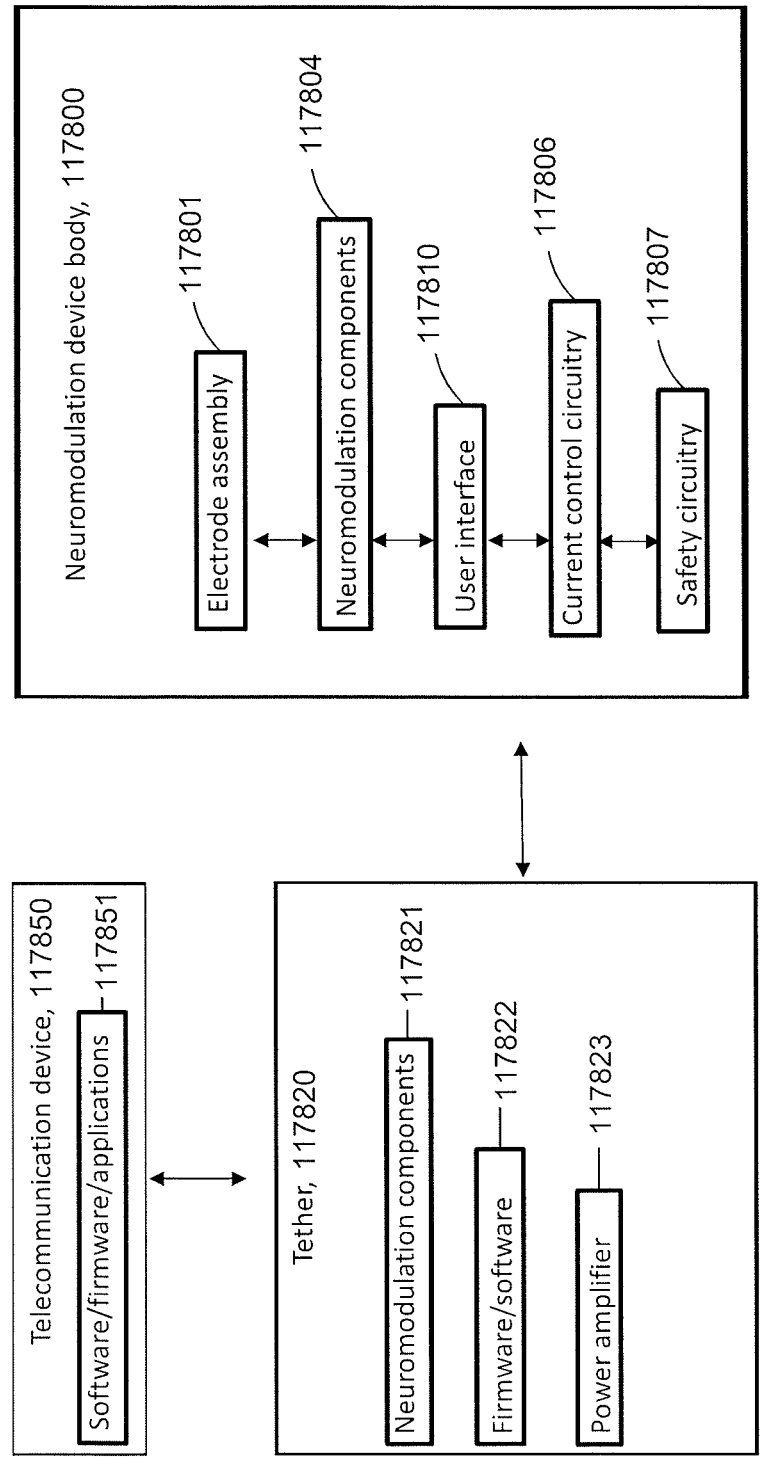

FIG. 117B is a diagram showing the configuration of an integrated neuromodulation device connected to a tether and a telecommunication device.

Figure 118C:
Figure 118F:
Figure 118B:
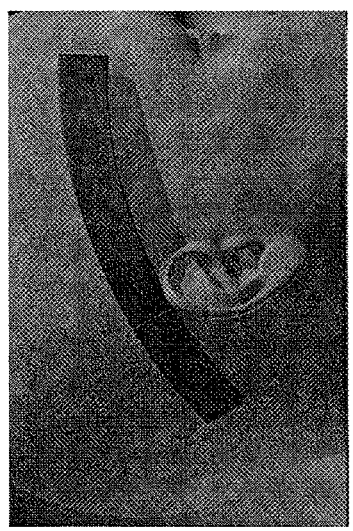
Figure 118E:
Figure 118A:
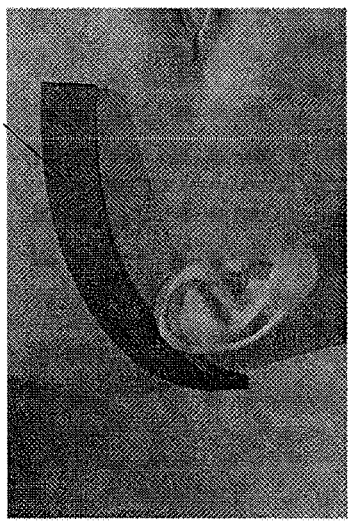

FIGS. 118A-118C show three views illustrating another variation of an electrode assembly having a rigid body.

Figure 118D:
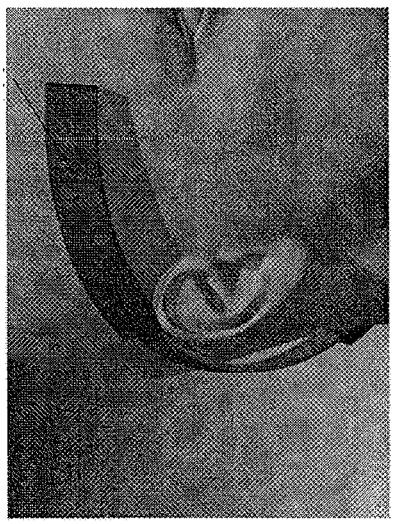

FIGS. 118D-118F show three views illustrating another variation of a cantilever electrode apparatus.

FIGS. 118G-118H show front and back views, respectively, of another variation of an electrode assembly.

Figure 118I:
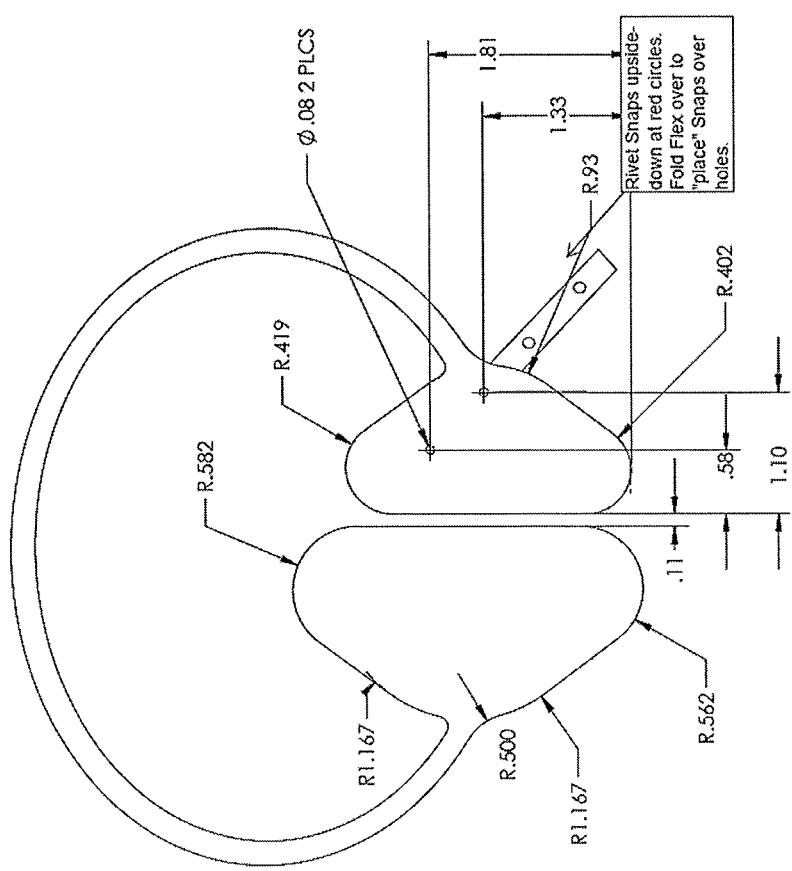

FIG. 118i is a front view of another variation of an electrode apparatus.

FIGS. 119A-119D show perspective, front, side, and back views, respectively, of another variation of an electrode assembly.

FIGS. 120A-120C show perspective, front, and back views, respectively, of another variation of an electrode assembly.

Figures 121A, 121B:
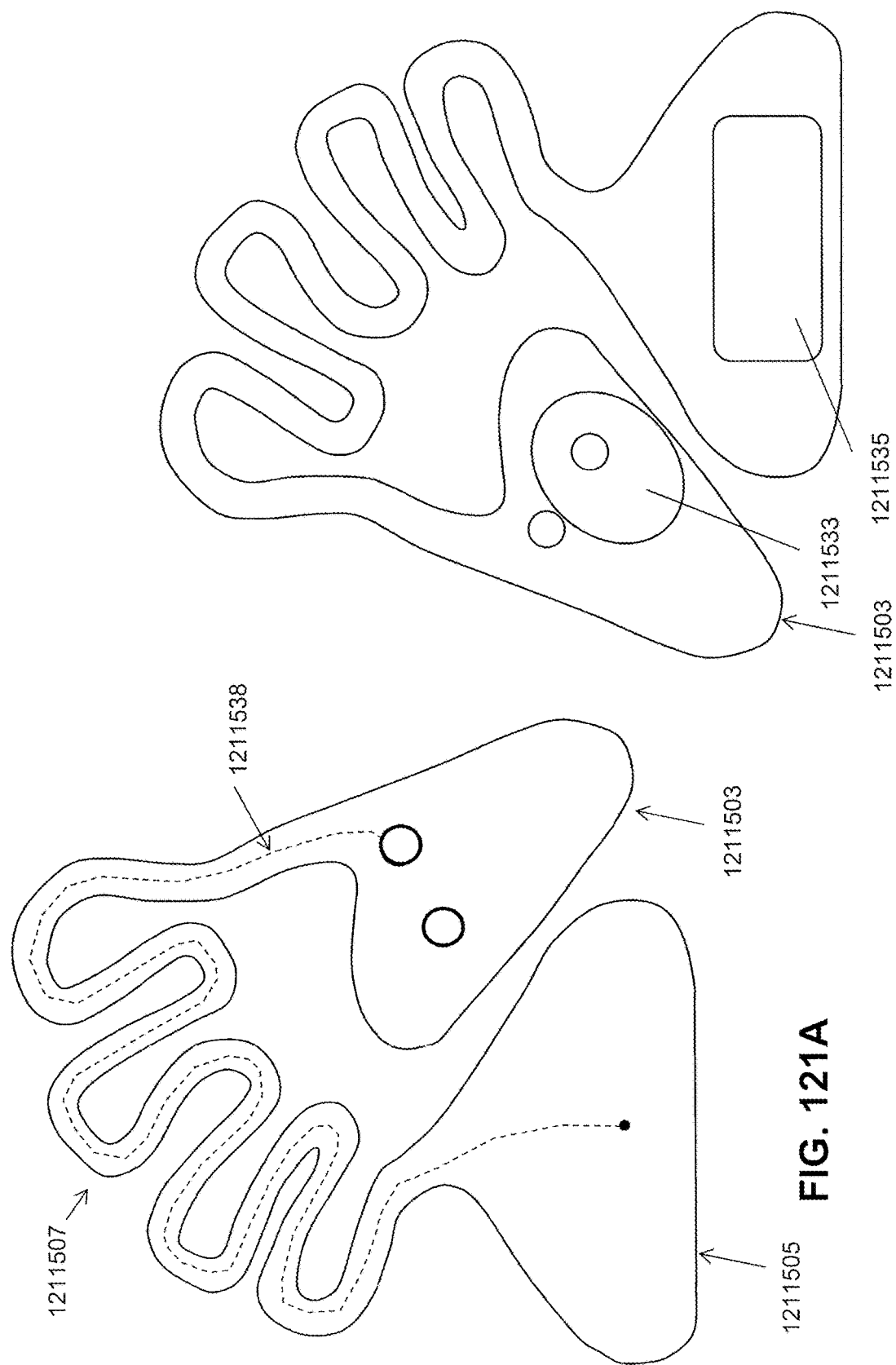

FIGS. 121A and 121B show top and bottom views, respectively, of another variation of an electrode assembly.

FIG. 122A is a perspective view of a variation of a cantilever electrode apparatus having a detectable electrical element between the first and second electrodes that can be sensed by a neurostimulator.

FIG. 122B is another example of a perspective view of a cantilever electrode apparatus having a detectable electrical element between the first and second electrodes that can be sensed by a neurostimulator.

Figure 123:
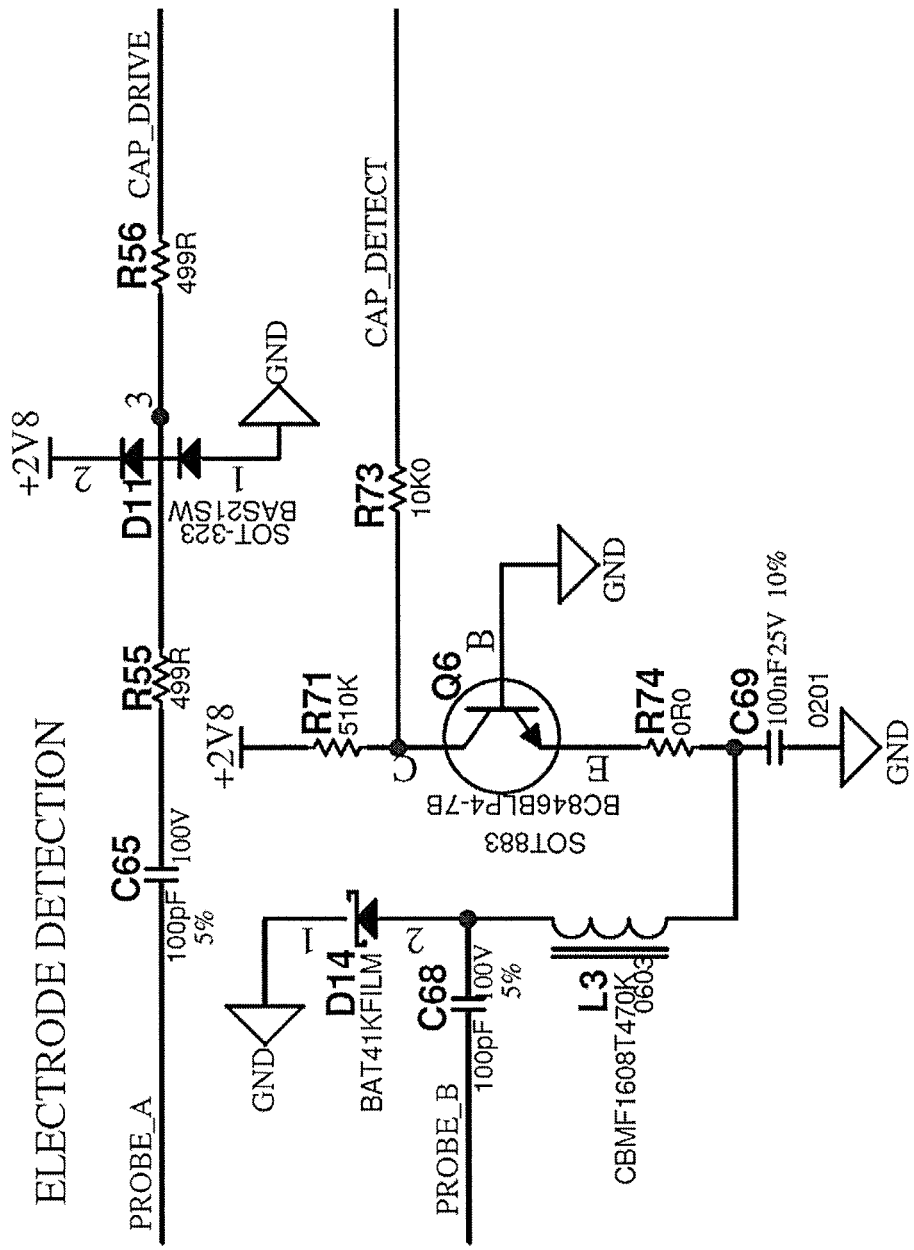

FIG. 123 is one example of a detection circuit that may be used to detect connection and or the type or identity of an electrode apparatus; the detection circuit may be included on a neurostimulator (e.g. cable neurostimulator) to detect some variations of the electrode apparatuses described herein.

Figure 124B:
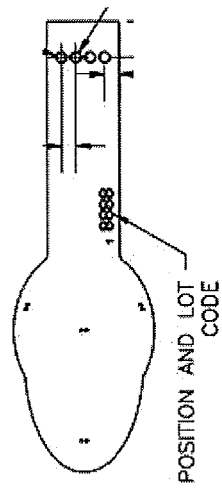
Figure 124A:
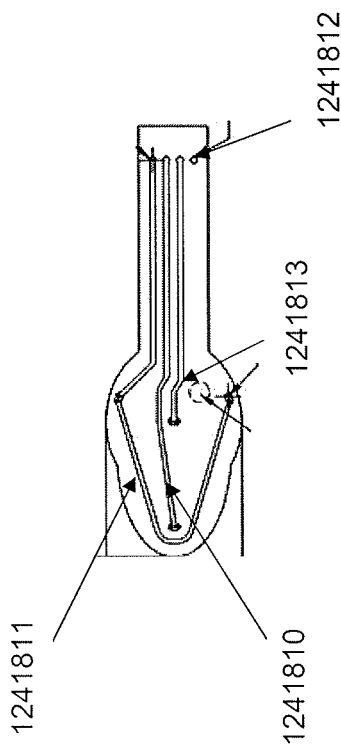
Figure 124C:
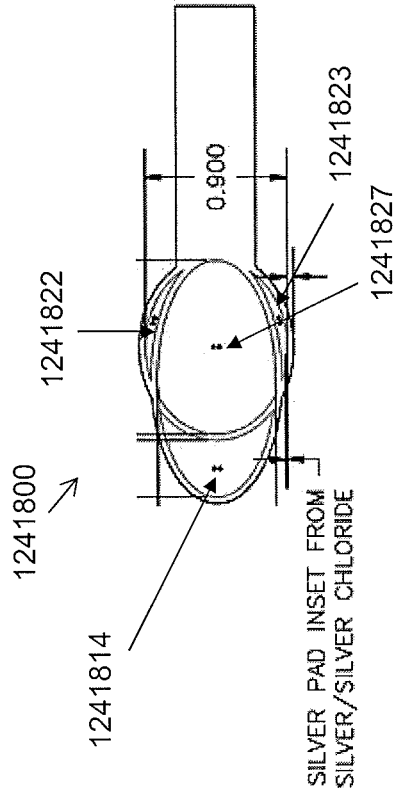

FIGS. 124A-124C illustrate a portion of an electrode apparatus including different sub-regions of active zones. FIG. 124A is a top view showing traces connecting through the substrate (shown in FIG. 124B) to multiple sub-regions forming an active region of the electrode on the bottom surface, shown in FIG. 124C.

FIG. 125A is a bottom view showing multiple sub-regions forming an active region of the electrode on the bottom surface, similar to that shown in FIG. 124C.

Figure 125C:
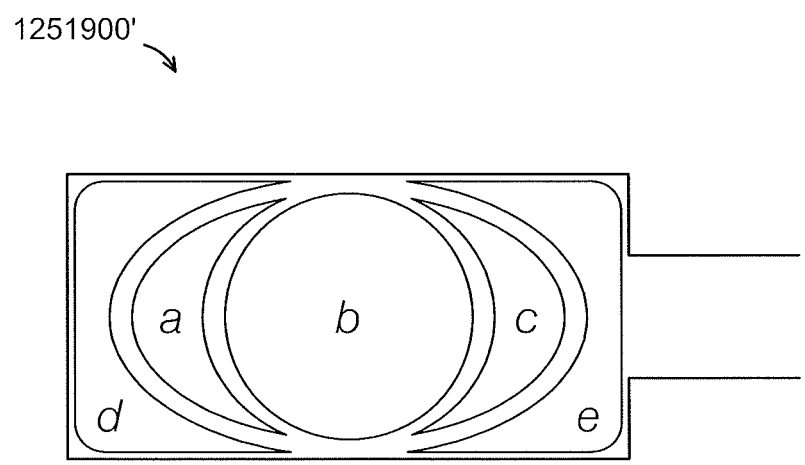

FIGS. 125B-125D show bottom, side sectional, and top views, respectively, of another variation of an electrode apparatus having multiple sub-regions forming an active region of the electrode on the bottom surface.

FIG. 126A shows an exemplary (not to scale) sectional view through an active region of an electrode fed by a conductive trace.

FIG. 126B shows a section view though an active region directly connected to a (snap) connector for coupling to a neurostimulator.

FIG. 126C is a slightly enlarged view of FIG. 126B.

FIG. 126D illustrates another example (not to scale) of a section view though an active region of an electrode fed by a conductive trace; in this example, the active region includes a weakly insulating layer (e.g., a thin carbon layer between the silver and silver chloride layers).

FIG. 126E shows a section view though an active region directly connected to a (snap) connector for coupling to a neurostimulator and including a weakly insulating layer (e.g., carbon).

FIG. 126F is a slightly enlarged view of FIG. 126E.

Figure 127:
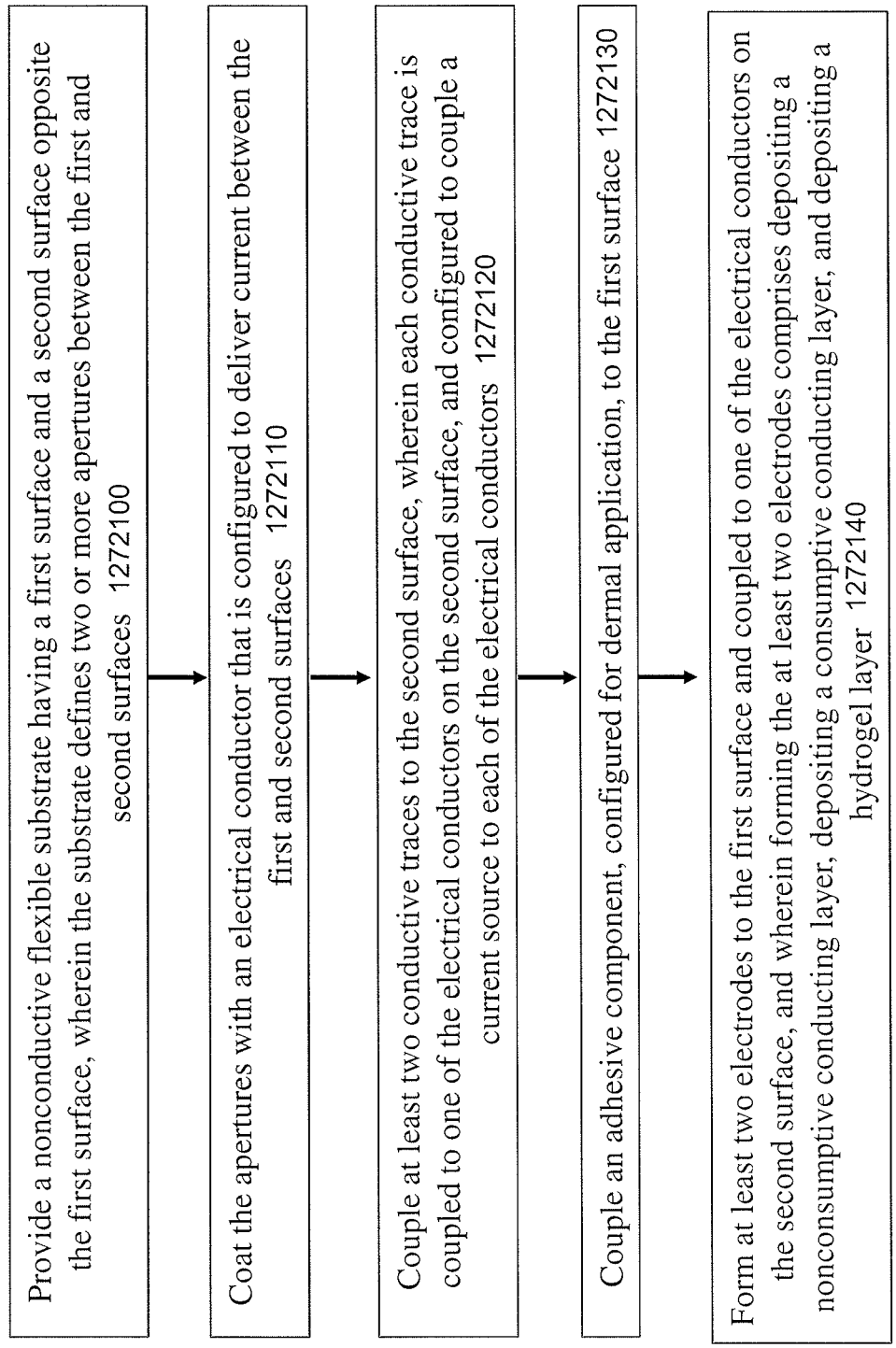

FIG. 127 schematically illustrates one method of forming an electrode apparatus such as a cantilever electrode apparatus.

FIGS. 128A and 128B illustrate another variation of an electrode assembly similar to the one shown in FIGS. 113A-113D and 114A-115, in which the two electrode skin-contacting portions (connected by the flexible elongate body region) are oriented differently, providing a more compact profile; the active regions of the electrode skin-contacting portions extend from edge-to-edge of a central region of both electrode skin-contacting portions. FIG. 128A is a front perspective view, and FIG. 128B is a back view.

FIGS. 129A and 129B illustrate another variation of a cantilevered electrode assembly similar to the one shown in FIGS. 116A-116C and 116D, in which the two electrode skin-contacting portions (connected by the flexible elongate body region) are oriented differently than shown in FIGS. 116A-116C; the active regions of the electrode skin-contacting portions extend from edge-to-edge of a central region of both electrode skin-contacting portions. FIG. 129A is a front perspective view, and FIG. 129B is a back view.

Figure 130:
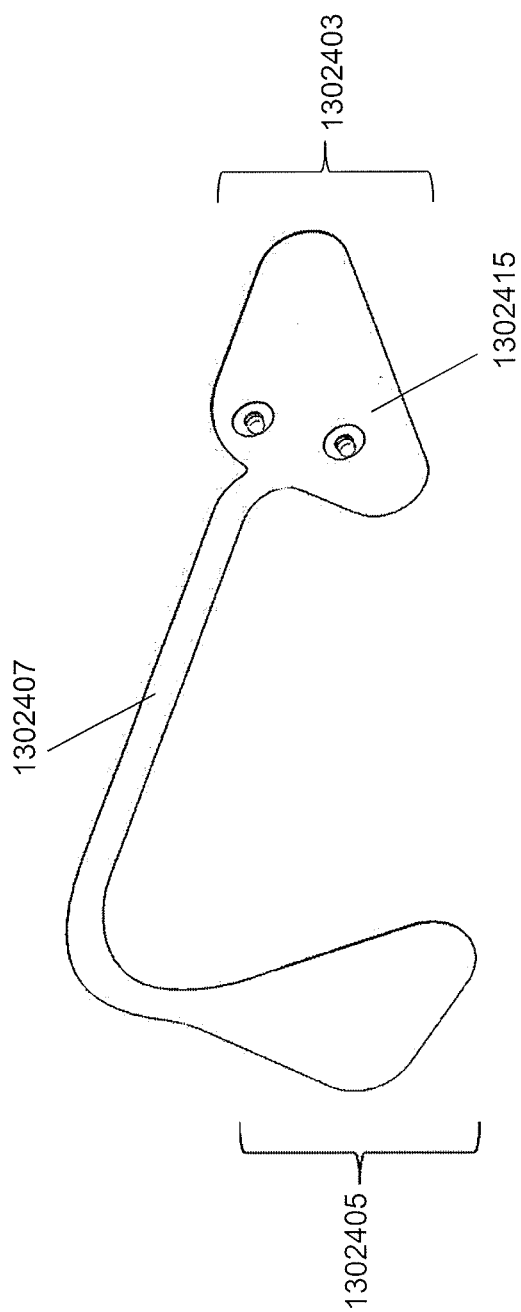

FIG. 130 shows a neuromodulation device with two external connectors for electrically contacting an external tether such as a cord or wire where the two external connectors are situated on the outer surface of the electrode region that contacts the user's head.

Figure 131:
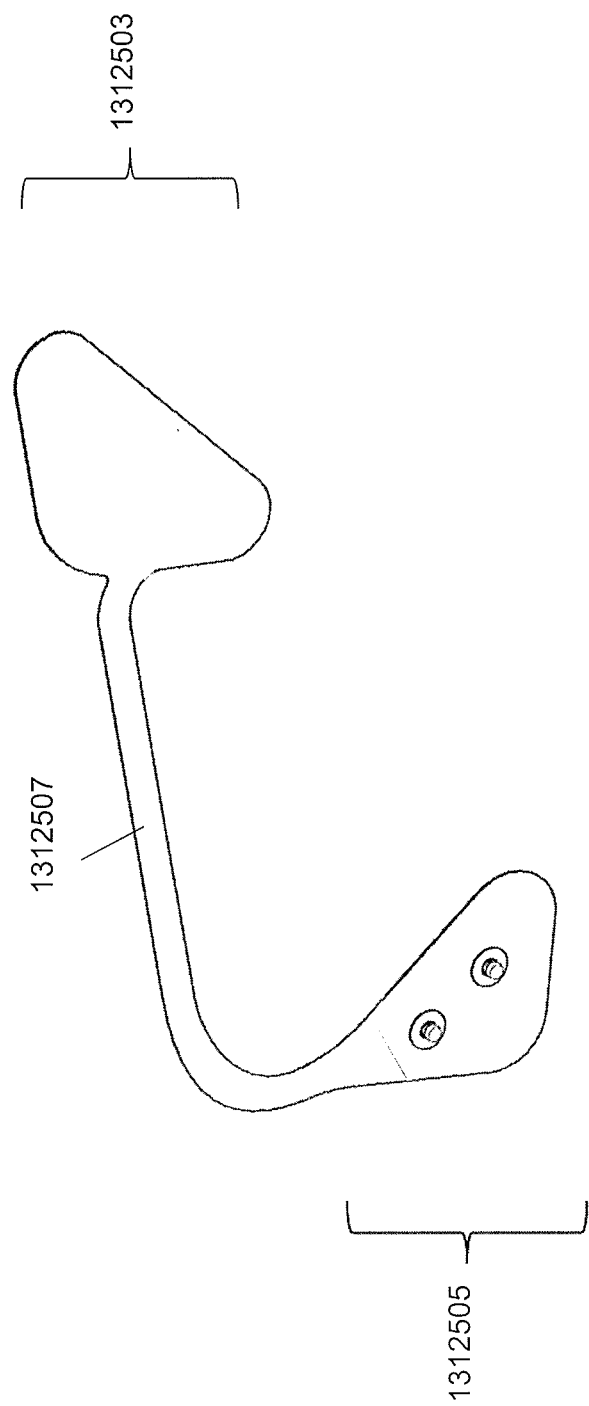

FIG. 131 shows a neuromodulation device with two external connectors for electrically contacting an external tether such as a cord or wire where the two external connectors are situated on the outer surface of the electrode region that contacts the user's neck.

Figure 132:
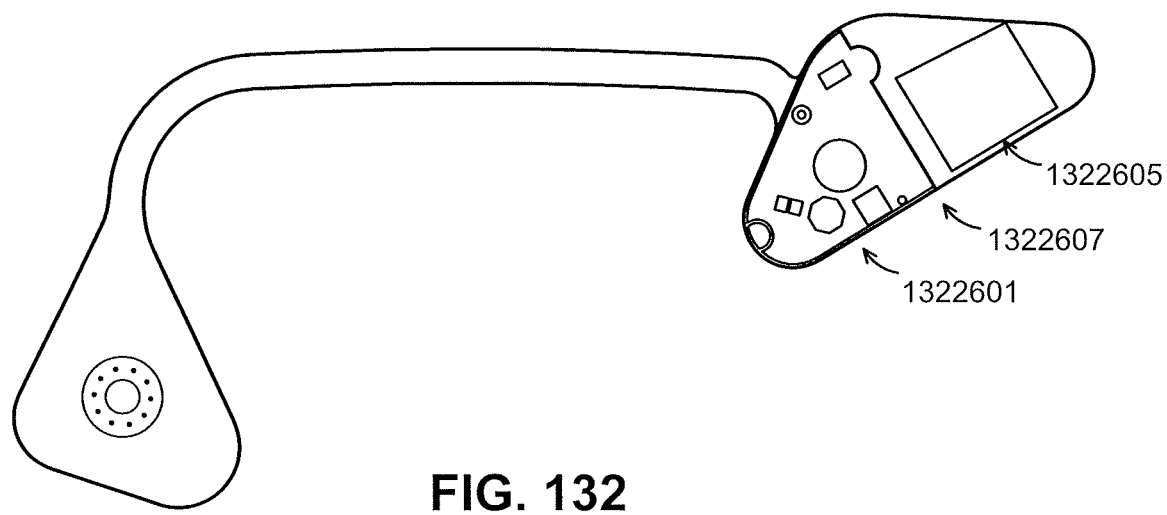

FIG. 132 is an example of a TES patch neurostimulator apparatus configured to be worn on a subject's head. The apparatus includes a pair of electrodes (not visible) connected through a flexible circuit body to a neurostimulator circuitry including a power source.

Figure 133A:
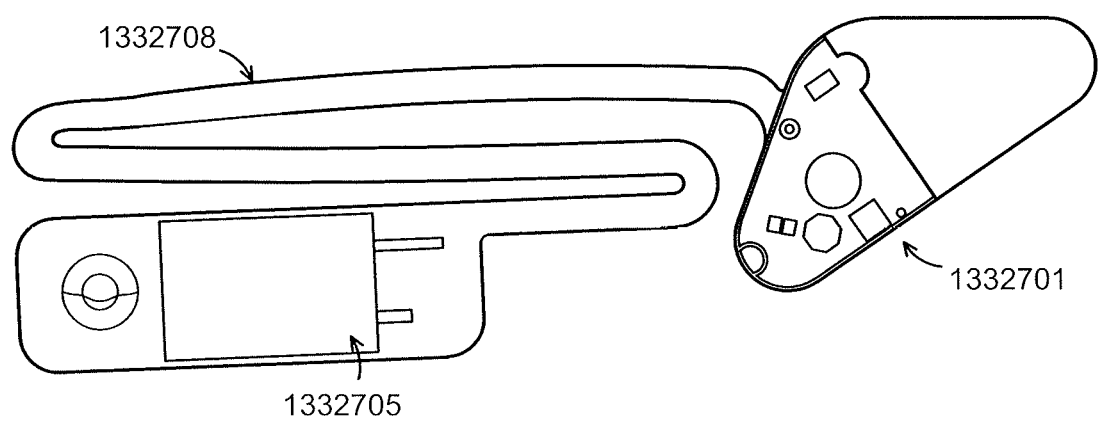

FIG. 133A is another example of a TES patch neurostimulator apparatus in which the neurostimulator circuitry is present on one end of the flexible substrate that also forms the electrodes, while the battery is another end.

Figure 133B:
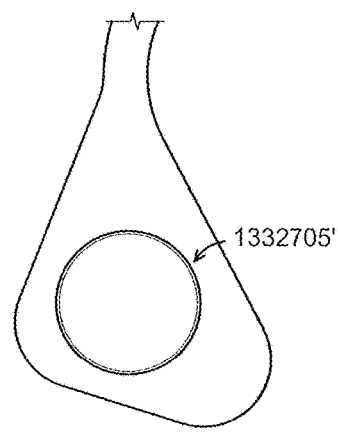

FIG. 133B illustrates a battery attached to one end of a flexible substrate forming the TES patch electrode.

Figure 134:
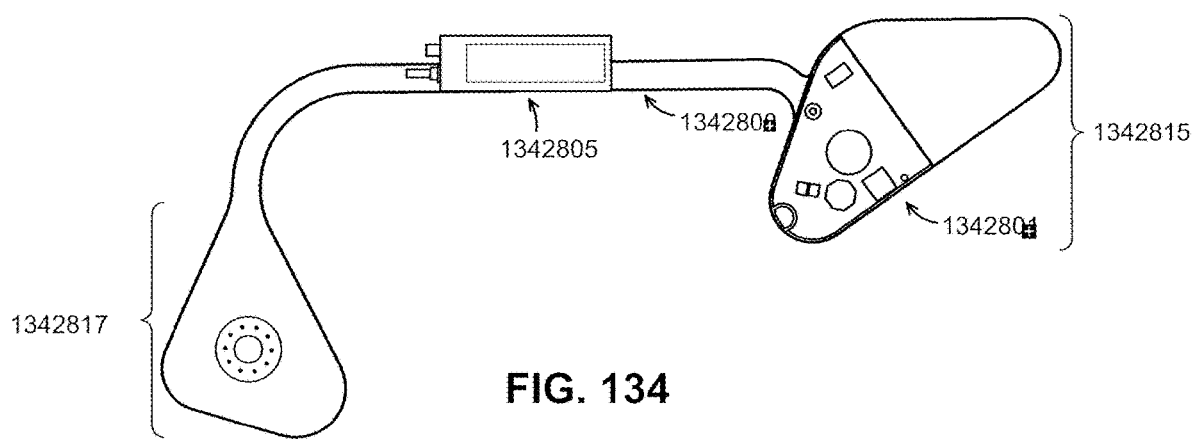

FIG. 134 illustrates an example in which the battery is located at an intermediate region between the two ends supporting the electrodes, configured to be positioned behind the wearer's ear when worn.

Figure 135:
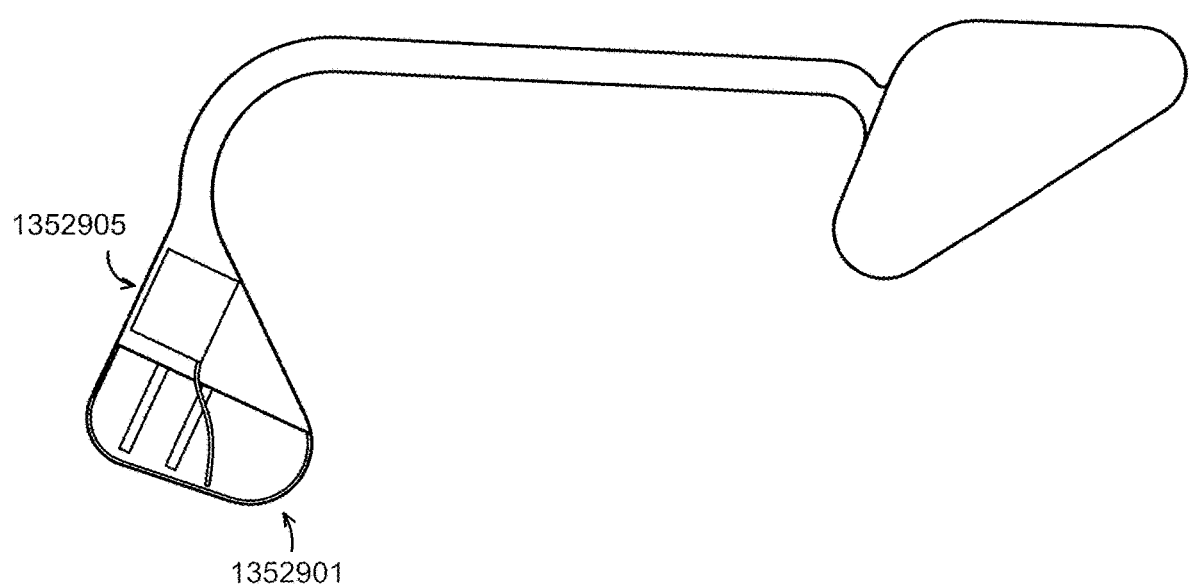

FIG. 135 illustrates another example of a TES patch neurostimulator apparatus in which the battery and neurostimulator circuitry are all located on one of the electrodes (e.g., to be worn behind the wearer's ear).

DETAILED DESCRIPTION

Lightweight and wearable apparatuses for applying transdermal electrical stimulation and methods of using them for inducing a cognitive effect are described. These apparatuses are typically self-contained, lightweight, and wearable devices and/or systems that include a primary unit and at least one secondary unit. The primary unit can include a first transdermal electrode, a processor or controller, which may include current controller, for applying current and, in some embodiments, a wireless communications module. The system also typically includes a secondary unit that is electrically connected to the primary unit by a cable such as a wire, cord, ribbon, etc. The secondary unit also typically includes a second transdermal electrode. The primary and secondary unit may be initially and conveniently stored together in a single housing (e.g., cover) and may be separated before applying or when applying to the subject's head and/or neck. The entire self-contained apparatus may be applied to and worn on the subject's head and/or neck, and the secondary unit is generally tethered to the primary unit by the cable so that the primary and secondary units can be independently connected to the subject and are connected only to each other by the cable, without requiring any additional cable connections. The apparatus can be configured to drive stimulation between the first and second electrode to induce a cognitive effect in the subject (for example, relaxation or excitement) while reducing any discomfort experienced by the subject at the locations where the electrodes are contacting the skin.

All of the components of the electrical stimulation device may be self-contained in one or more housings, and the entire device can easily be worn by a user. As described above, different components of the device can be worn by being adhered to skin of a user. Some or all of the components of the device can also or alternatively be held against the skin by an accessory such as a headband or wrap; alternatively or additionally the apparatus may be worn connected to an eyepiece or earpiece (e.g., eyeglasses, etc.). The simple wearability of the device can advantageously make it more comfortable and convenient to use for a user. It can also enhance the aesthetic effect of the device while being worn and/or used by a subject. The device may be particularly and specifically adapted to be wearable and lightweight; for example, the apparatus may weigh less than a predetermined amount (e.g., less than 8 ounces, less than 7 ounces, less than 6 ounces, less than 5 ounces, less than 4 ounces, less than 3 ounces, less than 2 ounces, less than about 1.5 ounces, less than about 1 ounce, less than about 0.5 ounces, less than about 0.25 ounces). The primary unit and the secondary unit may also be relatively flat or thin when worn against the head and/or neck (e.g., may be less than 30 mm thick, less than 25 mm thick, less than 20 mm thick, less than about 10 mm, less than 5 mm, etc.).

The lightweight and wearable transdermal electrical stimulation apparatus for inducing a cognitive effect in a subject may generally include hardware, software and/or firmware components that are configured to generate appropriate control sequences for the device, transmit signals to a current or voltage source and/or conditioner, and connect to electrodes that are configured to be placed on a user for generating electrical currents. For example, the apparatus may comprise a controller configured to transmit sequences to a current generator. Thus, the apparatus may be configured for mobile use.

The apparatus may generally be configured to receive control information for controlling the stimulation. This control may include control of the start, duration and timing of stimulation (e.g., on/off, duration, etc.) and/or may also include controls for the waveforms to be applied to induce a cognitive effect in a subject. In general, the induced cognitive effect is a function of the position of the electrodes (e.g., where on the head/neck the electrodes are positioned) and the stimulation parameters of the applied waveforms. An apparatus may include one or more manual controls (e.g., inputs) on the apparatus, and/or it may include wireless communication to a remote processor ("base station") that wirelessly transmits control information to the apparatus. For example, the apparatus may include a wireless module for wireless communication to the base station or via cellular networks to the Internet. A remote processor may be configured to transmit control signals to a current generator located in the device (e.g., within the primary unit). The remote processor may include non-transitory computer-readable storage mediums storing a set of instructions capable of being executed by a remote processor (such as a smartphone or the like), that when executed by the remote processor causes the processor to allow a subject to select one or more (or a set) of control parameters for controlling the lightweight, wearable apparatuses described herein. The set of instructions may include confirming a communication link with one or more lightweight, wearable apparatuses, presenting a list and/or menu of pre-selected control values (e.g., for one or more of current amplitude, current frequency, pulse width, pulse duration, pulse frequency, pulse waveform, burst duration, burst frequency, off-time, burst waveform, positive duty cycle, negative duty cycle, and on/off, etc.), or for allowing modification of one or more of these control values separately.

In general, inducing a cognitive effect can include inducing a response that a reasonable user is cognitively aware of. The effect can include a physiological change. For example, the effect can include a change in the amplitude or phase of brain rhythms. The effect can include a modulation of one or a plurality of the following biophysical or biochemical processes: (i) ion channel activity, (ii) ion transporter activity, (iii) secretion of signaling molecules, (iv) proliferation of the cells, (v) differentiation of the cells, (vi) protein transcription of cells, (vii) protein translation of cells, (viii) protein phosphorylation of the cells, or (ix) protein structures in the cells. The apparatus (device or system) may be configured so that the induced cognitive effect is perceived subjectively by the recipient as a sensory perception, movement, concept, instruction, other symbolic communication, or modifies the recipient's cognitive, emotional, physiological, attentional, or other cognitive state. Neurons and other cells in the brain and head area are electrically active, so stimulation using electric fields can be an effective strategy for modulating brain function. In various embodiments of the invention, the effect of electrical stimulation is one or more of inhibition, excitation, or modulation of neuronal activity.

Figure 1A:
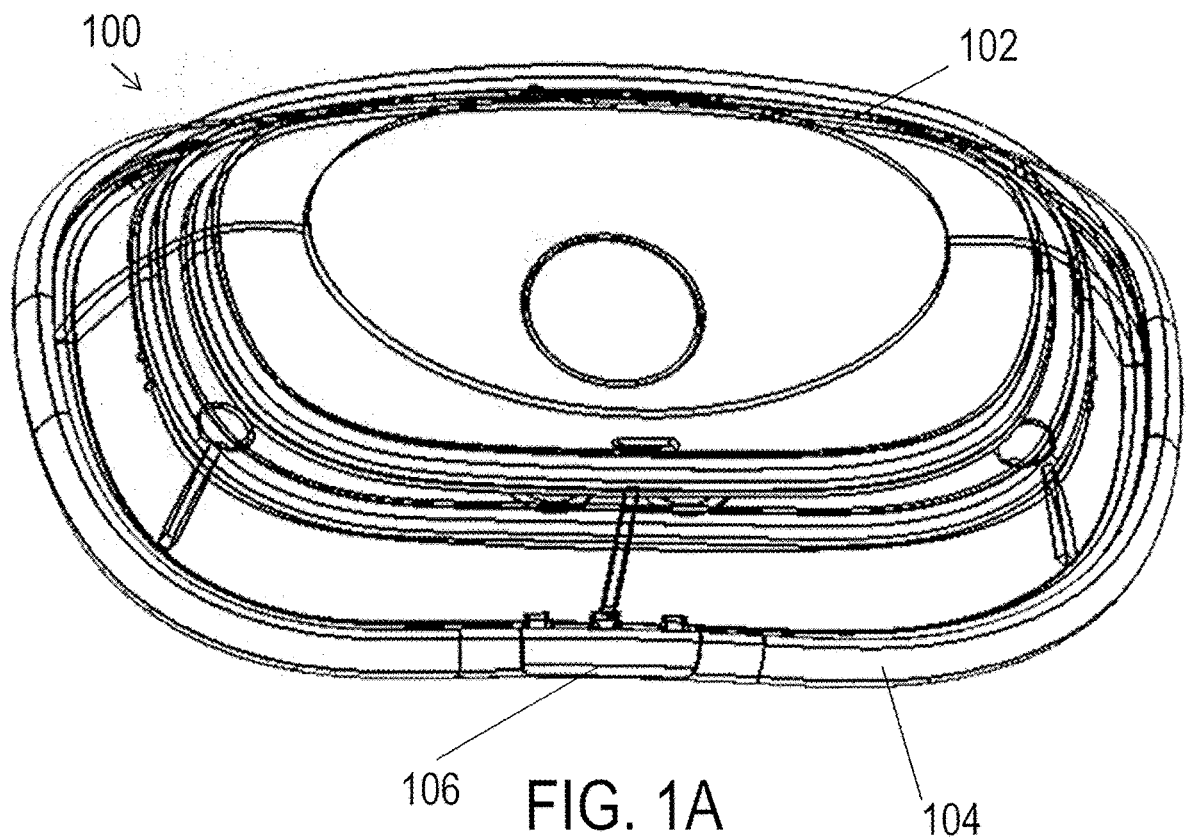
FIGS. 1A and 1B show front perspective and side perspective views, respectively, of one variation of a lightweight, wearable and self-contained electrical stimulation apparatus, as described herein.
Figure 1B:
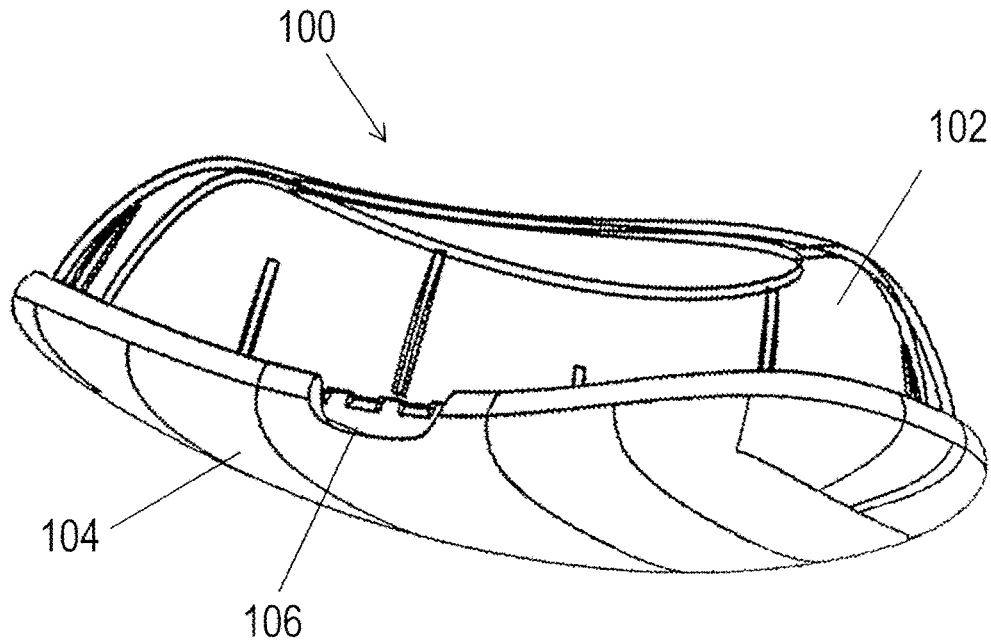
Figure 1C:
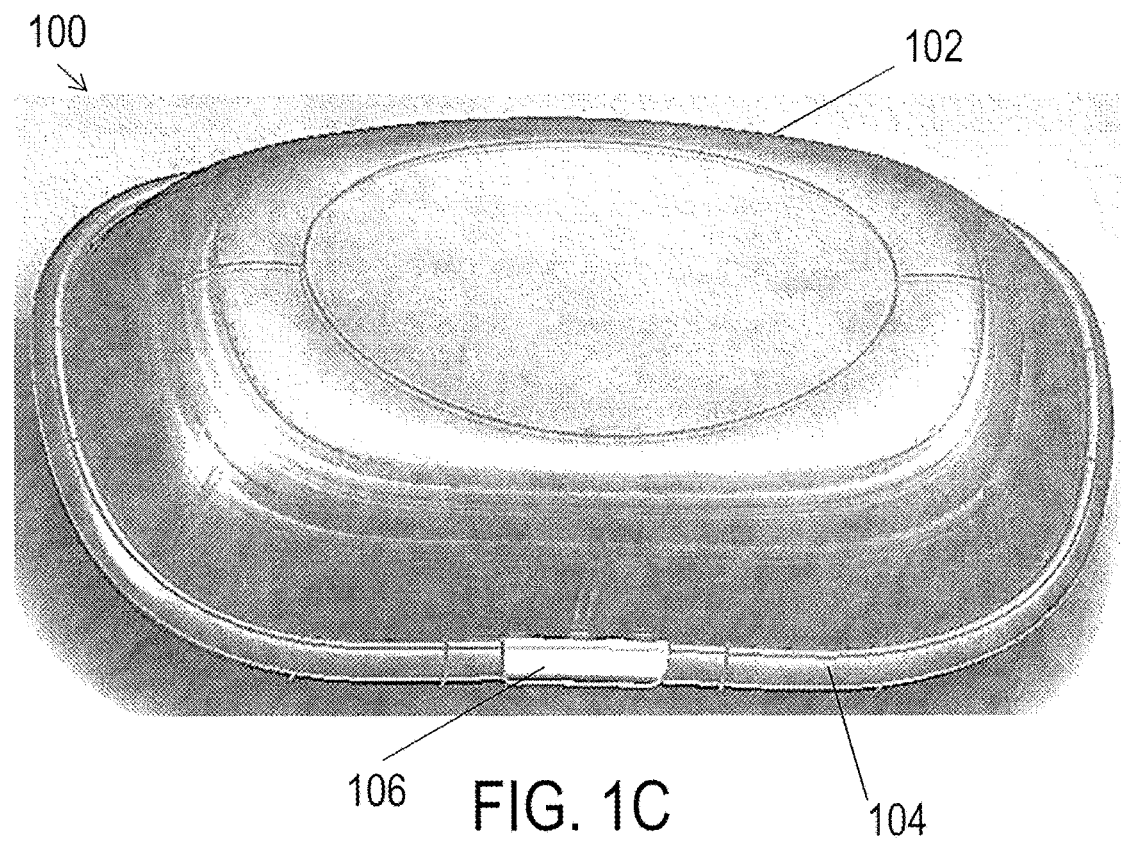
FIGS. 1C and 1D show side perspective and top views of the apparatus of FIGS. 1A and 1B.
Figure 1D:
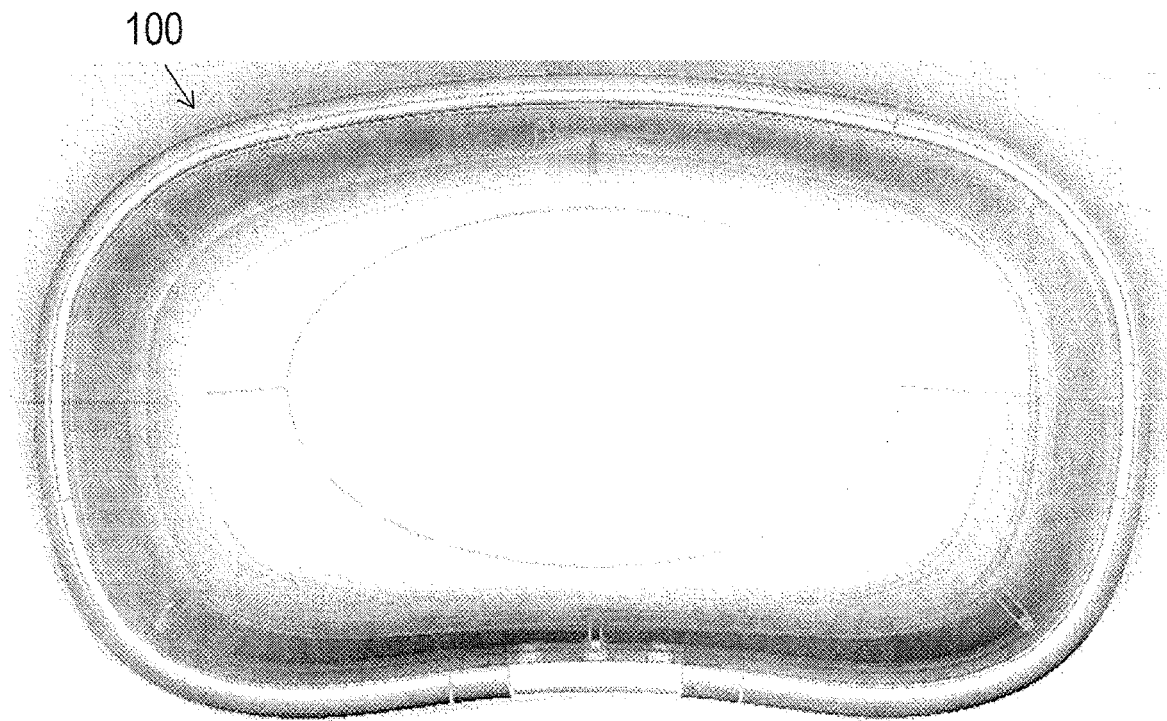
Figure 1E:
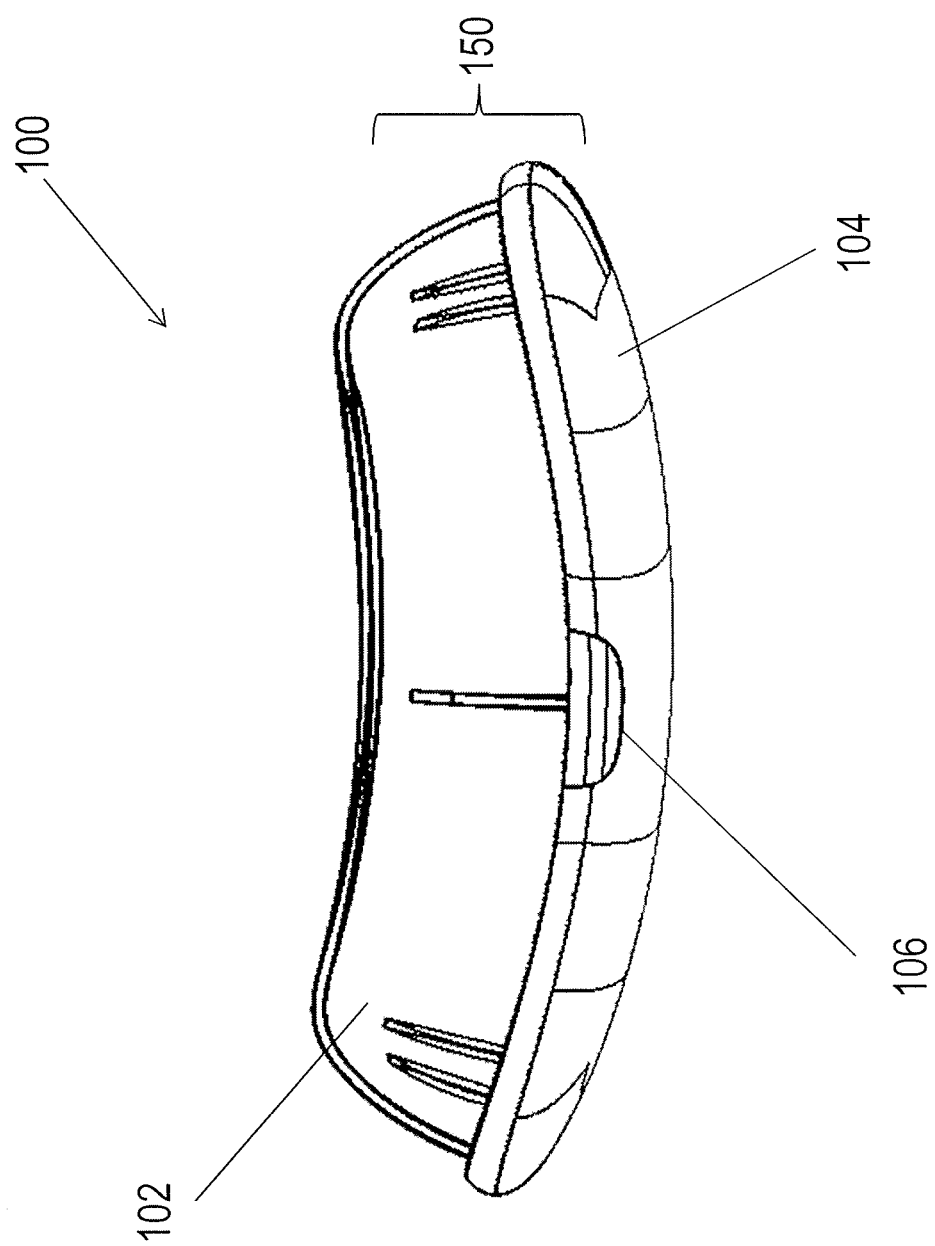
FIG. 1E shows a side view of the apparatus of FIGS. 1A-1D.

FIGS. 1A and 1B show perspective views of one variation of a wearable and lightweight apparatus 100 for applying transdermal electrical stimulation. The device shown in FIGS. 1A-1E includes a cover 102, although this cover may be optional. The cover 102 may allow storage of both the primary and secondary portions of the units together; prior to being applied, the cover may be removed and the secondary unit (and electrode) separated from the primary unit, though connected by a tethering cable (not visible in FIGS. 1A-1E). The primary unit 104 portion of the apparatus show in FIGS. 1A-1E is partially visible. In FIGS. 1A, 1B and 1E, the apparatus is shown partially transparent; in FIGS. 1C and 1D, the outer cover 102 obscures the inner components.

FIGS. 1A-1E show the apparatus (device 100) including an input control 106, for example a switch, touch-screen, button, or other user interface component that is present on an outer surface of the housing forming the primary unit 104. The input control can be used to control aspects of the function of the device 100. For example, the input control can be used to power the device off and on or turn the electrical stimulation off and on. Other functions are also possible. For example, the input control can be used to control wireless transmissivity. In some embodiments, the device can include more than one input control 106. For example, the device 100 can include two, three, four, or more input controls 106. In some embodiments, the device 100 does not include an input control 106. In some embodiments, the input control is positioned generally in the middle of the device 100. The input control 106 may be positioned elsewhere on the device, for example on a side of the device 100. In general, the device may have a thickness 150 that is relatively thin (e.g., less than 30 mm).

Figure 2A:
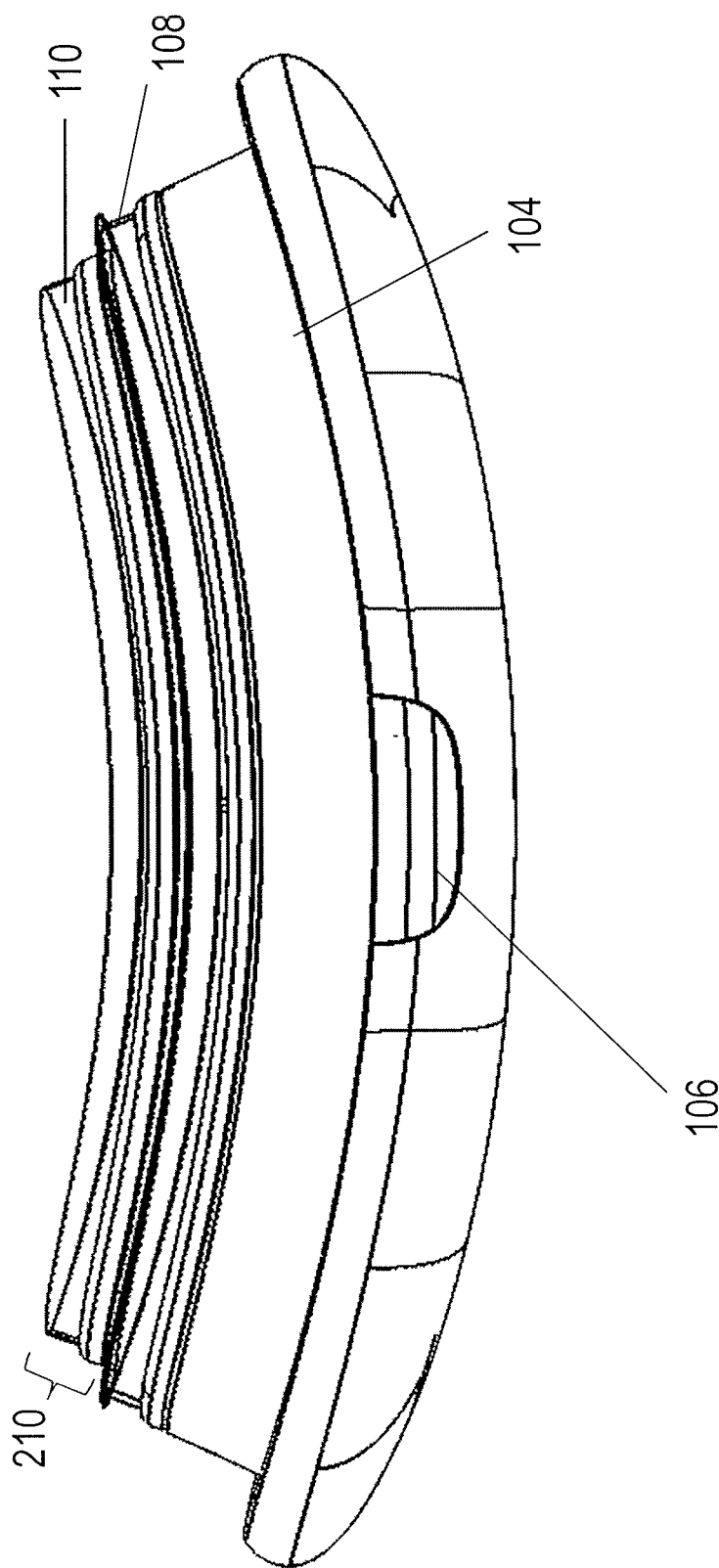
FIG. 2A shows a side perspective view of the apparatus of FIGS. 1A-1B with a cover removed, showing the secondary unit (including skin-contacting electrode) positioned above the primary unit (including skin-contacting electrode).

FIG. 2A shows a lightweight and wearable apparatus that includes a primary unit 104 with a primary electrode portion 108 and a secondary unit 210 with a secondary electrode portion 110 positioned adjacent to the primary unit 104. The cover 102 visible in FIGS. 1A and 1B has been removed to show the secondary unit held stored with the primary unit; a cable (not visible in FIG. 2A) connects the secondary unit to the rest of the apparatus.

Figure 2B:
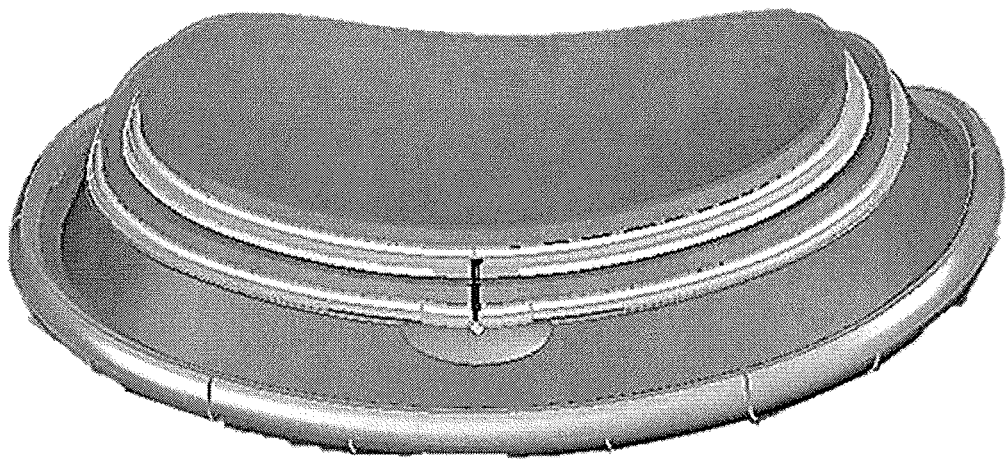
FIG. 2B shows an alternative view of the apparatus of FIG. 2A.
Figure 2C:
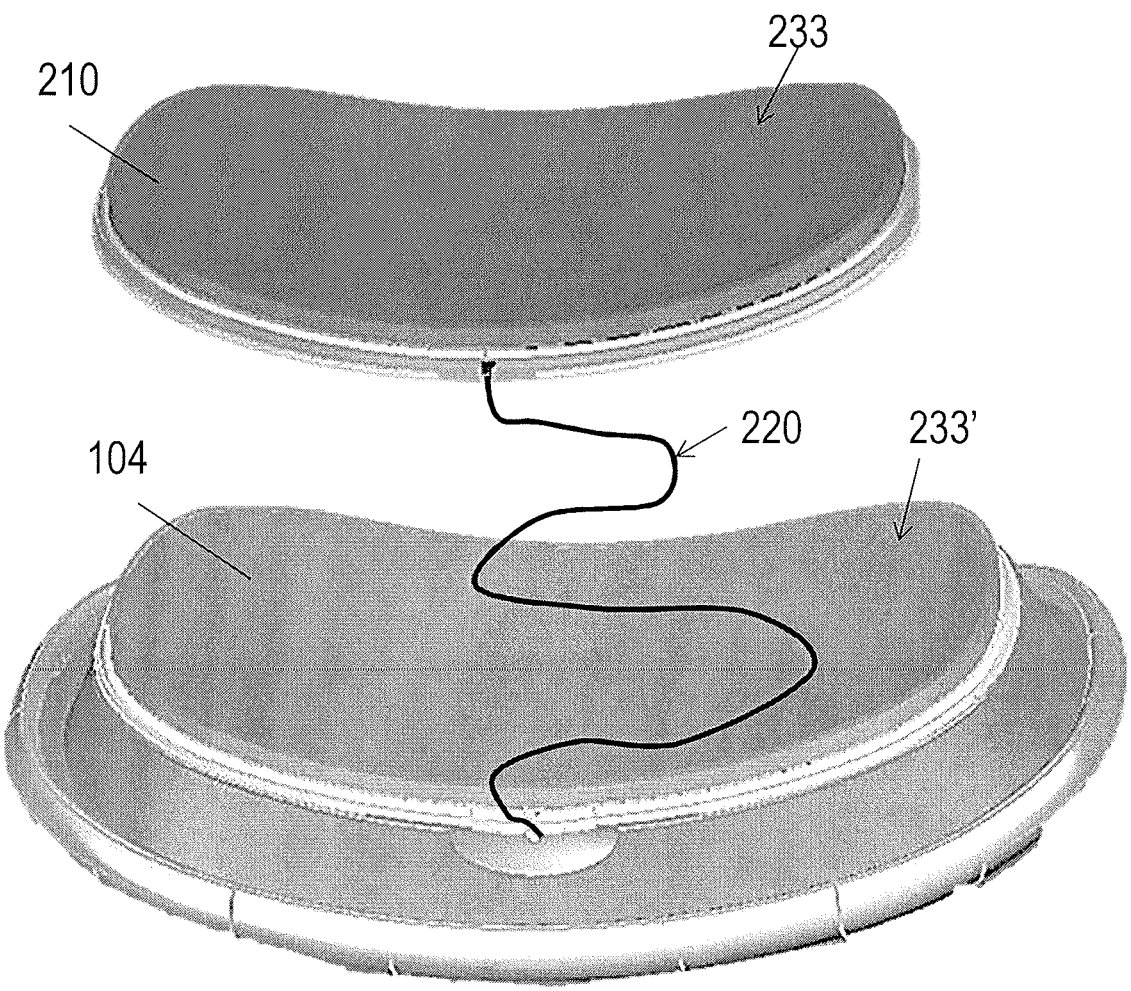
FIG. 2C illustrates the apparatus of FIG. 2B with the secondary unit separated from the primary unit.

FIG. 2B is a side perspective view of the apparatus of FIG. 2A. In FIG. 2C the secondary unit 210 has been separated from the primary unit 104, and the two units are connected by a cable 220. Thus, the two units may be separately positioned.

The primary unit and the secondary unit may both include a transdermal electrode for delivery of current to the subject to evoke a cognitive response. In FIGS. 2A-2C the electrodes are not visible as a removable cover 233, 233' (e.g., covering an adhesive layer) covers the contact surfaces of both units. The cable may be stored (e.g., wound) within either the primary or secondary units. In the example of FIGS. 2A-2C the cable is stored within the secondary unit (not visible in FIGS. 2A-2C).

Figure 3A:
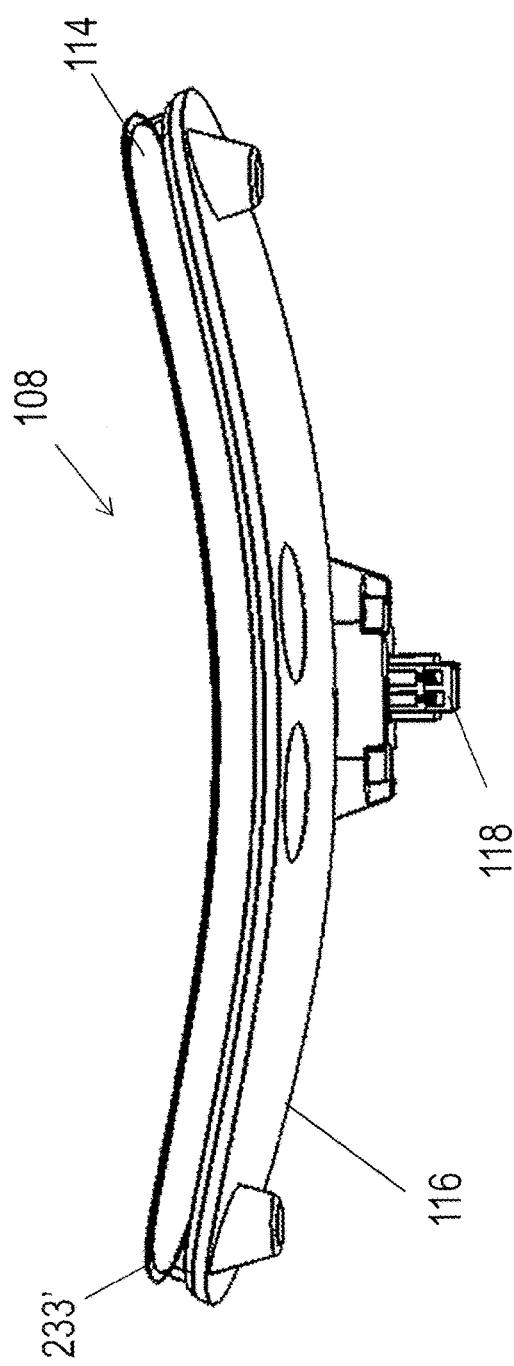
FIG. 3A is a side view of a primary electrode portion of a primary unit for an apparatus such as the one shown in FIG. 2A.
Figure 3B:
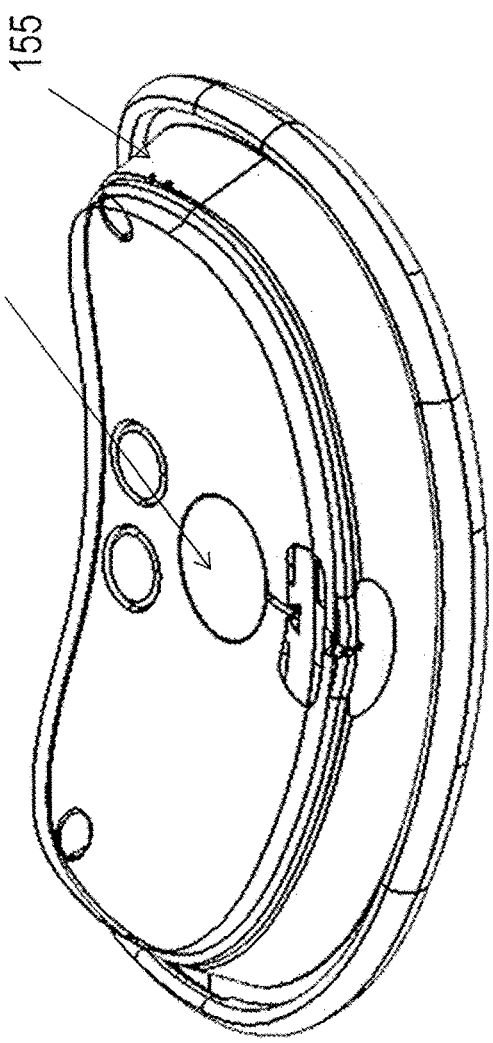
FIG. 3B is a top perspective view of a primary unit including the primary electrode portion of FIG. 3A.
Figure 3C:
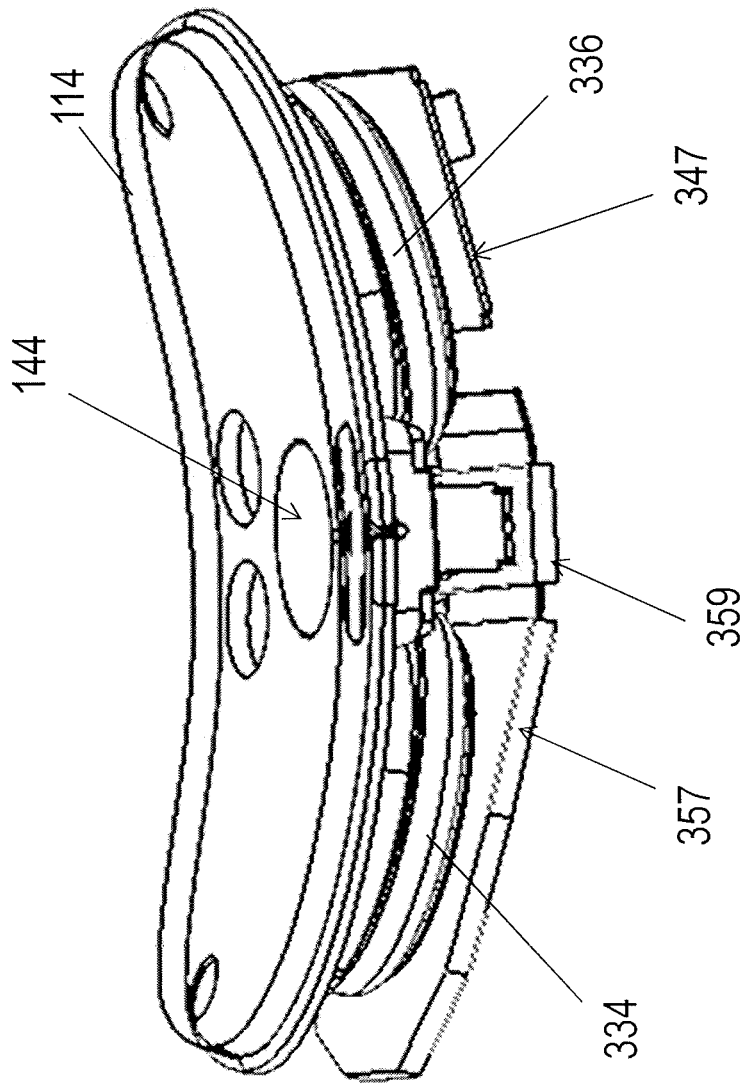
FIG. 3C is another view of the primary unit shown in FIG. 3B with the outer side housing removed.

FIG. 3A shows the primary electrode portion 108 of the apparatus of FIGS. 1A-2C. The primary electrode portion 108 comprises a cover 233' (e.g., an adhesive peel layer). Beneath the peel layer is the primary electrode 114 region. An adhesive (e.g., electrically conductive adhesive) may be positioned between the cover and an electrode base 116. The primary electrode portion 108 may also include a connector 118 (e.g. electrode connector) which can be used for attaching to and delivering current processor portion of the primary unit not shown in FIG. 3A). The electrode contact 144 for the primary electrode region 114 is shown in the partially transparent view of FIGS. 3B and 3C. FIG. 3B shows the primary unit housing 155 which may enclose the processor/controller of the primary unit as well as the power source (e.g., a pair of batteries in this example), as well as any additional and/or optional components including a wireless communications module. The housing also includes the one more controls and/or one or more indicators (e.g., LEDs) that may be present on the surface of the housing. FIG. 3C shows the primary unit with the housing removed, revealing a pair of batteries 334, 336, a wireless module 347 (e.g., Bluetooth) and circuitry (printed circuit boards) 357, 359 for controlling the power supply and generating and conditioning the current waveforms applied between the electrode in the primary unit and the electrode in the secondary unit.

The primary electrode region 114 region is configured to be positioned against the skin of a user during a stimulation session. The top surface of the electrode 114 region shown in FIG. 3A is the surface configured to be positioned on the skin of a user. As described below, the primary electrode region can be adhered to the skin or can be held in place by an accessory or other article.

The primary electrode 114 region shown in FIG. 3A is a transdermal adhesive electrode. The adhesive can be one of a variety of adhesives, for example pressure sensitive adhesives and dissolvable adhesives. The adhesive can be electrically conductive. Some examples of adhesive layers include acrylics (e.g., cyanoacrylate), silicone, polyurethane, and bio adhesives. The peel layer 233' can be used to maintain the adhesive properties of the electrode 114 when the device 100 is not being used. Embodiments of adhesives are described in more detail below. In some embodiments, the primary electrode 108 does not include an adhesive layer. In these embodiments, the primary electrode can be held against the skin of a user using a different technique. For example, the subject may wear an item configured to hold the electrode against the skin. In some embodiments, the subject wears a wrap or headband configured to hold the primary electrode against the skin. Other accessories and articles are also possible. For example, in some embodiments, a user uses a hat or glasses to hold the electrode in place. For example a glasses-like article can be used to hold an electrode over an ear of a user.

The primary electrode portion 108 may be formed integrally with the primary unit 104. In some embodiments, the primary electrode portion can be configured as a cartridge, to be detachably coupled to the primary unit 104 using the connector 118. In some embodiments, the primary and/or secondary electrode portion is disposable and can be used for a certain period of time, and can then be replaced with another primary electrode portion. The term 'disposable' can refer to the portion being used a number of times (e.g., 1-10, 10-25, 25-50, >50) and then being thrown away. In some embodiments, the portion is not thrown away, but is refurbished to be able to be used again. The term disposable is described in further detail herein.

The primary electrode base 116 is configured to be positioned within the primary unit 104. The primary electrode base 116 can comprise a bottom surface configured to mate with an inner surface of the primary unit 104. The connector 118 is a snap connector, but other configurations are also possible. For example, the connector can comprise a latch, screw-on, or micro-snap configuration. The connector 118 can provide both a physical and electrical connection between the primary electrode 114 and the primary unit 104. In some embodiments, the primary electrode portion 108 can include one or more electrical connectors and one or more separate physical connectors.

Figure 4B:
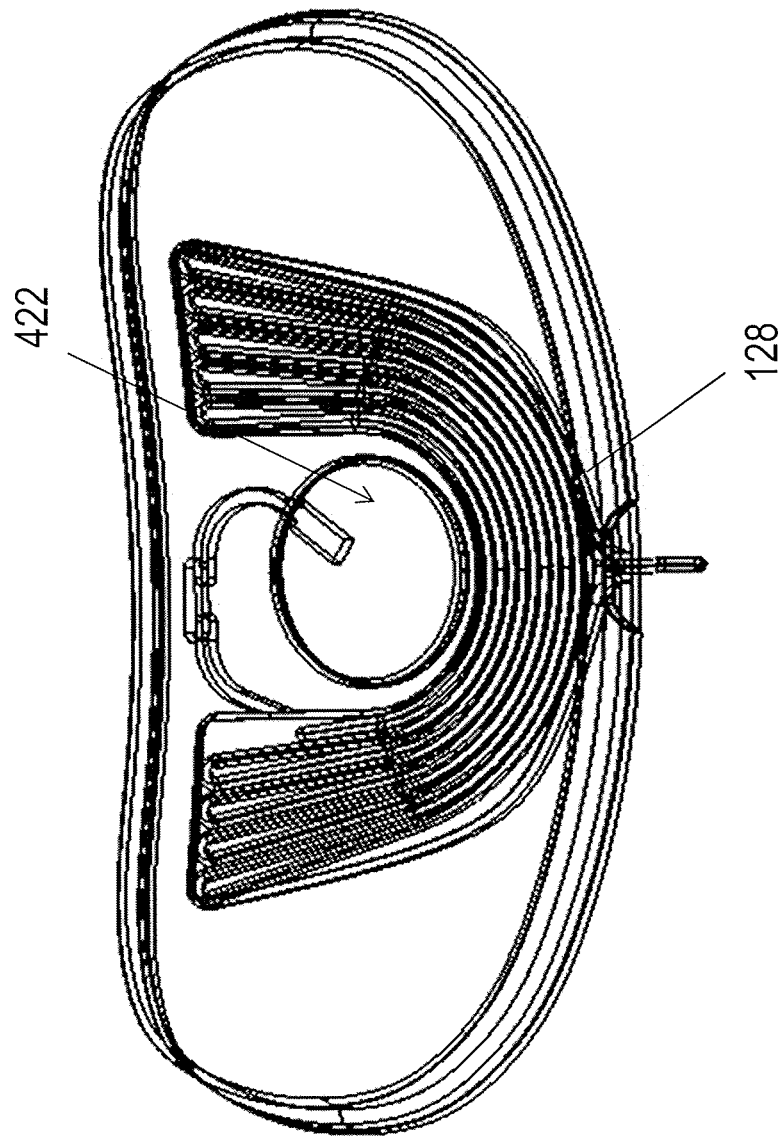
FIG. 4B shows a partially transparent view of the secondary unit of FIG. 4A.

FIGS. 4A and 4B illustrates one variation of a secondary electrode portion 110 of a secondary unit such as the one shown in FIGS. 2A-2C. The secondary electrode portion 110 shown in FIG. 4A includes a peel layer 233. The peel layer 233 can be similar to the peel layer 233' described with respect to FIGS. 3A-3C. Beneath the peel layer 120 is positioned the secondary electrode region 122, including an electrode (secondary electrode) 422. A secondary electrode base 124 is positioned beneath the secondary electrode 122. A secondary electrode cover 126 is positioned beneath the secondary electrode base 124.

In FIG. 4B the secondary unit has been made partially transparent to illustrate the internal elements, including an electrode 422 and cable 128. The cable is arranged within the layer formed by the secondary unit and may be extended from the secondary unit by pulling the secondary unit away from the primary unit.

As illustrated above in FIG. 2C, the secondary electrode portion 110 can be configured to be detached from the primary unit 104 and positioned against the skin (e.g., on the skin, on the hair, on the ear, etc.) of a user. The top surface of the secondary electrode, as viewed in FIG. 4A is configured to be positioned against the skin of a user. Similar to the primary electrode region 114, the secondary electrode region 122 can be adhered to the skin or can be held in place by an accessory or other article.

The secondary electrode region 122 may include a transdermal adhesive (which may be conductive) for coupling the electrode to the subject. The adhesive can be one of a variety of adhesives, for example pressure sensitive adhesives and dissolvable adhesives. The adhesive can be electrically conductive. Some examples of adhesive layers include acrylics (e.g., cyanoacrylate), silicone, polyurethane and bio adhesives. The peel layer 233 can be used to maintain the adhesive properties of the electrode region 122 when the device 100 is not being used. In some embodiments, the secondary electrode region 122 is not adhesive. In these embodiments, the primary electrode region can be held against the skin of a user using a different method. For example, the subject may wear an item configured to hold the electrode against the skin. In some embodiments, the subject wears a wrap or headband configured to hold the primary electrode region against the skin.

The secondary electrode base and cover 124, 126 can provide protection to the secondary electrode. The base 124, 126 can also provide packaging for the secondary electrode portion 110, for example when sold as a separate unit or cartridge. The base 124 and cover 126 can also be configured to hold the cable 128, as described with respect to FIGS. 4B and 4C. In some embodiments, the secondary electrode region 122 is connected to the primary electrode portion 108 or primary unit 104 using a connector (e.g., similar to connector 118) positioned at the secondary electrode base 124 and/or cover. In some embodiments, the secondary electrode 122, base 124, or cover 126 includes an adhesive that can be used to attach the secondary electrode portion 110 to the primary electrode portion 108. In some embodiments, the secondary electrode portion 110 can be held in place within the keeper 104 by a cover such as that shown in FIGS. 1A and 1B.

The secondary electrode portion 110 can be configured as a cartridge, to be detachably coupled to the primary unit 104 and/or the primary electrode portion 108 using a connector, adhesive, or the like. In some embodiments, the secondary electrode portion is disposable and can be used for a certain period of time, and can then be replaced with another or the same secondary electrode portion 110, as described with respect to the primary electrode portion 108 above.

FIG. 4C illustrates a bottom perspective view of the secondary electrode portion 110 with the cover 126 removed. The second electrode base 124 has a recessed portion sized to fit the cable 128 that connects the second electrode portion 110 to the primary unit 104 via connector 129. The cable 128 is shown furled within the base 124 in FIGS. 4B and 4C. In some embodiments, the furled cable 128 can serve to connect the two electrode portions 108, 110. In some embodiments, the base 124 will not include a recessed portion for the cable 128. The cable 128 can include one of a variety of wires, including a multicore cable (e.g., copper wire, carbon nanotube wire), a flexible flat wire (e.g., a ribbon cable), and the like. In some embodiments, the cable 128 can include a set of more than one wire or cable.

Figure 5A:
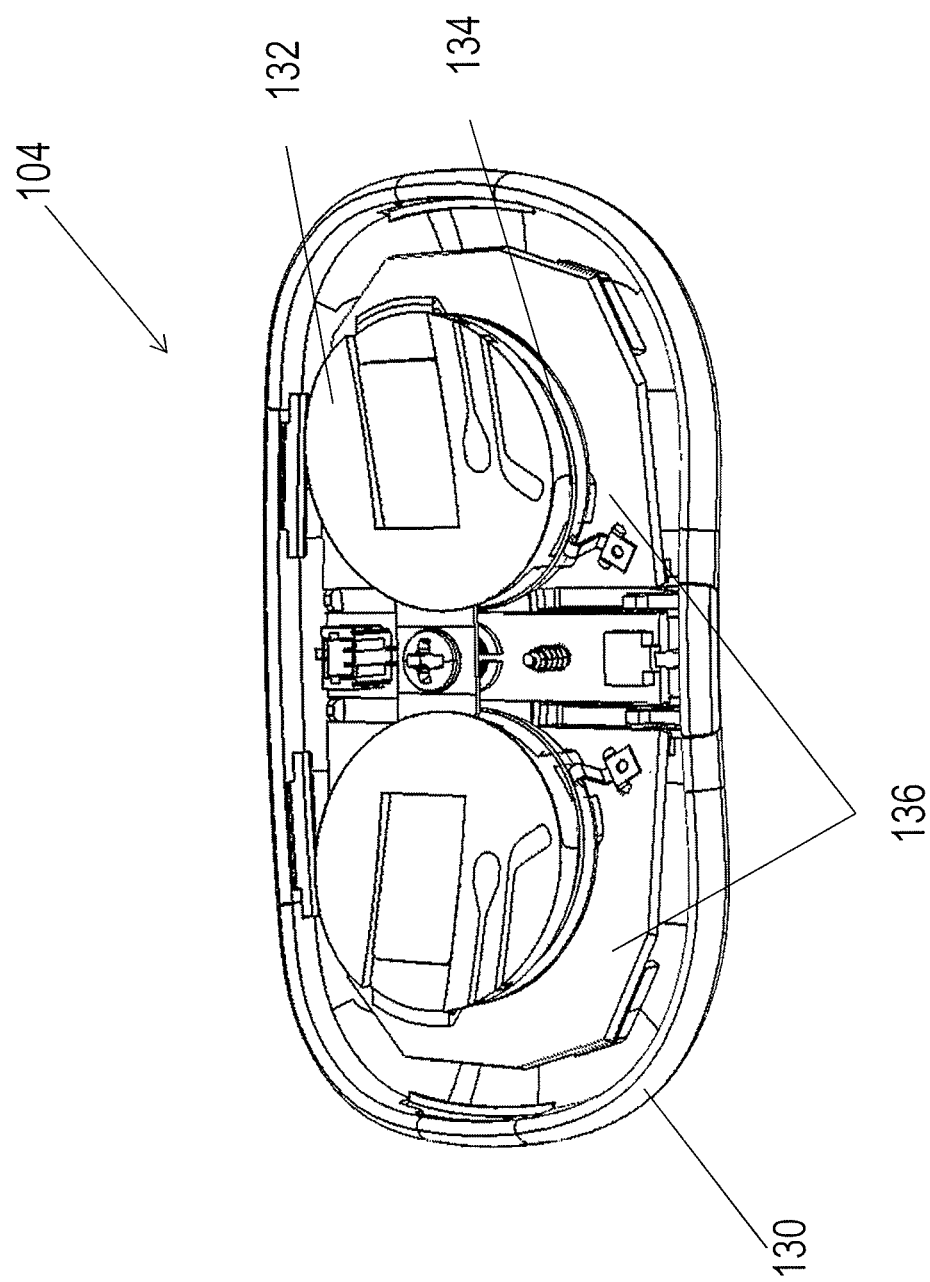
FIG. 5A illustrates some of the components that may be arranged and held within the housing of the primary unit.

FIG. 5A illustrates the interior of an embodiment of the housing (keeper 104) of the primary unit, as described above in reference to FIGS. 3A-3C. The keeper may include a housing 130 that serves as a base for the keeper 104. Situated within the housing 130 is a two-part PCB controller 136. In some embodiments, the controller 136 may have fewer or more than two parts. The parts may be oriented differently than the configuration shown in FIG. 5. The controller 136 can be configured to drive stimulation between the primary electrode 114 and the secondary electrode 122 when the electrodes 114, 122 are electrically connected. The controller 136 can be configured to drive stimulation based on a number of parameters, including current amplitude, current frequency, pulse width, pulse duration, pulse frequency, pulse waveform, burst duration, burst frequency, off-time, burst waveform, positive duty cycle, negative duty cycle, and on/off. Other parameters can also be utilized. For example, the controller can be configured to drive stimulation in which no current is provided between pulses or in which the current is short-circuited through a resistor between pulses (for instance, to provide sharper pulse boundaries due to reduction of capacitive current in the circuit). The controller 136 can utilize a current generator to drive stimulation. Other devices are also possible. For example, the controller 136 can utilize a voltage generator in some embodiments. A current generator or other similar device may be part of the controller 136. In some embodiments the current or voltage generator is positioned within the primary unit, but is not part of the controller 136. As described in further detail below, in some embodiments, the stimulation driven by the controller can depend on data received from items contained within or without the device 100. For example, measurements taken by devices such as impedance meters or physiological sensors can influence the stimulation provided. In some embodiments, the controller is configured to adjust current across the primary and secondary electrodes based on a detected impedance. In some embodiments, the stimulation can be triggered or controlled wirelessly from a remote device such as a smartphone.

In FIG. 5A two batteries 134 covered by doors 132 are illustrated. In some embodiments, the keeper 104 will not include doors 132 for the batteries 134. In some embodiments, one battery supply is configured to provide power to the electrodes while a second battery supply may be configured to provide power for stimulation delivered to control components and other components of the device (e.g., LED indicator or internal clock). In this manner, both the advantages of limitations on device usage can be achieved while maintaining convenience of having a reusable portion of the device that requires less maintenance in between uses. Certain embodiments may provide a battery supply integrated into the main housing of the device, while a second battery supply for the electrodes could be contained within a disposable portion of the device. In some embodiments, the device 100 comprises one battery. In some embodiments, the device 100 comprises more than two batteries. For example, the device 100 can comprise three batteries.

In some embodiments, coin cell batteries can be used. Other types of batteries are also possible. For example, in some embodiments, button cells can be used. An example of a suitable battery is the Energizer CR1220 lithium coin battery. Other possibilities include the CR 1025 and the CR1216. The CR1025 has enough power to delivery 1 mA for about 30 minutes (0.5 mAh). The CR1216 lithium coin battery is even smaller: about 0.5 inch round, $20^{th}$ inch high. These and other battery form factors can be advantageous for a disposable, limited use or single use system. Advantageously, usage of the device can be limited as to not allow a user to overuse or forget to turn off the device.

In some embodiments, a chain of batteries in series is used to generate higher voltages required for stimulation. For example, six 1.5V batteries in series can be used to create a 9V source. In some embodiments, transformer or buck-boost strategies are used to generate higher voltages from a low voltage battery source. One of ordinary skill in the art would appreciate that there are numerous strategies for generating higher voltages from lower voltage sources.

In some embodiments of the invention, the battery is charged by one or more solar panels or by harvesting energy from the movements of a user for example by using piezopolymers or piezoelectric fiber composites as disclosed in International Patent Application No. PCT/US2010/055527 (Publication No. WO/2011/057028) titled "DEVICES AND METHODS FOR MODULATING BRAIN ACTIVITY" by inventor Tyler).

Figure 5B:
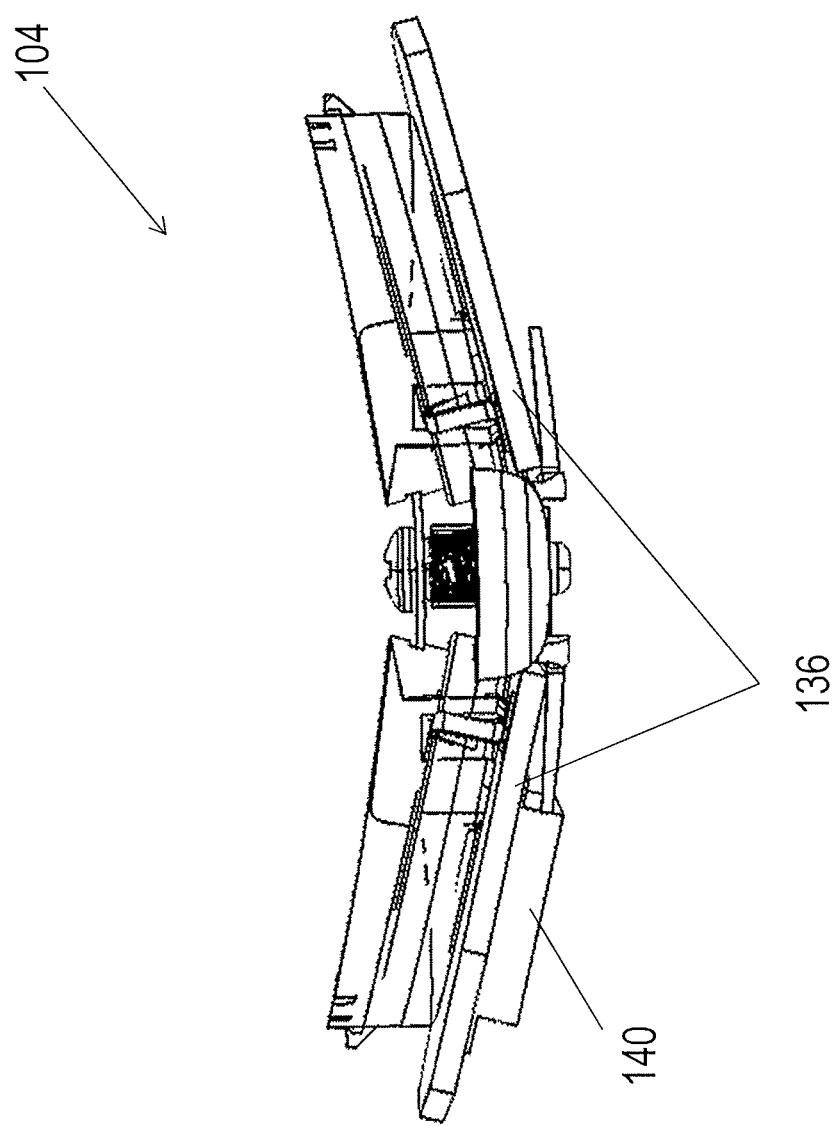
FIG. 5B is a side perspective view of FIG. 5A.

FIG. 5B depicts a side view of the primary unit 104 without the housing 130. This example includes a wireless communications module 140 positioned near one of the controller 136 components. The wireless communications module 140 can be configured to transmit information using one or more wireless modes such as Bluetooth, Wi-Fi, cellular data signals, or another form of wireless communication. In this manner, a remote server can trigger electrical stimulation via the Internet or other local or wide area network means, or a PC, laptop, smartphone, or tablet. Such wirelessly connected devices can be used to remotely control parameters of electrical stimulation (e.g., current amplitude, current frequency, pulse width, pulse duration, pulse frequency, pulse waveform, burst duration, burst frequency, off-time, burst waveform, positive duty cycle, negative duty cycle, and on/off). In some embodiments, the device is not configured to control parameters of electrical stimulation, such as those described above. In such embodiments, the device may advantageously be smaller as less room may be used for device circuitry.

The device 100 is shown as having a generally rectangular shape with rounded edges. In some embodiments, the primary unit 104 can have a different shape. For example, the primary unit 104 can have a generally ovular, rectangular, or circular shape.

The device 100 is shown as having a generally kidney bean-shaped profile, as seen from the view depicted in FIG. 1B. In some embodiments, the device has a differently shaped profile. For example, the profile can be generally rectangular, generally trapezoidal or generally ovular. The profile can have rounded edges or generally sharp edges. In some variations (as illustrated, the outer subject-contacting surface of the primary and secondary units is contoured to better fit the subject's head. For example, as illustrated, the primary and secondary unit subject-contacting surfaces are curved slightly (bowed inward) to better fit the subject's head or neck. In addition, these surfaces may be flexible, bendable or otherwise configured to contour to the shape of the subject. Thus, in general the primary and secondary units may be sufficiently curved, bendable, or flexible to conform to the shape of the subject's body where the primary and secondary units are coupled (and particularly where the electrode regions contact the subject's skin).

Figure 26:
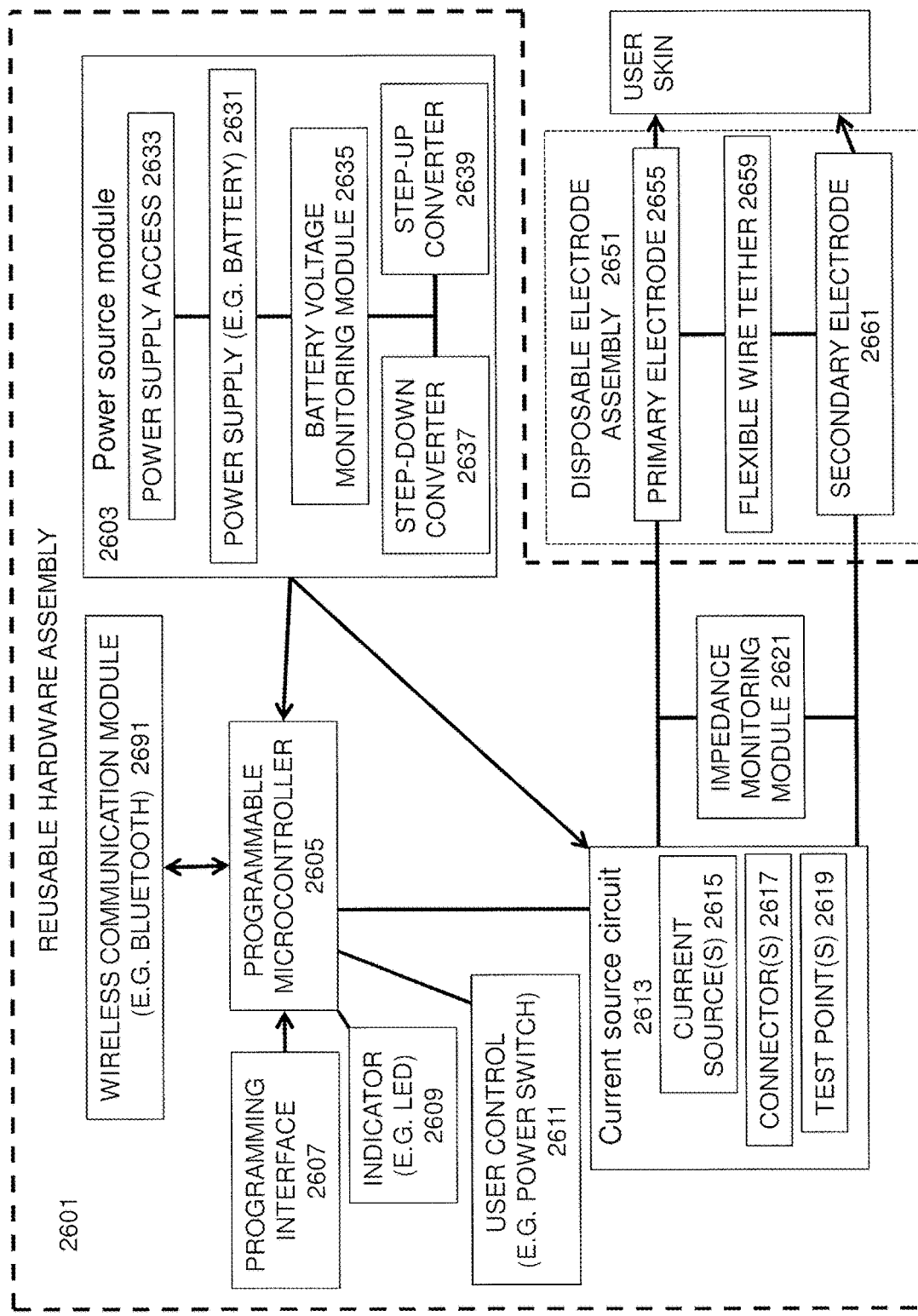
FIG. 26 is a schematic illustration of a lightweight, wearable and self-contained electrical stimulation apparatus.

FIG. 26 is a schematic illustration of a lightweight, wearable and self-contained electrical stimulation apparatus that illustrates both durable ("reusable") 2601 and disposable components 2603. In FIG. 26, the reusable assembly may include a processor (e.g., programmable microcontroller 2605, and programming interface 2607). The reusable components may also include one or more (or all) of: one or more indicators 2609, one or more user controls 2611, current source circuit 2613 (e.g., one or more current sources 2615, connector(s) 2617, test point(s) 2619), and one or more impedance monitoring module 2621. The impedance monitoring module is typically connected to microcontroller (not shown) which may act upon it or may adjust the applied current(s) based on information received from the impedance monitoring module. The power source module 2603 is also typically included in the reusable hardware assembly. Although one or more batteries may be replaceable or disposable, such power sources are typically intended for multiple uses, and may be rechargeable. In some variations, however, the power source (power supply 2631, such as batteries) may be disposable and included in the disposable assembly 2651. The power source module may also include a power supply access 2633, the power supply (e.g., battery, capacitive power source, etc.) 2631, a power monitor (e.g., battery voltage monitoring module 2635), and a step-down 2637 and/or step-up converter 2639.

As mentioned above, any of the apparatuses described herein may also include one or more wireless communication module 2691, which may also be part of the durable assembly. For example, a wireless communication module may include an antenna, encoder, D/A processor, filters, amplifiers, etc. The wireless communication module may be duplex (half-duplex, full-duplex, etc.) for both receiving and transmitting information. The durable/reusable assembly 2601 may also include a memory (not shown) for storing instructions and/or performance information about the apparatus; the memory may be coupled to either or both the controller/processor 2605 and the wireless communication module 2691.

Embodiments of methods of using a lightweight and wearable apparatus for inducing a cognitive effect will now be described. In some embodiments, a subject using the device or third party will detach the secondary electrode portion 110 from the primary unit, separating the two electrode portions, prior to initiating a stimulation session. In some embodiments, the primary electrode portion 108 and secondary electrode portion 110 are not positioned within the primary unit 104. In such embodiments, the user or third party can insert the first electrode portion (e.g., a replaceable or disposable cartridge) into the primary unit 104 (e.g., using snap 118). In some embodiments, the user or third party inserts the primary electrode portion 108 and secondary electrode portion 110 (e.g., as a replaceable or disposable cartridge) into the primary unit 104, and then detaches the secondary electrode portion 110 from the primary unit 104.

The user or third party can position the primary unit 104 including the primary electrode portion 108 at a first location on a user and position the secondary electrode portion 110 at a second location on a user. In some embodiments, one or both of the primary and secondary electrode portions 108, 110 are positioned on the head of a user. In some embodiments, one or both of the primary and secondary electrode portions 108, 110 are positioned on the neck of a user. For example, the primary electrode portion 108 can be positioned on the forehead of a user and the secondary electrode portion 110 can be positioned on a neck of a user. In some embodiments, one or both of the primary and secondary electrode portions 108, 110 is positioned on the periphery of a user (e.g., locations other than the head or neck). As described above, the electrode portions can be adhered to the skin of a user or worn using an accessory or article.

The secondary electrode portion 110 can be electrically connected to the primary electrode portion 108 by using the cable 128 and connector 129 either before or after positioning the electrode portions 108, 110 on the skin. In some embodiments the two electrode portions may already be connected. Once the two electrode portions 108, 110 are electrically connected, the user can drive stimulation between the electrodes 114, 122. As described above, the stimulation can be driven based on predetermined parameters. In some embodiments, a user can control the stimulation driven using the input control. In some embodiments, the device receives stimulation parameters wirelessly. In some embodiments, a user or third party can control the stimulation parameters on a separate device such as a smartphone, laptop, tablet, etc., and can transmit the parameters to the device 100 using a wired or wireless connection.

As described above, the device 100 includes a modular secondary electrode portion 110 that can be attached to the primary unit 104. In some embodiments, the device 100 includes more than one secondary electrode portion. Each secondary electrode portion can have its own adherent pad and one or more electrodes as well as a connection means allowing for connection (e.g., wired, wireless) to the primary unit 104. The multiple electrode portions can be arranged in an array with shapes including: round, elliptical, triangular, square, rectangular, trapezoidal, polygonal, oblong, horseshoe-shaped, hooked, or irregularly-shaped. In some embodiments, the secondary portion 110 can be attached to the primary portion 108 via a flexible wire, as described above. In these embodiments, power and control signals can be sent by way of the flexible wire. In other embodiments, the secondary units include an independent power source (e.g., battery) and receive control signals from the primary unit via the connection means either wirelessly (e.g., Bluetooth Low Energy) or through a wired connection (e.g., flexible wiring extending from the primary unit).

In some embodiments, an indicator communicates to the user (and/or a third party) that electrical stimulation is underway. In an embodiment of the invention, an indicator communicates to the user (and/or a third party) that electrical stimulation will end in a certain amount of time. In an embodiment of the invention, an indicator communicates to the user (and/or a third party) that electrical stimulation will begin soon.

In embodiments wherein an indicator communicates to the user, the indicator can take the form of an LED or other visual stimulus; transducer, buzzer, or other tactile transducer; a speaker or skull-coupled transducer for transmitting vibration that can be detected as an auditory stimulus; an emitted chemical signal detected as an olfactory or gustatory signal by the user; or a signal transmitted via an application used by the subject on a PC, laptop, tablet, smartphone, or other mobile computing device.

In some embodiments, the recipient of electrical stimulation triggers their own electrical stimulation. In alternative embodiments, a third party triggers electrical stimulation.

In embodiments of the invention, one or more of the electrodes is a dry electrode. In some embodiments that incorporate one or more dry electrodes, the dry electrodes are designed to have finger-like projections useful for contacting the skull through hair and composed of a material chosen from the group of: fabric, foam, rubber, or another material or materials known to one skilled in the art of creating dry electrodes.

As described above, the electrical stimulation device can include disposable components. In some embodiments, the entire assembly is disposable. In some embodiments, the device is composed of separable non-disposable and disposable components. For example, the primary unit 104 may be non-disposable, while the first and second electrode portions 108, 110 can be disposable. In this manner, robust and reusable components of the system can be reused, saving resources and reducing cost, while permitting the replacement of other components such as single-use (or limited use) electrodes (which may not reliably adhere to the head after a single use) or a battery.

In some embodiments, the system is configured to be a "single use" system that is only used once and then disposed. In other embodiments, the system is configured to be disposable after a certain number of uses and is thus referred to as "multiple use". In some embodiments, the system is configured to be disposed after a number of uses within a range. In alternative embodiments of the invention, the system is configured to be disposed after a fixed number of uses chosen from the group of: more than once, more than twice, more than 3 times, more than 4 times, more than 5 times, more than 10 times, more than 25 times, more than 50 times, more than 100 times, more than 1000 times, or more than 10000 times. In alternative embodiments of the invention, the system is configured to be disposed after a fixed period of time of use chosen from the group of: more than 10 seconds, more than 30 seconds, more than 1 minute, more than 2 minutes, more than 3 minutes, more than 4 minutes, more than 5 minutes, more than 7 minutes, more than 10 minutes, more than 15 minutes, more than 30 minutes, more than 45 minutes, more than 1 hour, more than 2 hours, more than 3 hours, more than 5 hours, more than 10 hours, more than 20 hours, or longer. In an embodiment of the invention, a fixed-use fuse, burnout circuit, limited battery, or other electronic or mechanical system is used to cease device operation once the limit in uses or time has been reached. In an embodiment of the invention, a machine readable memory is used to count the number of uses or length of time a disposable device or system component has been used, then a microcontroller or other electrical component compares the value in memory to a maximum number of uses or length of time to determine whether stimulation is triggered by the system. In some embodiments, a radiofrequency identification (RFID) tag is a component of a disposable component of a stimulation device and configured to make certain that the disposable component is not used more often or for longer than intended. The number of uses and/or length of use is transmitted wirelessly to a PC, laptop, smartphone, tablet, or other mobile computing device.

In some embodiments in which the stimulation device is configured to be semi-disposable, reusable components integrated into a main housing can be permanently used for all sessions of stimulation. In some embodiments, the reusable components incorporated into the main housing can be designed for re-use a number of times chosen from the group of: more than once, more than twice, more than 3 times, more than 4 times, more than 5 times, more than 10 times, more than 25 times, more than 50 times, more than 100 times, more than 1000 times, or more than 10000 times.

In some embodiments in which the stimulation device is configured to be semi-disposable, the disposable portion includes one or more electrodes. In some embodiments in which the stimulation device is configured to be semi-disposable, the disposable portion includes a battery. In some embodiments in which the stimulation device is configured to be semi-disposable, the disposable portion includes an electrical connector. In some embodiments in which the stimulation device is configured to be semi-disposable, the disposable portion includes an electrically conductive adhesive. In some embodiments in which the stimulation device is configured to be semi-disposable, the disposable portion includes a fuse or limiting switch configured to terminate (or burn out in the case of a fuse) after exceeding a desired time or current level, protecting the user from over use or undesirable current surges or fluctuations (e.g., permitting use without the need to have predefined range for the stimulation). In some embodiments in which the stimulation device is configured to be semi-disposable, the disposable portion includes a microcontroller. In some embodiments in which the stimulation device is configured to be semi-disposable, the disposable portion includes a user interface component. In some embodiments in which the stimulation device is configured to be semi-disposable, the disposable portion includes packaging, a tactile transducer, a speaker, or an LED. One of ordinary skill in the art will appreciate that the various elements of the disposable portions of the stimulation device are not necessarily a single disposable component. For example, in some embodiments, the disposable portion may be two or more separate components, such as a disposable contact pad, comprising an adherent and one or more electrodes, while a disposable battery may be detachably integrated within a semi-disposable or non-disposable portion of the device (e.g., battery compartment).

In some embodiments, a disposable stimulation device or disposable portion of a stimulation device is configured to be returned to the company or a third party for recycling. In an embodiment of the invention, a refund is provided for a disposable system returned by a user. One or more new disposable systems may be provided to a user or sent to them as a replacement for a returned or disposed of disposable stimulation device component. In some embodiments, return packaging is provided for the user to mail a used system or used component of a system. Users can subscribe to receive disposable stimulation devices or components of stimulation devices and/or disposable portions of stimulation devices regularly or when they have used previously received systems. Embodiments incorporating recycling can be advantageous, because they may benefit the environment, particularly with respect to batteries or other electrical components that may be toxic if disposed of improperly.

In some embodiments, the device is configured to be user-actuated and/or automated. In this manner, embodiments of the present invention may be utilized without the need to have a skilled practitioner (e.g., medical technician) available in order to oversee the placement, control and operation of the electrical stimulation.

The above features of embodiments of stimulation devices provided herein differ from existing TES systems and offer key advantages for the widespread, portable use of TES systems, including:

1) Single use or limited use electrodes that adhere to the skin, hair, face, or head can simplify system design by reducing requirements for robustness of the electrode itself, as well as its properties with respect to adherence to the head, electrical conductivity, and effectiveness of stimulation.

2) Smaller, lighter, and structurally flexible form factor can enable users to undertake normal, daily activities throughout stimulation sessions and make the device more comfortable and convenient to use.

3) Electrical, structural, and energy-storage components can be designed to lower tolerances and need not achieve long-term performance, permitting significantly reduced product pricing relative to existing TES systems (e.g., 5-10× less), significantly expanding their use and reducing the barrier to adoption versus traditional devices.

4) By eliminating the requirement for field support for hardware or long term performance requirements customer satisfaction can be improved while also lowering operational costs to maintain working products in the field.

As described above, the device components (e.g., the first and second electrode portions) can include adhesive to make them self-adhering (e.g., adherent) to the skin, skull, face, hair, neck or other portions of the head or body. The adhesive can be reversibly self-adhering. After a user session, the self-adhering components (for instance adhesive) can be manually removed by the user by exerting a small amount of force. In some embodiments, the device is designed so that little or no hair is removed during device removal if the adhesive portion of the device was placed over an area with hair. In some embodiments, the adhesion is stronger and removal requires more force (e.g., similar to band aid removal).

Adhesive used can include hydrogel, acrylic conductive adhesive, and PIB (polyisobutylene) synthetic rubber conductive adhesive. A hydrogel used as an adhesive is soft conformable gel material that enables intimate contact and can be ionically conductive. However, hydrogels can provide a weak skin bond. Appropriate hydrogels can be manufactured by Corium International and other vendors. An example of an acrylic conductive adhesive are the EC-2 products which have been used for defibrillator pads and EKG sensors for use over minutes to hours. Adhesives Research Inc. is a provider of acrylic conductive adhesive. PIB (polyisobutylene) synthetic rubber conductive adhesive are designed for direct skin contact and electrical pulse applications with long term exposure (days to weeks). PIB adhesives can be tailored to be removable or high bond. One of ordinary skill in the art will appreciate that there are numerous pressure sensitive adhesives and hydrogels that could be used with embodiments of the present invention, and embodiments of the present invention are contemplated for use with any type of pressure sensitive adhesive and/or hydrogel. Particular adhesives can be chosen for their, adhesive strength, electrical conductivity, the amount of residue they leave behind (e.g., little or none), and force required for removability.

In some embodiments, the adhesive includes a suction device, or another system that adheres the device to the head. The self-adhering property of at least some components of the device can advantageously hold the device components in place at a fixed location on the head or neck for targeting a specific brain region. The self-adhering property of at least some components of the device can also advantageously provide a more desirable aesthetic effect than other devices that need to be attached or worn using intrusive articles.

In some embodiments, the device is less than about 8 oz. or about 226.8 g. In some embodiments, the device is less than about 7 oz. or about 198.4 g. In some embodiments, the device is less than about 6 oz. or about 170.1 g. In some embodiments, the device is less than about 5 oz. or about 141.7 g. In some embodiments, the device is less than about 4 oz. or about 113.4 g. In some embodiments, the device is less than about 3 oz. or about 85.0 g. In some embodiments, the device is between about 1 oz. and about 2 oz., or between about 28.3 g. and about 56.7 g. For example, the device can be about 1.25 oz. or about 35.4 g. In some embodiments, the device is less than about 1 oz. or 28.3 g. In some embodiments, the device is less than about 0.5 oz. or about 14.2 g. For example, the device can be about 0.25 oz. or about 7 g. A sufficiently low weight can aid in allowing the device to be self-adhering. In some embodiments, the device may not be sufficiently light to be self-adhering. A lightweight device may also increase comfort, reduce cost, and reduce the area of electrical stimulation on the scalp and/or in the brain in order to achieve tighter focusing of the induced electric field in the brain.

The electrical stimulation device can be configured for conformability to the head, face, neck, or other body region. In some embodiments, the device components are flexible. In some embodiments, all components larger than the curvature of the target body area are made of flexible materials. In some embodiments, flexible mechanical elements between inflexible components permit conformability to the body.

In some embodiments, the device long axis dimension is less than about 30 cm, less than about 20 cm, less than about 12 cm, less than about 10 cm, less than about 9 cm, less than about 8 cm, less than about 7 cm, less than about 6 cm, less than about 5 cm, less than about 4 cm, less than about 3 cm, less than about 2 cm, or less than about 1 cm.

In some embodiments, the device has a diameter of less than about 12 cm, less than about 10 cm, less than about 9 cm, less than about 8 cm, less than about 7 cm, less than about 6 cm, less than about 5 cm, less than about 4 cm, less than about 3 cm, less than about 2 cm, or less than about 1 cm.

In some embodiments, the device has a height or profile of less than about 30 cm, less than about 20 cm, less than about 30 mm, less than about 20 mm, less than about 10 mm, less than about 9 mm, less than about 8 mm, less than about 7 mm, less than about 6 mm, less than about 5 mm, less than about 4 mm, less than about 3 cm, less than about 2 mm, or less than about 1 mm. A low-profile device may advantageously have better adhesion properties than a larger-profile device. For example, its center of mass is closer to the adhesive at the user's skin.

In one embodiment, the footprint of the device is less than about 5 cm in diameter and less than about 0.625 cm in height and weighs less than about 2 ounces (or about 56.7 g). In some embodiments, the footprint of the device is less than about 3.75 cm in diameter and less than about 0.3 cm in height and weighs less than about 1 ounce (or about 28.3 g).

Figure 14A:
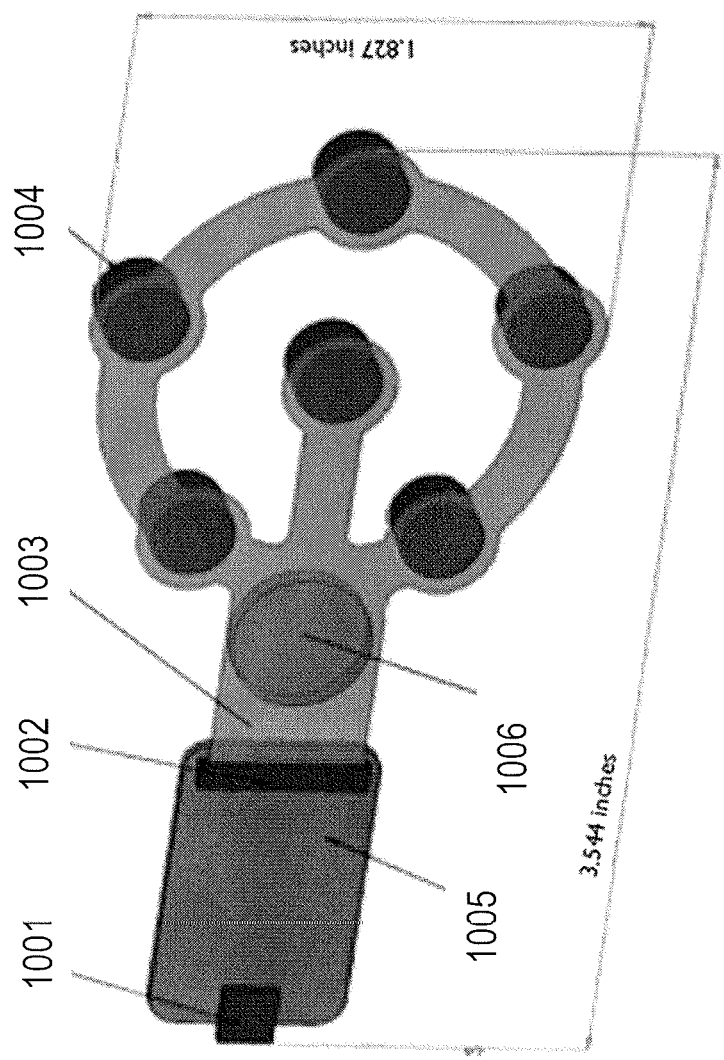
FIGS. 14A and 14B illustrate embodiments of an electrical stimulation device.
Figure 14B:
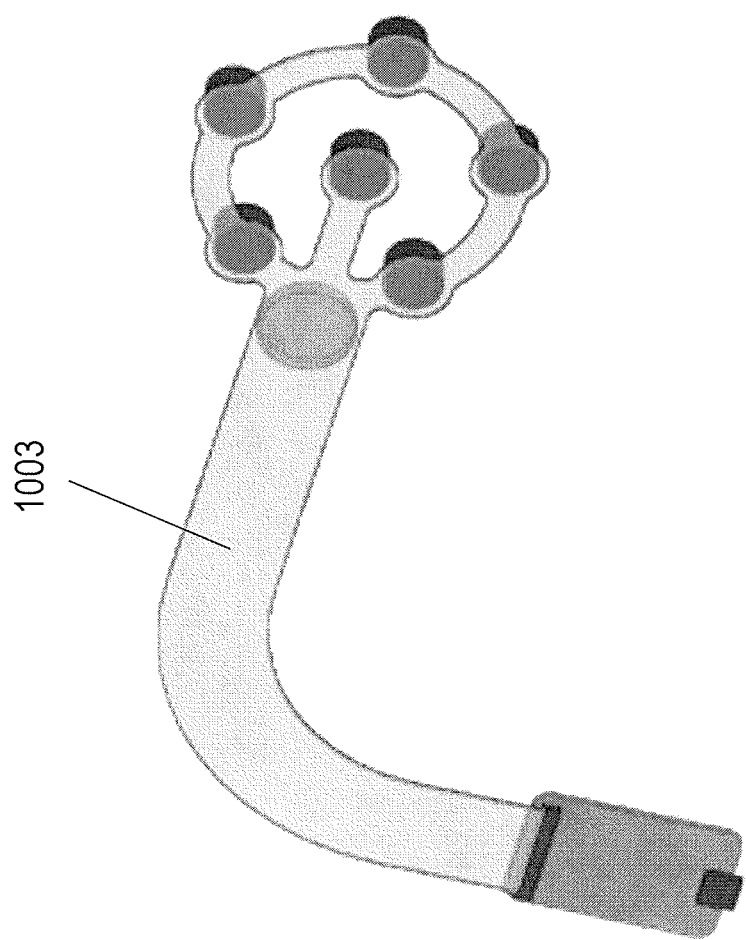

In alternative embodiments, the configuration of the device provides physical stability. For instance, a wrap-around-the-ear configuration can provide additional support for a TES assembly by transferring weight to the ear (FIG. 14B).

In some embodiments, the electrical stimulation device does not include user controllable elements for adjusting parameters of stimulation. In such embodiments, pre-determined stimulation protocols can be chosen for safety and efficacy and be stored in computer readable memory present in the device. The pre-determined setting can be triggered by toggling the on/off switch. The settings can also be triggered when the system senses a low impedance connection between electrodes occurring for instance when electrodes have been conductively adhered to a user's skin. In some embodiments, user controllable elements for adjusting parameters of stimulation can be located remotely from the device for example on a smartphone, computer, or other mobile computing device. In some embodiments, the device does not require user input concerning the time of stimulation, intensity of stimulation, frequency of stimulation, or other stimulation parameter.

In some embodiments, a GPS antenna, RFID tag, Bluetooth transmitter, Wi-Fi transmitter, and/or other wireless communication system are used for transmitting to and from the electrical stimulation device. In some embodiments, wireless communication is used to trigger electrical stimulation remotely or due to the presence of the device in a particular location. For example, a user may wear an electrical stimulation device configured for improved learning that is only triggered when they are in a classroom and a lecture has begun. In another embodiment, a device configured to improve motor learning and motor performance is worn by a golfer and activated when the subject is in proximity to their golf club.

As described above, transdermal electrical stimulation can include TES. TES can include transcranial direct current stimulation (tDCS), transcranial alternating current stimulation (tACS), cranial electrotherapy stimulation (CES), and transcranial random noise stimulation (tRNS). Unlike other forms of energy that can be transmitted transdermally or transcranially such as ultrasound, transmission of an electrical field in the brain occurs at the speed of light and is thus instantaneous on biological timescales.

In some embodiments, the device incorporates a built-in impedance meter. Impedance meters can advantageously provide the user with feedback about the impedance of each electrode (or electrode pair) to guide the user or other individual as to the effectiveness with which an electrode has been electrically coupled to their head. In various embodiments of the invention, feedback about electrode impedance is provided through one or more of: a graphical user interface (i.e. one presented on the screen of a mobile computing device), one or more indicator lights, or other user interface or control unit. In an embodiment of the invention, feedback to the user about the impedance is designed to inform the user to adjust a stimulation device to couple it more firmly to the body and thus reduce impedance. In an embodiment of the invention, feedback to the user about the impedance is designed to inform the user if a short circuit is present (i.e. that the impedance is too low) so that the user can resolve the short circuit (e.g. dry their head if it is raining). In an embodiment of the invention that uses dry electrodes, the device is configured to adjust, pause, or otherwise modulate stimulation due to capacitive interference as is known to occur for dry electrodes during movement such as raising a hand near the head.

Lower impedance between electrodes can indicate conductance via the head, scalp, face, or other body part of the user. In an embodiment, the device is engineered to automatically trigger electrical stimulation when the impedance between one or more pairs of electrodes falls below a threshold value. In other embodiments, the device is engineered such that impedance is determined upon an event (e.g., toggling of an on/off switch) in order to verify sufficient contact with the skin of a user prior to engaging stimulation. In an embodiment, the device is engineered to gate electrical stimulation so that it only occurs when the impedance between one or more pairs of electrodes falls below a threshold value chosen from the group of: less than about 250 k$\Omega$, less than about 100 k$\Omega$, less than about 50 k$\Omega$, less than about 251 k$\Omega$, less than about 10 k$\Omega$, less than about 5 k$\Omega$, or less than about 1 k$\Omega$. In an embodiment, the device is engineered to gate electrical stimulation so it only occurs when the impedance between one or more pairs of electrodes exceeds a threshold value to confirm that no electrical shorts are present (e.g. due to rain or wet hair) and the threshold value is chosen from the group of: greater than about 1$\Omega$, greater than about 5$\Omega$, greater than about 10$\Omega$, greater than about 50$\Omega$, greater than about 100$\Omega$, or greater than about 500$\Omega$. In some embodiments, the stimulation driven by the controller is influenced by the impedance measured (e.g. at least one of current amplitude, current frequency, pulse width, pulse duration, pulse frequency, pulse waveform, burst duration, burst frequency, off-time, burst waveform, positive duty cycle, negative duty cycle, and on/off).

The device can be configured to deliver alternating current (AC), direct current (DC), or a combination of alternating and direct current. In some embodiments in which the device is configured to deliver alternating current, alone or in combination with direct current, the waveform of the alternating current is chosen from the group of sine, square, saw tooth, triangle, and other waveform, including composite, complex, and stochastic waveforms.

In some embodiments, the device is configured deliver current at one or more frequencies between about 0.01 Hz and about 20 kHz. In some embodiments, the device is configured to deliver current at between about 400 Hz and about 20 kHz. In some embodiments, the device is configured to deliver current at between about 650 Hz and about 20 kHz. In some embodiments, the device is configured to deliver current at between about 500 Hz and about 10 kHz. In some embodiments, the device is configured to deliver current at between about 650 Hz and about 10 kHz. In particular, any of the apparatuses and methods of using them described herein may include a peak power that is within a frequency band between any of these ranges (e.g., peak power in the range of 650 Hz and about 20 kHz, etc.). Thus, a primary frequency component for the applied power (e.g., current) may be within the range, for example, of about 650 Hz to about 20 kHz (e.g., 650 Hz to about 10 kHz, etc.). This primary frequency component may be greater than other frequency components of the signal, as determined by a frequency domain (e.g., Fourier) analysis. In some variations, the primary frequency component is the first (principle) frequency component, having the greatest power, compared to any other frequency component of the applied signal (e.g., in some variations, by an order of magnitude).

Particularly advantageous frequencies for tACS are at frequencies of brain rhythms that naturally occur between about 0.5 Hz and about 130 Hz. In embodiments of the electrical stimulation device, higher frequencies between 1 kHz and 10 kHz are used to modulate neuronal function. In some embodiments of the invention, the components of the system that deliver alternating current stimulation are configured to deliver time-varying patterns of electrical stimulation with one or more dominant frequencies at a biologically relevant range of between about 0.01 Hz and about 500 Hz.

Skin irritation can be much less for AC or RNS than for DC stimulation, permitting higher current intensities without discomfort. In common embodiments of the invention, the current delivered through a single pair of electrodes is chosen from the group of: less than about 10 mA, less than about 5 mA, less than about 4 mA, less than about 3 mA, less than about 2 mA, less than about 1 mA, less than about 0.5 mA, less than about 0.25 mA, less than about 0.1 mA. In some embodiments of the invention, the sum of currents transmitted by all or a subset of electrodes is limited to a maximum instantaneous level chosen from the group of: less than about 10 mA, less than about 5 mA, less than about 4 mA, less than about 3 mA, less than about 2 mA, less than about 1 mA, less than about 0.5 mA, less than about 0.25 mA, less than about 0.1 mA, One of ordinary skill in the art would appreciate that there are numerous current levels that could be utilized with embodiments of the present invention, and embodiments of the present invention are contemplated for use with any appropriate level of current. Particularly advantageous stimulation protocols have a minimum peak current amplitude of 2 mA.

In some embodiments, the maximum current level permitted for a single pair of electrodes or group of electrodes is an average or cumulative value over a period of time chosen from the group of: less than about 100 minutes; less than about 30 minutes; less than about 10 minutes; less than about 5 minutes; less than about 2 minutes; less than about 1 minute; less than about 30 seconds; less than about 10 seconds; less than about 5 seconds; less than about 2 seconds; less than about 1 seconds; less than about 300 milliseconds less than about 100 milliseconds; less than about 50 milliseconds; less than about 10 milliseconds; less than about 5 milliseconds; or less than about 1 millisecond. One of ordinary skill in the art would appreciate that there are numerous periods of time that could be utilized with embodiments of the present invention, and embodiments of the present invention are contemplated for use with any period of time.

In some embodiments, the device may deliver random noise stimulation, similar to tRNS. The noise may be purely random (i.e. white noise). In some embodiments, the noise is structured (e.g. pink noise). In some embodiments, the electrical stimulation is delivered with higher power in the frequency band between about 100 Hz and about 640 Hz. One of ordinary skill in the art would appreciate that there are numerous types of noise, structured or unstructured, that could be utilized with embodiments of the present invention, and embodiments of the present invention are contemplated for use with any type of noise.

In some embodiments, the device is configured so that the effect induced by the stimulation is mediated at least in part by neurons. In alternative embodiments of the invention, the device is configured so that the effect is mediated at least in part by non-neuronal cells. In some embodiments of the invention, the device is configured so that the induced electric field has higher intensity in one or more targeted white matter tracts, nerves, or ganglia. In alternative embodiments of the invention, the device is configured so that the induced electric field has higher intensity in one or more targeted regions of grey matter. In some embodiments of the invention, the directionality of one or more electrical fields is modulated during a user's session. In alternative embodiments of the invention, the location and/or intensity of one or more electrical fields is modulated during a user's session.

The number and placement of electrodes, along with the stimulation parameters, determines the induced cognitive effect on a user. In some embodiments, multiple electrodes are used with a single current generator such that there are one or more anode and cathode electrodes. In other embodiments, multiple current generators create multiple current source-sink pairs to create a desired spatial pattern of electrical current density at one or more target sites in the brain. In various embodiments of the invention, the number of electrodes used is chosen from the group of: more than 2 electrodes, more than 3 electrodes, more than 4 electrodes, more than 5 electrodes, more than 7 electrodes, more than 10 electrodes, more than 15 electrodes, more than 25 electrodes, more than 50 electrodes, more than 100 electrodes, more than 500 electrodes, more than 1000 electrodes, more than 5000 electrodes, or more than 10000 electrodes.

In some embodiments, one or more dominant frequencies of AC are individualized for a user based on their own endogenous brain rhythms. The peak frequency for behaviorally relevant rhythms such as alpha rhythms can vary by several Hz between individuals. Thus, in some embodiments of the invention, the device is configured to modulate alpha or other rhythms at the frequency observed in that user with EEG or another form of brain recording. In an embodiment of the invention, brain rhythms are modulated by transmitted alternating current electrical stimulation at a similar frequency and either in phase or out of phase with an endogenous brain rhythm.

In some embodiments, one or more dominant AC frequencies are chosen such that electrical coupling is more effective or optimal for one or more cell types (pyramidal neurons, interneurons, glial cells, or other cell types) based on their membrane time constants, ion channel kinetics, or other biophysical property. In other embodiments, one or more dominant AC frequencies are chosen to optimize coupling for a subcellular compartment such as the dendrite, axon hillock, cell body, or synapse.

Figure 6:
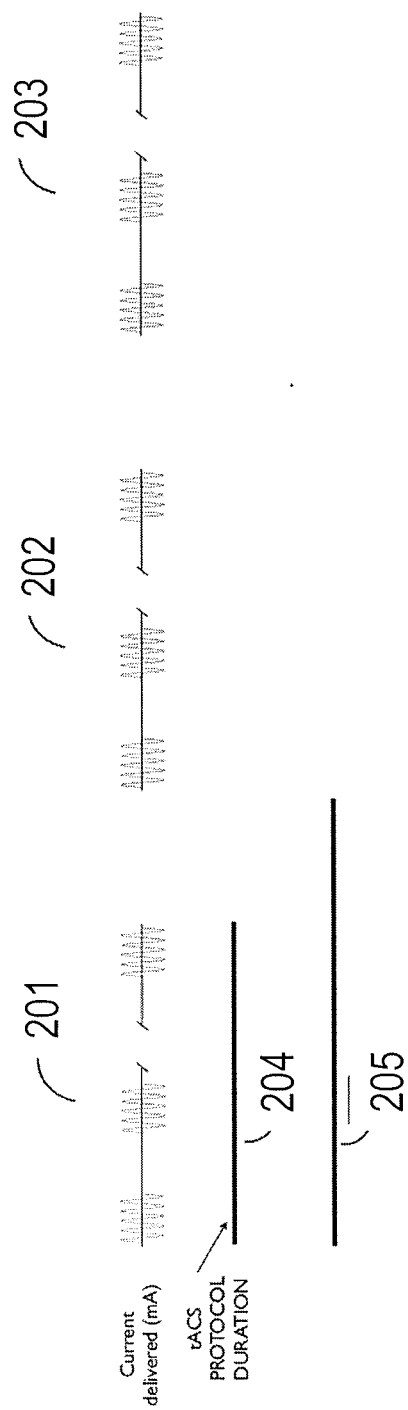
FIG. 6 illustrates an embodiment of an AC stimulation protocol.

In some embodiments of the invention, the electrical stimulation is pulsed, as shown in FIG. 6. FIG. 6 illustrates a targeted AC stimulation protocol involving repeated pulsing shown in waveforms 201, 202, and 203. FIG. 6 also depicts the protocol duration 204 and repetition period 205. As shown, the protocol repetition period is the inverse of the repetition frequency. Pulsing electrical stimulation can be an effective strategy for inducing a cognitive effect.

Figure 7:
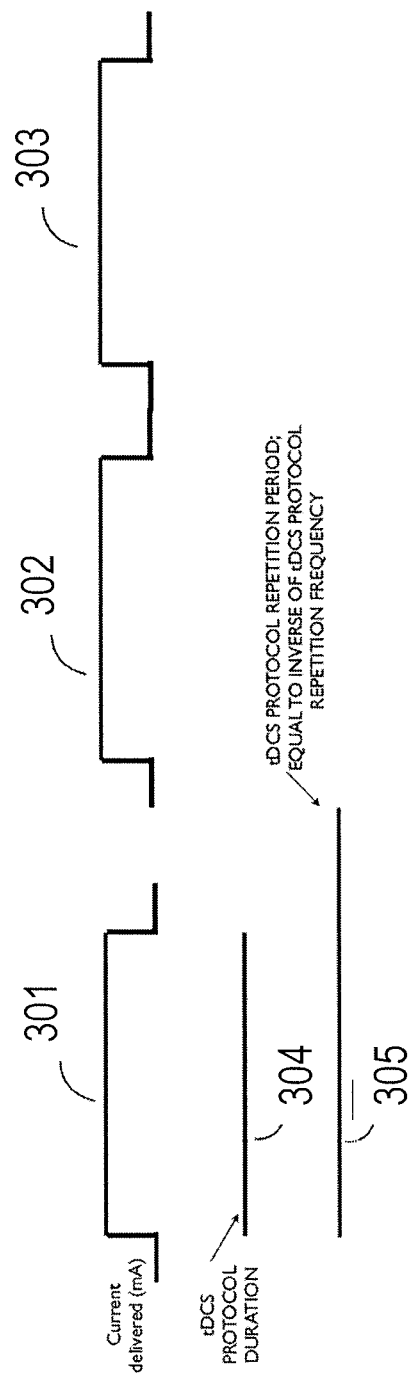
FIG. 7 illustrates an embodiment of a DC stimulation protocol.

Pulsed stimulation can use AC and/or DC, as shown in FIG. 7. FIG. 7 depicts a DC stimulation protocol including pulsing and repeating shown in waveforms 301, 302, 303. The protocol duration 304 is also shown. The protocol repetition period 305 is equal to the inverse of the repetition frequency. In some embodiments, the device delivers a protocol of two or more pulses 201, 301 chosen from the group of: about more than 2 pulses, about more than 3 pulses, about more than 4 pulses, about more than 5 pulses, about more than 10 pulses, about more than 20 pulses, about more than 50 pulses, about more than 100 pulses, about more than 500 pulses, about more than 1000 pulses, about more than 10000 pulses, or more pulses. The inter-pulse time and the number of pulses can determine the stimulation protocol duration 204, 304. In some embodiments, a pulsed protocol is repeated 202, 203, 302, 303 at a protocol repetition frequency 205, 305 chosen from the group of: about more than 0.001 Hz, about more than 0.01 Hz, about more than 0.1 Hz, about more than 1 Hz, about more than 5 Hz, about more than 10 Hz, about more than 20 Hz, about more than 50 Hz, about more than 100 Hz, about more than 250 Hz, about more than 500 Hz, about more than 1000 Hz, or faster. In some embodiments of the invention the pulse repetition rate is modulated during a user session. In some embodiments of the invention, the pulse repetition rate is specific to a subset of one or more electrodes. Different electrodes or subsets of electrodes are pulsed with different repetition rates. Similarly, in some embodiments different electrodes or subsets of electrodes are driven at different frequencies and/or with different amplitudes.

FIG. 8A illustrates various example waveforms. Amplitude modulated stimulation is shown at waveforms 401, 402, 403. Frequency modulated stimulation is shown at waveforms 404, 405, 406. Frequency and amplitude modulated stimulation is shown at waveforms 407, 408, 409. FIG. 8B illustrates various electrode positions 411, 412, 413 arranged on a head 410 of a user. The stimulation protocol 414 is used in FIG. 8B. FIG. 8C illustrates how each pulse in the overall stimulation applied 414 comes from a different electrode position 411, 412, 413.

Computational models can be advantageous for modeling the transmission of electric fields in the brain. Effective computational models account for differential field shaping effects of different tissue types (e.g. skin, skull, white matter, grey matter, etc.) to derive an accurate estimate of induced electric fields.

In some embodiments, two or more electrodes are configured to optionally record EEG by switching appropriate electrically connected circuits. In other embodiments, two or more EEG electrodes and electrical hardware for amplifying, filtering, and otherwise processing EEG signals are incorporated into the electrical stimulation device. In some embodiments, EEG electrodes and electrical hardware are contained in one or more separate housings and further comprise wired or wireless systems for transmitting raw and/or processed EEG signals to an electrical stimulation device.

A finite element model (FEM) can aid in estimating electric fields in the body, including the brain, spinal cord, and nerves (e.g. cranial nerves) and can be used to determine the number, location, size, and shape of stimulating electrodes to use for delivering current to a desired target area. The FEM also determines stimulation parameters for each electrode (if there is a single reference electrode) or pair of electrodes (if multiple reference electrodes are used) in order to create a focused electric field in a brain region of interest. FEM models can be configured to optimize for both intensity and direction of current with a particular spatial and temporal profile. Both the strength and direction of an induced electric field determine the neuromodulation that occurs. The direction of an electrical field is thought to most significantly affect neuromodulation of white matter.

FEM electric field calculations can be employed to estimate the spatial distribution of current density in the brain for a particular electrode montage and stimulation protocol. FEM's that use a Standard Model assume a fixed anatomy. The electric field distribution during electrical stimulation is strongly dependent on the electric tissue properties of skin, skull, cerebrospinal fluid, and brain tissue. These anatomical and biophysical parameters are incorporated into FEM models. To determine useful electrode configurations and stimulation protocols, an algorithm optimizes electrode positions and currents for a search space that includes one or more of: electrode positions and maximum and/or minimum currents at the electrodes, electrode size, and electrode shape. The optimization maximizes the electric field in a certain brain area and minimizes field strength at surrounding regions to achieve desired focality.

Recent research and disclosures have described workflows and related methods for FEM of electric fields in the brain. Some of these FEM models have used an idealized spherical model of the head (DaSilva et al., 2011 and Tyler et al. U.S. Patent application 61/663,409), the full disclosures of which are incorporated herein by reference.

Figures 9A, 9B, 9C:
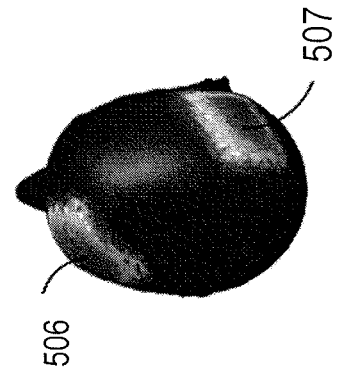
FIG. 9A shows standard model anatomy in which two large electrodes have been placed over the motor cortex (anode) and orbitofrontal cortex (cathode).
FIG. 9B shows the resulting electric potentials on the scalp.
FIG. 9C shows the absolute magnitude of the electric field on the scalp.
Figures 9D, 9E:
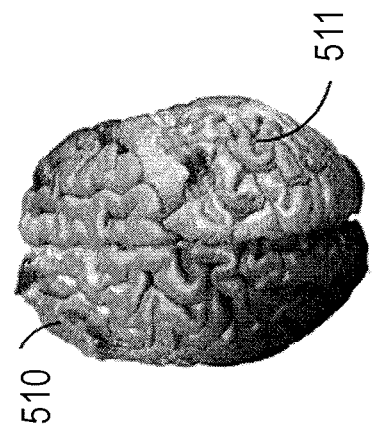
FIG. 9D similarly shows the absolute magnitude of the electric field in the brain from the arrangement shown in FIG. 9A.
FIG. 9E shows the direction and magnitude of electric fields in the brain.

FIGS. 9A-9E shows the results of FEM analysis, depicting common large electrode montage for DC stimulation and modeled fields. FIG. 9A shows Standard Model anatomy 501 and a common arrangement of two large electrodes (5 cm×7 cm, rectangular) placed over the motor cortex (anode) 503 and orbitofrontal cortex (cathode) 502. FIG. 9B shows the electric potential on the scalp. The magnitude of electric potential is indicated by shading in all figure panels. The potential of the anode 505 is set to 1 Volt and the potential of the cathode 504 is set to 0 Volt. By adjusting the potential difference between the anode and cathode an intended current strength can be achieved. FIG. 9C shows the absolute magnitude of the electric field on the scalp. Note that the highest field strength occurs at the edges of the electrodes 506, 507 where the gradient of the electric potential is strongest. Current gradient occurs at the boundaries but not under a TES electrode, because each electrode is at iso potential. FIG. 9D shows the absolute magnitude of the electric field in the brain. Peak electric fields occur underneath the electrode edges 508, 509. FIG. 9E shows the direction and magnitude of electric fields in the brain. The electric field is directed from the anode 511 to the cathode 510.

Figure 10B:
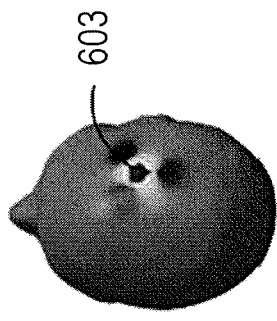
FIGS. 10A-10D show the results of FEM analysis with electrodes arranged in a triangle shaped configuration over premotor cortex. The anode is placed in the center and the cathodes are placed in the triangle corners, as shown in FIG. 10A.
Figure 10D:
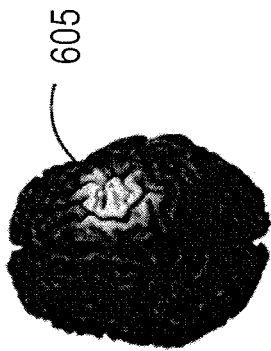
Figure 10A:
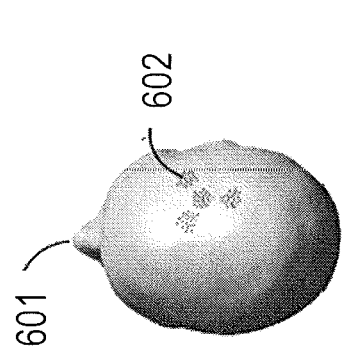
Figure 10C:
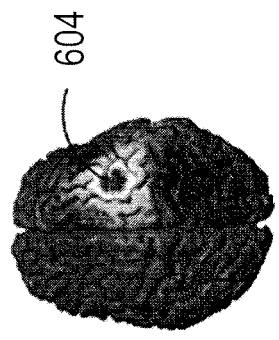

More focused electric fields can be achieved with electrode configurations with one or more electrodes that surround a central electrode and are configured to pass current between the central electrode and the one or more surrounding electrodes. In embodiments of the invention, a set of cathodes surrounds a single anode. In alternative embodiments, a set of anodes surrounds a single cathode. FIGS. 10A-10D shows the results of FEM analysis with a Standard Model 601 for a triangle shaped electrode configuration. For each panel, four circle shaped electrodes (radius 1 cm) 602 are modeled over premotor cortex. The anode is placed in the center and the cathodes are placed in the triangle corners. FIG. 10B shows the distribution of electric potential on the scalp. The potential of the anode is set to 1 Volt 603 and the potential of the cathodes is set to 0 Volt. By adjusting the potential difference between the anode and cathodes current is induced. FIG. 10C shows the distribution of electric potential in the brain. High potentials 604 are confined to a small volume underneath the anode. FIG. 10D shows the absolute magnitude of the electric field in the brain. Compared to the large electrodes of FIG. 9, high electric fields are confined to a small volume underneath the electrodes 605.

Figure 11A:
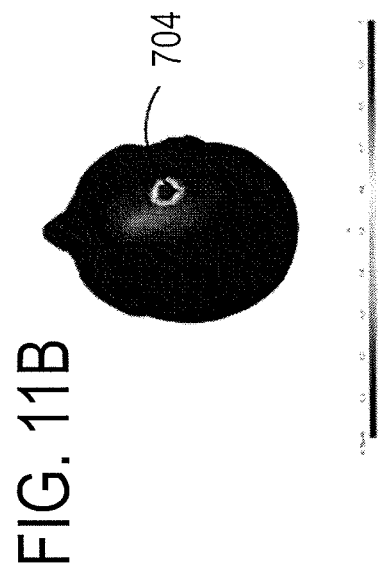
FIGS. 11A-11D show the results of FEM analysis with concentric ring electrodes. The anode is placed over the premotor cortex, and the cathode surrounds the anode. FIG.
Figure 11B:
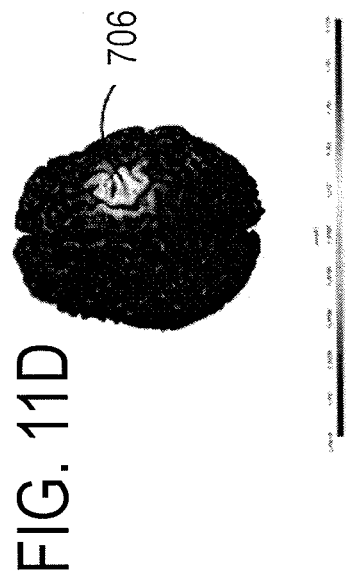
Figure 11C:
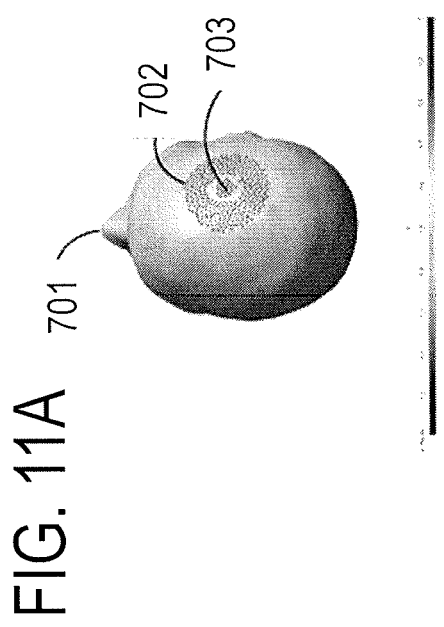
Figure 11D:
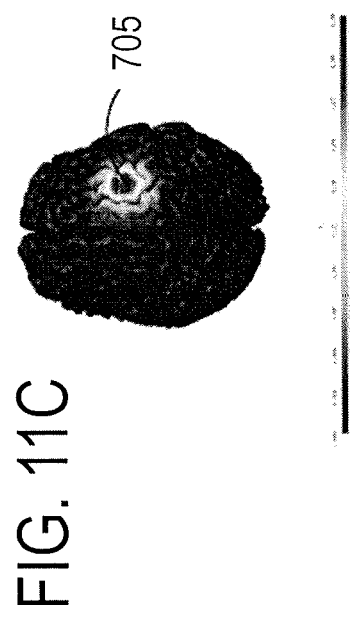

In an alternative embodiment, similar targeting is achieved with two ring electrodes in a concentric arrangement that is also an effective embodiment for a single enclosure TES assembly. FIGS. 11A-D shows the results of FEM analysis with a Standard Model 701 concentric ring electrodes. The anode 703 (radius 1 cm) is placed over the premotor cortex. The cathode 702 (inner radius 1.5 cm, outer radius 4 cm) surrounds the cathode. FIG. 11B shows the electric potential on the scalp by shading. The potential of the anode is set to 1 Volt 704 and the potential of the cathode is set to 0 Volt. FIG. 11C shows the distribution of electric potential in the brain. High potentials 705 occur underneath the anode. FIG. 11D shows the absolute magnitude of the electric field in the brain. Shown is the absolute magnitude of the electric field. High electric field strengths are confined to a limited area underneath the concentric electrode configuration.

Figure 12B:
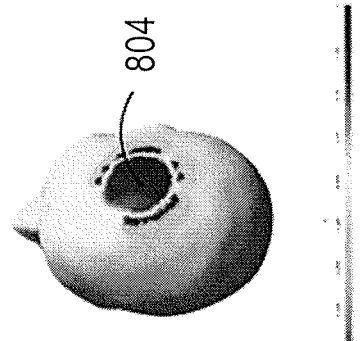
FIGS. 12A-12D show the results of FEM analysis with a large central anode placed over premotor cortex and a thin outer electrode, as shown in FIG. 12A.
Figure 12D:
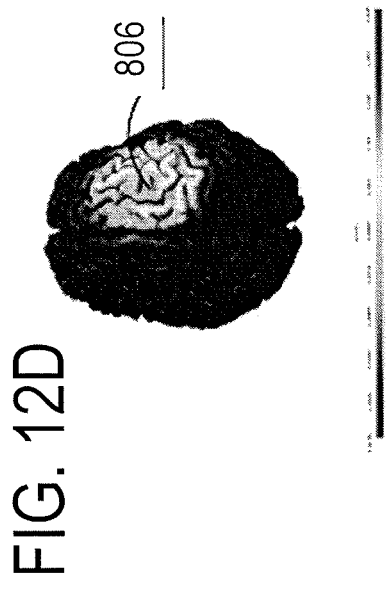
Figure 12A:
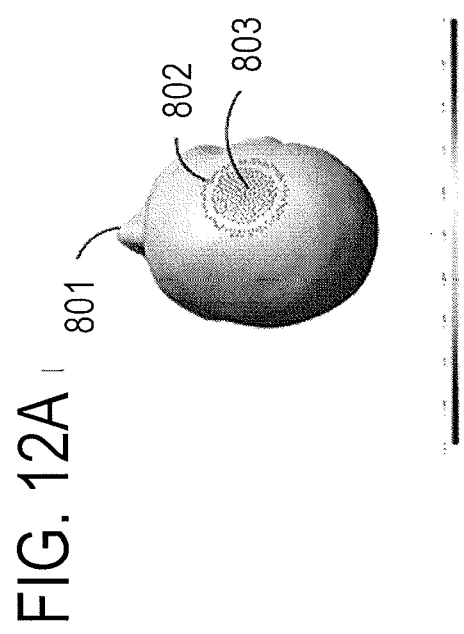
Figure 12C:
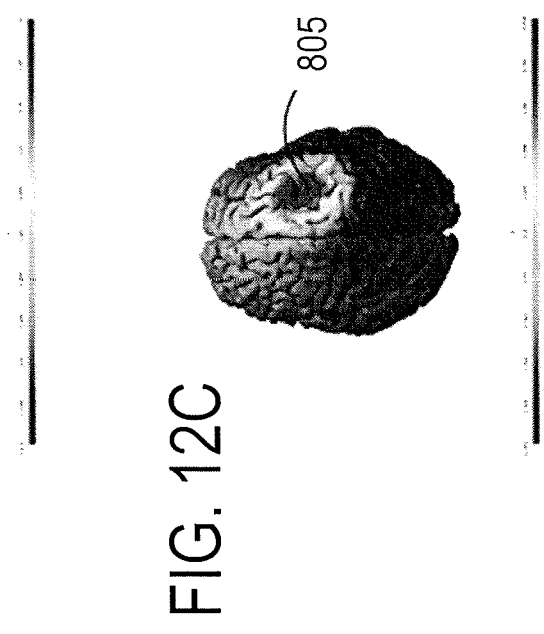

Changing the relative size of the concentric electrodes is effective for altering the size of the area stimulated. FIGS. 12A-12D use a Standard Model 801 with a large central anode 803 (radius 3 cm) placed over premotor cortex and a thin outer electrode 802 (inner radius 3.5 cm, outer radius 4 cm). A broad cortical area is activated. FIG. 12B shows electric potential on the scalp. The potential of the anode is set to 1 Volt 804 and the potential of the cathode is set to 0 Volt. FIG. 12C shows electric potential in the brain. The area of high potential 805 is larger spatially compared to the configuration in FIGS. 11A-D. FIG. 12D shows the absolute magnitude of electric fields in the brain. The area of strong electric fields 806 is more extended compared to the configuration in FIGS. 11A-11D. By changing the relative sizes of the electrodes the electric field distribution in the brain can be focused or defocused.

It will be appreciated that each electrode configuration and combination of electrode configurations described herein can be used with any other embodiments of stimulation devices or protocols described herein.

Figure 13:
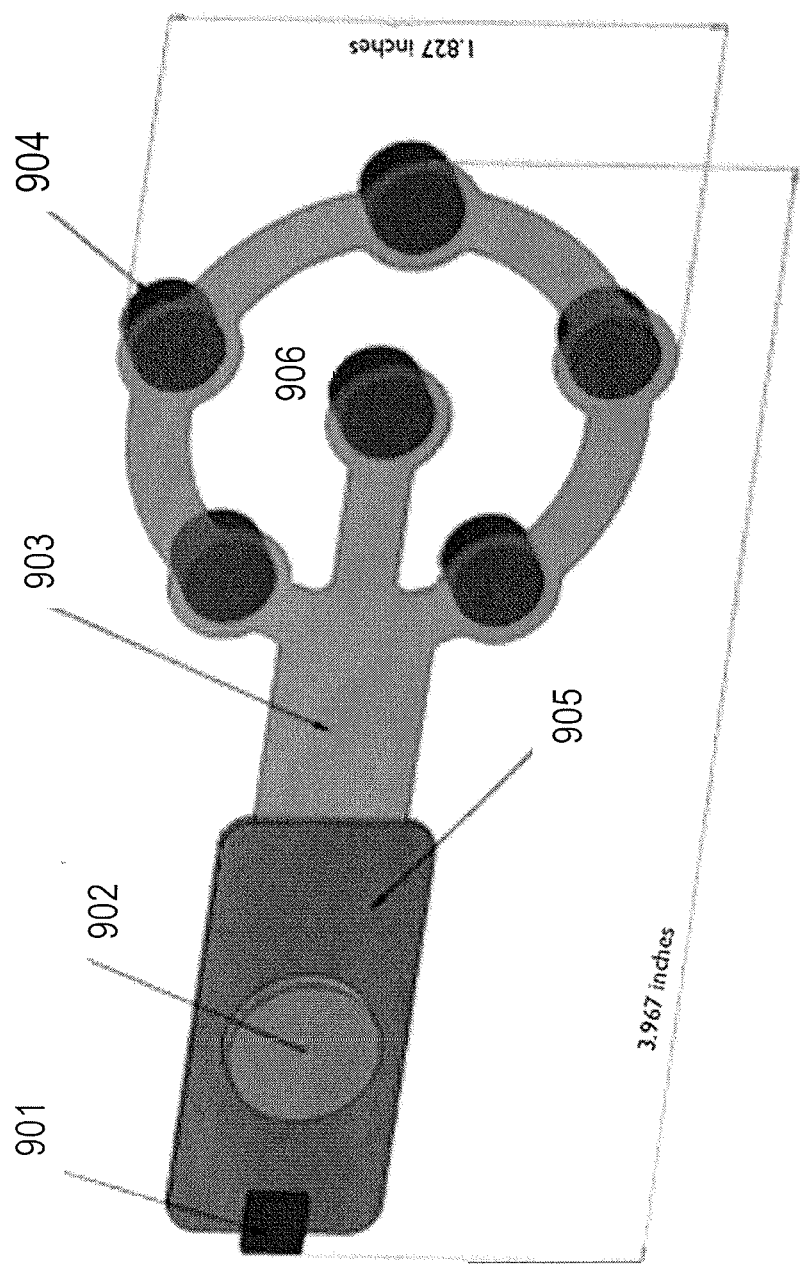
FIG. 13 illustrates another embodiment of an electrical stimulation device.

An alternative embodiment of a disposable electrical stimulation device is shown in FIG. 13. Six electrodes are arranged in a concentric manner with five electrodes 904 surrounding a central electrode 906 in a fixed pentagram arrangement. In some embodiments, all surrounding electrodes 904 are configured as cathodes and the central electrode 906 is the anode. The electrodes can be foam electrodes. In some embodiments, all surrounding electrodes 904 are configured as anodes and the central electrode 906 is the cathode. In an alternative embodiment, some of the surrounding electrodes 904 form a set with the central electrode 906 as either the anode (or cathode) and one or more of the remaining electrodes is the cathode (or anode). The flex portion comprising the electrodes 904 may conform to the curvature of a body part (e.g., the head). The flex circuit 903 incorporates electrical conductive wires used to transmit stimulation from an electrical circuit 905. In some embodiments the electrical circuit is constructed on a printed circuit board (PCB) or silicon chip. The electrical circuit includes a battery 902. In some embodiments, there is an on/off switch 901 for the user to control activation of the electrical stimulation system. In the schematic of FIG. 13, a housing for the assembly is not shown.

In an alternative embodiment, the system is semi-disposable. FIG. 14A shows the same six electrode 1004 configuration as FIG. 13 and also incorporates a battery 1006 in the flex circuit 1003 portion of the assembly. The battery 1006 and the electrodes 1004 are disposable. The flex portion comprising the electrodes 1004 may conform to the curvature of a body part (e.g., the head). The electrodes 1004 can connect to the flex circuit 1003 using a connector (e.g., a micro snap). A connector 1002 is used to interface with a rigid board containing electrical components for achieving the desired form of electrical stimulation 1005 and an on/off switch 1001 for user actuated control of the system. The disposable flex circuit can be disconnected from the reusable printed circuit board (or other electrical circuit assembly) 1005 at the connector 1002. As shown in FIG. 14B, in some embodiments, the flex circuit 1003 is longer and shaped to go behind a subject's ear in a similar fashion to an eyeglass frame. The flex circuit can be any shape for convenience and comfort of placing the assembly on the user's head.

Figure 15A:
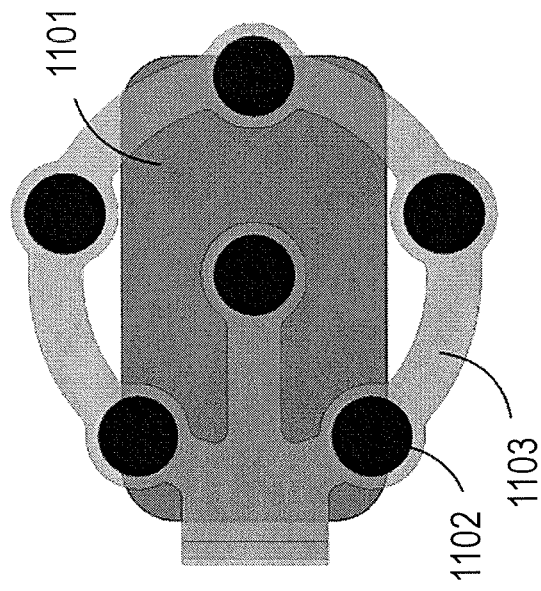
FIGS. 15A-15D illustrate another embodiment of an electrical stimulation device.
Figure 15B:
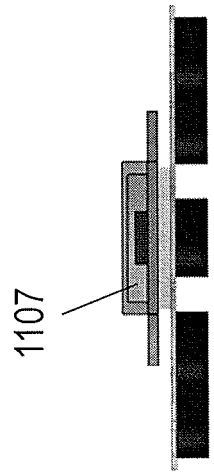
Figure 15C:
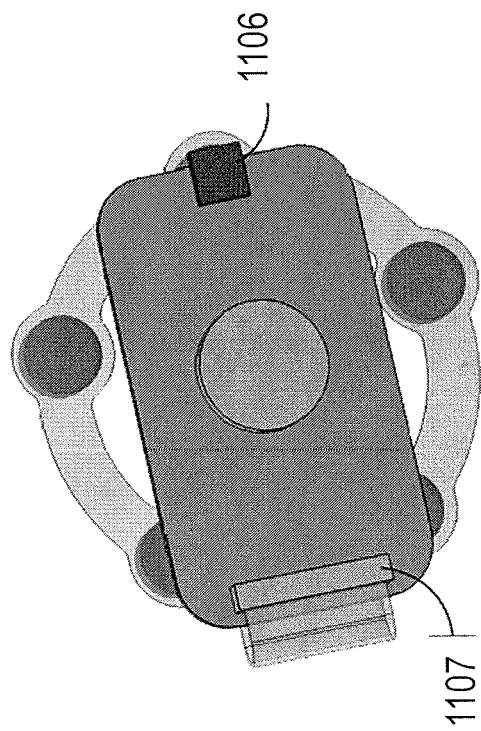
Figure 15D:
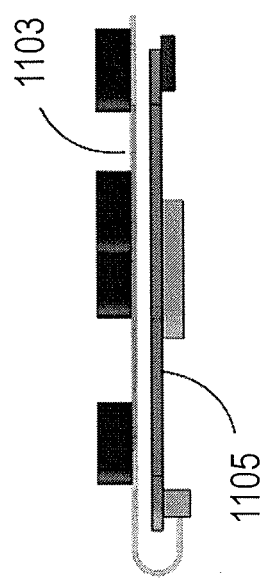
Figure 16A:
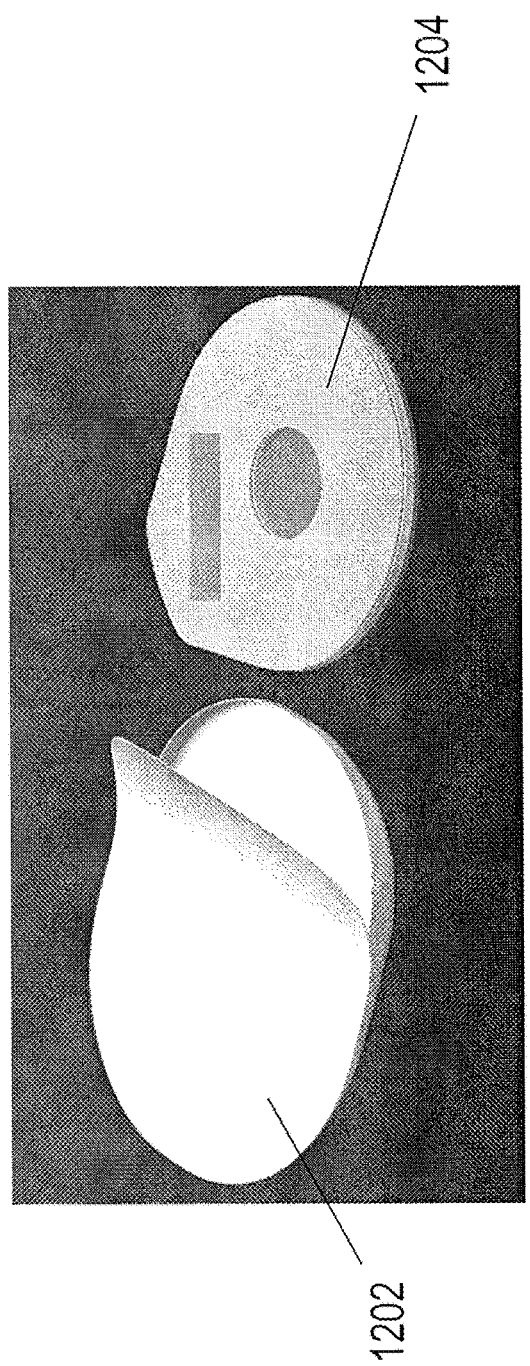
FIGS. 16A and 16B illustrate one variation of an apparatus including a disposable portion and a durable (reusable) portion.
Figure 16B:
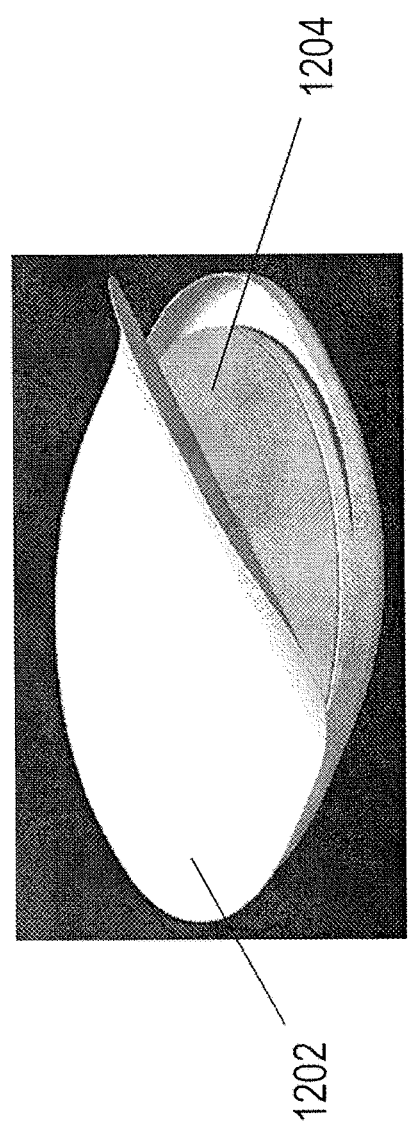
Figure 17:
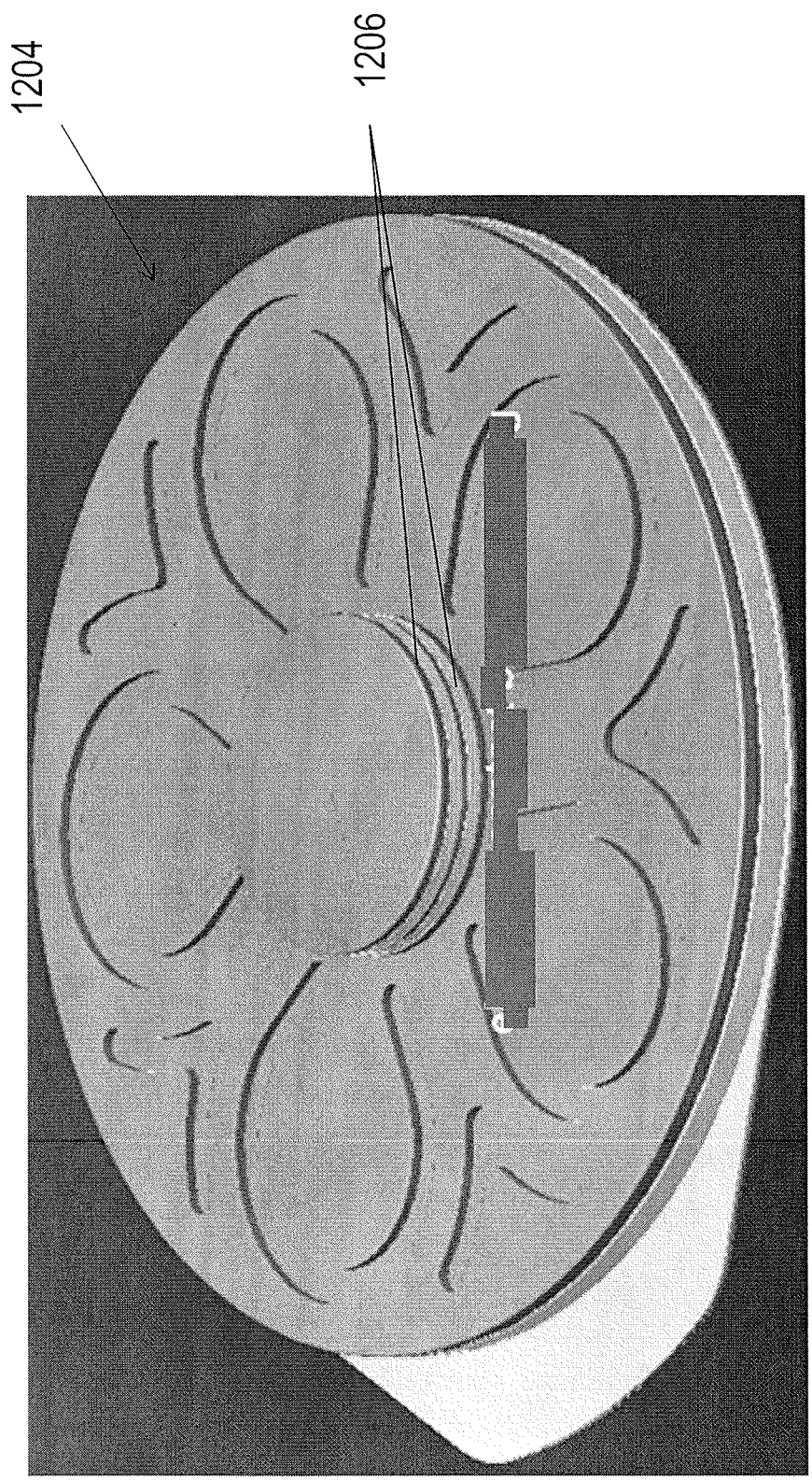
FIG. 17 illustrates a flexible support disk for a secondary unit, supporting one or more electrodes and having one or more relief cuts to increase flexibility of the device.

An embodiment of a fully disposable stimulation device designed to be contained in a single housing with a small cross-sectional area (footprint) is shown in FIGS. 15A-15D. FIG. 15A depicts a top view of the device, showing the on/off switch 1106 on the circuit board 1101. FIG. 15A also illustrates the connector 1107 connecting the circuit board 1101 to the flex circuit 1103. FIG. 15B depicts a bottom view showing the electrodes 1102 and flex circuit 1103 beneath the circuit board 1101. FIGS. 15C and D depict views of the profile of the device.

FIGS. 16A-23 illustrate an alternative embodiment of a semi-disposable stimulation device. In this embodiment, an optional blister pack 1202, shown in FIGS. 16A and B, is configured to protect a disposable portion 1204 of a puck and keep the disposable portion clean (or even sterile) prior to contact with the skin of a user. FIG. 16B illustrates the disposable portion 1204 positioned within the blister pack 1202. Further, the disposable portion 1204 of the stimulation device comprises a flexible support disk (FIG. 17), having one or more relief cuts to increase flexibility of the device, allowing for more conformal attachment to a user's head or other body part. Electrical contact bands 1206 may be present in the disposable portion, allowing for electrical contact with the main housing of the device of the present embodiment.

Figure 18B:
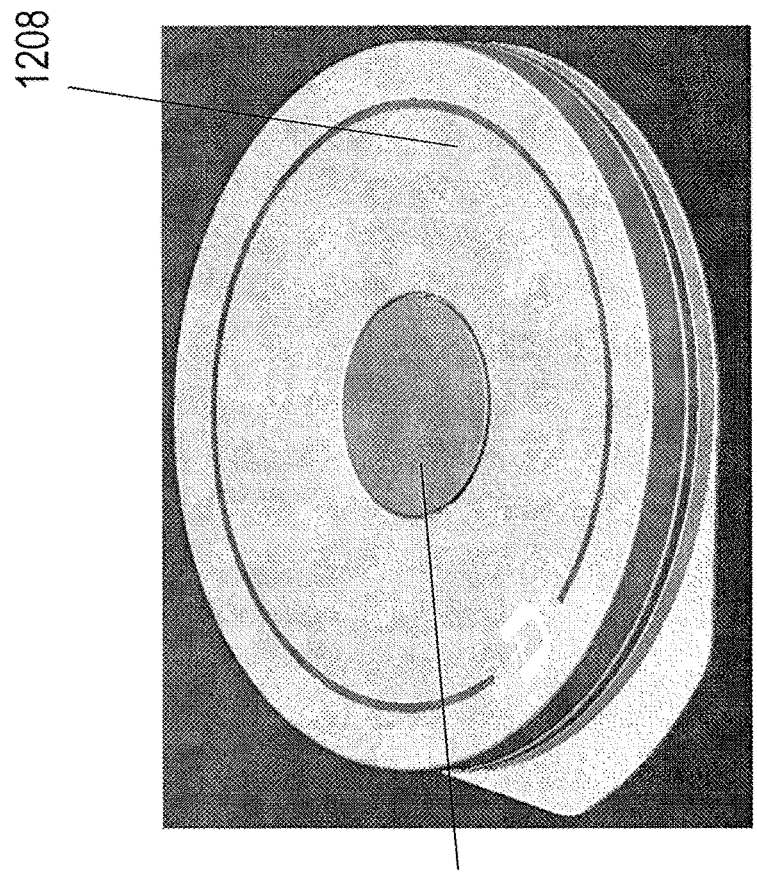
FIG. 18B shows the disposable portion snapped into position within the main housing of the primary unit.
Figure 18A:
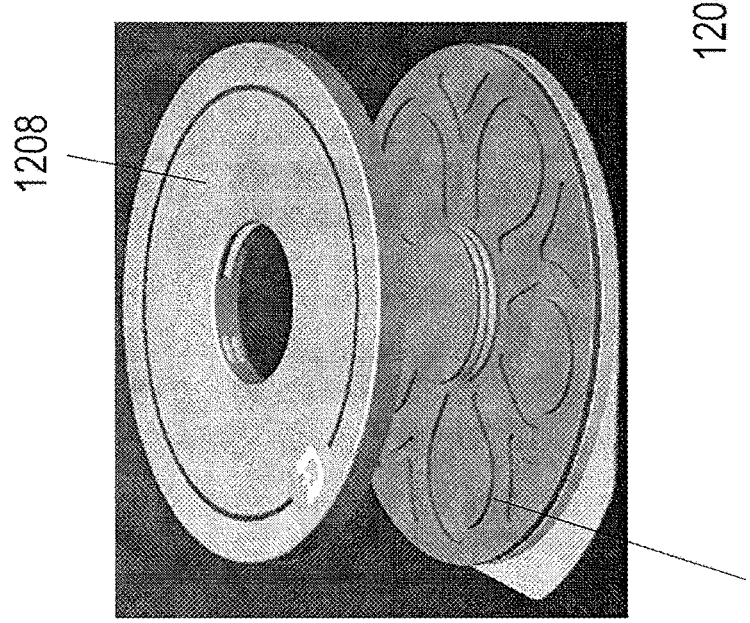
FIG. 18A shows a disposable portion of one variation of an apparatus that is configured to snap into a durable portion of the apparatus.
Figure 20A:
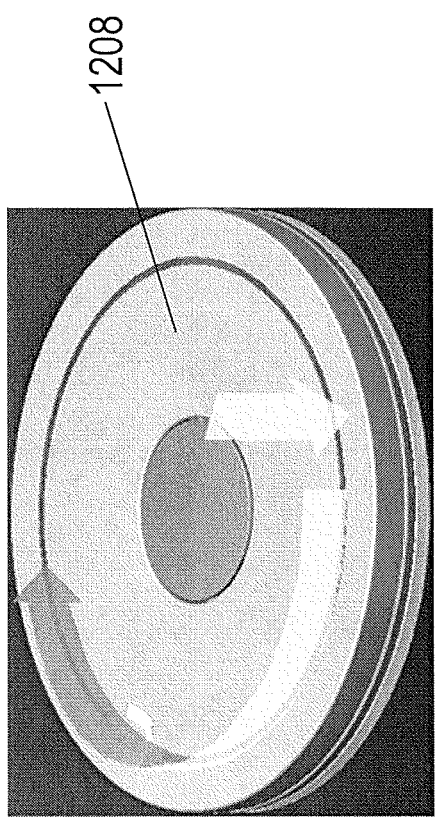
FIG. 20A illustrates the separation of a disposable component including the electrodes and adhesive from a durable holding component when the two are attached, as shown in FIG. 18B.
Figure 20B:
FIG. 20B shows the adhesive, electrodes and backer assuming a curved configuration, e.g., on the curvature of the body part onto which it is placed.

As shown in FIG. 18A, the disposable portion 1204 in the present embodiment is configured to snap into the main housing 1208 of the device. FIG. 18B shows the disposable portion 1104 snapped into position within the main housing of the stimulation device. Once inserted into the main housing, an optional backer 1210, shown in FIG. 19A may be removed from the side of the disposable portion that is opposite to the main housing side, revealing one or more electrodes 1212 and an adherent 1214 (e.g., adhesive foam), shown in FIG. 19B. The adherent and electrodes are configured to be removably or reversibly secured to the skin of a user through the application of a mild to moderate amount of force. As indicated by the arrows in FIG. 20A, the force can be applied to a first spot and then in a circular pattern around the housing 1208. As shown in FIG. 20B, the adherent 1214, electrodes 1212, and/or backer 1210 may gap depending on the curvature of the body part onto which it is placed.

Figure 21:
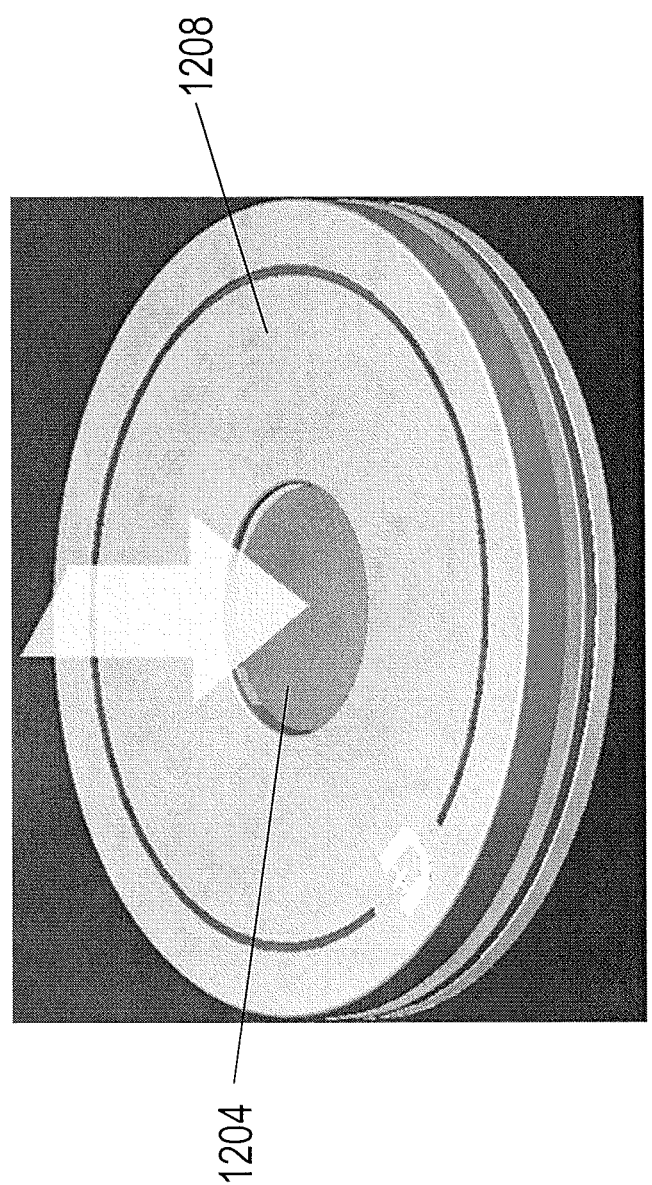
FIG. 21 shows the disengagement of a disposable portion from a durable main housing by pushing on the center of the disposable portion, indicated with an arrow, to release the housing from the disposable portion.
Figure 22:
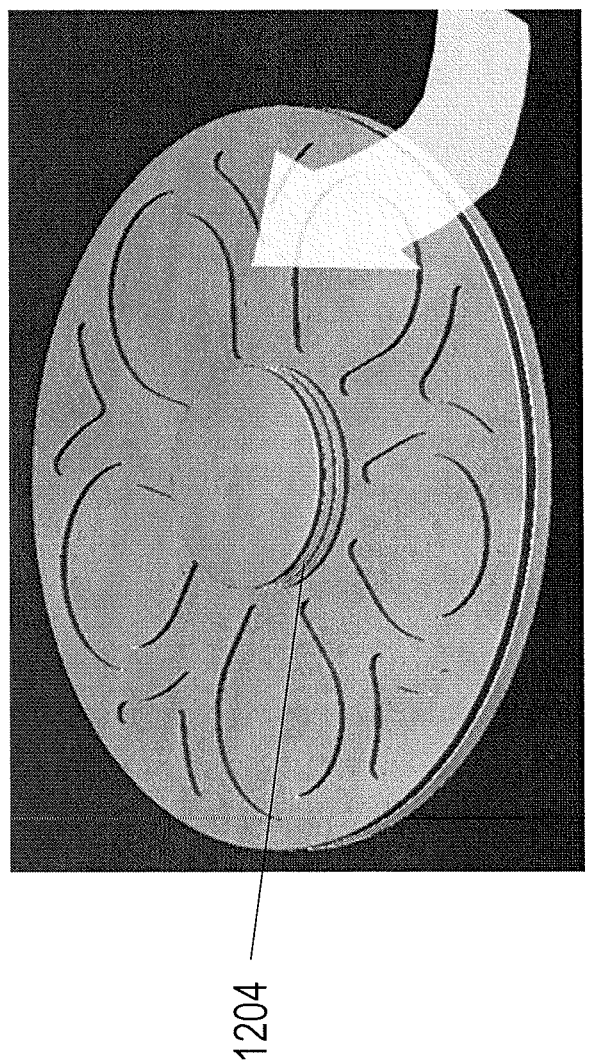
FIG. 22 shows the disengagement of the disposable portion from the skin of a subject by peeling from the skin.

Continuing from the example and embodiment above, FIG. 21 shows the disengagement of the disposable portion from the main housing. A user can push the center of the disposable portion, indicated with an arrow in FIG. 21, to release the housing 1208 from the disposable portion 1204. FIG. 22 shows the disengagement of the disposable portion 1204 from the skin of the user by peeling the portion 1204 from the skin.

Figure 23A:
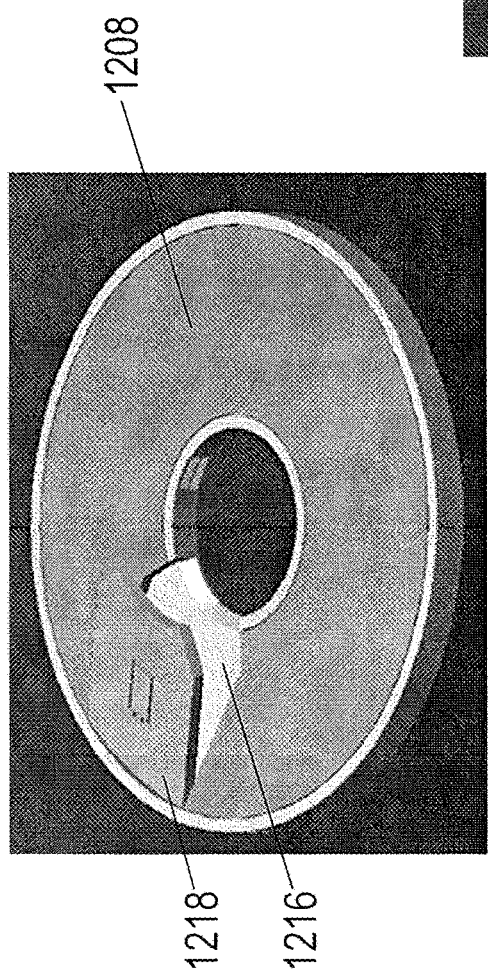
FIGS. 23A and 23B illustrate the location of an integrated replaceable or disposable battery on the underside of a housing.
Figure 23B:
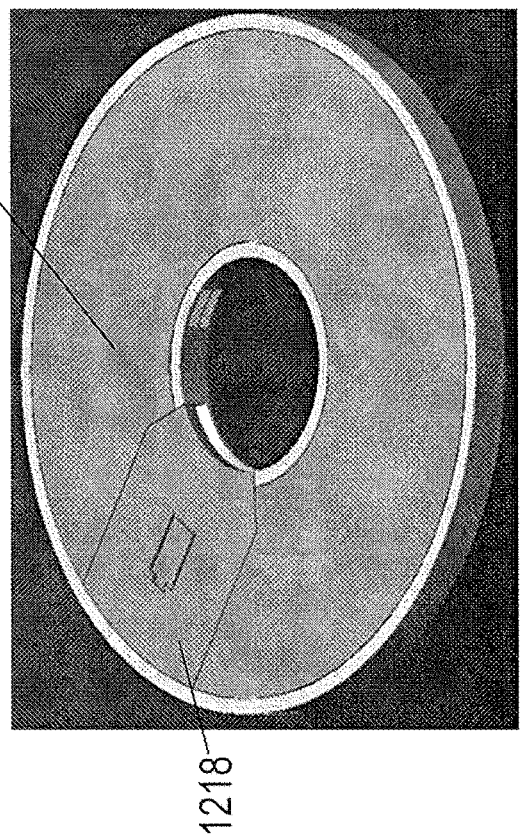

According to an embodiment of the present invention, FIGS. 23A and 23B show the location of an integrated replaceable or disposable battery 1216 on the underside of the device housing 1204. FIG. 23A illustrates the battery door 1218 open, while FIG. 23B illustrates the battery door 1218 closed.

In some embodiments, the device electrode assembly incorporates tracks for moving one or more electrodes. FIG. 24 shows an embodiment of a four electrode configuration but a similarly configurable system can use any number of electrodes. Electrodes on the outer track 1301 can move around the assembly 1303 along a track 1302. In various embodiments, the three outer electrodes are equidistant from each other (FIGS. 24A, 24D) or grouped asymmetrically (FIGS. 24B, 24C, 24E, 24F). In some embodiments a central electrode 1305 can also move laterally along a track 1307 until stopped by a tab or other mechanical component 1304. By moving the position of both the central electrode and the surrounding electrodes, a rich set of stimulation areas and directions can be achieved in the underlying brain tissue.

Figure 25B:
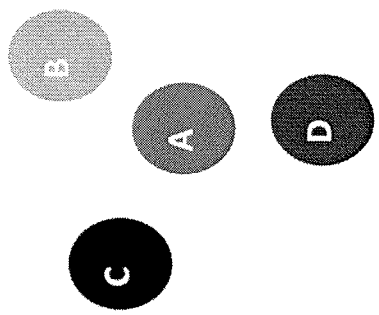
FIGS. 25A-25C illustrate configurable electrode configurations that may be used with the apparatuses described herein.
Figure 25C:
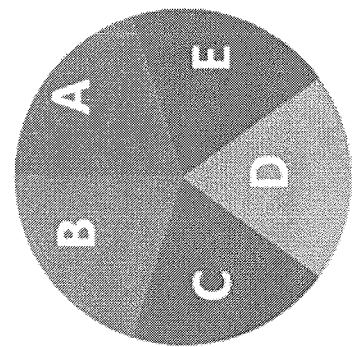
Figure 25A:
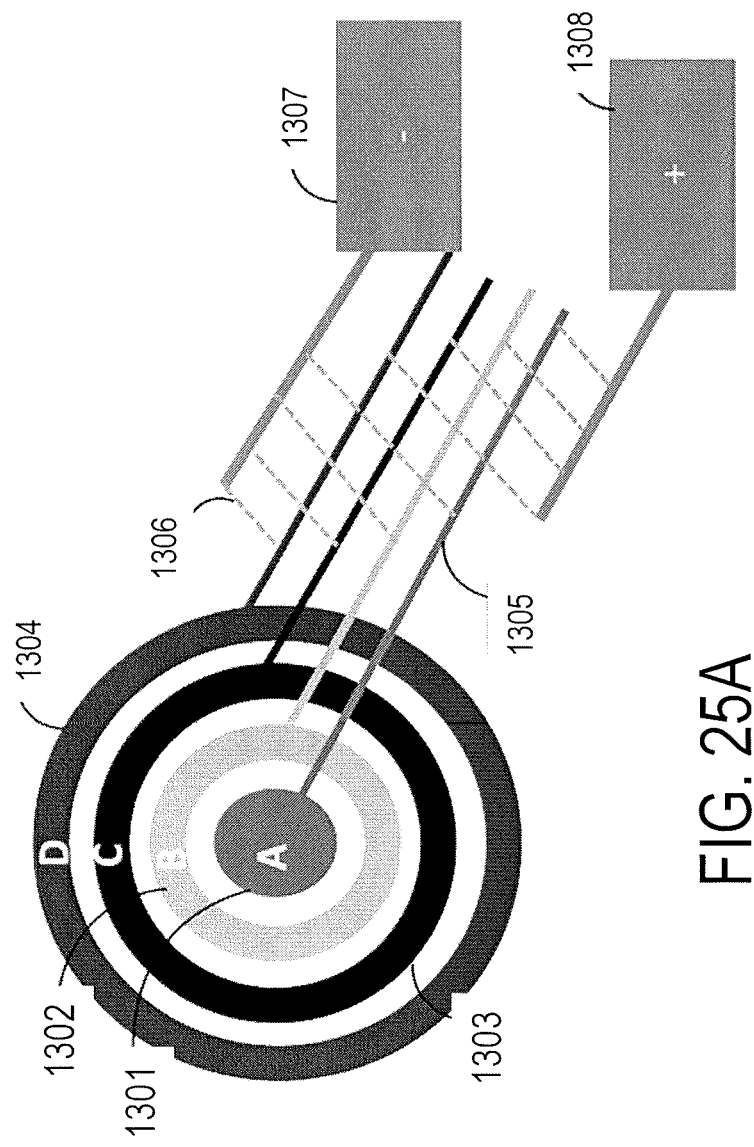

FIGS. 25A-25C illustrate embodiments of configurable electrode configurations for use with the stimulation devices described herein. The electric field induced in neural tissue by transdermal electrical stimulation can depend on the relative surface area and positioning of the anode and cathode. Modeling and experimental results indicate that the magnitude of the electric field around a given electrode (anode or cathode) is directly related to the current density (current strength/electrode area) at that electrode. Moreover, the spatial spread of direct current stimulation over the cortical surface around a given electrode is directly related to the area of the electrode. Thus, for example, given constant current, a small anode (e.g. FIG. 25A electrode A in each of the subpanels) and large cathode (e.g. FIG. 25A electrodes B+C+D in each of the subpanels) will maximize both the stimulation intensity and spatial resolution of the anodic effect, whereas a large anode (e.g. combined electrodes A+B+C in FIG. 25A) and small cathode (e.g. electrode D in FIG. 25A) will maximize the stimulation intensity and spatial resolution of the cathodic effect. Furthermore, by keeping the current and size of the cathode constant (e.g. electrode D in FIG. 25A) and manipulating the size of the anode (e.g. electrodes C+B+A vs. electrodes B+A vs. electrode B in FIG. 25A), it is possible to effectively zoom in on a region for anodic stimulation (in this case near electrode B). These examples illustrate the possibilities that result from being able to flexibly adjust the role of each electrode (as part of the anode, part of the cathode, or inactive) with the touch of a button or under the control of an algorithm. Since the parameters of effective stimulation are likely to vary between people and within the same person for different tasks, effective stimulation may require adjusting the site(s), extent, and current density in a given individual.

In some embodiments, the focality of stimulation can be controlled for a fixed set of electrodes by changing which electrodes serve as anodes or cathodes. In an embodiment, the electrodes are concentric 1401 1402 1403 1404 and connect 1405 to gates or switches 1406 that determine whether a particular electrode is connected to the positive 1408 or negative 1407 terminal. This allows adjusting focus or direction of the electric field without requiring changing the placement of the electrodes or changing the peak current. This adjustment could be done by the user, by pressing a button or automatically by the system. The general idea is to have multiple gates in the PCB that allow connecting or disconnecting the positive and negative leads to any set of the electrodes, thus specifying each electrode as part of the anode, part of the cathode, or inactive. A similar configurable system for focusing electric fields can be achieved with a triangle configuration, as shown in FIG. 25B or pie configuration, as shown in FIG. 25C of electrodes.

In some embodiments, application software (e.g., an 'app') installed on a PC, laptop, smartphone, tablet, or other computerized platform running an iOS, Android, Windows or other operating system is configured to transmit a time-varying voltage or current signal through the headphone jack output or other plug interface on the device. This application software may be configured as non-transitory control logic that causes the processor (e.g., of the computer, smartphone, etc.) to perform the functional and transformative steps described herein. For example in such embodiments, the timing and amplitude of stimulation by the device can be transmitted from the remote processor executing the control logic. In an embodiment, the trigger signal is transmitted wirelessly by the smartphone or tablet via Bluetooth low energy (BTLE) or another wireless communication protocol. In an embodiment, the stimulation device is powered by a USB or other wired communication port of the PC, laptop, smartphone, tablet, or other computerized platform. In an embodiment, specialized hardware permits analog communication via the headphone jack such as the HiJack system developed at the University of Michigan and available via Seed Studios. In this manner, control signals for the timing, intensity, pulsing, or alternating current carrier frequency can be generated by the mobile device and transmitted directly to the electrical circuitry of the stimulation device. Configurations that use a smartphone, tablet, laptop, or other external processor can be advantageous, because they remove the requirement for a microcontroller in the electrical circuit of the stimulation device by shifting the processing burden to the mobile device. In some embodiments, a program running on a desktop or laptop computer transmits a control signal for the stimulation device via serial, USB, or other transmission protocol.

Figure 27A:
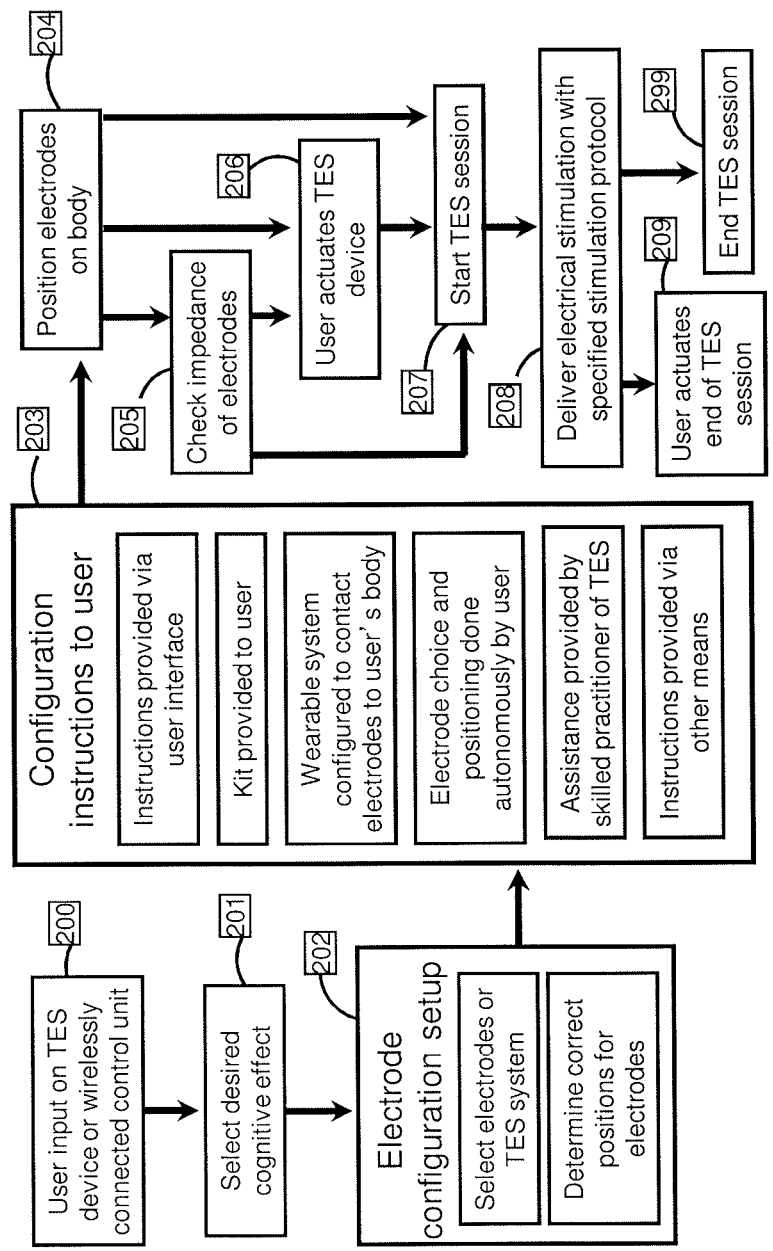
FIGS. 27A-27D schematically illustrates non-transitory control logic that causes a remote processor (e.g., of the computer, smartphone, etc.) to wirelessly transmit control instructions to a lightweight, wearable, and self-contained electrical stimulation apparatus.
Figure 27B:
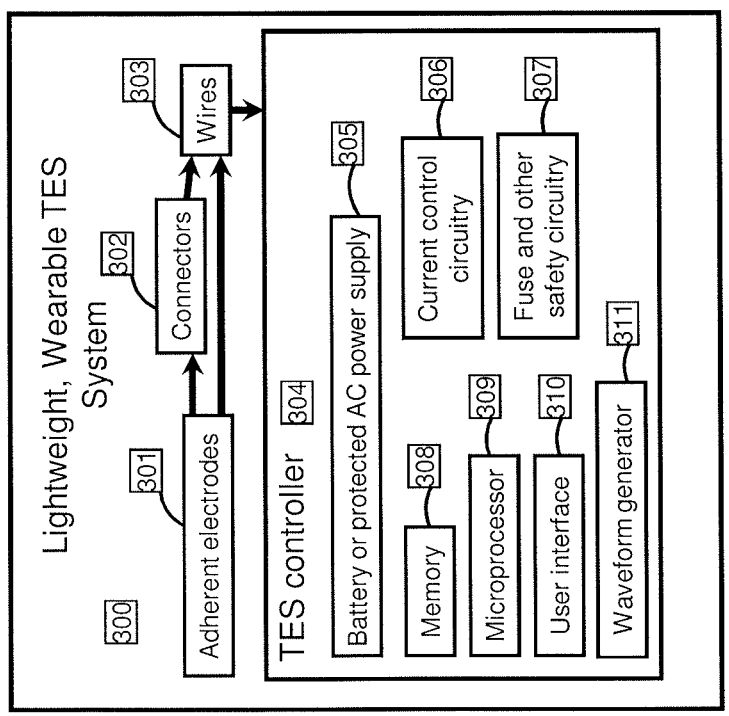
Figure 27C:
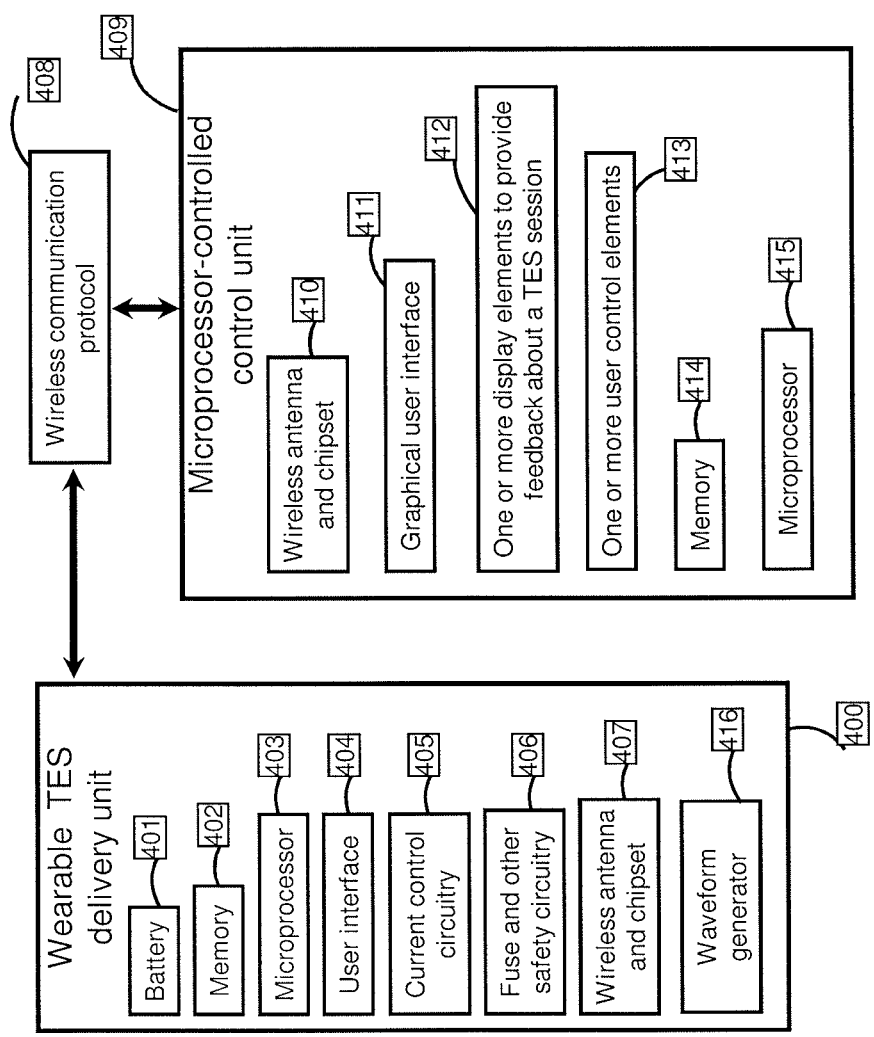
Figure 27D:
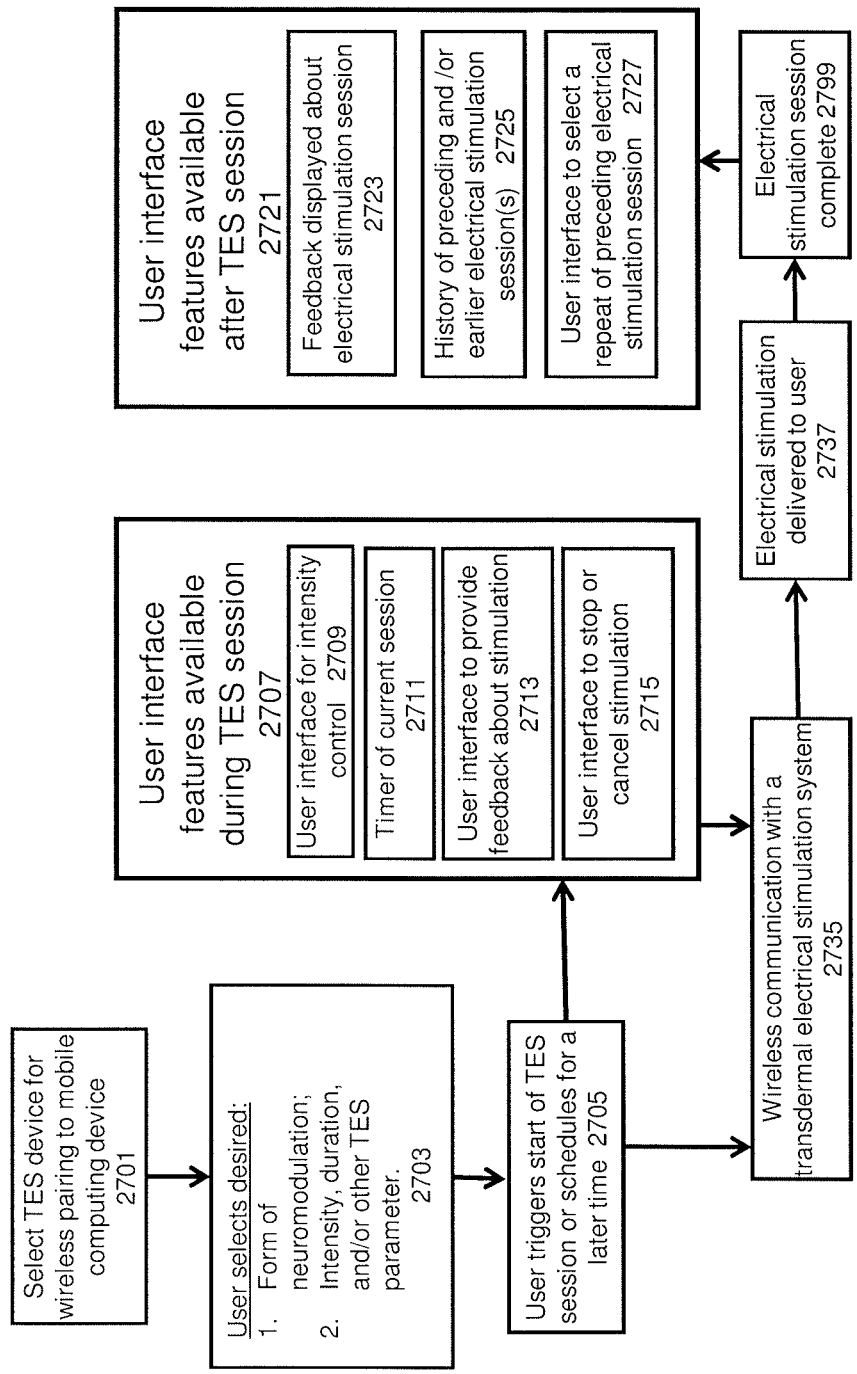

FIGS. 27A-27D schematically illustrate the operation of an apparatus as described herein to evoke a desired cognitive response. FIGS. 27C and 27D in particular illustrate variations in which a remote processor to transmit control information to a lightweight, wearable apparatus to produce a cognitive effect as described herein.

FIG. 27A shows an exemplary workflow for configuring, actuating, and ending a TES session using an apparatus as described herein. For example, in FIG. 27A, a subject (e.g., "user") may input control information directly on an apparatus being worn by the user, or may input control information wirelessly by connecting to a remote control unit 200.

In any of the apparatuses described herein, the apparatus may include an input to the controller/processor, which may be referred to as a control input; the control input may be a manual input on the device (e.g., button, dial, switch, etc.) or it may be a wireless receiver, receiving wireless information (or both).

In some variations, the remote processor can be used to select a desired cognitive effect 201 which corresponds to the electrode configuration setup 202 to achieve the desired cognitive effect. In operation, this may include selection of electrodes or a TES system that contains electrodes and determination of correct positions for electrodes. In FIGS. 27A-27D the TES system referenced may include any of the apparatuses described herein. The user may be provided configuration instructions 203 by one or more ways, as indicated in FIG. 27A, including but not limited to: instructions provided via user interface; kit provided to user; wearable system configured to contact TES electrodes to appropriate portions of a user's body; electrode choice and positioning done autonomously by user (e.g. due to previous experience with TES); assistance provided by skilled practitioner of TES; and instructions provided via other means.

Based on these instructions or knowledge, a subject (or technician) may position electrodes on body 204. The apparatuses and method of using them described herein may advantageously be self-applied by the subject, although a third party may also apply the device (or assist in application). In some embodiments, the TES session starts 207 automatically after electrodes are positioned on the body. In other embodiments, the impedance of the electrodes 205 is checked by a TES system before the TES session starts 207. In some embodiments, after impedance of the electrodes 205 is checked by a TES system, user actuates TES device 206 before the TES session starts 207. In other embodiments, after positioning electrodes on the body 204 the user actuates the TES device 206 to start the TES session 207. Once the TES session starts, the next step is to deliver electrical stimulation with specified stimulation protocol 208. In some embodiments, a user actuates end of TES session 209. In other embodiments, the TES session ends automatically when the stimulation protocol completes 299.

FIG. 27B shows another variation of a wearable, lightweight apparatus ("TES system") 300. In this variation, adherent electrodes 301 connect to controller 304 via connectors 302 and/or one or more cables (e.g., wires 303). The primary unit includes a controller 304 and may include several additional components including battery or protected AC power supply 305, fuse and other safety circuitry 307, memory 308, microprocessor 309, user interface 310, current control circuitry 306, and waveform generator 311.

FIG. 27C shows a TES system comprising an adherent or wearable TES delivery unit 400 that communicates wirelessly with microprocessor-controlled control unit 409 (e.g. a smartphone running an Android or iOS operating system such as an iPhone or Samsung Galaxy, a tablet such as an iPad, a personal computer including, but not limited to, laptops and desktop computers, or any other suitable computing device). In this exemplary embodiment, adherent or wearable TES delivery unit 400 holds two or more electrodes in dermal contact with a subject with one or more of: an adhesive, a shaped form factor that fits on or is worn on a portion of a user's body (e.g. a headband or around-the-ear 'eyeglass' style form factor). The TES delivery unit 400 may include: battery 401, memory 402, microprocessor 403, user interface 404, current control circuitry 405, fuse and other safety circuitry 406, wireless antenna and chipset 407, and waveform generator 416. The remote microprocessor-controlled control unit 409 may include: wireless antenna and chipset 410, graphical user interface 411, one or more display elements to provide feedback about a TES session 412, one or more user control elements 413, memory 414, and microprocessor 415. As described herein, the TES delivery unit 400 may include additional or fewer components.

A wearable TES delivery unit 400 may be configured to communicate bidirectionally (e.g. duplex) with wireless communication protocol 408 to microprocessor-controlled system 409. The system can be configured to communicate various forms of data wirelessly, including, but not limited to, trigger signals, control signals, safety alert signals, stimulation timing, stimulation duration, stimulation intensity, other aspects of stimulation protocol, electrode quality, electrode impedance, and battery levels. Communication may be made with devices and controllers using methods known in the art, including but not limited to, RF, WIFI, WiMax, Bluetooth, BLE, UHF, NHF, GSM, CDMA, LAN, WAN, or another wireless protocol. Pulsed infrared light as transmitted for instance by a remote control is an additional wireless form of communication. Near Field Communication (NFC) is another useful technique for communicating with a neuromodulation system. One of ordinary skill in the art would appreciate that there are numerous wireless communication protocols that could be utilized with embodiments of the present invention, and embodiments of the present invention are contemplated for use with any wireless communication protocol.

In some variations, the apparatuses (e.g., TES delivery unit 409) do not include a user interface 404 and is controlled exclusively through wireless communication protocol 408 to control unit 409. In some variations, the apparatus (e.g., a wearable TES delivery unit 409) does not include wireless antenna and chipset 407 and is controlled exclusively through user interface 404.

The pattern of currents delivered into tissue of a subject (e.g. transcranially into the brain) may depend on the electrode configuration and stimulation protocol. For example, an electrode configuration may be used with one or more set of parameters. The set of parameters may be selected based on the desired cognitive effect and the number of electrodes, positions of electrodes, sizes of electrode, shapes of electrode, composition of electrodes, and anode-cathode pairing of electrodes (i.e. whether a set of electrodes is electrically coupled as an anode or cathode; also whether multiple independent channels of stimulation are present via current sources driving independent anode-cathode sets). A stimulation protocol may define the temporal pattern of current delivered to an anode-cathode set and can incorporate one or more waveform components selected from the list including but not limited to: direct current, alternating current, pulsed current, linear current ramp, nonlinear current ramp, exponential current ramp, modulation of current, and more complex (including repeated, random, pseudo-random, and chaotic patterns). In operation, the device may provide current flow at target areas (e.g., in the brain) to induce neuromodulation when appropriate electrode configurations and stimulation protocols are delivered.

FIG. 27D schematically illustrates a method of operating a remote processor to provide control information to a wearable, lightweight apparatus as described herein. For example, the apparatus ("TES device") may be paired with the remote device 2701. The user (subject) may then select the desired cognitive effect ("form of neuromodulation") and/or the control parameters 2703. In some variations the control parameters for a particular cognitive effect may be predetermined; however, the user may modify them from this predetermined baseline in some variations. The subject may then initiate the session or indicate the start time (e.g., after a delay) 2705.

Any of these control steps 2703, 2705 may be performed via a user interface. Further, the user interface may include features available before/during the session 2707, and/or after the session 2721. For example, feedback during the session may include intensity control 2709, a timer 2711, user feedback collection/monitoring 2713, and stop/cancel control 2715. User interface features available after the session may include feedback about the electrical stimulation 2723, historical information about the operation of the apparatus 2725, and user controls to repeat prior session parameters 2727. The remote processor may also be controlled to communicate wirelessly with the apparatus 2735 and to control the delivery of electrical stimulation to the subject 2737 as well as control (and indicate) when the session is complete 2799. The apparatus may also include a stop override (not shown) to stop stimulation immediately, regardless of the control from the remote processor.

Figures 28A, 28B:
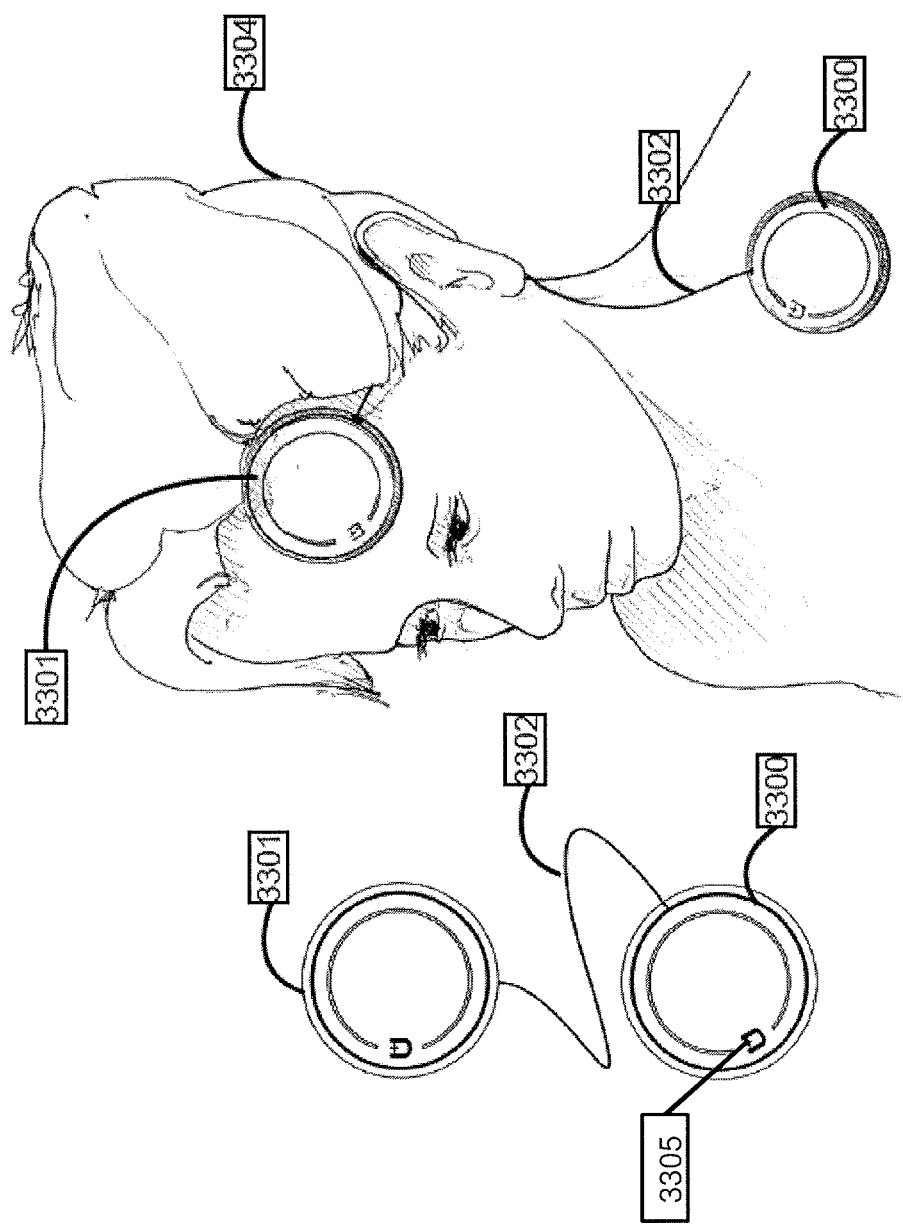
FIG. 28A shows another variation of a lightweight, wearable and self-contained electrical stimulation apparatus including a primary unit having a secondary unit tethered by a cable.
FIG. 28B illustrates the apparatus of FIG. 28A worn on a subject.

Another variation of a lightweight, wearable and self-contained electrical stimulation apparatus is shown in FIG. 28A. In this example, the apparatus includes a primary unit 3300 housing a power source, processor/controller, and wireless communication module. The outer housing of the apparatus includes an indicator 3305 which can be illuminated when the device is on and ready to operate; an LED light may indicate status (e.g., on/off, transmit/receive, etc.). The primary unit also includes an electrode that can be placed in contact with the subject's skin, as illustrated in FIG. 28B. A secondary unit 3301 is connected to the primary unit by a cable 3302. The secondary unit also includes an electrode and can be adhesively attached to the subject. In this example, the primary unit 3300 is connected to the subject's neck/shoulder region and the secondary unit 3301 is independently positioned and adhesively connected to the subject's head, as illustrated in FIG. 28B. The positions of the primary and secondary units may be reversed.

In some embodiments configured to be powered by a USB or other connection to a computerized system, electrical isolation hardware is incorporated in the stimulation device to protect the user from unexpected electrical surges and voltage boosting hardware is optionally configured to boost 1V, 3V, 5V, or other low voltage inputs to about 9V or about 12V or another higher voltage level.

In some embodiments, the device comprises sensors and related components to record measurements related to brain activity, detect skin resistance, salinity, or humidity, temperature, electromyogram (EMG), galvanic skin response (GSR), heart rate, blood pressure, respiration rate, pulse oximetry, pupil dilation, eye movement, gaze direction or measure other physiological or ambient signals. For example, in some embodiments, the device may be configured to perform an electroencephalogram (EEG). The stimulation device can include sensors and electrical control and signal processing hardware.

In some embodiments, the stimulation protocol is adjusted based on a physiological measurement of the body that takes the form of one or more measurements chosen from the group of: electromyogram (EMG), galvanic skin response (GSR), heart rate, blood pressure, respiration rate, pulse oximetry, pupil dilation, eye movement, gaze direction, or other physiological measurement known to one skilled in the art. For example, the device may be configured to utilize the one or more physiological measurements to start or stop one or more functionalities (e.g., begin or end a stimulation session).

In some embodiments, a physiological or cognitive measurement is used to detect a cognitive state of the user. For example, in an embodiment, the unit turns on when the user is tired and is configured to increase a user's energy, alertness, and/or wakefulness. In another embodiment, anxiety or stress is detected in a user by measuring galvanic skin response or another physiological measurement that correlates anxiety or stress, and the stimulation device is configured to reduce anxiety and/or stress. In another embodiment, the device is configured to modify the amplitude or phase of a brain rhythm. For instance, in an embodiment, the device can be triggered to enhance synchrony in an alpha, beta, or gamma frequency band to affect attention, working memory, and/or decision-making.

In some embodiments, the placement of electrodes is adjusted based on a procedure that delivers a test pulse of known electrical current through one or more electrodes and measures the induced electric field.

In some embodiments, a stimulation device is configured for therapeutic use in a user who is a patient. In some embodiments of the invention, the device is configured for use by a consumer without oversight by a technician, medical professional, or other skilled practitioner.

In some embodiments, targeted stimulation is combined with other neuromodulatory stimulation techniques to achieve effects in the brain. These embodiments are advantageous for neuromodulation that is not possible with either effect by itself. Other brain stimulation modalities include transcranial ultrasound neuromodulation, transcranial magnetic stimulation (TMS), deep brain stimulation (DBS), optogenetic stimulation, one electrode or an array of electrodes implanted on the surface of the brain or dura (electrocorticography (ECoG) arrays), and other modalities of brain stimulation known to one skilled in the art.

In some embodiments, the one or more effects of using multiple forms of neuromodulation are chosen from the list of: increasing the spatial extent of stimulation; decreasing the spatial extent of stimulation; reshaping the spatial extent of stimulation; modifying the nature of the induced neuromodulation; increasing the intensity of neuromodulation; decreasing the intensity of neuromodulation; mitigating a cognitive or behavioral affect; enhancing a cognitive or behavioral affect; modifying the cells affected by neuromodulation; modifying the cellular compartments affected by neuromodulation; or another modification of the neuromodulating energy transmitted into the brain and/or nervous system.

Combining targeted stimulation with transcranial ultrasound neuromodulation can be advantageous for more effectively targeting the temporal and/or spatial extent of neuromodulation. Combining targeted stimulation with transcranial ultrasound neuromodulation can also be beneficial for shaping the induced cognitive, behavioral, perceptual, motor, or other change in brain function. For instance, stimulation could be used to "clamp" shallow areas near the brain surface so that no change in brain function occurs during the transmission of ultrasound to a deeper brain region desired to be affected by transcranial ultrasound neuromodulation. In another embodiment of the invention that combines electrical stimulation and transcranial ultrasound neuromodulation, supralinear enhancement of neuromodulation is achieved so that low energy levels to improve the safe operation of the system. In an embodiment, components for delivering transcranial ultrasound neuromodulation are integrated in an electrical stimulation device.

In some embodiments, neuromodulation is targeted to more than one brain region or other portion of the nervous system (e.g. spinal cord or cranial nerves). In some embodiments, targeted stimulation or another technique for neuromodulation targets a first brain region to induce a set of behavioral, cognitive, or other effects, while concurrently (or in close temporal relation) targeting a second brain region to counteract a subset of the effects of stimulation targeting the first brain region. In this manner, the functional effect of neuromodulation can be shaped to reduce unwanted side effects. In some embodiments that target multiple brain regions, the brain regions are anatomically nearby brain regions. In other embodiments that target multiple brain regions, the brain regions are anatomically distant brain regions.

In some embodiments of the invention in which multiple brain regions are targeted with a pre-defined temporal relationship, the device is configured to target a first brain region and a second brain region to counteract an unwanted effect occurring in or mediated by the second brain region caused by stimulation of the first region. In some embodiments of the invention in which multiple brain regions are targeted with a pre-defined temporal relationship, the device is configured to target additional brain regions to counteract the effects of stimulating a first and/or second brain region. In some embodiments of the invention in which multiple brain regions are targeted with a pre-defined temporal relationship, the device is configured for concurrent stimulation of the first and second brain regions. In some embodiments of the invention in which multiple brain regions are targeted with a pre-defined temporal relationship, the device is configured such that stimulation of the first and second brain regions occurs with a specified latency, where the latency is chosen from the group of: less than about 30 seconds; less than about 10 seconds; less than about 5 seconds; less than about 1 second; less than about 500 milliseconds; less than about 250 milliseconds; less than about 100 milliseconds; less than about 50 milliseconds; less than about 40 milliseconds; less than about 30 milliseconds; less than about 20 milliseconds; less than about 10 milliseconds; less than about 5 milliseconds; less than about 2 milliseconds; or less than about 1 millisecond.

In some embodiments of the invention in which multiple brain regions are targeted with a pre-defined temporal relationship, parameters of stimulation of multiple brain regions and relative timing of stimulation are determined based on feedback from a measurement of brain activity, behavior, cognition, sensory perception, motor performance, emotion, or state of arousal.

In some embodiments, the device is configured to induce spike-timing dependent plasticity in one or more targeted brain regions. In some embodiments for inducing spike-timing dependent plasticity, the device is configured to re-create patterns of neural activity in and/or between distinct brain regions during which transduction delays of between about 1 ms and about 30 ms occur.

In some embodiments, random noise stimulation is delivered. Random noise stimulation has been shown to induce neuroplasticity (Terney et al., 2008). Advantageous embodiments that use random noise stimulation delivered by TES target specific brain regions for neuroplasticity or broader areas as large as a cortical hemisphere or the entire brain.

In some embodiments, the timing of targeted stimulation is designed to modulate brain activity that occurs in the temporal domain. In some embodiments, stimulation is used to activate, inhibit, or modulate brain rhythms in one or more brain regions. In some embodiments, stimulation is targeted to multiple connected regions in the brain that normally communicate with a known temporal latency. By stimulating multiple brain regions, communication or coupling between disparate brain regions can be enhanced, disrupted, phase-shifted or otherwise modulated.

In some embodiments, brain recordings are used to measure the effect of targeted stimulation. This technique is advantageous for providing feedback (in some embodiments, real-time feedback) concerning the targeting, timing, and stimulation parameters for targeted stimulation and/or other techniques for neuromodulation used. In this embodiment of the invention, the measurement of brain activity takes the form of one or a plurality of: electroencephalography (EEG), magnetoencephalography (MEG), functional magnetic resonance imaging (fMRI), functional near-infrared spectroscopy (MRS), positron emission tomography (PET), single-photon emission computed tomography (SPECT), computed tomography (CT), functional tissue pulsatility imaging (fTPI), xenon 133 imaging, or other techniques for measuring brain activity known to one skilled in the art.

In some embodiments, the effect on the brain is measured by a cognitive assessment that takes the form of one or more of: a test of motor control, a test of cognitive state, a test of cognitive ability, a sensory processing task, an event related potential assessment, a reaction time task, a motor coordination task, a language assessment, a test of attention, a test of emotional state, a behavioral assessment, an assessment of emotional state, an assessment of obsessive compulsive behavior, a test of social behavior, an assessment of risk-taking behavior, an assessment of addictive behavior, a standardized cognitive task, an assessment of "cognitive flexibility" such as the Stroop task, a working memory task (such as the n-back task), tests that measure learning rate, or a customized cognitive task.

In some embodiments, physiological monitoring is used to measure the effect of electrical stimulation. This technique is advantageous for providing feedback (in some embodiments, real-time feedback) concerning the targeting, timing, and stimulation parameters for targeted stimulation and/or other techniques for neuromodulation used. In this embodiment of the invention, the measurement of physiological signals takes the form of one or a plurality of: electromyogram (EMG), galvanic skin response (GSR), heart rate, blood pressure, respiration rate, pulse oximetry, pupil dilation, eye movement, gaze direction, or other physiological measurement known to one skilled in the art.

In another aspect of an embodiment of the invention, a device assists a user or other individual in placing electrodes at appropriate locations to achieve a desired form of neuromodulation. Methods for guiding the user or other individual to place electrodes at the one or more desired locations includes one or more from the group of: fiduciary markers on the head; ratiometric measurements relative to fiduciary markers on the head; alignment components that detect relative location of electrode components by proximity as measured by radiofrequency energy, ultrasound, or light; or a grid or other alignment system, such as the position of the electrodes themselves, projected onto the head of the user. In some embodiments of the invention, an indicator provides feedback when the electrode positioning is achieved through a light-, sound-, or tactile-based indicator.

In some embodiments of the invention, a user or other individual identifies fiduciary markers to assist in targeting. Fiduciary markers on the head include those used for placing EEG electrodes in the standard 10/20 arrangement. The nasion is the point between the forehead and the nose. The inion is the lowest point of the skull from the back of the head and is normally indicated by a prominent bump.

In some embodiments, neuromodulation is achieved exclusively via electrodes placed on portions of the head, face, and neck that do not have hair to reduce the need for additional material or system components for coupling the electrical current to the scalp. Targeted stimulation is achieved with a system that includes one or more electrodes placed on hairless portions of the head, face, and neck. In some embodiments, an electrode placed on the periphery (below the neck) is used to deliver a spatially broad electrical field to the brain.

In some embodiments of the invention, multiple stimulation devices are used to deliver a focused electric field to a deeper brain region. One method for targeting an electrical field at depth in the brain is to deliver AC from multiple sets of electrodes and select anode-cathode pairs, stimulus amplitude and frequency, and relative timing or phase delay of stimulation so that constructive and destructive interference among transmitted electric fields create a focused region of neuromodulation. In some embodiments, a master device controls the timing and stimulus parameters among one or more slave devices in order to achieve improved focusing of stimulation.

In another aspect of an embodiment of the invention, the placement of electrodes and spatiotemporal pattern of stimulation delivered through the electrodes is configured for targeting the ventromedial prefrontal cortex for neuromodulation (VmPFC; Brodmann area 10). Targeting to the VmPFC can be advantageous for modulating emotion, risk, decision-making, and fear.

In another aspect of an embodiment of the invention, the placement of electrodes and spatiotemporal pattern of stimulation delivered through the electrodes is configured for targeting the orbitofrontal cortex for neuromodulation (OFC; Brodmann 10, 11, 14; 16). Targeting to the OFC can be advantageous for modulating executive control and decision making.

In some embodiments, the system or device is configured to target one or more regions of cerebral cortex, where the region of cerebral cortex chosen from the group of: striate visual cortex, visual association cortex, primary and secondary auditory cortex, somatosensory cortex, primary motor cortex 4, supplementary motor cortex, premotor cortex, the frontal eye fields, prefrontal cortex, orbitofrontal cortex, dorsolateral prefrontal cortex, ventrolateral prefrontal cortex, anterior cingulate cortex, and other area of cerebral cortex.

In some embodiments, the system or device is configured to target one or more deep brain regions chosen from the group of: the limbic system (including the amygdala), hippocampus, parahippocampal formation, entorhinal cortex, subiculum, thalamus, hypothalamus, white matter tracts, brainstem nuclei, cerebellum, neuromodulatory nucleus, or other deep brain region.

In some embodiments, the system or device is configured to target one or more brain regions that mediate sensory experience, motor performance, and the formation of ideas and thoughts, as well as states of emotion, physiological arousal, sexual arousal, attention, creativity, relaxation, empathy, connectedness, and other cognitive states.

In some embodiments, modulation of neuronal activity underlying multiple sensory domains and/or cognitive states occurs concurrently or in close temporal arrangements.

In some embodiments, a device can be configured via a user interface on the device (e.g., selector switch) or wireless interface via another device (e.g. smartphone, tablet, laptop, or desktop computer) for targeting a particular brain region. For instance, a user may be able to configure the particular type of neuromodulation utilized by using a smartphone application connected to an application programming interface (API) provided by the device over a wireless connection via a local area network. In this manner, the device can be conveniently changed between two or more types of stimulation.

In some embodiments, coupling between a stimulating electrode and the skin is achieved with a semi-permeable sack between the electrode and the skin that releases a small amount of water or other conductive liquid when squeezed. In some embodiments of this aspect of the invention, the water or other conductive liquid evaporates after the TES session and does not require cleanup.

The electrode apparatuses described herein may also be referred to as cantilever electrode apparatuses. The cantilever electrode apparatuses described herein may act as an interface between a wearable, lightweight and self-contained neurostimulator (e.g., a primary unit, which may also be referred to herein as an "electrical stimulator" and/or neuromodulation system) and a subject's body, particularly the head or head and neck region, where stimulation is to be applied. As mentioned, these cantilever electrode apparatuses may be disposable (or semi-disposable) components that are connected to the neurostimulator and applied directly to the subject; energy (typically current) from the neurostimulator is guided and delivered to the subject by the cantilever electrode apparatus. Although the neurostimulator may be small and lightweight, the cantilever electrode apparatus may allow it to secure to the subject's body and deliver energy to two or more regions on the body (e.g., temple, neck, chest, etc.) that are separated by a distance that is much greater than the size of the neurostimulator.

The cantilever electrode apparatuses described herein generally include at least two electrode regions, separated from each other along an elongate body. The cantilever electrode apparatus typically attaches to the neurostimulator device by two (or more) electrical connectors (which may be referred to herein as connectors) that are in electrical contact with the electrode regions. The electrical contacts may be positioned on the cantilever electrode apparatus adjacent each other and in a particular manner that permits both the secure attachment to the neurostimulator and prevents disruption of the electrical contact while the cantilever electrode apparatus is worn by the subject, even while the subject moves about. For example, the spacing of the connectors may be between 0.6 and 0.9 inches apart on center (from center to center), and more preferably between about 0.7 inches and about 0.8 inches. The electrical connectors typically extend from the otherwise substantially flat surface of the cantilever electrode apparatus, and may plug into the neurostimulator. The electrical connectors may mechanically engage with the neurostimulator (e.g., they may be snaps), which may also provide mechanical support for the connection between the cantilever electrode apparatus and the neurostimulator, and thereby help support and hold the neurostimulator on the subject's body when the cantilever electrode apparatuses is attached to the subject's.

In general the cantilever electrode apparatuses include two or more connectors at or near one end of the elongate body of the cantilever electrode apparatus, and two (or more) electrode regions are positioned along the elongate body of the cantilever electrode apparatus. The two or more connectors (which may also be referred to as electrical connectors) may be at one end and help secure the entire cantilever electrode apparatus to the neurostimulator, even while a second electrode region is positioned at a distance (e.g., greater than 2 inches, greater than 3 inches, greater than 4 inches, etc.) along the elongate body of the cantilever electrode apparatus from the connectors and another electrode region.

Each electrode region of the cantilever electrode apparatuses described herein typically includes an active region on a back side of the electrode region that is adapted to contact the subject. The active region may include a hydrogel that transfers energy (e.g. current) from the neurostimulator to the subject's skin. The active region is in electrical communication with the connector.

In general, the elongate body forming the cantilever electrode apparatuses may be made of a material that is rigid in at least one direction, even while flexible in another direction. For example, the elongate body of the cantilever electrode apparatus may be formed of a relatively flat sheet of material (e.g., flex circuit material) that is relatively thin (e.g., less than 3 mm, less than 2 mm, less than 1 mm). The sheet of material may extend in a plane, and the material may not be bendable in the direction of the plane although it may be bendable out of the direction (e.g., can be curved up/down), and may twist. This partial rigidity may help support the cantilever electrode apparatus on the body while allowing it to conform to a wide variety of subject body sizes. In some variations the cantilever electrode apparatus is made of a material that is rigid, but can be bent by the application of force to hold a shape. For example, the elongate body of the cantilever electrode apparatus may be ductile, e.g., may be made (at least in part) of a shape memory material that allows bending.

The configuration of the cantilever electrode apparatuses described herein may provide numerous benefits compared to other possible arrangements, including variations in which a wire or separate connection connects a second (or more) electrode region to a neurostimulator. For example, the cantilever electrode apparatuses described herein may include least a few mm of adhesive surrounding the active area of each electrode, which may help make good contact with the skin when the cantilever electrode apparatus is attached to a wearable neurostimluator. For electrode apparatuses and microstimulators that are configured to be worn on the temple (e.g., adjacent to the eye), the amount of adhesive in one portion of the electrode apparatus may be limited; in particular, the portion that will be positioned below a lower edge of the electrode, to prevent the unit from extending too far towards the eye and/or towards the hairline at the temple. In some variations it is desirable to have the cantilever electrode apparatus and the electrical stimulator with its overlaying hardware unit positioned on the face so that it does not interfere with a temple portion of a pair of glasses that may be worn while wearing the device (e.g., the region adjacent to the ear). In addition, it may be beneficial for the bottom edge of the cantilevered electrode assembly (at the first electrode portion) to correspond with the bottom edge of the electrical stimulator to help guide self-placement using the lower edge of the device to align horizontally with the edge of the eye, an easy landmark for self-placement; thus, it may be beneficial to limit the amount of adhesive below/around the lower section of the electrode.

As mentioned above, there are also numerous benefits of using a connector for electrically connecting the active regions of the cantilever electrode apparatus to the electrical stimulator both mechanically and electrically. For example, an apparatus that uses a mechanical and electrical connector, such as a snap connector or other connector that stands proud from the relatively thin cantilever electrode apparatus may prevent miss-adjustment of the apparatus. In particular, it may be beneficial to have two connectors (e.g., snaps) rather than just wires or one snap and a wire to connect the wearable apparatus and the cantilevered electrode apparatus. The second mechanical/electrical connector such as a snap may improve the physical connection between electrode adhesive pad and hardware unit (neurostimulator/electrical assembly). In addition, the hardware unit (neurostimulator/electrical stimulator) any electrode apparatus must fit under the temple portion of an eyeglass frame for users wearing glasses; thus the portion of the combined assembly (electrode assembly and neurostimulator) should ideally be thin enough to fit between glasses and the temple region. However, it may also be beneficial to have some portions of the system (e.g., the neurostimulator) be sufficiently thick to allow the apparatus to contain a sufficient battery (or other power portion) so that the unit can be used for a reasonable amount of time between charges. Thus one portion of the neurostimulator may be thick enough to allow a standard battery and/or circuitry and at one end (e.g., an end that is worn higher up on the face). Thus, it may be beneficial to locate the mechanical/electrical connectors such as snaps the extend proud from the cantilevered electrode assembly toward the thinner end, separated from the battery compartment of the neurostimulator to reduce the overall thickness of the system in come variations, allowing the connectors to under a PCB rather than under a thick battery portion (or under both). However, in some variations it may be beneficial to have the connector(s) be positioned under the batter portion or have one connector under the battery portion and one connector under the thinner region separated from the battery portion.

For example, in some variations it may be beneficial to have one connector on the electrode assembly (e.g., cantilevered electrode assembly) near the portion of the neurostimulator hardware that is highest up on the forehead; this may help ensure that this upper portion of the device doesn't pull away from the electrode. If that happens, then the weight of the hardware unit may pull the electrode further from the head and eventually lead to poor contact between the electrode active area and the skin. An adhesive may be used between the neurostimulator and the electrode assembly to prevent this; alternatively or additionally an additional mechanical connector may be used (an adhesive may be considered on type of mechanical connector, and may be present on the electrode assembly and/or on the neurostimulator body).

It may also be beneficial to have at least one of the electrical/mechanical connectors (such as a snap) at or near (and preferably behind) the active area of the first electrode portion, as this may make the electrical connection with the hardware unit easier and more robust.

As will be described in greater detail in reference to FIGS. 35A-35F, the overall shape of the neurostimulator may be triangular, and particularly the surface of the neurostimulator (though curved/concave and twisted) adapted connect to the electrode apparatus and face the patient may be three-sided (e.g., roughly triangular). This roughly triangular shape may include rounded edges, and the thickness of the stimulator (in the direction perpendicular to the surface contacting the cantilevered electrode apparatus) may vary, e.g., be thinner along one side, and particularly the side (the portion between the orbital edge and the auricular edge) that will extend between the eye and the temple. This shape may also be beneficial when helping to fit/be worn on most people in a region of the face/head that tend to not have hair. This thin lower corner (the orbital/auricular corner) may fit between the eyebrow and hairline, while the wider portion is positioned up in the forehead area where there is less likely to be hair.

FIGS. 29A-29D and 2 illustrate one variation of a cantilevered electrode apparatus ("electrode apparatus") that may be used with a neurostimulator that is worn on a subject's head. In this example, the cantilevered electrode apparatus 2900 includes a plurality of electrode portions (two are shown) 2903, 2905. In FIG. 29A, a front perspective view is shown. The front side is the side that will face away from the subject when worn. The cantilevered electrode apparatus is thin, so that the electrode portions include a front side (visible in FIGS. 29A and 29B) and a back side (visible in FIG. 29D). As shown in the side view of FIG. 29C, the device has a thin body that includes the electrode portions 2903, 2905 as well as an elongate body region 2907 extending between the two electrode portions. The elongate body is also thin (having a much larger diameter and height than thickness (the thickness is shown in FIG. 29C).

In this example, two connectors 2915, 2917 (electrical and mechanical connectors, shown in this example as snaps) extend from the front of the cantilevered electrode apparatus. The front of the first electrical portion 2903 may also include an optional foam and/or adhesive material 2921 through which the snaps extend proud of the first electrical portion. The first electrical portion is shaped and sized so that the snaps will connect to plugs (ports, holders, opening, female mating, etc.) on the electrical stimulator. As described above, the connectors may be separated by between about 0.6 and about 0.9 inches (e.g., between about 0.7 and about 0.8 inches, etc., shown in FIGS. 29A-29D and 2 as about 0.72 inches). The second electrode portion may also include a foam or backing portion 2923. This foam/backing region may be optional.

FIG. 29D shows a back view of this first example of a cantilevered electrode apparatus. In this example, the first 2903 and second 2905 electrode portions are also shown and include active regions 2933, 2935. The active regions are bordered by adhesive 2940. The first 2903 electrode portion includes, on the back (patient-contacting) side, a first active region 2933, surrounded by an adhesive material 2940 that extends. The active region may include a conductive material (e.g., electrically conductive gel). Similarly, the back of the second electrode portion 2905 includes the second active region 2935 which is bounded on an upper and lower side by an adhesive 2940. The adhesive may be any biocompatible adhesive that can releasably hold the material to the skin.

FIGS. 30A and 30B show exploded views of the exemplary cantilevered electrode apparatus of FIGS. 29A-29D. In FIG. 30A, the front side of the cantilevered electrode apparatus is shown with the foam backing 2921, 2923 (which may be adhesive on one or both sides) materials and snaps 2917, 2915 removed. The snaps may include two parts (not shown in FIG. 30A), a base and a post, and the base may be positioned on the back side of the elongate body forming the substrate (or base) 2908 for the cantilevered electrode apparatus. The base may be a flex circuit material, e.g., that is relatively insulating, flexible out of the plane of the material, but rigid in the plane (meaning it can be bent up/down out of the plane, but has rigidity when pushed/pulled in the direction of the plane of the material). Many of the structures used to form the electrode regions and connectors may be printed directly onto the base or attached to the base. For example, in FIG. 30B, the back (patient-facing) side of the base of the cantilevered electrode apparatus is shown with the snaps attached so that the base of the snaps extends along the back side and can be in electrical contact in one case with the electrically conductive first active region forming part of the first electrode portion. The second snap is offset from the electrically active region and may contact a conductive trace (e.g., printed on the body 2908 of the base) and extending along the elongate body region 2907 until it contacts the second active region. In this manner, the first and second connectors may establish electrical communication between the active regions and the neurostimulator. In FIG. 30B the active regions includes a conductive gel (although additional materials, including sacrificial materials, pH buffer materials, antibacterial/germicidal materials, etc.). The adhesive portion 2940 is also shown in this exploded view.

As described above, the foam material over either or both of the front sides of the first and second electrode portions may be omitted. FIG. 31 shows an example in which the foam material, which may also or alternatively be an adhesive to help secure the cantilevered electrode apparatus to the neurostimulator is not included in the cantilevered electrode apparatus. In this example, the connectors (snaps 2917, 2915) alone may be used to secure the cantilevered electrode apparatus to the neurostimulator.

Figures 33, 34:
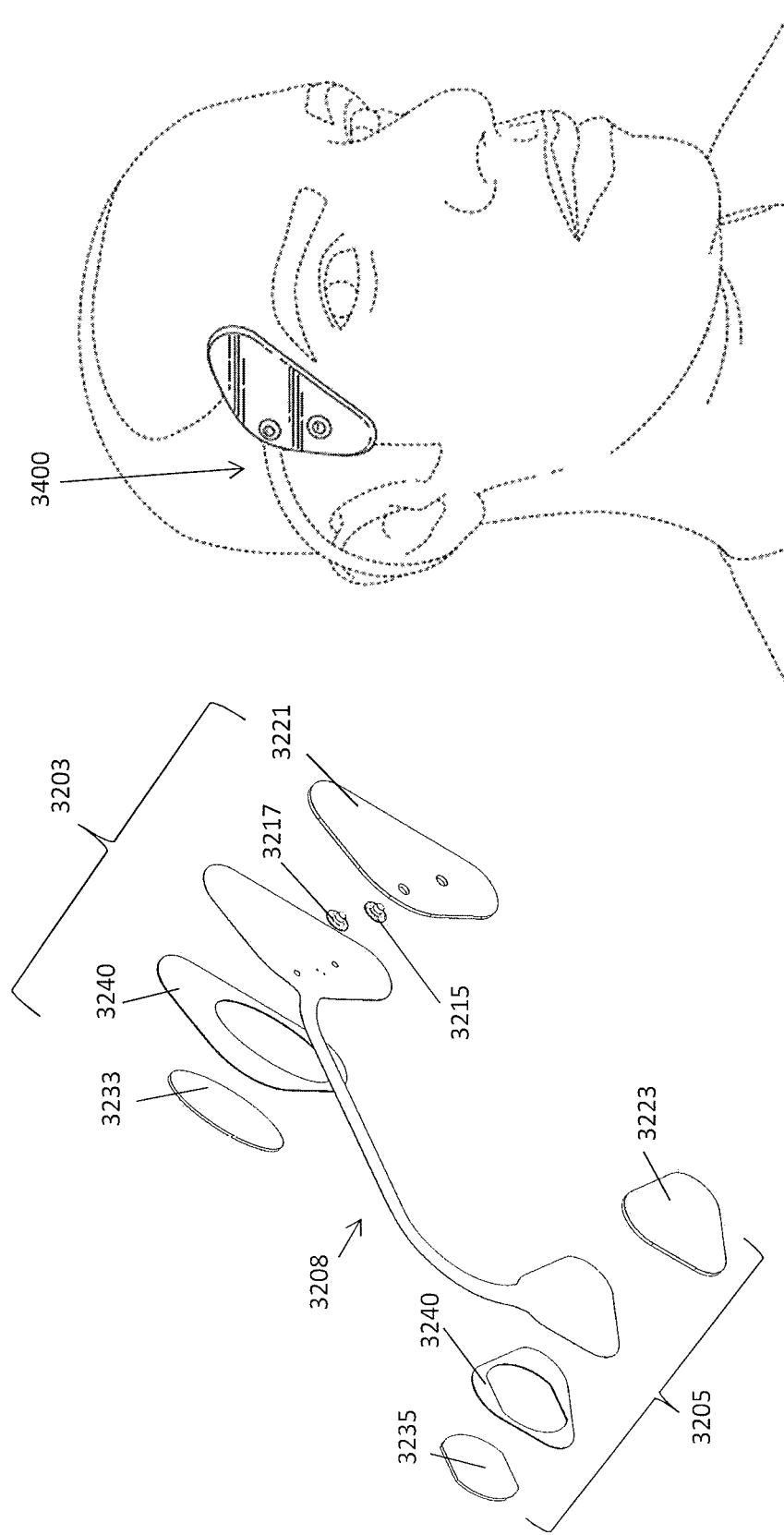
FIG. 33 is an exploded view of the cantilever electrode apparatus of FIG. 32A.
FIG. 34 illustrates a cantilever electrode apparatus (similar to those shown in FIGS. 29A and 32A) worn on a subject's head.
Figures 3, 70B:
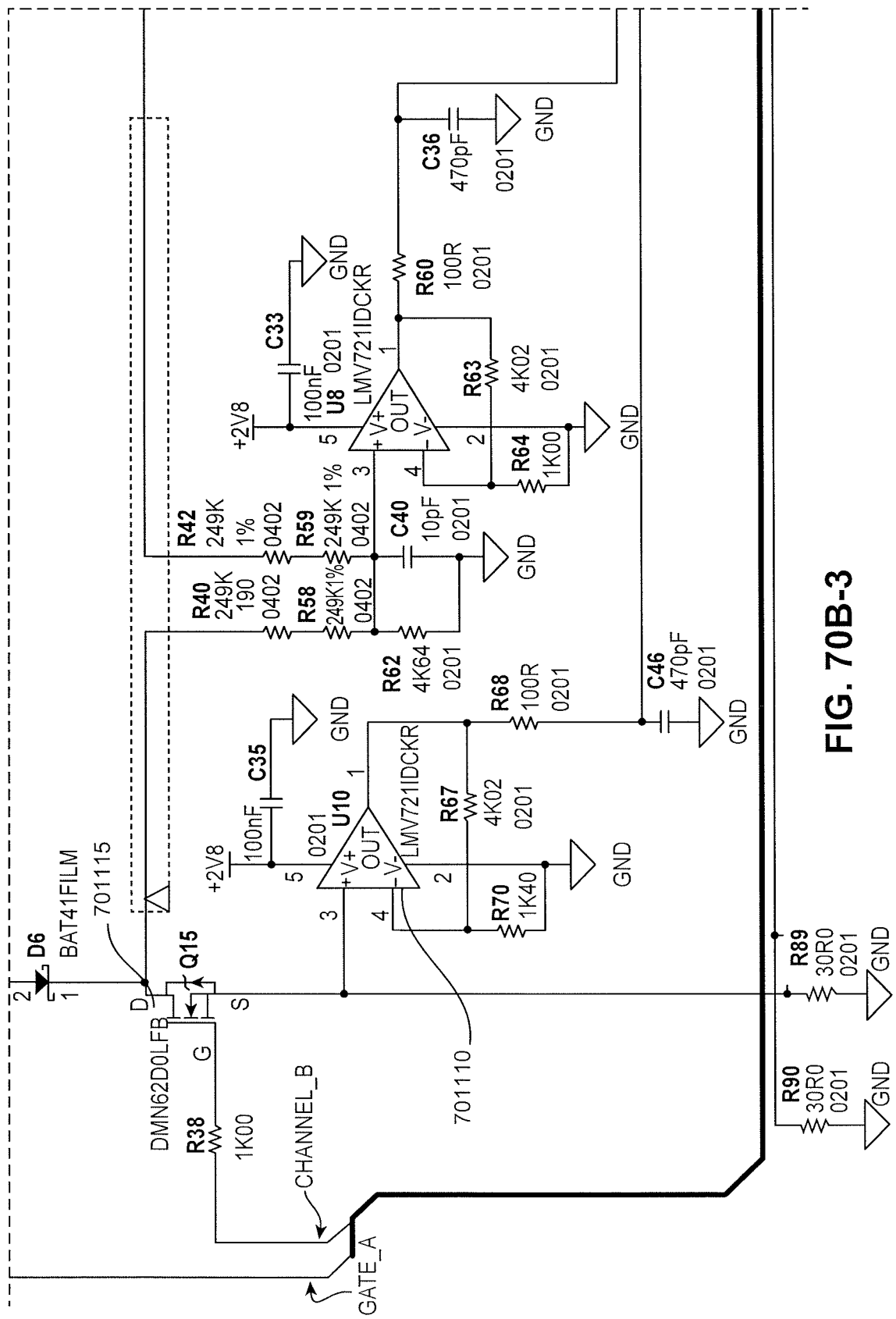
Figures 4, 70B:
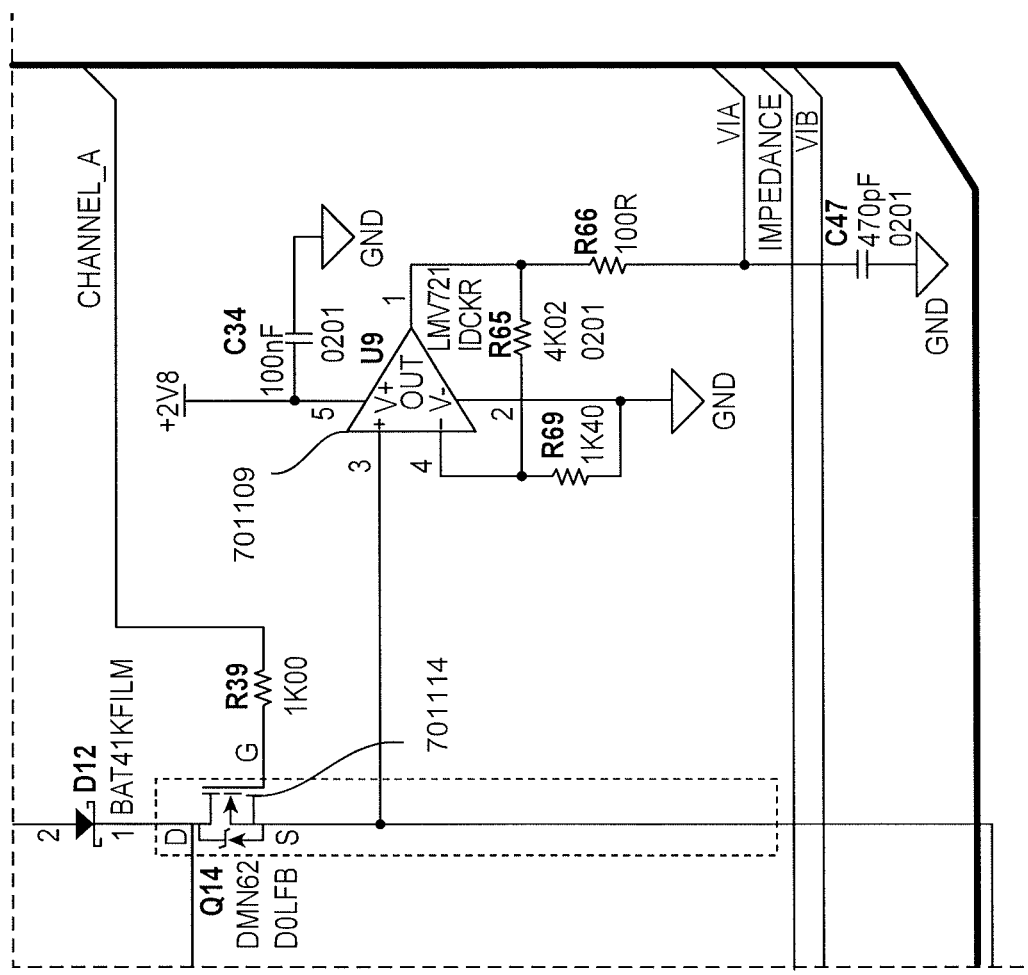
FIG. 4A shows on example of a secondary unit of an apparatus such as the apparatus of FIGS. 1A-3C.
FIG. 4C is a bottom view of the secondary unit of FIG. 4A.

The cantilevered electrode apparatus show in FIGS. 29A-3 may be particularly useful, for example, to connect a neurostimulator to a subject's head (as illustrated in FIG. 34, below) and so that the neurostimulator is attached to the front side of the cantilevered electrode apparatus by snapping onto the proud connectors, while the elongate body region 2907 is bent to extend behind the subject's head and down to a portion on the midline of the back of the patient's neck. Both the first electrode portion and the second electrode portion may be adhesively held with the electrically active regions against the skin, allowing the neurostimulator to apply energy, and in particular the waveforms as described in U.S. patent application Ser. No. 14/320,443, titled "TRANSDERMAL ELECTRICAL STIMULATION METHODS FOR MODIFYING OR INDUCING COGNITIVE STATE" and filed Jun. 30, 2014, and herein incorporated by reference in its entirety.

FIGS. 32A-32D illustrate another example of a cantilevered electrode apparatus. This example is very similar to the variation shown in FIGS. 29A-30B. The connectors (snaps 3317, 3315) are in the same position as shown in FIGS. 29A-29D, as are the shape of the first electrode portion 3303 and foam/backing material 3321 (which may also or alternatively be an adhesive material). However, the example shown in FIG. 32A-32D includes a different overall shape, and may be used to connect, for example, to different regions of the patient's head/neck. In particular, the portion of the substrate forming the elongate body region 407 extending between the two electrode portions 3303, 3305 is shaped slightly differently. In this example, the cantilevered electrode apparatus may be configured to connect, for example, to the subject's temple with the first electrode portion (to which the neurostimulator may be connected) and the elongate body region may be bent around the subject's head so that the second electrode portion maybe in electrical contact with a region behind the subject's ear (e.g., at or near the mastoid). By placing the first active region 3333 of the first electrode portion 3305 in electrical contact with the skin at the temple region, using the adhesive material 3340 surrounding the electrically active region 3333 to hold the electrically active region (and the attached neurostimulator) in position, and the second electrically active region may also be adhesively 3340 held to skin so that the second electrically active region 3335 is in contact with the mastoid region.

Figure 36B:
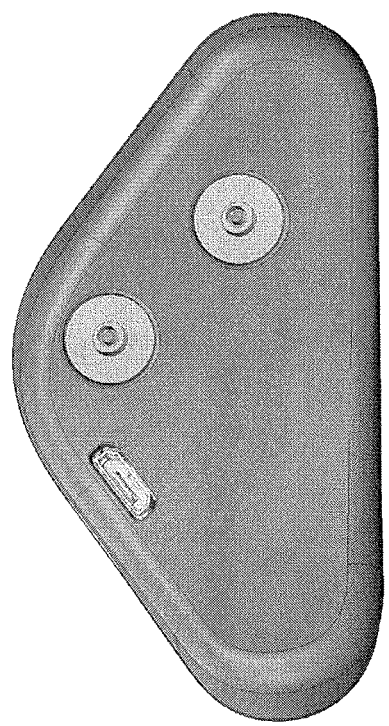
FIG. 36B is a back perspective view of a neurostimulation device similar to the device shown in FIGS. 35A-35F.
Figure 36A:
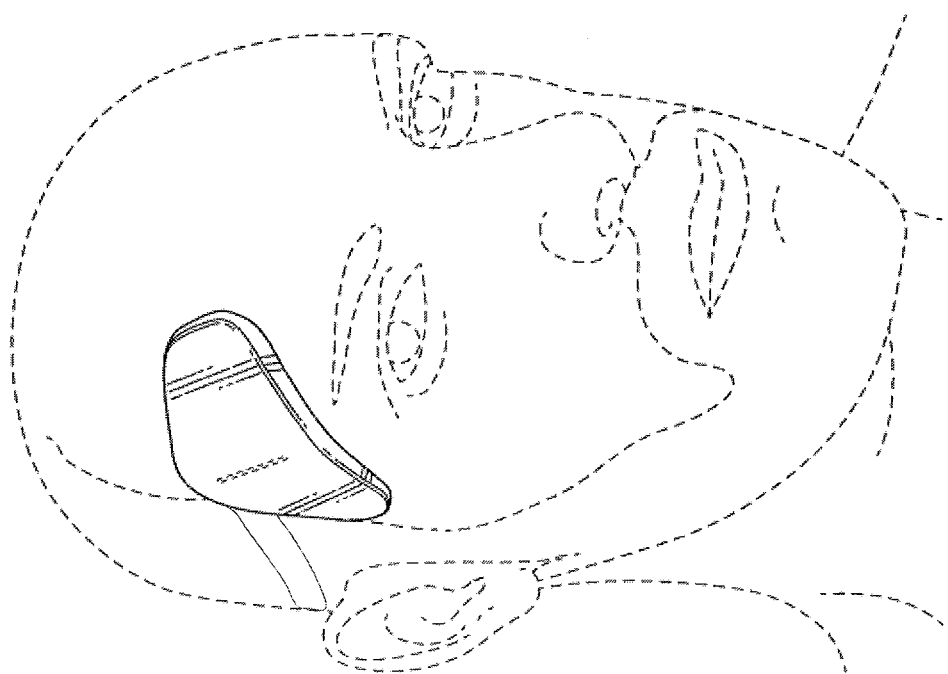
FIG. 36A illustrates the neurostimulation device shown in FIGS. 35A-35F worn with a cantilever electrode apparatus on a subject.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc. The elongate body region may also be bent or curved, as illustrated in both the variations of FIGS. 29A-3 and FIGS. 32A-5. The bend or curve, in which the elongate body may even double back on itself, may allow the material to flex or bend to allow it to be adjustably positioned over and/or around the subject's head, as shown in FIGS. 6 and 36A, for example.

FIG. 33 shows an exploded view of the cantilevered electrode apparatus of FIGS. 32A-32D. In this example, the substrate (elongate body 3308) forms the elongate body region between the first electrode portion (formed of the first electrically active region having conductive material 3333 and adhesive 3340 and optional backing material 3321, as well as a portion of the substrate 3308) and the second electrode portion (formed of the second electrically active region 3335, adhesive 3340, and optional backing material 3323, as well as a portion of the substrate 3308). One or more electrical traces may also be included, e.g., directly printed onto the substrate 3308, connecting the second electrically conductive region 3335 to the second connector 3317.

As mentioned above, the connectors (pins 3315, 3317) are spaced a predetermined distance apart (e.g., between about 0.7 and 0.8 inches) with the first pin 3315 behind, and in direct electrical contact with the first electrically conductive region 3333 of the first electrode portion 3303. The second connector (pin 3317) is electrically insulated from the first connector and the first electrically conductive material, and may be positioned so that it is not directly behind the first electrically active region 3333, but it is still in the first electrode portion 3303, and extends proud of the back of the first electrode portion (e.g., the back of the substrate forming the first electrode portion).

FIG. 34 illustrate a variation of a cantilevered electrode apparatus 3400 worn on a subject's head. As illustrated, the apparatus is positioned with the first electrode portion on the temple region and a second electrode portion behind the head (e.g., behind the ear or neck region, not shown).

In this example, a neurostimulator (not shown in FIG. 34) may be attached to the cantilevered electrode apparatus either before or after it is applied to the subject. FIGS. 35A-35F illustrate perspective views of one variation of a neurostimulation apparatus, and FIG. 36A shows the apparatus applied to a subject's head with a cantilevered electrode apparatus. FIG. 36B shows a back view of the neurostimulator (electrical applicator) of FIGS. 35A-36A.

In FIGS. 35A-35F the various edges are labeled, based on where the apparatus will be worn by the subject, similar to what is illustrated in FIG. 36A. In general, the side of the unit worn toward the ear is the auricular edge, the side worn highest on the forehead is the superior edge, and the side worn nearest the eye/eyebrow is the orbital edge. The overall shape of the neurostimulator is triangular (including rounded edges). As used herein triangular includes shapes have rounded/smooth transitions between the three sides, as illustrated. The subject-facing surface is specifically contoured to fit in the predefined orientation, making it difficult or impossible for a subject to misapply, and risk placing the active region of the attached cantilevered electrode apparatus in the wrong place. When attaching the cantilevered electrode apparatus to the neurostimulator, the cantilevered electrode apparatus may flex or bend so that it is contoured to match the curved and twisted surface. This surface is a section of a saddle shape, in which there is an axis of curvature around which the surface is concavely curved, and an axis of twisting, which may distort the curved surface (the two axes may be different or the same).

As shown in FIG. 36B, the bottom surface of the neurostimulator, to which the cantilevered electrode apparatus attaches, including mating junctions (openings, receptacles, female receivers, etc.) to receive and make electrical and mechanical contact with the connectors on the cantilevered electrode apparatus. These receivers may also be positioned to optimize the placement of the cantilevered electrode apparatus, allowing it to make sufficient contact with the neurostimulator and subject, and prevent the cantilevered electrode apparatus from bending or breaking contact, even while the subject is mobile and/or active.

Although the variations described above for the cantilevered electrode apparatus illustrate a flexible structure, in which a substrate (e.g., flex circuit) material is thin and permitted to bend in at least one axis, in some variations the cantilevered electrode apparatus may be rigid. FIGS. 37A-37C and 38A-38C illustrate two variations of rigid, or semi-rigid cantilevered electrode apparatuses.

In FIGS. 37A-37C, the device is shown as a CAD rendering of an exemplar neurostimulator 3703 attached to a cantilevered electrode apparatus 3701 that may be bendable (ductile) or hinged to achieve a wearable form factor allowing contact with different regions of the head/neck. A neurostimulator (not shown) may include all or a subset of electronic components and may be attached to the projecting pins 3705. For example, an anode electrode (the electrically active region of the first electrode portion) may be positioned on the right temple area and electrically. When the posterior portion (e.g., the second electrode region) of the cantilevered electrode apparatus may be positioned so that a cathode electrode targeting the right mastoid behind the ear is positioned correctly (electrode active region not shown).

Similarly, the example shown in FIGS. 38A-38C illustrates a region 3801 having a rigid elongate body (including connector region of the elongate body), the elongate body extends further and may allow contact with the second active region on the back of the subject's neck. All or a portion of the body may be ductile so that it can be bent into a shape allowing it to conform to the neck. In some variations the elongate body may be hinged to allow it to bend/flex during use.

Figures 39A, 39B:
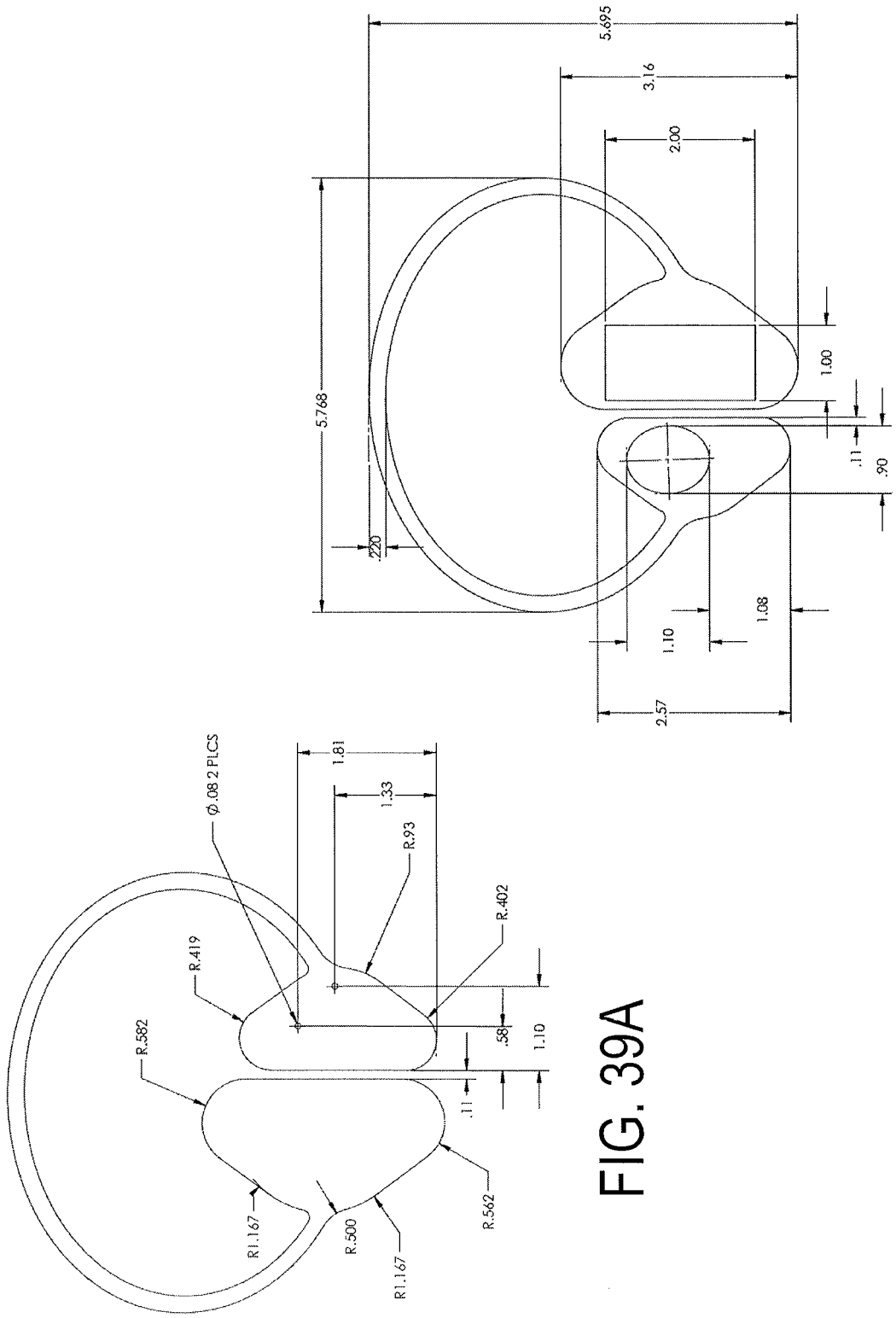
FIGS. 39A and 39B show front and back views, respectively of another variation of a cantilever electrode apparatus.

FIGS. 39A and 11B illustrate another variation of a flexible (at least in one axis of freedom) cantilevered electrode apparatus which may also be formed of a flex circuit material. FIG. 39A shows a front view and FIG. 39B shows a back view of the substrate portion onto which the other elements may be attached (e.g., the active regions, the connectors, adhesive, etc.). In this example, the device includes an elongate thin connector portion of the substrate body, similar to the variations shown in FIGS. 29A-3 and 32A-5, above. Exemplary dimension (in length units of inches) are shown for illustrative purposes only, and may be varied.

Figure 40:
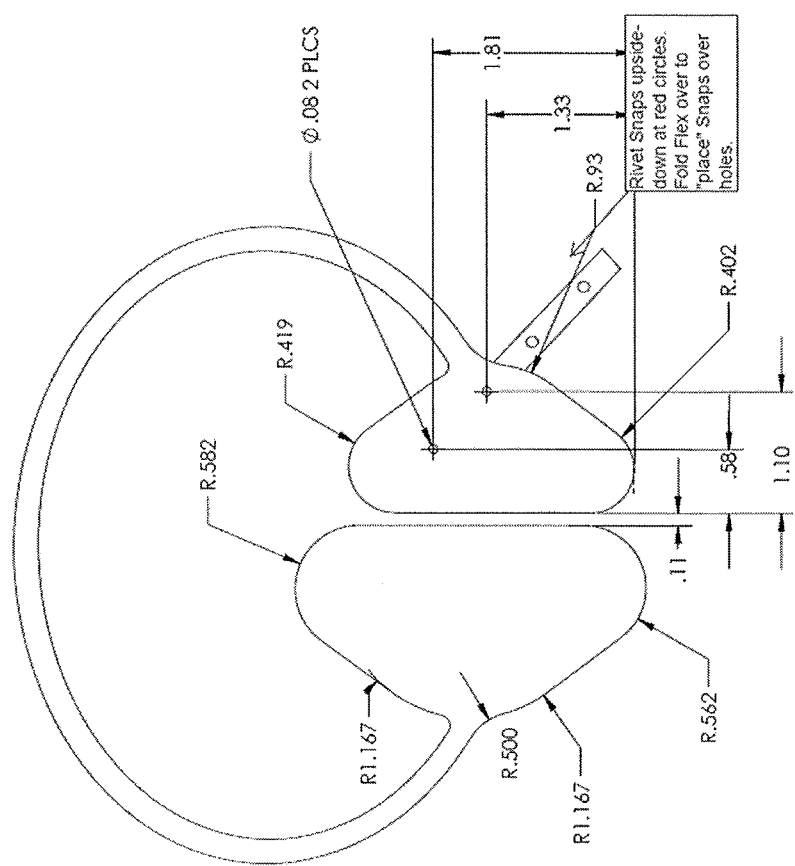
FIG. 40 is a front view of another variation of a cantilever electrode apparatus.

FIG. 40 is another variation of a cantilevered electrode apparatus in which the connectors are coupled to a different portion of the substrate and folded back over so that they may be positioned on the first electrode region, similar to what is illustrated in FIGS. 29A-3, and 32A-5 above. This may allow a better fit for larger electrodes.

In any of the apparatuses described herein, the electrodes may include an adhesive, as described and illustrated above. Good adherence is generally a beneficial property of transdermal electrodes that permits uniform, low-impedance contact with a user's skin. Adhesive materials of an adhesive transdermal electrode may include a portion of the electrode intended for delivering electrical stimulation (i.e. adhesive and conductive) and/or a portion of the electrode that is not intended for delivering electrical stimulation that is configured to cause an electrically conductive portion of the electrode to be in close physical contact (i.e. low impedance) contact with a user's skin.

Any of the electrodes described may include a buffer (e.g., pH buffer). Any of the electrodes described herein may also include a silver/silver chloride material (Ag and AgCl). For example, buffering pH and even distribution of current across the transdermal face of an electrode are beneficial properties of transdermal electrodes that improve the comfort of electrical stimulation, particularly at high peak currents above 5 mA. Uniform current distribution and pH buffering can be improved by features of transdermal electrodes, including the water composition of a hydrogel component of a transdermal electrode for TES and the amount of Ag and AgCl contained in a component that couples an electric current through the electrode to the skin. Water in a hydrogel component of a transdermal electrode (or other water-containing conductive material) is consumed as net charge is transferred into a subject's body. Ag/AgCl components of an electrode (including components coated with Ag/AgCl and Ag/AgCl ink) improve the efficiency of charge transfer to tissue (essentially a salt solution) and are also consumed during electrical stimulation.

Charge imbalanced TES waveforms are often necessary for inducing cognitive effects, but these waveforms can consume Ag, AgCl, and water, causing the degradation of transdermal electrodes and limited their effective use.

In some embodiments, one or both electrodes includes a nonconsumptive conducting layer, a consumptive conducting layer, and a conductive hydrogel layer. In some embodiments, the consumptive layer may be a buffer layer disposed between the nonconsumptive layer and the hydrogel layer. Further, the consumptive layer may extend beyond the boundary of the nonconsumptive layer at each edge of the nonconsumptive layer and may be configured to reduce hydrolysis in the hydrogel layer, such that the consumptive layer donates electrons for redox reactions. The nonconsumptive and consumptive layers may include silver, gold, copper, or any other type of conductive metal or non-metallic material, such as carbon or conductive polymers (e.g. poly(3,4-ethylenedioxythiophene). Preferably, the nonconsumptive and consumptive layers include silver. An important feature of the nonconsumptive layer is that any electrochemical reactions occurring in that layer do not cause the quality of the layer as an electrical conductor (i.e. impedance) to change during a transdermal or transcranial stimulation session. This feature ensures that current delivered to the layer is, for the most part, distributed evenly over its surface first before entering the consumptive layer. In some embodiments, the nonconsumptive layer experiences reduced consumption, such as when the nonconsumptive layer includes silver. Alternatively, the nonconsumptive layer may experience essentially zero consumption, such as when the nonconsumptive layer includes carbon. In some embodiments, the nonconsumptive layer experiences reduced consumption since it does not include an anion that can be electrically consumed during electrical stimulation. The nonconsumptive layer may disperse the electrical current over its surface area before reaching the consumptive layer. If the electrical current is not dispersed over the surface area of the nonconsumptive layer before reaching the consumptive layer, the consumptive layer may be overconsumed, such that AgCl becomes Ag(0) in a local area of the consumptive layer surface, causing uneven current distribution and the potential for local hydrolysis. In embodiments, the consumptive layer is composed of a ratio of silver to silver chloride (Ag:AgCl) for efficient consumption and electrochemistry. Optimal ratios can be selected based on the charge balance of stimulation or empirically based on comfort and cognitive effect induced in users. In some embodiments, the ratio of Ag to AgCl particles in the consumptive layer may be between 40%:60% to 95%:5%, preferably 65%:35% to 85%:15%. Alternatively, the consumptive layer may include any suitable ratio of Ag:AgCl such that the chloride may be consumed but not depleted. The AgCl in the consumptive layer is consumed during alternating current or direct current stimulation (DC) because it acts as a sacrificial anode/cathode. If the consumptive layer does not fully cover the dermal side of the nonconsumptive layer, the current may travel directly to the hydrogel layer and cause a site of high current density, for example a current hotspot. A conductive hydrogel layer ensures that the current is transmitted substantially evenly to the skin of a user. Further, the hydrogel layer creates a uniform connection between the multi-electrode assembly and the skin of a user.

A flexible transdermal multi-electrode assembly may further include an adhesive component. The adhesive component is configured to couple the flexible transdermal multi-electrode assembly to a body portion of a user or any other device or system. The adhesive component may surround and/or be adjacent to the boundary of the consumptive layer. In some embodiments, the adhesive component and the three layers (consumptive, nonconsumptive, and hydrogel) of the electrode may be substantially the same thickness, such that substantially all areas of the flexible assembly may be flush with the skin of a user. In some embodiments, the hydrogel layer may extend slightly beyond the adhesive layer so that the hydrogel makes a more uniform contact through slight compression when the electrode is adhered to the skin.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected," "attached" or "coupled" to another feature or element, it can be directly connected, attached or coupled to the other feature or element or intervening features or elements may be present. In contrast, when a feature or element is referred to as being "directly connected," "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 370 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Alternatively or additional, also described herein are methods and apparatuses (including device and/or systems) for invoking a mental state (such as a calm, relaxed mental state or an energized mental state), or for modifying a user experience (such as enhancing a sensory experience, including audio, visual, or audiovisual experiences) by delivering transcranial/transdermal neurostimulation, e.g., transdermal electrical stimulation, hereinafter 'TES'. An enhanced sensory experience may generally be understood as sensory experiences (primary sensory effects, as well as secondary and higher order sensory-driven cognitive effects, including emotion, arousal, mood, etc.) that, when concurrently paired with an appropriate TES waveform and electrode montage (i.e. electrode size, shape, composition, and position) induce a change in cognitive state in the subject that is different than the sum of the parts (i.e. sensory experience and TES session) in quality and/or intensity. The systems (apparatuses, devices) and methods described herein may cause the cognitive effects of a subject's sensory experience to be enhanced, mitigated, or otherwise modulated.

TES may also induce sensory experiences in a subject that, though strictly speaking also cognitive effects, are generally considered to be distinct from the cognitive effects of TES such as an induction of calmness or enhanced energy. These include: skin sensations (slight pain, itchiness, prickliness, etc.), proprioception of muscles contracting, and artificial visual impulses (such as bursts of light and/or colors, e.g., phosphenes). In general, these sensory experiences of TES may also be timed with a temporally structured sensory experience, e.g. music, video, etc. to enhance the experience of the temporally structured sensory experience.

In general the apparatuses (devices, systems) and methods described herein may be used to deliver a TES waveform concurrently (and in some variations, choreographed) with music, including both recorded tracks and live performances (including in-person and streaming, e.g. Coachella via YouTube™). TES electrodes for TES sessions delivered concurrently with music are placed on the head and/or neck to elicit a cognitive effect and the neurostimulator for delivering TES may further comprise speakers (e.g. headphones or earbuds) so that a musical track may be delivered directly from the neurostimulator. In other variations, an image of a video may be delivered by a component of the neurostimulator. Alternatively, a user computing device (e.g. smartphone) may trigger or control (e.g. by Bluetooth or via a wired connection) the neurostimulator and also deliver a temporally aligned audio signal via a plug of the user computing device (e.g. headphone jack) and, optionally, video via a smartphone. In variations, the neurostimulator may fit on or in one or both ears and apply transdermal electrical stimulation targeting the cranial and/or cervical spinal nerves present in the pinna(e). Any of the neurostimulator devices described herein, including pinna neurostimulators, may include a speaker for easily delivering auditory stimuli concurrently with TES. For example, an earbud style form factor may fit in the auditory canal for delivering sound and have an assembly that press fits into the concha with stimulation electrode(s), or any other wearable neurostimulator as described herein.

Temporally structured sensory experiences are defined as generally predictable and repeatable in their timing, making them amenable to pairing with an ensemble TES waveform that itself has an ordered temporal structure of waveform components. Temporally structured sensory experiences are beneficial for coordination with a TES session. The time course of such sensory experiences may be more easily and more reliably associated with the cognitive effects of a TES session and thus more strongly and reliably enhance the combined effect of TES and the sensory experience or create a novel cognitive effect through their combination. As described in greater detail below and in specific examples herein, examples of temporally structured and/or predictable sensory experiences include music (e.g. concerts, auditory tracks on a portable music player, a DJ at a club), naturalistic sounds (e.g. waves on the beach; birds chirping; a car accelerating and shifting gears), performances involving spoken word (e.g. a play, public reading of a poem or other text, political stump speech), an event (e.g. fireworks show, light show), a video (e.g. film, TV show, movie, YouTube™ clip), a primarily visual art presentation (e.g. dance performance, visual art display, fashion show), a predictable vestibular experience (e.g. a somersault or other acrobatics by the subject, a rollercoaster, a train or subway taking a regular path), or a pattern of somatosensory activation (e.g. from a massage chair, haptic transducer array, or refreshable braille display).

According to an embodiment of the invention, a 'track' of neuromodulation is aligned (or choreographed) temporally with a sensory (or multisensory) experience experienced subjectively by a user via one or more sensory transduction pathways. As mentioned above, transdermal electrical stimulation targeting the nervous system and transcranial ultrasound neuromodulation are two forms of neuromodulation effective for a neuromodulation track, but other forms of neuromodulation can also be used, including but not limited to: transcranial magnetic stimulation (TMS), transcranial direct current stimulation (tDCS), transcranial alternating current stimulation (tACS), targeted electrical stimulation (TES), deep brain stimulation (DBS), stimulation through one electrode or an array of electrodes implanted on the surface of the brain or dura, and light activation of specially engineered proteins for neuromodulation known as optogenetics. In an exemplar embodiment, a temporal pattern of neuromodulation is combined with a musical performance or presentation. In variations, visual, tactile, olfactory, vestibular and/or gustatory stimuli are aligned temporally with neuromodulation to induce changes in cognitive function or cognitive state not possible with neuromodulation or sensory input alone.

A skilled technician can create a neuromodulation track aligned to other sensory stimuli, much as a sound engineer in a studio or lighting control person at performance do for auditory and visual stimuli. At its core, this embodiment combines raw sensory stimuli (sound, light, etc.) with neuromodulation to create contextually relevant subjective experiences that represent nonlinear responses to sound, music, film, video, performance, dance, other produced/organized sensory experiences. Artists, producers, and audience members seek further ways to control the subjective experiences associated with artistic performance in the fields of music, film, and other forms of performance art. The systems and methods described herein are designed to create new and subjectively enjoyable experiences by concurrently stimulating the brain via direct neuromodulation as well as one or more sensory transduction pathway.

One embodiment of a 'neuromodulation track' combines time varying neuromodulation with time varying sensory input in order to create enhanced experience of music for instance by making the emotional connection of music more intense or making the experience of a musical event more memorable. A musical, light show, or other sensory experience is intended to induce a particular change in cognitive state (e.g. emotional response; mood, relaxed/euphoric state; energized state).

The timescale of changes in cognitive state by a particular form of neuromodulation is an important parameter because it determines how quickly neuromodulation parameters can change relative to changing elements of other sensory inputs (e.g. musical features; lighting show effects). In some embodiments, neuromodulation occurs over a slower timescale and changing sensory inputs via traditional sensory transduction pathways occurs over a faster timescale in parallel.

In some embodiments, a particular neuromodulation protocol (and resulting change in cognitive state) is the starting point, and musical, lighting, or other sensory inputs are designed to complement the experience of (and time course of) the induced neuromodulation. Alternatively, a particular sensory experience (e.g. album, song, or symphony) may be a starting point for an artist and a neuromodulation track is designed to fit the flow of the (for instance) music.

In some embodiments, musical elements are algorithmically assessed for likely emotional states induced and neuromodulation protocols (and thus effects) are selected to be matched to a musical element or song. For instance, a transdermal electrical stimulation waveform can be offered as a complement to a song downloaded electronically, much as a music video for that song is complementary to the auditory experience and offers a different type of experience for a user or customer.

In another variation of the invention, kits are provided to designers of neuromodulation tracks so that they can experience subjectively the core neuromodulatory elements (with regards to subjective or other cognitive effects induced) and thus estimate the form of neuromodulation expected for a given temporal sequence of neuromodulation track elements.

A software or other system can complement the kit by indicating when a particular sequence of effects is impossible, unsafe, or likely to be uncomfortable.

The systems and methods described herein include systems for associating music, video, and other sensory experiences with neuromodulation. By appropriately pairing a neuromodulation stimulation regime with appropriate music, video, and other sensory experiences, a more significant cognitive effect can be induced in a subject than by either neuromodulation or sensory experience (i.e. music) alone.

In general, a system for concurrently inducing cognitive effects from a temporally structured sensory experience and a TES session may trigger a TES waveform and the temporally structured sensory experience concurrently or about at the same time. In variations, a single controller controls the TES waveform delivered via dermal electrodes and generates the sensory experience (e.g. a video on a screen of the controller or an audio signal provided via a speaker (e.g. headphones)). A portable or wearable user computing device (e.g. smartphone, smartwatch, tablet, virtual reality headset) may control a neurostimulator device for delivering TES and also generate, control, or cause to be generated (i.e. by triggering a third device) the temporally structured sensory experience (e.g. sound from the audio jack; video on the screen of the smartphone; tactile sensations from a haptic array). See, e.g., U.S. Provisional Patent Application No. 62/168,615, filed May 29, 2015 titled "METHODS AND APPARATUSES FOR TRANSDERMAL ELECTRICAL STIMULATION".

Alternatively, alignment of music or another temporally structured form of sensory experience may enforce a delay in either a neuromodulation protocol or the music experienced by a subject. Systems and methods for enforcing a delay in neuromodulation can also apply to other forms of sensory experience such as a movie or video. Enforcing a delay on the temporally structured sensory experience (e.g. music or movie) may permit a user to start a combined TES-sensory experience (e.g. song) session with a single user input (e.g. on a user computing device controlling a neurostimulator and playing a song) and automatically delaying the onset of the temporally structured sensory experience (e.g. song) so that the cognitive effects of TES (which may have slower onset on the tens of seconds to minutes to timescale) have an onset closer in time to the onset of the song, video, etc.

Transdermal electrical stimulation, including transcranial electrical stimulation, is one form of neuromodulation for which combination with music or another form of sensory stimulation is beneficial, though other forms of neuromodulation are also beneficial including, but not limited to: transcranial pulsed low frequency ultrasound neuromodulation, transcranial magnetic stimulation, and other forms of (generally noninvasive) neuromodulation.

Improved cognitive effects can be achieved in a subject when there is a correspondence between a particular musical element and a particular neuromodulation element or event. For instance, music generally associated with a state of high energy (i.e. high tempo music or electronic dance music (EDM)) would complement and improve effects of a form of neuromodulation that causes an increase in a user's subjective feeling of energy. Associations may be personalized for a particular user to associate songs, musical elements, or genres that most effectively complement the subjective effect of a neuromodulation event or experience. Alternatively, associations between music and a form of neuromodulation may be selected according to a user's demographic profile, psychographic profile, age, gender, physiological recording, brain recording, etc.

To achieve effective match of a form of neuromodulation (e.g. one or more targets, modalities, stimulation protocols, and induced cognitive effect(s)), systems and methods for tagging, marking, or otherwise curating matched sets (e.g. pairs) of music with a form of neuromodulation and a cognitive effect induced. Elements of this system include systems and methods for building databases and distributing these matched sets (i.e. via an API).

Statistical analysis of music or other forms of sensory experience can automatically derive moods, cognitive effects, or states of mind associated with features of a piece or element of music and automatically select or suggest a matched neuromodulation protocol (one or more of target, modality, protocol, etc.). For example, as described at https://github.com/gracenote/timeline-metadata-api/blob/master/README.md (accessed on 11/5/14) "Gracenote's Timeline Metadata API gives developers access to detailed information about a track. The API currently returns four types of features for an uploaded track: beats, BPM, segments and moods." These data can be used to select an appropriate neuromodulation protocol from a database that includes metadata for induced cognitive effects and/or musical elements that have been positively associated with the neuromodulation protocol or element by a user.

A structured database containing elements of neuromodulation (including but not limited to: modality, target, intensity, and protocol) with associated performance elements, including musical elements (e.g., tempo, genre, musical key, etc.) that has been built manually, by user input (i.e. by users of a neuromodulation system) is beneficial for selecting an appropriate neuromodulation protocol, target, and/or modality based on a user's current and desired state of mind, as well as the context (i.e. music being played) for that user. A change in one or more waveform parameter that defines a shift from one block of a TES ensemble waveform to a subsequent block of a TES ensemble may be timed to occur synchronously or at a defined latency relative to a change in an auditory sensory experience (e.g. musical track), including but not limited to: a change in the frequency distribution, musical phrasing, timing of instruments and vocals, instrumentation, tempo, tonality, musical key, loudness, or directionality (i.e. from stereo or 3D speakers). In some embodiments, a band, musician, DJ, or other artist defines an element of neuromodulation (i.e. target, protocol, modality, intended cognitive effect) to associate with a musical track or other generated sensory experience.

Also described herein are methods of generating TES waveforms for concurrent delivery with a temporally structured sensory experience. For example, methods for generating TES waveforms designed to align with temporally structured experienced (i.e. a song, video, rollercoaster ride, etc.) include manual and/or computer-aided methods. For example, a practitioner of TES waveform design may use an interface on a computing device similar to common video or music editing software, wherein the waveform parameters are aligned in time with the music or video as one or more 'tracks'. The TES waveform parameters may be displayed visually for the waveform designer, as rows in the editing software, similar to how a different musical instrument is represented as a distinct class, separated visually (i.e. in its own row) in common music editing software. For example, one 'track' (or row in a TES waveform editing user interface) may represent a specific waveform parameter (i.e. a frequency, a duty cycle, a charge imbalance, the presence or absence of a capacitive discharge pulse, a bursting frequency, a bursting duty cycle, etc.). Alternatively, a TES waveform row may indicate with blocks (i.e. rectangles distinguished by color, shading, etc.) epochs of an ensemble waveform comprising different sets of waveform parameters, while another track (i.e. row) shows the ramping between (and/or within) blocks, and a third track (i.e. row) shows add-in effects such as eliciting visually perceived bursts of light and/or color (e.g., phosphenes).

Methods for generating TES waveforms designed to align with temporally structured experiences (i.e. a song, video, rollercoaster ride, etc.) include computerized, automated methods. In a first step, one or more rules is defined to associate a feature of a TES waveform with a feature of the temporally structured experience (e.g. song, video, rollercoaster ride, etc.). Examples of TES waveform features that may be used for this type of automated alignment and coordination of a TES waveform with a temporally structured experience include a TES waveform parameter including one selected from the list of: intensity, frequency, duty cycle, percent charge imbalance, bursting frequency, bursting duty cycle, etc.; a ramping or other shift between one TES waveform value and another (i.e. time period over which the ramping occurs, start and stop values for the ramping, and shape (e.g. linear vs. exponential) of the ramp); or a brief 'add-in' TES waveform component intended, for example, to elicit a visual or particular skin sensation. For a video (film, TV show, and the like), the associated feature from the video may be a scene change (detectable through machine vision algorithm or manual entry of times of scene changes), the presence of a particular character (detectable e.g. through facial recognition), a change in a musical or psychoacoustic property of the video's score (detectable through musical analysis), or spoken language (detectable through semantic or lexical analysis for mood, valence, meaning, etc.).

Coutinho et al. (Musical emotions: Predicting second-by-second subjective feelings of emotion from low-level psychoacoustic features and physiological measurements. Coutinho; Cangelosi, Angelo Emotion, Vol 11(4), August 2011, 921-937.) defined psychoacoustic categories including loudness, pitch level, pitch contour, timbre, tempo, and texture and assessed the second-by-second levels of emotional arousal and valence by measuring physiology (i.e. heart rate and skin conductance) and collecting subjective reports from subjects. The authors observed statistically significant correlations between a subset of psychoacoustic categorical variables and subject's emotional arousal and valence:

TABLE 1

Correlated musical psychoacoustic variable and subject emotional arousal or valence (Coutinho et al. 2011)

| Type of emotional effect | Psychoacoustic property of music |
| --- | --- |
| arousal | loudness |
| arousal | tempo |
| arousal | pitch level |
| arousal | sharpness |
| valence | tempo |
| valence | pitch level |

The Coutinho et al. findings show example correlations between music and emotional responses that can be used to define an algorithm for to match, complement, or otherwise modulate the musically-induced changes in cognitive state (i.e. emotion) by TES delivered concurrently to the subject. Though it should be recognized that the relationships observed are exemplary only and should not be considered as the only potential relationships between features of music and emotional, physiological, or cognitive states.

The aforementioned examples are not meant to be limiting and one skilled in the art will recognize that other aspects of a temporally structured sensory experience (i.e. music, video, rollercoaster ride, etc.) and other algorithmic rules may be used for defining TES waveform parameters to associate with features of the sensory experience.

In other embodiments, a hybrid semi-automated method (i.e. manual with automated suggestions for timing and parameters of TES waveform elements of an ensemble TES waveform) is a third method for designing TES waveforms for alignment of TES sessions with a temporally structured sensory experience. For example, a TES waveform designer (of an ensemble TES waveform) may select from a list of suggested waveform parameter sets. Further, suggestions for the timing of when and over what period of time (i.e. by ramping) to select a new set of waveform parameters may be generated automatically. For example, sharp transitions in musical tempo or timbre may be identified automatically and suggested as time periods for integrating a phosphene to be delivered to a TES recipient. As mentioned above, the timing (and/or parameters) of the TES delivery may be choreographed with the concurrent audiovisual performance, and may include a delay in the delivery of the audio and/or visual experience so as to synchronize with the evoked cognitive effect (which will typically occur with a slower onset than the audiovisual impact being choreographed with). Thus, any of the apparatuses described herein may communicate with and/or control the application of the audiovisual input(s) including coordinating a delay between the applied TES and the audiovisual performance.

For example, a first method for generating TES waveforms to align to a temporally structured sensory experience is to adjust the length of TES session to match a song or album (e.g. from a user's music library on the smartphone). To expand or contract a TES waveform to match the length of a song, album, video, podcast, or playlist certain blocks (of an ensemble waveform) may be designated as appropriate to be shortened, lengthened, or repeated. In at least some instances, the start and end of a TES waveform, which generally ramp in a particular way for comfort, are fixed, while intermediate periods of the TES waveforms may be appropriate for changing in length and/or repeating an appropriate number of times.

TES waveforms may be configured to match songs in a streaming music service and to auto-select matched TES waveforms by using an API for the streaming service (e.g. Spotify, Radio, etc.) and/or for the TES waveform service in order to download, select, or stream a TES waveform appropriate for delivery concurrently with the song.

In variations, TES waveforms may be integrated with virtual reality environments. For example, TES waveforms in a virtual reality environment may be dynamically adjusted based on a user's interaction with and experience in the environment in order to maintain a well-matched experience despite the absence of a fully predictable temporal structure to the virtual reality experience (due to the user's agency).

In variations, TES systems may be integrated with an augmented reality environment (e.g. via a smartphone, smartwatch, or tablet screen, wearable glasses-style display which may, in some variations, serve as a controller for both the augmented reality experience and a neurostimulator). The reality viewed and parsed via an augmented reality system may be used to start, stop, select, adjust, amend, or otherwise modulate a TES session. For example, in a stressful situation (e.g. traffic, facial recognition of an angry client entering your office), the controller may automatically trigger the neurostimulator to deliver a TES session for enhancing calmness.

In general, a TES controller may be configured to start, stop, select, adjust, amend, or otherwise modulate a TES session based on a reading of a physiological sensor. For example, the controller may cause the neurostimulator to start a TES session to enhance a state of calmness when sympathetic activity is too high (e.g. as assessed by: EEG, infrared facial thermography (e.g. with a forward looking infrared (FLIR) camera), heart rate, heart rate variability, breathing rate, etc.). In another example, the controller may cause the neurostimulator to start a TES session to increase alertness and energy when sympathetic activity is too low (as assessed by a physiological recording or measurement, as in the list above).

In variations, the neurostimulator or controller of the neurostimulator comprises a microphone to record sound in a user's environment (e.g. music as at a concert, a nature sound, or spoken word (to which linguistic analysis may be applied to determine valence, etc.)), then applies signal processing and control logic algorithms to start, stop, select, adjust, amend, or otherwise modulate a TES session (i.e. change one or more parameter of the waveform such as intensity, frequency, duty cycle, charge imbalance, bursting frequency, and bursting duty cycle, etc.). In a social variation, the recording of sound may be in one environment (i.e. location) via either a fixed microphone or microphone array (e.g. at a concert venue, at the beach, on a whale, in a lecture hall or courtroom, etc.) or recorded by another individual. In a next step, the audio recording may be processed locally (e.g. with a user computing device or a processor on the neurostimulator) to parse triggers for selecting, starting, stopping, or modulating a TES waveform. Alternatively, the audio may be transmitted via the Internet (or other communications protocol) to a remote server or other computing device to parse triggers for selecting, starting, stopping, or modulating a TES waveform. Then in a third step instructions are transmitted to the neurostimulator to start, stop, select, adjust, amend, or otherwise modulate a TES session (i.e. change one or more parameter of the waveform such as intensity, frequency, duty cycle, charge imbalance, bursting frequency, and bursting duty cycle, etc.) to complement the user's experience in a unique and interesting way. A similar approach may be used with a camera and machine vision algorithms. Similar to the application of TES sessions during virtual reality, the TES waveforms in this case are not pre-defined.

Delivering TES Waveforms at a Group Event

As described in pending PCT/US2014/018061 (filed Feb. 24, 2014), published as WO 2014/130960, more than one TES apparatuses may be coordinated to modulate the experience of a group of individuals to an audiovisual experience, including a performance. This application is herein incorporated by reference in its entirety.

In variations, the experience of film, musical, political, sporting, and other events experienced in groups are enhanced or modulated by concurrently delivering TES to modify the cognitive state of two or more individuals. For example, members of an audience at a concert, club with a DJ, other musical experience, sporting event, political rally, religious service, or other group experience use a TES system during the event that induces neuromodulation and enhances the audience members' experience of the event. The venue may be an intimate and small with a small audience (e.g. less than 50 people) or large at an outdoor music festival or stadium (e.g. with an audience exceeding 10,000 people). In at least some instances wherein multiple members of an audience all receive TES, their shared experience of the event is enhanced.

In embodiments, TES users may bring a TES system to the venue and stimulation is triggered to audience members based on proximity, geographic location, or request by the user (e.g. by entering a code into a TES app or scanning a QR code specific to the event on their smartphone, so that an app can trigger an appropriate waveforms at times selected by one or more of the performers or staff of the performance). Wireless communication directly to a TES system is one way to communicate with a TES system so that stimulation can be triggered with timing and waveform selected by one or more of the performers or staff of the performance. In some embodiments, the system is configured so that a performer (e.g. musician, DJ, dancer, etc.) triggers TES stimulation directly (e.g. with a foot pedal; a button on an electronic instrument such as a synthesizer; or a remote control). In other embodiments, the system is configured so that a supporting staff member controls TES stimulation of members of the audience, similar to the way that a mixer at a sound board or a person controlling a light show can control delivery of sensory stimuli to the audience.

In some systems and methods for TES integration with a musical performance, a performer also wears a TES system and receives neuromodulation during a performance. The performer's neuromodulation may be concurrent with the audience's neuromodulation or may alternatively occur at a different time. The performer may have their TES system configured so that the form of neuromodulation they receive is the same as the audience or, alternatively, the form of neuromodulation received by the audience is different than that received by the performer.

TES can be similarly configured so that leaders of other forms of group experiences such as sporting events, political rallies, motivational speeches, or religious events control TES stimulation received by members of the audience.

In an alternative embodiment, an individual who wishes to share in the experience of a musical performance or other group experience listens to a recording in their home by themselves or in a small group while wearing a TES system that is activated at appropriate times relative to the audio so that the user can experience a version of the event without being there, much as listening to a recording of a live concert permits an enjoyable proxy to being at the event.

In an exemplar embodiment, attendees at a club with a DJ performing a set of electronic dance music or other music receive a wearable TES system upon entry to the club, adhere TES electrodes at appropriate locations based on instructions provided by the performer and/or kit, and receive electrical stimulation triggered remotely.

An advantageous feature of this system is the capacity to integrate TES with the musical performance and light show in order to enhance the concert experience.

In embodiments, the performer or other member of the performance staff defines the timing of TES and each user controls one or more aspects of the TES protocol selected from the list including but not limited to: waveform, intensity, cognitive state induced, and length. In an alternative embodiment, the performer or other member of the performance staff defines the timing of TES as well as an aspect of the waveform (e.g. ramping of the waveform to control the relative intensity of an induced cognitive effect in a member of the audience.

In variations, the timing and other features of TES controlled by a performer or other member of the performance staff are: (1) controlled in real-time to respond to the energy of the audience; (2) prerecorded or otherwise pre-determined; or (3) triggered based on a pattern of sound, light, or other stimulus.

In variations, all participants or attendees experience the same form, duration, and timing of TES. In other embodiments one or more of TES form (e.g. change in cognitive state induced), TES duration, and TES timing differs among members of the audience, for instance in groups, sections, sets, or by demographics of audience members (e.g. males experience one form of TES and females receive a different timing or form of TES).

Systems

Figure 43A:
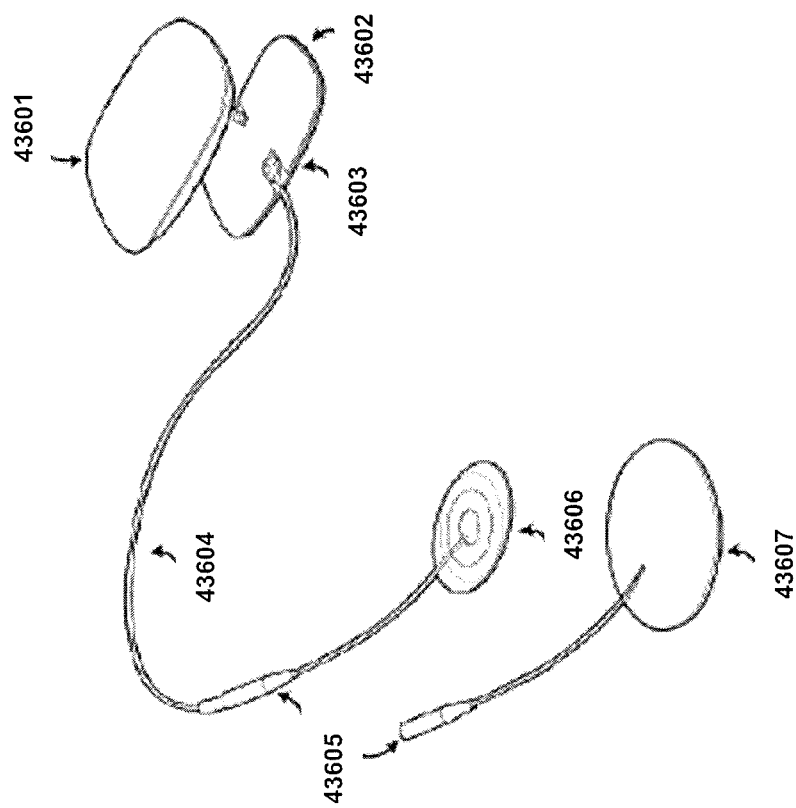
FIG. 43A illustrates one example of a neurostimulator that may be configured for use with (and may deliver) the ensemble waveforms described herein.
Figure 43Q:
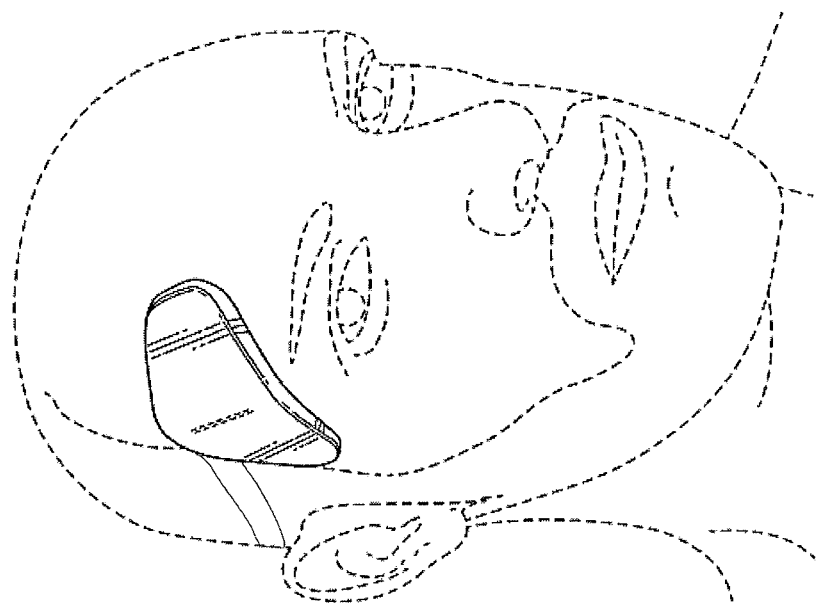
FIG. 43Q illustrates the neurostimulator device worn on the subject's head.

In general, any appropriate neurostimulation system may be used for delivering TES to a subject concurrently with a temporally structured sensory experience as described herein. FIGS. 43A-43Q describe and illustrate an example of a neurostimulation system (neurostimulator, electrodes, controller, etc.) that may be used. For example, a neurostimulation system may include a lightweight, wearable, neurostimulator device (neurostimulator) that is configured to be worn on the head and a consumable/disposable electrode assembly; in addition a device that may be worn and/or held by the user ("user device") which includes a processor and wireless communication module may be used to control the application of neurostimulation by the wearable neurostimulator. The neurostimulator and/or user device may be particularly adapted to deliver TES waveforms during a temporally structured sensory experience (e.g. music, video) as described herein. For example, the neurostimulator device may comprise a memory, a music player, and a speaker for playing songs matched to the TES waveform. In another example, the neurostimulator control may also contain a screen, a memory, and a video player (and, optionally, speaker) for displaying a video concurrently with an ensemble TES waveform. For example, the user device may present a list of ensemble waveforms and allow the user to select among them in order to select a desired cognitive effect. The ensemble waveforms may be ordered by the desired effect (e.g., calm, energy, etc.) and/or by time and/or by ranking, and the associated music or video or other temporally structured sensory experience may be indicated, etc. Further, the user device may be adapted to communicate with the wearable neurostimulator and may transmit an identifier of the selected ensemble waveform, and/or waveform parameters that define all or a portion (e.g., component waveforms or portions of component waveforms) of the ensemble waveform, as well as any user adjustments such as user modification to the perceived intensity to be used to modify the actual waveforms delivered by, for example, attenuating the ensemble waveform parameters. Thus, for example, the user device maybe configured to send, and the neurostimulator to receive, the ensemble waveform parameters (duration, ramping parameter/ramping time, capacitive discharge parameters, current amplitude, frequency, percent duty cycle, percent charge imbalance, bursting frequency, bursting duty cycle, etc.).

The user device may also be referred to herein as a controller, and the controller (user device or user computing device) may typically be separate from but communicates with the neurostimulator. For example, in some variations the controller may be a user device that wirelessly communicates with the neurostimulator. In some variations the controller is a mobile telecommunications device (e.g., smartphone or tablet) or wearable electronics (e.g., Google glass, smartwatch, virtual reality headset, etc.), being controlled by an application that sends instructions and exchanges 2-way communication signals with the neurostimulator. Any of these embodiments may be referred to as handheld devices, as they may be held in a user's hand or worn on the user's person. However, non-handheld control user devices (e.g., desktop computers, etc.) may be used as well. The user device may be a general purpose device (e.g., smartphone) running application software that specifically configures it for use as a controller, or it may be a custom device that is configured specifically (and potentially exclusively) for use with the neurostimulators described herein. For example, the controller may be software, hardware, or firmware, and may include an application that can be downloaded by the user to run on a wireless-connectable (i.e., by Bluetooth) device (e.g., handheld device such as a smartphone or tablet) to allow the user to select the waveforms delivered by the neurostimulator, including allowing real-time modulation of the delivered neurostimulation to modify the user's cognitive state as described herein. The controller may be a component of the neurostimulator apparatus itself. In some variations, the controller, including general purpose devices, may play music or display video configured to be associated with the TES waveform.

For example the system can be operated to induce either "calm" states of mind or "energetic" states of mind. Operating the system to induce a state of increased energy can be alternatively described as one or more of: enhancing focus and attention; enhancing alertness; increasing focus and/or attention; enhancing wakefulness; an increase psychophysiological arousal associated with changes in the activity of the hypothalamic-pituitary-adrenal axis and/or the reticular activating system; increasing subjective feeling of energy; increasing objective physiological energy levels; increasing motivation; increasing physiological arousal; and evoking a physical sensation of warmth in the subject's chest. Operating the system to induce a state of enhancing a calm or relaxed mental state can be alternatively described as one or more of: a state of calm within about 5 minutes of starting a TES session; a care-free state of mind; a mental state free of worry; induction of sleep; facilitating falling asleep; maintaining a state of sleep; a perception of slowing of a passage of time; muscular relaxation; enhanced concentration; inhibition of distractions; increased cognitive clarity; increased sensory clarity; a dissociated state; a mild intoxication; a euphoric state; a relaxed state; enhanced enjoyment of auditory and visual experiences; reduced physiological arousal; increased capacity to handle emotional or other stressors; a reduction in psychophysiological arousal associated with changes in the activity of the hypothalamic-pituitary-adrenal axis and/or the reticular activating system; a reduction in biomarkers of stress, anxiety, and mental dysfunction; anxiolysis; a state of mental clarity; enhanced physical performance; resilience to stress; a physical sensation of relaxation in the periphery; and a perception of feeling the heartbeat.

Figure 45A:
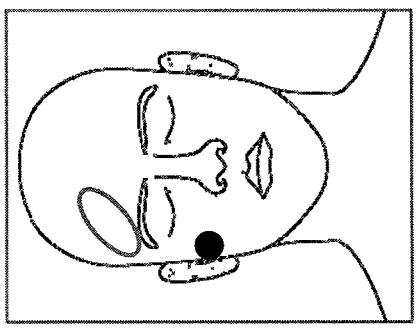
FIGS. 45A-45F illustrate locations for electrodes on the forehead/temple and upper cheek of a TES neurostimulator system for inducing a state of enhanced energy.
Figure 45B:
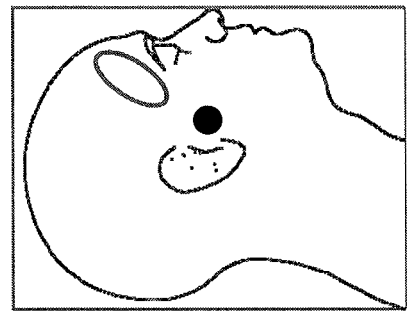
Figure 45C:
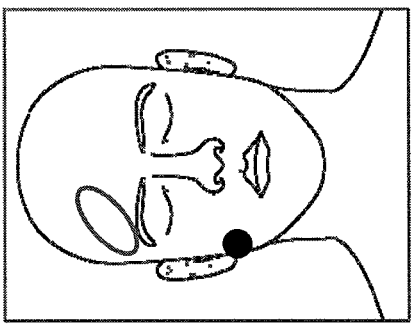
Figure 45D:
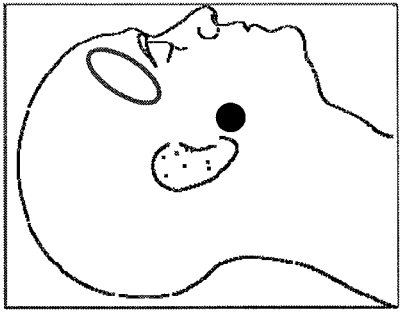
Figure 45E:
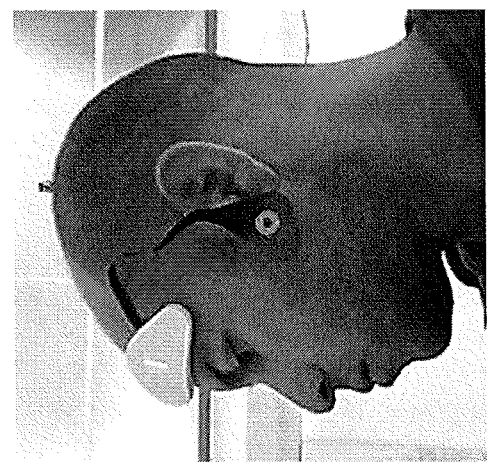
Figure 45F:

For example, to induce energy, the electrode apparatus may be attached to the user's temple (and/or forehead) and behind the user's ear (e.g., mastoid region) and/or behind the user's cheek in front of the user's ear and/or in front and slightly below the user's ear (e.g., FIGS. 45E and 45F). To induce calm, the electrodes may be attached to the user's temple (and/or forehead) and the back of the user's neck. In general, the neurostimulator may apply an ensemble waveform for about 3-30 min (or longer) that is made up of different "blocks" having repeated waveform characteristics; the waveform ensemble may include transition regions between the different blocks. In general, at least some of the waveform blocks (and in some variations most or all of them) generally have a current amplitude of >3 mA (e.g., between 5 mA and 40 mA, between 5 mA and 30 mA, between 3 mA and 22 mA, etc.), and a frequency of >700 Hz (e.g., between 700 Hz and 25 kHz, between 700 Hz and 20 kHz, between 700 Hz and 15 kHz, etc.), the current is typically biphasic and is charge imbalanced, and has a duty cycle of between 10-99% (e.g., between 20-95%, between 30-80%, between 30-60%, etc.). The waveform blocks may include bursting, defined by a bursting frequency and a bursting duty cycle. One or more of these characteristics may be changed during stimulation over timescales of every few seconds to minutes as the ensemble waveform shifts between subsequent component waveforms.

When worn, the system may resemble the system shown in FIG. 43Q, having an electrode assembly attached at two locations (points or regions) on the subject's head and/or neck) and a neurostimulator attached to the electrode assembly, as shown; in some variations a separate controller may be attached to coordinate the application of stimulation.

As will be described in greater detail herein, the neurostimulator may be lightweight (e.g., less than 30 g, less than 25 g, less than 20 g, less than 18 g, less than 15 g, etc.), and self-contained, e.g., enclosing the circuitry, power supply, and wireless communication components such as a rechargeable battery and charging circuit, Bluetooth chip and antenna, microcontroller, and current source configured to deliver waveforms with a duration of between 10 seconds and tens of minutes. A neurostimulator may also include safety circuitry. The neurostimulator may also include circuits to determine that the electrode is attached and what "kind" of electrode it is (i.e., for the calm or the energy mode; or indicating the batch and/or source of manufacture, etc.). FIGS. 43A and 43B-43G illustrate two variations of a neurostimulator.

For example, FIG. 43A illustrates a first example of a neurostimulator as described herein. In FIG. 43A, the neurostimulator is shown with a pair of electrodes attached (though the particular electrodes shown may not be configured to target the locations for electrodes according to the variations of the invention as described herein, they serve as a helpful example of an electrode assembly for use with the system). A first electrode 43601 is coupled directly to the body 43603 of the TES applicator 43602, and a second electrode 43606 is connected by a cable or wire 43604 to the body 43603 of the applicator 43602. These electrodes are separate from each other, and may be replaceable/disposable. Different shaped electrodes 43607 may be used with the same re-usable neurostimulator. The neurostimulator in this example includes a rigid outer body, to which the pair of electrodes is attachable, making electrical contact via one or more plug-type connectors.

FIGS. 43B-43G illustrate another, preferred embodiment of a neurostimulator as described herein. In this variation the neurostimulator is also a lightweight, wearable neurostimulator that attaches to an electrode, and includes contacts for making an electrical connection with two (or potentially more) electrically active regions (e.g., anodic and cathodic regions) on the electrode(s). However, in this example, the neurostimulator is configured to operate with a cantilevered electrode apparatus, and to attach both mechanically and electrically to the electrode apparatus at a region that is off-center on the bottom (underside or skin-facing side) of the neurostimulator, allowing one end region to be held securely to the skin while the other edge region is not pinned in this way. The "floating" end may therefore adjust slightly to different curvatures of the head, even while the electrode assembly (which may be flexible) is securely held to the skin. Thus, this cantilevered attachment mechanism may enhance comfort and adjustability of the device. In addition, the neurostimulator device may be configured specifically so that it can be comfortably worn at the user's temple, even in users wearing glasses. For example, the apparatus may be configured so that the skin-facing side (which connects to the electrode assembly via one or more connectors) is curved with a slightly concave surface having a slight twist angle. This curve shape may help the apparatus fit more snugly (more uniformly) to the surface of the temple. In addition, one end of the device (the end to be positioned in-line with the edge of the user's eye and the user's ear) may be thinner (e.g., less than 2 cm, less than 1.5 cm, less than 1 cm, less than 0.8 cm, etc.) than the opposite end, which may be worn higher up on the temple.

For example, FIGS. 43B-43G illustrate front, back, left side, right side, top and bottom perspective views, respectively of a variation of a neurostimulation device (neurostimulator or electrical stimulator) that may be used with cantilever electrode apparatuses. The overall shape of the neurostimulator may be triangular, and particularly the surface of the neurostimulator (though curved/concave and twisted) adapted to connect to the electrode apparatus and face the patient may be three-sided (e.g., roughly triangular). This roughly triangular shape may include rounded edges, and the thickness of the stimulator (in the direction perpendicular to the surface contacting the cantilever electrode apparatus) may vary, e.g., be thinner along one side, and particularly the side (the portion between the orbital edge and the auricular edge) that will extend laterally from the edge of the eye in the direction of the ear. This shape may also be beneficial when helping to fit/be worn on most people in a region of the face/head that tends to not have hair. Both adhesive and conductive hydrogel that may cover an active electrode region function more effectively on skin with little or no hair. This thin lower corner (the orbital/auricular corner) may fit between the eyebrow and hairline, while the wider portion is positioned up in the forehead area where there is less likely to be hair.

In FIGS. 43B-43G the various edges of the neurostimulator are labeled, based on where the apparatus will be worn by the subject, as is illustrated in FIG. 43Q. In general, the side of the unit worn toward the ear is the auricular edge, the side worn highest on the forehead is the superior edge, and the side worn nearest the eye/eyebrow is the orbital edge. The overall shape of the neurostimulator is triangular (including rounded edges; i.e. trianguloid). As used herein triangular includes shapes having rounded/smooth transitions between the three sides, as illustrated. The subject-facing surface is specifically contoured to fit in the predefined orientation, making it difficult or impossible for a subject to misapply, and risk placing the active region of the attached cantilever electrode apparatus in the wrong place. When attaching the cantilever electrode apparatus to the neurostimulator, the cantilever electrode apparatus may flex or bend so that it is contoured to match the curved and twisted surface. This surface is a section of a saddle shape, in which there is an axis of curvature around which the surface is concavely curved, and an axis of twisting, which may distort the curved surface (the two axes may be different or the same).

Within the housing, any of the neurostimulators described herein may include a processor (e.g., microprocessor) or controller, a wireless communication module that is connected to the processor, and a power source (e.g., battery, etc.). The power source may be configured to provide power to the internal circuitry and/or the circuitry driving current between anodic and cathodic regions of the electrodes when worn by the user. The power supply may be a high-voltage power supply, e.g., able to provide up to 60 V across these electrode terminals. In general, the apparatus may also include circuitry that is configured to regulate the energy (e.g., current) delivered as required by the processor, which may in turn receive instructions via the wireless communications module from a controller. The controller may also communicate information, and in particular information about the electrodes, including confirming that the electrode assembly is connected and/or what type (e.g., calm, energy, make/model, batch, etc.) of electrode assembly is attached, and an indicator of the contact with the user's skin (e.g., conductance, a parameter proportional to conductance, or a value from which an estimate of the conductance of the electrode(s) may be derived).

The electrode assembly may mechanically and/or electrically connect to the neurostimulator, e.g., by snapping to the underside of the neurostimulator at one or more (e.g., two) connectors such as snap receivers. Thus in some variations the neurostimulator may be held onto the subject's (user's) head by the electrode assembly; the electrode assembly may be adhesively connected to the user's head and/or neck to form an electrical contact with the desired regions on the user, and the neurostimulator may be connected e.g., adhesively and/or electrically, to the electrode assembly. As described below, the connectors between the neurostimulator and the electrode assembly may be positioned in a particular and predetermined location that allows the neurostimulator to be robustly connected to the electrode assembly and therefore the user's head/neck without disrupting the connection, and while permitting the system to be worn on a variety of different body shapes.

Electrode assemblies are generally described in detail below, along with specific examples and variations. In particular, described herein are electrode assemblies that are thin (e.g., generally less than 4 mm, less than 3 mm, less than 2 mm, less than 1 mm, etc. thick, which may not include the thickness of the connectors that may extend proud from the thin electrode assembly), and flexible, and may be flat (e.g., formed in a plane). For example, they may be printed on a flex material, such as the material used to print a flex circuit. In use, they can be wrapped around the head to contact it in at least two locations (e.g., at the temple and the back of the neck and/or behind the ear). The electrode assembly may include a connector (electrical and/or mechanical) that extends proud of the otherwise flat/planar surface to connect the active regions of the electrode assembly to the neurostimulator. For example, the neurostimulator may be mechanically and electrically connected by one or more snaps extending from the front of the electrode assembly. In some examples, one snap connects to a first active electrode region (anodic or cathodic region) that is surrounded by an adhesive to adhere the active region to the user's head (e.g. temple/forehead or mastoid region). A second electrode region (anodic or cathodic) on a separate part of the electrode assembly may be electrically connected to the other connector. For example, the second electrode region may be adapted to fit either on the region over the (other) mastoid bone, behind the subject's ear or a region on the user's neck (e.g., at the base of the hairline, e.g., near the midline of the neck.

The electrode apparatus may be printed (e.g., by flexographic printing, laser printing with conductive ink, silk-screening, etc.) on a flexible (e.g., plastic) substrate (flex substrate) and may also include a pair of connectors (snaps) on the side opposite the skin-facing electrodes. The electrode active regions on the back of the assembly may include a layer of conductor (e.g., silver), a layer of a higher resistance conductor than silver (e.g. a conductive carbon), over which a layer of Ag/AgCl is placed that is sacrificial and acts as a pH buffer. A next layer of hydrogel overlays the Ag/AgCl electrode so that it can uniformly transfer charge across the active region into the skin. A portion of the electrode assembly around the active electrode area may have an adhesive that permits good contact with a user's skin.

There may be multiple configurations (e.g., shapes) of the electrode assembly, and, as described in greater detail herein, the electrode assembly may generally be formed on a flexible material ('flex circuit' material) and mechanically and electrically connected to the neurostimulator.

FIGS. 43H-43K illustrate one variation of a cantilever electrode apparatus ("electrode apparatus") that may be used with a neurostimulator and may be worn on a subject's head. Again, this example may be instructive of electrode assembly design in general for a wearable TES neurostimulator it but may not be necessary to target the specific electrode locations as described herein. This variation may be referred to as a "calm" configuration, as it is adapted to connect to a user's temple or forehead and the back of a user's neck. In this example, the cantilever electrode apparatus 400 includes a plurality of electrode portions (two are shown) 43403, 43405. In FIG. 43H, a front perspective view is shown. The front side is the side that will face away from the subject when worn. The cantilever electrode apparatus is thin, so that the electrode portions include a front side (visible in FIGS. 43H and 43I) and a back side (visible in FIG. 43K).

As shown in the side view of FIG. 43J, the device has a thin body that includes the electrode portions 43403, 43405 as well as an elongate body region 43407 extending between the two electrode portions. The elongate body is also thin (having a much larger diameter and height than thickness). The thickness is shown in FIG. 43J.

In this example, two connectors 43415, 43417 (electrical and mechanical connectors, shown in this example as snaps) extend from the front of the cantilever electrode apparatus. The front of the first electrical portion 43403 may also include an optional foam and/or adhesive material 43421 through which the snaps extend proud of the first electrical portion. The first electrical portion is shaped and sized so that the snaps will connect to plugs (ports, holders, opening, female mating, etc.) on the electrical stimulator. As described above, the connectors may be separated by between about 0.6 and about 0.9 inches (e.g., between about 0.7 and about 0.8 inches, etc., shown in FIGS. 43H-43K as about 0.72 inches). The second electrode portion may also include a foam or backing portion 43423. This foam/backing region may be optional. In some variations the separation between the connectors is not limited to 0.7 to 0.8, but may be larger (e.g., between 0.7 and 1.2 inches, 0.7 and 1.1 inches, 0.7 and 1.0 inches, 0.7 and 0.9 inches, etc.) or smaller (e.g., between 0.2 and 0.7, 0.3 and 0.7, 0.4 and 0.7, 0.5 and 0.7, 0.6 and 0.7 inches, etc.).

FIG. 43K shows a back view of this first example of a cantilever electrode apparatus. In this example, the first 43403 and second 43405 electrode portions are also shown and include active regions 43433, 43435. The active regions are bordered by adhesive 43440. The first 43403 electrode portion includes, on the back (patient-contacting) side, a first active region 43433, which is bounded, e.g., around its entire circumference, or at least on, by an adhesive 43440. The active region may include a conductive material (e.g., electrically conductive gel). Similarly, the back of the second electrode portion 43405 includes the second active region 43435 surrounded on two sides by an adhesive material 43440 that extends to the edge of the electrode region. The adhesive may be any biocompatible adhesive that can releasably hold the material to the skin.

FIGS. 43L-43o illustrate another example of a cantilever electrode apparatus. This example is very similar to the variation shown in FIGS. 43H-43K, but may be referred to as an "energy" configuration as it is configured to contact both the user's temple or forehead and a region behind the user's ear, over the mastoid region. This example is just one example of an electrode assembly design for a wearable TES neurostimulator, and is not limited to the specific electrode locations as described herein.

The connectors (snaps 43417, 43415) are in the same position as shown in FIGS. 43H-43K, as are the shape of the first electrode portion 43403 and foam/backing material 43421 (which may also or alternatively be an adhesive material). An advantage of having multiple electrode apparatuses with the same shape is that they can be used interchangeably with a single neurostimulator device. However, the example shown in FIGS. 43L-43o includes a different overall shape, and may be used to connect, for example, to different regions of the patient's head. In particular, the portion of the substrate forming the elongate body region 43407 extending between the two electrode portions 43403, 43405 is shaped slightly differently. In this example, the cantilever electrode apparatus may be configured to connect, for example, to the subject's temple with the first electrode portion (to which the neurostimulator may be connected) and the elongate body region may be bent around the subject's head so that the second electrode portion may be in electrical contact with a region behind the subject's ear (e.g., at or near the mastoid). By placing the first active region 43433 of the first electrode portion 43405 in electrical contact with the skin at the temple or forehead and using the adhesive material 43440 surrounding the electrically active region 43433 to hold the electrically active region (and the attached neurostimulator) securely in position on the subject's skin, the second electrically active region may also be adhesively 43441 held to skin so that the second electrically active region 43435 is in contact with the mastoid region.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 43H-43K and 43L-43o. The bend or curve, in which the elongate body may even double back on itself, may allow the material to flex or bend to allow it to be adjustably positioned over and/or around the subject's head, as shown in FIGS. 43P and 43Q, for example.

Figure 43P:
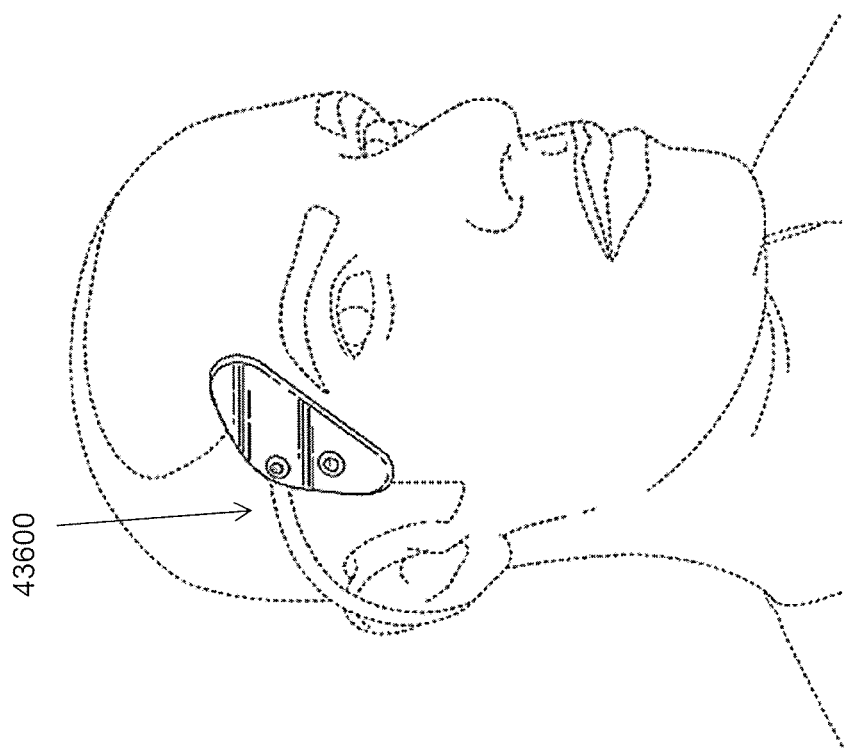
FIG. 43P illustrates the application of an electrode assembly that may be worn on the subject's head, and/or head and neck to induce a cognitive effect.

FIG. 43P illustrates a cantilever electrode apparatus (similar to those shown in FIGS. 41 and 44A) worn on a subject's head. As illustrated, the apparatus is positioned with the first electrode portion adhesively attached at the temple or forehead and a second electrode portion attached to a region behind the head (e.g., behind the ear or neck region, not shown). A neurostimulator (not shown in FIG. 43P) may be attached to the cantilever electrode apparatus either before or after it is applied to the subject. As shown in FIG. 43Q, the neurostimulator may be attached to the front side of the cantilever electrode apparatus by snapping onto the proud connectors, while the elongate body region 43407 is bent to extend behind the subject's head and down to a portion on the midline of the back of the patient's neck. Both the first electrode portion and the second electrode portion may be adhesively held with the electrically active regions against the skin, allowing the neurostimulator to apply energy, and in particular the waveforms as described in U.S. patent application Ser. No. 14/320,443, filed Jun. 30, 2014 titled "TRANSDERMAL ELECTRICAL STIMULATION METHODS FOR MODIFYING OR INDUCING COGNITIVE STATE," now U.S. Pat. No. 9,014,811 and U.S. patent application Ser. No. 14/715,476, filed May 18, 2015 titled "METHODS AND APPARATUSES FOR AMPLITUDE-MODULATED ENSEMBLE WAVEFORMS FOR NEUROSTIMULATION," each of which are herein incorporated by reference in their entirety.

In use, a user may interact with a controller (e.g., a smartphone controlled by application software/firmware) that pairs with the neurostimulator (e.g., i.e., by Bluetooth). The user may operate the controller to select the operational mode, e.g., the type of cognitive effect to be induced, such as an energy mode or calm mode, and/or the device could automatically detect based on the configuration of an electrode to which the apparatus is attached. The user may select, for example, from a set of ensemble waveforms which ensemble waveform to execute. There may be separate waveforms to evoke a desired experience/effect (e.g., "calm" or "energy" ensemble waveforms). An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, i.e., current amplitude, frequency, duty cycle, charge imbalance, shorting/capacitive discharge, bursting parameters, etc., and these parameters may change at pre-specified times for subsequent component waveforms. Once the user selects an ensemble waveform, the user can start the neurostimulation and the user can control or change the perceived intensity (e.g., by dialing the perceived intensity up or down), pause, or stop the session using the phone (app). In general, the perceived intensity can be scaled by the user between 0-100% of a target perceived intensity (e.g., a target current, frequency, duty cycle, charge imbalance, and/or shorting/capacitive discharge), using a control such as one or more buttons, sliders, dials, toggles, etc., that may be present on the controller (e.g., smartphone) in communication with the neurostimulator. The controller may also allow a user to activate ("on demand") a waveform configuration that is designed to evoke a predetermined response. For example, the control device could be adapted to display one or more icons to trigger phosphenes or an intensification of the perceived cognitive effect or skin sensation intensity. In addition, the controller may be configured to allow the user to press an icon to help in applying the electrode apparatus and/or neurostimulator. For example, activating this control may cause the smartphone to activate a front-facing camera on the phone to help the user to attach the apparatus to the head. During or after a session, a user can access help screens, a profile page, social sharing interfaces (i.e., tweet your experience), feedback about a session, and analysis & history of previous use. In general, the system may also be configured to pass data to and from the controller and/or the neurostimulator and to/from a remote server via the Internet. These data may include user information, waveform data, information about the function or state of the hardware device or electrode assembly, etc.

In general, described herein are general TES waveforms parameters that may be used to invoke, enhance, or modify a variety of cognitive states. Although the apparatuses and methods described herein may be used to provide TES to induce and/or modify a variety of cognitive states, two particular examples are described in detail herein, including enhancing attention, alertness, or mental focus and inducing a calm or relaxed mental state. Configurations of apparatuses and methods specific to enhancing attention, alertness, or mental focus and inducing a calm or relaxed mental state, including specific configurations for causing neuromodulation that achieves one of these particular cognitive effects in a subject are described in particular detail.

In general, a user may wear a neuromodulation device and apply one or more waveforms using the neuromodulation device to induce a cognitive effect. In general, the user may control the wearable neuromodulation device through a user device. A user device may be used to control the applied waveforms ("ensemble waveforms") for use in a transdermal electrical stimulation protocol, and in some variations may be used to control the application of waveforms concurrently with music, video, a performance, or another temporally structured sensory experience. A system may include the wearable neuromodulation device, and the user computing device for control of the transdermal electrical stimulation (TES) waveforms.

A time-varying pattern of electrical stimulation delivered transdermally (and, optionally, to some extent, transcranially) to induce neuromodulation may be referred to as a transdermal electrical stimulation waveform ('TES waveform'). A stimulation protocol may define the temporal pattern of current delivered to an anode-cathode set and can incorporate one or more waveform components including but not limited to: direct current, alternating current, pulsed current, linear current ramp, nonlinear current ramp, exponential current ramp, modulation of current (e.g., amplitude modulation at one or more frequencies), pulsed current (e.g., amplitude modulation where part of the modulated cycle is at zero intensity), and more complex time-varying patterns of electrical stimulation (including repeated, random, pseudo-random, and chaotic patterns). In operation, the device may provide current flow at target areas (e.g., in the brain, facial nerves (cranial nerves and/or cervical spinal nerves), vagal nerve, or other neuronal targets) to induce neuromodulation when appropriate electrode configurations and stimulation protocols are delivered.

TES waveform parameters that may be used to invoke, enhance, or modify a variety of cognitive states may be considered compound waveforms including a number of different sub-portions that are temporally connected together and delivered to a user in sequence. In general, the ensemble waveform and the component portions can be defined by four waveform parameters that may be used by the neurostimulator to define the component waveforms and, in combination with the duration of each waveform component and in some variations a ramping parameter, may define an ensemble waveform. In some variations, more complex waveforms are used for TES, and additional components may be included, such as transient capacitive discharges, multiple pulses per cycle, phase relationships of two or more pulses per cycle, complex pulse shapes, non-sinusoidal alternating current, etc. In some variations, an ensemble waveform (or portion of an ensemble waveform) may be modulated by an envelope of slower-frequency amplitude modulation (e.g., modulation of the current amplitude parameter). For example different types of amplitude modulation may be applied (e.g., amplitude modulation at frequencies between 0.5 Hz and 1000 Hz may be applied on top of the ensemble waveform. In some variations the amplitude modulation is applied as a sinusoidal (e.g., pure sinusoid, saw tooth, square pulses, etc.); in some variations the amplitude modulation is bursting, and results in an amplitude modulation duty cycle, in which stimulation intensity is decreased or turned off for a pre-determined period and switched on for a pre-determined period (where the amplitude modulation duty cycle can be calculated as the on period duration divided by the sum of the on period duration and off period duration).

Figure 41:
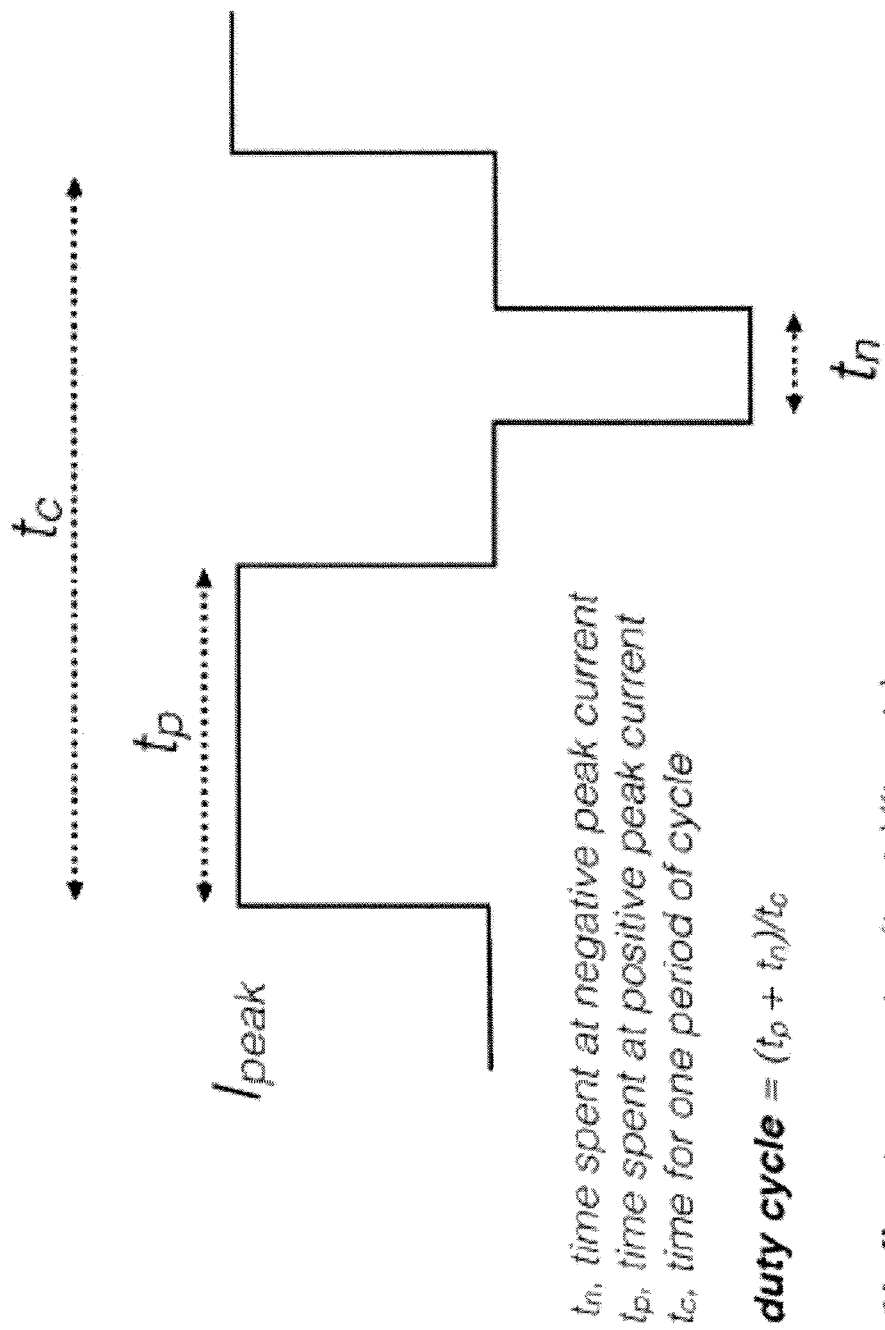
FIG. 41 schematically illustrates a base waveform which may be repeated and modified according to waveform parameters to form component waveforms which may be combined to form ensemble waveforms, as described herein, for use with TES.

The TES waveform components described herein may generally be formed of a basic unit comprising a plurality of biphasic pulses that may be asymmetric with respect to positive and negative going phases and may be charge imbalanced (although one or more capacitive discharging pulses may also be included within each repeating pulse to offset a charge imbalance as described herein). The component waveforms described herein may be defined by a duration and a set of waveform parameters including: a peak current amplitude (in mA), a frequency (in Hz or kHz), a percent charge imbalance, and a duty cycle. FIG. 41 schematically illustrates a basic waveform unit. This example shows the basic unit as a combination of square-waves (steps), however, rounded (including sinusoid), saw-toothed, triangular, and other shapes may be used. The waveform parameters for this basic unit waveform are defined by a duty cycle (or percent duty cycle), percent charge imbalance (also referred to as percent direct current, or percent DC), ramping or other amplitude modulation, one or more multiple frequency components, phase relationship of biphasic current, flat or structured noise, wave shapes (i.e., saw tooth, triangular, sine wave, square wave, exponential, or other wave shape), capacitance compensation features, or other parameters as discussed in U.S. patent application Ser. No. 14/091,121, filed Nov. 26, 2013 titled "WEARABLE TRANSDERMAL ELECTRICAL STIMULATION DEVICES AND METHODS OF USING THEM," now U.S. Pat. No. 8,903,494, which is herein incorporated by reference in its entirety.

In FIG. 41, the biphasic waveform includes a positive-going pulse having an amplitude $I_{peak}$, and a duration $t_p$ (time spent in the positive direction, relative to baseline), a negative-going pulse having an amplitude (in this example, Ipeak but in the negative direction) and a duration to (time spent in the negative direction, relative to baseline). The total time of the base unit is tc (time for one period of a cycle).

As used herein, 'percent duty cycle' may refer to the proportion of a cycle of a waveform that causes non-zero (or nominally non-zero) current to be delivered transdermally (though for waveforms incorporating capacitive discharge, the nominally non-zero portion of the duty cycle may not include the non-zero portions of the cycle caused by capacitive discharge). For example, the duty cycle in FIG. 41 is the sum of tp and tn divided by tc. Further, the percent charge imbalance (or 'percent direct current') refers to the non-zero portion of a waveform cycle that is positive-going or negative-going (again, excluding capacitive discharges, if present). In FIG. 41, the percent charge imbalance is the ratio of the difference of tp and tn and the sum of tp plus tn.

Inducing significant, robust, and/or reliable cognitive effects typically requires an appropriate ensemble waveform defined by a set of parameters for each component waveform. A stimulation protocol typically includes a composite waveform that defines the temporal pattern of current delivered to an anode-cathode set and can incorporate one or more waveform components including but not limited to: direct current, alternating current, pulsed current, linear current ramp, nonlinear current ramp, exponential current ramp, modulation of current, and more complex patterns (including repeated, random, pseudo-random, and chaotic patterns). In operation, the device may provide current flow at target areas (e.g., in facial nerves, cranial nerves, vagal nerve, in the brain, etc.) to induce neuromodulation when appropriate electrode configurations and stimulation protocols are delivered.

Although the apparatuses and methods described herein may be used to provide TES to induce and/or modify a variety of cognitive states, two particular examples are described in detail herein: (1) enhancing attention, alertness, or mental focus and (2) inducing a calm or relaxed mental state. Configurations of apparatuses and methods for causing neuromodulation that specifically achieve enhanced attention, alertness, or mental focus as opposed to an increased calm or relaxed mental state are described in particular detail.

Thus, a generic neurostimulator for modifying a cognitive state may include a pair of electrodes (or two sets of electrodes), referred to herein for convenience as an anode and a cathode (where the anode and cathode may loosely refer to their function as primarily anode and primarily cathode for biphasic waveform components), that can be applied to specific regions of the subject's body and used to provide TES stimulation within the relatively high-intensity, high-frequency ranges described as effective herein. Current is typically applied between the anode and cathode electrodes (or groups of anode and cathode electrodes). Without being bound by a particular theory of operation, the current may be passed through the body between the anode and cathode electrodes (or groups of anode and cathode electrodes), potentially applying energy in an appropriate treatment regime to underlying neural tissue (nerves, e.g., cranial, cervical spinal, vagal, etc., brain, etc.) in a particular neural pathway to result in the desired target effect (e.g., attention, alertness, or mental focus; inducing a calm or relaxed mental state). Thus, the placement locations of the electrodes on the subject's body are important to provide the desired cognitive effect. The placement positions for the pairs of electrodes (anodal and cathodal electrodes) specific to a desired cognitive effect may be referred to as a placement regime or configuration. For example, a first placement configuration for inducing a cognitive state of attention, alertness, or mental focus may include a first electrode applied to the subject near the temple and/or forehead area (e.g., laterally to the eye, such as slightly above and to the right of the right eye or above and to the left of the left eye) and a second electrode positioned behind the ear on the same side as the first electrode in the mastoid region (e.g., on or near the mastoid). High-intensity stimulation (as described in greater detail below) of this region may result in enhanced attention, alertness, or mental focus.

Another configuration of electrode positions may include an electrode positioned on the subject's skin near the subject's temple and/or forehead area (e.g., above and to the right of the right eye) and a second electrode on the subject's neck (e.g., on a superior portion of the neck centered at or near the midline and at least partially overlapping the midline). Appropriate TES stimulation of this region may result in enhancing a calm or relaxed mental state. Either of these configurations may also be used with an appropriate TES stimulation regime (waveform) to induce phosphenes by noninvasive transdermal electrical stimulation using the apparatuses described herein.

Generally speaking, peak stimulation intensities above at least 3 mA (e.g., greater than 5 mA, e.g., between 5 mA and 25 mA, etc.) may be advantageous for transdermal electrical stimulation that causes neuromodulation by targeting the brain, nerves (e.g., cranial nerves, vagal nerve, peripheral nerves, spinal nerves), and/or spinal cord. To achieve these peak intensities without causing significant pain, irritation, or discomfort in a subject may require appropriate electrodes and appropriate ensemble waveforms as described herein. Beneficial electrodes may have pH buffering properties and may contain components for uniformly (or more uniformly) delivering current across the dermal-facing portion of the electrode.

The TES waveforms for use with any of the configurations described herein may be a pattern of currents delivered into tissue of a user (e.g., transdermally). Although there may be variations (optimizations) of these waveforms and electrical protocols for each configuration (electrode placement) and each target cognitive state, in general, the patterns may be within the same range of values to provide biphasic, high-intensity, high-frequency and asymmetric with regard to the positive-going and negative-going phases of the waveform (in some cases not charge balanced) signals that are applied to robustly evoke a response in most individuals while causing at most a low level (e.g., minimal or none) of discomfort and/or pain.

Figure 44A:
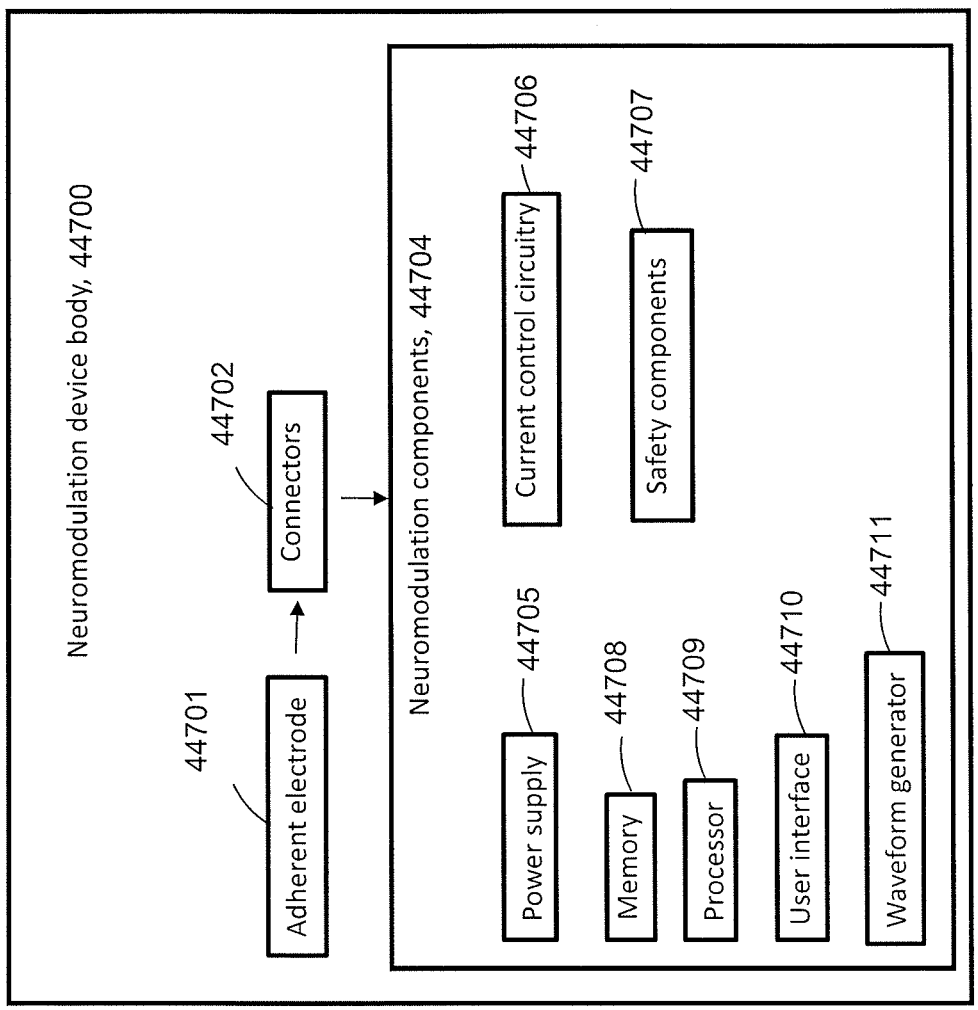
FIG. 44A is a diagram showing the overall configuration of the integrated neuromodulation device.

These waveforms may be ensemble waveforms including a plurality (e.g., 3 or more) of component waveforms having a predetermined value for each of: current amplitude ("intensity"), frequency, percent charge imbalance, duty cycle, and in some variations capacitive discharge. These component waveforms may each have a duration (time), and may be connected together in a sequence to evoke the desired cognitive effect. Some of these component waveforms forming the ensemble waveform are ramps, in which one or more waveform parameter (current amplitude, frequency, duty cycle, percent charge imbalance) of the waveform is ramped up to the target/peak value of the waveform components from the previous value of the waveform components after transitioning to the new component waveform when delivering the ensemble waveform. Generally, tDCS studies have used between about 1 mA and about 2 mA peak currents for longer stimulation periods (e.g., more than a few minutes or seconds), and tACS typically uses relatively low frequencies (e.g., <650 Hz). However, these current levels and frequencies are sub-threshold for at least some forms of neuromodulation. In particular, the inventors have found that higher currents may be necessary for inducing significant and beneficial cognitive effects. Unfortunately, such higher currents may lead to pain, irritation, and damage to skin under high current stimulation conditions. Higher currents than have traditionally been used for TES are required for inducing a change in a cognitive state in at least some instances. Described herein are systems configured to deliver higher currents (optimally 3 mA or higher), at relatively high frequency (>750 Hz, e.g., between 750 Hz and 30 kHz, between 1 kHz and 30 kHz, etc.) to achieve a desired cognitive effect. The ensemble waveforms described herein may reduce irritation, pain, and burning sensations in the dermis, muscles, and other tissues of users receiving TES. These embodiments permit higher current intensities to be transmitted comfortably so that desirable changes in a subject's cognitive function, cognitive state, mood, and/or energy levels can be attained. In addition to the high current amplitudes, high frequency (e.g., repeating the base waveform of FIG. 41 between about 650 Hz and about 50 kHz (e.g., between about 750 Hz and about 40 kHz, between about 1 kHz and about 35 kHz, etc.) may provide biphasic pulsed and/or alternating current stimulation that minimally activates sensory pathways and minimizes pH changes in tissue due to stimulation. As can be seen in FIG. 44A, the neuromodulation device body contains an electrode assembly 44701, and neuromodulation components 44704. The neuromodulation components 44704 further contain power supply 44705, memory 44708, processor 44709, user interface 44710, current control circuitry 44706, and safety components 44707. A skilled artisan will appreciate that FIG. 44A is one representation of how the neuromodulation device components can be laid out and there are numerous other ways for both the electrodes 44701 and neuromodulation components 44704 to be integrated.

Figure 44B:
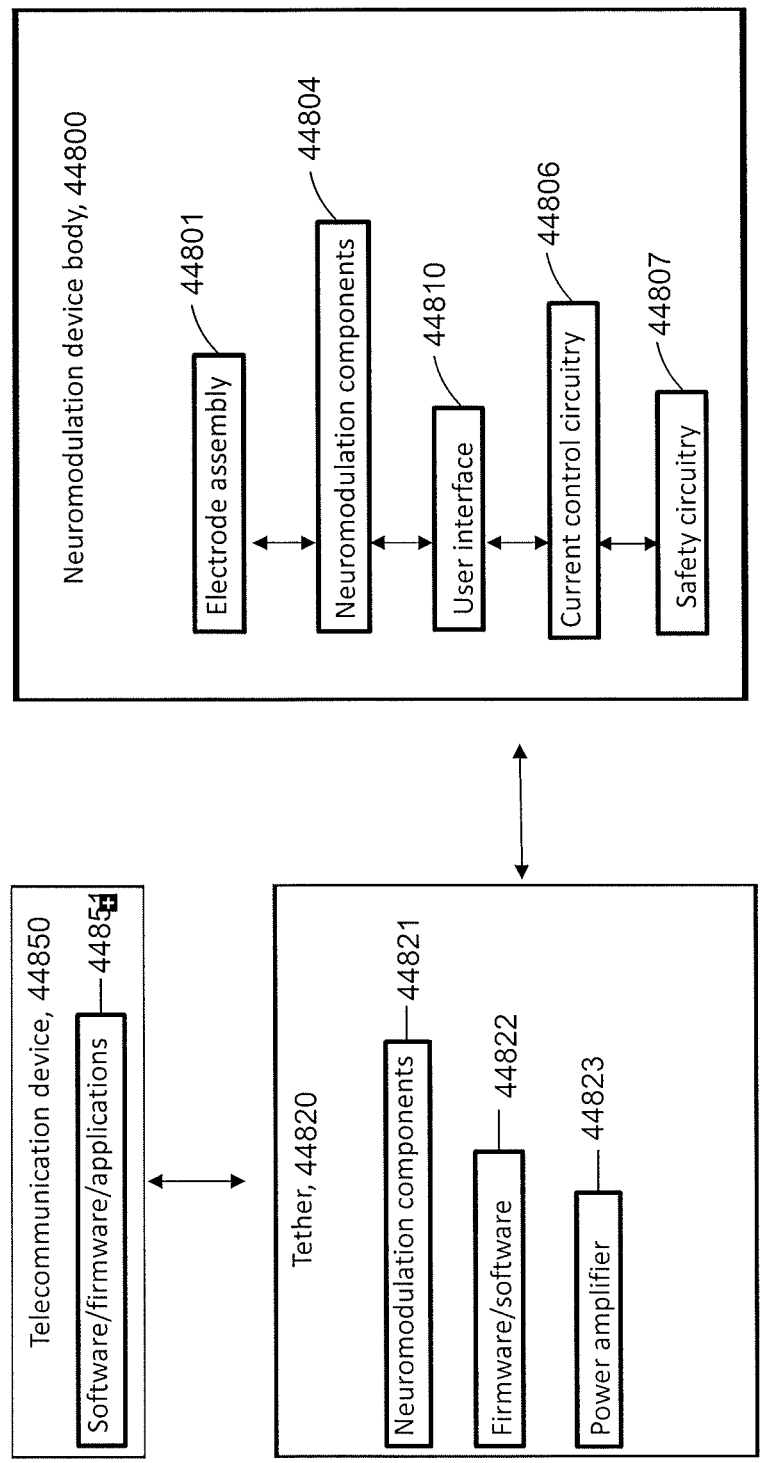
FIG. 44B is a diagram showing the configuration of integrated neuromodulation device connected to a tether and a telecommunication device.

In a second embodiment of the present neuromodulation device as shown in FIG. 44B, a physical tether, such as a wire or cord, can be established between the neuromodulation device and a communication device (such as a smartphone or a tablet). The tether 44820 can contain some of the neuromodulation components 44821 as well as firmware/software 44822 for controlling the neuromodulation device body 44800, and a power amplifier 44823 for boosting the power available to the neuromodulation device. In this embodiment, the neuromodulation device can also draw power from the communication device for outputting any particular waveform session. This can prove useful, because the primary power drain on the neuromodulation device will be the delivery of the stimuli from the first and second electrode to the subject's skin. Having a secondary source of power to draw from can decrease the size of the power supply used within the actual neuromodulation device. In one example of this second embodiment, the cord or wire used to connect the neuromodulation device to the control device can be a standard wire or cord. In a second example of the second embodiment, some components related to the neuromodulation aspect of the device (such as creating the waveforms, outputting the waveforms) can be placed external to the main neuromodulation device and retained within or hardwired to the cord or wire in a housing.

In various embodiments, the controller of the TES neurostimulator may include a capacitive discharge circuit configured to discharge a capacitance on the electrodes during the delivery of the biphasic electrical stimulation signal. TES neurostimulators that incorporate discharging the capacitance on the electrodes may be useful for pulsed stimulation regimes, and may help reduce or prevent pain and discomfort. In some variations the apparatus includes capacitance discharging circuitry in connection with the electrodes. For example, capacitance discharging circuitry may include electronic components and firmware features that short the anode-cathode path to permit discharge of capacitance that builds up during a pulse (e.g., in the subject's skin). In some instances, short-circuiting is beneficial for reducing discomfort and accordingly increasing the cognitive effects induced by TES (due to one or both of: reducing the distraction of discomfort so that other cognitive effects can be experienced by a subject and permitting higher peak current intensities to be delivered that induce more significant cognitive effects). In general, controlling the maximum current of a capacitance discharging pulse may be beneficial for tuning the comfort of a TES waveform (e.g. to vary the maximum current of discharge based on the estimated amount of capacitance built up, which is expected to correlate with increasing imbalance (i.e. duration and/or peak current) between positive-going and negative-going pulses, as well as by frequency, where lower frequency stimulation at a fixed duty cycle will cause relatively more capacitance build-up per cycle).

In some embodiments, the wearable transdermal electrical stimulator may comprise a control module having the capacitive discharging features (which may be referred to as a 'short circuiting' applicator) described. For example, the wearable transdermal electrical stimulator may include: a housing configured to be connected to a first electrode and a second electrode, a control module at least partially within the housing including: a processor, a waveform generator configured to deliver a biphasic electrical stimulation signal between the first electrode and the second electrode, and a capacitive discharge circuit configured to discharge a capacitance on the first electrode and the second electrode during the delivery of the biphasic electrical stimulation signal. The TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset; and a capacitive discharge circuit, wherein the TES control module is configured to occasionally trigger the capacitive discharge circuit to discharge capacitance on the electrodes during the delivery of the biphasic electrical stimulation.

Figure 42A:
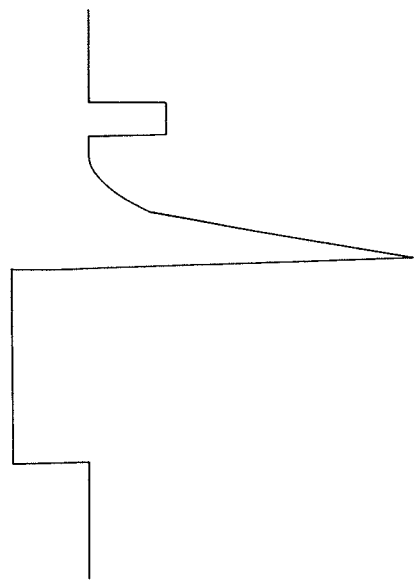
FIG. 42A schematically illustrates a biphasic electrical stimulation waveform with a positive pulse and a negative pulse in one cycle.

FIG. 42A schematically illustrates a biphasic electrical stimulation waveform with a positive pulse and a negative pulse in one cycle. In some embodiments, the firmware may create segments in a waveform cycle. The smallest segment may be limited by the clock of the processor. For example, in some embodiments, the shortest segment per cycle can be 2, 5, or 10 microseconds or any values there between. For example, in some embodiments, the firmware may create 10, 12, 15, or 20 segments per cycle. For each segment of the cycle, the controller may instruct the waveform generator to generate a positive intensity value, a negative intensity value, a value of "zero" which indicates an open circuit mode, or a capacitive discharge.

Figure 42B:
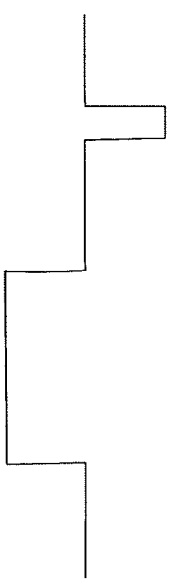
FIG. 42B schematically illustrates a capacitive discharge pulse triggered immediately after the positive pulse.
Figure 42C:
FIG. 42C schematically illustrates a capacitive discharge pulse triggered immediately after the negative pulse.
Figure 42D:
FIG. 42D schematically illustrates capacitive discharge pulses triggered immediately after the positive pulse and the negative pulse.

In some embodiments, the capacitive discharge (which may be referred to as "short-circuiting" although it is not the result of shorting) can be triggered immediately after the positive pulse or negative pulses as shown in FIGS. 42B-42D. For example, as shown in FIG. 42B, at the time when the positive pulse ends, the controller triggers the capacitive discharge circuit to short the anode-cathode path, resulting in a capacitive discharging pulse to permit discharge of capacitance. The minimum duration of the capacitive discharging pulse may be limited by the shortest segment of the cycle as discussed above. Thus the duration of the pulse can be larger than 2, 5, or 10 microseconds. However, the duration of the pulse may not be too short. It might be advantageous to have a more gradual pulse to prevent pain in the subject. It might be advantageous to have a limited peak value of the pulse to further prevent pain and discomfort. The peak value and the time constant of the capacitive discharging pulse may be controlled by the capacitive discharge circuit. In some other embodiments, the capacitive discharge can be triggered immediately after the negative pulse as shown in FIG. 42C. In some embodiments, the capacitive discharge can be triggered both after the positive pulse and after the negative pulse as shown in FIG. 42D.

Figure 42E:
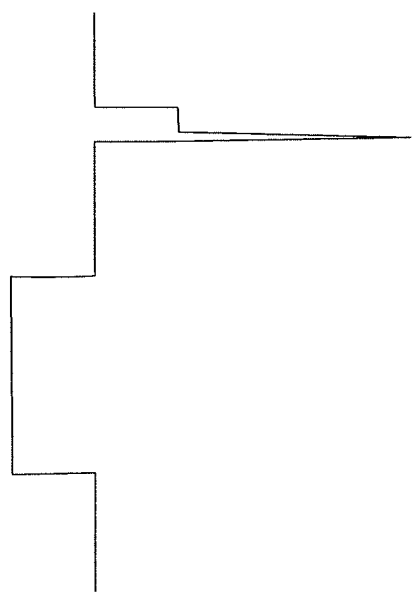
FIG. 42E schematically illustrates a capacitive discharge pulse in the negative going direction that occurs at the onset of a negative going pulse.

In some alternative embodiments, the capacitive discharging pulse can be triggered at the onset of each negative-going pulse in the negative-going direction as shown in FIG. 42E. For example, in the "energy" mode, the capacitive discharging pulse can be triggered at the onset of each negative-going pulse in the negative-going direction to induce an enhanced cognitive state. In some other embodiments, the capacitive discharging pulse may be triggered at the onset of each positive-going pulse in the positive-going direction. In some other embodiments, the capacitive discharging pulse can be triggered both at the onset of each negative-going pulse in the negative-going direction and at the onset of each positive-going pulse in the positive-going direction.

An advantage of the ear-based TES systems and methods described herein may include co-delivery with an audible signal. Novel cognitive effects may be induced by aligning in time (in some cases, with a temporal offset) an auricular TES waveform with an audible signal through coordinated activation of auditory pathways with cranial and/or cervical spinal nerve downstream pathways. For example, any of these methods may include delivering an audible signal to the subject from the TES applicator. Any audible signal may be used, including one or more of: a song (e.g., music), a tone or tones, a chant, spoken language, instrumental music, white noise, structured noise (e.g. pink noise, brown noise, frequency-modulated noise), binaural beats, recorded or synthesized sounds (e.g. ocean noise, wind noise, running water, etc.), or the like. In variations, the audible signals may take the form of instructions or advisements about the TES applicator (e.g. 'recharge device' or 'one minute remaining'); may take the form of music, chants, recorded sounds, and/or synthesized sounds timed and temporally sequenced to match, enhance, or otherwise modulate the cognitive effects induced from auricular TES alone; or may take the form of binaural beats in bilateral variations of the system (i.e. higher frequency audible signals (generally frequencies above 200 Hz) with phase offsets at frequencies of brain rhythms (generally less than 200 Hz).

For example, any of these methods may include delivering an audible signal to the subject from the TES applicator wherein the audible signal is delivered from an earbud TES applicator.

Temple and Mastoid Electrode Pairs

The exemplary apparatuses descried above and shown in FIGS. 43B-43Q and 45A-45D illustrate examples configured to apply stimulation to a subject's head and/or neck. In general, the location in which neurostimulation is applied, in conjunction with the applied TES waveform(s), may profoundly affect the efficacy and effect of the resulting neurostimulation. For example, stimulation in regions other than those described herein may not be effective at all, or may result in discomfort, and undesirable effects (e.g., may evoke anxiety, rather than calm, etc.).

Also described herein are methods and systems for inducing cognitive effects by delivering transcranial/transdermal electrical stimulation (hereinafter 'TES') with electrodes on the temple and mastoid. This configuration, illustrate in FIGS. 45E and 45F may provide an alternative placement option and may be beneficial compared to other electrode placement options. For example, in some variations one electrode of the TES system is placed on the temple or forehead region and a second electrode is placed on the upper cheek area on the same side of the head. The upper cheek region includes areas anterior to the ear, as well as anterior and below the auditory canal. The advantage of placing both electrodes on the same side of the head in this configuration is that the overall footprint of the system may be made small. That is, because there is relatively little distance between the electrode (generally less than 3 inches and more frequently less than 2 inches, e.g., between 1 inch and 3 inches, between 1.5 inches and 3 inches, between 2 inches and 3 inches, etc.) the overall footprint of the electrode assembly (and neurostimulator assembly attached thereto which delivers current through the electrode assembly into the skin) is small, improving the portability and wearability of the system (e.g. permitting weaker adhesive or smaller adhesive areas to hold the system in place on the user's skin). With these electrode locations, a cognitive effect of enhanced energy may be induced using stimulation waveforms as described below. Exemplar locations for TES dermal electrodes on the temple/forehead and cheek according to these variations of the invention are shown in FIGS. 45A-45F.

Figure 46:
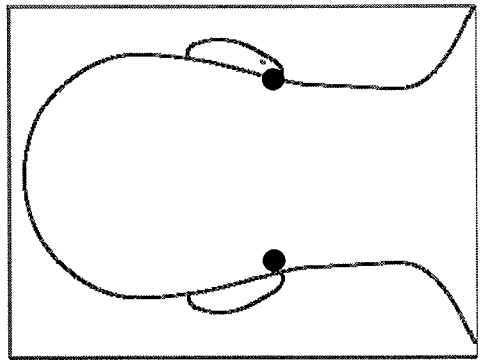
FIG. 46 illustrates electrode positions on the mastoid bilaterally for inducing various muscle contractions and inducing changes in cognitive state (e.g. through proprioceptive pathways) by stimulating the facial nerve.

In other variations of the system, two electrodes are placed bilaterally over the mastoids (i.e. bilaterally) and apply waveforms as described below to induce various contractions of facial musculature via stimulation of branches of the facial nerve. Stimulating via electrodes in this configuration may be effective for inducing changes in mood and cognitive state via proprioceptive pathways. For example, by placing electrodes in these locations near the stylomastoid foramen (bilaterally), the facial nerve may be activated (or otherwise modulated), causing various patterns of facial muscle contraction by projections of the facial nerve. Exemplar locations for TES dermal electrodes bilaterally on the mastoid according to these variations of the invention are shown in FIG. 46.

User Interface

Any of the TES neurostimulation apparatuses and methods described herein may be configured for use by a consumer (e.g., user) for personal use. Also described herein are user interfaces and methods and system for operating and servicing these TES apparatuses, as well as methods and systems for improving user experiences and compliance. As will be described in greater detail below, FIGS. 47A-53E illustrate one variation of a user interface (UI) for controlling operation and servicing of a TES apparatus that modulates a user's cognitive state. FIGS. 54A-59F illustrate methods of operation, reordering, and user guidance; these principles may be provided to a user with a TES apparatus. In general, the UI may be, for example, an application software ("app") running on the user electronics device.

Any of the TES apparatuses described herein may include client or user software, firmware and/or hardware that may include or be adapted for operation on a user electronics device such as a handheld or wearable electronics device (e.g., smartphone, pad, computer, smartwatch, etc.). The user electronics device may communicate and/or control operation of the TES apparatus. In particular, the user electronics may include a user interface for controlling operation of the TES apparatus.

Figure 47A:
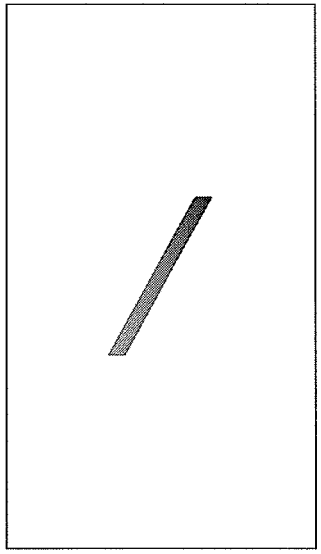
FIGS. 47A-47F show screens of an app for controlling a neurostimulator for TES that allow a user to log in, pair a neurostimulator wirelessly via Bluetooth, and view Warnings and Terms.
Figure 47B:
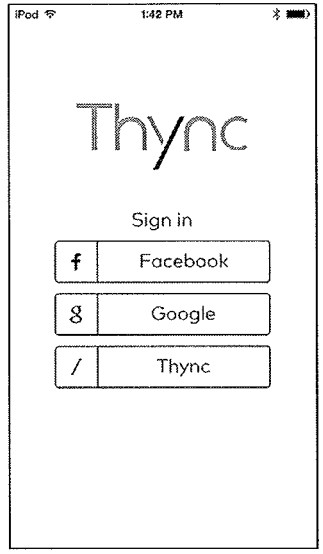
Figure 47C:
Figure 47D:
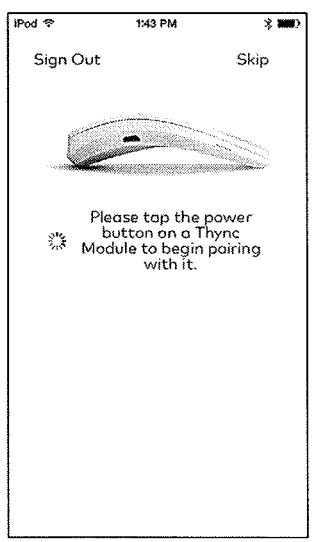
Figure 47E:
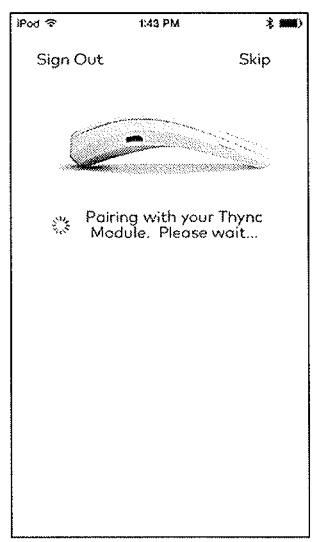
Figure 47F:
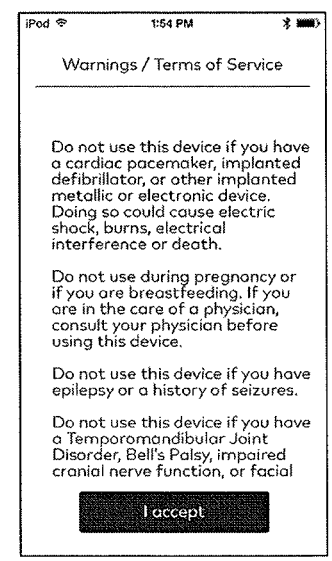

For example, FIGS. 47A-47F illustrate introductory information from a UI that may be used to communicate between a user wearing the TES applicator and the control for the device. In FIG. 47A the user may be presented with an introductory screen, and in FIGS. 47B and 47C may be presented with sign-in and/or registration prompts that allow the UI and therefore the TES apparatus to identify the user. The TES applicator may be locked or otherwise prevented from operating until login and/or registration has occurred. The apparatus may also coordinate with remote servers and/or processes (FIG. 47B). The UI may also prompt or walk the user through the pairing or otherwise communicating with the wearable TES apparatus, as shown in FIGS. 47D-47E, and may present information such as warnings, terms of use, and the like (FIG. 47F).

Figure 48:
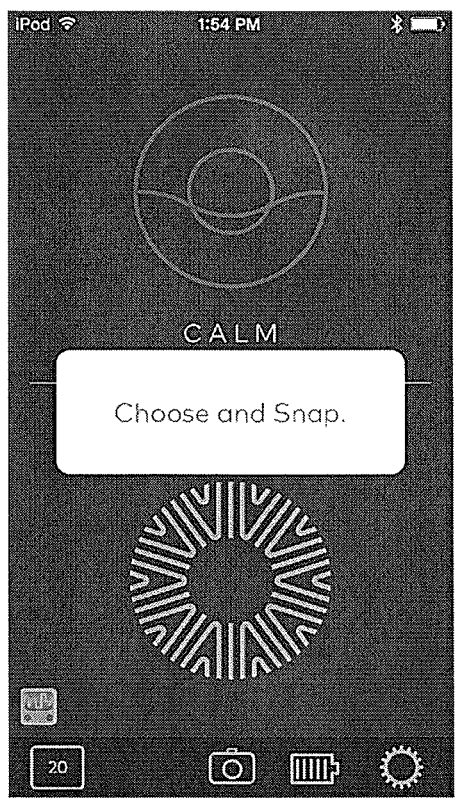
FIG. 48 shows a screen of an app for controlling a neurostimulator for TES that instructs a user to choose a subtype of an electrode assembly and snap it (connect mechanically and electrically) to a neuromodulator.

In general, the US may allow the user electronics device to control the TES apparatus, including the attachment and confirmation of an electrode. For example, as shown in FIG. 48, the UI may coordinate attachment of a particular electrode (and may include instructions stepping the user through attachment, including presenting video, text and/or audio instructions). The UI may also include automatic detection of the 'type' of electrode (e.g., a 'calm' configured electrode for attachment at the temple and back of the neck, an 'energy' configured electrode for attachment to the temple and region behind the ear, etc.).

Figure 49:
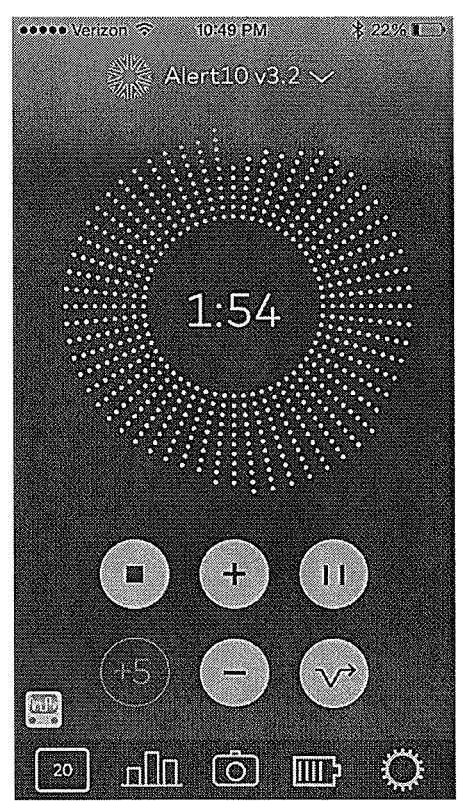
FIG. 49 shows a screen of an app for controlling a neurostimulator for TES that provides various user controls for electrical stimulation and information (i.e. time remaining, intensity) for the TES session.
Figure 50A:
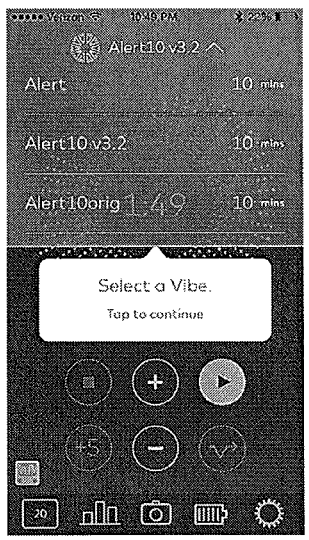
FIGS. 50A-50L show screens of an app for controlling a neurostimulator for TES that display a series of messages to instruct a user on the function of various user interface elements.
Figure 50B:
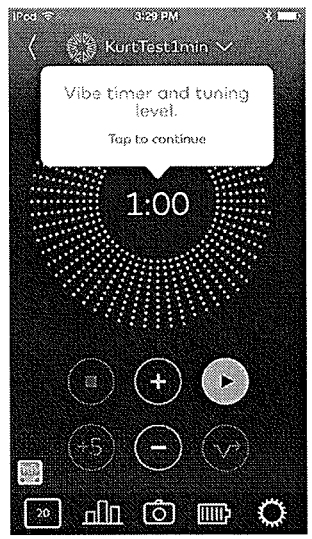
Figure 50C:
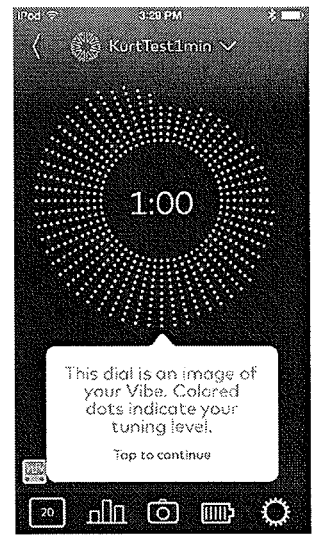
Figure 50D:
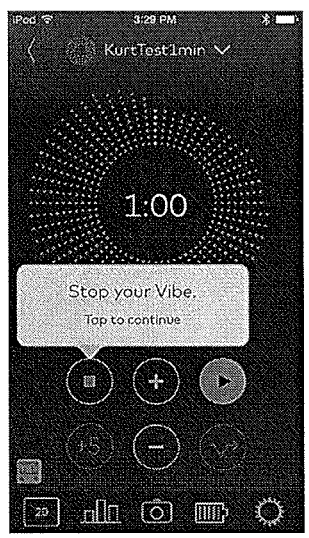
Figure 50E:
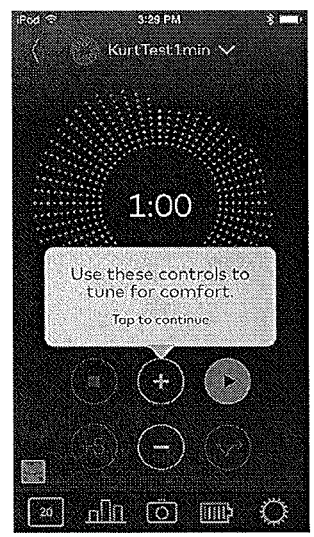
Figure 50F:
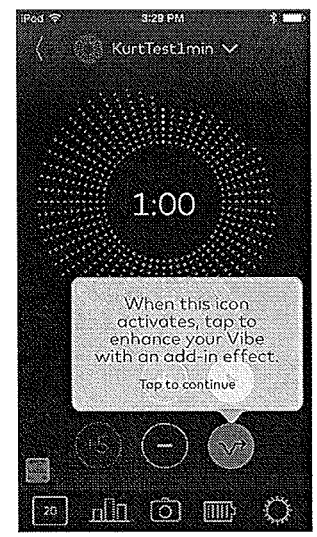
Figure 50G:
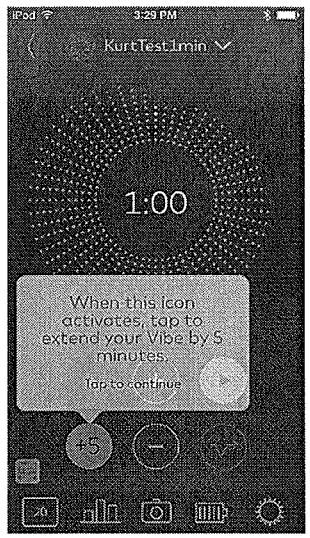
Figure 50H:
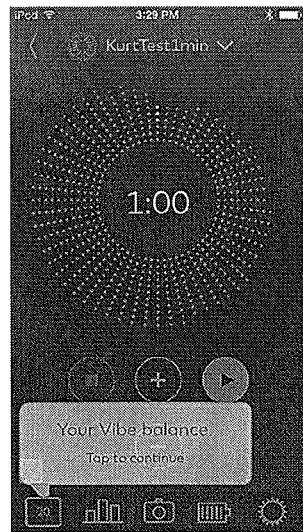
Figure 50I:
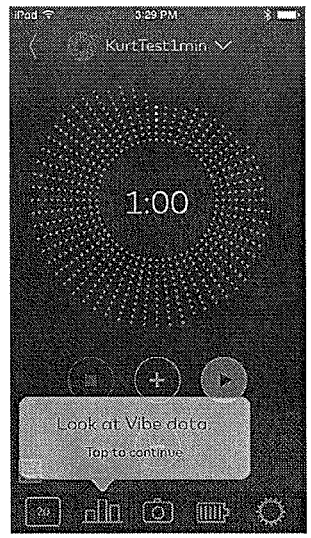
Figure 50J:
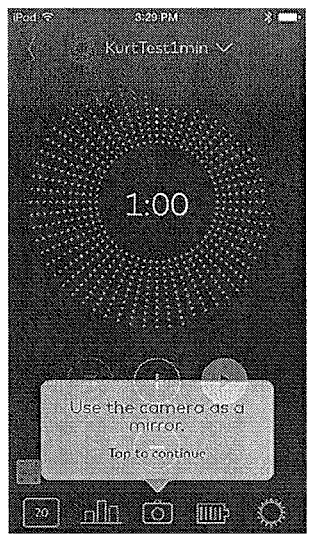
Figure 50K:
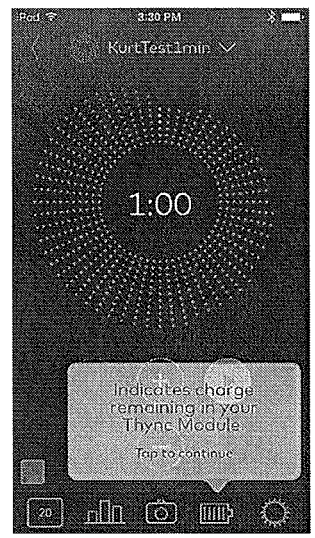
Figure 50L:
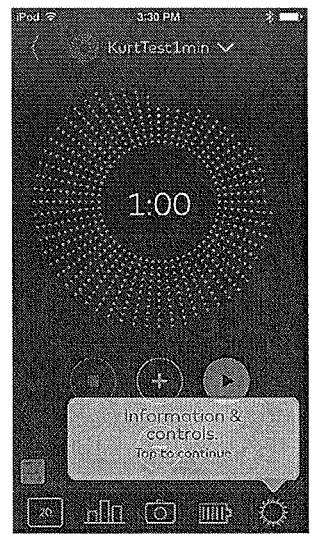
Figure 51:
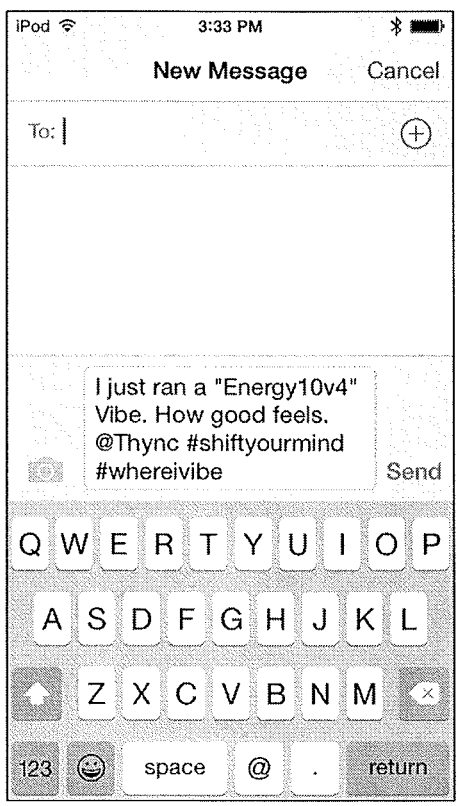
FIG. 51 shows a messaging screen on a smartphone with auto-populated content for sharing by a user of a TES system.

In general, the apparatus may allow a user to select a particular ensemble waveform (vibe) and modify the properties of that vibe during use, as shown in FIG. 50A, and to modify the selected ensemble waveform as it is being applied. For example, as shown in FIG. 49, the UI may allow the user to adjust the intensity (e.g., current, frequency, DC offset, etc. or some combination thereof) using one or more controls (buttons, sliders, knobs, etc.), to pause operation, to add additional duration (time) and/or to trigger a transient increase in intensity or other signal change. The UI may also show the current location within an ensemble waveform and may show what to expect (duration, intensity) in the future. FIGS. 50B-50L illustrate one example of a UI, describing the features. These figures may also be presented by the UI to a user to explain operation of the UI.

Figure 52:
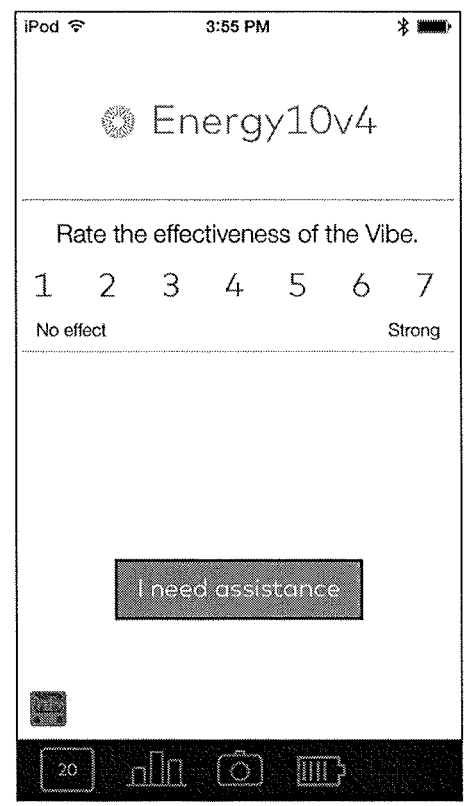
FIG. 52 shows a screen of an app for controlling a neurostimulator for TES that enables a user to provide feedback on efficacy and request customer support assistance.

Any of the UIs described herein may also be configured to communicate with social media, including existing general-purpose social media platforms (e.g., Facebook, Twitter, etc.) or dedicated (e.g., TES-specific social medial) platforms. As already mentioned, any of these apparatuses may present user rankings associated with each ensemble waveform, and/or may also prompt a user for user-reported information about any of the TES ensemble waveforms, as shown in FIG. 52; in addition, the apparatuses described herein may also collect and/or present unprompted user or ranking information, including number of downloads, number of completed runs ("popularity"), intensity modifications, number of aborted runs, etc.

A UI may also be used to determine and/or present analytics about the operation of the TES apparatus. For example, FIGS. 53A-53E illustrate analytics user interfaces for a sample user. As shown in FIG. 53A, the UI may be used to select information about the user's usage history (vibe history, etc.), the devices used by the user (device), and account information, and may also be used to purchase additional electrode strips, purchase or modify ensemble waveforms, or to view information about the individual's operation of the apparatus. The UI may also be configured to allow a user to login/logout, as mentioned, or to log in as a guest. The UI may also be configured to associate with one or more specific devices, and may be configured to control operation of the TES apparatus (see, e.g., FIG. 53B). The UI may also provide information specific to the UI and/or the TES apparatus (see, e.g., FIG. 53C). The UI may provide user analytics (e.g., number, duration, frequency of one or more, or all, ensemble waveforms, etc.), including historical information (FIG. 53E) such as a history of operation of the apparatus.

Rental/Purchase and Tracking of "Vibes"

As mentioned above, the TES waveforms referred to herein may be called waveforms, ensemble waveforms or "vibes". Any of these ensemble waveforms may be preconfigured and offered, sold, set, rented, or otherwise made available to a user having a TES neurostimulator as described and shown herein (and incorporated by reference above). For example, a vibe may be tracked (usage and/or possession), and may provide accounting for eCommerce (i.e., buying a credit to play a particular TES waveform/waveform ensemble, which is distinct from purchasing an electrode, a neurostimulator module, an app, etc.). For example, users may purchase packages (e.g., a combo pack) of electrode assemblies (also referred to as electrode strips, i.e. calm strips and energy strips for different electrode locations and cognitive effects induced) and/or TES sessions (also referred to as ensemble waveforms or vibes). The system may maintain a count of a user's available vibes (e.g. on the neurostimulator, on a user computing device that controls or otherwise communicates with the neurostimulator, on a remote server connected to the neurostimulator (or to the user computing device connected to the neurostimulator) via the Internet. A user may have login credentials or other security that indicates they are the user (their account is to be debited for) a TES session (e.g., a vibe), and their 'vibe balance' may be decremented. A vibe credit may be associated with a single TES session (of any length), by a length of time during TES session(s), by a duration from the onset of a first TES session, etc.

The system may make the electrodes reusable many more times and will sell or lease (rent) Vibes rather than (or in addition to) electrode assemblies.

For example, described herein are systems for operating a marketplace of ensemble TES waveforms. Each of a plurality of TES waveforms may be associated with an outcome or evoked cognitive effect, such as calm, relaxation, energy, etc. The system may include a database of such ensemble waveforms, and may also include additional associated information, such as: a summary/description of the vibe (intended effect, duration, recommended electrode configuration, recommended audio and/or visual accompaniment, etc.), rankings/ratings, creator, recommended or required electrode configurations, date of creation, music or other audiovisual accompaniment, and the like. Ensemble waveforms (vibes) from the database may be accessed by the one or more users, who may purchase, rent and/or contribute vibes to/from the database. The system may present a description of each vibe and a rental and/or purchase price for each vibe. The system may track purchases/rentals, and may regulate distribution of purchased/rented vibes.

Fitting

In general, the methods and apparatuses (including the UIs) described herein may be configured to optimize the application of TES ensemble waveforms, including optimization (by the apparatus and/or by the user, including automatically guiding the user) of the fit of the electrodes with the apparatus. For example, for fitting an electrode strip and/or TES apparatus, the apparatus may be configured (e.g., using the UI) to instruct a user to try 'dry fit' first the electrode first, by figuring out placement with just the neurostimulator module before attaching it to the adhesive electrode assembly. This may permit ease of sliding, rotating, shifting unit on the head to find correct positioning with regard to placement and contour of module vs. head. Once the user has determined the correct position for themselves, they may attach the adhesive electrode assembly and position it again at the same location (e.g. by using a front facing camera, including one that automatically compares the real-time position to the one selected earlier during the dry fit phase) and/or a mirror. See, e.g., FIGS. 54L-54N.

Customization

As mentioned above, any of these apparatuses may be used to customize the delivery of TES via the device, including selecting one or more specific ensemble waveforms. For example, an ensemble waveform may be purchased having specific properties and/or for use with a specific electrode strip. Custom ensemble waveforms (vibes) may control the wearable apparatus to deliver a particular type of TES (controlling frequency, current, timing, duration, DC offset, etc. as described above). A database and UI as described herein may "push" (electronically distribute) a particular TES waveform to a particular user based on their login, and/or based on the user's selection, rental or purchase of a particular TES waveform. This may allow creation and distribution of vibes customized for particular users or classes of users. See, e.g., FIG. 54o.

Methods of Operation

Figure 54A:
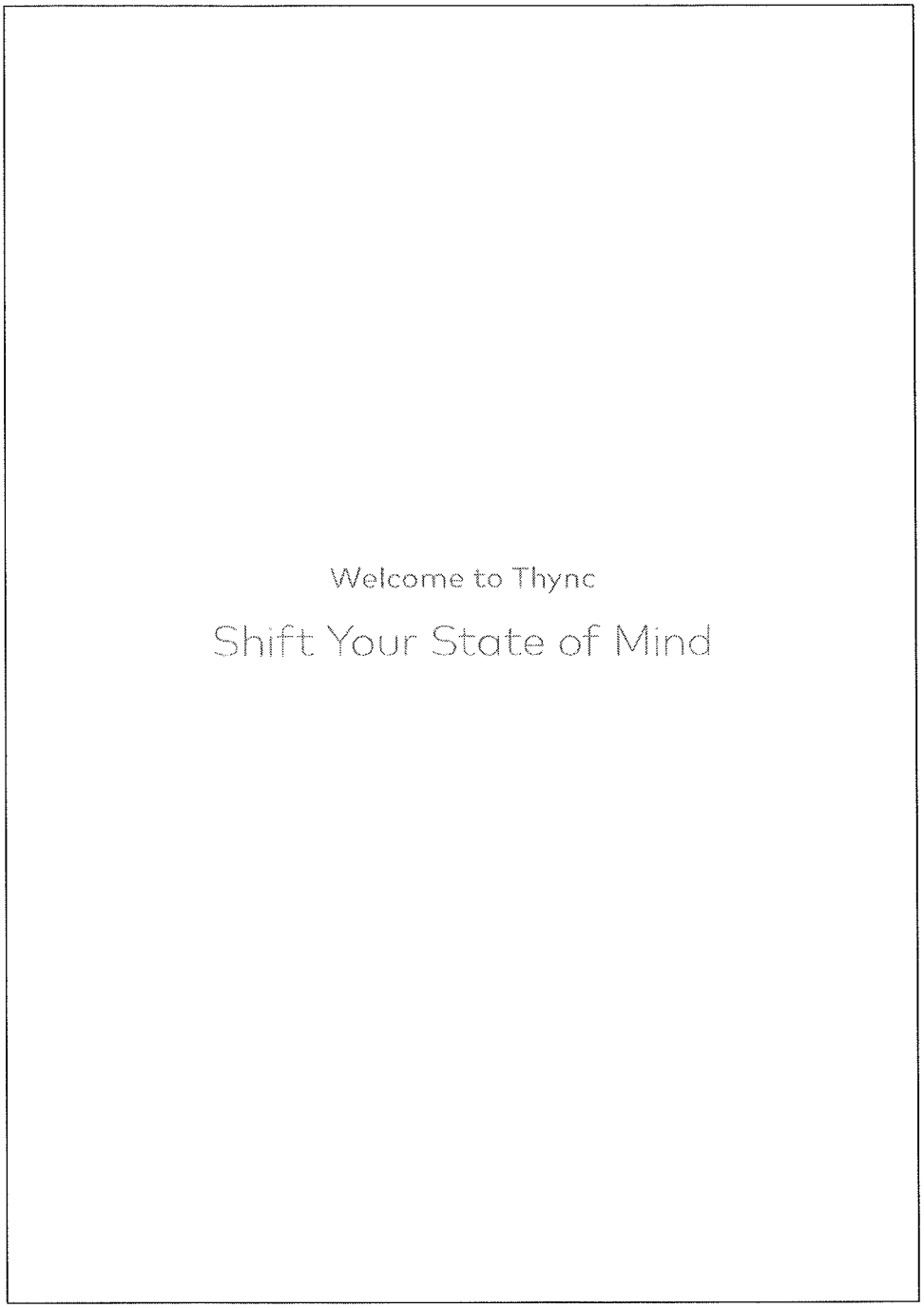
FIG. 54A shows a title page of a user guide for a TES system.
Figure 54B:
FIG. 54B shows a table of contents page of a user guide for a TES system.
Figure 54D:
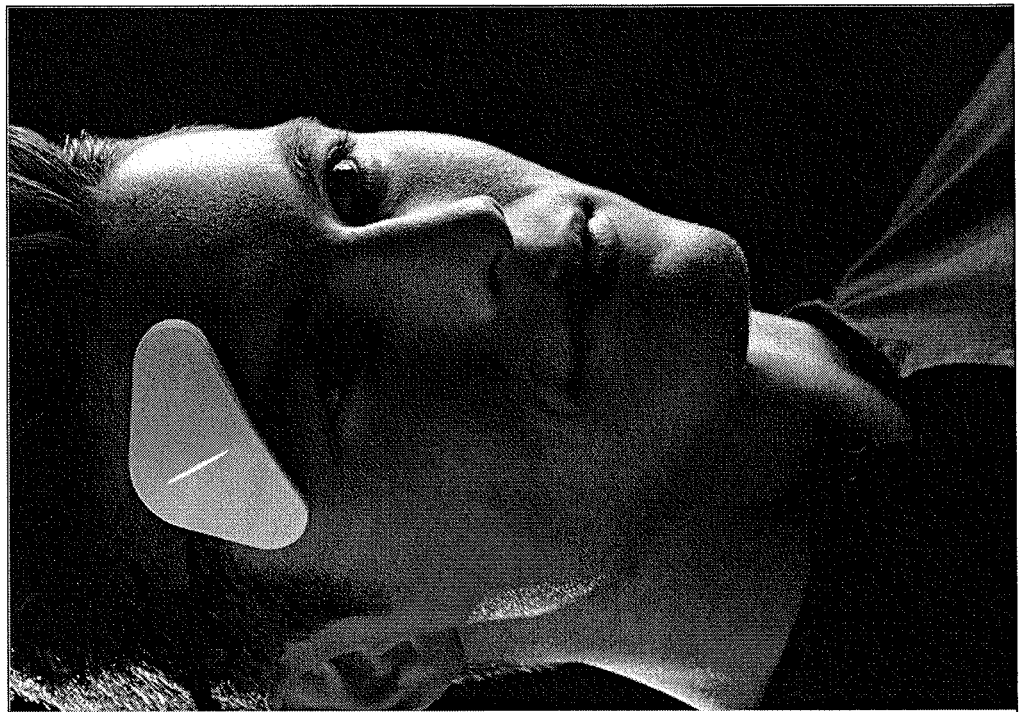
FIG. 54D shows a first TES experience (i.e. 'Vibe') description page of a user guide for a TES system.
Figure 54E:
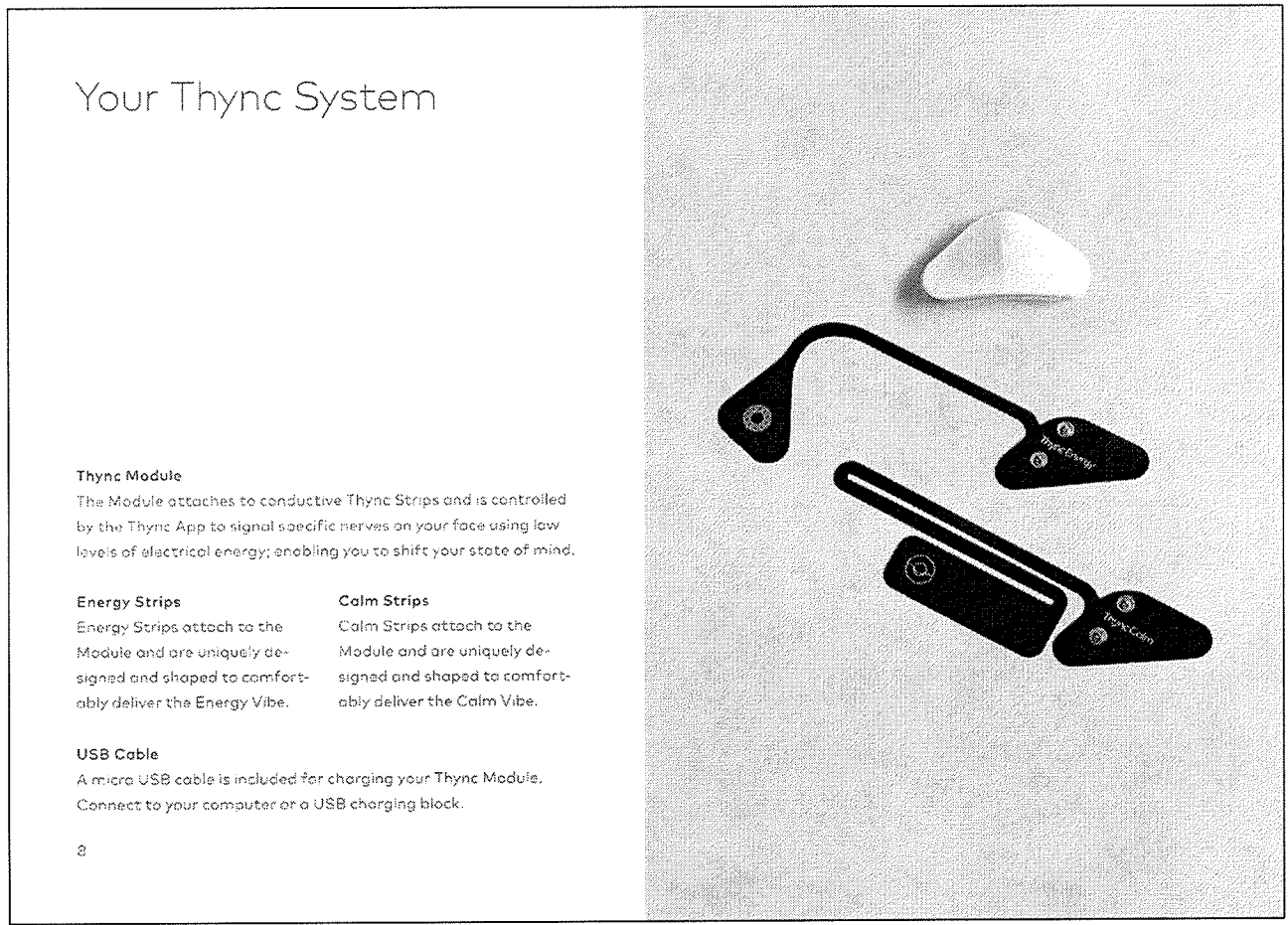
FIG. 54E shows a system description page of a user guide for a TES system.
Figure 54F:
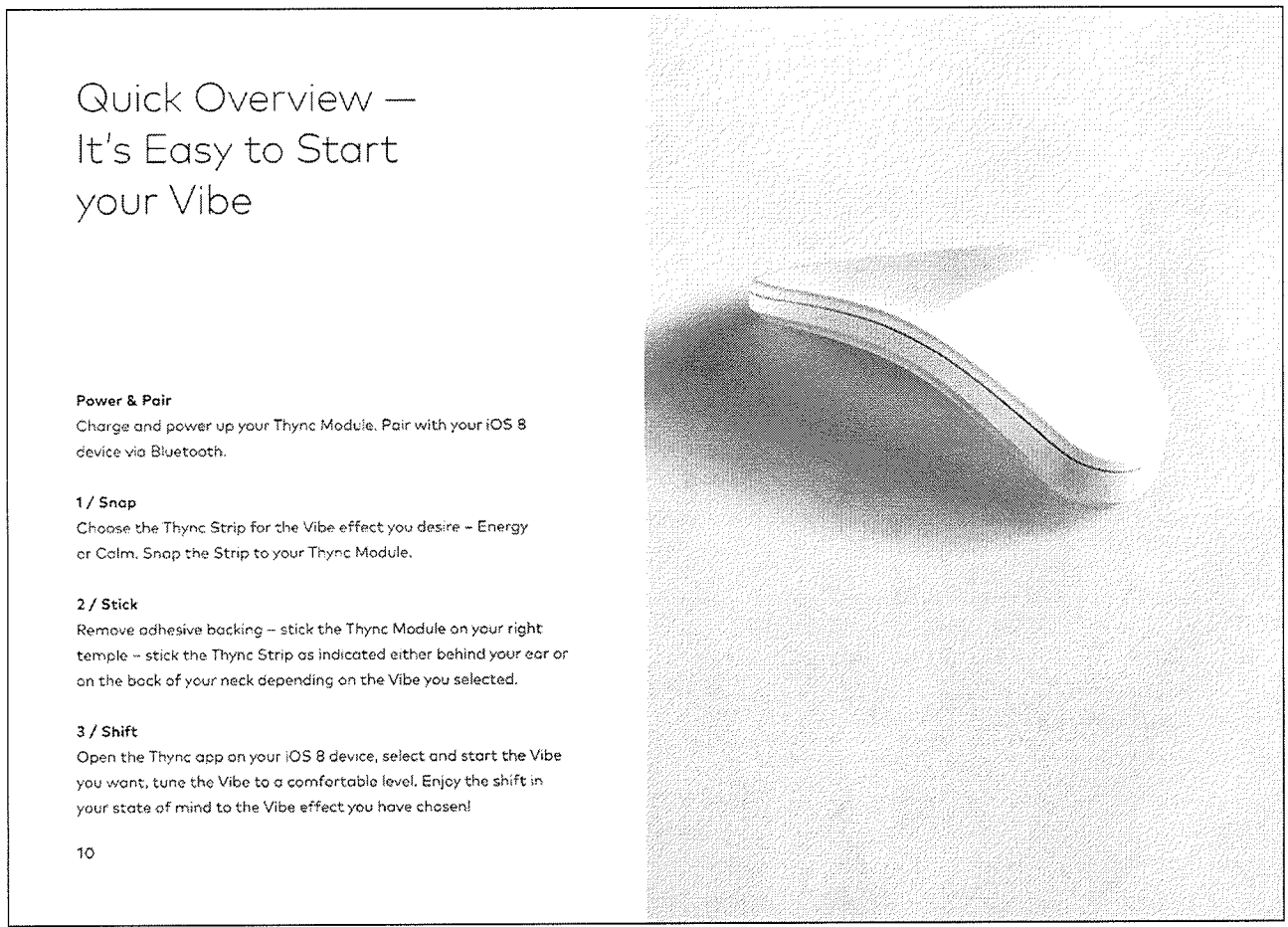
FIG. 54F shows an overview page of a user guide for a TES system.
Figure 54G:
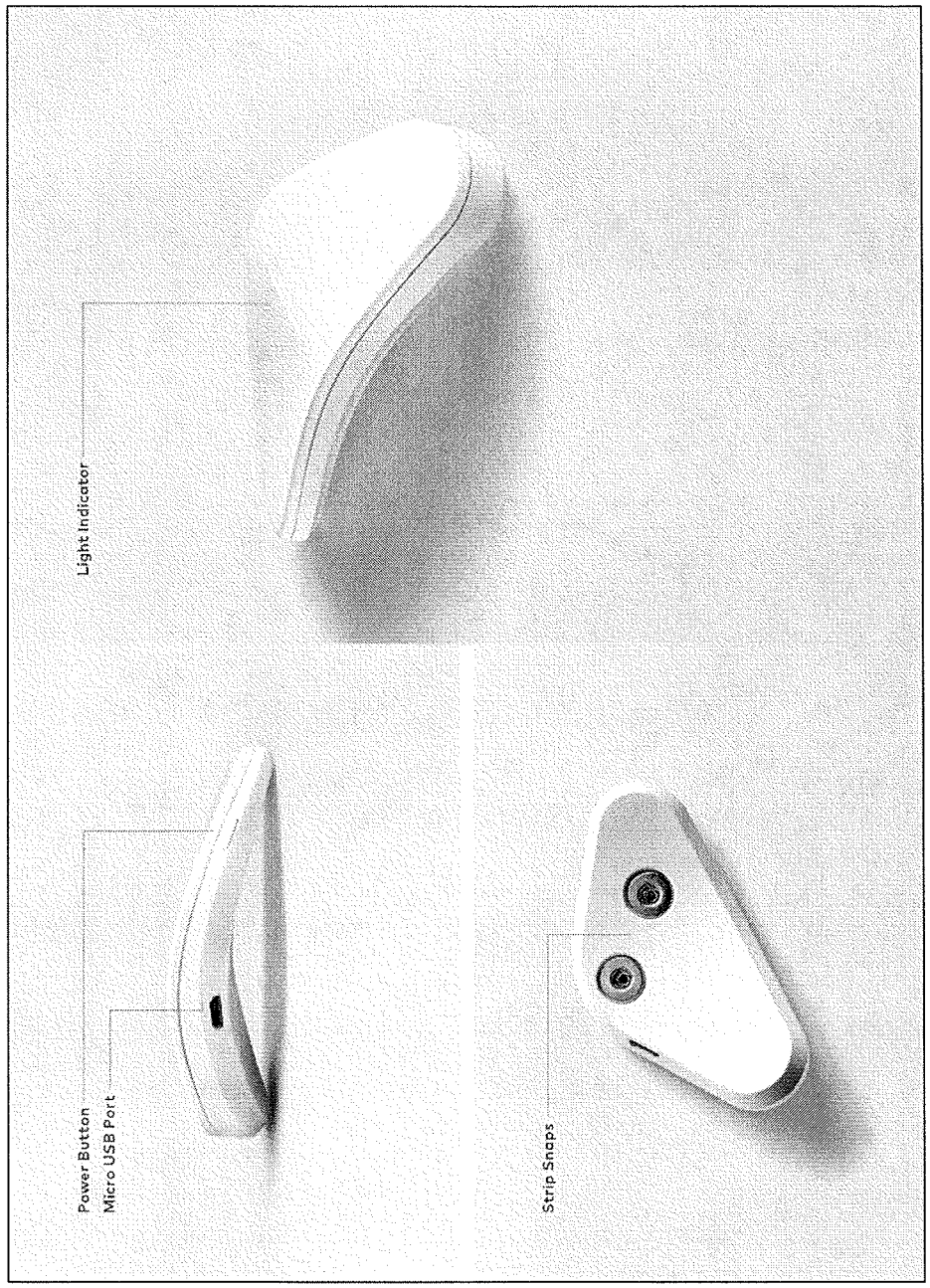
FIG. 54G shows a page of a user guide for a TES system indicating components of a wearable TES neurostimulator.
Figure 54H:
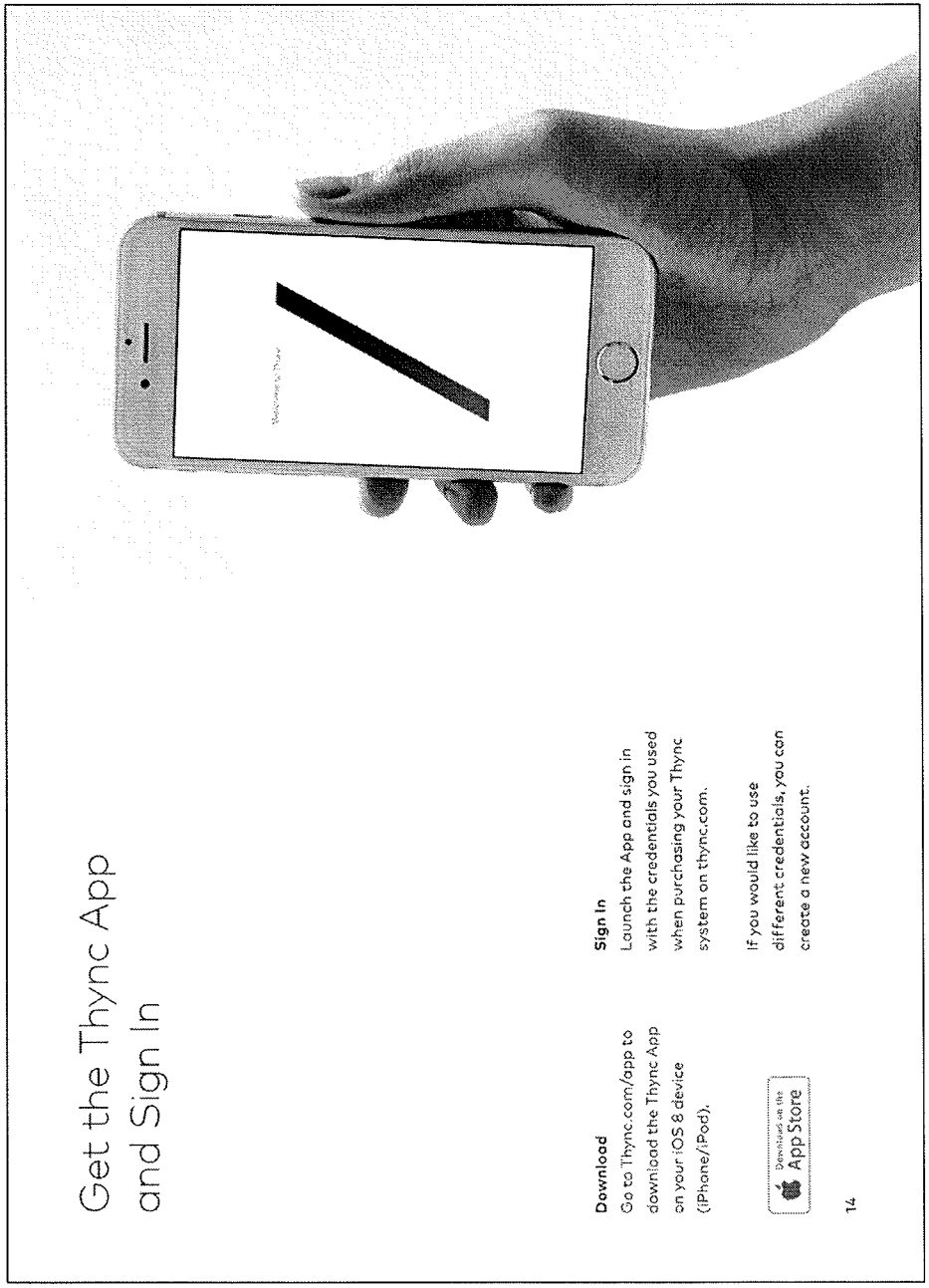
FIG. 54H shows a page of a user guide for a TES system that guides a user to download an app for controlling the TES neurostimulator from a smartphone.
Figure 54I:
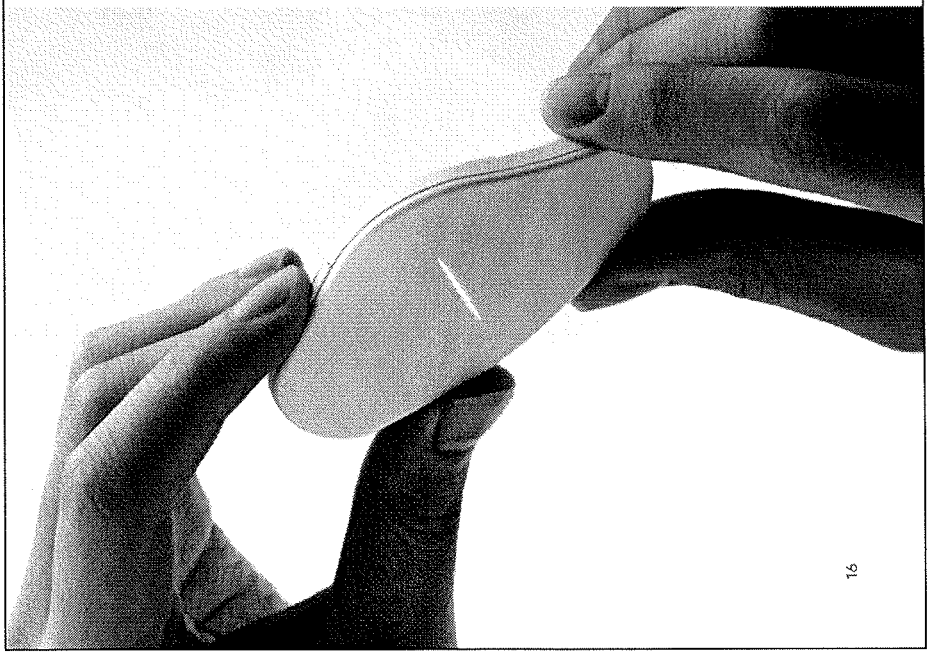
FIG. 54i shows a page of a user guide for a TES system with instructions for wirelessly pairing to a smartphone and power/charging of a wearable TES neurostimulator.
Figure 54J:
FIGS. 54J and 54K show pages of a user guide for a TES system with instructions for attaching an electrode assembly (i.e. 'strip') to a wearable TES neurostimulator (i.e. 'Module').
Figure 54K:
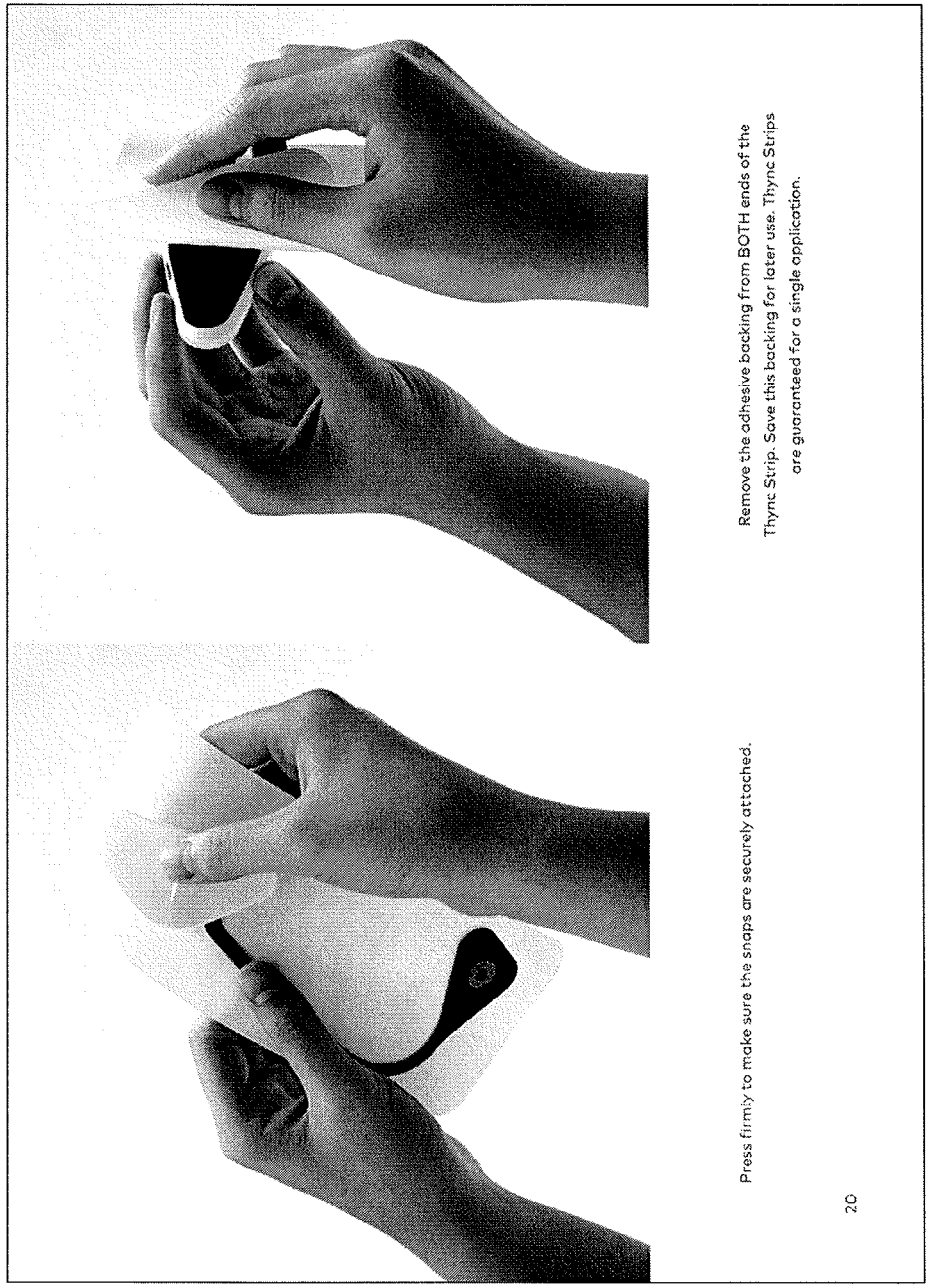
Figure 54L:
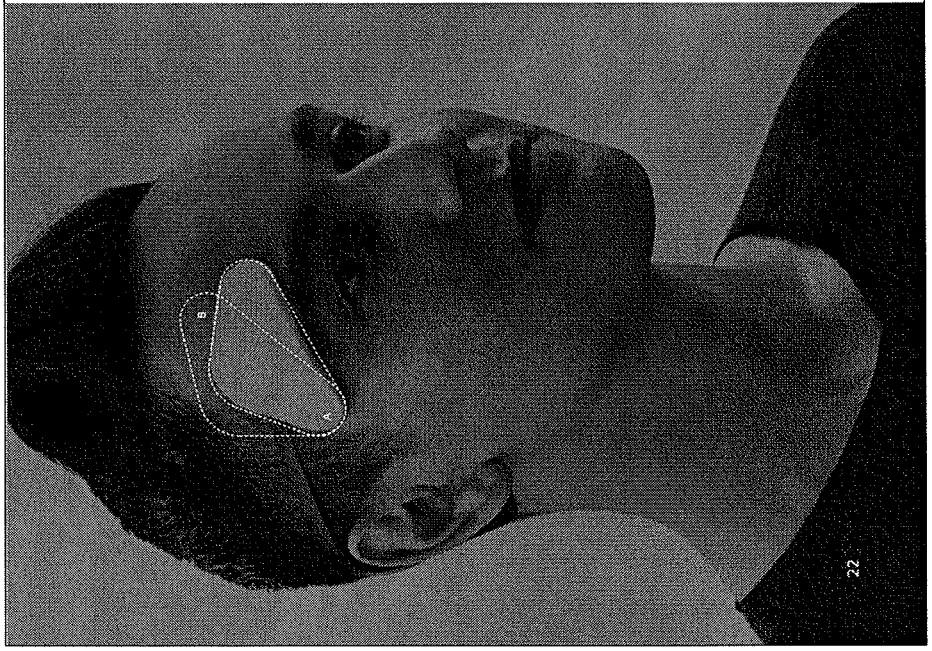
Figure 54M:
Figure 54O:
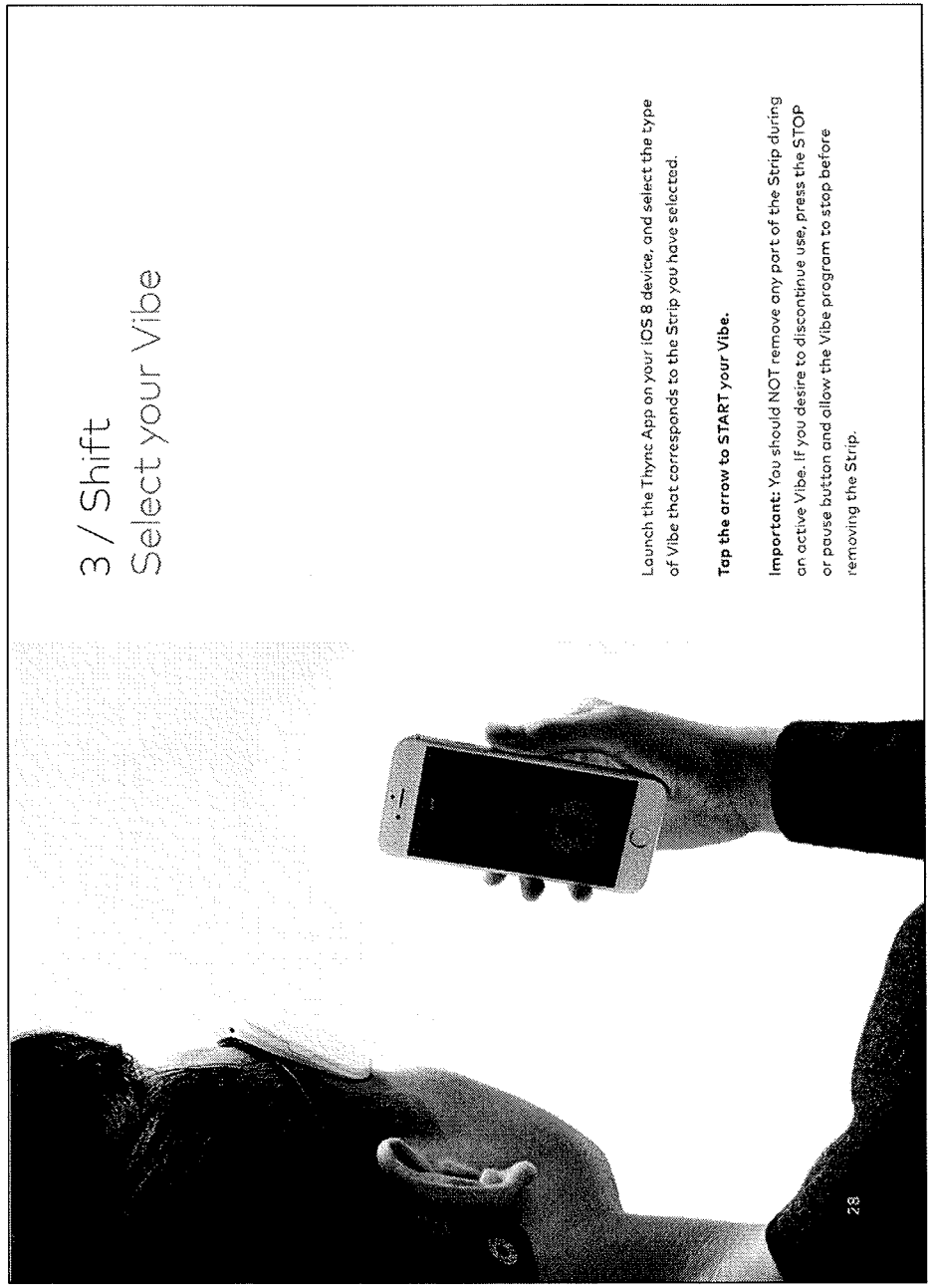
Figure 54P:
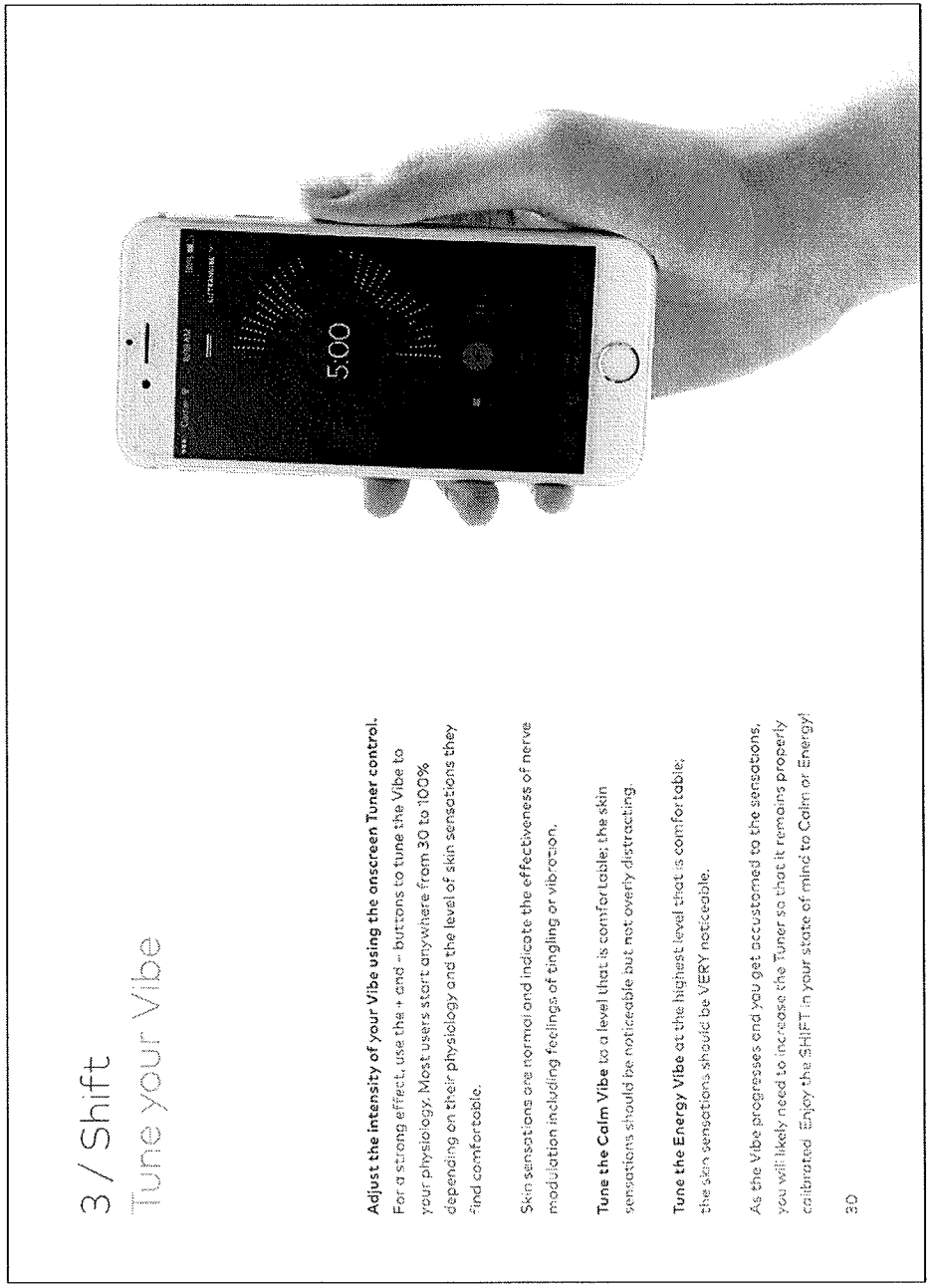
Figure 55:
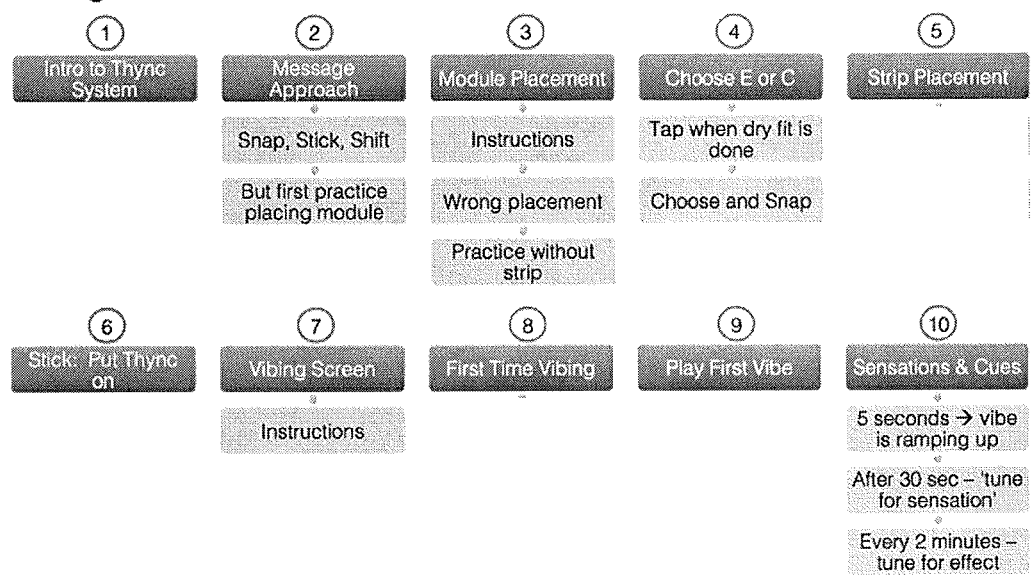
FIG. 55 shows a workflow for instructions, including text, video, and user interaction for teaching a naïve user how to use a wearable neurostimulator system for TES.
Figure 56A:
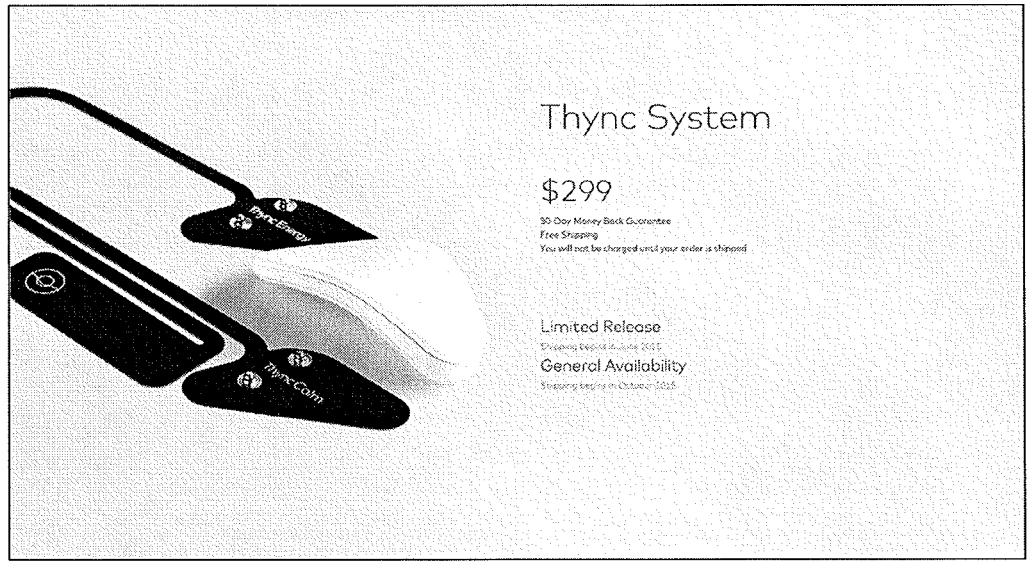
FIG. 56A shows a resource (e.g. website) describing a wearable TES neurostimulator, electrode assemblies, and app (referred to as the 'Thync System') for user-actuated TES to induce a cognitive effect.
Figure 56B:
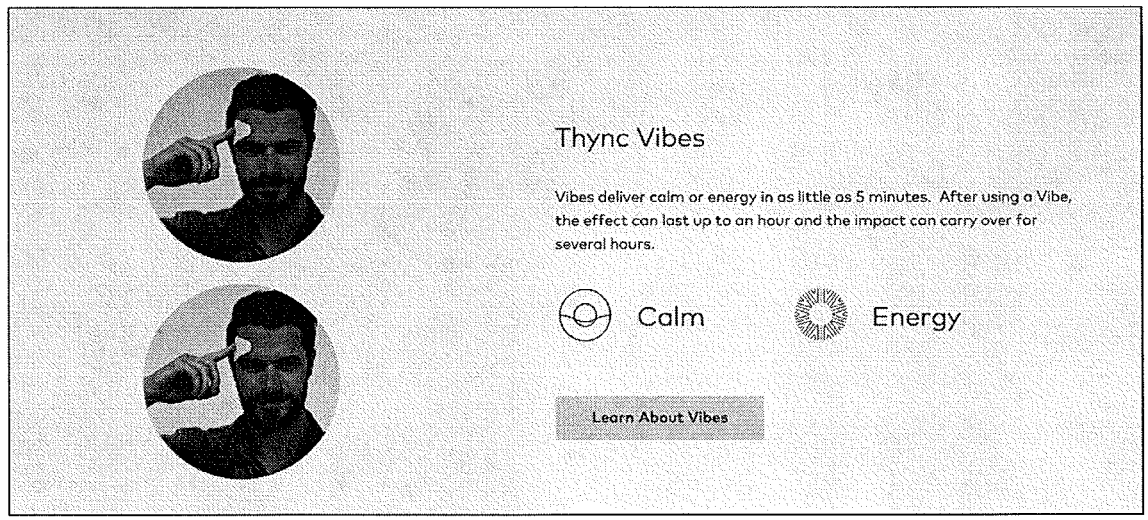
FIG. 56B shows a resource (e.g. website) describing two categories of TES (i.e. Calm Vibes and Energy Vibes) that can be delivered to a user by a wearable TES neurostimulator to induce a cognitive effect.
Figure 56C:
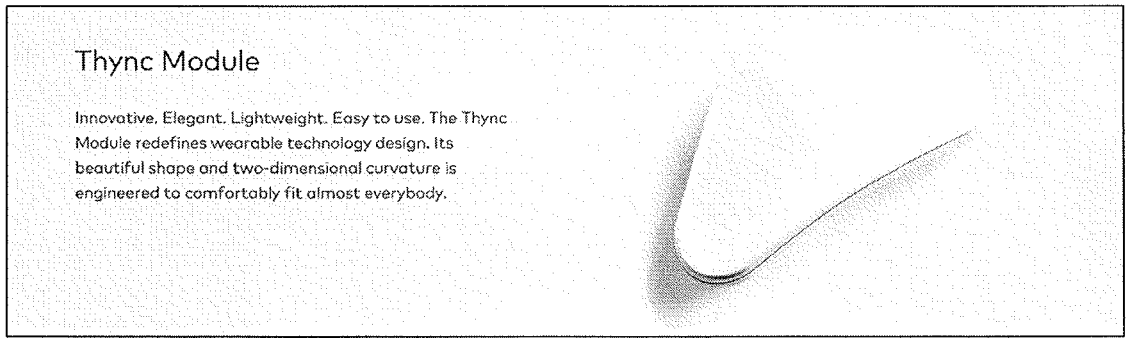
FIG. 56C shows a resource (e.g. website) describing a wearable neurostimulator (also referred to as a 'Thync Module').
Figure 56D:
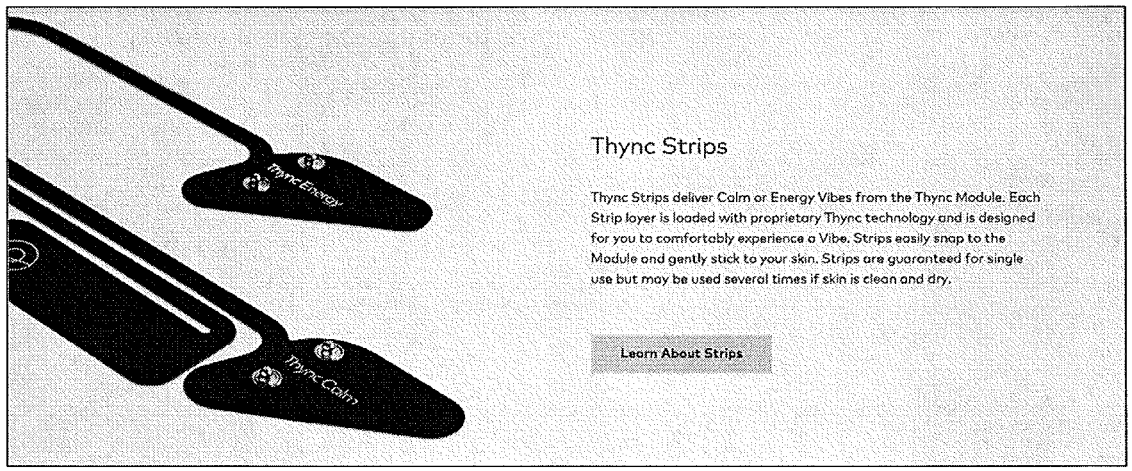
FIGS. 56D and 56E show resources (e.g. websites) describing electrode assemblies for inducing a cognitive effect via a wearable neurostimulator (also referred to as a 'Thync Strips').
Figure 56E:
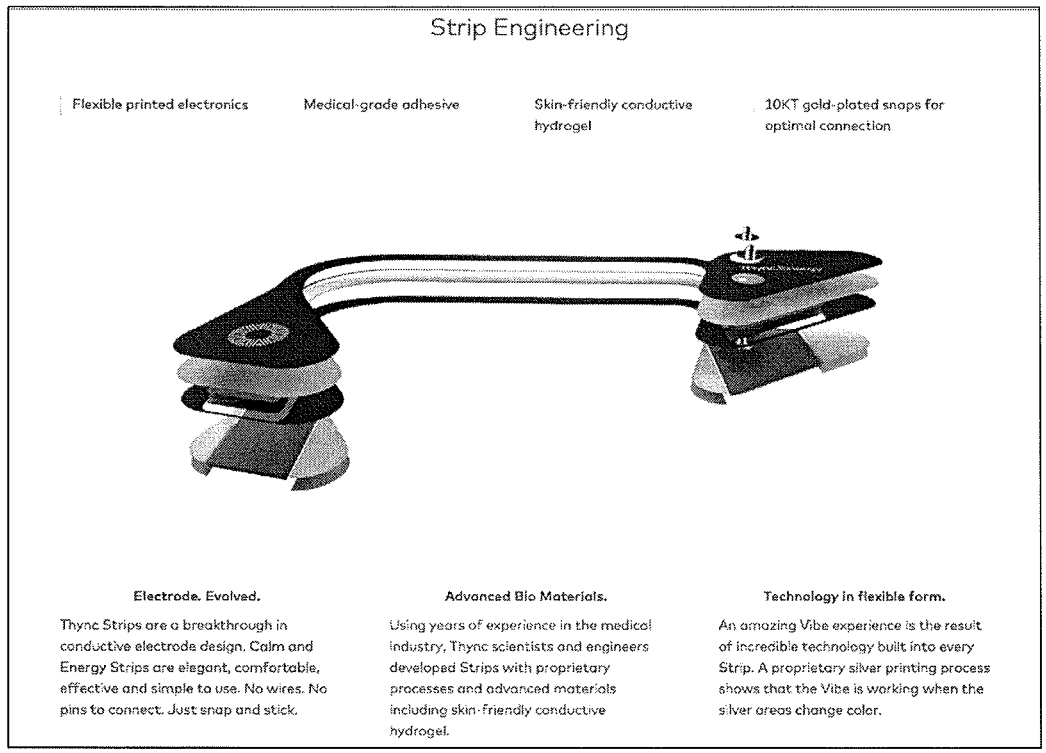
Figure 56F:
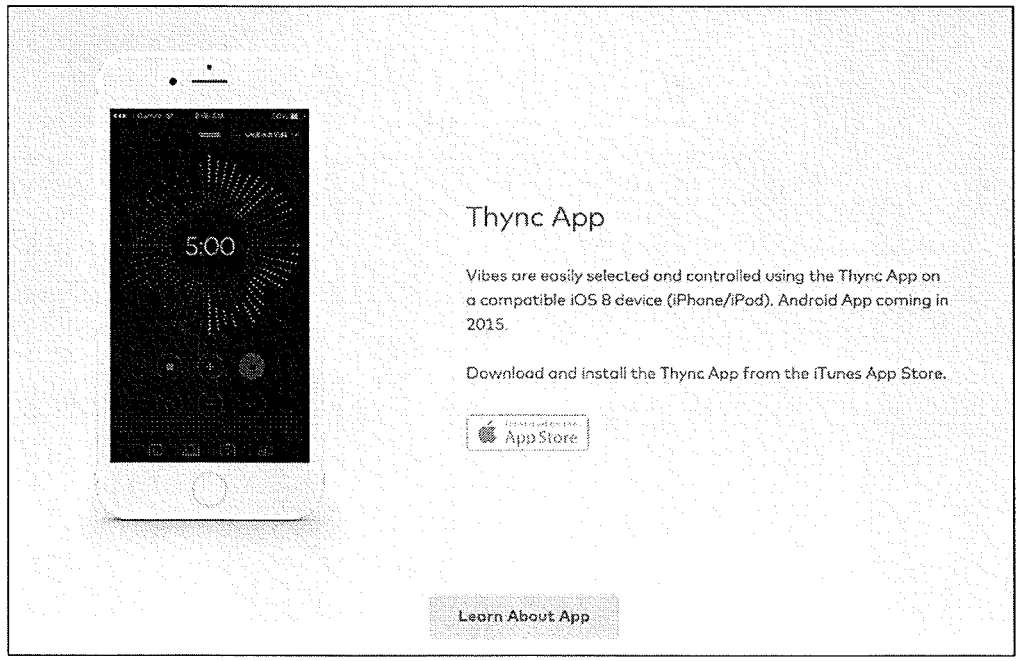
FIG. 56F shows a resource (e.g. website) describing a dedicated software (also referred to as a 'Thync App') on a user computing device for controlling a wearable neurostimulator.
Figure 57A:
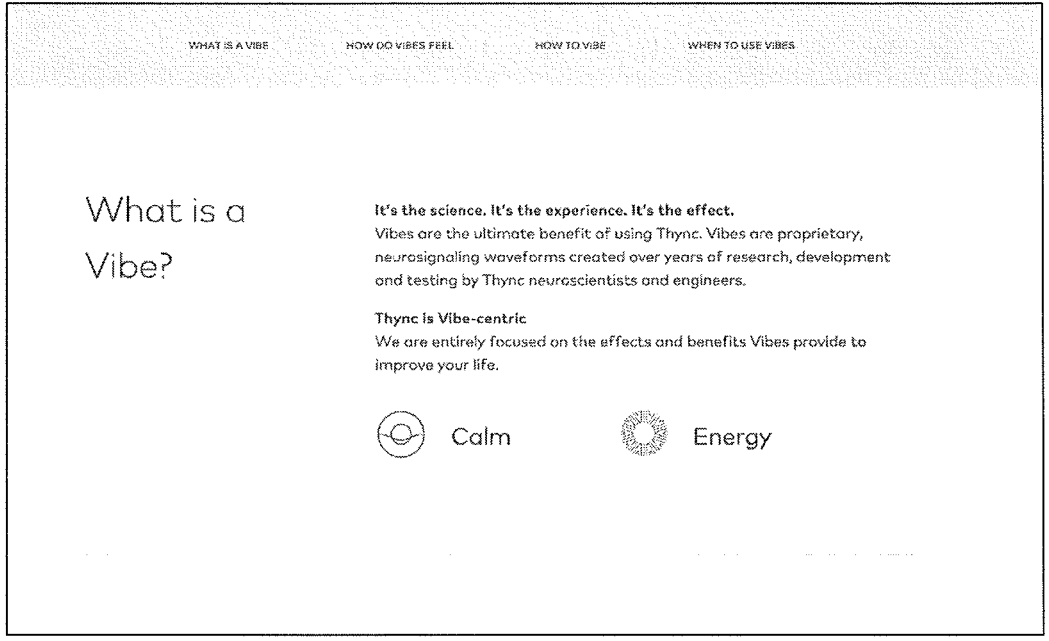
Figure 57B:
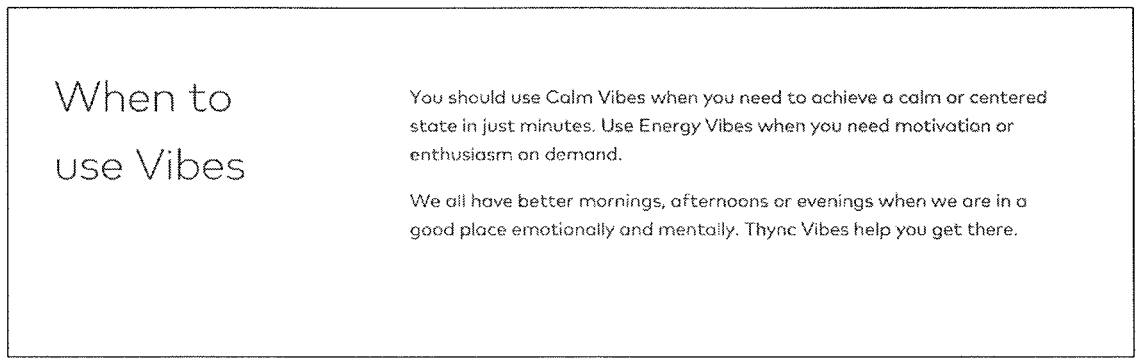
Figure 58C:
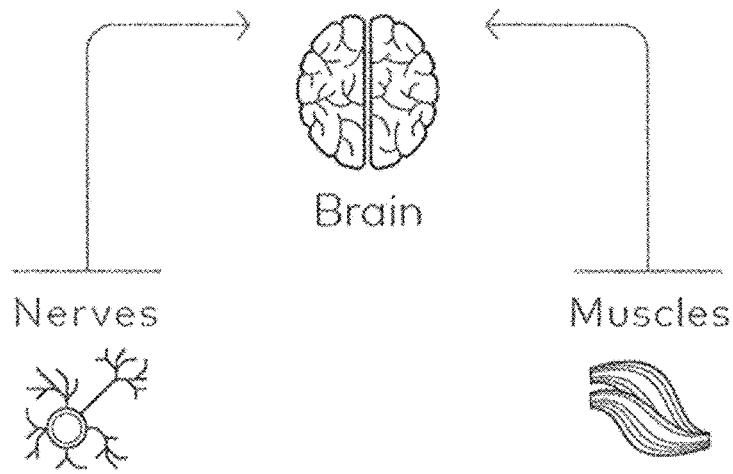
Figure 58D:
Figures 59A, 59B:
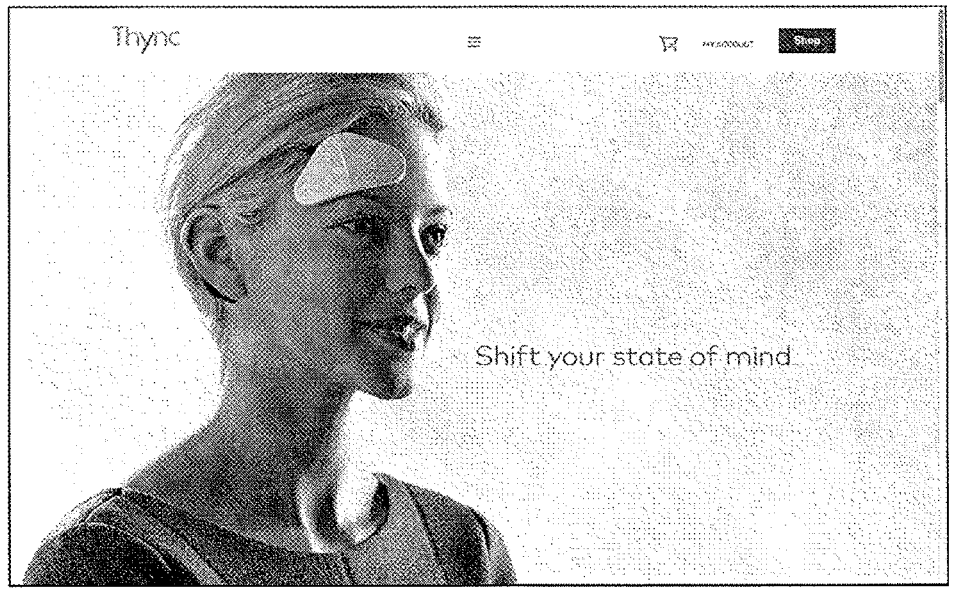
FIGS. 59A-59F show resources (e.g. websites) that describe a high level summary of a wearable neurostimulator system that uses TES to induce cognitive effects of increased energy or enhanced calmness in users.
Figure 59C:
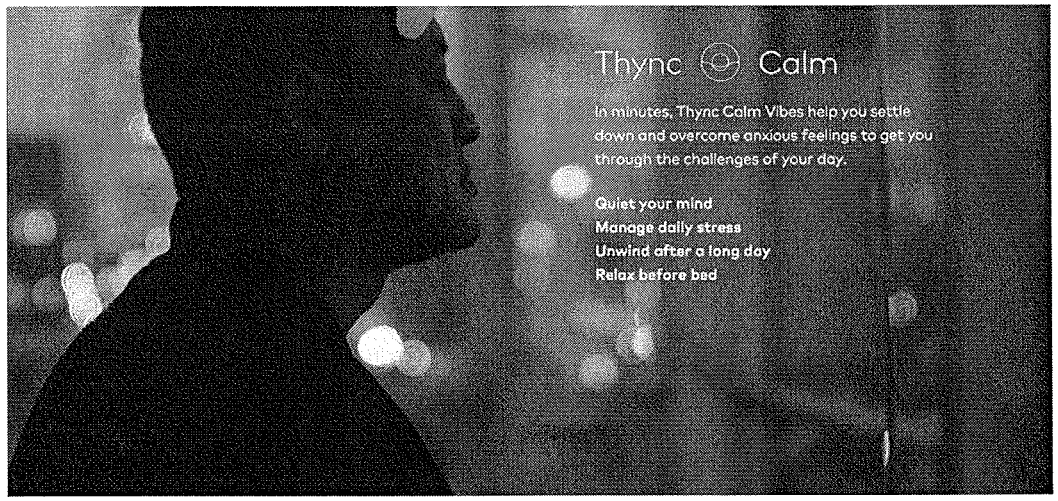
Figure 59D:
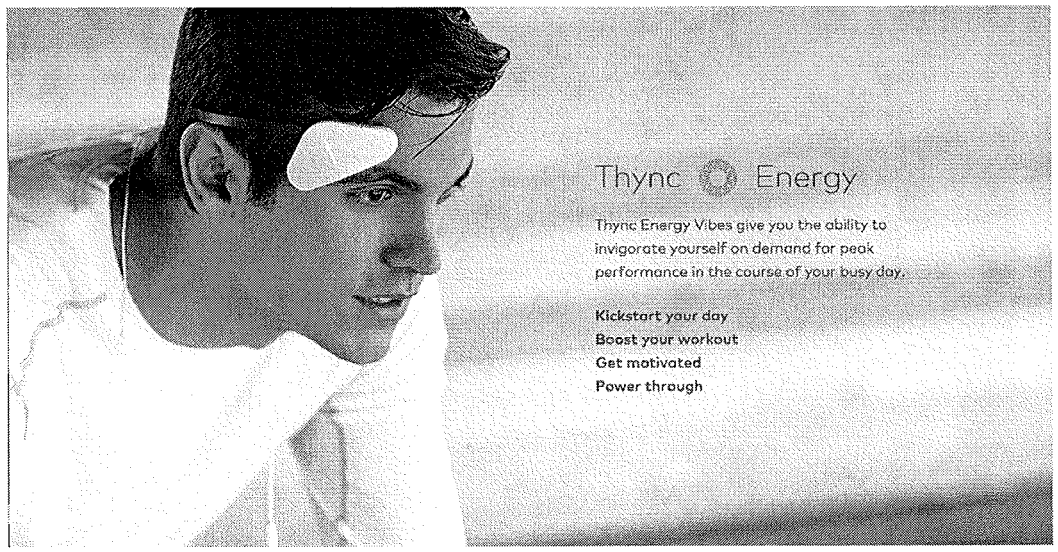
Figure 59E:
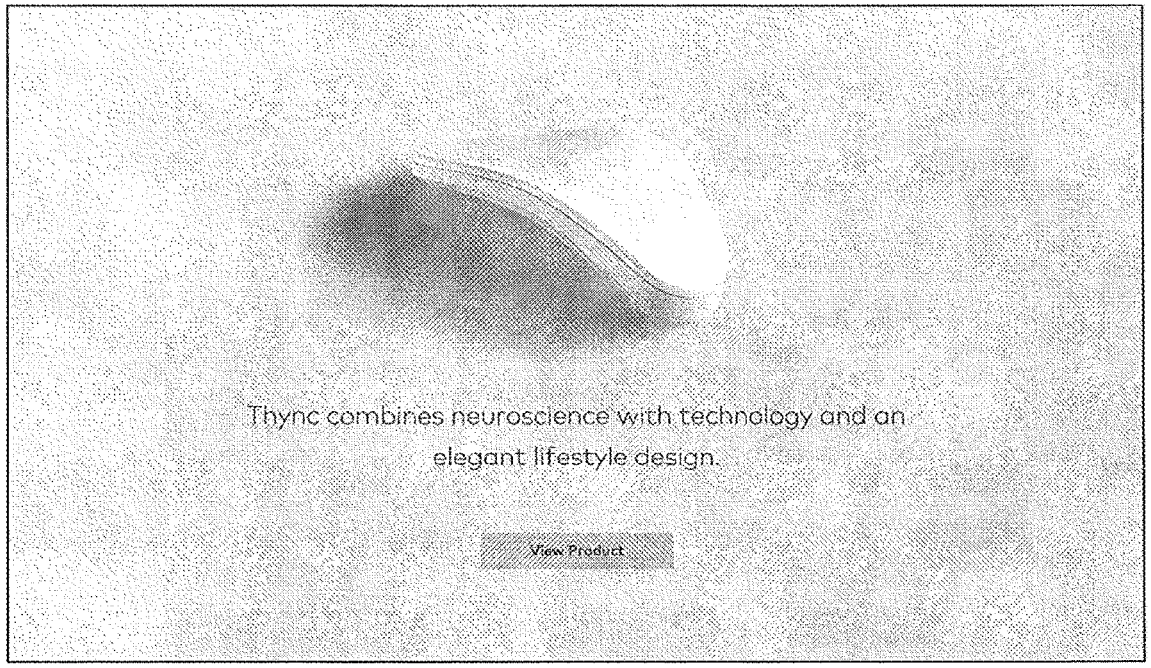
Figure 59F:
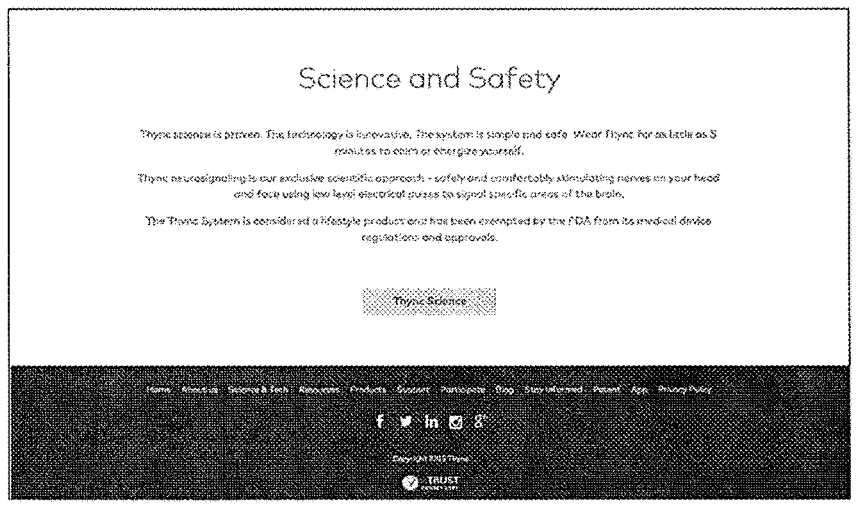

As illustrated in FIGS. 54P-55, the user may control delivery of the TES ensemble waveform, including modulating the intensity as the waveform is being delivered. Messages during a TES session may be displayed, e.g., by an app on a user interface of a user electronics device, and may instruct a user (especially beneficially for less experienced or naïve users) to find the correct intensity to achieve a cognitive effect with minimal discomfort by changing the intensity the right amount at the right time.

These messages occur at specific times relative to TES waveform onset with messaging appropriate for that epoch of the waveform. For example, within 5 seconds the UI may inform a user that: "vibe is ramping up"—No need to adjust Vibe tuner unless you find it comfortable to reduce the intensity; within 1 minute, the app may instruct the user that: "time to calibrate tuner," "tune the Energy Vibe to the highest level that is comfortable, "tune the Calm Vibe to the level where you start to feel pressure and then back off," etc. The app may also inform the user (e.g., at five minutes: "find your sweet spot" Adjust+/−6 and see how that feels after 15-20 seconds), or for "energy" vibes "look for heightened alertness, feeling of wanting to move around," or for calm vibes, "look for pleasurable tingles running up your neck, feeling detached and lighter," etc.

The apparatus may instruct new users in how to use a self-actuated wearable TES neurostimulator system is critical to ensure they use the system safely and correctly to achieve a cognitive effect. An animated video with a descriptive voice-over is an effective means for training naïve users. For example, any of the methods of operating or instructing a user to operate a TES apparatus such as those described herein may include the information (which may be presented by, e.g., an animated video that may use visuals and/or a voice over text) as follows: "The apparatus is wearable technology that uses neurosignaling to deliver on demand calm or energy in minutes. Using the apparatus to shift your state of mind is as easy as Snap-Stick-Shift." "This system has three components—the Applicator module, Vibe strips, and Vibes delivered through the app on your iOS device." "Turn ON by pressing the POWER button until the white light blinks. Make sure your module is fully charged. Then, turn on BLUETOOTH on your iOS device." "To PAIR the module, open the app on your device and follow the screen prompts. The white light will pulse to indicate pairing is underway and will become SOLID WHITE when successfully paired." "Energy strips have a different shape than Calm Vibe strips." "Select your Vibe strip and SNAP it directly onto the Applicator Module." "The module is designed and contoured to precisely fit this area on most people. Find the place where it rests FLUSH against your skin." "PLACE the module so that it lies on both your temple and forehead area, above your right eyebrow. You may need to move it around until it feels just right. Make sure no hair, oils or lotions are on the skin." "Remove the adhesive backing from the strip and press firmly for several seconds to STICK the module in place." "The Energy strip should be placed on the bone directly behind your right ear. The lower half of this bone, directly between your ear and your hairline, is the ideal location. The edge of the strip should just touch the back of your ear." "You may have trouble positioning this strip correctly on your first use. If you notice strong skin sensations at this location during a vibe, try pressing the strip down firmly—if this significantly reduces the skin sensations, this indicates that the strip is not making good contact with your skin and you will want to pause and adjust it." "The Calm strip should be placed horizontally and centered on the back of your neck, just below your hairline." "Remove the adhesive backing. Again, make sure no hair, oils or lotions are on the skin in this area. Press firmly for several seconds to STICK the end of the strip in place." "Once the Applicator module and Vibe strip are in place, running the vibe is easy to SHIFT your state of mind. Open the app on your iOS device, and select the type of Vibe that corresponds to the strip you have selected, 'Energy' or 'Calm.'" "For each vibe, there are 10 and 20 minute sessions available. A 10 minute vibe will give you the option to add two 5 minute extensions. Choose your desired session and the vibe TUNING screen will appear." "Press PLAY to start and wait at least 30 seconds before tuning the intensity of your Vibe. Press PAUSE or STOP before removing the unit." "After 30 seconds, use the + and—buttons to tune the intensity and comfort of your vibe to your unique physiology. Now . . . enjoy your Vibe!" Any method of operating the systems described herein (including incorporated by reference above) may include one or more of these statements, or an equivalent statement.

Alternatively or additionally, the following additional descriptions of the various embodiments of the invention is not intended to limit the invention to these embodiments, but rather to enable any person skilled in the art to make and use this invention. Disclosed herein are methods and apparatuses, and systems for user control of neurostimulation waveforms.

Lightweight and wearable apparatuses for applying transdermal electrical stimulation and methods of using them for inducing a cognitive effect are described. These apparatuses are typically self-contained, lightweight, and wearable devices and/or systems. The lightweight and wearable transdermal electrical stimulation apparatus for inducing a cognitive effect in a subject may generally include hardware, software and/or firmware components that are configured to generate appropriate control sequences for the device, transmit signals to a current or voltage source and/or conditioner, and connect to electrodes that are configured to be placed on a user for generating electrical currents. For example, the apparatus may comprise a controller configured to transmit sequences to a current generator. Thus, the apparatus may be configured for mobile use.

The apparatus may generally be configured to receive control information for controlling the stimulation. This control may include control of the start, duration, and timing of stimulation (e.g., on/off, duration, etc.) and/or may also include controls for the waveforms to be applied to induce a cognitive effect in a subject. In general, the induced cognitive effect is a function of the position of the electrodes (e.g., where on the head/neck the electrodes are positioned) and the stimulation parameters of the applied waveforms. An apparatus may include one or more manual controls (e.g., inputs) on the apparatus, and/or it may include wireless communication to a remote processor ("base station") that wirelessly transmits control information to the apparatus. For example, the apparatus may include a wireless module (e.g., sub-system, wireless circuit/circuitry, etc.) for wireless communication to the base station or via cellular networks to the Internet. A remote processor may be configured to transmit control signals to a current generator located in the device (e.g., within the primary unit). The remote processor may include non-transitory computer-readable storage mediums storing a set of instructions capable of being executed by a remote processor (such as a smartphone or the like), that when executed by the remote processor causes the processor to allow a subject to select one or more (or a set) of control parameters for controlling the lightweight, wearable apparatuses described herein. The set of instructions may include confirming a communication link with one or more lightweight, wearable apparatuses, presenting a list and/or menu of pre-selected control values (e.g., for one or more of current amplitude, current frequency, pulse width, pulse duration, pulse frequency, pulse waveform, burst duration, burst frequency, off-time, burst waveform, positive duty cycle, negative duty cycle, and on/off, etc.), or for allowing modification of one or more of these control values separately.

In general, inducing a cognitive effect can include inducing a response that a reasonable user is cognitively aware of. The effect can include a physiological change. For example, the effect can include a change in the amplitude or phase of brain rhythms. The effect can include a modulation of one or a plurality of the following biophysical or biochemical processes: (i) ion channel activity, (ii) ion transporter activity, (iii) secretion of signaling molecules, (iv) proliferation of the cells, (v) differentiation of the cells, (vi) protein transcription of cells, (vii) protein translation of cells, (viii) protein phosphorylation of the cells, or (ix) protein structures in the cells. The apparatus (device or system) may be configured so that the induced cognitive effect is perceived subjectively by the recipient as a sensory perception, movement, concept, instruction, other symbolic communication, or modifies the recipient's cognitive, emotional, physiological, attentional, or other cognitive state. Neurons and other cells in the brain and head area are electrically active, so stimulation using electric fields can be an effective strategy for modulating brain function. In various embodiments of the invention, the effect of electrical stimulation is one or more of inhibition, excitation, or modulation of neuronal activity.

The cognitive effects of TES may be transduced in part and in at least some instances via neuromodulation of a cranial nerve. Thus, improved TES systems and methods improve targeting and activation of appropriate cranial nerves by mapping the particular location (and/or physiology) of a cranial nerve in a subject. Personalization of electrode position(s) and/or TES waveforms so that a cranial nerve can be targeted effectively by TES (and off target effects minimized in cranial nerves that do not induce a desired cognitive effect) would be advantageous for improved intensity and reliability of an induced cognitive effect while also minimizing side effects (e.g. discomfort due to higher than necessary stimulation intensity being necessary to activate a cranial nerve via less than ideal electrode positioning). Mapping of cranial nerves may be achieved by one or more of the group including, but not limited to: imaging, electrical stimulation, muscle recording, nerve recording, or other physiological measurement known to correlate with activation of a particular cranial nerve.

The neurostimulator apparatus can be small and lightweight to be wearable. For example, in some variations the maximum dimension of the housing is less than about 10 cm (e.g., less than about 9 cm, 8 cm, 7 cm, 6 cm, 5 cm, 4 cm, 3 cm, etc., between about 10 cm and about 2 cm, etc.) The wearable neuromodulation devices can be configured to be worn on a subject's head or on the subject's head and neck. The electrode apparatuses can be used with the wearable neuromodulation devices. These electrode portions may also be referred to as cantilevered electrodes. Any of the neurostimulator apparatuses described herein may be used with or may include an electrode apparatus (e.g., a cantilevered electrode, electrode assembly, or cantilevered electrode apparatus); in some variations the electrode assembly (or sub-assembly) may be included as part of the neurostimulator apparatus or may be integrated into/onto the neurostimulator apparatus. Although the single-piece electrode assemblies (that are flat, adhesive members having a first portion onto which the housing of the neurostimulator attaches), as shown in FIGS. 63A-67B are described herein, any electrode apparatus/assembly may be used, including two or more pieces that are separate (and connected by wires, etc.).

FIG. 60A illustrates one variation of a lightweight and wearable electrical stimulation apparatus (e.g., neurostimulator apparatus) that may be worn on a subject via attachment to an electrode assembly; the electrode assembly is a flat, adhesive member that is worn on the user's head, directly against the skin, while the neurostimulator apparatus is connected to the back (non-user facing side) of the electrode assembly. The neurostimulator devices may be small, lightweight and specifically adapted to be conforming to the subject so that they can be worn while the subject goes about their daily activities. Described herein are features or elements that allow or enhance this functionality. These apparatuses (which generally may include systems and devices) may be adapted to be worn on the subject's head (e.g., at the temple and/or forehead region) comfortably even while wearing headgear such as hats, glasses, hoods, scarves, or the like. These neurostimulator devices typically can have a first surface (subject-facing surface) that has a curved and/or twisted shape so that an electrode on the surface conforms to a subject's temple and/or forehead region. The apparatus may also be configured to cantilever off of the electrode assembly, as described below.

In some embodiments, the subject-facing surface can be specifically contoured to fit in the predefined orientation, making it difficult or impossible for a subject to misapply, and risk placing the active region of the attached cantilevered electrode apparatus in the wrong place. This surface can be a section of a saddle shape, in which there is an axis of curvature around which the surface is concavely curved, and an axis of twisting, which may distort the curved surface (the two axes may be different or the same). In addition, these surfaces may be flexible, bendable or otherwise configured to contour to the shape of the subject. As will be described in greater detail below, in some other embodiments, this subject-facing surface can be configured to generally conform to a contour of the head (e.g., include having a user-facing surface that is curved and/or twisted as described herein) but be adapted to cantilever relative to the electrode assembly and/or head, so that one end may "float" at a distance away from the user's head (that may vary between different users or even on the same user from one use to the next) to allow the apparatus to fit various sizes of the heads of the subjects. The electrode apparatus/assembly (which can be referred to as a cantilevered electrode assembly), can be attached to the neurostimulator. The electrode assembly may flex or bend so that it may be secured directly against (e.g., to match the curvature) of the users head. The electrode assembly can be configured to contact the skin of the head of the subject to provide tight fit and good electrical connection. The neurostimulator apparatus may be connected directly to the electrode assembly, so that the electrode assembly holds the neurostimulator apparatus to the user's body.

In general, a neurostimulator apparatus may be adapted to conform to any region of a subject's head. In particular, described herein are neurostimulator apparatuses that are configured to conform to a subject's forehead and/or temple region by having a user-facing surface that is curved and/or twisted so that it approximately conforms to the outer curvature of this region of a generic user's head, but may be oversized, so that it is slightly less curved and/or twisted than the forehead and/or temple region of an average adult. FIGS. 75A-76C illustrate this portion of a user's head, and a configuration of a user-facing surface of a neurostimulator apparatus as described above.

FIG. 75A illustrates a right temple region (more generally a temple/forehead region) onto which a neurostimulator apparatus may be connected, including connected through an electrode apparatus. For example, as described above, the neurostimulator apparatus may have a low profile, particularly on the end to be worn closest to the cheek when worn correctly, so that the user can wear glasses and the frames of the glasses can fit around/over the neurostimulator apparatus when the unit is coupled to the user's temple/forehead region.

When the neurostimulator apparatus is configured so that the user-facing surface is curved to fit this region, the curvature and shape may also help guide the user in applying/wearing the apparatus. For example, the user-facing curvature of the transdermal neurostimulator apparatus may guide the user in positioning the device correctly relative to landmarks on the head, such as the eyes (e.g., a line between the corner of the eye and the ear 751604), eyebrow, hairline, or forehead (e.g. midline of forehead). FIG. 75A shows a rendering of a user 751601 with a generic neurostimulator apparatus housing 751603 positioned over the right temple and forehead region so that an edge of the neurostimulator apparatus is at or near the line between the edge of the user's right eye and the ear. Line 751602 indicates an axis (which may be referred to as a primary axis, or as a temple axis) along which the user-facing surface of the neurostimulator apparatus may be curved. This is similar to the positioning of the neurostimulator apparatus shown in FIG. 60A, described above.

FIG. 75B shows a workflow for using a plastic contour gauge to measure the curvature of a user along line 751602 (the temple axis). In this example, a contour gauge may be pressed against the user's temple and forehead region, capturing an impression on the contour gauge that may be captured by a processed (e.g. thresholded) image 751605. By applying an edge-finding algorithm 751606, a curvature 751607 and alignment/scaling bar 751608 may be determined. This process has been repeated multiple times from a population of human adults to generate an empirical determination of the surface characteristics, including the curvature (including twist about a twist axis), and an example of this is shown in FIG. 75C.

FIG. 75C shows aligned temple/forehead contours for n=20 subjects, as well as two exemplar curvatures of a surface (which may be used to generate a surface for a neurostimulator apparatus to be worn at the temple/forehead region). Surprisingly, the information between different users, even users of a diverse range of body shapes and sizes, as well as users of different ages, are remarkably similar over this region. By using a derived curvature to generate a user-facing surface of a neurostimulator apparatus that is matched to facial curvature at the correct position for the electrode, the apparatus may be more comfortably worn, and users may also be more likely to place (adhere) the unit correctly. In some embodiments, additional features can be added to the housing so that misalignments (e.g. adhere to left rather than right side; adhere too low, too close to eye, too medial (towards midline of forehead)) are more uncomfortable for a user and thus easier to recognize. As mentioned above, the resulting data may be multiplied by a factor (e.g., 1.1×, 1.2×, 1.3×, etc.) when using this information to generate the curvature/twist of the user-facing surface of a neurostimulator apparatus configured to be worn there. Multiplying by a factor may be beneficial for neurostimulators configured for use with a cantilevered electrode.

In any of the transdermal neurostimulators described herein, and particularly those that are connectable to a subject via attachment with an electrode apparatus (as illustrated in FIGS. 60A and 60B, above), the neurostimulator may include a housing that both encloses much of the electronics (e.g., a controller, current source, etc.) and also has a user-facing surface that is curved based on the region of the head where it will be positioned. In particular, the user-facing housing, which may be referred to herein for convenience as a bottom surface, may be concave and twisted along an axis of twist so that it fits this temple/forehead region. As shown in FIGS. 75A-75C, this region may be curved (e.g., along the temple axis) as shown, and it may be twisted along an axis of curvature.

FIGS. 76A-76F illustrate how a surface, such as the surface of a neurostimulator apparatus, may be twisted. In FIG. 76A, the surface of the block (rectangular piece 761702) is shown; FIG. 76B shows the same piece 761702, twisted about the axis of twist (twist axis 761704). This twisting is illustrated in FIGS. 76C and 76D, looking down from a top view along the axis of twist 761704, before (FIG. 76C) and after (FIG. 76D) twisting approximately α degrees (where the angle of twist, α) may be determined as the angle between two lines (in FIGS. 76E and 76F, 761722 and 761723) that are perpendicular to the axis of twist 761704 (the vertex of the angle) along a predetermined length of the axis of twist (e.g., the distal L in FIG. 76A). In this example, the angle α is approximately 15 degrees over the length L of the surface 761702. This surface may also be curved, which may result in curvature of the axis of rotation 761704.

In practice, any of the apparatuses described herein may include a user-facing surface that is twisted along an axis of twist. For example, FIGS. 77A-77B illustrate one example of a neurostimulator apparatus having a user-facing surface with an axis of twist 771804 about which the ends of the device are twisted, which may enhance the comfort and wearability of the neurostimulator apparatus, even when connected to an electrode apparatus that is connected to the users head (e.g., temple/forehead region). In FIG. 77A, the axis of twist extends along the user-facing surface of the apparatus; in other variations it may also be curved, and ill particular, may be concave. The twist angle in this example may be estimated from the acute angle formed between the lines that extend normal (perpendicular) to the twist axis over a length, L. As shown in FIGS. 77A, 77B, and 77C, this angle between vectors 771822 and 771823 is approximately 30 degrees over a length of approximately 30 mm (which may be expressed as 1 degree/mm in this example). As described above, the twist of the user-facing surface may vary between, for example, 0.07 degrees/mm and 1.5 degrees/mm.

Tactile and shape cues are beneficial features of TES electrodes and housings for durable components (i.e. power source, microprocessor, current control circuitry, wireless transmitter, etc.) for TES systems intended for self-placement. In general, an edge, corner, or other feature of the shape of a component of a TES system is configured to align, orient, or otherwise position relative to a feature of a user's anatomy. A mirror or video camera (i.e. front-facing camera on a smartphone or tablet) can help a user to guide placement for electrodes in a visible area (e.g. on their face). However, tactile and shape cues for correct placement are useful for circumstances when visual feedback is not possible, including when a mirror or camera is not available, as well as for electrode placements in areas that cannot easily be viewed with a single mirror such as the back of the neck or behind the ear.

For methods that use shape and/or tactile cues for correct electrode or housing self-placement by a user, appropriate instructions (e.g. contained within a kit or provided by a set of images or video) may help a user to understand how to effectively use the shape or tactile cues in placement. In general, shape or tactile cues are beneficial for guiding a user to orient an electrode or TES housing containing an electrode correctly and to place it (wear it) in an appropriate location for delivering electrical stimulation to a target neural region to induce a desired cognitive effect. Cues that relate to common anatomical landmarks are particularly advantageous. The following several examples illustrate how shape and tactile cues can guide positioning of electrode components.

Returning now to FIG. 75A, the rendering shows a TES controller assembly 751603 that contains an electrode in its dermal-facing portion (electrode not shown) on a user 751601. The housing shape of has several anatomical guides so that a user can more easily self-place the housing and underlying electrode in a correct location for inducing a cognitive effect via TES neuromodulation. For instance, the shape of the unit makes it less comfortable when placed on the incorrect side of the face (left) rather than the correct side (right). Instructions provided to a user may identify the shape and tactile cues so that correct anatomical placement is achieved. Straight edge 751604 is designed to be horizontal and aligned to the edge of the right eye. Curved edge nearest the eye wraps around the eye and eyebrow. A raised line may be aligned to the edge of the eyebrow and provide a clear tactile cue such that a user can extend their finger along his/her eyebrow and continue along the raised line. The alignment cue may also be achieved by a button, tab, or any other aligned tactile cue. Alternatively, an LED (which may be observable by the eye beneath, with a mirror, or by a front-facing camera e.g. on a smartphone) can be incorporated in a TES controller housing and may be further configured so that it only turns on when aligned properly. The LED or set of LEDs may be configured similarly to lights on an airport runway that are only observable from particular orientations and thus guide approach angle for landing.

FIG. 85 shows a CAD rendering of a curved, crescent-shaped electrode unit designed to target the right mastoid area behind the ear. The curve of the electrode guides the user to place it on his/her right mastoid (rather than his/her left). A silicone printed logo (alternatively a tab or button or any other tactile cue) is positioned near the center of the electrode and guides a user to place that section directly overlying the bony process of the mastoid. The adhesive areas are positioned so that they do not cover the center of the mastoid yet also do not overlap significantly with areas having hair.

FIG. 86 shows a CAD rendering of a round electrode unit designed to target the neck, centered slightly to the right of the midline. The active electrode area is off center from the full unit (i.e. the white adhesive area is wider on the left than on the right). Also a silicone printed logo tab (alternatively a tab or button or any other tactile cue) is positioned so that a user can align it with a vertebra. An alternative electrode shape for guiding neck placement slightly to the right of the midline is shaped like a capital 'D' and intended for the straight edge to be aligned with the spine.

FIG. 87 shows a CAD rendering of an oblong electrode unit designed to target the right temple area above and to the right of the right eye. A first silicone printed logo tab (alternatively a tab or button or any other tactile cue) is positioned so that a user aligns it to the right of their forehead and a second silicone printed logo tab (alternatively a tab or button or any other tactile cue) is positioned so that a user aligns it to their cheekbone. The asymmetric shape guides correct placement on the right side of the face rather than the left.

In general, a transdermal electrode assembly or TES controller assembly that incorporates a transdermal electrode may include a buzzer, piezoelectric material, ultrasound transducer (e.g. CMUT), or other transducer for activating a sensory transduction pathway as a signal for alignment (align the buzzing portion to the side of your eyebrow) or signal of alignment (buzzer activates for correct placement or changes its frequency to indicate closeness to an optimal location).

In general, a transdermal electrode assembly or TES controller assembly that incorporates a transdermal electrode intended for placement near the right temple area may be designed with a low profile on the end closest to the cheek when worn correctly so that glasses frames can fit around the unit when the unit is adhered to a subject's skin (or otherwise worn by the user).

In general, TES systems may improve targeting and effective electrode positioning by using an array of electrodes. For instance, the circuit may be designed so that all active electrodes in the array are isoelectric (i.e. shorted). By selecting a subset of an array of electrodes based on positioning of the entire unit, the accuracy of placement of the active electrode region can be improved without requiring that a subject accurately place the entire assembly or array. These embodiments require components and/or methods to determine the actual location of the entire assembly or array, then a way to manually or automatically select a subset based on desired targeting. Any shaped array, any number of electrodes, and any means of determining the location and orientation of the array can be combined to select an appropriate subset of electrodes for improved targeting.

For example, FIG. 88A shows a schematic of an electrode arrays with long, radial electrodes 882901, 882902, 882903, 882904, 882905, and 882906. In FIG. 88A, the array is positioned correctly to target a right temple area, so all electrodes are active. In FIG. 88B, the unit is placed too low, so only electrodes 882903, 882904, and 882905 are active. In FIG. 88C, the unit is rotated and too medial, so only electrodes 882904, 882905, and 882906 are active.

In general, the housing of the neurostimulator apparatus may also have a top surface that is opposite from the user-facing bottom surface. The housing generally includes a thickness in a direction that is generally transverse (or normal) to the bottom and/or top surface, defining the region between these surfaces. Any of the surfaces referred to herein may refer to generally smooth surfaces, though they may include one or more gaps, protrusions, or the like. For example, the user-facing surface 771819 in FIG. 77A includes two openings where the connectors (connector receivers 771805 and 771807) are located.

Figure 62E:
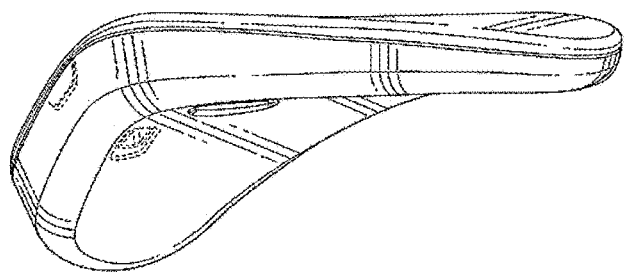
FIGS. 62A-62F illustrate front, back, left side, right side, top and bottom perspective views, respectively, of a variation of a neurostimulation device (electrical stimulator) in accordance with some embodiments of the disclosure.
Figure 62D:
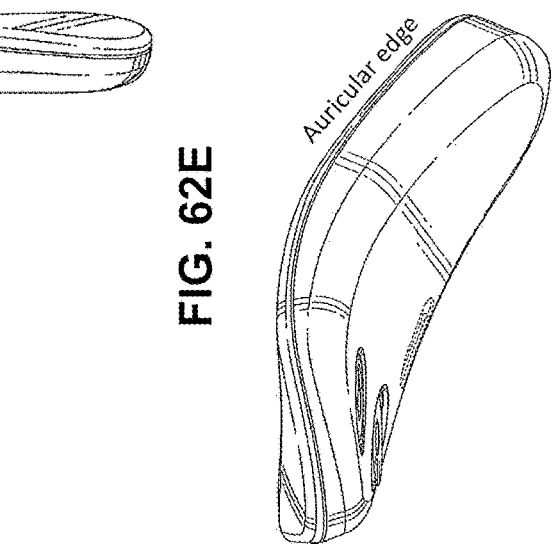
Figure 62C:
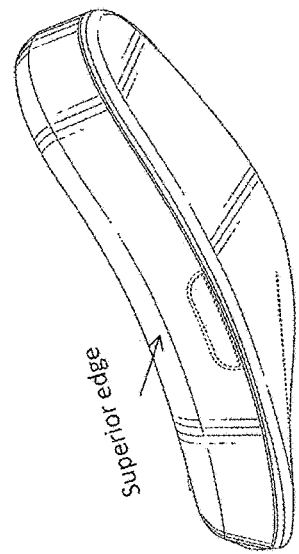
Figure 62F:
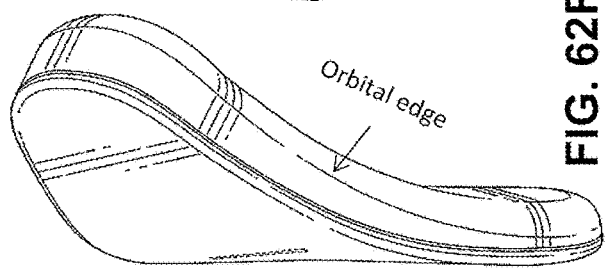
Figure 62A:
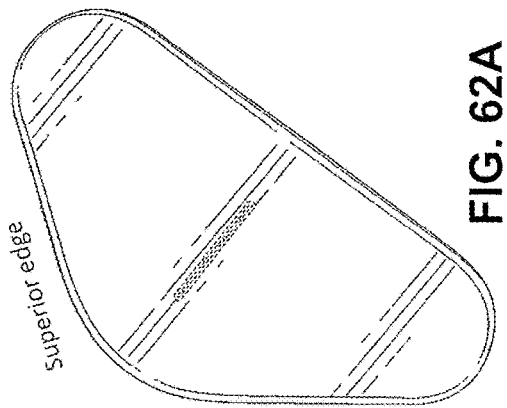
Figure 62B:
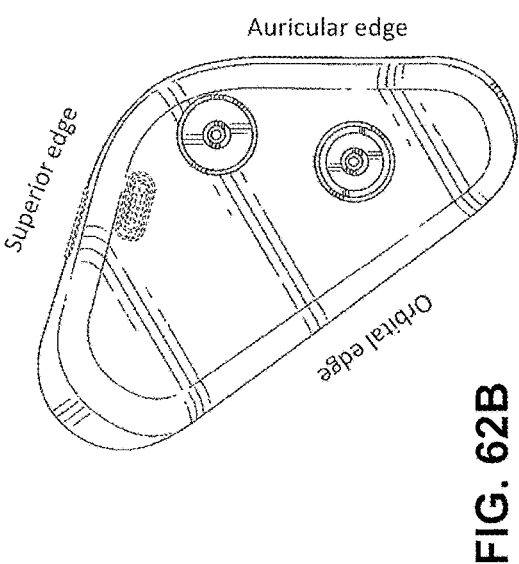

As described above, the thickness of the housing of the neurostimulator apparatus may be non-uniform, and may be thicker in some regions than in others. Thus, the upper surface may have a different shape (twist, curvature, etc.) than the lower surface. Returning to FIG. 61B, showing an example of a housing of a neurostimulator apparatus, the housing includes a first edge region 61250 at one end having a first thickness 61256 and a second edge region 61252 at second end having a different (and in this example, larger) thickness 255. The thicknesses in this example are measured between the user-facing concave bottom surface and the top surface, and the first edge region 61250 is thinner than the second edge region 61252. Other edge regions may be taken, but in this example, the two edge regions are opposite of each other along the longest dimension of the apparatus (the orbital edge shown in FIG. 62B). In general, the housing is thin, and may have an average thickness of less than about 30 mm (e.g., less than about 25 mm, less than about 20 mm, less than about 15 mm, less than about 10 mm, less than about 8 mm, etc.).

The housing may have a thickness between the user-facing surface and the top surface that is more than 15% greater at one end of the neurostimulator than at an opposite end of the neurostimulator. In the example shown in FIG. 62E, the thickness of one corner end/edge region (between the auricular and orbital edges) is approximately 0.5× the thickness of the opposite edge region (e.g., the corner region between the superior and orbital edges). Thus, one region has a thickness that is approximately 2× the thickness of another region (approximately 100% thicker). In general, the thickness of the housing between the top surface and first surface may be more than 50% greater at one end of the neurostimulator than at an opposite end of the neurostimulator (or greater than 60%, greater than 70%, greater than 80%, greater than 90%, greater than 100%, etc., though generally less than 500%).

As mentioned above, the neurostimulator apparatuses described herein generally include one or more connectors on, in, or extending from the user-facing surface. In FIGS. 60B, 62B, 62D, 77A, and 77B, apparatuses are shown having a pair of connectors, both configured as female (receiving) connectors that can receive protruding snaps from an electrode assembly, such as the one shown in FIGS. 63A-67B, described in greater detail below. Referring, for example, to FIG. 77A, the first 771805 and second 771807 connectors on the user-facing concave surface 771819 are positioned off-center relative to the user-facing concave surface. As mentioned, in this example, the connectors are snap receivers. The first 771805 and second 771807 connectors are each configured to make an electrical and a mechanical connection with a connector mate (a snap) on an electrode apparatus, as illustrated and described herein with reference to FIGS. 61A-61C. The first and second connectors may be separated by any appropriate length, which will be described in greater detail below. In FIG. 77A, they are separated by between about 0.7 and 0.8 inches (approximately 17.78 mm and 20.32 mm) on center, or about 0.74 inches (approximately 18.80 mm).

In many of the examples shown here, the neurostimulator apparatus is configured so that the first and second connectors secure an edge region of the user-facing concave surface to the electrode apparatus while permitting an end of the user-facing concave surface opposite from the edge region to move relative to the electrode apparatus. This allows the neurostimulator apparatus to be cantilevered over the electrode apparatus (and the user) as illustrated in FIGS. 61B and 61C, so that one end or edge region 61250 is mechanically held relatively fixed to the electrode apparatus 61239 and the user by the pair of connectors (not visible in FIG. 61B), while an opposite end region 61250 is allowed to float, held cantilevered over the electrode apparatus 61239, as shown by the arrows 61230. Thus, as the user wearing the apparatus moves her face (including changing her expression, talking, etc.) the separation between the second end region 61252 and the electrode assembly 61239 (and user) may change without putting stress on the electrical and mechanical connection between the electrode assembly and the neurostimulator housing. Reducing stress on the connectors between the electrode assembly and snap receptacles of the neurostimulator may improve comfort and efficacy of TES waveforms by eliminating or mitigating transients (i.e. 'shocks') caused by intermittency of connection between the connectors of the electrode assembly and neurostimulator.

In general, a connector between a transdermal electrode and a durable assembly of a TES system may use a connector that has a magnet (i.e. a 'maglock' or magnetic power connector), wherein one polarity of the magnet is on the connector of the electrode and a magnet of the opposite polarity is contained within a durable portion of the TES system. Magnetic connectors can enable automated alignment of electrically conductive and/or mechanically matched components (e.g. to fit together and transmit current from the controller to the electrode).

The spacing between the connectors connecting the electrode assembly and the housing of the neurostimulator apparatus may be configured to permit the cantilevered connection. For example, spacing that is less than about 0.5 inches (approximately 12.7 mm) may be too close and may permit torqueing or dislodgement of the housing of the neurostimulator, particularly when the housing is sized as described herein (e.g., having a largest length dimension of greater than about 4 cm, and in some instances less than about 15 cm) and weighing less than about 7 ounces (e.g., between 0.1 ounces and 7 ounces). Spacing that is larger than about 1 inch may, in some variations, make the connection overly stiff, and prevent the apparatus from connecting to different head curvatures. The inventors have found that spacing generally between about 0.5 and 1 inch may provide a stable and comfortable attachment, preventing a large moment arm from developing even for larger sizes/weights of devices.

By positioning the connectors off-center relative to the user-facing surface (e.g., along a first end/edge region, the opposite end/edge region may be allowed to move somewhat relative to the electrode assembly beneath it, as described above. For example, returning to FIG. 62B, the pair of connectors (snap receivers) shown are positioned off-center from the bottom of the device nearest the auricular edge of the device, while the opposite end (the intersection between the superior edge and the orbital edge) would be allowed to float relative to the other end/edge region when connected to an electrode assembly.

In many of the examples described herein, the neurostimulator housing is trianguloid, having three sides (in FIG. 62B, the superior edge, auricular edge and orbital edge, each slightly curved) with three "corners" that are rounded.

In some embodiments, the neurostimulator can be configured to fit under the temple portion of an eyeglass frame for users wearing glasses, thus the portion of the combined assembly (electrode assembly and neurostimulator) can be thin enough to fit between glasses and the temple region. In some embodiments, the thickness at a first end of the neurostimulator that is configured to extend between an eye and a temple of the subject can be sufficiently thin to fit under an eyeglass frame of the subject. For example, the thickness at the first end can be between 0.1 and 10 mm (e.g., between 1 mm and 8 mm, between 2 mm and 7 mm, etc.).

In some embodiments, however, it may also be beneficial to have some portions of the neurostimulator be sufficiently thick to allow the apparatus to contain a sufficient battery (or other power portion) so that the unit can be used for a reasonable amount of time between charges. Thus one portion of the neurostimulator may be thick enough to allow a standard battery and/or circuitry at one end (e.g., an end that is worn higher up on the face). Thus, it may be beneficial to locate the mechanical/electrical connectors, such as snaps, that extend proud from the cantilevered electrode assembly toward the thinner end, separated from the battery compartment of the neurostimulator to reduce the overall thickness of the system in some variations, allowing the connectors to fit under or within through-holes of a PCB rather than under a thick battery portion (or under both). However, it may be beneficial to have the connector(s) positioned under the battery portion or have one connector under the battery portion and one connector under the thinner region separated from the battery portion.

For example, in some variations it may be beneficial to have one connector on the electrode assembly (e.g., cantilevered electrode assembly) near the portion of the neurostimulator hardware that is highest up on the forehead; this may help ensure that this upper portion of the device doesn't pull away from the electrode. If that happens, then the weight of the neurostimulator may pull the electrode further from the head and eventually lead to poor contact between the electrode active area and the skin. An adhesive may be used between the neurostimulator and the electrode assembly to prevent this; alternatively or additionally an additional mechanical connector may be used (an adhesive may be considered one type of mechanical connector, and may be present on the electrode assembly and/or on the neurostimulator body). It may also be beneficial to have at least one of the electrical/mechanical connectors (such as a snap) at or near (and preferably behind) the active area of the first electrode portion, as this may make the electrical connection with the hardware unit easier and more robust.

In some embodiments, the thickness of the device (measured from the first surface) can be thinner at one end and thicker at the other end. As shown in FIG. 60A, the thinner end 1 may be configured to be oriented relative to the subject's eye, with the thicker region 2 worn higher on the subject's head. The neuromodulation devices described herein are also configured to include attachments to the cantilevered electrodes on the underside (e.g., the first surface), providing electrical connection to at least two electrodes on the cantilevered electrode assembly. These neuromodulation devices may also be referred to as neurostimulation devices, neurostimulators, neuromodulators, applicators, neuromodulation applicators, electrical stimulators, or the like.

In some embodiments, for example, the overall shape of the neurostimulator can be triangular (including rounded edges) as shown in FIG. 60A. As used herein triangular includes shapes that have rounded/smooth transitions between the three sides, as illustrated. The side of the unit 3 worn toward the ear can be the auricular edge, the side 4 worn highest on the forehead can be the superior edge, and the side 5 worn nearest the eye/eyebrow can be the orbital edge. In some other embodiments, the device may have a differently shaped profile. For example, the profile can be generally rectangular, generally trapezoidal or generally ovular. The profile can have rounded edges or generally sharp edges.

As shown in FIG. 60B, the first surface of the neurostimulator, to which the cantilevered electrode apparatus attaches, may include mating junctions (openings, receptacles, female receivers, etc.) to receive and make electrical and mechanical contact with the connectors on the cantilevered electrode apparatus. These receivers may also be positioned to optimize the placement of the cantilevered electrode apparatus, allowing it to make sufficient contact with the neurostimulator and subject, and prevent the cantilevered electrode apparatus from bending or breaking contact, even while the subject is mobile and/or active.

In some embodiments, the wearable transdermal electrical stimulator may include a button for control by the subject. The subject may use the button to stop or reset the neurostimulator when necessary. In some embodiments, the wearable transdermal electrical stimulator may include a light indicator configured to provide visual feedback or a transducer for providing tactile feedback. For example, the light indicator can be used to indicate the connection of the electrodes, the status and progress of the TES stimulation session. For example, the tactile indicator can be used to indicate function of the device (e.g. 1 minute left in waveform; batteries low; placement incorrect, etc.) while worn on the head when a user cannot easily view a visual indicator without a mirror or front-facing camera of a smartphone or the like.

FIG. 61A illustrates a variation of an electrode apparatus 61200 worn on a subject's head. Examples of electrode apparatuses may also be seen in U.S. patent application Ser.

No. 14/634,664, titled "CANTILEVER ELECTRODES FOR TRANSDERMAL AND TRANSCRANIAL STIMULATION," and filed Feb. 27, 2015 and herein incorporated by reference in its entirety. As illustrated, the apparatus is positioned with the first electrode portion on the temple and forehead region and a second electrode portion behind the head (e.g., behind the ear or neck region, not shown). In this example, a neurostimulator (not shown in FIG. 61A) may be attached to the cantilevered electrode apparatus either before or after it is applied to the subject. For example, the mechanical and electrical connectors may be snapped together between the housing of the neurostimulator and the electrode apparatus.

FIGS. 62A-62F illustrate perspective views of one variation of a neurostimulation apparatus. In some embodiments, the overall shape of the neurostimulator may be triangular, and particularly the surface of the neurostimulator (though curved/concave and twisted) adapted to connect to the electrode apparatus and face the user may be three-sided (e.g., roughly triangular). As mentioned above, this roughly triangular shape may include rounded edges, and the thickness of the stimulator (in the direction perpendicular to the surface contacting the cantilevered electrode apparatus) may vary, e.g., be thinner along one side, and particularly the side (the portion between the orbital edge and the auricular edge) that will extend between the eye and the temple. This shape may also be beneficial when helping to fit and/or be worn on most people in a region of the head (e.g., face) that tends to not have hair. This thin lower corner (the orbital/auricular corner) may fit between the eyebrow and hairline, while the wider portion is positioned up in the forehead area where there is less likely to be hair.

In FIGS. 62A-62F the various edges are labeled, based on where the apparatus will be worn by the subject, similar to what is illustrated in FIG. 60A. In general, the side of the unit worn toward the ear is the auricular edge, the side worn highest on the forehead is the superior edge, and the side worn nearest the eye/eyebrow is the orbital edge. In some embodiments, the overall shape of the neurostimulator can be triangular (including rounded edges). In some other embodiments, the overall shape of the neurostimulator can be of a variety of shapes. The subject-facing surface can be contoured to fit in the predefined orientation. This surface can be a section of a saddle shape, in which there is an axis of curvature around which the surface is concavely curved, and an axis of twist, which may distort the curved surface. When attaching the cantilevered electrode apparatus to the neurostimulator, the cantilevered electrode apparatus may flex or bend so that it is contoured to match the curved and twisted surface.

In general, the electrode apparatuses described herein may act as an interface between the wearable, lightweight and self-contained neurostimulator ("electrical stimulator") and a subject's body, particularly the head or head and neck region, where stimulation is to be applied. These cantilever electrode apparatuses may be disposable (or semi-disposable) components that are connected to the neurostimulator and applied directly to the subject; energy (typically current) from the neurostimulator is guided and delivered to the subject by the cantilever electrode apparatus. Although the neurostimulator may be small and lightweight, the cantilever electrode apparatus may allow it to secure to the subject's body and deliver energy to two or more regions on the body (e.g., temple, neck, chest, etc.) that are separated by a distance that is much greater than the size of the neurostimulator.

The cantilever electrode apparatuses described herein generally include at least two electrode regions, separated from each other along an elongate body. The cantilever electrode apparatus typically attaches to the neurostimulator device by two (or more) electrical connectors (which may be referred to herein as connectors) that are in electrical contact with the electrode regions. The electrical contacts may be positioned on the cantilever electrode apparatus adjacent each other and in a particular manner that permits both the secure attachment to the neurostimulator and prevents disruption of the electrical contact while the cantilever electrode apparatus is worn by the subject, even while the subject moves about. For example, the spacing of the connectors may be between 0.6 and 0.9 inches apart on center (from center to center), and more preferably between about 0.7 inches and about 0.8 inches. The electrical connectors typically extend from the otherwise substantially flat surface of the cantilever electrode apparatus, and may plug into the neurostimulator. The electrical connectors may mechanically engage with the neurostimulator (e.g., they may be snaps), which may also provide mechanical support for the connection between the cantilever electrode apparatus and the neurostimulator, and thereby help support and hold the neurostimulator on the subject's body when the cantilever electrode apparatuses is attached to the subject's body.

In general the cantilever electrode apparatuses include two or more connectors at or near one end of the elongate body of the cantilever electrode apparatus, and two (or more) electrode regions are positioned along the elongate body of the cantilever electrode apparatus. The two or more connectors (which may also be referred to as electrical or mechanical and electrical connectors) may be at one end or edge region and help secure the entire cantilever electrode apparatus to the neurostimulator, even while a second electrode region is positioned at a distance (e.g., greater than 2 inches, greater than 3 inches, greater than 4 inches, etc.) along the elongate body of the cantilever electrode apparatus from the connectors and another electrode region.

Each electrode region of the electrode apparatuses described herein typically includes an active region on a back side of the electrode region that is adapted to contact the subject. The active region may include a hydrogel that transfers energy (e.g. current) from the neurostimulator to the subject's skin. The active region is in electrical communication with the connector.

In general, the elongate body forming the cantilever electrode apparatuses may be made of a material that is rigid in at least one direction, even while flexible in another direction. For example, the elongate body of the cantilever electrode apparatus may be formed of a relatively flat sheet of material (e.g., flex circuit material) that is relatively thin (e.g., less than 3 mm, less than 2 mm, less than 1 mm, etc.). The sheet of material may extend in a plane, and the material may not be bendable in the direction of the plane although it may be bendable out of the direction (e.g., can be curved up/down), and may twist. This partial rigidity may help support the cantilever electrode apparatus on the body while allowing it to conform to a wide variety of subject body sizes. In some variations the cantilever electrode apparatus is made of a material that is rigid, but can be bent by the application of force to hold a shape. For example, the elongate body of the cantilever electrode apparatus may be ductile, e.g., may be made (at least in part) of a shape memory material that allows bending.

Usability and miniaturization of a wearable TES system may be improved by the use of flexible or stretchable components, including but not limited to: electronic circuits, power source (i.e. flexible solar panel or flexible/bendable batter), and communications module (e.g. wireless communications module). Recent advances in materials science and the design and manufacture of flexible/stretchable electronic circuits support a miniaturized, wearable TES system that is worn on or adhered to the body. Various components and technologies may be used for constructing a flexible and/or stretchable TES system. One skilled in the art of flexible circuits, flexible sensors, or flexible power sources will recognize that other materials, methods, and technologies may be used to improve the conformability, comfort, and disposability of a wearable TES system.

Examples of materials and technologies which can be used to improve the flexibility and wearability of a TES system include: elastic strain sensors for sensing muscle contraction (e.g. stretch sensors from Danfoss Poly Power A/S); 'tattoo' electronics developed by companies, including MC10, Inc. (Cambridge, Mass.) and Electrozyme (San Diego, Calif.), including those with features described in U.S. Pat. Nos. 8,536,667 and 8,097,926 to de Graff et al., as well as technologies that can integrate solid state components (e.g. those developed by John Rogers et. al); thin film batteries (e.g. batteries composed of polymers, carbon nanotubes, and/or nanoporous nickel fluoride); a flexible supercapacitor made of graphene and carbon nanotubes; flexible OLED display; components containing single layer graphene developed by Samsung; and components containing molecularly stretchable electronics.

Improved adherence of electrodes and other TES components would benefit from the use of 'geckskin' developed by Irschick and Crosby at the University of Massachusetts-Amherst, which can hold strongly to a smooth surface yet can be removed easily without leaving a residue.

The configuration of the cantilever electrode apparatuses described herein may provide numerous benefits compared to other possible arrangements, including variations in which a wire or separate connection connects a second (or more) electrode region to a neurostimulator. For example, the cantilever electrode apparatuses described herein may include least a few mm of adhesive surrounding the active area of each electrode, which may help make good contact with the skin when the cantilever electrode apparatus is attached to a wearable neurostimulator. In another example, the cantilever electrode apparatuses described herein may include at least a few mm of adhesive in sections bordering an active electrode area. For electrode apparatuses and microstimulators that are configured to be worn on the temple (e.g., adjacent to the eye), the amount of adhesive in one portion of the electrode apparatus may be limited; in particular, the portion that will be positioned below a lower edge of the electrode, to prevent the unit from extending too far towards the eye and/or towards the hairline at the temple. In some variations it is desirable to have the cantilever electrode apparatus and the electrical stimulator with its overlaying hardware unit positioned on the face so that it does not interfere with a temple portion of a pair of glasses that may be worn while wearing the device (e.g., the region adjacent to the ear). In addition, it may be beneficial for the bottom edge of the cantilevered electrode assembly (at the first electrode portion) to correspond with the bottom edge of the electrical stimulator to help guide self-placement using the lower edge of the device to align horizontally with the edge of the eye, an easy landmark for self-placement; thus, it may be beneficial to limit the amount of adhesive below/around the lower section of the electrode.

In some embodiments, an electrically conductive tethering wire may be part of a disposable electrode assembly that couples to the neurostimulator. A subject may unfurl the electrically conductive tethering wire as needed so that two or more electrode portions can be adhered to appropriate parts of the head to deliver TES neuromodulation to a brain region of interest.

As mentioned above, there are also numerous benefits of using a connector for electrically connecting the active regions of the cantilever electrode apparatus to the electrical stimulator both mechanically and electrically. For example, an apparatus that uses a mechanical and electrical connector, such as a snap connector or other connector that stands proud from the relatively thin cantilever electrode apparatus may prevent misadjustment of the apparatus. In particular, it may be beneficial to have two connectors (e.g., snaps) rather than just wires or one snap and a wire to connect the wearable apparatus and the cantilevered electrode apparatus. The second mechanical/electrical connector such as a snap may improve the physical connection between electrode adhesive pad and hardware unit (neurostimulator/electrical assembly). In addition, the hardware unit (neurostimulator/electrical stimulator) and electrode apparatus may fit under the temple portion of an eyeglass frame for users wearing glasses; thus the portion of the combined assembly (electrode assembly and neurostimulator) should ideally be thin enough to fit between glasses and the temple region. However, it may also be beneficial to have some portions of the system (e.g., the neurostimulator) be sufficiently thick to allow the apparatus to contain a sufficient battery (or other power portion) so that the unit can be used for a reasonable amount of time between charges. Thus one portion of the neurostimulator may be thick enough to allow a standard battery and/or circuitry at one end (e.g., an end that is worn higher up on the face). Thus, it may be beneficial to locate the mechanical/electrical connectors such as snaps that extend proud from the cantilevered electrode assembly toward the thinner end, separated from the battery compartment of the neurostimulator to reduce the overall thickness of the system in some variations, allowing the connectors to fit under or within a through hole of a PCB rather than under a thick battery portion (or under both). However, in some variations it may be beneficial to have the connector(s) positioned under the battery portion or have one connector under the battery portion and one connector under the thinner region separated from the battery portion.

For example, in some variations it may be beneficial to have one connector on the electrode assembly (e.g., cantilevered electrode assembly) near the portion of the neurostimulator hardware that is highest up on the forehead; this may help ensure that this upper portion of the device doesn't pull away from the electrode. If that happens, then the weight of the hardware unit may pull the electrode further from the head and eventually lead to poor contact between the electrode active area and the skin. An adhesive may be used between the neurostimulator and the electrode assembly to prevent this; alternatively or additionally an additional mechanical connector may be used (an adhesive may be considered one type of mechanical connector, and may be present on the electrode assembly and/or on the neurostimulator body).

It may also be beneficial to have at least one of the electrical/mechanical connectors (such as a snap) at or near (and preferably behind) the active area of the first electrode portion, as this may make the electrical connection with the hardware unit easier and more robust.

FIGS. 63A-63D illustrate one variation of an electrode apparatus ("cantilevered electrode apparatus") that may be used with a neurostimulator that is worn on a subject's head. In this example, the cantilevered electrode apparatus 63100 includes a plurality of electrode portions (two are shown) 63103, 63105. In FIG. 63A, a front perspective view is shown. The front side is the side that will face away from the subject when worn. The cantilevered electrode apparatus is thin, so that the electrode portions include a front side (visible in FIGS. 63A and 63B) and a back side (visible in FIG. 63D). As shown in the side view of FIG. 63C, the device has a thin body that includes the electrode portions 63103, 63105 as well as an elongate body region 63107 extending between the two electrode portions. The elongate body is also thin (having a much larger diameter and height than thickness (the thickness is shown in FIG. 63C)).

In this example, two connectors 63115, 63117 (electrical and mechanical connectors, shown in this example as snaps) extend from the front of the cantilevered electrode apparatus. The front of the first electrical portion 63103 may also include an optional foam and/or adhesive material 63121 through which the snaps extend proud of the first electrical portion. The first electrical portion is shaped and sized so that the snaps will connect to plugs (ports, holders, opening, female mating, etc.) on the electrical stimulator. As described above, the connectors on the electrode apparatus may be spaced in the same manner as the complimentary connectors on the housing of the neurostimulator apparatus. For example, the connectors on the electrode apparatus may be separated by between about 0.5 and about 1 inches (e.g., between about 0.6 and about 0.9 inches, between about 0.7 and about 0.8 inches, etc., shown in FIGS. 63A-63D as about 0.72 inches). The second electrode portion may also include a foam or backing portion 63123. This foam/backing region may be optional.

FIG. 63D shows a back view of this first example of a cantilevered electrode apparatus. In this example, the first 63103 and second 63105 electrode portions are also shown and include active regions 63133, 63135. The active regions are bordered by adhesive 63140. The first 63103 electrode portion includes, on the back (user-contacting) side, a first active region 63133, surrounded by an adhesive material 63140 that extends to the edge region of the electrode assembly. The active region may include a conductive material (e.g., electrically conductive gel). Similarly, the back of the second electrode portion 63105 includes the second active region 63135 which is bounded on an upper and lower side by an adhesive 63140. The adhesive may be any biocompatible adhesive that can releasably hold the material to the skin.

FIGS. 64A and 64B show exploded views of the exemplary cantilevered electrode apparatus of FIGS. 63A-63D. In FIG. 64A, the front side of the cantilevered electrode apparatus is shown with the foam backing 63121, 63123 (which may be adhesive on one or both sides) materials and snaps 63117, 63115 removed. The snaps may include two parts (not shown in FIG. 64A), a base and a post, and the base may be positioned on the back side of the elongate body forming the substrate (or base) 64108 for the cantilevered electrode apparatus. The base may be a flex circuit material, e.g., that is relatively insulating, flexible out of the plane of the material, but rigid in the plane (meaning it can be bent up/down out of the plane, but has rigidity when pushed/pulled in the direction of the plane of the material). Many of the structures used to form the electrode regions and connectors may be printed directly onto the base or attached to the base. For example, in FIG. 64B, the back (user-facing) side of the base of the cantilevered electrode apparatus is shown with the snaps attached so that the base of the snaps extends along the back side and can be in electrical contact in one case with the electrically conductive first active region forming part of the first electrode portion. The second snap is offset from the electrically active region and may contact a conductive trace (e.g., printed on the body 64108 of the base) and extending along the elongate body region 63107 until it contacts the second active region. In this manner, the first and second connectors may establish electrical communication between the active regions and the neurostimulator. In FIG. 64B the active regions include a conductive gel (although additional materials, including sacrificial materials, pH buffer materials, antibacterial/germicidal materials, etc. may also be included). The adhesive portion 63140 is also shown in this exploded view.

As described above, the foam material over either or both of the front sides of the first and second electrode portions may be omitted. FIG. 65 shows an example in which the foam material, which may also or alternatively be an adhesive to help secure the cantilevered electrode apparatus to the neurostimulator is not included in the cantilevered electrode apparatus. In this example, the connectors (snaps 63117, 63115) alone may be used to secure the cantilevered electrode apparatus to the neurostimulator.

The cantilevered electrode apparatus shown in FIGS. 63A-65 may be particularly useful, for example, to connect a neurostimulator to a subject's head so that the neurostimulator is attached to the front side of the cantilevered electrode apparatus by snapping onto the proud connectors, while the elongate body region 63107 is bent to extend behind the subject's head and down to a portion on the midline of the back of the user's neck. Both the first electrode portion and the second electrode portion may be adhesively held with the electrically active regions against the skin, allowing the neurostimulator to apply energy, and in particular the waveforms as described in U.S. patent application Ser. No. 14/320,443, titled "TRANSDERMAL ELECTRICAL STIMULATION METHODS FOR MODIFYING OR INDUCING COGNITIVE STATE" and filed Jun. 30, 2014, now U.S. Pat. No. 9,014,811 and herein incorporated by reference in its entirety.

FIGS. 66A-66D illustrate another example of a cantilevered electrode apparatus. This example is very similar to the variation shown in FIGS. 63A-64B. The connectors (snaps 66417, 66415) are in the same position as shown in FIGS. 63A-63D, as are the shape of the first electrode portion 66403 and foam/backing material 66421 (which may also or alternatively be an adhesive material). However, the example shown in FIGS. 66A-66D includes a different overall shape, and may be used to connect, for example, to different regions of the user's head/neck. In particular, the portion of the substrate forming the elongate body region 66407 extending between the two electrode portions 66403, 66405 is shaped slightly differently. In this example, the cantilevered electrode apparatus may be configured to connect, for example, to the subject's temple with the first electrode portion (to which the neurostimulator may be connected) and the elongate body region may be bent around the subject's head so that the second electrode portion may be in electrical contact with a region behind the subject's ear (e.g., at or near the mastoid). By placing the first active region 66433 of the first electrode portion 66405 in electrical contact with the skin at the temple region, using the adhesive material 66440 surrounding the electrically active region 66433 to hold the electrically active region (and the attached neurostimulator) in position, the second electrically active region may also be adhesively 66440 held to skin so that the second electrically active region 66435 is in contact with the mastoid region.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 63A-65 and FIGS. 66A-66D.

In alternative embodiments, an electrically conductive tethering wire may be a durable portion of the TES system and intended for long-term use. FIG. 83A shows exemplar schematic embodiments of a TES system comprising primary durable housing 832402, secondary durable housing 832401, connectors 832403 and 832404, and electrically conductive tethering wire 832405. Not shown are disposable electrodes that couple electrically and mechanically to housings 832401 and 832402 and contain a dermally-facing adhesive so that the TES system can be wearably attached to the user. Other variations of TES systems as described herein may be non-adherent and otherwise wearably attached to a user's body (e.g. by a headband, cap, etc.).

As shown in FIG. 83A the tethering wire may be permanently attached to the primary and secondary units, or it may be configured to unplug from either or both of the primary or secondary TES system housing (FIG. 83B, FIG. 83C) with standard or custom connector 832406, 832407.

In some embodiments, one of the durable housing may have a standard plug component (e.g. a male USB or male micro-USB connector) for charging and communication with other electronic or computing devices. For example, the smaller, secondary durable housing may contain a male USB connector, a charging circuit, and a battery.

In general, TES systems containing an electrically conductive cable that is permanently or detachedly attached may contain all components in a single housing. In such instances, the electrically conductive cable would include at least a connector at or near its end distal from the unit containing the electrical components to which a disposable electrode can be electrically connected.

In general, TES systems containing an electrically conductive cable that is permanently or detachedly attached may contain components in two or more housings. These embodiments are advantageous because they permit miniaturization of each of the housings relative to having all components in a single housing. This miniaturization may improve comfort, wearability, durability, and/or fit of a TES system. Any set of necessary or optional components may be selected to be in a first housing or a second housing (or a third housing, etc.). FIG. 84 shows an exemplar TES system schematic with first durable TES housing 842512 containing current control circuitry 842505, fuse and other safety circuitry 842506, wireless antenna and chipset 842507, waveform generator 842508, memory 842509, microprocessor 842510, and connector to first electrode (842514) connected by electrically conductive cable 842511 to second durable TES housing 842513 containing a battery 842501, recharging circuitry 842502, connector to second electrode 842503, and other electrical components 842504.

A method of using the TES systems described herein can include connecting two TES controller housings with a detachable, reusable electrically-conductive cable, followed by connecting the two electrodes to the cable and/or TES controller. Alternative methods can employ the opposite ordering of connecting necessary and detachable system components.

A TES apparatus with a durable cable connecting two housings with electrode connectors—or a single housing with two or more electrode connectors—may be used with disposable electrodes that do not have a wire connecting them. This system architecture reduces the cost and complexity of a disposable set of transdermal electrodes, which only require a connector (e.g. electrically conductive button snap connector) configured to connect with the TES controller system.

FIGS. 67A and 67B illustrate two different types of cantilever electrode apparatuses, each having an electrically detectable element, for example, a capacitor connecting the electrode contacts. The electrically detectable element can be a capacitor or a capacitive element in some embodiments. In some other embodiments, the electrical detectable element may be another type of electrical element. In some embodiments, each of the cantilever electrode apparatuses can have an electrically detectable element. In some other embodiments, only one of the cantilever electrode apparatuses may have an electrical detectable element (so that it can easily be distinguished from the version of the electrode apparatus having the electrically detectable element). The detection circuit in the neurostimulator can be configured to detect the electrically detectable element and distinguish the two different types of cantilever electrode apparatuses.

As shown in FIG. 67A, the first and second electrical/mechanical contacts 671615, 671617 can be connected by a detectable electrical element 671646. In some embodiments, the detectable electrical element may be a capacitor or capacitive element that is chosen so that at frequencies within the neurostimulation operating frequency range (e.g., at frequencies below about 18 kHz, below about 20 kHz, below about 25 kHz, below about 30 kHz, etc.) the capacitor or capacitive element behaves like an open circuit and therefore does not interfere with the application of the ensemble waveforms to the user. At higher frequencies (e.g., above about 18 kHz, above about 20 kHz, above about 25 kHz, above about 30 kHz, etc., and particularly in the MHz range), the capacitor or capacitive element has a characteristic response that can be sensed by the detection circuitry in the neurostimulator.

For example, in FIG. 67A, which illustrates one example of an "energy" electrode apparatus that may be used to evoke an energy effect as described above, the electrically detectable element may be a capacitor 671646 with a capacitance 180 pF (or any capacitor having a capacitance of between about 10 pF and 2 nF, e.g., 10 pF, 100 pF, 200 pF, 300 pF, etc.). In contrast, the electrode apparatus shown in FIG. 67B, which may describe a "calm" type of electrode apparatus, may have a different electrically detectable element 671646', such as a capacitor with a second capacitance of 680 pF (any capacitance between about 20 pF and 2 nF, e.g., 20 pF, 200 pF, 400 pF, 600 pF, 800 pF, etc.). In FIG. 67B, the electrically detectable element 671646' is also connecting the two electrical contacts 671615' and 671617' that each connect to an active region on the back of the electrode apparatus. The capacitance of the second capacitor can be any value that is distinguishable by the detection circuit, for example, the capacitance of the second capacitor can be two times, three times, four times larger than the capacitance of first capacitor.

Figure 68A:
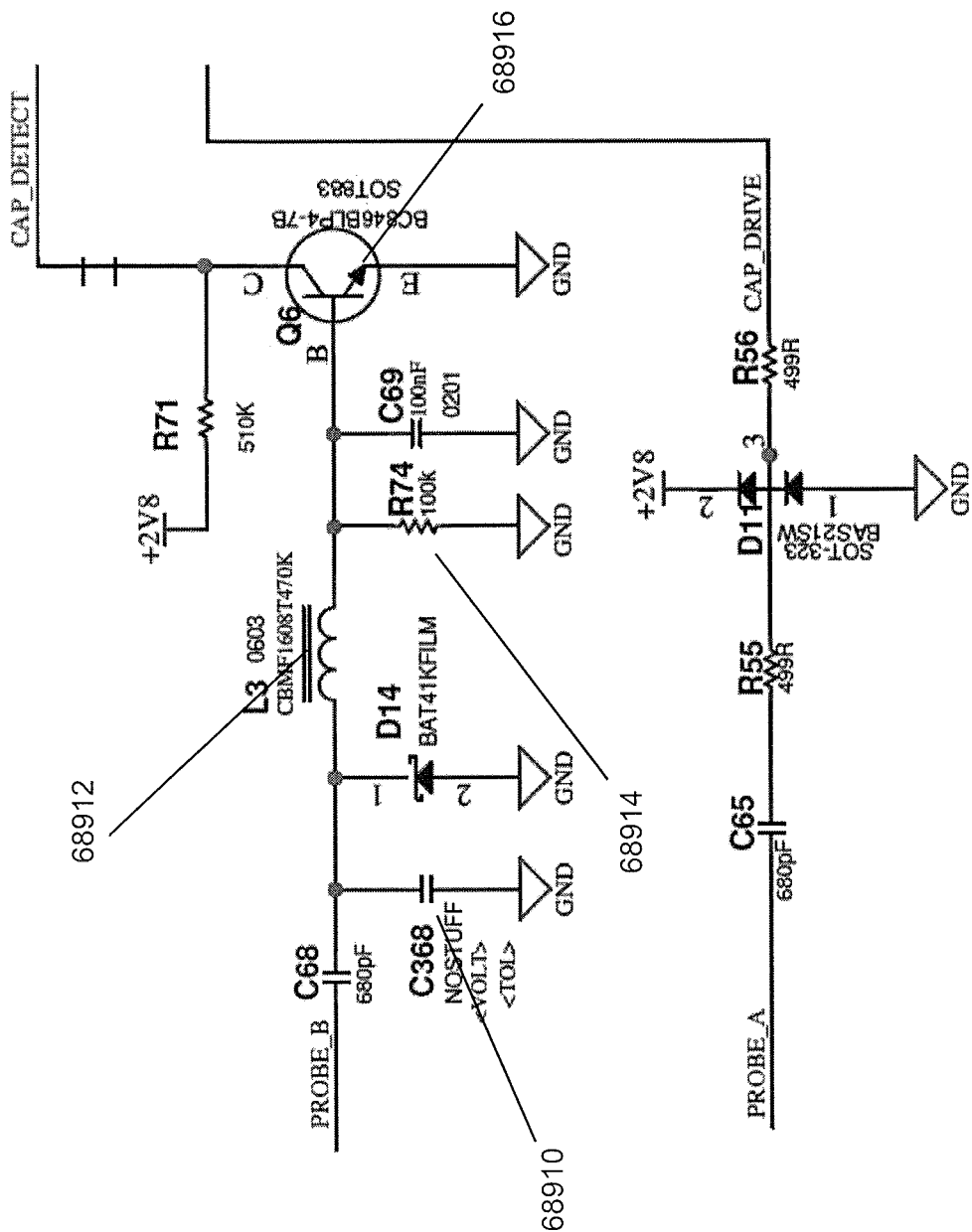

FIG. 68A illustrates one embodiment of a detection circuit that may be used (e.g., included in a neurostimulator) to determine if an, and what type of, electrode apparatus is attached to the neurostimulator. In this example, the probe A and probe B portions communicate with the first and second contacts, respectively, on the electrode apparatus to which the neurostimulator is attached. Probe A acts as the drive line to the capacitor or capacitive element on the electrode assembly (which may be referred to as a detection capacitor or detection capacitive element) connected between the electrical (or electrical and mechanical, e.g., snaps) connectors of the electrode apparatus, while probe B includes the capacitive detection circuit. The capacitive detection circuit can be an RLC resonant circuit (the letters R, L and C can be in other orders) including a resistor, an inductor, and a capacitor, connected in series. The RLC resonant circuit can form a harmonic oscillator for current and resonate at the resonance frequency. The resonance frequency can be defined as the frequency at which the impedance of the RLC resonant circuit is at a minimum. The resonance frequency in a series resonant circuit has the value of:

$$\omega_0 = \frac{1}{\sqrt{LC}}$$

The capacitive detection circuit of the neurostimulator shown in FIG. 68A may be connected to a microcontroller or other logic circuit to detect a signal (i.e. voltage) indicating resonance of the circuit. The microcontroller or other logic circuit may also incorporate a clock or other timing circuit. The presence and/or amplitude of resonance can be used to distinguish the different type of electrode apparatus in some embodiments. The latency at which resonance begins can be used to distinguish the different type of electrode in some embodiments.

In some other embodiments, as shown in FIG. 68A, the capacitive detection circuit can include a capacitor 68910 (C368) and an inductor 68912 (L3) in parallel. The resonant frequency of the LC circuit is defined by the capacitance of the capacitor 68910 and the inductance of the inductor 68912. When the frequency is the resonant frequency of the RL circuit, the charge over the node B of the transistor 68916 can accumulate quickly. The transistor 68916 can begin to conduct, and the node C of the transistor 68916 can switch from status "0" to "1". The capacitance of the capacitor or capacitive element on the electrode assembly connected between the electrical connectors of the electrode apparatus (e.g., 671646 in FIG. 67A or 671646' in FIG. 67B) can affect the time for the node C of the transistor 68916 to switch. By measuring the time for the node C of the transistor 68916 to switch, the capacitive detection circuit can determine what type of electrode apparatus is attached to the neurostimulator. The detection circuit to detect the capacitor or capacitive element can have high sensitivity by using the resonant circuit. The detection circuit can detect the small difference in capacitance. For example, the detection circuit can detect the difference in capacitance when the first capacitance is 2 times, 3 times, or 4 times larger than the second capacitance in some embodiments. The detection circuit can detect the difference in capacitance when the difference between the first capacitance and the second capacitance is larger than 50 pF, 100 pF, 200 pF, 300 pF, 400 pF, and 500 pF in some embodiments.

Figure 68B:
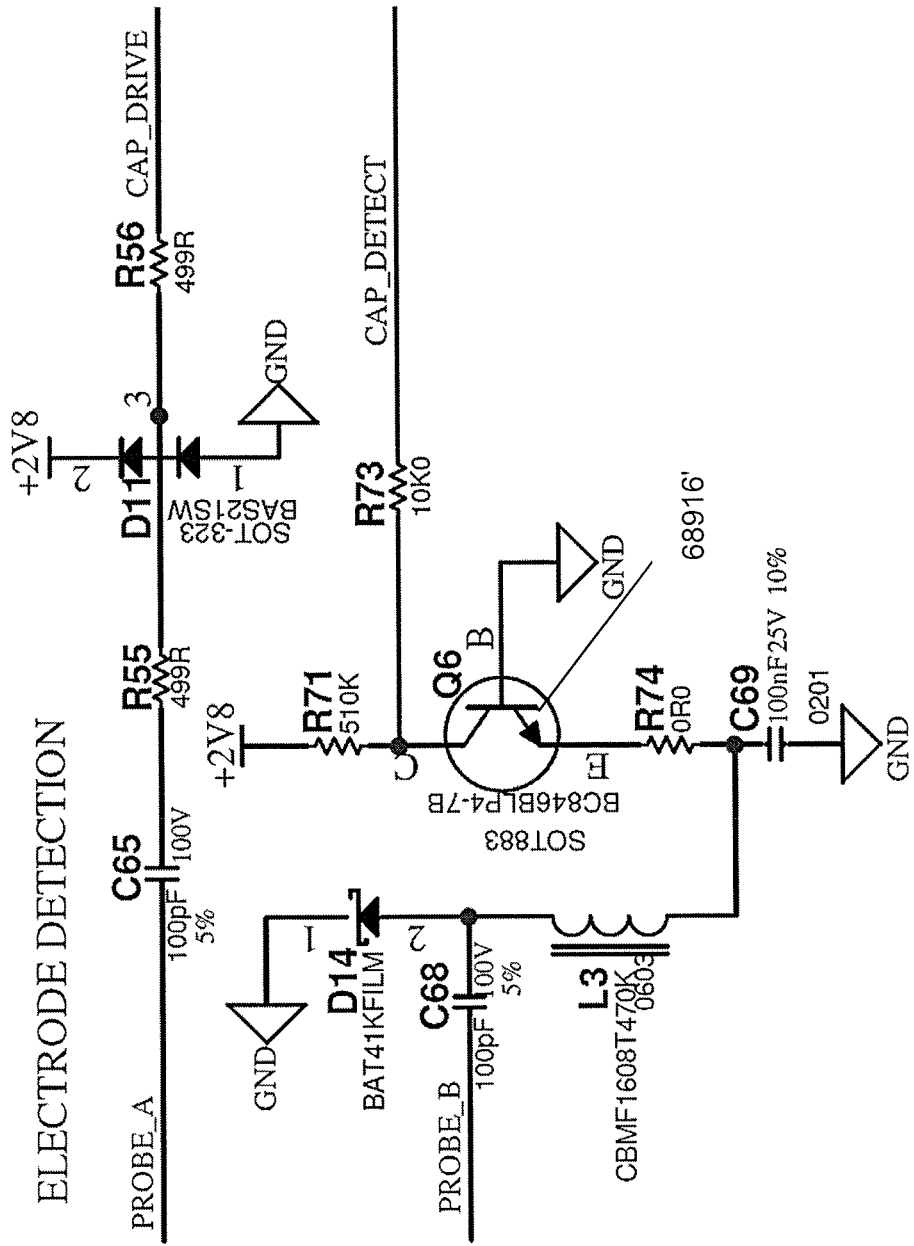

FIG. 68B illustrates another embodiment of a detection circuit that may be used to determine if an, and what type of, electrode apparatus is attached to the neurostimulator. Similar to the embodiment in FIG. 68A, the probe A and probe B portions communicate with the first and second contacts on the electrode apparatus to which the neurostimulator is attached. Probe A acts as the drive line to the capacitive element (e.g., 671646 in FIG. 67A or 671646' in FIG. 67B), while probe B includes the capacitive detection circuit. The capacitive detection circuit can be another RLC resonant circuit, a slight variation of the embodiment shown in FIG. 68A. When sweeping the frequencies at frequencies higher than the neurostimulation operating frequency range, the RLC circuit can have resonance at the resonant frequency. Therefore, the detection circuit can determine the type of electrode apparatuses attached to the neurostimulator.

Figure 68C:
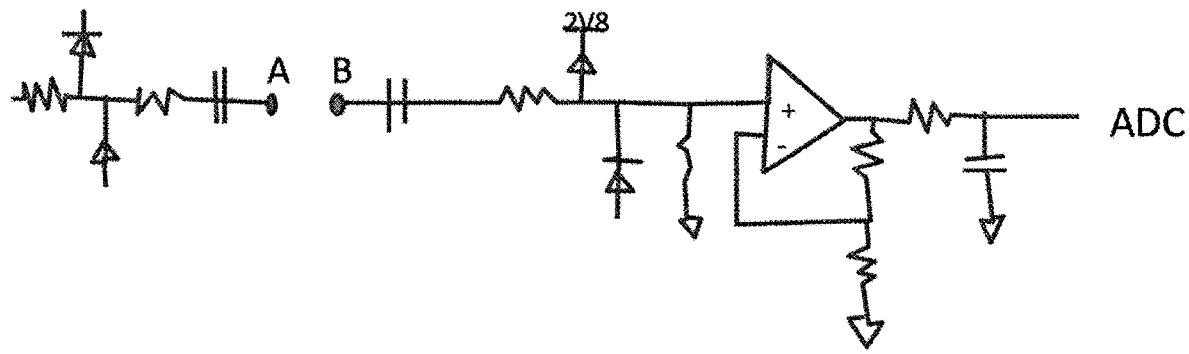

FIG. 68C illustrates a circuit using a pulse to detect the capacitor on the electrode apparatus in another variation of a capacitance detection circuit that may be used to uniquely identify an electrode apparatus. The embodiments shown in FIG. 68A and FIG. 68B are based on a resonant circuit to detect the capacitor or capacitive element on the electrode apparatus. Alternatively, a capacitor detection circuit may use a pulse to detect the capacitor or capacitive element on the electrode apparatus. As shown in FIG. 68C, the pulse may be generated by a controller output coupled to the circuit. The pulse may propagate through the circuit including the capacitor or capacitive element on the electrode apparatus (for e.g., 671646 in FIG. 67A or 671646' in FIG. 67B), the response may be affected by the capacitor or capacitive element. By measuring the response, the detection circuit can determine the type of electrode apparatus attached to the neurostimulator.

FIGS. 78A-78B also illustrate another example of a capacitance detection circuit that may be used to identify different types of electrode apparatuses once they are connected to a neurostimulator apparatus as described herein. FIG. 78A illustrates one example of the circuit that may be used. In FIG. 78A, the circuit acts by examining pulse length, e.g., the time required for the pulse to decay below a threshold. In FIG. 78A, the circuit includes two capacitors in the test circuit that, when placed in series with the capacitor in the electrode assembly, allows a pulse of signal transmitted between the electrodes (probe A and probe B) to decay at a rate that is characteristic and dependent on the capacitor in the electrode assembly. The detection circuit detects the time that the pulse returned through the electrode assembly remains above a threshold (e.g., non-zero threshold), and compares to an expected value (e.g., within the controller, or via a comparator). In FIG. 78A, the controller is configured to directly read the value of the returned pulse and determine the time above threshold. This is possible in this example because although the returned signal is mostly a decaying exponential, when the amplification gain is high, the pulse is saturated. Although the exponential size of the pulse returned is on order of 2.8V, the amp wants to amplify it to 28V, however because it is limited to 2.8V from the power supply, the signal is saturated to this value.

Thus, in this example, the three capacitors are connected in series and the decay time of the pulse will be based on the value of the three capacitors, two of which are constant (in the circuit). Depending on the value of the capacitor in the electrode assembly, the time to pass below a threshold will be different for different capacitors.

FIG. 78C shows an example of a workflow for distinguishing a plurality of electrode strip types (electrode assembly 781904, shown in FIG. 78B). Electrode assembly 781904 may be held on a non-conductive (or minimally conductive) releasable liner 781901 to which the adhesive may be attached until it is removed and placed on the skin (it may be returned to the adhesive liner later). The electrode assembly in this example includes two connectors (snaps

781903) on a first (outwardly-facing, away from the user) side of the electrode assembly for connecting to snap receptacles on a neurostimulator apparatus, such as shown in FIGS. 60B and 62A-62F. In general, two (or more) types of electrode assemblies may be distinguished by detecting the value of a capacitor on the electrode assembly as discussed above and shown in, e.g., FIGS. 67A-67B that shorts between the two snaps on the electrode apparatus. The neurostimulator apparatus may include detection circuitry including or working with a controller that controls a current source. The detection circuitry for detecting the value and/or the presence of a (shorting) capacitor on the electrode apparatus, and the controller may also contain a wireless communication module for communicating with an 'app' running on a personal computing device. When the electrode assembly and the neurostimulator apparatus are connected (e.g., via the snaps and snap receptacles), the neurostimulator apparatus may be adherently worn on a subject's head and/or neck for delivering transdermal electrical stimulation to cause a cognitive effect as described above.

In FIG. 78C, showing an example workflow, a user connects the neurostimulator to the electrode apparatus (e.g. via snap receptacles and snaps). Software (and/or firmware) running on the neurostimulator module may be configured to detect when an electrode apparatus is electrically (and mechanically) connected and deliver capacitor identification waveform 781909. In the exemplary flowchart shown in FIG. 78C, the apparatus is configured to determine between one of two possible electrode apparatuses (e.g., between two different capacitor values). The capacitor-detection circuit and control logic on the neurostimulator apparatus may determine if there is no capacitor on the electrode apparatus 781910 (in which case it may prompt the user), or if it detects a low 781913 or high 781912 capacitor value on the electrode apparatus. The capacitor-detection circuit and control logic on the neurostimulator apparatus may also determine whether the electrode assembly and neurostimulator apparatus are adhered to the subject's head or head and neck, though in some variations it may not be possible to reliably distinguish between different capacitor values of electrode assembly sub-types when the assembly is adhered to the subject's skin due to the relatively high capacitance of the body.

In some variations, when the capacitor identification circuit (detection circuit) determines that no capacitor is present (e.g., shorting the snaps of the electrode apparatus), the system may enter a locked state that disables electrical stimulation. This functionality may be beneficial for improved safety so that a user may not use the neurostimulator module to deliver transdermal electrical stimulation with an inappropriately configured electrode apparatus. Alternatively, absence of a capacitor on the electrode apparatus may trigger a user interface on a personal computing device (smartphone, laptop, desktop, pad, etc., that is communicating with the neurostimulator apparatus) to provide a selection screen to be shown so that a user may select an appropriate waveform type matching an electrode apparatus type connected to the neurostimulator apparatus 781917 (e.g. allowing selection between one of two types of electrode assemblies, such as a "Calm"-type waveform, by tapping the top half of the screen, or an "Energy"-type waveform by tapping the bottom half of the screen).

Alternatively, if the neurostimulator apparatus detects a low capacitor value 781913, it may transmit this information wirelessly to the user computing device which may automatically select waveforms that are appropriate for the type of electrode assembly that correspond to the low capacitor value shorting the electrode connector snaps 781914 and may also display a user interface for selecting a specific waveform from the matching type via pull-down menu 781919, and controlling the commencement, intensity, modulation, pausing, or stopping of a transdermal electrical stimulation waveform for inducing a cognitive effect 781919. A similar workflow and functionality may occur for the detection of high capacitor value 781912 for automatic selection of waveforms appropriate for the electrode assembly type that corresponds to the high value capacitor, and may provide a user interface allowing the selection of appropriate waveforms to match this electrode type or auto-selection and commencement of an appropriate waveform, as well as the control of the starting, stopping, and intensity of the waveform 781916.

FIGS. 68A-68C and 78A-78B are examples of sensing circuitry that may be used to detect the capacitor or capacitive element on the electrode apparatus. The detection circuit of the neurostimulator may be connected to a microcontroller or other logic circuit. The microcontroller or other logic circuit may also incorporate a clock or other timing circuit. In some embodiments, the capacitor detection circuit may include a RLC resonant circuit. In general, sensing circuitry based on a RLC resonant circuit may identify the capacitor or capacitive element on the electrode apparatus by applying high-frequency current between the electrical connections (anodic, cathodic) of the electrode apparatus. In some alternative embodiments, the capacitor detection circuit may generate a pulse, and determine the type of electrode apparatuses attached to the neurostimulator by measuring the response (e.g. duration of a signal) after the pulse propagates through the capacitor or capacitive element on the electrode apparatus.

A variety of different detection circuits (electrode assembly detection/identification circuit) may be used as part of the neurostimulator apparatus, and the electrode detection circuits are not to be limited to the examples discussed above. In some embodiments, both types of electrode assemblies may include capacitors or capacitive elements with different capacitance. In some other embodiments, only one electrode apparatus may include a capacitor or capacitive element. In some alternative embodiments, other electrically detectable elements, such as a resistor or an inductor may be included in both types of electrode assemblies, or in only one type of electrode assembly; the detection circuit can be configured to detect the electrically detectable element. In some other embodiments, a switch may be included in the detection circuit, which can be configured to be turned on when one type of electrode apparatus is used and turned off when the other type of electrode apparatus is used.

FIG. 79 shows data taken from three types of exemplary electrode assemblies: a first set that does not include a capacitor (e.g., a capacitor between the electrical connectors as shown in FIGS. 67A-67B), referred to in FIG. 79 as "sticker no cap.;" a second set that includes a 180 pF capacitor on the electrode assembly between the connectors (electrodes); and a third set that includes a 680 pF capacitor on the electrode assembly between the connectors (electrodes). These different sets may correspond to different types of electrode assemblies, such as electrode assemblies specifically designed to be used to induce different cognitive effects. For example, an electrode assembly used to induce a "calm" cognitive state may include a capacitor having a first value (e.g., 680 pF) that connects between a first electrode to attach at the user's temple/forehead region and a second electrode to be worn at the back of the user's neck, such as the electrode assembly variation shown in FIGS.

63A-65 and 67B. Another type of electrode assembly, such as the one shown in FIGS. 66A-67A, may be configured to be used for inducing a cognitive state of enhanced energy, and may include a capacitor having a different value (e.g., 180 pF) that connects between a first electrode to be attached to the user's temple/forehead and a second electrode that attaches behind the user's ear. In this example, there is a rather large and detectable distinction between these different configurations of electrode assemblies, including a large distinction between electrode assemblies that have no capacitor. Notwithstanding the large and detectable difference between the electrode assembly types having different capacitor values, the measured values may include unaccounted variability, such that the distribution of durations measured for a capacitive element with a first value (capacitance) may overlap with the distribution of durations measured for a capacitive element with a second value (capacitance). To improve the reliability of electrode assembly type detection based on capacitance differences of capacitive elements on the electrode assembly, an algorithm may be applied that samples multiple values and applies a statistical algorithm (e.g. calculating an average, calculating a median, requiring that n consecutive measurements be classified as the same electrode subtype (where n may be two measurements, three measurements, four measurements, five measurements, or more measurements), etc. In general, ongoing, sequential measurements of the electrode assembly capacitance by the circuit may continue until a statistical threshold is reached (e.g. according to an algorithm such as those listed above). In addition, the apparatus may readily detect when no electrode has been attached ("no sticker"). The data shown represents the number of clock cycles for a 12 MHz clock (about 83 nanoseconds) occurring during a pulse detection period, when the electrode assembly ("sticker") is not yet attached to the subject. These values may be different when the electrode assembly is attached to the user, and the capacitive detection circuit (and/or controller) may detect these different values to determine if the electrode assembly is attached to the user, and guide the user in confirming the type of electrode assembly connected or to be connected, as described above.

Alternatively or additionally, in some variations, an electrode assembly such as the cantilever electrode apparatuses described herein may include active circuitry such as a surface mounting chip to identify the electrode apparatus and/or for security. For example, when the electrode apparatus includes a substrate that is a flex circuit, the circuitry may be configured to provide a unique identifier, and/or a counter that may increment with use(s).

Any of the electrode assembly embodiments described herein may additionally or alternatively include an identification tag (e.g., a near-field identification tag) configured to designate the electrode assembly type (e.g., energy, calm) and/or other identifying information or use information about the electrode assembly. An identification tag may be disposed on a surface of the substrate, for example, on an outer (not skin-facing) surface of the substrate, or on a connector physically coupled to the substrate. Any suitable identification tag(s) may be used, for example, a Bluetooth transmitter, a Bluetooth Smart beacon, an RFID tag, a near-field communication tag, a resistive element, a capacitive element, a microcontroller, and/or a visual identifier such as a bar code, a QR code, a light transmitter, or an image. The identification tag may serve to identify one or more characteristics of a particular electrode assembly. For example, the identification tag may uniquely identify an electrode assembly's: model (e.g., calming effect, energizing effect, or focusing effect), brand, manufacturer, date and/or time of manufacture, physical size (e.g., small, medium, or large), security tag, or stimulation capacity (for example, as determined by the amount of Ag and Ag/AgCl and/or hydrogel present in the electrode assembly).

As described above in reference to a capacitive element for identification of the electrode assembly, an electrical stimulation system may be adapted for use with an identification tag of an electrode assembly. Further, any of the controllers that may be used with the neurostimulators described herein may be configured to recognize (and the electrode assembly and marker may be configured so as to be recognizable) by a controller, e.g., a specialized remote control, smartphone, tablet, etc. In some such variations, the controller may include an electronic reader, electronic receiver, or image reader configured to detect and recognize the identification tag. In some variations the neurostimulator may pass along the identifying information to the controller specifically (i.e. may both read and write to the identification tag). For example, in one embodiment of the system, the controller includes a Bluetooth receiver, and the electrode assembly includes a Bluetooth transmitter or Smart beacon; in another embodiment, the controller includes an RFID reader, and the electrode assembly includes an RFID tag. In another embodiment, the controller includes a near-field communication antenna, and the electrode assembly includes a near-field communication tag. Additionally or alternatively, the controller may include an electrical connector and resonating circuit, such as a series of electrical pins, and the electrode assembly may include a resistive element or a capacitive element.

In one embodiment of a system including an electrode assembly, the electrode assembly and the controller (and/or the neurostimulator) each includes a microcontroller (e.g., a microprocessor or a programmable chip) programmed with firmware. The firmware, when run, allows for one-way or two-way communication between the coupled microcontrollers and further allows the microcontrollers to run an authentication protocol to query and confirm that the controller and the electrode assembly are authentic and authorized for use together.

In another embodiment, the controller (and/or neurostimulator) may include an image reader configured to detect a visual identification tag, and the electrode assembly may include a visual identification tag. In some embodiments, the image reader includes an image capturing mechanism (e.g., a camera, a lens, a bar code reader, a QR code reader, or a diode) and a microprocessor, and the visual identification tag of the electrode assembly includes: a bar code, a QR code, a light transmitter, an image, or other visual identifier.

The controller and/or neurostimulator of various embodiments may be programmed such that, if the controller cannot recognize the identification tag of an electrode assembly, the controller will not provide a stimulating current to the electrode assembly. For example, if a controller is communicatively coupled to an electrode assembly having an unrecognized identification tag (or lacking such a tag), the controller may render the coupled electrode assembly inoperable. No stimulating current will be delivered to the electrode assembly. In such a manner, the electronic identification tag may prevent the system from operating with unauthorized electrode assemblies and thus ensure safe operation of the system.

In some embodiments, when a controller and/or neurostimulator is communicatively coupled to an electrode assembly having an identification tag, the microprocessor of the controller and/or neurostimulator may compare the detected identification tag to a database of identification tags stored in a memory to confirm that the detected identification tag matches a known identification tag. Additional electrode-specific information may be stored in the database with each known identification tag, such as, for example: the appropriate stimulation protocol for the respective electrode, acceptable threshold levels (e.g., temperature, pH, and/or current values), acceptable operating parameters (e.g., temperature, humidity, etc.), and the like. In other embodiments, the microprocessor of the controller and/or neurostimulator may transmit data indicative of the detected identification tag to a remote server where a database of known identification tags is stored, and the remote server may compare the detected identification tag to the known tags, and if there is a match, transmit data associated with the known tag back to the controller. With the information obtained from the database, the controller and/or neurostimulator may test the electrode assembly and current conditions to confirm the electrode(s) are still within acceptable operating specifications (e.g. temperature, humidity, force, etc.); the controller may then deliver a programmed stimulation protocol to a user appropriate for the operating conditions of the electrode assembly.

For example, the neurostimulator, a user computing device, or a remote server connected via, e.g., the Internet, may in a first step store information about a specific electrode assembly unit (unique identifier contained in the detected information of the tag) associated with information about the electrical stimulation delivered. If the same electrode identifier is detected by that neurostimulator (or another neurostimulator connected via the Internet to a database storing information about the previous use of that electrode assembly unit), the duration, intensity, or another quality of stimulation may be adjusted to ensure efficacious and comfortable delivery of an electrical stimulation waveform for inducing a cognitive effect. For example, the detected information from the electrode assembly tag may contain a quantity of consumptive electrode material (i.e. Ag—AgCl layer) and limit use of the electrode to comply with this limit, across one or more electrical stimulation sessions. In general, this information may be stored locally on the neurostimulator device, in a database on a user computing device that communicates wirelessly with the neurostimulator, or in a database on a remote server connected to the neurostimulator (and/or user computing device), e.g., via the Internet.

FIG. 69 schematically illustrates a TES waveform configured to deliver a biphasic electrical stimulation signal according to various embodiments of the disclosure. In general, a TES waveform may be defined by a duration, direction, peak current, and frequency. In some embodiments, a TES waveform is further defined by a percent duty cycle, percent direct current, ramping or other amplitude modulation, one or multiple frequency components, phase relationship of biphasic current, flat or structured noise, wave shapes (i.e. saw tooth, triangular, sine wave, square wave, exponential, or other wave shape), capacitance compensation features, or other parameters as discussed in U.S. patent application Ser. No. 14/091,121, titled "WEARABLE TRANSDERMAL ELECTRICAL STIMULATION DEVICES AND METHODS OF USING THEM," filed Nov. 26, 2013, now U.S. Pat. No. 8,903,494, which is herein incorporated by reference in its entirety. A TES waveform may also be defined for bursting wherein one or more cycles of the waveform are repeated at a bursting frequency and with a bursting duty cycle that defines, as a percentage of the bursting frequency, the proportion of the cycle comprising a burst versus a quiescent period.

In some embodiments, the neurostimulator may include a high voltage supply, for example, 30V, 60V, or 80V. TES systems described herein incorporate electronic circuitry to achieve high voltage electrical stimulation, where high voltage corresponds to a circuit supply voltage generally greater than 10 V and optionally greater than 15 V, greater than 20 V, greater than 30 V, greater than 40 V, greater than 50 V, or greater than 75 V. An apparatus for delivering high current stimulation comprises a power source (generally a battery) with rapid discharge properties (e.g. a Li-ion 2 C battery of 200 mAh capacity with a maximum charging current of 1 C (200 mA), maximum continuous discharge current of 1 C (200 mA), and maximum peak discharge current of 2 C (400 mA)) so that peak currents can be delivered; a transformer (buck boost or other) to take lower voltage output of a battery or other power source and provide high voltage levels needed to provide the specified power level; and other electronic circuit components designed to operate predictably and reliably at high voltage.

FIG. 70A and FIG. 70B illustrate an example of a circuit of a controller of the neurostimulator configured to adjust an applied voltage. In various embodiments, the controller of the neurostimulator can include a feature to control the applied (or available) supply voltage, Vs, instead of using the maximum available voltage. FIG. 70A illustrates the power supply of the controller. As shown in FIG. 70A, a power converter 701112 can be configured to output the supply voltage, $V_s$, which can be different than the available maximum voltage of the power supply.

For example, FIG. 70B illustrates a circuit including an H-bridge configured to deliver electrical stimulation to a subject and control the applied supply voltage, $V_s$, 701105. In some embodiments, the circuit can be a double H-bridge configuration. In one direction of the outside H-bridge, a transistor 701113 and a transistor 701111 can be configured to generate a first current pulse, which can be a first portion of a TES waveform. The first current pulse can propagate to probe A 701101, to the subject, to probe B 701102, and then propagate to a MOSFET transistor 701114. The first current pulse can be measured by an amplifier 701109, and the measurement can be sent to a microprocessor 701103. The microprocessor 701103 can use the measurement of the first current pulse as a first feedback signal to adjust the applied supply voltage $V_s$ 701105. In the other direction of the outside H-bridge, a pair of transistors 701125 can be configured to generate a second current pulse, which can be a second portion of the TES waveform. The second current pulse can propagate to probe B 701102, to the subject, to probe A 701101, then to a second MOSFET transistor 701115. The second current pulse can be measured by a second amplifier 701110, and the measurement can be sent to the microprocessor 701103. The microprocessor 701103 can use the measurement of the second current pulse as a second feedback signal to adjust the applied supply voltage $V_s$ 701105.

In some embodiments, the circuit may measure and/or calculate the peak voltages delivered to the electrodes. In some other embodiments, the circuit may include other electrical elements to perform the measurements of the peak voltages delivered to the probes. The measured voltage can be used to calculate the effective impedance, resistance, and/or capacitance, then a communication signal can be sent to the microprocessor 701103 of the controller, which may adjust the applied supply voltage $V_s$ 701105 depending on the historical pattern of peak voltages delivered to the probes. In general, the circuit may perform the measurements of the peak voltages delivered to the probes only during positive-going and/or negative-going pulses of the TES waveform.

In some embodiments, the controller can be configured to adjust the applied supply voltages V, from the historical demand of the peak voltages and/or the applied voltages during the TES stimulation session. The impedance and/or capacitance of skin may be varied during the TES stimulation session. For example, the impedance of the skin may be affected by electrical signal frequencies, local skin temperature, etc. and capacitance on the skin can build up during individual pulses, requiring greater voltage at the end of a pulse than at the beginning for a constant current. Although the maximum available voltage may be high, (for example, 60 V in some embodiments), the applied voltages may be adjusted according to the demand of the user to avoid overheating. In some embodiments, the controller may measure the peak voltages delivered to the probes over several cycles, (for example, 2, 5, 8, or 10 cycles). The measured peak voltages may be used as feedback control signals to adjust the applied voltages. For example, the average measured peak voltage measured over a few cycles (for example, 2, 5, 8, 10, or more cycles) may be some measured value, for example, 10V. The controller may adjust the applied voltage by setting the applied voltage to be 5 V or 7 V over the measured value 10V, thus the overall applied voltage may be adjusted to be 17V, instead of using the maximum voltage of 60 V. This automatic feedback adjustment feature may avoid overheating of the neurostimulator or skin of the user and save electrical energy to improve efficiency and enable longer TES waveforms to be delivered between recharging or replacing the batteries of a neurostimulator.

In order for the transistors 701111, 701113 and 701125 to work properly, the voltage drops between Vs and the upper nodes of the MOSFET transistors 701115 and 701114 can be configured to be in an appropriate working range. In some embodiments, the voltages drops can be 2V, 3V, 4V, 5V, 6V, 7V, 8V or any values there between. The applied supply voltage $V_s$ 701105 can be adjusted using the feedback signals to ensure the voltage drops are in the appropriate working range. When the voltage drops are too high, the circuit can adjust the current to reduce the voltage drops.

In general, any electrical stimulators, including in particular (but not limited to) the wearable transdermal neurostimulator apparatuses described herein, may be configured to regulate the power of a wearable transdermal neurostimulator device. The electrical stimulators may be configured with circuitry to deliver biphasic electrical signals between a first electrode and a second electrode. Any of these apparatuses may include a high-voltage power supply that is configured to provide an adjustable supply voltage ($V_s$) and a waveform generator receiving the supply voltage. The apparatus may include control circuitry to adjust the Vs after comparing the available $V_s$ to the voltage needed to drive the current (and/or the voltage actually applied between the electrodes or the connectors configured to connect to the electrodes). This control circuitry may be integrated into the controller of the electrical stimulation apparatus, or it may be discrete circuitry. FIG. 70B, discussed above, illustrates one example of this control circuitry, including an H-bridge configuration to compare a difference between the supply voltage ($V_s$) and the applied voltage ($V_{applied}$) to a target voltage offset, allowing the control circuitry to adjust the supply voltage and increase the supply voltage if the difference between the supply voltage and the applied voltage is below the target voltage offset, or to decrease the supply voltage if the difference between the supply voltage and the applied voltage is above the target voltage offset.

In general, the target voltage offset may be a range of values (e.g., between 1V and 12V, between 2V and 10V, between 3V and 9V, between 4V and 8V, etc., including between any lower value of about 1 V, 2V, 3V, 4V, etc. and any upper value of 5V, 6V, 7V, 8V, 9V, 10V, etc.). Although broad ranges of target voltage offsets (e.g., between 1-12V) are possible, in some variations it may be preferable to use a narrower range (such as between 4-6V or other similar ranges), to avoid heating at high end of the range and distortions in waveform at low end of range. In some embodiments, the range may be narrow such that the $V_s$ adjustments are made to target a specific offset voltage (i.e. 4 V, 5 V, 6 V, 6.5 V, 7 V, etc.).

Without control circuitry configured to adjust the supply voltage (Vs) as described herein, the apparatus may heat, and may waste a large amount of the available charge in heat loss. Further, the shape of the waveforms delivered may be less precise, as illustrated in FIGS. 80A-80D. For example, FIG. 80A shows an "ideal" biphasic waveform which may be repeated at a desired frequency, and may be modulated (e.g., amplitude modulated), and controlled to regulate either or both the positive-going pulse and the negative-going pulse for the duration (pulse width), amplitude, and presence (and direction) of any capacitive discharge component. In FIG. 80A, the waveform element is a square-wave, biphasic, charge-imbalanced current, having a positive-going pulse 802103 with a larger duration than the negative-going pulse 802105; no capacitive discharging is shown (examples showing capacitive discharging are shown in FIGS. 71A-71E and 73A-73B, discussed above). FIG. 80B illustrates how this current waveform signal may be distorted if the supply voltage ($V_s$) is not regulated as described herein, particularly when the value of the supplied voltage is close to the value of the applied voltage needed to deliver the desired current (which may vary with skin impedance and other factors); in this case, the current source may saturate due to capacitance built up in the electrodes (and subject), as illustrated in FIG. 80B, resulting in distortion of the applied waveforms. FIGS. 80C and 80D illustrate the voltage delivered to the probes connected to the electrodes to supply the currents shown in the TES waveforms of FIGS. 80C and 80D, respectively. This saturation may be avoided using the control circuitry described herein.

Thus, any of the transdermal neurostimulator apparatuses described herein may include any of the elements mentioned above, including a housing enclosing a high-voltage power supply (e.g., having a maximum voltage of greater than 10V) that is configured to provide a supply voltage of less than the maximum voltage, in which the supply voltage is adjustable, a pair of connectors configured to electrically connect with a first electrode and a second electrode, and a controller (e.g., within the housing) that includes a waveform generator configured to deliver a pulsed, asymmetric, biphasic electrical signal between the first and the second connectors, wherein the waveform generator receives the supply voltage from the high-voltage power supply. The controller may be specifically configured to compare a difference between the supply voltage ($V_s$) and an applied voltage between the first and second connectors (e.g., $V_s-V_{applied}$) to a target voltage offset, and the controller may adjust the supply voltage based on the comparison. For example, the controller may be configured to decrease the supply voltage ($V_s$) if the difference between the supply voltage and the applied voltage is greater than the target voltage offset, and to adjust the supply voltage by increasing the supply voltage if the difference between the supply voltage and the applied voltage is less than the target voltage offset. FIG. 81 illustrates one example of a method for adjusting the supply voltage based on this comparison. In this example, the target voltage offset is a target range that extends between $V_b$, and $V_a$ (e.g., from 4 to 7 V, $V_a$=7 V, $V_b$=4 V). In other examples, the target voltage offset is a threshold value (e.g., 6.5V). As the applied voltage between the electrodes ($V_{applied}$) varies, the difference between this applied voltage and the supply voltage ($V_s$), $V_s$-$V_{applied}$, is compared to the target voltage offset. In FIG. 81, this range is shown graphically as $V_s$-$V_b$ and $V_s$-$V_a$. As the applied voltage moves out of the range window of the target voltage offset (between $V_a$ and $V_b$) relative to the supply voltage, the supply voltage is adjusted up or down, to try and keep it at or near the target voltage offset value(s). Thus, in FIG. 81, at times $t_1$, $t_2$ and $t_3$, the supply voltage is adjusted as shown. FIG. 81 is a simplified case, in practice, the controller may also consider other states when determining how (or if) to adjust $V_s$—and the adjustments to Vs may occur frequently (i.e. every cycle, every other cycle, every $5^{th}$ cycle, every $8^{th}$ cycle, every $10^{th}$ cycle, etc.). For example, FIGS. 82A and 82B are state diagrams indicating how $V_s$ may be adjusted ($V_{adjust}$). The state diagram indicates boundary conditions for adjusting voltage (FIG. 82A) and/or applied current (FIG. 82B) under conditions that require $V_s$ adjustment to attain a target $V_s$-$V_{applied}$ (generally, increased $V_s$ is required for fields under '$V_s$ saturation' and reduced $V_s$ is required for fields not under '$V_s$ saturation'), saturation of the voltage source, or overheating. FIGS. 82A and 82B illustrate a control loop logic to adjust the target current (i.e. peak current of an electrical stimulation pulse) and supply voltage (Vs) that the controller may execute depending on logical criterion of $V_s$ saturation (i.e. $V_s$-$V_{applied}$ is outside of its target region, as shown in FIG. 81), overheat limit (to protect the user, as well as maintain components within safe operating limits), and maximum ('max') $V_s$ reached. $V_s$ saturation may mean the current sources do not have enough voltage across them to operate linearly, and are not capable of supplying sufficient voltage during a stimulation pulse, leading to distortions of square pulses (as described above in reference to FIGS. 80B and 80D). To remove the saturation the supplied voltage (power supply voltage) may be increased and/or the applied current may be decreased. If the maximum supply voltage is already being supplied as $V_s$ then no change is made to $V_s$ (FIG. 82B) and the target current delivered at the electrodes is reduced (FIG. 82A). Generally, $V_s$ is increased when $V_s$ saturation occurs, unless the maximum $V_s$ is already being delivered or an overheating condition is present, in which cases the delivered peak current is reduced instead. In general, the control logic may reduce the peak current delivered rather than distort a current waveform or maintain an overheating condition. Overheating may be derived (e.g., calculated) from the current sources transistor power. When the dissipated power is excessive, the current may be reduced. The power supply voltage may then be reduced to a level that dissipates less power by means of the Vs adjustment feedback control. Both voltages and current may be controlled to match the target values. Thus, in addition to adjusting the supply voltage, the controller may (in some instances) regulate the current applied and adjust it based on these conditions (see, e.g., the middle rows in FIGS. 82A-82B). For example, the control logic may reduce the target current delivered under conditions of an overheat limit, even if the $V_s$ is not saturated.

When the supply voltage has to be adjusted as described above, it may be adjusted in any number of ways, including adjusting by a fixed amount, and/or adjusting by a percentage of the difference (e.g., between the $V_s$ and the $V_{applied}$), and/or adjusting based on recent historical values of the applied voltage (e.g., over some recent time period). In some embodiments, the supply voltage may be adjusted in an open loop manner based on an upcoming change in a waveform (e.g. a change that requires higher probe voltages such as a longer duty cycle or reduced frequency) in order to avoid an expected deviation from the acceptable voltage offset range. For example, in some variations, $V_s$ may be adjusted by, e.g., 85% of measured excursion of ($V_s$-$V_{elec}$) outside of the acceptable range. This may provide improved stability of the system, so that the changes in $V_s$ are somewhat dampened. In some variations, large adjustments may be made by adjusting by fixed increments (e.g., of about 0.5V, 1V, 1.5V, 2V, 2.5V, 3V, etc.). This may allow enough adjustment to quickly get to (e.g., approach) the acceptable range of $V_s$-$V_{elec}$ without making such a large immediate change that there could be an unsafe or uncomfortable shock from the apparatus.

As indicated above, if the adjustment to $V_s$ would exceed the maximum available power for the voltage supply, then the controller may override the requested max current. After the override, the current has a lower maximum intensity (note that the alternative would distort the signals as illustrated in FIGS. 80B and 80D, e.g., so that current falls off at the end of the pulse once the voltage supply reaches maximum).

For example, a transdermal neurostimulator apparatus may include a housing enclosing a high-voltage power supply having maximum voltage (e.g., of greater than 10V, greater than 15V, greater than 20V, greater than 25V, greater than 30V, etc.) and further configured to provide a supply voltage of less than the maximum voltage, wherein the supply voltage is adjustable. These apparatuses generally include a first connector configured to electrically connect with a first electrode and a second connector configured to electrically connect with a second electrode. Any of these apparatuses may also include a controller (e.g., within the housing) that includes, e.g., a waveform generator configured to deliver a pulsed, asymmetric, biphasic electrical signal between the first and the second connectors, wherein the waveform generator receives the supply voltage from the high-voltage power supply. Any of these controllers may also include a sensing circuit configured to detect an applied voltage between the first and second connectors (the $V_{applied}$). The sensing circuit may comprise an amplifier connected to one or both of the first and second connectors. The controller may also be configured as described herein to compare a difference between the supply voltage ($V_s$) and the applied voltage ($V_{applied}$) with a predetermined target voltage offset, and to adjust the supply voltage by decreasing the supply voltage if the difference between the supply voltage and the applied voltage is greater than the target voltage offset and to adjust the supply voltage by increasing the supply voltage if the difference between the supply voltage and the applied voltage is less than the target voltage offset.

In general, any appropriate high-voltage power supply may be used. For example, the high-voltage power supply may be configured to provide between 20V and 100V.

As mentioned above, the controller may be configured to decrease the supply voltage if the difference between the supply voltage and the applied voltage is above the target voltage offset and to increase the supply voltage if the difference between the supply voltage and the applied voltage is below the target voltage offset. The controller may be configured to adjust the supply voltage as a function of the difference between the supply voltage and the applied voltage.

In any of the apparatuses and methods described herein, the controller is configured to determine if the apparatus is in an overheating state based on an applied current and the difference between the supply voltage and the applied voltage.

As mentioned above, in various embodiments, the controller of the TES neurostimulator may include a capacitive discharge circuit configured to discharge a capacitance on the electrodes during the delivery of the biphasic electrical stimulation signal. TES neurostimulators that incorporate discharging the capacitance on the electrodes may be useful for pulsed stimulation regimes, and may help reduce or prevent pain and discomfort. In some variations the apparatus includes capacitance discharging circuitry in connection with the electrodes. For example, as described above, capacitance discharging circuitry may include electronic components and firmware features that short the anode-cathode path to permit discharge of capacitance that builds up during a pulse (e.g., in the subject's skin). In some instances, short-circuiting is beneficial for reducing discomfort and accordingly increasing the cognitive effects induced by TES (due to one or both of: reducing the distraction of discomfort so that other cognitive effects can be experienced by a subject and permitting higher peak current intensities to be delivered that induce more significant cognitive effects). In general, controlling the maximum current of a capacitance discharging pulse may be beneficial for tuning the comfort of a TES waveform (e.g. to vary the maximum current of discharge based on the estimated amount of capacitance built up, which is expected to correlate with increasing imbalance (i.e. duration and/or peak current) between positive-going and negative-going pulses, as well as by frequency, where lower frequency stimulation at a fixed duty cycle will cause relatively more capacitance build-up per cycle).

In some embodiments, the wearable transdermal electrical stimulator may comprise a control module having the capacitive discharging features (which may be referred to as a 'short circuiting' applicator) described. For example, the wearable transdermal electrical stimulator may include: a housing configured to be connected to a first electrode and a second electrode, a control module at least partially within the housing including: a processor, a waveform generator configured to deliver a biphasic electrical stimulation signal between the first electrode and the second electrode, and a capacitive discharge circuit configured to discharge a capacitance on the first electrode and the second electrode during the delivery of the biphasic electrical stimulation signal. The TES control module is adapted to deliver a biphasic electrical stimulation signal of 10 seconds or longer between the first and second electrodes having a frequency of 400 Hz or greater, a duty cycle of greater than 10 percent, an intensity of 3 mA or greater, with a DC offset; and a capacitive discharge circuit, wherein the TES control module is configured to occasionally trigger the capacitive discharge circuit to discharge capacitance on the electrodes during the delivery of the biphasic electrical stimulation.

FIG. 71A schematically illustrates a biphasic electrical stimulation waveform with a positive pulse and a negative pulse in one cycle. In some embodiments, the firmware may create segments in a waveform cycle. The smallest segment may be limited by the clock of the processor. For example, in some embodiments, the shortest segment per cycle can be 2, 5, or 10 microseconds or any values there between. For example, in some embodiments, the firmware may create 10, 12, 15, or 20 segments per cycle. For each segment of the cycle, the controller may instruct the waveform generator to generate a positive intensity value, a negative intensity value, a value of "zero" which indicates an open circuit mode, or a capacitive discharge.

In some embodiments, the capacitive discharge (which may be referred to as "short-circuiting" although it is not the result of shorting) can be triggered immediately after the positive pulse or negative pulses as shown in FIGS. 71B-71D. For example, as shown in FIG. 71B, at the time when the positive pulse ends, the controller triggers the capacitive discharge circuit to short the anode-cathode path, resulting in a capacitive discharging pulse to permit discharge of capacitance. The minimum duration of the capacitive discharging pulse may be limited by the shortest segment of the cycle as discussed above. Thus the duration of the pulse can be larger than 2, 5, or 10 microseconds. However, the duration of the pulse may not be too short. It might be advantageous to have a more gradual pulse to prevent pain in the subject. It might be advantageous to have a limited peak value of the pulse to further prevent pain and discomfort. The peak value and the time constant of the capacitive discharging pulse may be controlled by the capacitive discharge circuit. In some other embodiments, the capacitive discharge can be triggered immediately after the negative pulse as shown in FIG. 71C. In some embodiments, the capacitive discharge can be triggered both after the positive pulse and after the negative pulse as shown in FIG. 71D.

In some alternative embodiments, the capacitive discharging pulse can be triggered at the onset of each negative-going pulse in the negative-going direction as shown in FIG. 71E. For example, in the "energy" mode, the capacitive discharging pulse can be triggered at the onset of each negative-going pulse in the negative-going direction to induce an enhanced cognitive state. In some other embodiments, the capacitive discharging pulse may be triggered at the onset of each positive-going pulse in the positive-going direction. In some other embodiments, the capacitive discharging pulse can be triggered both at the onset of each negative-going pulse in the negative-going direction and at the onset of each positive-going pulse in the positive-going direction.

FIG. 72 schematically illustrates an example of a capacitive discharge circuit including a double H-bridge according to some embodiments of the disclosure. The double H-bridge circuit can be configured to generate a gradual capacitive discharging pulse with controlled time constant and peak value. As discussed above, the outside H-bridge can be configured to adaptively adjust the applied voltage $V_s$ based on feedback signals. In addition to the outside H-bridge, the circuit can further comprise an inside H-bridge including transistors 721324, 721305 and 721310. The transistors 721305 and 721310 can be configured to form a current source, driving the current to the ground. When probe B is negatively charged, and probe A is positively charged, the transistors 721305 and 721310 can pull probe B to ground with a gradually discharging pulse. In the other direction, the transistors 721324 can be configured to form a second current source, driving the current to the ground. When probe A is negatively charged, and probe B is positively charged, the transistors 721324 can pull probe A to ground with a second gradually discharging pulse. Therefore, the inside H-bridge including transistors 721324, 721305 and 721310 can be configured to generate gradual capacitive discharging pulses with controlled time constants and peak values. In general, the double H-bridge circuit can be configured to generate gradual capacitive discharging pulses, in addition to adaptively adjust the applied voltage Vs using feedback signals.

For example, the TEST waveform may have a frequency of 11 kHz, the time constant of the capacitive discharging pulse can be between 0.00001 to 100 microseconds. The peak value can be controlled to be between 0.001 and 10 mA in some embodiments. In some embodiments, the controller of the neurostimulator may include a switch configured to turn off the current source when the capacitive discharge circuit is triggered.

FIG. 73A illustrates an example of the capacitive discharging pulse from the double H-bridge capacitive discharge circuit. The discharging pulse immediately after the positive pulse can be controlled to have a gradual slope with a controlled peak value. The discharging pulse immediately after the negative pulse is small because there is only small amount of capacitance built up.

FIG. 73B illustrates another example of the capacitive discharging pulse from the capacitive discharge circuit with the double H-bridge. The discharging pulse is triggered at the onset of the negative going pulse in the negative going direction with a controlled time constant and peak value. The discharging pulse can be configured to enhance the "energy" cognitive state and minimize user discomfort.

In some other embodiments, the capacitance discharging circuitry may include electronic components and firmware features that short the anode-cathode path with a low ohm resistor (e.g. 50 Ohms) to permit discharge of capacitance that builds up during a pulse (e.g., in the subject's skin). In some other embodiments, the capacitive discharging circuitry may include a fixed current source similar to the main current source in the device, but saturating at 0V and allowing discharge of the accumulated charges. The discharge time may be fixed or may depend on the voltage and electrode capacitance. In one example a nominal short-circuit current may be adjustable (e.g., to 40 mA), which could be changed by changing a resistor. The discharge could be made by the regular current source with an adjustable current inside the range, e.g., up to 20 mA; turning on the two rectified bottom switches may avoid reverse charging in this case. In general, a capacitive discharge can be very quick (e.g. on the microsecond timescale) and could use a very high current, e.g., tens of mA to 100 mA.

In general, a biphasic pulse may include a positive-going pulse following (either immediately or after some delay) by a negative-going pulse. As described herein, these pulses are not limited to square-wave pulses, but may be saw tooth, or other shapes. In some variations, the positive-going and negative-going pulses may have different shapes. In some variations, the biphasic pulse includes a positive-going (or negative-going) monophasic square wave pulse and a capacitive discharge (from a capacitive discharge circuit) in the other direction. For example, the apparatus may be configured to apply a uniphasic square wave pulse (positive or negative going) and a capacitive discharge in the opposite direction. In general, TES waveforms may include bursting regimes wherein cycles of stimulation occur intermittently.

FIG. 74 schematically illustrates an example of safety comparison circuits according to some embodiments of the disclosure. In various embodiments, the controller of the neurostimulator can include safety comparison circuits configured to prevent the current and/or the voltage from exceeding maximum values. For example, the maximum DC current may be set at 5 mA, 8 mA, or 10 mA, or any values there between. Similarly, the voltage may have a maximum value for the safety of the subject as well. The circuit can be configured to shut down the power supply when the current or voltage exceeds the maximum value. For example, the safety circuit can comprise a current safety comparison circuit section 741510. The section 741510 can be configured to compare the current values in both directions and output a fault signal to the microprocessor if the current value in any direction exceeds the maximum value. The safety circuit can further comprise a voltage safety comparison circuit section 741520. The section 741520 can be configured to compare the voltage values in both directions and output a second fault signal to the microprocessor if the voltage value in any direction exceeds the maximum value. The voltage safety comparison circuit section 741520 can comprise a transistor 741527 to increase the sensitivity of the safety circuit.

The systems, devices, and methods of the preferred embodiments and variations thereof can be embodied and/or implemented at least in part as a machine configured to receive or include a computer-readable medium storing computer-readable instructions. The instructions are preferably executed by computer-executable components preferably integrated with the system including the computing device configured with software. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

Alternatively or additional, also described herein are methods and apparatuses for transdermal electrical stimulation (e.g., neurostimulation) of a subject using ensemble waveforms that generally include a sequence of different periods (component waveforms) having predetermined values (e.g., peak values) for at least four waveform components, in which one or more (typically two) of these waveform components is changed between adjacent component waveforms in the series forming the ensemble waveform. Also described herein are methods of modulating a subject's cognitive state by applying ensemble waveforms, and apparatuses configured to apply these ensemble waveforms. Also described herein are methods and apparatuses (including devices and systems) for user control of ensemble waveforms, particularly transdermal electrical stimulation (TES) ensemble waveforms. In general, the methods and apparatuses may allow effective neuromodulation with electrical stimulation to induce a beneficial or desired change in cognitive function and/or cognitive state. Finally, described herein are methods and apparatuses for controlling a neurostimulator including transmitting waveform information (e.g., component waveform information) to a processor of a wearable neurostimulator where it may be used to set the parameter values necessary to deliver the ensemble waveform as described herein.

In general, a user may wear a neuromodulation device and apply one or more waveforms using the neuromodulation device to induce a cognitive effect. In general, the user may control the wearable neuromodulation device through a user device. A user device may be used to control the applied waveforms ("ensemble waveforms") for use in a transdermal electrical stimulation protocol. A system may include the wearable neuromodulation device, and the user computing device for control of the transdermal electrical stimulation (TES) waveforms.

A time-varying pattern of electrical stimulation delivered transdermally (and, optionally, to some extent, transcranially) to induce neuromodulation may be referred to as a transdermal electrical stimulation waveform ('TES waveform'). A stimulation protocol may define the temporal pattern of current delivered to an anode-cathode set and can incorporate one or more waveform components including but not limited to: direct current, alternating current, pulsed current, linear current ramp, nonlinear current ramp, exponential current ramp, modulation of current (e.g., amplitude modulation at one or more frequencies), pulsed current (e.g., amplitude modulation where part of the modulated cycle is at zero intensity), and more complex time-varying patterns of electrical stimulation (including repeated, random, pseudo-random, and chaotic patterns). In operation, the device may provide current flow at target areas (e.g., in the brain, facial nerves (cranial nerves and/or cervical spinal nerves), vagal nerve, or other neuronal targets) to induce neuromodulation when appropriate electrode configurations and stimulation protocols are delivered.

TES waveform parameters that may be used to invoke, enhance, or modify a variety of cognitive states may be considered compound waveforms including a number of different sub-portions that are temporally connected together and delivered to a user in sequence. In general, the ensemble waveform and the component portions can be defined by four waveform parameters that may be used by the neurostimulator to define the component waveforms and, in combination with the duration of each waveform component and in some variations a ramping parameter, may define an ensemble waveform. In some variations, more complex waveforms are used for TES, and additional components may be included, such as transient capacitive discharges, multiple pulses per cycle, phase relationships of two or more pulses per cycle, complex pulse shapes, non-sinusoidal alternating current, etc. In some variations, an ensemble waveform (or portion of an ensemble waveform) may be modulated by an envelope of slower-frequency amplitude modulation (e.g., modulation of the current amplitude parameter). For example different types of amplitude modulation may be applied (e.g., amplitude modulation at frequencies between 0.5 Hz and 1000 Hz may be applied on top of the ensemble waveform. In some variations the amplitude modulation is applied as a sinusoidal (e.g., pure sinusoid, saw tooth, square pulses, etc.); in some variations the amplitude modulation is bursting, and results in an amplitude modulation duty cycle, in which stimulation intensity is decreased or turned off for a pre-determined period and switched on for a pre-determined period (where the amplitude modulation duty cycle can be calculated as the on period duration divided by the sum of the on period duration and off period duration).

The TES waveform components described herein may generally be formed of a basic unit comprising a plurality of biphasic pulses that may be asymmetric with respect to positive and negative going phases and may be charge imbalanced (although one or more capacitive discharging pulses may also be included within each repeating pulse to offset a charge imbalance as described herein). The component waveforms described herein may be defined by a duration and a set of waveform parameters including: a peak current amplitude (in mA), a frequency (in Hz or kHz), a percent charge imbalance, and a duty cycle. FIG. 89A schematically illustrates a basic waveform unit. This example shows the basic unit as a combination of squarewaves (steps), however, rounded (including sinusoid), sawtoothed, triangular, and other shapes may be used. The waveform parameters for this basic unit waveform are defined by a duty cycle (or percent duty cycle), percent charge imbalance (also referred to as percent direct current, or percent DC), ramping or other amplitude modulation, one or more multiple frequency components, phase relationship of biphasic current, flat or structured noise, wave shapes (i.e., saw tooth, triangular, sine wave, square wave, exponential, or other wave shape), capacitance compensation features, or other parameters as discussed in U.S. patent application Ser. No. 14/091,121, titled "Wearable Transdermal Electrical Stimulation Devices and Methods of Using Them," filed Nov. 26, 2013, which is herein incorporated by reference in its entirety.

In FIG. 89A, the biphasic waveform includes a positive-going pulse having an amplitude $I_{peak}$, and a duration $t_p$ (time spent in the positive direction, relative to baseline), a negative-going pulse having an amplitude (in this example, $I_{peak}$ but in the negative direction) and a duration $t_n$ (time spent in the negative direction, relative to baseline). The total time of the base unit is $t_c$ (time for one period of a cycle).

As used herein, 'percent duty cycle' may refer to the proportion of a cycle of a waveform that causes non-zero (or nominally non-zero) current to be delivered transdermally (though for waveforms incorporating capacitive discharge, the nominally non-zero portion of the duty cycle may not include the non-zero portions of the cycle caused by capacitive discharge). For example, the duty cycle in FIG. 89A is the sum of $t_p$ and $t_n$ divided by $t_c$. Further, the percent charge imbalance (or 'percent direct current') refers to the non-zero portion of a waveform cycle that is positive-going or negative-going (again, excluding capacitive discharges, if present). In FIG. 89A, the percent charge imbalance is the ratio of the difference of $t_p$ and $t_n$ and the sum of $t_p$ plus $t_n$.

Inducing significant, robust, and/or reliable cognitive effects typically requires an appropriate ensemble waveform defined by a set of parameters for each component waveform. A stimulation protocol typically includes a composite waveform that defines the temporal pattern of current delivered to an anode-cathode set and can incorporate one or more waveform components including but not limited to: direct current, alternating current, pulsed current, linear current ramp, nonlinear current ramp, exponential current ramp, modulation of current, and more complex patterns (including repeated, random, pseudo-random, and chaotic patterns). In operation, the device may provide current flow at target areas (e.g., in facial nerves, cranial nerves, vagal nerve, in the brain, etc.) to induce neuromodulation when appropriate electrode configurations and stimulation protocols are delivered.

Although the apparatuses and methods described herein may be used to provide TES to induce and/or modify a variety of cognitive states, two particular examples are described in detail herein: (1) enhancing attention, alertness, or mental focus and (2) inducing a calm or relaxed mental state. Configurations of apparatuses and methods for causing neuromodulation that specifically achieve enhanced attention, alertness, or mental focus as opposed to an increased calm or relaxed mental state are described in particular detail.

Thus, a generic neurostimulator for modifying a cognitive state may include a pair of electrodes (or two sets of electrodes), referred to herein for convenience as an anode and a cathode (where the anode and cathode may loosely refer to their function as primarily anode and primarily cathode for biphasic waveform components), that can be applied to specific regions of the subject's body and used to provide TES stimulation within the relatively high-intensity, high-frequency ranges described as effective herein. Current is typically applied between the anode and cathode electrodes (or groups of anode and cathode electrodes). Without being bound by a particular theory of operation, the current may be passed through the body between the anode and cathode electrodes (or groups of anode and cathode electrodes), potentially applying energy in an appropriate treatment regime to underlying neural tissue (nerves, e.g., cranial, cervical spinal, vagal, etc., brain, etc.) in a particular neural pathway to result in the desired target effect (e.g., attention, alertness, or mental focus; inducing a calm or relaxed mental state). Thus, the placement locations of the electrodes on the subject's body are important to provide the desired cognitive effect. The placement positions for the pairs of electrodes (anodal and cathodal electrodes) specific to a desired cognitive effect may be referred to as a placement regime or configuration. For example, a first placement configuration for inducing a cognitive state of attention, alertness, or mental focus may include a first electrode applied to the subject near the temple and/or forehead area (e.g., laterally to the eye, such as slightly above and to the right of the right eye or above and to the left of the left eye) and a second electrode positioned behind the ear on the same side as the first electrode in the mastoid region (e.g., on or near the mastoid). High-intensity stimulation (as described in greater detail below) of this region may result in enhanced attention, alertness, or mental focus.

Another configuration of electrode positions may include an electrode positioned on the subject's skin near the subject's temple and/or forehead area (e.g., above and to the right of the right eye) and a second electrode on the subject's neck (e.g., on a superior portion of the neck centered at or near the midline and at least partially overlapping the midline). Appropriate TES stimulation of this region may result in enhancing a calm or relaxed mental state. Either of these configurations may also be used with an appropriate TES stimulation regime (waveform) to induce phosphenes by noninvasive transdermal electrical stimulation using the apparatuses described herein.

Generally speaking, peak stimulation intensities above at least 3 mA (e.g., greater than 5 mA, e.g., between 5 mA and 25 mA, etc.) may be advantageous for transdermal electrical stimulation that causes neuromodulation by targeting the brain, nerves (e.g., cranial nerves, vagal nerve, peripheral nerves, spinal nerves), and/or spinal cord. To achieve these peak intensities without causing significant pain, irritation, or discomfort in a subject may require appropriate electrodes and appropriate ensemble waveforms as described herein. Beneficial electrodes may have pH buffering properties and may contain components for uniformly (or more uniformly) delivering current across the dermal-facing portion of the electrode.

The TES waveforms for use with any of the configurations described herein may be a pattern of currents delivered into tissue of a user (e.g., transdermally). Although there may be variations (optimizations) of these waveforms and electrical protocols for each configuration (electrode placement) and each target cognitive state, in general, the patterns may be within the same range of values to provide biphasic, high-intensity, high-frequency and asymmetric with regard to the positive-going and negative-going phases of the waveform (in some cases not charge balanced) signals that are applied to robustly evoke a response in most individuals while causing at most a low level (e.g., minimal or none) of discomfort and/or pain.

These waveforms may be ensemble waveforms including a plurality (e.g., 3 or more) of component waveforms having a predetermined value for each of: current amplitude ("intensity"), frequency, percent charge imbalance, duty cycle, and in some variations capacitive discharge. These component waveforms may each have a duration (time), and may be connected together in a sequence to evoke the desired cognitive effect. Some of these component waveforms forming the ensemble waveform are ramps, in which one or more waveform parameter (current amplitude, frequency, duty cycle, percent charge imbalance) of the waveform is ramped up to the target/peak value of the waveform components from the previous value of the waveform components after transitioning to the new component waveform when delivering the ensemble waveform.

Generally, tDCS studies have used between about 1 mA and about 2 mA peak currents for longer stimulation periods (e.g., more than a few minutes or seconds), and tACS typically uses relatively low frequencies (e.g., <650 Hz). However, these current levels and frequencies are sub-threshold for at least some forms of neuromodulation. In particular, the inventors have found that higher currents may be necessary for inducing significant and beneficial cognitive effects. Unfortunately, such higher currents may lead to pain, irritation, and damage to skin under high current stimulation conditions. Higher currents than have traditionally been used for TES are required for inducing a change in a cognitive state in at least some instances. Described herein are systems configured to deliver higher currents (optimally 3 mA or higher), at relatively high frequency (>750 Hz, e.g., between 750 Hz and 30 kHz, between 1 kHz and 30 kHz, etc.) to achieve a desired cognitive effect. The ensemble waveforms described herein may reduce irritation, pain, and burning sensations in the dermis, muscles, and other tissues of users receiving TES. These embodiments permit higher current intensities to be transmitted comfortably so that desirable changes in a subject's cognitive function, cognitive state, mood, and/or energy levels can be attained. In addition to the high current amplitudes, high frequency (e.g., repeating the base waveform of FIG. 89A between about 650 Hz and about 50 kHz (e.g., between about 750 Hz and about 40 kHz, between about 1 kHz and about 35 kHz, etc.) may provide biphasic pulsed and/or alternating current stimulation that minimally activates sensory pathways and minimizes pH changes in tissue due to stimulation.

In addition to the waveform parameters described herein, it may be helpful to achieve higher transdermal currents while minimizing pain and irritation by using electrodes that distribute current evenly across the electrode and/or mitigate pH changes known to occur in tissue due to direct current stimulation or other charge imbalanced stimulation waveforms. Embodiments include TES systems and methods that use appropriate electrodes configured to reduce pain, irritation, itching, and burning sensations in a subject due to one or more of: mitigation of pH changes in tissue due to direct current stimulation or charge imbalanced stimulation; hydrogels or other electrically conductive media for more effectively coupling an electrode to a user's skin with low impedance; and components of an electrode assembly that achieve a more even distribution of current across the face of the dermally coupled electrode. Examples of electrode designs that may be used are provided herein, but additional examples may include Axelgaard Manufacturing Co., LTD., Axelgaard Little PALS (neonatal pediatric ECG electrodes)

and PALS Platinum Blue (conductive cloth neurostimulation electrodes designed for peripheral transcutaneous electrical nerve stimulation (TENS) and muscle stimulation), which are particularly effective for delivering higher tDCS currents while minimizing pain, irritation, and tissue damage. Electrodes configured to spread current evenly across the face of the electrode and mitigate pH changes due to direct current stimulation and/or charge imbalanced stimulation are advantageous for safely and comfortably delivering higher current intensities (e.g., direct currents above about 1.5 mA) that would otherwise be painful, irritating, or damaging to a subject. One skilled in the art will recognize that other commercially available and custom-designed electrodes that mitigate pH changes in tissue and/or spread current evenly across the electrode surface in dermal contact are advantageous for high current TES.

The waveforms described herein may minimize pain and irritation by delivering ensemble waveforms in which one or more of the waveform parameters (current intensity, frequency, duty cycle and percent charge imbalance) is varied and/or changed and held fixed or ramped for predetermined time intervals as the ensemble waveform progresses. The duration of each component waveform may be between 100 ms and 30 minutes (e.g., 20 min), e.g., between 1 second and 240 seconds and an ensemble waveform may include a gradual ramping of the one (or more than one) parameter being changed between component waveforms, with intermittent periods of stable current delivery (which may habituate a subject to the current level delivered and accordingly reduce or eliminate perceptions of pain and/or irritation due to electrical stimulation, though these static waveforms may also cause habituation to the induced cognitive effect intended from the waveform). Ramping strategies that deliver component portions of the TES waveforms with gradually changing current amplitude, frequency, duty cycle and/or percent charge imbalance can cause habituation or otherwise inhibit a user's sensory receptors or other components of a user's nervous system that transmit painful stimuli or transduce the subjective feeling of pain or discomfort, allowing relatively higher intensities of current (previously considered just to be a function of current amplitude, rather than the time course of the stimulation waveform).

For example, pain and irritation from TES may be reduced by ramping the changing waveform parameter gradually (e.g., over tens of seconds to a few minutes) up or down. This can be done various ways: e.g., with a linear ramp, a ramp with a different temporal profile, or a series of ramps between intermediate levels of static current delivery (e.g., ramp and hold, ramp and hold, etc.).

As an illustrative example, a TES system configured for applying an ensemble waveform according to a protocol to minimize pain and irritation while evoking a robust response in a subject is illustrated in FIG. 89B. In this example, there are ten waveform components shown (time is on the x-axis, not shown to scale). The first component waveform has a zero current amplitude 892014, but a first frequency (e.g., 10 kHz), and duty cycle (e.g., 40%), and percent charge imbalance (e.g., 80%). Thus, once the ensemble waveform is applied, there is initially no current (since current is 0 mA). After a few seconds duration, the second component waveform starts 892015. The second component waveform has a value for the peak current amplitude (e.g., 5 mA), a frequency (e.g., 10 kHz, in this example, the same as the first component waveform), a percent charge imbalance (e.g., 80%, in this example, the same as the first component waveform), and a percent duty cycle (e.g., 40%, in this example, also the same as the first component waveform). This second component waveform also has a predetermined duration (e.g., 1 min), and ramping is on, so that the parameter that changes from the first component waveform (amplitude) is ramped over the 1 minute duration to the peak value. In some variations the waveform components may indicate which parameters (amplitude, frequency, etc.) are to be ramped and/or a separate duration and/or a method of ramping for each of the waveform components that has changed. The third component waveform 892016 has all of the same waveform parameters as the second, but with ramping off (or ramping time set to zero) and a duration of about 3 minutes. The fourth component waveform 892017 has ramping on again, a duration of one minute, and an increase in the peak current amplitude (e.g., 10 mA). The fifth component waveform 892018 has the same waveform parameter values as the fourth, but with ramping off, maintaining the waveform parameters for several minutes until the sixth component 892019, in which the frequency is increased (e.g., to 15 kHz) and ramping is on. The seventh component waveform 892020 increases the current value (e.g., to 12 mA), while keeping the frequency and other waveform parameters the same, with ramping on for the duration of the component (e.g., 5 min). The 8th component waveform 892020 has the same waveform parameters, but with ramping off for the duration (e.g., 2 min). The 9th component waveform has an increase in the frequency (e.g., to 17 kHz) and ramping on, while all other parameters stay the same. The 10th component waveform has all the same waveform parameters as the 9th, but with ramping off. Also not shown in this example, a capacitive discharge may be "on" during all of the component waveforms (or some of them).

This example shows primarily increasing current and frequency, however, any of the other components may be modified (e.g., duty cycle, percent current imbalance), or decreased as well as increased.

In any of the ensemble waveforms described herein, a capacitive discharge may be incorporated into any or all of the composite waveforms. As used herein, a capacitive discharge may be referred to as a controlled transient short circuiting of the electrodes at some point (or more than one point) during the pulsing waveform (e.g., every cycle, after every pulse, etc.). Capacitive discharge may be a beneficial feature for TES waveforms, because it may relieve capacitance built up in the subject's body (and electrodes coupled to the subject's skin) that can lead to pH changes and discomfort. Reducing capacitance in the subject's body also may improve the efficiency of stimulation by decreasing the voltage required for delivering a current (i.e., a high current such as one greater than 5 mA) transdermally. For example, FIGS. 89C and 89D illustrate two kinds or types of capacitive discharge that may be used. In FIG. 89C the basic waveform unit, such as the one shown and described above in FIG. 89A, includes a pair of capacitive discharges that occur following each positive-going or negative-going pulse. In some variations, e.g., the "calm" ensemble waveforms described herein, a capacitive discharge occurs at the end of the positive-going pulse and at the end of the negative-going pulse. The time constant for the return of the capacitive discharge may be sufficiently long so that the adjacent negative-going pulse rides on the return portion of the capacitive discharge, as shown in FIG. 89C. In some variations, such as the "energy" ensemble waveforms described herein, the capacitive discharge may occur at the start of a pulse. For example, in FIG. 89D, each base unit includes at least one capacitive pulse that occurs at the start of the negative-going pulse. These examples are not meant to be limiting with regard to the types of capacitive discharge that may be used in component waveforms for TES. Thus, in general, any of the ensemble waveforms may also include a parameter (e.g., an overall parameter and/or an individual parameter for each composite waveform) indicating if a capacitive pulse (or pulses) is included. In some variations, the capacitive pulse parameter may also indicate the type of capacitive pulse (e.g., positive-going, negative-going). The capacitive pulse parameter may also indicate the timing of a capacitive discharge during a cycle (i.e., relative to pulses or other features of the waveform, including after each positive-going pulse, after each negative-going pulse, before each positive-going pulse, before each negative-going pulse, etc.). The capacitive pulse parameter may also indicate the time constant for the capacitive pulse parameter and/or it may be set by the system. The capacitive pulse parameter may also indicate the number of capacitive discharges during a cycle (including values less than one, i.e., those that occur on every other cycle; every $3^{rd}$ cycle; every $4^{th}$ cycle; every $n^{th}$ cycle, etc.; and also including capacitive discharge that occurs on cycles selected randomly or pseudo-randomly). The capacitive pulse parameter may also indicate the maximum current (and/or maximum voltage) of the capacitive discharge, which is defined by elements of the electric circuit of the neurostimulator device configured for allowing the capacitive discharge to occur.

These ensemble waveforms may be delivered to the subject wearing the neurostimulator, or in some variations they may be modified (e.g., by scaling them down) as mentioned above. Scaling or otherwise modifying a waveform may be controlled in real-time or near-real-time by the user (subject) during a TES session, for instance as discomfort develops or to increase the strength of an intended cognitive effect. Scaling will typically change (e.g., by a percentage) one or more of the waveform parameters (e.g., current amplitude, frequency, duty cycle, charge imbalance, etc.). When a subject modifies a waveform to reduce discomfort (e.g., by one or more of: reducing current amplitude, increasing frequency, decreasing duty cycle, decreasing charge imbalance), the modified waveform may allow habituation to the current delivered so that the subject experiences reduced irritation or discomfort.

Biphasic transcranial alternating current stimulation (and biphasic pulsed current stimulation as shown in FIGS. 89A, 89C, and 89D) may yield stronger cognitive effects compared to transcranial direct current stimulation due to dramatically reducing discomfort in the skin under the electrodes (and, in at least some cases, enabling higher peak stimulation currents). Putative mechanisms for reduced irritation include: (1) reduced pH changes in tissue relative to pH changes occurring from direct current stimulation; and (2) reduced skin impedance at higher stimulation frequencies.

Another example of a composite waveform that may be used as described herein is shown in FIGS. 90A-90C. FIG. 90A shows the peak intensity for each of the component waveforms forming the ensemble waveform. This waveform may be used to evoke a cognitive state referred to herein as a "calm" ensemble waveform (e.g., for evoking a feeling of calm when applied with electrodes positioned at the temple (and/or forehead) and back of the neck). FIG. 90B shows labels for the component waveforms indicating their order, duration, and timing. FIG. 90C shows the carrier frequency of stimulation for each of the component waveforms. For all waveform segments shown, the peak intensity listed is the maximum peak intensity, which may be delivered at a reduced level (i.e., percentage of the peak intensity) based on automatic or manual (user-controlled) intensity selection, as mentioned above. Also, this example shows that not all waveform parameters need to change during an ensemble waveform. In this example, the duty cycle is fixed at 40% for all component waveforms.

The waveform begins with component waveform 90100 during which stimulation is turned on gradually to improve the comfort of the experience for the user and thus increase the likelihood that a cognitive effect can be induced without causing undue discomfort, pain, or tissue damage. Similarly, at the end of the waveform, component waveform 90116 gradually ramps down the intensity of stimulation gradually as the ensemble waveform completes. In the intervening time period, the ensemble waveform comprises three primary waveform components, as well as waveform components that provide transition periods between the primary waveform components.

A first primary waveform component ('primary waveform component X') 90101, 90107, 90115 is defined by a maximum peak intensity of 8 mA, 40% duty cycle, 40% charge imbalance, and 5 kHz carrier frequency.

A second primary waveform component ('primary waveform component Y') 90103, 90109, 90113 is defined by a maximum peak intensity of 17 mA, 40% duty cycle, 45% charge imbalance, and 12 kHz carrier frequency.

A third primary waveform component ('primary waveform component Z') 90105, 90111 is defined by a maximum peak intensity of 20 mA, 40% duty cycle, 55% charge imbalance, and 18 kHz carrier frequency.

In this example, the waveform parameters for the component waveforms making up this ensemble waveform are shown, in order, in Table 1, below:

TABLE 1

| First ensemble waveform example | | | | | | | | | | |
|---|---|---|---|---|---|---|---|---|---|---|
| FIGS. 90A-C label | Start time (sec) | Duration (sec) | Start peak intensity (mA) | End peak intensity (mA) | Start duty cycle (%) | End duty cycle (%) | Start charge imbalance (%) | End charge imbalance (%) | Start carrier freq. (kHz) | End carrier freq. (kHz) |
| 90100 | 0 | 30 | 0 | 8 | 40 | 40 | 40 | 40 | 5 | 5 |
| 90101 | 30 | 90 | 8 | 8 | 40 | 40 | 40 | 40 | 5 | 5 |
| 90102 | 120 | 15 | 8 | 17 | 40 | 40 | 40 | 45 | 5 | 12 |
| 90103 | 135 | 75 | 17 | 17 | 40 | 40 | 45 | 45 | 12 | 12 |
| 90104 | 210 | 15 | 17 | 20 | 40 | 40 | 45 | 55 | 12 | 18 |
| 90105 | 225 | 75 | 20 | 20 | 40 | 40 | 55 | 55 | 18 | 18 |
| 90106 | 300 | 15 | 20 | 8 | 40 | 40 | 55 | 40 | 18 | 5 |
| 90107 | 315 | 75 | 8 | 8 | 40 | 40 | 40 | 40 | 5 | 5 |
| 90108 | 390 | 15 | 8 | 17 | 40 | 40 | 40 | 45 | 5 | 12 |
| 90109 | 405 | 75 | 17 | 17 | 40 | 40 | 45 | 45 | 12 | 12 |

TABLE 1-continued

First ensemble waveform example

| FIGS. 90A-C label | Start time (sec) | Duration (sec) | Start peak intensity (mA) | End peak intensity (mA) | Start duty cycle (%) | End duty cycle (%) | Start charge imbalance (%) | End charge imbalance (%) | Start carrier freq. (kHz) | End carrier freq. (kHz) |
|---|---|---|---|---|---|---|---|---|---|---|
| 90110 | 480 | 15 | 17 | 20 | 40 | 40 | 45 | 55 | 12 | 18 |
| 90111 | 495 | 75 | 20 | 20 | 40 | 40 | 55 | 55 | 18 | 18 |
| 90112 | 570 | 15 | 20 | 17 | 40 | 40 | 55 | 45 | 18 | 12 |
| 90113 | 585 | 75 | 17 | 17 | 40 | 40 | 45 | 45 | 12 | 12 |
| 90114 | 660 | 15 | 17 | 8 | 40 | 40 | 45 | 40 | 12 | 5 |
| 90115 | 675 | 90 | 8 | 8 | 40 | 40 | 40 | 40 | 5 | 5 |
| 90116 | 765 | 30 | 8 | 0 | 40 | 40 | 40 | 40 | 5 | 5 |

In the exemplary waveform of FIG. 90A, the first component waveform has a 30 second ramp phase 90100 from 0 to 8 mA with primary waveform component X. The second component waveform is a 90 second maintenance component waveform 90101 with primary waveform component X at 8 mA maximum peak intensity. The third component waveform is a 15 second ramp phase 90102 that gradually changes the peak intensity, percent charge imbalance, and carrier frequency between primary waveform component X and primary waveform component Y. The fourth component waveform is a 75 second maintenance component waveform 90103 with primary waveform component Y at 17 mA maximum peak intensity. The fifth component waveform is a 15 second ramp phase 90104 that gradually changes the peak intensity, percent charge imbalance, and carrier frequency between primary waveform component Y and primary waveform component Z. The sixth component waveform is a 75 second maintenance component waveform 105 with primary waveform component Z at 20 mA maximum peak intensity. The seventh component waveform is a 15 second ramp phase 90106 that gradually changes the peak intensity, percent charge imbalance, and carrier frequency between primary waveform component Z and primary waveform component X. The eighth component waveform is a 75 second maintenance component waveform 90107 with primary waveform component X at 8 mA maximum peak intensity. The ninth component waveform is a 15 second ramp phase 90108 that gradually changes the peak intensity, percent charge imbalance, and carrier frequency between primary waveform component X and primary waveform component Y. The 10th component waveform is a 75 second maintenance component waveform 90109 with primary waveform component Y at 17 mA maximum peak intensity. The 11th component waveform is a 15 second ramp phase 90110 that gradually changes the peak intensity, percent charge imbalance, and carrier frequency between primary waveform component Y and primary waveform component Z. The 12th component waveform is a 75 second maintenance component waveform 90111 with primary waveform component Z at 20 mA maximum peak intensity. The 13th component waveform is a 15 second ramp phase 90112 that gradually changes the peak intensity, percent charge imbalance, and carrier frequency between primary waveform component Z and primary waveform component Y. The 14th component waveform is a 75 second maintenance component waveform 90113 with primary waveform component Y at 17 mA maximum peak intensity. The 15th component waveform is a 15 second ramp phase 90114 that gradually changes the peak intensity, percent charge imbalance, and carrier frequency between primary waveform component Y and primary waveform component X. The 16th component waveform is a 90 second maintenance component waveform 90115 with primary waveform component X at 8 mA maximum peak intensity. The final, $17^{th}$, component waveform is a 30 second ramp phase 90116 from 8 to 0 mA with primary waveform component X.

FIGS. 90D-90F illustrate another example of an ensemble waveform that may be particularly effective as an "energy" waveform (inducing or enhancing focus and attention, enhancing alertness, enhancing wakefulness, increasing subjective feeling of energy, etc.), with electrodes positioned on the temple (and/or forehead) and mastoid region. For example, FIGS. 90D, 90E, and 90F schematically illustrate the ensemble waveform, which is composed of 15 component waveforms, of which several are repeating (i.e., have identical waveform parameters and duration), with a composite duration of 417 seconds. This ensemble waveform also includes a number of rapid transitions.

For example, FIG. 90D shows the peak intensity for each of the component waveforms, FIG. 90E shows labels for the component waveforms indicating their order, duration, and timing, and FIG. 90F shows the carrier frequency of stimulation for each of the component waveforms. The long period of the ensemble waveform at the 11 kHz frequency 90215 is the frequency for all component waveform segments 90200-90211. Table 2, below, illustrates the waveform parameters for the individual component waveforms, in order, making up this ensemble waveform:

TABLE 2 second Ensemble waveform example

| FIGS. 90D-F label | Start time (sec) | Duration (sec) | Start peak intensity (mA) | End peak intensity (mA) | Start duty cycle (%) | End duty cycle (%) | Start charge imbalance (%) | End charge imbalance (%) | Start carrier freq. (kHz) | End carrier freq. (kHz) |
|---|---|---|---|---|---|---|---|---|---|---|
| 90200 | 0 | 30 | 0 | 16 | 41 | 41 | 85 | 85 | 11 | 11 |
| 90201 | 30 | 30 | 16 | 18 | 41 | 41 | 85 | 85 | 11 | 11 |
| 90202 | 60 | 60 | 18 | 18 | 41 | 41 | 85 | 85 | 11 | 11 |
| 90203 | 120 | 2 | 18 | 11 | 41 | 41 | 85 | 85 | 11 | 11 |

TABLE 2-continued second Ensemble waveform example

| FIGS. 90D-F label | Start time (sec) | Duration (sec) | Start peak intensity (mA) | End peak intensity (mA) | Start duty cycle (%) | End duty cycle (%) | Start charge imbalance (%) | End charge imbalance (%) | Start carrier freq. (kHz) | End carrier freq. (kHz) |
|---|---|---|---|---|---|---|---|---|---|---|
| 90204 | 122 | 3 | 11 | 18 | 41 | 41 | 85 | 85 | 11 | 11 |
| 90205 | 125 | 60 | 18 | 18 | 41 | 41 | 85 | 85 | 11 | 11 |
| 90206 | 185 | 2 | 18 | 11 | 41 | 41 | 85 | 85 | 11 | 11 |
| 90207 | 187 | 3 | 11 | 18 | 41 | 41 | 85 | 85 | 11 | 11 |
| 90208 | 190 | 90 | 18 | 18 | 41 | 41 | 85 | 85 | 11 | 11 |
| 90209 | 280 | 2 | 18 | 11 | 41 | 41 | 85 | 85 | 11 | 11 |
| 90210 | 282 | 15 | 11 | 18 | 41 | 41 | 85 | 85 | 11 | 11 |
| 90211 | 297 | 30 | 18 | 18 | 41 | 41 | 85 | 85 | 11 | 11 |
| 90212 | 327 | 15 | 18 | 11 | 41 | 38 | 85 | 100 | 11 | 7.5 |
| 90213 | 342 | 60 | 11 | 11 | 38 | 38 | 100 | 100 | 7.5 | 6.7 |
| 90214 | 402 | 15 | 11 | 0 | 38 | 38 | 100 | 100 | 6.7 | 6.7 |

In the example shown in FIGS. 90D-90F, as in FIGS. 90A-90C, the current amplitude shown is a peak current amplitude or maximum peak intensity, which may be delivered at a reduced level (i.e., percentage) based on automatic or manual (user-controlled) adjustment of the perceived intensity.

In this example, the ensemble waveform begins with component waveforms 90200, 90201 during which stimulation is turned on gradually to improve the comfort of the experience for the user and thus increase the likelihood that a cognitive effect can be induced without causing undue discomfort. Similarly, at the end of the ensemble waveform, component waveform 90214 gradually ramps down the intensity of stimulation as the ensemble waveform completes. In the intervening time period, the ensemble waveform comprises four primary waveform components, as well as waveform components that provide transition periods between the primary waveform components.

In this example, a first primary waveform component ('primary waveform component T') 90202, 90205, 90208, 90211 is defined by a maximum peak intensity of 18 mA, 41% duty cycle, 85% charge imbalance, and 11 kHz carrier frequency. A second primary waveform component ('primary waveform component U') is defined by a maximum peak intensity of 11 mA, 41% duty cycle, 85% charge imbalance, and 11 kHz carrier frequency. A third primary waveform component ('primary waveform component V') is defined by a maximum peak intensity of 11 mA, 38% duty cycle, 100% charge imbalance, and 7.5 kHz carrier frequency. A fourth primary waveform component ('primary waveform component W') 90213 is defined by a maximum peak intensity of 11 mA, 38% duty cycle, 100% charge imbalance, and 6.7 kHz carrier frequency.

As described in Table 2, above, the ensemble waveform is composed of 15 component waveforms each having a set of waveform parameters that differ from the immediately preceding set of waveform parameters in one or more of the frequency, peak current amplitude, percent duty cycle, or percent charge imbalance. For example, the first component waveform is a 30 second ramp phase 90200 from 0 to 16 mA with primary waveform component T. The second component waveform is a 30 second ramp phase 90201 from 16 to 18 mA with primary waveform component T. The third component waveform is a 60 second maintenance component waveform 90202 with primary waveform component T at 18 mA maximum peak intensity. The fourth component waveform is a 2 second ramp phase 90203 that rapidly changes the peak intensity between primary waveform component T and primary waveform component U. The fifth component waveform is a 3 second ramp phase 90204 that rapidly changes the peak intensity between primary waveform component U and primary waveform component T. The sixth component waveform is a 60 second maintenance component waveform 90205 with primary waveform component T at 18 mA maximum peak intensity. The seventh component waveform is a 2 second ramp phase 90206 that rapidly changes the peak intensity between primary waveform component T and primary waveform component U. The eighth component waveform is a 3 second ramp phase 90207 that rapidly changes the peak intensity between primary waveform component U and primary waveform component T. The ninth component waveform is a 90 second maintenance component waveform 90208 with primary waveform component T at 18 mA maximum peak intensity. The $10^{th}$ component waveform is a 2 second ramp phase 90209 that rapidly changes the peak intensity between primary waveform component T and primary waveform component U. The $11^{th}$ component waveform is a 15 second ramp phase 90210 that gradually changes the peak intensity between primary waveform component U and primary waveform component T. The $12^{th}$ component waveform is a 30 second maintenance component waveform 90211 with primary waveform component T at 18 mA maximum peak intensity. The $13^{th}$ component waveform is a 15 second ramp phase 90212 that gradually changes the peak intensity, percent duty cycle, percent charge imbalance, and carrier frequency between primary waveform component T and primary waveform component V. The $14^{th}$ component waveform is a 60 second ramp phase 90213 that gradually changes the carrier frequency between primary waveform component V and primary waveform component W; and the $15^{th}$ component waveform is a 15 second ramp phase 90214 from 11 to 0 mA with primary waveform component W.

System Description

In general, any appropriate neurostimulation system may use (and/or be configured to use or operate with) the ensemble waveforms as described herein. FIGS. 91A-91Q describe and illustrate an example of a neurostimulation system (neurostimulator, electrodes, controller) that may be used. For example, a neurostimulation system may include a lightweight, wearable, neurostimulator device (neurostimulator) that is configured to be worn on the head and a consumable/disposable electrode assembly; in addition a device that may be worn and/or held by the user ("user device") which includes a processor and wireless communication module may be used to control the application of neurostimulation by the wearable neurostimulator. The neurostimulator and/or user device may be particularly adapted to deliver the ensemble waveforms as described herein. For example, the user device may present a list of ensemble waveforms and allow the user to select among them in order to select a desired cognitive effect. The ensemble waveforms may be ordered by the desired effect (e.g., calm, energy, etc.) and/or by time and/or by ranking, etc. Further, the user device may be adapted to communicate with the wearable neurostimulator and may transmit an identifier of the selected ensemble waveform, and/or waveform parameters that define all of a portion (e.g., component waveforms or portions of component waveforms) of the ensemble waveform, as well as any user adjustments such as user modification to the perceived intensity to be used to modify the actual waveforms delivered by, for example, attenuating the ensemble waveform parameters. Thus, for example, the user device maybe configured to send, and the neurostimulator to receive, the ensemble waveform parameters (duration, ramping parameter/ramping time, capacitive discharge parameters, current amplitude, frequency, percent duty cycle, percent charge imbalance, etc.).

The user device may also be referred to herein as a controller, and the controller (user device or user computing device) is typically separate from but communicates with the neurostimulator. For example, in some variations the controller may be a user device that wirelessly communicates with the neurostimulator. In some variations the controller is a mobile telecommunications device (e.g., smartphone or tablet) or wearable electronics (e.g., Google glass, smart watch, etc.), being controlled by an application that sends instructions and exchanges 2-way communication signals with the neurostimulator. Any of these embodiments may be referred to as handheld devices, as they may be held in a user's hand or worn on the user's person. However, non-handheld control user devices (e.g., desktop computers, etc.) may be used as well. The user device may be a general purpose device (e.g., smartphone) running application software that specifically configures it for use as a controller, or it may be a custom device that is configured specifically (and potentially exclusively) for use with the neurostimulators described herein. For example, the controller may be software, hardware, or firmware, and may include an application that can be downloaded by the user to run on a wireless-connectable (i.e., by Bluetooth) device (e.g., handheld device such as a smartphone or tablet) to allow the user to select the waveforms delivered by the neurostimulator, including allowing real-time modulation of the delivered neurostimulation to modify the user's cognitive state as described herein. The controller may be a component of the neurostimulator apparatus itself.

For example the system can be operated to induce either "calm" states of mind or "energetic" states of mind. Operating the system to induce a state of increased energy can be alternatively described as one or more of: enhancing focus and attention; enhancing alertness; increasing focus and/or attention; enhancing wakefulness; an increase psychophysiological arousal associated with changes in the activity of the hypothalamic-pituitary-adrenal axis and/or the reticular activating system; increasing subjective feeling of energy; increasing objective physiological energy levels; increasing motivation; increasing physiological arousal; and evoking a physical sensation of warmth in the subject's chest. Operating the system to induce a state of enhancing a calm or relaxed mental state can be alternatively described as one or more of: a state of calm within about 5 minutes of starting a TES session; a care-free state of mind; a mental state free of worry; induction of sleep; facilitating falling asleep; maintaining a state of sleep; a perception of slowing of a passage of time; muscular relaxation; enhanced concentration; inhibition of distractions; increased cognitive clarity; increased sensory clarity; a dissociated state; a mild intoxication; a euphoric state; a relaxed state; enhanced enjoyment of auditory and visual experiences; reduced physiological arousal; increased capacity to handle emotional or other stressors; a reduction in psychophysiological arousal associated with changes in the activity of the hypothalamic-pituitary-adrenal axis and/or the reticular activating system; a reduction in biomarkers of stress, anxiety, and mental dysfunction; anxiolysis; a state of mental clarity; enhanced physical performance; resilience to stress; a physical sensation of relaxation in the periphery; and a perception of feeling the heartbeat.

For example, to induce energy, the electrode apparatus may be attached to the user's temple (and/or forehead) and behind the user's ear (e.g., mastoid region). To induce calm, the electrodes may be attached to the user's temple (and/or forehead) and the back of the user's neck. In both examples, the neurostimulator may apply an ensemble waveform for about 3-30 min (or longer) that is made up of different "blocks" having repeated waveform characteristics; the waveform ensemble may include transition regions between the different blocks. In general, at least some of the waveform blocks (and in some variations most or all of them) generally have a current amplitude of >3 mA (e.g., between 5 mA and 40 mA, between 5 mA and 30 mA, between 3 mA and 22 mA, etc.), and a frequency of >700 Hz (e.g., between 700 Hz and 25 kHz, between 700 Hz and 20 kHz, between 700 Hz and 15 kHz, etc.), the current is typically biphasic and is charge imbalanced, and has a duty cycle of between 10-99% (e.g., between 20-95%, between 30-80%, between 30-60%, etc.). One or more of these characteristics may be changed during stimulation over timescales of every few seconds to minutes as the ensemble waveform shifts between subsequent component waveforms.

When worn, the system may resemble the system shown in FIG. 91Q, having an electrode assembly attached at two locations (points or regions) on the subject's head and/or neck) and a neurostimulator attached to the electrode assembly, as shown; in some variations a separate controller may be attached to coordinate the application of stimulation.

As will be described in greater detail herein, the neurostimulator may be lightweight (e.g., less than 30 g, less than 25 g, less than 20 g, less than 18 g, less than 15 g, etc.), and self-contained, e.g., enclosing the circuitry, power supply, and wireless communication components such as a rechargeable battery and charging circuit, Bluetooth chip and antenna, microcontroller, and current source configured to deliver waveforms with a duration of between 10 seconds and tens of minutes. A neurostimulator may also include safety circuitry. The neurostimulator may also include circuits to determine that the electrode is attached and what "kind" of electrode it is (i.e., for the calm or the energy mode; or indicating the batch and/or source of manufacture, etc.). FIGS. 91A and 91B-91G illustrate two variations of a neurostimulator.

For example, FIG. 91A illustrates a first example of a neurostimulator as described herein. In FIG. 91A, the neurostimulator is shown with a pair of electrodes attached. A first electrode 91601 is coupled directly to the body 91603 of the TES applicator 91602, and a second electrode 91606 is connected by a cable or wire 91604 to the body 91603 of the applicator 91602. These electrodes are separate from each other, and may be replaceable/disposable. Different shaped electrodes 91607 may be used with the same reusable neurostimulator. The neurostimulator in this example includes a rigid outer body, to which the pair of electrodes is attachable, making electrical contact via one or more plug-type connectors.

FIGS. 91B-91G illustrate another, preferred embodiment of a neurostimulator as described herein. In this variation the neurostimulator is also a lightweight, wearable neurostimulator that attaches to an electrode, and includes contacts for making an electrical connection with two (or potentially more) electrically active regions (e.g., anodic and cathodic regions) on the electrode(s). However, in this example, the neurostimulator is configured to operate with a cantilevered electrode apparatus, and to attach both mechanically and electrically to the electrode apparatus at a region that is off-center on the bottom (underside or skin-facing side) of the neurostimulator, allowing one end region to be held securely to the skin while the other edge region is not pinned in this way. The "floating" end may therefore adjust slightly to different curvatures of the head, even while the electrode assembly (which may be flexible) is securely held to the skin. Thus, this cantilevered attachment mechanism may enhance comfort and adjustability of the device. In addition, the neurostimulator device may be configured specifically so that it can be comfortably worn at the user's temple, even in users wearing glasses. For example, the apparatus may be configured so that the skin-facing side (which connects to the electrode assembly via one or more connectors) is curved with a slightly concave surface having a slight twist angle. This curve shape may help the apparatus fit more snugly (more uniformly) to the surface of the temple. In addition, one end of the device (the end to be positioned in-line with the edge of the user's eye and the user's ear) may be thinner (e.g., less than 2 cm, less than 1.5 cm, less than 1 cm, less than 0.8 cm, etc.) than the opposite end, which may be worn higher up on the temple.

For example, FIGS. 91B-91G illustrate front, back, left side, right side, top and bottom perspective views, respectively of a variation of a neurostimulation device (neurostimulator or electrical stimulator) that may be used with cantilever electrode apparatuses. The overall shape of the neurostimulator may be triangular, and particularly the surface of the neurostimulator (though curved/concave and twisted) adapted to connect to the electrode apparatus and face the patient may be three-sided (e.g., roughly triangular). This roughly triangular shape may include rounded edges, and the thickness of the stimulator (in the direction perpendicular to the surface contacting the cantilever electrode apparatus) may vary, e.g., be thinner along one side, and particularly the side (the portion between the orbital edge and the auricular edge) that will extend laterally from the edge of the eye in the direction of the ear. This shape may also be beneficial when helping to fit/be worn on most people in a region of the face/head that tends to not have hair. Both adhesive and conductive hydrogel that may cover an active electrode region function more effectively on skin with little or no hair. This thin lower corner (the orbital/auricular corner) may fit between the eyebrow and hairline, while the wider portion is positioned up in the forehead area where there is less likely to be hair.

In FIGS. 91B-91G the various edges of the neurostimulator are labeled, based on where the apparatus will be worn by the subject, as is illustrated in FIG. 91Q. In general, the side of the unit worn toward the ear is the auricular edge, the side worn highest on the forehead is the superior edge, and the side worn nearest the eye/eyebrow is the orbital edge. The overall shape of the neurostimulator is triangular (including rounded edges). As used herein triangular includes shapes having rounded/smooth transitions between the three sides, as illustrated. The subject-facing surface is specifically contoured to fit in the predefined orientation, making it difficult or impossible for a subject to misapply, and risk placing the active region of the attached cantilever electrode apparatus in the wrong place. When attaching the cantilever electrode apparatus to the neurostimulator, the cantilever electrode apparatus may flex or bend so that it is contoured to match the curved and twisted surface. This surface is a section of a saddle shape, in which there is an axis of curvature around which the surface is concavely curved, and an axis of twisting, which may distort the curved surface (the two axes may be different or the same).

Within the housing, any of the neurostimulators described herein may include a processor (e.g., microprocessor) or controller, a wireless communication module that is connected to the processor, and a power source (e.g., battery, etc.). The power source may be configured to provide power to the internal circuitry and/or the circuitry driving current between anodic and cathodic regions of the electrodes when worn by the user. The power supply may be a high-voltage power supply, e.g., able to provide up to 60 V across these electrode terminals. In general, the apparatus may also include circuitry that is configured to regulate the energy (e.g., current) delivered as required by the processor, which may in turn receive instructions via the wireless communications module from a controller. The controller may also communicate information, and in particular information about the electrodes, including confirming that the electrode assembly is connected and/or what type (e.g., calm, energy, make/model, batch, etc.) of electrode assembly is attached, and an indicator of the contact with the user's skin (e.g., conductance, a parameter proportional to conductance, or a value from which an estimate of the conductance of the electrode(s) may be derived).

The electrode assembly may mechanically and/or electrically connect to the neurostimulator, e.g., by snapping to the underside of the neurostimulator at one or more (e.g., two) connectors such as snap receivers. Thus in some variations the neurostimulator may be held onto the subject's (user's) head by the electrode assembly; the electrode assembly may be adhesively connected to the user's head and/or neck to form an electrical contact with the desired regions on the user, and the neurostimulator may be connected e.g., adhesively and/or electrically, to the electrode assembly. As described below, the connectors between the neurostimulator and the electrode assembly may be positioned in a particular and predetermined location that allows the neurostimulator to be robustly connected to the electrode assembly and therefore the user's head/neck without disrupting the connection, and while permitting the system to be worn on a variety of different body shapes.

Electrode assemblies are generally described in detail below, along with specific examples and variations. In particular, described herein are electrode assemblies that are thin (e.g., generally less than 4 min, less than 3 mm, less than 2 mm, less than 1 mm, etc. thick, which may not include the thickness of the connectors that may extend proud from the thin electrode assembly), and flexible, and may be flat (e.g., formed in a plane). For example, they may be printed on a flex material, such as the material used to print a flex circuit. In use, they can be wrapped around the head to contact it in at least two locations (e.g., at the temple and the back of the neck and/or behind the ear). The electrode assembly may include a connector (electrical and/or mechanical) that extends proud of the otherwise flat/planar surface to connect the active regions of the electrode assembly to the neurostimulator. For example, the neurostimulator may be mechanically and electrically connected by one or more snaps extending from the front of the electrode assembly. In some examples, one snap connects to a first active electrode region (anodic or cathodic region) that is surrounded by an adhesive to adhere the active region to the user's head. A second electrode region (anodic or cathodic) on a separate part of the electrode assembly may be electrically connected to the other connector. For example, the second electrode region may be adapted to fit either on the region over the mastoid bone, behind the subject's ear (energy electrode configuration) or a region across the user's neck at the base of the hairline, e.g., near the midline of the neck (calm electrode configuration).

The electrode apparatus may be printed (e.g., by flexographic printing, laser printing with conductive ink, silk-screening, etc.) on a flexible (e.g., plastic) substrate (flex substrate) and may also include a pair of connectors (snaps) on the side opposite the skin-facing electrodes. The electrode active regions on the back of the assembly may include a layer of conductor (e.g., silver), a layer of a higher resistance conductor than silver (e.g. a conductive carbon), over which a layer of Ag/AgCl is placed that is sacrificial and acts as a pH buffer. A next layer of hydrogel overlays the Ag/AgCl electrode so that it can uniformly transfer charge across the active region into the skin. A portion of the electrode assembly around the active electrode area may have an adhesive that permits good contact with a user's skin.

There may be multiple configurations (e.g., shapes) of the electrode assembly, and, as described in greater detail herein, the electrode assembly may generally be formed on a flexible material ('flex circuit' material) and mechanically and electrically connected to the neurostimulator.

FIGS. 91H-91K illustrate one variation of a cantilever electrode apparatus ("electrode apparatus") that may be used with a neurostimulator and may be worn on a subject's head. This variation may be referred to as a "calm" configuration, as it is adapted to connect to a user's temple or forehead and the back of a user's neck. In this example, the cantilever electrode apparatus 91400 includes a plurality of electrode portions (two are shown) 91403, 91405. In FIG. 91H, a front perspective view is shown. The front side is the side that will face away from the subject when worn. The cantilever electrode apparatus is thin, so that the electrode portions include a front side (visible in FIGS. 91H and 91i) and a back side (visible in FIG. 91K). As shown in the side view of FIG. 91J, the device has a thin body that includes the electrode portions 91403, 91405 as well as an elongate body region 91407 extending between the two electrode portions. The elongate body is also thin (having a much larger diameter and height than thickness). The thickness is shown in FIG. 91J.

In this example, two connectors 91415, 91417 (electrical and mechanical connectors, shown in this example as snaps) extend from the front of the cantilever electrode apparatus. The front of the first electrical portion 91403 may also include an optional foam and/or adhesive material 91421 through which the snaps extend proud of the first electrical portion. The first electrical portion is shaped and sized so that the snaps will connect to plugs (ports, holders, opening, female mating, etc.) on the electrical stimulator. As described above, the connectors may be separated by between about 0.6 and about 0.9 inches (e.g., between about 0.7 and about 0.8 inches, etc., shown in FIGS. 91H-91K as about 0.72 inches). The second electrode portion may also include a foam or backing portion 91423. This foam/backing region may be optional. In some variations the separation between the connectors is not limited to 0.7 to 0.8, but may be larger (e.g., between 0.7 and 1.2 inches, 0.7 and 1.1 inches, 0.7 and 1.0 inches, 0.7 and 0.9 inches, etc.) or smaller (e.g., between 0.2 and 0.7, 0.3 and 0.7, 0.4 and 0.7, 0.5 and 0.7, 0.6 and 0.7 inches, etc.).

FIG. 91K shows a back view of this first example of a cantilever electrode apparatus. In this example, the first 91403 and second 91405 electrode portions are also shown and include active regions 91433, 91435. The active regions are bordered by adhesive 91440. The first 91403 electrode portion includes, on the back (patient-contacting) side, a first active region 91433, which is bounded, e.g., around its entire circumference, or at least on, by an adhesive 91440. The active region may include a conductive material (e.g., electrically conductive gel). Similarly, the back of the second electrode portion 91405 includes the second active region 91435 surrounded on two sides by an adhesive material 91440 that extends to the edge of the electrode region. The adhesive may be any biocompatible adhesive that can releasably hold the material to the skin.

FIGS. 91L-91o illustrate another example of a cantilever electrode apparatus. This example is very similar to the variation shown in FIGS. 91H-91K, but may be referred to as an "energy" configuration as it is configured to contact both the user's temple or forehead and a region behind the user's ear, over the mastoid region. The connectors (snaps 91417, 91415) are in the same position as shown in FIGS. 91H-91K, as are the shape of the first electrode portion 91403 and foam/backing material 91421 (which may also or alternatively be an adhesive material). An advantage of having multiple electrode apparatuses with the same shape is that they can be used interchangeably with a single neurostimulator device. However, the example shown in FIGS. 91L-91o includes a different overall shape, and may be used to connect, for example, to different regions of the patient's head. In particular, the portion of the substrate forming the elongate body region 91407 extending between the two electrode portions 91403, 91405 is shaped slightly differently. In this example, the cantilever electrode apparatus may be configured to connect, for example, to the subject's temple with the first electrode portion (to which the neurostimulator may be connected) and the elongate body region may be bent around the subject's head so that the second electrode portion may be in electrical contact with a region behind the subject's ear (e.g., at or near the mastoid). By placing the first active region 91433 of the first electrode portion 91405 in electrical contact with the skin at the temple or forehead and using the adhesive material 91440 surrounding the electrically active region 91433 to hold the electrically active region (and the attached neurostimulator) securely in position on the subject's skin, the second electrically active region may also be adhesively 91441 held to skin so that the second electrically active region 91435 is in contact with the mastoid region.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 91H-91K and 91L-91o. The bend or curve, in which the elongate body may even double back on itself, may allow the material to flex or bend to allow it to be adjustably positioned over and/or around the subject's head, as shown in FIGS. 91P and 91Q, for example.

FIG. 91P illustrates a cantilever electrode apparatus (similar to those shown in FIGS. 89A and 92A) worn on a subject's head. As illustrated, the apparatus is positioned with the first electrode portion adhesively attached at the temple or forehead and a second electrode portion attached to a region behind the head (e.g., behind the ear or neck region, not shown). A neurostimulator (not shown in FIG. 91P) may be attached to the cantilever electrode apparatus either before or after it is applied to the subject. As shown in FIG. 91Q, the neurostimulator may be attached to the front side of the cantilever electrode apparatus by snapping onto the proud connectors, while the elongate body region 91407 is bent to extend behind the subject's head and down to a portion on the midline of the back of the patient's neck. Both the first electrode portion and the second electrode portion may be adhesively held with the electrically active regions against the skin, allowing the neurostimulator to apply energy, and in particular the waveforms as described in application Ser. No. 14/320,443, titled "TRANSDERMAL ELECTRICAL STIMULATION METHODS FOR MODIFYING OR INDUCING COGNITIVE STATE" and filed Jun. 30, 2014, and herein incorporated by reference in its entirety.

In use, a user may interact with a controller (e.g., a smartphone controlled by application software/firmware) that pairs with the neurostimulator (e.g., i.e., by Bluetooth). The user may operate the controller to select the operational mode, e.g., the type of cognitive effect to be induced, such as an energy mode or calm mode, and/or the device could automatically detect based on the configuration of an electrode to which the apparatus is attached. The user may select, for example, from a set of ensemble waveforms which ensemble waveform to execute. There may be separate waveforms to evoke a desired experience/effect (e.g., "calm" or "energy" ensemble waveforms). An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, i.e., current amplitude, frequency, duty cycle, charge imbalance, shorting/capacitive discharge, etc., and these parameters may change at pre-specified times for subsequent component waveforms. Once the user selects an ensemble waveform, the user can start the neurostimulation and the user can control or change the perceived intensity (e.g., by dialing the perceived intensity up or down), pause, or stop the session using the phone (app). In general, the perceived intensity can be scaled by the user between 0-100% of a target perceived intensity (e.g., a target current, frequency, duty cycle, charge imbalance, and/or shorting/capacitive discharge), using a control such as one or more buttons, sliders, dials, toggles, etc., that may be present on the controller (e.g., smartphone) in communication with the neurostimulator. The controller may also allow a user to activate ("on demand") a waveform configuration that is designed to evoke a predetermined response. For example, the control device could be adapted to display one or more icons to trigger phosphenes or an intensification of the perceived cognitive effect or skin sensation intensity. In addition, the controller may be configured to allow the user to press an icon to help in applying the electrode apparatus and/or neurostimulator. For example, activating this control may cause the smartphone to activate a front-facing camera on the phone to help the user to attach the apparatus to the head. During or after a session, a user can access help screens, a profile page, social sharing interfaces (i.e., tweet your experience), feedback about a session, and analysis & history of previous use. In general, the system may also be configured to pass data to and from the controller and/or the neurostimulator and to/from a remote server via the Internet. These data may include user information, waveform data, information about the function or state of the hardware device or electrode assembly, etc.

In general, described herein are general TES waveforms parameters that may be used to invoke, enhance, or modify a variety of cognitive states. Although the apparatuses and methods described herein may be used to provide TES to induce and/or modify a variety of cognitive states, two particular examples are described in detail herein, including enhancing attention, alertness, or mental focus and inducing a calm or relaxed mental state. Configurations of apparatuses and methods specific to enhancing attention, alertness, or mental focus and inducing a calm or relaxed mental state, including specific configurations for causing neuromodulation that achieves one of these particular cognitive effects in a subject are described in particular detail.

EXAMPLES

Three additional examples of parameters for ensemble waveforms are described below. In these examples the waveforms may be implemented in the neurostimulation systems described above and illustrated in FIGS. 91A-91Q. These waveforms may be defined as a vector array including the duration and waveform parameters (frequency that the basic waveform unit is repeated, peak current amplitude, percent charge imbalance of the basic waveform unit, percent duty cycle of the basic waveform unit, and, optionally, capacitive discharge parameters and/or amplitude modulation or burst mode parameters). The basic waveform unit may be defined, or may be set by the system, e.g., as biphasic, square pulses having a predetermined or variable period cycle (i.e., by composing waveforms having chirped pulses).

Example 1 is shown in FIG. 92A, and is another example of a calm ensemble waveform. The table shown in FIG. 92A lists the waveform parameters for each of the component waveforms. In this example the ensemble waveform is configured with short circuiting on (meaning that a capacitive discharge pulse occurs in the opposite direction after each of the biphasic pulses).

In operation, the system transfers chunks (e.g., 400 ms segments) securely between the user device and the worn neurostimulator every about 400 ms (or on multiples of about 400 ms), including the neurostimulation start frequency, end frequency, starting amplitude, end amplitude, start duty cycle, end duty cycle, start percent charge imbalance, end charge imbalance, etc. The timing of wireless communication chunks at about 400 ms should not be construed as limiting the timing of communication between a controller unit and the neurostimulator.

FIG. 92B illustrates a second example of a calm ensemble waveform having a slightly longer running time, running over 12 minutes. Similarly, 92C illustrates a third example of a calm ensemble waveform having a yet longer running time (over 16 minutes).

FIG. 93A illustrates another example of an energy ensemble waveform. In these examples of ensemble waveforms for inducing enhanced energy, short circuiting (capacitive discharge) may be set to 'on' (or off). In this example, the capacitive discharge may also be configured to occur in the opposite direction after each of the biphasic pulses. In contrast, FIG. 93B illustrates an example of an energy ensemble waveform in which a capacitive discharge is formed in the negative going direction and occurs at the onset of each negative going pulse (see FIG. 89D, above).

The ensemble waveforms described herein may be divided up into at least two categories, including energy and calm types of ensemble waveforms. These two categories or classes of waveforms may have different characteristics, which may make them appropriate for the physiological delivery location and the induced effect. In some variations, the energy waveforms and/or the calm waveforms are specific in their effects; for example a calm ensemble waveform may not induce any effect when applied using an energy treatment regime, and vice versa. In general, the calm ensemble waveforms described herein may have higher frequency waveform parameters (for example, a larger percentage of ensemble waveforms may have a frequency above 10 kHz, e.g., 50%, 60%, 70%, etc.) compared with energy waveforms, and the current amplitude may vary more often (e.g., between component waveforms) than with energy component waveforms. In contrast, the energy ensemble waveforms may typically have a lower range of frequency waveform parameters (e.g., down to 750 Hz), and may not need short circuiting (capacitive discharge). In addition, the percentage of charge imbalance in the energy waveforms may be in a 30-50 percent range. In addition, in energy ensemble waveforms there may be more shifting of frequency between component waveforms than with calm ensemble waveforms (e.g., shifting from 11 KHz to 7500 Hz to 9 kHz, etc., typically shifting by approximately 1-3 kHz, e.g., 2 kHz jumps), which may occur on a longer time scale (e.g., longer than every 30 seconds) or over a very brief timescale of less than 10 seconds.

There may also be general features that are shared between many of the ensemble waveforms described herein. For example, in general, when ensemble parameters are changed after longer duration blocks, two or more waveform parameters may be adjusted at once. Further, when shifting frequency between component waveforms by 2 kHz or more, at least one other waveform component may also be shifted. In general, rapid shifts in frequency or current amplitude (e.g., shifting down and back up within a 10 sec, period, e.g., 1 sec, 2 sec, 5 sec, etc. period) may be useful to intensify the desired effect for either calm or energy. For example, FIG. 94 illustrates one example of an add-in that may be applied onto an ensemble waveform to intensify an effect. In this example, the add-in provides a gradual ramp down of the intensity (e.g., applied current amplitude) of the ensemble waveform currently being applied by scaling it by the intensity factor shown (intensity factor %) over the duration (e.g., 0.8 s) provided; thereafter the intensity may be quickly returned to 100% of the value otherwise delivered but for the add-in (e.g., which may also be adjusted by a user-selected intensity control and by the value of the ensemble waveform at that time). The result of the add-in shown in FIG. 94 may, in some users, be to intensify the cognitive effect being evoked (e.g., enhanced calm, increased energy, etc.).

Another exemplary ensemble waveform to induce a state of increased energy (e.g. with electrodes positioned on the right temple/forehead area and the right mastoid, as described above) is approximately 10 minutes in length and incorporates capacitive discharge current (discharges) after each positive-going and negative-going pulse of the waveform. For example, this TES ensemble waveform for inducing an increase in energy (or related cognitive effects of alertness and physiological arousal, etc.) may include three component waveform types delivered in sequence. A first component waveform ("A") of the ensemble waveform has a duration of 60 seconds, during which time the peak intensity gradually and linearly increases from 0 mA to 14 mA with waveform parameters including: 7 kHz frequency, 85% charge imbalance, 49% duty cycle, 90 Hz bursting frequency, and 50% bursting duty cycle. A second component waveform ("B") of the ensemble waveform has a duration of 535 seconds, during which time all parameters of the waveform remain constant except the duty cycle percentage, which gradually increases to 55%. In a third and final component waveform ("C") of the ensemble waveform has a duration of five seconds, and the current ramps down to 6 mA (and then to zero mA, as the ensemble waveform completes) while all other waveform parameters (frequency, percent duty cycle, etc.) are identical to those during the second waveform segment of the ensemble waveform. These component waveforms (e.g., A, B, C) may then be repeated (or may be repeated as A, B, A, B, A, B, . . . , C).

Another exemplary ensemble waveform has a five minute total duration, and may be used to induce a state of increased energy (physiological arousal, etc. as described above). This example includes two core waveforms with component waveforms of an ensemble providing gradual onsets, offsets, and shifts of these waveform components. A first set of waveform parameters ("A1") of this component of the ensemble waveform gradually ramps the intensity of stimulation up to 12 mA over 30 seconds for a waveform with a frequency of 7600 Hz, a charge imbalance of 81%, a duty cycle of 52%, a bursting frequency of 90 Hz, and a bursting duty cycle of 22%. A second set of component waveform parameters ("B1") of this ensemble waveform gradually increases the peak intensity to 13 mA with all other parameters identical to the first ensemble component. The gradual increase in intensity over 120 seconds of the second component may help counteract any habituation that may occur in response to electrical stimulation of the subject's skin. A third set of component waveform parameters ("C1") of the ensemble waveform shifts several waveform parameters gradually over 25 seconds to: 8600 Hz frequency, 14 mA peak intensity, 81% charge imbalance (unchanged from the preceding waveform component), 57% duty cycle, 90 Hz bursting frequency (unchanged from the preceding waveform component), and a 32% bursting duty cycle. By slightly increasing the duty cycle, bursting duty cycle, and peak intensity, the relative (perceived) intensity of the waveform to the subject may be minimally changed despite increasing the stimulation frequency by 1 kHz. In general, higher stimulation frequencies in this range may correspond to more comfortable waveforms. In a fourth set of component waveform parameters (D1), the parameters to which the waveform adjusted during the preceding waveform component are maintained for 120 seconds, then in a fifth set of component waveform parameters (E1) the intensity of stimulation is gradually ramped down to 7 mA over 5 seconds (then, as the ensemble waveform completes, the intensity gradually ramps to 0 mA over a duration of a few seconds).

In general, an ensemble TES waveform may include component waveforms with continuous stimulation (i.e. no quiescent periods between presentations of a waveform cycle). In a third exemplary ensemble waveform, which may be used to induce an increase in energy, alertness, physiological arousal, etc., no bursting occurs in waveform components for the first 8 minutes of the ensemble waveform (e.g., no amplitude modulation is applied over this time), then the last two minutes of the ensemble waveform include components with bursting (amplitude modulation using a square pulse waveform, as described in greater detail below).

In any of the ensemble waveforms described herein, the peak intensity may generally be scaled according to a user input to a peak intensity value that is a percentage of the peak intensity indicated (e.g. 5%, 30% of the peak intensity, 40%, 50%, 60%, 70%, 80%, 90%, 100% and values there between).

The use of ensemble waveforms, which are made up of discrete periods of component waveforms each having one or more distinct parameters as described above have proven to be particularly effective when evoking cognitive states by TES. In part, this may be because the use of ensemble waveforms may help avoid habituation. Further, the inventors have found from empirical data across a population of users that different users prefer different parameter sets for comfort and efficacy of inducing a cognitive effect. The application of ensemble waveforms as described herein allows cycling through multiple different parameter sets that, while perhaps not optimal for all users, has proven surprisingly effective for a wider range of people. Shifting parameters as described herein when using ensemble waveforms may also be more effective than static waveforms by both preventing desensitization on one time scale (e.g. at the neuronal level) while evoking cognitive effects at a different level (e.g., neural network) over a longer timescale.

For example, the use of multiple (e.g., greater than 3, 4, 5, etc.) component waveforms each having a duration of between 100 msec and about 600 seconds may also provide functional translation between cranial nerve modulation and brainstem modulation. The component waveforms themselves are configured to penetrate the skin and soft tissue to reach the nerves. For example, the high-frequency, higher-intensity component waveforms may allow relatively deeper penetration than lower-intensity signals. However, the cognitive effects seen are not just due to the activation/modulation of nerves. The evoked effects may depend on these nerves reliably modulating brainstem nuclei. An analogy may be found with TENS for the gate control theory of pain; whereas nerves can be activated in the first second of stimulation, in many systems, the durations used are instead on the order of 30-45 seconds to (hypothetically) modulate brainstem nuclei involved in pain control. This suggests that the time course for nerve modulation to yield brainstem modulation is much slower (seconds to tens of seconds) than the time course for nerve modulation (which is less than a second). Most neural circuits typically adapt to constant inputs and become less sensitive. To avoid adaptation in cranial nerves, the ensemble waveforms described herein may use rapid changes in the underlying waveform that occur, e.g., in less than a second. Similarly, these signals may be at least partially amplitude modulated, which may also help prevent adaptation in the brainstem, using transitions that occur on the timescale that it takes to modulate the brainstem using cranial nerve inputs (e.g., seconds to tens of seconds). Slower effects may be mediated by signal processing and signal transduction cascades involving brain stem nuclei. This may be analogous to descending pain control systems for example which are well understood to involve a cascade of second messenger systems. In pain applications TENS also rather immediately affects brainstem and spinal pathways. Delayed effects may be due to slower intracellular second messenger systems.

Amplitude Modulation (AM)

As mentioned above, any of the waveforms (compound or ensemble waveforms) described herein may be amplitude modulated, which may modify, including enhancing, the cognitive effects achieved. In particular a subset of the component waveforms forming an ensemble waveform may be amplitude modulated as described herein. Any of the apparatuses and methods described herein may include amplitude modulation of all or some of the component waveforms, and the amplitude modulation applied to different component waveforms may be the same or it may be different, for example, having different AM envelope shapes (square, saw tooth, sinusoidal, etc.), different AM frequency (burst frequency), different AM percent duty cycle (e.g., burst duration), etc.

Thus, any of the component or ensemble waveforms described herein may be modified by amplitude modulation so that a second, generally lower, frequency component (and this second frequency component may be varied or constant) may be applied atop the component or ensemble waveform. Amplitude modulation may be considered another type of add-on effect, because it may intensify or qualitatively modify (i.e. cause a distinct subjective cognitive experience) the desired cognitive effect.

In general, the inventors have found that amplitude modulation (AM) is a beneficial feature in the use of TES waveforms, because cognitive effects can be induced with improved comfort.

Amplitude modulation as described herein typically results in overlaying a bursting of some or all of the component waveforms of an ensemble waveform, which may both decrease the overall power requirement of the system, since less overall current is applied (thereby potentially expanding battery life or reducing the demand for larger power sources), and may also be more effective in evoking a modification of a subject's cognitive state, as mentioned above. Finally, the use of amplitude modulation has been found to enhance comfort, and surprisingly allow even greater current intensities to be used, despite decreasing desensitization.

The frequency of the applied AM is typically lower than the carrier frequencies of stimulation (the component and/or ensemble waveform frequencies), and may generally be between about 0.5 Hz and 1 kHz; strictly speaking any frequency below a dominant frequency of a carrier wave may be used for AM, although particularly effective AM frequencies may be between about 10 Hz and about 1 kHz, including neurobiologically relevant frequencies below about 200 Hz.

One advantage of amplitude modulation may be that the total energy delivered transdermally per unit time may be reduced while still evoking a robust response. This principle motivates the use of amplitude modulation duty cycles less than 100% (preferably less than 80%, less than 70%, less than 60%, etc.). However, significantly lower duty cycles (i.e. less than 20%) may be less effective due to discomfort occurring as a result of a larger proportion of the frequency-spectrum power of stimulation in a lower frequency range for which skin impedance is lower and somatosensory receptors are more likely to be activated.

The amplitude modulation waveform applied may be any appropriate shape, including square waves, triangular ("saw tooth") waves, sinusoidal waves, or the like. For example, amplitude modulation by a sine wave or similar smoothly varying curve may be particularly beneficial for modulating (i.e. entraining, strengthening, phase-shifting) brain rhythms. Brain rhythms are well known in the art and include frequencies of oscillation associated with brain function (i.e. delta, beta, alpha, theta, gamma, etc.).

TES waveforms that include bursting generally deliver pulsed stimulation waveforms with high peak currents (i.e. greater than 2 mA, greater than 5 mA, etc.) and a relatively high carrier frequency of greater than 750 Hz (i.e. above 1 kHz, above 5 kHz, above 10 kHz, etc.) that are delivered intermittently, with periods of lower (preferably, zero) stimulation. Burst mode TES waveforms are a form of amplitude modulation TES waveform. Any of the amplitude modulation waveforms described herein may further incorporate other time-varying features of ensemble waveforms. That is, amplitude modulation may be an additional control structure that can be used to deliver more comfortable electrical stimulation for inducing a cognitive effect, as illustrated and described below.

For example, FIGS. 96A-96D, 97A-97D, 98A, 98D, and 100A all illustrate amplitude modulation on a zero to one (or −1 to 1) scale, where a value of zero represents a cessation of stimulation of the underlying carrier wave (defined by frequency, pulsing regimen, duty cycle, intensity, etc. as outlined herein), a value of one represents a maximum stimulation intensity as defined by the underlying carrier wave, a value of negative one represents a maximum stimulation intensity in the negative-going direction, and values intermediate between zero and one represent a modulation of the underlying waveform to have an associated intermediate intensity (e.g. envelope).

FIG. 96A shows an exemplar AM burst stimulation framework for TES and defines terms used to describe AM herein. The extent of amplitude modulation is generally defined from 0 to 1 and may represent a time-varying multiplier for a pulsed stimulation regime. In the example shown in FIG. 96A, the amplitude modulation is applied by square wave pulses (which may result in bursts of the applied component waveforms in the ensemble waveform applied). In this example, either a multiplier of zero (i.e. no current delivered) or one (full amplitude of stimulation delivered) is applied to the ensemble waveform (or a component portion thereof). The relative length of a pulse and inter-pulse time may define the duty cycle of the resulting bursting due to amplitude modulation in the applied ensemble waveform. The combined time may be equal to a burst period which is equal to the inverse of the AM pulse frequency. Bursting generally continues due to the multiple cycles of amplitude modulation. In FIG. 96A, the amplitude modulation duty cycle (AM duty cycle) is the percentage defined as the burst length 96811 divided by the burst period 96813, which is approximately 30% in FIG. 96A.

FIG. 96B shows how a duty cycle of AM (and therefore the 'bursting' duty cycle seen in the resulting ensemble waveform) may vary between TES waveforms. The AM applied by the AM waveform in FIG. 96B has a similar frequency as shown in FIG. 96A, but a larger (approximately 50%) AM duty cycle resulting in the larger bursting duty cycle in the resulting applied waveform (ensemble waveform or one or more component waveforms in the ensemble). The total charge transfer when applying the waveform of FIG. 96B is higher than that of FIG. 96A (for a fixed ensemble, or 'carrier', wave structure, intensity, and frequency), which may be beneficial for more strongly modulating a nerve or brain region.

FIG. 96C shows an AM waveform with the same AM pulse width ("burst length") as FIG. 96A and higher AM pulse frequency ("AM frequency" or "burst frequency"). Changing the frequency or duty cycle of the AM waveform may induce stronger cognitive effects. For example, effective TES waveforms may shift the frequency and/or duty cycle of stimulation during an ensemble waveform on a timescale between 1 sec and 10 minutes (optimally, 10 seconds to 5 minutes). FIG. 96D shows a set of AM pulses for TES with fixed length, but the AM wave applied changes frequency, which may be a beneficial characteristic of some ensemble AM waveforms.

FIG. 99 illustrates one example of a square-wave envelope for amplitude modulation shown modulating an exemplary portion of one component waveform of an ensemble waveform. In this example, three burst cycles are shown (as indicated by black rectangles at top of figure). The AM is applied to a portion of an ensemble waveform (or component waveform) having a biphasic pulsed 5 kHz carrier signal delivered with a 50% bursting duty cycle and a 500 Hz burst frequency. The resulting waveform has defined bursting periods ("bursts") and quiescent periods ("inter-burst periods"). Without amplitude modulation, these quite periods would resemble the bursts; the AM in this example acts to turn off the current during the inter-burst periods (when the AM envelope is zero). As described in greater detail below, the burst duration (e.g., percent duty cycle of the amplitude modulation waveform) as well as the amplitude modulation frequency (AM frequency) may be selected so that the bipolar pulses in the underlying component waveform (the base pulses 991104) are not truncated, e.g., so that the edge of the burst envelope does not cut off a burst but instead corresponds with the start of the next pulse cycle.

Figure 97A:
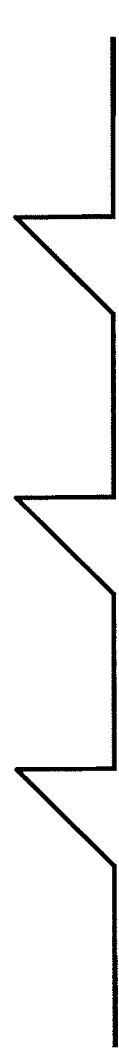
Figure 97B:
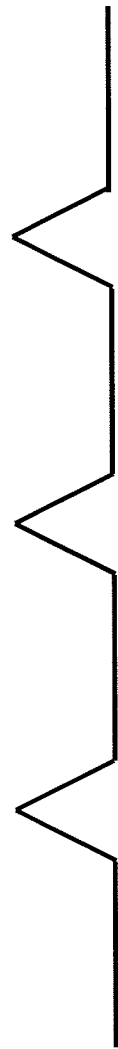
Figure 97C:
Figure 97D:

The amplitude modulation envelope shapes are not limited to square waves. Other shapes for applied amplitude modulation may be effective for improving comfort and/or enhancing or modifying a cognitive effect induced in a user receiving TES. FIG. 97A shows a saw tooth wave-shaped amplitude modulation for bursts in which the start of each burst ramps up the intensity of stimulation gradually (i.e. which may improve comfort). FIG. 97B shows a triangle wave-shaped amplitude modulation for bursts in which the start and end of each burst ramps the intensity of stimulation gradually. FIG. 97C shows a roughly exponential-shaped amplitude modulation for bursts in which the start of each burst ramps up the intensity of stimulation gradually (i.e. to improve comfort). FIG. 97D shows a roughly exponential wave-shaped amplitude modulation for bursts in which the start and end of each burst ramps the intensity of stimulation gradually.

Another envelope shape for amplitude modulation is sine-wave amplitude modulation, which may result in gradually shifting peak intensities. One skilled in the art will recognize that various smoothly varying forms of AM may be as potentially effective (and comfortable) as a sine-wave AM envelope. FIG. 98A shows three cycles of a sine-wave amplitude modulation between zero and one (though other sine-wave AM frameworks are also possible that vary between values greater than zero and/or less than one, such as that shown in FIG. 98D, where amplitude modulation occurs with a minimum value greater than zero during the sine wave modulation). The arrows pointing to FIGS. 98B and 98C illustrate two cycles of pulsed waveforms as in FIG. 89C, where the cycles from FIG. 98B are roughly half the amplitude of those in FIG. 98C based on the time during the AM cycle when they are delivered.

FIG. 100A shows another example, including a 500 Hz sine-wave amplitude modulation curve, and FIG. 100B shows the stimulation waveform delivered with a constant 5 kHz pulsed frequency (e.g., "carrier wave," which may correspond to the component waveform parameters) throughout the three cycles of amplitude modulation displayed. In some ensemble waveforms, the frequency, shape, or modulation factor of amplitude modulation may vary while the higher frequency carrier wave remains constant. In some ensemble waveforms, the frequency, shape, or modulation factor of amplitude modulation may remain constant while the higher frequency carrier wave changes by one or more intensity, frequency, duty cycle, charge imbalance, capacitive discharge, ramping, etc.

Amplitude modulation may allow a reduction of the applied intensity while retaining the robustness of the cognitive effect. For example, an ensemble waveform applied at 750 Hz, 4 mA with 30-40% duty cycle without applied AM may be equivalent to a 750 Hz, 3 mA, 30-40% duty cycle stimulation. In general, the use of amplitude modulation within the lower frequency ranges described herein may therefore allow a reduction in one or more of current amplitude, duty cycle and/or frequency. For example, one way to comfortably achieve the effects attributed to low duty cycle stimulation (including invoking cognitive effects, and/or, for example, phosphenes) may be to apply somewhat low frequency AM (e.g., between 100 Hz and 1 kHz, e.g. 200 Hz) to an ensemble waveform having carrier frequency values outside of this range that are more easily tolerated, e.g., the carrier waveform may have a frequency of 8 KHz and an amplitude of 10 mA). The amplitude modulation envelope may define in an AM burst mode of the carrier waveform resulting in a comfortable while still robust effect.

For example, FIG. 95 illustrates one variation of an ensemble waveform designed for use to evoke a calming cognitive effect. In this example, the 10 minute waveform includes square-wave modulated AM (resulting in "bursts") of the ensemble waveform at frequencies between 500-800 Hz, with an AM duty cycle (atop the ensemble waveform duty cycles) of between 40-85%. In some variations, the use of AM at a burst (e.g., pulse) frequency of between about 200-900 Hz, and between about 20-95% duty cycle (e.g., AM duty cycle or burst duty cycle) may be particularly effective to potentiate the cognitive effects seen with the non-AM ensemble waveforms, particularly when the AM parameter (e.g., frequency and/or duty cycle) is changed during the application of the ensemble waveform. This may be referred to as AM mode stimulation or the application of amplitude modulated ensemble waveforms, which may make the evoked cognitive effect experienced by the user stronger. Rapid shifts in the AM within a few seconds to minutes may be particularly helpful.

For example, FIGS. 101-103 show examples of the stimulation parameters that may be used (e.g., by a neurostimulator) to deliver ensemble waveforms. For example, in FIG. 101, the parameters of a 5 minute ensemble waveform configured to evoke a calm cognitive state are shown. In this example the ensemble waveform has 3 component waveforms of different durations. For example, the first component waveform is a brief, 1 sec, ramp to 1 mA at 7000 Hz and 85% duty cycle; the second component waveform is 60 seconds long, during which time the current increases to 11 mA; the third component waveform lasts for 540 additional seconds, during which the duty cycle increase from 49% to 70%. The entire ensemble waveform is amplitude modulated by a 70 Hz modulation (e.g., using a square pulse modulation) having a duty cycle of 35%. Each of the intensities listed is a maximum intensity, and a user may manually adjust intensity (or another variable such as the duty cycle or frequency of the carrier wave) to achieve a desired subjective intensity of stimulation. This user adjustment may result in modifying the ensemble waveform during application by a user intensity adjustment factor. A user intensity adjustment factor may be transmitted by a controller, and may scale one or more parameters (e.g., current amplitude, percent duty cycle, frequency, etc.) of each of the component waveforms of the ensemble waveform.

FIG. 102 illustrates another example of an ensemble waveform, showing (in tabular form) the parameters of each of the component waveforms, including the use of a specific, and potentially distinct amplitude modulating for some or all of the component waveforms making up the ensemble waveform. In the example of FIG. 102, the ensemble waveform has 11 component waveforms. The amplitude modulation varies multiple times during the application of the ensemble waveform (in this example, between each of the $2^{nd}$ to $11^{th}$ component waveforms). Thus, the applied amplitude modulation is configured so that the AM frequency and/or duty cycle changes over the application of the component waveforms, even as the ensemble waveform ("carrier") changes or remains constant between different component waveforms (e.g., component waveforms 2-4 in the series are identical except for the applied amplitude modulation). Also, in general, the change in amplitude modulation between different component waveforms may be instantaneous (e.g., applying the AM parameters and envelope immediately at the start of the component waveform), or they may be ramped up, as with changes in other component waveform parameters (e.g., current, percent duty cycle, charge offset, frequency, as discussed above).

FIG. 103 shows another example of a "calm" evoking waveform having a 10 minute duration in which the amplitude modulation (e.g., AM duty cycle and AM frequency) change during the application of the ensemble waveform with different sequential component waveforms forming the ensemble waveform.

Although the examples shown above are configured to evoke a calm cognitive state, waveforms configured to evoke any other cognitive states (in conjunction with proper electrode placement) may also be used. For example, waveforms configured to evoke a cognitive state of energy (as described above) may be amplitude modulated (see, e.g., FIGS. 98A-98C). Amplitude modulation frequencies between 20 and 200 Hz may be particularly useful for energy ensemble waveforms. Amplitude modulation of energy waveforms may allow comfortable and effective stimulation at a broader range of frequencies (including as high as 10-11 KHz or higher), and for duty cycle of component waveforms that may be higher than would be comfortable and effective for inducing a cognitive effect without amplitude modulation. Interestingly, lower frequency AM (e.g., less than 20 Hz, such as around 8-10 Hz AM) may result in evoking phosphenes. In some variations this may be desirable and AM may offer one means of reliably triggering phosphenes. For example, the apparatuses and methods described herein may be configured to allow a user to select triggering of phosphenes by selecting a control (e.g., button, knob, key, slider, etc.) which adjusts the amplitude modulation (e.g., percent duty cycle of AM and/or frequency of AM), e.g., triggering the apparatus to adjust the frequency of the AM to between about 5 and about 50 Hz (e.g., between about 5-30 Hz, between about 5-20 Hz, between about 5-15 Hz, etc.). The AM frequency may be maintained ongoing, or for a predetermined period (e.g., 1 sec, 2 sec, 3 sec, 4 sec, 5 sec, 10 sec, 20 sec, 30 sec, 40 sec, 50 sec, 1 min, 2 min, 5 min, etc., or less than any of these times, e.g., less than 1 sec, less than 2 sec, etc.) to induce repeated or ongoing phosphenes experienced by a user.

As mentioned above, in any of the examples of amplitude modulation described above, the frequency and/or percent duty cycle of the amplitude modulation (e.g., burst frequency and/or burst duration) may be adjusted to prevent truncation of pulses (e.g., bipolar pulses) of the component waveform. In general, this may be achieved in any appropriate manner, but may be done by setting and/or adjusting the frequency and/or percent duty cycle of the amplitude modulation relative to the frequency of the fundamental (e.g., base) pulses of the underlying component waveform (the "carrier wave" that is being amplitude modulated or made to burst, as described above).

For example, FIG. 104 illustrates the correction, adjustment or selection of a modulation frequency for an amplitude modulated component waveform. As mentioned above, each component waveform of an ensemble waveform may be separately amplitude modulated (or not amplitude modulated), and thus, may have a different burst frequency and/or burst duration. In general, the use of square-wave (burst inducing) amplitude modulation envelopes may be adjusted or configured to avoid truncation of the base/fundamental pulses 1601 within the component waveforms. FIG. 104A shows a simplified example of a portion of a component waveform. In this example the frequency of the component waveform is shown as 5 Hz, merely for purposes of this general illustration. As illustrated and described above, the frequency of a component waveform may typically be much higher, e.g. between 500 Hz and 30 kHz, etc. FIG. 104B shows an example of an amplitude modulation signal envelope (shown here as a square pulse envelope) having a frequency of 2 Hz; as described above, the frequency of the amplitude modulation (envelope) may be different, and typically may be one or more orders of magnitude less than the frequency of the component waveform. In this example, when amplitude modulation of the component waveform of FIG. 104A is applied using the envelope of FIG. 104B, the amplitude modulated component waveform (shown in FIG. 104C) includes truncated (partial) fundamental pulses 1041603, 1041605. Truncated pulses may be tolerated, and even, in some variations, beneficial, however, in general they may be eliminated by modifying the frequency of the amplitude modulation envelope.

Preventing truncation within the component waveforms forming the ensemble waveform may improve the cognitive effect and prevent undesirable and potentially painful charge imbalance and pH changes in the skin beneath the electrodes. As mentioned, any appropriate technique to remove or eliminate the truncated pulses may be used, including filtering of the signal (to remove truncated signals) or modification of the frequency of the amplitude modulation. For example, the duration (and therefore the frequency, which is one over the duration) of the amplitude modulation envelope may be set or adjusted to be a multiple of the duration of one period of a cycle of the component waveform ($t_s$), which may help prevent truncation of pulses of the component waveform; similarly, the burst length of the amplitude modulation may be set or adjusted to be a multiple of the $t_s$.

In some variations, it may be beneficial to adjust a target frequency and/or percent duty cycle (burst length) so that the resulting AM does not truncate pulses of the component waveform. For example, the duration of an amplitude modulation waveform may be adjusted to subtract out the fraction of the component waveform that is truncated. The original desired frequency for amplitude modulation may be adjusted by determining the duration of the fraction of the initial fundamental pulse of the component waveform that is truncated by the envelope, and subtracting the duration (e.g., when both the envelope and the component waveforms start at the same time) from the duration of the amplitude modulation envelope.

In FIG. 104D, the duration of the amplitude modulation envelope has been adjusted by subtracting the duration of the partial pulse 1041603. The resulting AM duration (burst period) is close to the desired initial frequency and is a multiple of the component waveform duration (as is the burst duration) thereby preventing truncation of pulses within the component waveform. This is illustrated in FIG. 104E. In this example, the resulting envelope (burst) duration is twice the duration of the fundament frequency of the component waveform (e.g., the duration of the adjusted/corrected amplitude modulation envelope in this example is 0.4 seconds, with a frequency of 2.5 Hz).

Waveform Controller

Also described herein are method for efficient, compact and rapid communication of ensemble waveform control information from a controller (waveform controller) to a wearable neurostimulator. The controller may be remotely located relative to the wearable neurostimulator. FIG. 105A is a schematic illustration of a wearable neurostimulator 1051701 such as the ones described herein (e.g., FIGS. 91A-91Q), which may wirelessly receive control information (e.g., ensemble waveform information and/or command controls from a waveform controller 1051705). In this example, the wearable neurostimulator includes at least two electrodes 1051721 that are integral with or connectable to the neurostimulator 1051701, and a processor 1051707 that connects to wireless communication circuitry 1051715 (e.g., wireless transducer), a power source 1051709, and a pulse generator 1051713 to apply the waveforms via the electrodes 1051721. The processor may also include a memory 1051723 having one or more registers for storing waveform information, including one or more of a: a current and/or next component waveform. The waveform controller 1051705 may also include wireless communication circuitry 1051715' for transmitting (and/or receiving) control information, including component waveform control information.

The processor 1051707 is generally configured to receive and handle waveform information. Specifically, the processor described herein is configured to operate in real-time to communicate with and receive information from the waveform controller. The waveform controller may transmit (e.g., in real-time or near-real time) sequential component waveforms from the series of waveforms forming an ensemble waveform; to achieve this, the controller and processor share a specific communication architecture that allows the rapid and reliable transmission of component waveforms to the wearable apparatus, allowing the wearable apparatus to deliver the potentially complex ensemble waveform in an energy-efficient and reliable manner.

Specifically, the controller may transmit one or more control codes that may be received by the processor. A variety of control codes may be transmitted, for controlling any of the functions of the wearable neurostimulator, including self-reporting codes (instructing the device to run and/or return diagnostic information including power charge status), LED controls, pairing controls, power-down controls, and the like. In particular, the controller may transmit control codes instructing the neurostimulator to receive waveform information and in particular component waveform information. A command control may tell the processor to prepare to receive and/or deliver a new component waveform, or it may tell the processor to edit or modify an existing component waveform; the command control may also specific the number of segments to expect for the new component waveform or which segments in a stored (including currently running) component waveform to modify.

For example, a first command message (e.g., "new waveform" message/command control) may instruct the processor of the wearable apparatus to prepare a memory register ("shadow register") to receive waveform information. This message may indicate that the processor should start a "new" component waveform or use a component waveform already stored (which may be the waveform most recently delivered by the device). In general, the command messages may be structured to include a message identifier (message ID) that indicates what the message will contain (e.g., which may be recognized by the processor via a look-up table or other mechanism), and/or routing information (e.g., destination and/or source endpoints), and a message payload, which may be the message, such as the new waveform message or the waveform segment message discussed below.

FIG. 106A is a schematic illustration of a generic command message structure that may be used. In this example, the message is a finite size (e.g., 20 bytes, though the systems described herein may be configured to handle any appropriate size, more or less than 20 bytes, e.g., 21, 22, 23, 24, 25, 26, 27, 28, 29, 30 bytes, etc.). The message includes a message identifier (Message ID) and a message payload. The command message may also (optionally) include destination and source endpoints. This message structure may be used for any of the command messages described herein, including the new waveform command messages (see FIG. 106B) and segment command messages (see FIG. 106C).

FIG. 106B illustrates one example of a message payload portion of a first command message (e.g., a new waveform message 1061801) to instruct the wearable neurostimulator to prepare to receive a new set of waveform parameters or a modification of a stored set of waveform parameters. In this example, the controller is configured to transmit, and the processor to receive, a 4 byte message payload that instructs the processor to prepare to either receive a new set of component waveform parameters into a set of memory registers, or to copy and/or modify a stored set of component waveform parameters.

In the message payload for the first command message shown in FIG. 106B, one byte (e.g., byte 0) 1061805 indicates what component waveform to expect, e.g., a modification of a currently playing component waveform, a new waveform, or a saved component waveform (e.g., already in a register or set of registers). The new waveform command message payload may also indicate (e.g., byte 1) 1061807 a number of segments to expect encoding particular waveform parameters (e.g., when a 'new' waveform will be expected). In this example, the new waveform message payload may also indicate if amplitude modulation is going to be applied (e.g., bytes 3-2) 1061809, and may indicate information about the amplitude modulation (e.g., burst frequency, burst duration, etc.), or may indicate if bursting (amplitude modulation) is not to be used.

FIG. 106C also illustrates the transmission of one or more (e.g., n) segment command message payloads 1061803 from the controller to the processor. In this example, each segment command payload includes the waveform parameters for a component waveform of an ensemble waveform. For example, the segment command message payloads may be (as a non-limiting example) a seven byte message in which the segment command information ("waveform segment message") includes the segment definition information for running a portion of an ensemble waveform (e.g. a component waveform or portion of a component waveform). For example, a message waveform segment may include a segment index (e.g., byte 0) 1061813 which corresponds to the sequence of the segment in the waveform when bursting is on (e.g., with amplitude modulation 'on'). The segment may also define the duration of the portion of the waveform (component waveform) being transmitted. For example, bytes one to three 1061815 in FIG. 106B may indicate as a 24 bit number the duration in counts of 12 MHz. The segment message may also indicate the current amplitude (peak current amplitude), e.g., in mA as an 8 fraction bit (e.g., in bytes 4 and 5) 1061821. Finally, the segment message may include a state indicator (e.g., state byte, shown in FIG. 106B as byte 6), which may include a code indicating what state the applied current for the waveform is, such as positive current, negative current, capacitive discharge, and open circuit (no current delivered). Additional segment messages (segment message payloads 1061803') may be transmitted (e.g., a total of n), as shown schematically in FIG. 1068B, and may each encode a portion of a component waveform.

Other command messages may include waveform control messages (e.g., commands to start or stop waveforms), and/or to exchange/swap an actual playing waveform with a stored ('shadow') waveform in a memory register.

In general, any of the apparatuses described herein (e.g., within the processor of the neurostimulator) may include firmware and communication protocols for receiving and responding to the command messages. Any of the processors (neurostimulators) described herein may also be configured to transmit error codes back to the controller. For example, the processor may, during communication (e.g., via a communication circuit) check whether received waveform parameters comply with limitations of hardware and safety standards. Examples of error codes that may be safety conditions (e.g., current requested too high, electrode contact lost or poor connection, DC limit reached, communication lost), error codes related to the received command messages/communication (e.g., too many wave segments, fewer segments received than expected, received segments too short, received segments too long, etc.)

Any of the apparatuses for neurostimulation described herein may be configured to receive a plurality of neurostimulation command messages, including in particular the new waveform message and subsequent segment messages, which may include parameters from a controller such as a computing device (e.g., smartphone, etc.) and apply them as stimulation. The neurostimulator may also adjust them and/or send one or more response error messages back to the controller if the parameters contained in the messages do not comply with hardware limitations and/or safety limits which may be included in the neurostimulator.

FIGS. 106A-106C described above illustrate one possible framework for transmitting waveforms parameters and/or instructions (e.g., as 400 ms segments). This framework, including the specific segment definitions included herein provide a robust way to send waveform parameters in small and manageable pieces that allow very quick response between the controller and the neurostimulator (allowing the system to nearly-immediately respond to user modifications, stops or changes in the applied waveforms), while transmitting a minimum of required information.

In use, the system may be configured so that the controller (e.g., a control apparatus) controls the wearable neurostimulator by transmitting a first message (e.g., new waveform message) from the control apparatus instructing the wearable neurostimulator to prepare to receive a new set of waveform parameters or a modification of a stored set of waveform parameters. The controller may then transmit one (or more likely, more than one) segment messages from the control apparatus, where each segment message defining a segment of the new waveform parameters or the modification to the stored waveform parameters. The segment messages may each comprise a message encoding: a segment index number, a segment duration, a current amplitude, and a state code, wherein the state code indicates one of: positive current, negative current, capacitive discharge, and open circuit.

In general, the segments may correspond to sub-regions of the ensemble waveform that have a particular value (e.g. positive-going current, negative-going current, capacitive discharge current, no current), and segments may be sequentially stitched together to form a single unit pulse, then repeated to form the component waveform of an ensemble waveform.

In general, the hardware of a controller (waveform controller) may be a dedicated device or it may be an apparatus, such as a smartphone, etc. that can be configured to wirelessly transmit the control information as described above. Although wireless configurations are described above, FIG. 105B also provides an example of an integrated or hard-wired connection between a controller 1051705' and a processor 1051707', in which the two components are attached to the same apparatus 1051701', such as a single-use neurostimulator which may be formed, e.g., as a device in which the processor and controller are physically connected (e.g., by a wire or trace) rather than wirelessly connected.

Any of the transdermal electrical stimulation (TES) apparatuses (devices and systems) may be used to modulate a subject's cognitive state, for example, to induce or enhance a state of relaxation, clarity, tranquility, calm, etc. (a "calm" state), or alternatively to induce or enhance a state of excitation, mental agility, energy, etc. (an "energy" state). All of the variations described herein typically include an electrode assembly, which may be a single piece, having a substrate with two end regions, a proximal region and a distal region, linked by a connecting region. A first electrode region (including first electrically active region) may be present at one end, while a second electrode region (including a second electrically active region) may be present at the opposite end; the connection between the two may be flexible in at least one direction. In some variations the substrate is a flexible circuit (also referred to as a flex circuit) onto which the electrode regions and other components (including conductive components) are placed. The electrode assemblies may be adhesive (e.g., may be adhesively held to the subject).

Described herein are single-use or limited-use TES apparatuses comprising flexible and wearable apparatuses with integrated TES hardware, a power source, and an electrode assembly. Such apparatuses may be referred to herein as "integrated TES apparatuses". For example, an electrode assembly may be configured as an integrated, autonomous TES neuromodulation apparatus, in which all of the control circuitry, safety circuitry, waveform generators, power sources and processors necessary for applying a TES session are integrated into the electrode assembly along with the electrically active regions. Such apparatuses may be configured for single-use or for limited-use (e.g., configured to be used between 2, 3, 4, 5, 6, 7, 8, 9, 10, 11, 12, etc. uses and 3, 4, 5, 6, 7, 8, 9, 10, 11, 12, 13, 14, 15, 20, 25, etc. uses before needing to be reconditioned, recycled or disposed of).

Such apparatuses may have a user interface for a user to control the function of the apparatus (i.e. a mechanical component, touchscreen, or accelerometer-detected input (e.g. finger tap) to start or stop a waveform, increase or decrease the intensity of stimulation, etc.) However, such apparatuses may not need to communicate or be controlled by a separate component. In some variations the apparatuses may include near-field communication to receive input (e.g., control input) to enable activity (turn it on), select waveforms, and control a stimulation parameter (e.g. intensity) of the waveform to be delivered. For example FIGS. 107A-109C, described below, illustrate integrated TES assemblies.

Also described herein are TES apparatuses comprising a TES cable neurostimulator that is configured to couple between a wearable (e.g. flex circuit) electrode assembly and a control device (which may be a portable electronic device such as a smartphone, tablet, smartwatch, virtual reality headset, and the like); the TES cable neurostimulator translates control information into TES waveforms that are applied by the electrode assembly. In a simplest form, the electrode assembly is simplified so that it does not include any of the control circuitry to generate and deliver TES waveforms; these functions may be divided between the reusable cable and the control device. For example, the control device may provide command instructions for delivering the TES waveforms as well as power to drive the TES waveforms, and the TES cable neurostimulator may receive this information (e.g., waveform parameter information or analog waveform signals) from the control device and may format the waveforms, including amplifying the signal from the control device, or forming the actual waveforms, for delivery to the simple electrode assembly. The TES cable neurostimulator may include TES circuitry to communicate with the control device, form and modulate the waveforms as instructed by the control device, and may also receive information back from the electrode assembly, including impedance measurements (e.g., indicating that the apparatus has been applied to a user) and/or electrode assembly identification information (e.g., capacitive or resistive information indicating that an electrode assembly is attached to the TES cable neurostimulator and/or what type of electrode assembly is attached, or any other information about the electrode assembly). Examples of these TES cable neurostimulator apparatuses are described below and shown in FIGS. 110A-111B, described below.

Also described herein are intermediate apparatuses, in which a TES cable neurostimulator couples between a control device such as a smartphone and an electrode assembly, but in which the control device provides both control information and power to deliver TES through the electrode assembly, while the electrode assembly may include at least some of the TES circuitry configured to form and apply the TES waveforms. FIGS. 112A-112B illustrate one example of this hybrid or intermediate apparatus, in which the TES cable neurostimulator and the electrode assembly share the TES circuitry that receives TES waveforms or waveform information from a control device (e.g., running an application software and providing a user interface), builds the TES waveforms and delivers them to a user wearing the electrode assembly in a predetermined location (e.g., on the head or head and neck).

FIGS. 107A-107D illustrate a first example of an integrated TES apparatus in which the power source (e.g., battery 107195) and TES control circuitry are formed on or in the substrate 107190 forming the electrode assembly. In general the TES control circuitry 107198 may be any circuitry that is necessary or useful for generating and safely delivering TES waveforms to be applied between the electrodes 107180, 107181 (shown in profile in FIG. 107B and most visible in FIG. 107C). Examples of TES waveform parameters are described in greater detail below, and may also be found in U.S. patent application Ser. No. 14/715,476, filed May 18, 2015 ("METHODS AND APPARATUSES FOR AMPLITUDE-MODULATED ENSEMBLE WAVEFORMS FOR NEUROSTIMULATION"), including ensemble waveforms formed of sequences of different component waveforms having one or more different peak current amplitudes, frequencies, percent duty cycle, percent charge imbalance, capacitive discharge periods, bursting frequency, and/or bursting duty cycle. For example, the TES control circuitry 107198 may include one or more controllers (which may include or be separate from one or more processors). The TES control circuitry may include a current generator (e.g., waveform generator), which may be controlled by the processor/controller, and a memory (e.g., for storing waveform information), a skin-impedance sensing circuit (which may be incorporated into the processor), a timer, etc. The TES circuitry may also include a near-field communication circuit 107183. The near-field communication circuitry 107183 may be used as described below in FIGS. 109A-109C, for receiving control information and/or instructions (e.g., waveform parameter information).

The substrate may also include conductive traces 107193 to connect the TES control circuitry to the electrodes.

FIG. 107B shows a side view of the apparatus of FIG. 107A. In this example, the TES control circuitry stands slightly proud of the substrate, but this is not mandatory. The circuitry may also be positioned elsewhere on the substrate (e.g., over the opposite electrode as shown in FIG. 108A, and/or distributed along the connecting region 107190 between the electrodes, etc.). A cover may be used to cover and/or protect the TES control circuitry e.g. epoxy or a silicone, rubber, etc.). The cover may be a material or foam covering, etc., or the TES control circuitry may be uncovered.

The exemplary substrate shown in FIGS. 107A-107D is configured to be worn on a user's head at temple/forehead region 107177 and on the back of the neck (a "calm" configuration, as described in greater detail herein), although other configurations of the substrate, electrodes and integrated TES circuitry are possible. FIG. 107D shows the exemplary integrated TES apparatus of FIGS. 107A-107C worn on a user's head.

FIGS. 108A-108B illustrate another example of an integrated TES apparatus. In this example, the TES control circuitry is positioned at a different location, over the second electrode region 107181; when worn, this region may be positioned on the back of the neck, and may therefore be less visible.

As mentioned, any of these apparatuses may include a power-source, such as a battery, capacitor, or the like. The power source may be of sufficient power to drive the TES stimulation for the desired duration (e.g., 10 minutes, 15 minutes, 20 minutes, 25 minutes, 30 minutes, etc.) using the TES waveforms, e.g., ensemble waveforms. Generally, apparatuses that integrate an electrode assembly and neurostimulator can operate with a small battery, in part because a wireless transmitter may be eliminated. If very small, a battery may have sufficiently low charge so that some or all safety circuitry may be excluded from the integrated neurostimulator, further reducing the size and weight of the integrated neurostimulator-electrode assembly system.

Any of the apparatuses described herein, including the integrated apparatuses shown in FIGS. 107A-108B, may include one or more controls 107179 for allowing user control of their operation. For example, a power control (button, knob, etc.), intensity control (slider, dial, touchscreen, etc.), waveform selector, etc., may be incorporated onto the apparatus either with or separate from the TES control circuitry (though it will typically be connected thereto).

In any of the integrated TES apparatuses described herein, which may also be referred to as TES patch apparatuses, a TES waveform control and/or waveform selector may be used. In general a TES waveform control/selector (which may be referred to herein as a selector or waveform selector for convenience) is a separate element that can be used to provide information to the integrated apparatus, such as waveform information (selecting a particular type, duration, or intensity of TES waveform(s)), and/or control information (including unlocking the device for use). The waveform selector may communicate with the integrated device in any appropriate manner, including, for example, near-field communication. Alternatively, an onboard removable memory (e.g. microSD card) may contain waveform information that can be loaded from a user computing device or purchased pre-loaded with a waveform and other information for neurostimulator control.

FIGS. 109A-109B illustrate one example of a near-field communication selector (waveform selector) to be used with a TES patch neurostimulator apparatus such as those shown in FIGS. 107A and 108A. In this example, the near-field communication selector 109300 is configured as a sticker or stamp that may be applied to the apparatus before operation, as illustrated in FIG. 109C. The patch includes an adhesive 109317 and can be placed on or near a near-field communication circuit 107183 forming part of the TES control circuitry. The near-field communication selector may include a coil and circuitry and may encode control information (to "unlock" the device) and/or waveform information, e.g., encoding one or more ensemble waveforms for delivery to the wearer of the apparatus.

FIGS. 132-135 illustrate examples of integrated TES apparatuses in which the power source and TES control circuitry are formed on or in the substrate forming the electrode assembly, similar to those shown in FIGS. 107A-109B above. For example, FIG. 132 shows the back of one exemplary device in which the flexible, electrode assembly is lightweight (e.g., has a weight of less than 9 grams). The electrodes (not visible) are on the front side; the assembly is adapted to be worn over the user's temple region and behind an ear. A separate attachment (e.g., snap, pin, etc.) to an additional piece is not necessary. In this example, there is space 1322607 between the circuitry 1322601 (e.g., controller, signal generator, etc.) and the battery 1322605, which may allow some level of bending or flexing to better conform to anatomy. The circuitry may create a relatively stiffer region. The total thickness is approximately 5.5 mm.

FIGS. 133A-133B illustrate another variation of an integrated TES apparatus, configured to be worn on the wearer's (user's) forehead/temple and the back of the wearer's neck. In this example, the battery 1332705 is separated from the majority of the neurostimulator circuitry 1332701 by the more than the two inch long path of flexible substrate 1332708 connecting the two electrodes (not visible). This may make the battery less visible, and may also help the apparatus conform better to the anatomy, as the larger battery may be attached at only one point. FIG. 133A illustrates a variation in which the second electrode portion is rather large and rectangular (e.g., having a length of more than 17 mm in this example). FIG. 133B illustrates the second electrode portion in another configuration of an integrated TES apparatus in which the second electrode portion is smaller and includes a battery 2705' having a round profile.

FIG. 134 is another example of an integrated TES apparatus in which the battery is positioned in an intermediate position between the somewhat enlarged first and second electrode portions. The circuitry 1342801 is integrated on the flexible substrate on the back of the first electrode portion, while the battery 1342805 is positioned along the connecting region 1342808 between the first electrode portion 1342815 and the second electrode portion 1342817, and is configured so that it will be held above the wearer's ear when the device is worn with the first electrode region attached to the temple and the second electrode region behind the back of the ear (e.g., at or near the mastoid). This position may feel particularly balanced as it conforms well to the wearer's anatomy, while allowing a fairly long-lasting battery.

FIG. 135 illustrates another example in which all of the circuitry and battery 1352901, 1352905 are coupled to the second electrode region of the flexible substrate. In this example, the entire apparatus may weigh between 5-10 grams (e.g., 6.5 grams) and the majority of the weight is supported behind the user's ear, near the mastoid region. The electrode may be held against the skin by an appropriate skin adhesive. Although the addition of the circuitry and battery to the second electrode portion may make the otherwise highly flexible substrate more rigid, particularly if an additional printed circuit board (PCB) is used, this additional rigidity in this limited region may not be problematic, given the flexibility of the rest of the apparatus. In addition, the total PCB space used (as in this example) may be relatively small (e.g., less than approximately 2.5 $cm^2$). In the exemplary apparatus shown in FIG. 135, the battery is 90 mAh and approximately 6.5 mm thick, including the flexible substrate, but may provide sufficient power for at least 3 to 4 energy waveforms (i.e. tens of minutes of TES). The front (first electrode portion) may feel particularly comfortable, as it allows excellent compliance with the anatomy.

Other variations of TES neurostimulation apparatuses that are not integrated, but may include external power and/or control are also described herein, as mentioned above. For example, FIGS. 110A-111B illustrate variations of a TES apparatus in which the electrode assembly is formed on a flexible material, but include one or more connectors (e.g., U.S. patent application Ser. No. 14/634,664, filed Feb. 27, 2015, titled "CANTILEVER ELECTRODES FOR TRANSDERMAL AND TRANSCRANIAL STIMULATION") such as snap connectors or other mechanical and electrical connectors that may be connected to a cable, and (through the cable) to a hand-held or otherwise portable computing device, such as a general-purpose smartphone (e.g., iPhone™, Android™, Google phone) or other portable or wearable electronics. The portable computing device may function by running software and/or firmware for controlling operation of the TES neurostimulator, including in some variations, selecting and preparing the TES waveforms to be delivered, confirming connection of the electrode assembly to the user, and/or confirming the type/state of the electrode apparatus. Although the electrode apparatus may be single-use or limited-use, and may include no or very little of the TES control circuitry (unlike the variation shown in FIGS. 107A-109C), the cable 110499 may be configured as a "smart" cable, which includes TES control circuitry receiving power and control information from the portable computing device (control device) and forming the TES waveform for delivery by the electrode assembly. The smart cable may also be referred to herein as a TES cable neurostimulator, and it may include all or some of the TES control circuitry described above, e.g., current control circuitry, including at least amplification circuitry for amplifying the power provided by the control device to the TES waveforms.

In FIG. 110A, the TES cable neurostimulator 110499 is configured to plug into the control device 110490, so that it may drive delivery of TES waveforms appropriate for the type of electrode assembly (e.g., calm 110485 or energy 110486). In any of the apparatuses described herein, the apparatus may detect the type of electrode apparatus and provide or allow only waveforms appropriate for this type of electrode (e.g., to elicit a calm and/or energy state). In FIG. 110A, the proximal end of the TES cable neurostimulator includes a housing region which may house some of the TES control circuitry as well as forming the connector (e.g., a "Lightning" type connector when connecting to an appropriate iPhone). The distal end of the TES cable neurostimulator may include a set of connectors (e.g., snap connectors, magnetic connectors, multi-pin connectors, concentric connectors, etc.) complimentary to the connectors on the electrode assembly. In FIG. 110A the connectors are held in a fixed spacing appropriate to mate with the mechanical/electrical connectors on the electrode assembly. FIG. 110B shows another example of the distal end region of an apparatus in which the connectors are separately positionable relative to each other. In other variations of the TES cable neurostimulator, a larger housing containing TES control circuitry may be present at or near the distal end of the cable (i.e., near the electrode assembly) or in-line along the cable, similar to how music controls may be present along the cable of earbuds.

FIG. 110C illustrates an alternative view of a TES cable neurostimulator 110499' connectable to two alternative configurations of electrode assemblies 110485', 110486'. In this example, the TES cable neurostimulator is configured to be connected to a region of the electrode assembly that is worn away from the face (e.g., on the back of the neck and/or behind the ear). This is illustrated in FIG. 111B. For comparison, a system such as that shown in FIGS. 110A-110B is illustrated worn on a user in FIG. 111A.

As shown in FIGS. 112A and 112B, in some variations the TES circuitry may be distributed between the TES cable neurostimulator 112699 and the electrode assembly 112693, 112693'. In FIG. 112A, at least some of the TES control circuitry is present on the electrode assembly 112693, so that power and control information from the control device (e.g., phone 112688) is passed on to the circuitry on the electrode assembly. In some variations some of the circuitry may be on the TES cable neurostimulator, though in some variations, the cable may merely include connectors at the distal end to connect to the electrode assembly which may include the TES control circuitry, while the proximal end of the TES cable neurostimulator may include a connector appropriate to connect to the control device (e.g., smartphone 112688), while the rest of the cable includes a conductive path to communicate between the two.

In general in any of the TES neurostimulators (including wired and wireless stimulators), when a control device such as a phone communicates with TES control circuitry to apply a TES waveform, the communication may be digital, analog, or a combination of analog and digital. In some variations, as described in U.S. application Ser. No. 14/639,015 previously incorporated by reference, the TES waveform information may be digital and discrete, so that the communicated TES information is divided up into waveform parameters that are interpreted by the TES control circuitry (including processor) to form the actual waveforms to be delivered. However, in some variations it may be beneficial to provide actual analog and/or digitized TES waveforms, similar to how the waveform of an audible signal, e.g. song, is encoded. This may be particularly useful in the wired configurations shown in FIGS. 110A-112B; the TES circuitry may then modulate (e.g., amplify, limit, etc.) the applied TES waveforms. Alternatively or additionally, the system may be configured to transmit from the control device (e.g., smartphone) an analog waveform signal that is modulated by a second signal from the control device (which may be digital or analog) to form the final TES waveform. For example, an analog signal may be modulated by a defined set of amplitude modulation parameters, defining the addition/removal of capacitive discharge currents, etc. Alternatively, a digital signal on a second channel may be present on the cable that defines the presence of a capacitive discharge current at a particular time point in the waveform.

EXAMPLES

In general, described herein are neuromodulation devices having an integrated electrode and neuromodulation unit, systems including them, and methods of wearing and using them for delivering neurostimulation to a subject. The described integrated neuromodulation device will largely contain disposable or semi-disposable components that may be entirely or partially recyclable. It is conceptualized that the integrated neurostimulation device can be geared toward a more disposable device that a person can use for a certain number of sessions before requiring replacing the integrated neuromodulation device. Thus, multiple layers of adhesive may be present on portions of the electrode assembly, such that they may be peeled before a subsequent use to reveal a fresh adhesive area (similar to how a layer of a lint roller is removed to reveal a new, fresh adhesive patch).

The integration of the electrode assembly and the neuromodulation control components has many benefits. For one, having the entire neuromodulation device on a strip means a much more portable and lighter weight device compared to related designs. In related designs, having a detachable neuromodulation unit meant that having proper electrical contact was always a concern. The issue of proper electrical contact is eliminated, because the electrodes and the neuromodulation components are in electrical communication internally within the neuromodulation device strip.

A neuromodulation system as described herein may be an integrated system that combines two main features of related neuromodulation systems. More specifically, these devices may combine and integrate previously described lightweight, wearable neurostimulator devices that were configured to couple to a consumable, disposable electrode assembly. The present disclosure is directed to neuromodulation output-generating components combined with a plurality of electrodes that are all located on a flex circuit strip or having a strip-like shape.

In one embodiment, all the components (including but not limited to electrodes, neuromodulation components, controls for powering on and off the device, and controls for selecting a particular waveform session) associated with the neuromodulation device strip are integrated into an integrated flex circuit device. There are numerous advantages of integrating the neuromodulation components with the electrode within one unit. For one, having an overall lighter weight device attached to one's facial and neck region is more comfortable and less intrusive for the wearer. Also, having even a slightly lighter neuromodulation device strip enables the use of weaker adhesives (and/or smaller adhesive areas), improving usability while reducing cost and the likelihood of skin irritation. Using weaker adhesives is less damaging to the user's skin. Along the same vein, because all the components for controlling the neurostimulation output are integrated into the device strip, there is no requirement that the neuromodulation device strip contains means for wireless connections (i.e. Bluetooth capabilities). There would also be no requirements for a corresponding smartphone mobile application for controlling the waveform sessions. Another very relevant advantage for both a manufacturer and a potential consumer is that the neuromodulation device strip with integrated components would be more cost effective to manufacture and produce and as a result can be brought to consumers at a price an order of magnitude cheaper than other versions.

Similar to related designs, the electrode assembly may have a variety of shapes and be formed on a flexible material, such as flex circuit material, and in electronic communication with the neuromodulation components that are also located on the flexible circuit strip. In general, the flexible circuits described herein are amenable to high throughput automated pick and place manufacture using surface mount technology. In one possible embodiment, the neuromodulation device may include a number of pre-loaded waveforms or "vibe" sessions. A user simply has to turn on the neuromodulation device and select the desired waveform. In some embodiments, a wireless or wired connection may be established between the neuromodulation device and a mobile telecommunication device. For example, it would be possible for the mobile telecommunication device to include downloadable software, firmware, or applications aimed at controlling and delivering an assortment of waveform sessions and wirelessly or in a wired configuration transmit to the integrated neuromodulation device commands for operating said device. Further, it would also be possible in this current example for the mobile telecommunication device to receive output from the integrated neuromodulation device such as a physiological parameter. In general, the flex circuit may include sensors (e.g. electrodes for recording EEG, EMG, EOG; temperature sensors; heart rate sensors; accelerometers and gyroscopes; etc.) and may, in variations using a TES cable neurostimulator, may transmit this information to the user computing control device (i.e. smartphone).

In general, the neuromodulation device strip is flexible. All the electronic components contained within the flexible strip are formed in a manner that allows for some degree of flexibility and movement. Flexibility may permit bending up or down along the longitudinal axis of the device strip as well as allow for a some twisting of the strip. The neuromodulation device strip may also have flexibility about its horizontal axis. Flexibility of the neuromodulation device strip along both its longitudinal and horizontal axes allows for movements associated with the user placing the neuromodulation device strip on his head and neck region as well as allowing for natural movements of the user's head and neck during use of the neuromodulation device strip with a lower likelihood that all or part of the dermal electrode will dislodge from a low-impedance contact with the skin.

The neuromodulation devices described herein may incorporate some or all of the components needed for controlling and outputting the transdermal electrical stimuli. The incorporation of all the requisite components for the neuromodulation device eliminates the need for a separate neuromodulation applicator and the drawbacks of maintaining electrical connection between the neuromodulation applicator and the electrode assembly.

In the example where some of the neuromodulation components are contained within the neuromodulation device, an external tether can contain the remaining neuromodulation components. The tether can contain a means for amplifying the neuromodulation output or a chip for contributing to the control or output of the waveform sessions. The tether can also be connected to a telecommunication device (e.g. a smartphone, a tablet, a laptop, a smartwatch, a virtual reality headset, or a computer). In this latter scenario, the telecommunication device can include software, firmware, or applications for controlling or modulating the waveform session outputs.

In reference to FIGS. 113A-113D, an electrode assembly is shown. In this example, the electrode assembly 113100 includes a plurality of electrode portions (two are shown) 113103, 113105. In FIG. 113A, a front perspective view is shown. The front side is the side that will face away from the subject when worn. The electrode assembly is thin, so that the electrode portions include a front side (visible in FIGS. 113A and 113B) and a back side (visible in FIG. 113D). As shown in the side view of FIG. 113C, the device has a thin body that includes the electrode portions 113103, 113105 as well as an elongate body region 113107 extending between the two electrode portions. The elongate body is also thin (having a much larger diameter and height than thickness). The thickness is shown in FIG. 113C.

FIG. 113D shows a back view of this first example of an electrode assembly. In this example, the first 113103 and second 113105 electrode portions are also shown and include active regions 113133, 113135. The active regions are bordered by adhesive 113140. The first 113103 electrode portion includes, on the back (patient-contacting) side, a first active region 113133, surrounded by an adhesive material 113140 that extends. The active region may include a conductive material (e.g., electrically conductive gel). Similarly, the back of the second electrode portion 113105 includes the second active region 113135 which is bounded, e.g., around its entire circumference, or at least on, by an adhesive 113140. The adhesive may be any biocompatible adhesive that can releasably hold the material to the skin.

In FIG. 114A, the front side of the electrode assembly is shown with the foam backing 113121, 113123 (which may be adhesive on one or both sides) materials. A foam backing material is advantageous for apparatuses that incorporate TES components on the front side of the electrode assembly, because it can protect these components from short-circuiting (i.e. via touching to a conductive surface, moisture, etc.). The base may be composed of a flex circuit material, e.g., that is relatively insulating, flexible out of the plane of the material, and rigid in the plane (meaning it can be bent up/down out of the plane, but has rigidity when pushed/pulled in the direction of the plane of the material). The flex circuit may have a dielectric layer covering all or part of the front and/or back side, covering and insulating conductive traces. Many of the structures used to form the electrode regions and connectors may be printed directly onto the base or attached to the base (e.g. by flexographic printing, silk screening, or laser printing with conductive ink). As described above, the foam material over either or both of the front sides of the first and second electrode portions may be omitted (or replaced with another electrically insulating material such as epoxy).

Electrode assemblies are generally described in detail below, along with specific examples and variations. In particular, described herein are electrode assemblies that are thin (e.g., generally less than 10 mm, less than 9 mm, less than 8 mm, less than 7 mm, less than 6 mm, less than 5 mm, less than 4 mm, less than 3 mm, less than 2 mm, less than 1 mm, etc. thick, which may not include the thickness of the connectors that may extend proud from the thin electrode assembly), and flexible, and may be flat (e.g., formed in a plane). For example, they may be printed on a flex material, such as the material used to print a flex circuit. In use, they can be wrapped around the head to contact it in at least two locations (e.g. at the temple and the back of the neck and/or behind the ear). In some examples, one snap connects to a first active electrode region (anodic or cathodic region) that is surrounded by an adhesive to adhere the active region to the user's head. A second electrode region (anodic or cathodic) on a separate part of the electrode assembly may be electrically connected to the other connector. For example, the second electrode region may be adapted to fit either on the region over the mastoid bone, behind the subject's ear (energy electrode configuration) or a region across the user's neck at the base of the hairline, e.g., near the midline of the neck (calm electrode configuration). Other electrode locations on the head, neck, or other parts of the body below the neck are possible by adjusting the shape of the flex circuit and position of the electrode areas.

The electrode apparatus may be printed (e.g., by flexographic printing, laser printing with conductive ink, silk-screening, etc.) on a flexible plastic substrate (flex substrate). The electrode active regions on a first side of the assembly may include a layer of conductor (e.g., silver), over which a layer of Ag/AgCl is deposited that is sacrificial and acts as a pH buffer. A next layer of hydrogel overlays the Ag/AgCl electrode so that it can uniformly transfer charge across the active region into the skin. A portion of the electrode assembly around the active electrode area may have an adhesive that permits good contact with a user's skin. The electrodes conceived generally have the active region on a first side that is adapted to contact the user's skin. The active region may include a hydrogel that transfers energy (e.g. current) from the neuromodulation device to the subject's skin. The active region of the electrodes is in electrical communication with the neuromodulation components on the neuromodulation device strip.

Both the first electrode portion and the second electrode portion may be adhesively held with the electrically active regions against the skin, allowing the neurostimulator to apply energy, and in particular the waveforms as described in U.S. patent application Ser. No. 14/320,443, titled "TRANSDERMAL ELECTRICAL STIMULATION METHODS FOR MODIFYING OR INDUCING COGNITIVE STATE," filed Jun. 30, 2014, Publication No. US-2015-0005840-A1 and herein incorporated by reference in its entirety.

Another example of an electrode assembly similar to the variation shown in FIGS. 113A-115 is shown in FIGS. 119A-119D. In this example, the electrode assembly 1191300 includes two electrode portions 1191303, 1191305 each having at least one active region 1191333, 1191335. FIG. 119A shows a front perspective view, FIG. 119B is a front view, FIG. 119C is a side view and FIG. 119D is a back view. The front side is the side that will face away from the subject when worn. Electrode portions 1191303, 1191305 are connected by an elongate body region 1191307 extending between the two electrode portions. The elongate body is also thin (having a much larger diameter and height than thickness). The thickness is apparent in FIG. 119C. None of the figures herein are to scale, unless indicated otherwise.

The width of the connection region between two electrode regions in any of the variations described herein may be relatively small (though wider than the thickness of the electrode apparatus body region), e.g., between about 0.5 mm and 20 mm, between about 1 mm and 15 mm, between about 2 mm and 15 mm, between about 3 mm and 10 mm, etc.

FIG. 119D shows a back view in which the first 1191303 and second 1191305 electrode portions are also shown and include active regions 1191333, 1191335. The active regions are bordered by adhesive 1191340. The first 1191303 electrode portion includes, on the back (patient-contacting) side, a first active region 1191333, surrounded by an adhesive material 1191340 that surrounds the entire circumference of the active region. Adhesive regions that surround all or most of the circumference of an active region are beneficial in curved and/or hairy (e.g. with vellus hair) body regions to ensure as uniform electrical contact as possible between the active region and the subject's skin. The active region may include a conductive material (e.g., electrically conductive hydrogel). Similarly, the back of the second electrode portion 1191305 includes the second active region 1191335 which is bounded on an upper and lower side by an adhesive 1191340. The adhesive may be any biocompatible adhesive that can releasably hold the material to the skin.

FIGS. 128A-128B illustrate another variation of an electrode assembly similar to the one shown in FIGS. 113A-113D and FIGS. 119A-119D. In this example, the second electrode region (which may be positioned on the wearer's neck, for instance) is oriented horizontally, in the direction of the elongate connecting member. This may allow the entire assembly to be more compact for packaging and manufacture. FIG. 128B shows a back view of the apparatus, including the electrically active regions 1282205, 1282209 which may include a conductive hydrogel. In this example, the electrically active regions 1282205, 1282209 may extend from edge-to-edge of the two skin-contacting electrode regions 1282227, 1282229, improving the efficiency and yield of manufacture. For example, the first conductive layer and/or the sacrificial layer (and any intervening layer) may comprise a portion of the area underlying the conductive hydrogel (e.g. 1282205) so that the active electrode region is targeted and sized correctly while still permitting a strip of hydrogel 1282205 to cover the electrode region from one end to another for improved manufacturability. This configuration may simplify the construction of the apparatus (as it may be formed without having to pick and place the hydrogel "islands" as shown in FIGS. 113D and 119D). These conductive regions are bracketed on either side by adhesive 1282207, 1282207' and 1282217, 1282217'. For example, during manufacture, parallel lanes of adhesive and hydrogel may be placed on the flex circuit without requiring a pick and place or additional die-cut step for placing a hydrogel island surrounded by an adhesive region. In the example electrode apparatus shown in FIG. 128B, manufacturing may use three lanes of adhesive with appropriate width parallel to the adjoining strips or lanes of adhesive and hydrogel on the two electrode regions 1282227, 1282229. For example, a first lane of adhesive having width appropriate for adhesive region 1282207, a second lane of adhesive having width appropriate for the combined area of adhesive regions 1282207' and 1282217', and a third lane of adhesive having width appropriate for adhesive region 1282217. (In another example, separate lanes of adhesive may be used for adhesive regions 1282207' and 1282217'.) Also during manufacture, two lanes of hydrogel of appropriate width to cover hydrogel regions 1282205 and 1282229 of the electrode apparatus. In some examples, a first manufacturing step places the strips of adhesive and hydrogel onto a disposable, temporary substrate so that the combined parallel strips of adhesive and hydrogel may be die cut to have the shape appropriate for the electrode regions 1282227 and 1282229 (including separating adhesive regions 1282207' and 1282217' from a single lane of material into two distinct adhesive regions for the two electrode regions), then the die cut hydrogel-adhesive regions are transferred from the temporary, disposable substrate to the electrode apparatus at the appropriate location. A beneficial feature of this design is that the electrode apparatus (and components in its manufacture) do not need to be turned, rotated, or placed and can be more readily manufactured in an efficient roll-to-roll framework.

FIGS. 116A-116C illustrate another example of an electrode assembly. This example is very similar to the variation shown in FIGS. 113A-114B. In general, virtually any form factor for the electrode strips (e.g., a flexible elongate, flat electrode strip) may be used and integrated with TES control circuitry and/or power source and/or cable connection, as described herein. In the example shown in FIGS. 116A-116C, the shape of the first electrode portion 116403 and foam/backing material 116421 (which may also or alternatively be an adhesive material) are similar to those previously shown. An advantage of having multiple electrode apparatuses with the same shape is that they can be used interchangeably with a single neurostimulator device. However, the example shown in FIGS. 116A-116C includes a different overall shape, and may be used to connect, for example, to different regions of the patient's head/neck. In particular, the portion of the substrate forming the elongate body region 116407 extending between the two electrode portions 116403, 116405 is shaped slightly differently. In this example, the electrode assembly may be configured to connect, for example, to the subject's temple with the first electrode portion and the elongate body region may be bent around the subject's head so that the second electrode portion may be in electrical contact with a region behind the subject's ear (e.g., at or near the mastoid). By placing the first active region 116433 of the first electrode portion 116405 in electrical contact with the skin at the temple region and using the adhesive material 116440 surrounding the electrically active region 116433 to hold the electrically active region securely in position on the subject's skin, the second electrically active region may also be adhesively 116441 held to skin so that the second electrically active region 116435 is in contact with the mastoid region.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in both the variations of FIGS. 113A-115 and FIGS. 116A-116D. The bend or curve, in which the elongate body may even double back on itself, may allow the material to flex or bend to allow it to be adjustably positioned over and/or around the subject's head, as shown in FIGS. 112A-112B and 116i, for example.

FIG. 116D shows an exploded view of the electrode assembly of FIGS. 116A-116C. In this example, the substrate (elongate body 116408) forms the elongate body region between the first electrode portion 116403 (formed of the first electrically active region having conductive material (not visible in FIG. 116D), hydrogel overlying the electrically active region 116443, adhesive 116440 and optional backing material 116421, as well as a portion of the substrate 116408) and the second electrode portion 116405 (formed of the second electrically active region (not visible), hydrogel overlying the electrically active region 116445, adhesive 116441 and optional backing material 116423, as well as a portion of the substrate 116408). One or more electrical traces may also be included, e.g., directly printed (or silk-screened, etc.) onto the substrate 116408.

FIGS. 116E and 116F show examples of exploded views of electrode assemblies. FIGS. 116G and 116H show front and back views, respectively, of this variation of a flexible electrode assembly.

FIG. 116F shows an exploded view of the flexible electrode assembly components for transdermal electrical stimulation configured similar to the variation shown in FIG. 116A. The apparatus is configured with a shape so that a first electrode active region may be placed on or near a subject's right temple and a second electrode active region may be placed on a subject's right mastoid region In some variations, the apparatus may be formed of multiple substrate layers. For example in FIG. 116F, the electrode apparatuses includes a skin-facing dielectric 116510 layer that is an insulative layer. An additional dielectric layer 116515 may be positioned to face outwards (distal from the skin and the skin-facing layer) and may have cut-out regions (exclusions) so that two snap connectors can pass through the layer. The layer may also include one or more small rectangular exclusions so that a capacitor soldered onto the internal flexible electrode substrate 116511 has sufficient clearance. The top 116515 (outward facing) and bottom 116510 (skin facing) layers may be coatings or may be formed of solid materials that are adhesively attached to the inner substrate material 116511.

In this example, an oval region 116555 is a printed (silk screened, etc.) region that is formed or attached to the flexible substrate 116511, and may be formed of a conductor and/or sacrificial layer (e.g., Ag/AgCl layer as described in more detail below), forming the first electrode active region. In this example, the Ag/AgCl region has a round exclusion area so that the eyelet portion of a snap electrode does not directly contact the active electrode area. Direct contact between a snap and the electrode may cause oxidation of the electrode area or create a galvanic cell due to the chemistry of the included components.

FIGS. 116F-116H also illustrate various conductive traces which may be present on any of the variations described herein, to connect the electrically active regions to the electrical/mechanical connectors, such as the second electrode active region. For example, a conductive trace 116553 may be formed on the skin-facing side of the flexible electrode apparatus and may conduct current through a conductive via passing from the second (outward-facing) side of the apparatus to the electrode area. A conductive, non-consumed (i.e. metal) layer (e.g. Ag, Cu, Au, conductive carbon, etc.) may also be included (not shown in FIG. 116F) as one layer forming the first and/or second electrically active regions. This conductive, non-consumed layer may be printed as a contiguous region from trace 116553 and has a similar shape as the Ag/AgCl layer 116555 ("sacrificial layer"), which extends slightly beyond the underlying conductive region at all boundaries (including the interior boundary of the circular exclusion, if present) in order to ensure there are no shorts between the conductive layer printed on the flexible substrate and the overlying hydrogel. Such a short may cause current to bypass the pH buffering Ag/AgCl layer and reduce the comfort and efficacy of transdermal electrical stimulation.

Similarly, for a second electrically active region (which may be configured to position over the mastoid, as shown in FIG. 116F), a conductive trace 116519 may be functionally similar to the conductive trace 116553 in the first electrically active region and may be positioned and shaped to be co-incident with the Ag/AgCl layer 116561 or with a conductive non-consumed layer that is in contact (and surrounded on all peripheral sides by) the Ag/AgCl layer.

In this example, flexible substrate 116511 (e.g. formed of a material such as polyethylene) may form the base onto which the electrodes and any circuit elements are printed and/or attached, glued, adhered, silk-screened, etc.

In this example, two or more conductive carbon circular regions 116514 and 116517 may be coupled between the conductive traces. Traces 116512 and 116513 in this example are connected by a capacitor (as described in greater detail below) that may be used as part of a capacitive element for electrode assembly identification. A capacitor is not shown in FIG. 116F, but would connect between, for example, the first and second active region, e.g., between the two electrical connectors (e.g., snaps) by traces 116512, 116513. Trace 116518 may carry current to conductive vias (not shown) to trace 116553 on the skin-facing side of the electrode assembly that is contiguous with the first electrode region (e.g., the conductive non-consumed layer, if included).

Similarly, trace 116516 may carry current through a conductive via to trace 116519 on the skin-facing side of the flexible electrode assembly that is contiguous with the second electrode active region (e.g., a conductive non-consumed layer, if included).

FIGS. 116G and 116H show front (away-facing) and back (skin-facing) views, respectively, of a flexible electrode assembly such as the one shown in FIG. 116F. In the plane of the electrode apparatus, the first electrode active region is at a proximal 116520 end, and the second electrode apparatus is at a distal end region 116530.

In any of the variations described herein, a conductive layer such as conductive carbon or another conductive material (e.g., annulus 116523) may connect to an electrical stimulator unit, as well as traces that transmit current to a first electrode 116534. One of the conductive carbon annuluses 116521 may connect to one or more traces that transmit current to the second electrode active region 116536.

In this example, a conductive trace 116524 on the front (facing away from the subject's skin) side of the apparatus transmits current from the conductive connector (e.g., from the conductive carbon layer) through a conductive via (not shown) to trace 116533 on the skin-facing (back) side and then to the first electrode active region 116534, which may be formed of the conductive layer(s) (e.g., non-consumed conducting layer and overlaid consumed conductive layer, and hydrogel layer). A through hole 116531 in the substrate may provide clearance for a second electrical connector (e.g., conductive snap) to be riveted through the flexible substrate. In FIG. 116G the traces 116522 and 116526 may act to short the two electrode paths through a capacitive element (e.g., capacitor, not shown) which may be used to identify the type and veracity of an electrode assembly as described in detail below.

FIG. 116i illustrates a variation of an electrode assembly 116600 worn on a subject's head. As illustrated, the apparatus is positioned with the first electrode portion adhesively attached at the temple region and a second electrode portion attached to a region behind the head (e.g., behind the ear or neck region, not shown).

FIGS. 120A-120C shows another example of an electrode assembly similar to the variation shown in FIGS. 116A-116D. The electrode apparatus includes a first electrode portion 1201403 and a second electrode portion 1201405. FIGS. 120A and 120B show front perspective and front views, respectively. In this example, the front side does not include any foam/backing material or additional adhesive material around either electrode portions, although such may be included. As in FIGS. 116A-116C the overall shape of the electrode apparatus may be adapted to connect to a subject's temple with the first electrode portion 1201403, the elongate body region may be bent around the subject's head, and the second electrode portion 1201405 may be in electrical contact with a region behind the subject's ear (e.g., at or near the mastoid). By placing the first active region 1201433 of the first electrode portion 1201405 in electrical contact with the skin at the temple region and using the adhesive material 1201440 surrounding the electrically active region 1201433 to hold the electrically active region (and the attached neurostimulator) in position, the second electrically active region may also be adhesively 1201441 held to skin so that the second electrically active region 1201435 is in contact with the mastoid region.

FIGS. 129A-129B also illustrate another example of an electrode array, similar to those described above in FIGS. 116A-116D and 120A-120C. As described above, the electrode apparatus/assembly includes a pair of skin-contacting electrode regions 1292327, 1292329. The second skin-contacting electrode region 1292329 will be positioned away from the first skin-contacting electrode region 1292327 and the neuromodulation components, but will also be held against the subject's skin, for example, behind the ear.

FIG. 129B shows the back of the electrode assembly, which is configured to face (and contact) the subject wearing the apparatus. In this example, both skin-contacting electrode regions include active regions that extend from at least one edge of the apparatus across the skin-contacting electrode region to form the active zones on the skin-contacting electrode regions. For example, in FIG. 129B, the first skin-contacting electrode region 1292327 has an active region 1292205 that forms a central strip across the skin-contacting electrode region 1292327. In other examples, the hydrogel 1292205, 1292209 may extend from one edge of the electrode region to another edge of the electrode region, while the underlying electrode active area only covers a subset of this region in order to ensure the electrode is appropriately sized and located in order to be positioned effectively for inducing a cognitive effect. As described in more detail in reference to FIGS. 126A-126F, below, this active region may include a layered structure of conductive metal, sacrificial conductive layer, and hydrogel to spread the current across the entire active region; in some variations one or more additional layers may be included, such as a less-conductive (than the conductive metal and sacrificial layer) layer, e.g., comprised of carbon, between the conductive metal and sacrificial layer, that may help spread out the current across the surface of the active region before it passes into the sacrificial layer and therefore allow higher current intensities to be delivered more uniformly across the electrode-dermal contact area and thus reduce discomfort in the user. The second skin-contacting electrode region 1292229 is similarly constructed and is electrically connected to the other electrode active region 1292205 by a conductive trace on or in the portion of the flexible substrate 1292307 extending between the two skin-contacting electrode regions.

Any electrode assembly described herein (including the electrode assembly shown in FIGS. 129A-129B) may be formed of a substrate such as a Kapton (e.g., a polyimide film) and/or vinyl (e.g., coated vinyl, polyvinyl chloride or related polymer) onto which the different regions are formed by layering or attaching. The active region may include a hydrogel (e.g., AG602 Hydrogel, having a resistance of approximately 350 Ohm-cm), and Ag coating (e.g., Ag ink), Ag/AgCl coating (e.g., Ag/AgCl ink), and (optionally) a carbon conductor (e.g., Exopack Z-flo carbon filled Vinyl having a resistance of approximately <90 Ohms/cm$^2$).

In another variation, an electrode assembly such as the one shown in FIGS. 129A-129B (or FIGS. 128A-128B) may include a substrate (e.g., Kapton or other polymeric material) and may include the active region with a hydrogel (e.g., AG602 Hydrogel, at 350 Ohm-cm), a silver/silver chloride sacrificial layer (e.g., ECM Ag/AgCl ink (85/15) with <0.2 Ohm/cm2), the optional carbon layer (e.g., DuPont Carbon 5000 ink, <50 Ohm/cm2), and silver layer (e.g., EMC Silver ink with <0.2 Ohm/cm2).

As mentioned above, the elongate body region of the electrode apparatus that connects the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc., between 2 and 12 inches, between 2 and 10 inches, between 3 and 9 inches, etc.). In the plane of the electrode apparatus, the elongate body region may travel in a bent or curved path, as illustrated in the variations of FIGS. 113A-115, FIGS. 116A-116D, FIGS. 119A-119D and FIGS. 120A-120D, helping to allow the material to flex or bend to be adjustably positioned over and/or around the subject's head, as shown in FIGS. 112A, 112B and 116i.

Although the variations described above for the electrode assembly illustrate a flexible structure, in which a substrate (e.g., flex circuit) material is thin and permitted to bend in at least one axis, in some variations the electrode assembly may be rigid. FIGS. 118A-118C and 118D-118F illustrate two variations of rigid, or semi-rigid assembly electrode apparatuses.

In FIGS. 118A-118C, the device is shown as a CAD rendering of an exemplar neurostimulator 118901 attached to an electrode assembly that may be bendable (ductile) or hinged to achieve a wearable form factor allowing contact with different regions of the head/neck. For example, an anode electrode (the electrically active region of the first electrode portion) may be positioned on the right temple area and electrically conductive when the posterior portion (e.g., the second electrode region) of the electrode assembly may be positioned so that a cathode electrode targeting the right mastoid behind the ear is positioned correctly (electrode active region not shown).

Similarly, the example shown in FIGS. 118D-118E illustrates a region having a rigid elongate body (including connector region of the elongate body), the elongate body extends further and may allow contact with the second active region on the back of the subject's neck. All or a portion of the body may be ductile so that it can be bent into a shape allowing it to conform to the neck. In some variations the elongate body may be hinged to allow it to bend/flex during use.

FIGS. 118G and 118H illustrate another variation of a flexible (at least in one axis of freedom) electrode apparatus which may also be formed of a flex circuit material. FIG. 118G shows a front view and FIG. 118H shows a back view of the substrate portion onto which the other elements (e.g. components of a neurostimulator) may be attached (e.g., the active regions, the connectors, adhesive, etc.). In this example, the device includes an elongate thin connector portion of the substrate body, similar to the variations shown in FIGS. 113A-115 and 116A-116D, above. Exemplary dimension (in length units of inches) are shown for illustrative purposes only, and may be varied.

FIG. 118*i* is another variation of an electrode assembly including connectors. In this example, the connectors are coupled to a different portion of the substrate in an upside-down configuration, connected by conductive traces (not shown), and folded back over so that they may be positioned over the first electrode region but without requiring the connector be riveted through the flexible substrate into the active region, similar to what is illustrated in FIGS. 113A-115, and 116A-116D above. Also, this may allow a better fit for larger electrodes while reducing the constraint of where a connector for the active region is located. As described herein, it may be advantageous to avoid coupling to a separate neurostimulator, or instead connecting to a cord, cable, or tether that integrates some or all of the TES neurostimulator circuitry, as shown in FIGS. 107A-110C, above. When connectors, such as snaps, buttons, etc., are used, they may be configured so that they engage with the separate device (e.g., neurostimulator, cord, etc.) on the top surface opposite from the skin, or in some variations on the bottom surface, facing the skin.

FIGS. 121A and 121B illustrate another variation of an electrode assembly that includes a winding connector region to adapt comfortably to different anatomies by extending without substantial force pulling adhesive-containing electrode areas off of the skin. A second electrode portion (region 1211505) is connected to the first electrode region by elongate body region 1211507. In FIG. 121A, the connecting trace extends down the elongate body region 1211507 on the top surface, and may be insulated. As with any of the layers forming the electrically active region, the trace (and/or insulator) may be printed, silk-screened, deposited, or otherwise applied to the substrate. In this example, the second connector 1211517 is not positioned over the first active region, which may prevent shorting of the first and second active regions; however in some variations the connectors may both be entirely or partially positioned over (on the opposite side of) the first active region.

As discussed above, any of the electrode apparatuses herein may be flexible multi-electrode assemblies that are typically flexible such that two separate but connected regions of the electrode assembly conform to two or more body regions of a user, such as a portion of the user's forehead and/or neck and/or an area surrounding an ear. Conforming the multi-electrode assembly to the body portion of the user may result in increased comfort during electrical stimulation, increased uniformity in impedance, and improved cognitive effects. In some embodiments, the use of a unified assembly with multiple electrodes (e.g., multiple electrically active regions) may eliminate the need for connectors and/or cables between electrically active regions on the electrode assembly. The substrate of the electrode assemblies described herein may be a flexible nonconductive substrate onto which the electrically active regions are formed or placed.

Any of the electrode apparatuses described herein, including the electrode apparatuses or multi-electrode assemblies, may be disposable, and single-use or multiple-use, allowing use for a plurality of times before being disposed. Alternatively, the electrode apparatuses may be durable and reusable for any length of time, for example only requiring replacement or refurbishing of certain components or elements of the device or system. An electrode apparatus as described herein is not limited to the neuromodulation systems and techniques described herein, but may be used in other fields and/or applications. For example, the electrode apparatuses described herein may be used in fuel cells, medical applications (e.g. EEG, ECG, ECT, defibrillation, etc. . . . ), electrophysiology, electroplating, arc welding, cathodic protection, grounding, electrochemistry, or any other electrode application. An electrode apparatus may be used to target non-neuronal tissues and may be placed on any portion of the body. For example a flexible electrode system as described herein may be used for muscle therapy for healing an injury.

FIGS. 124A-124C illustrate one variation of a flexible electrode apparatus that includes a flexible substrate, at least two conductive traces, an adhesive component, and at least two electrodes. The electrode apparatus is preferably used for noninvasive neuromodulation, but can additionally or alternatively be used for any suitable applications, clinical or otherwise.

In FIG. 124A, a flexible substrate 1241812 may include a first surface and a second surface, as shown in FIG. 124A (top view) and FIG. 124B (bottom view), respectively. The second (bottom) surface is opposite the first (top) surface. The flexible substrate may include two or more apertures each coated with an electrical conductor, such that the electrical conductor (e.g., carbon black, silver, etc.) delivers current between the first and second surfaces. As shown in FIG. 124C, the first surface may include one or more active regions 1241814, such that current from the second surface is delivered to the electrodes on the first surface.

In general, an active region of an electrode may be divided up into multiple zones or sub-regions that can be individually and/or collectively driven and/or sensed from so that the size of the active region of the electrode apparatus can be increased and/or decreased as needed. This modification may be controlled by the neurostimulator and/or the controller (e.g., a control unit, including a control application that is operating on a smartphone, etc.), which may determine which groups of active regions of an electrode (typically anode or cathode) is active at a particular time. In some variations, multiple regions (sub-regions) of the active region are tied together so that they may operate together. This is illustrated, for example, in FIGS. 124A-124C.

Each sub-region of the active region may be separately or collectively coupled to a trace that connects to the power supply and/or controller. For example, FIG. 124A shows a substrate having multiple (e.g., three) conductive traces printed on an upper surface (though any surface, e.g., the top or bottom surface, may be used). The conductive traces may be printed, silk-screened, etched, soldered, welded, or otherwise attached to the surface. In some embodiments, the conductive surface may include more than two traces (e.g. FIG. 124A, three traces are shown). For example, a first trace 1241810 on the back side of the portion of the apparatus shown is coupled though an opening in the substrate (which may be filled with a conductive material) to a first area of an electrode (1241814 in FIG. 124C); a second trace 1241811 is coupled to second and third electrode areas (1241822, 1241823 in FIG. 124C), where these regions are electrically shorted (connected) together; a third trace 1241813 is coupled to fourth electrode area (1241827 in FIG. 124C) or alternatively may be connected to a secondary electrode on either the same assembly or a second assembly. The traces may be connected to an electrical/mechanical connector for coupling to the neurostimulator. This connection may be direct, or they may be coupled to a chip, resistor, capacitor, or the like (including a capacitive element as discussed above). The sub-regions shown in this example may therefore be used to provide a single electrode apparatus that can have one or more (e.g., two) active regions that can have different dimensions, and therefore be used on different regions of the body. In practice this may allow a single electrode apparatus having at least one active region that is configured to have multiple sub-regions in which different combinations of sub-regions may be separately operated together to provide a particular shape and/or pattern for the active region. Thus, whereas separate electrode apparatuses configured for energy and relaxation are described above (e.g., FIGS. 122A and 122B, respectively), in some variations a single electrode apparatus may by dynamically configured or configurable to evoke either "energy" (using a large, relatively circular active region for placement behind the ear/on the mastoid region) or "calm" (using a more rectangular active region for placement behind the neck).

FIGS. 125A-125D show other variations of active region of an electrode apparatus in which the active region is formed of a plurality of sub-regions that may be operated together in different sub-combinations, so that they may be differentially stimulated or read from, and the size or shape of the effective active region on the surface, and thus the electrical stimulation area, may be adjusted to effect different neuromodulation outcomes. Selecting specific sub-regions of the active region from an array of active sub-regions on the surface can be used to focus stimulation to a preferred area, compensate for changes in impedance (e.g. if part of the array shifts away from the skin during use), avoid uncomfortable areas, compensate for changes in electro-chemistry to improve comfort (e.g. reduced AgCl in a particular electrode vs. another) or other uses. As shown in FIGS. 125A-125D, a conductive trace on the opposite (top) surface from the active region (see, e.g., FIG. 125D) may extend to a distinct active sub-region on the bottom surface, as shown in FIG. 125B. In this example, FIG. 125D is the top surface and FIG. 125B is the bottom surface of the same electrode region. Each conductive trace may control the electrical stimulation delivered by the sub-region or sub-area to which it is coupled. For example, activating electrode areas 1251901 and 1251902 may induce a first cognitive effect in a user, while activating electrode areas 1251901, 1251902, and 1251903 may induce an alternative or modified cognitive effect in a user. Any combination of electrode areas may be used to achieve the desired neuromodulation outcome. FIG. 125B illustrates how three conductive traces may be positioned to control three electrode areas. For example, trace 1251901 (FIG. 125D) controls areas d and e, trace 1251903 controls areas a and c, and trace 1251902 controls area b. In some embodiments, any number of electrode areas may be positioned on each electrode. Further, the electrode active sub-regions may be clustered in an area of the flexible assembly or distributed over a region of the flexible assembly. Electrical current from a controller or current delivery device (neurostimulator) may be delivered to the traces through one or more connectors or pins, for example pogo pins or conductive snaps, extending from the controller to the second surface or from the second surface to the controller, such that the pogo pins/snaps are electrically connected with the traces. Further, electrical current from the conductive traces on the top surface may be delivered to the electrode sub-regions on the bottom surface through one or more conductive apertures 1251927 or through holes in the nonconductive flexible substrate, as shown in the side sectional view of FIG. 125C. FIG. 125A shows another variation of a bottom portion having an active region for the electrode that includes a plurality of different sub-regions that may be differently operated together to provide different effective active regions (e.g., an active region formed of sub-regions 1251902 and 1251901 to provide a first oval configuration, an active region formed of sub-regions 1251903 and 1251901 to provide a second oval configuration, an active region formed of 1251904, 1251903, 1251902 and 1251901 to provide a large circular region).

In some variations, a second electrode having an active region formed of multiple sub-regions that may be operated in sub-combinations may be present on the electrode apparatus, e.g., in a spaced relationship from the first electrode. For example, the two electrodes may be spaced apart by about 1 inch, 2 inches, 3 inches, 4 inches, 5 inches, etc. The spacing may be along the connecting region of the substrate, as discussed above (e.g., following the shortest continuous path along the substrate). The electrodes may be spaced apart by any suitable distance so that they may target the two regions on the user's head.

As used herein the path length of the flexible elongate member separating the first and second electrode portions may refer to the length of the connector if it were made straight; this may also be referred to as the distance of travel between the first and second electrode portions. This distance is typically sufficient to allow the first electrode portion to be placed at a first location on the user's head (e.g., the front of the user's head), then adjust (e.g., bend, flex, etc.) the connecting region so that the second connecting region can be placed at a second region on the side of the head, back of the head or neck region. The connecting region extends between the two, so that the path length is the path taken by an electrical trace or wire extending from one of the proud connectors linking the first electrode portion to the electrical stimulator to the second electrode portion.

Within the same overall active region (e.g., 1241800 in FIG. 124C, 1251900 in FIG. 125A, 1251900' in FIG. 125B) the individual sub-regions may be arranged such that current resists traveling through the hydrogel to "inactive" electrode areas, which are not part of an active sub-region being used. Thus, in some variations the adjacent regions may be spaced apart from each other (e.g., so that there is at least 1 mm, 2 mm, etc. between the hydrogel of different regions). In some variations the unused sub-regions may be set to "float" (electrically unconnected to ground or to an active region). In general at least one sub-region is coupled to the first surface and electrically coupled to the second surface through two or more conductive apertures, as described above. Flexible electrode assemblies containing two or more spatially distinct electrodes are advantageous by permitting stimulation between the two electrodes when they are adhered to the skin.

In any of the electrode apparatuses described herein, the first conductive layer (e.g., a Ag layer) connects to the neuromodulation components. This first conductive layer is separated from the sacrificial layer (e.g., Ag/AgCl layer) that connects to the gel (e.g., hydrogel) by the intermediate, less conductive layer. This less conductive layer may also be referred to as a weakly conductive layer, a weakly insulating layer, or a more resistive layer (all in reference to the adjacent first conductive layer and sacrificial layer). In general, this weakly conductive layer has an electrical conductance that is lower than either the adjacent first conductive layer or the sacrificial layer, although the electrical properties of the sacrificial layer may change with use. Thus, in general the weakly conductive layer may be more resistive than the first conductive layer; for example, the weakly conductive layer may have a resistivity that is greater than 3×, 4×, 5×, 6×, 7×, 8×, 9×, 10×, 15×, 20×, etc., the resistivity of the first conductive layer. In some variations, the resistance of the weakly conductive layer is greater than 5× the resistance of the first conductive layer that it covers. In general, each successive layer distal from the flexible substrate (i.e. a polymeric material appropriate for use in a flexible circuit) extends beyond the edge of the more proximal layer along its entire circumference to ensure that current cannot short between non-successive layers.

The weakly conductive layer may be formed of any appropriate material having the electrical properties described herein. For example, the weakly conductive layer may include carbon. For example, the weakly conductive material may be a polymeric material (including rubbers, polyvinyl chlorides, etc.) that is mixed with or incorporates carbon (e.g., carbon particles), etc.

The optional less conductive layer 1262044 described above may be helpful to spread the current as it moves from the highly conductive metal layer such as the Ag layer 1262005 shown in FIGS. 126A-126F to the sacrificial layer (e.g., Ag/AgCl layer 1262007) and into the hydrogel. In effect, this carbon layer (or similar less-conductive layer) may make the electrodes much more comfortable for the user to wear them, even when delivering relatively high intensity current signals, by improving the uniformity of current density and electrochemistry occurring in the consumptive layer and/or hydrogel.

In some embodiments, the electrode apparatus (flexible electrode assembly) may include an adhesive component. The adhesive component may be configured to couple the electrode apparatus to a body portion of a user or any other device or system. An adhesive component may surround and/or be adjacent to the boundary of the consumptive layer. In some embodiments, the adhesive component and the three layers (consumptive, nonconsumptive, and hydrogel) of the electrode active region may be substantially the same thickness, such that substantially all areas of the flexible assembly may be flush with the skin of a user. In some embodiments, the hydrogel layer may extend slightly beyond the adhesive layer so that the hydrogel makes a more uniform contact through slight compression when the electrode is adhered to the skin.

Alternatively, a flexible multi-electrode assembly may be pressed against or held to a body portion of a user. In some embodiments, the flexible transdermal multi-electrode assembly may be pressed against a body portion of the user using a headband, helmet, head scarf, or any other type of wearable device.

As described above, a single flexible transdermal assembly may include two or more electrodes (active regions) for electrical stimulation, such that only one assembly is required for electrical stimulation. For example, a user may stimulate a forehead region with a first electrode region (active region) on the flexible transdermal assembly and the back of the neck with a second electrode region (active region) on the same assembly to achieve the desired neuromodulation effect. Alternatively, the system may utilize two separate or separable assemblies, such that each assembly includes one electrode for electrical stimulation. In some embodiments, the two assemblies may be electrically coupled by a coupling element. For example, a user may position one assembly on the forehead and the second assembly on the back of the neck to achieve the desired neuromodulation outcome. Alternatively, any number of electrodes in each assembly may be used to achieve the desired neuromodulation effect. In some embodiments, any number of electrode areas on the same or different assemblies may be coupled by one or more traces. For example, one trace may couple an electrode area on the forehead to an electrode area on the back of the neck. Alternatively, one or more electrode areas on the same or different assemblies may be independently and directly controlled by the controller, for example through pogo pins as described above.

One improvement over other designs of the neuromodulation device is the miniaturization and integration of these components (i.e. chip, firmware, software) into the main body of the neuromodulation device containing the electrode assembly as can be seen in FIG. 117A. As can be seen in FIG. 117A, the neuromodulation device body contains an electrode assembly 117701, and neuromodulation components 117704. The neuromodulation components 117704 further contain power supply 117705, memory 117708, processor 117709, user interface 117710, current control circuitry 117706, and safety components 117707. A skilled artisan will appreciate that FIG. 117A is one representation of how the neuromodulation device components can be laid out and there are numerous other ways for both the electrodes 117701 and neuromodulation components 117704 to be integrated.

In order to fit all the necessary neuromodulation components into the body of the electrode assembly, some or all of the neuromodulation components can be contained in the proximal end electrode body or some or all of the relevant neuromodulation components can be contained in the distal end electrode body, or some or all of the relevant neuromodulation components can be contained within the stem portion of the neuromodulation device body. In other variations, the neuromodulation components can be spread throughout the proximal end electrode, the distal end electrode, and the stem portion of the neuromodulation device. In other variations, the electrode apparatus has one contiguous area without a connector region and components may be distributed across the cross section for usability, comfort, and fit.

Another benefit to an integrated electrode and neuromodulation device is that it consumes less power than other configurations of the neuromodulation device when producing the desired waveform sessions (e.g., by eliminating wireless communication components). In one example, the neuromodulation components can be surface mounted components (SMC) and incorporated into the electrode assembly design. Benefits of using SMC is that they are small in size. For example, some SMC components can be approximately 0.25×0.125 mm. Also, components can be placed on either side of the flexible circuit board (ideally restricting components on the first, subject-facing side to the non-adhering (i.e. connector) portion of the flex circuit) for comfort and/or safety. Thus, due to their smaller size and ability to be fitted on either side of the circuit board, a larger number of components can be accommodated within a particular space. Furthermore, SMC components have lower resistance and inductance at the connections compared to traditional electrical components, and as a result, SMC components are able to provide cleaner and more predictable TES waveform frequencies.

In another example, it would be conceivable to design the neuromodulation components in a custom application specific integrated circuit (ASIC) for delivering TES waveform sessions. Because an ASIC would be constructed for a specific task and not a variety of different actions, an ASIC-based neurostimulator circuit may require less energy and may be physically smaller and/or more compact. Requiring less energy to power the neuromodulation components means that smaller batteries and smaller inducers can be used in the device or that the neuromodulation device has a longer overall life. Moreover, with sufficient reductions in power storage capacity, some or all safety circuits may not be necessary to protect the user.

As mentioned earlier, the integration of the electrode elements and the neuromodulation elements of the neuromodulation device could eliminate the need for external software and firmware, and also the need for wireless capabilities. In that case, additional components may be needed to be placed on the neuromodulation device strip. This might include a power on/off switch, a means for selecting the waveform session desired, and/or a means for increasing or decreasing the intensity of stimulation (or another parameter of the stimulation waveform).

In a second embodiment of the present neuromodulation device as shown in FIG. 117B, a physical tether, such as a wire or cord, can be established between the neuromodulation device and a communication device (such as a smartphone, smartwatch, virtual reality headset, or a tablet). The tether 117820 can contain some of the neuromodulation components 117821 as well as firmware/software 117822 for controlling the neuromodulation device body 117800, and a power amplifier 117823 (as part of current control circuitry) for boosting the power available to the neuromodulation device. In this embodiment, the neuromodulation device can also draw power from the communication device for outputting any particular waveform session. This can prove useful, because the primary power drain on the neuromodulation device will be the delivery of the stimuli from the first and second electrode to the subject's skin. Having a secondary source of power to draw from can decrease the size of the power supply used within the actual neuromodulation device. In one example of this second embodiment, the cord or wire used to connect the neuromodulation device to the control device can be a standard wire or cord. In a second example of the second embodiment, some components related to the neuromodulation aspect of the device (such as creating the waveforms, outputting the waveforms) can be placed external to the main neuromodulation device and retained within or hardwired to the cord or wire in a housing.

In this second embodiment, the tether connecting the neuromodulation device to the communication device can be disconnected from both the neuromodulation device and the communication device. In order for the neuromodulation components that are external to the main neuromodulation device to communicate and work in concert with the internal neuromodulation components, the neuromodulation device, in this instance, will also include at least one connector port with which the wire or cord may connect to the neuromodulation device with as can be seen in FIG. 130. FIG. 130 shows a connector 1302415 configuration on the electrode region of the neuromodulation body with two snaps, to which the tether can couple with. The tether can contain two separate connectors or two active regions of electrical contact within one integrated connector. Alternatively, the at least one connector for contacting the tether can be located on the electrode assembly that contacts the mastoid region as shown in FIG. 131.

There needs to be appropriate connections between the tether and the internal neuromodulation device components. FIGS. 126A-126F and 127 show how a snap connector can be integrated into the body of the neuromodulation device. In FIG. 126A, an electrode trace 1262011 extends on a top surface of a substrate 1262003 (such as a polymeric material appropriate for use in a flexible circuit, e.g., Kapton). This trace 1262011 may be insulated (e.g., by an insulating covering) 1262015. An opening through the flex circuit (e.g., hole 1262019) may include a conductive material (e.g., carbon black, silver, etc.) resulting in electrical communication between the trace 1262011 and a portion of the electrically active region 1262024, that (in this example) includes a layer of conductive metal (e.g., Ag) 1262005, a layer of sacrificial conductor (e.g., Ag/AgCl) 1262007 that completely covers the Ag layer and an outer, skin-contacting layer of hydrogel 1262009 that is in electrical contact with the Ag/AgCl layer, and may also completely cover it (or cover it in conjunction with an insulator). The sacrificial Ag/AgCl layer 1262007 in this example may also extend beyond the border of the conductive (i.e. Ag) layer 1262005 to avoid shorts between the conductive (i.e. Ag) layer and the skin-contacting layer of hydrogel 1262009 (i.e. extends beyond it around its entire circumference, including any internal exclusions or holes in the layer, for instance to permit a snap conductor to be placed).

In some variations, and in particular variations such as those shown in FIGS. 110A-110B, the flexible electrode strip may be configured so that the connectors (e.g., snaps, etc.) to couple to a cable or TES controller device are on the same surface as the electrodes, rather than being on the opposite (e.g., back or second) surface. Thus, all of the connectors and electrical contacts are on the same surface (the dermal facing, front or first surface). Thus connectors to connect to a tether, neurostimulator cable, etc. may be on the first surface of the electrode strip between the distal and proximal end, such as on the first end. This may simplify the manufacturing by having all the electrical traces on one side of the strip.

FIG. 126B shows a partial section through a portion of an active region that is electrically connected to an electrical and/or mechanical connector via an indirect connection pathway and thereby connects to an electrical stimulator (e.g., such as a neurostimulator). This configuration is similar to that seen in the second active region 113135 in FIG. 113D or 116435 in FIG. 116C. In some variations the electrode includes an active region that is directly connected to the connector, such as the first active region 113133 in FIG. 113D or the first active region 116433 in FIG. 116C. An example of this arrangement is shown in FIG. 126B and in detail in FIG. 126C.

In FIG. 126B the active region of the electrode includes a contact (shown as a snap or pin) for connection to the electrical stimulator (e.g., neurostimulator). In this example, the connector 1262020 penetrates the substrate 1262003 and a layer of conductive material (shown as a conductive metal, e.g., Ag) 1262005 and makes electrical contact with this Ag layer. The bottom of the post or connector 1262020 is electrically insulated (visible in FIG. 126C as the insulating layer 1262015). A sacrificial layer of Ag/AgCl covers the Ag layer (and the insulated base of the post 1262020), and a skin contacting layer of conductive hydrogel 1262009 contacts the Ag/AgCl layer. FIG. 126C shows a slightly enlarged view of FIG. 126B, and schematically illustrates the current flowing from the electrical/mechanical connector 1262020 into the hydrogel 1262009 through the sacrificial Ag/AgCl layer 1262007 and the Ag conductive layer 1262005. In this example, the connection is configured so that the current does not flow directly into the Ag/AgCl 1262007 or hydrogel 1262009, but first passes from an upper surface of the connector that is in electrical contact with the Ag layer 1262005 and then down into the Ag/AgCl layer 1262007 and the hydrogel to contact the user. Thus, in this example, the portion of the connector base in contact with the silver/silver chloride layer is insulated 1262015 so that the current primarily passes through the silver layer 1262005.

In general, an electrically active region of an electrode apparatus may include a nonconsumptive conducting layer (e.g., 1262005 in FIGS. 126A-126C), a consumptive conducting layer (e.g., 1262007 in FIGS. 126A-126C), and a conductive hydrogel layer (e.g., 1262009 in FIGS. 126A-126C). In some embodiments, the consumptive layer may be a buffer layer disposed between the nonconsumptive layer and the hydrogel layer. Further, the consumptive layer may extend beyond the boundary of the nonconsumptive layer at each edge of the nonconsumptive layer and may be configured to reduce hydrolysis in the hydrogel layer, such that the consumptive layer donates electrons for redox reactions. Examples of the conductive nonconsumptive layers may include silver, gold, copper, or any other type of conductive metal or non-metallic material, such as carbon or conductive polymers (e.g. poly(3,4-ethylenedioxythiophene). Preferably, the nonconsumptive and consumptive layers include silver. An important feature of the nonconsumptive layer is that any electrochemical reactions occurring in that layer do not cause the quality of the layer as an electrical conductor (i.e. impedance) to change during a transdermal (e.g., transcranial) stimulation. This feature ensures that current delivered to the layer is, for the most part, distributed evenly over its surface first before entering the consumptive layer. In some variations, an additional, higher impedance, layer is disposed between the nonconsumptive layer and the consumptive layer to more evenly spread current across the nonconsumptive layer before entering the higher impedance layer and, subsequently, the consumptive layer. In some embodiments, the nonconsumptive layer experiences reduced consumption, such that the nonconsumptive layer includes silver. Alternatively, the nonconsumptive layer may experience essentially zero consumption, such that the nonconsumptive layer includes carbon. In some embodiments, the nonconsumptive layer experiences reduced consumption since it does not include an anion that can be electrically consumed during electrical stimulation. The nonconsumptive layer may disperse the electrical current over its surface area before the current reaches the consumptive layer (i.e. there is lower impedance within the nonconsumptive layer than between the nonconsumptive layer and the consumptive layer). If the electrical current is not dispersed over the surface area of the nonconsumptive layer before reaching the consumptive layer, the consumptive layer may be over-consumed, such that AgCl becomes Ag(0) in a local area of the consumptive layer surface, causing uneven current distribution and the potential for local hydrolysis and local pH changes that may lead to discomfort in the subject. In embodiments, the consumptive layer is composed of a ratio of silver to silver chloride (Ag:AgCl) for efficient consumption and electrochemistry. Optimal ratios can be selected based on the charge balance of stimulation. In some embodiments, the ratio of Ag to AgCl particles in the consumptive layer may be between 40%:60% to 95%:5%, preferably 65%:35% to 85%:15%. Alternatively, the consumptive layer may include any suitable ratio of Ag:AgCl such that the chloride may be consumed but not depleted during an electrical stimulation session of sufficient length to induce a beneficial cognitive effect in a subject. The AgCl in the consumptive layer is consumed during alternating current or direct current stimulation (DC) because it acts as a sacrificial anode/cathode and is converted to Ag and a Cl− ion. The Ag+ in the consumptive layer is consumed during alternating current or direct current stimulation (DC) because it acts as a sacrificial anode/cathode and is converted to AgCl. In some embodiments, if the consumptive layer does not fully cover the dermal side of the nonconsumptive layer, the current may travel directly to the hydrogel layer and cause a site of high current density, for example a current hotspot. In some embodiments, the conductive hydrogel layer, as shown in FIG. 116i, ensures that the current is transmitted substantially evenly to the skin of a user. Further, the hydrogel layer creates a uniform connection between the multi-electrode assembly and the skin of a user.

In any of the electrode apparatuses described herein, an additional layer may be positioned between the conductive layer in electrical contact with the connector (e.g., snap connector) and the sacrificial anode/cathode layer in contact with the hydrogel. The additional layer may be a material that is less conductive than the adjacent conductive metal (e.g., Ag) layer and sacrificial (e.g., Ag/AgCl) layer, or even a weakly insulating material. In this example, the material is carbon, although other materials may be used. In general this layer may be less conductive than the layers immediately above (e.g., Ag) and below (e.g., Ag/AgCl). For example, FIGS. 126D-126F illustrate another variation of section through an active region of an electrode apparatus, showing different regions that may be used to form the active region and including an additional carbon layer. In FIG. 126D, the electrode trace 1262011 extends on a top surface of a substrate 1262003 (such as a polymeric material appropriate for use in a flexible circuit). This trace 1262011 may be insulated (e.g., by an insulating layer 1262015). An opening through the flex circuit (e.g., hole 1262019) may include a conductive material (e.g., carbon black, silver, etc.) making an electrical communication between the trace 1262011 and a portion of the electrically active region 1262024, that includes a layer of conductive metal (e.g., Ag) 1262005, a layer (e.g., carbon) having a lower conductance than the adjacent layers 1262044, a covering layer of sacrificial Ag/AgCl 1262007 that completely covers the Ag layer and it itself covered by the carbon layer 1262044, and an outer, skin contacting layer of hydrogel 1262009 in electrical contact with the Ag/AgCl layer.

The at least one connector port on the neuromodulation device can be either positioned on the proximal end electrode region, which corresponds to the temple area of the user or the distal end electrode region, which corresponds to the neck region of the user. The at least one connector port can make a "snap-on" type connection with the cord or wire. The snap-on connection here can be similar to the snap connectors in other designs where the neuromodulation unit "snapped on" and made connection with the proximal end electrode region. A person skilled in the art will also appreciate that other types of connectors can be used. The connection made between the neuromodulation device port and the cord or wire can electrically connect neuromodulation components outside of the neuromodulation device body to those neuromodulation components within the neuromodulation device, or also connect to the electrode elements contained within the neuromodulation device, or a combination thereof. Thus, to make the connection between the port and a viable region on the neuromodulation device, the connector or connectors need to be in electrical communication with the appropriate internal circuitry of the neuromodulation device.

For the neuromodulation assembly as a whole, a master control can be used to control the integrated neuromodulation components to communicate to the electrode assembly to deliver the desired waveform output and not dependent on the location of the various neuromodulation components relative to each other. The master control can include circuitry for controlling the current delivery, a battery, and other electronic circuitry for communicating with the electrode assembly and other electronic components present. In addition, because the neuromodulation device can function without the need for external controls, the neuromodulation components can be analog for outputting the waveform sessions. The use of purely analog signals simplifies the neuromodulation systems requirement compared to when digital signal are used.

In addition to the electrode assembly and the components controlling the neuromodulation, the incorporation of the neuromodulation components into the body of the device may necessitate some additional controls to allow the user to manipulate which waveform sessions to play. Additional controls can include a means for selecting the waveform sessions and a display for showing the user that the desired waveform session has been selected. Also, there may be an on/off switch for powering on and off the neuromodulation device. Examples for user interfaces include mechanical controls (i.e. toggles, switches, or knobs), touchscreen interfaces, and accelerometer-based controls (e.g. tap the device to cause a discrete movement event detected by a processor connected to an accelerometer). For example, any of the apparatuses described herein may include a touch-sensitive interface for controlling one or more aspects of the TES, such as the intensity, e.g., "swipe" up for higher intensity, "swipe" down for lower intensity, etc. Any of the apparatuses described herein may include an accelerometer to receive user input, such as taps or shakes, e.g., tap once to play/pause, tap twice to choose a different wave form, tap top of module for higher intensity, tap bottom of module for lower intensity, etc.

In use, any of the electrode apparatuses described herein may be connected to the user for neuromodulation. The neurostimulator may then electrically stimulate through the at least two electrodes, such that the neurostimulator delivers stimulation waveforms (or an ensemble of waveforms as discussed above) to the at least two electrodes for transdermal electrical stimulation and modification of the user's cognitive state. The method preferably functions to stimulate neural pathways, the brain, and/or nerves of a user using electrical stimulation delivered by a flexible electrode apparatus and neurostimulator.

Thus, neuromodulation using a multi-electrode assembly may include adhering a multi-electrode assembly to a body portion of a user to position a multi-electrode assembly on a body portion of a user such that the user may begin a transdermal or transcranial electrical stimulation protocol. In some embodiments, the system includes a single assembly containing two or more electrodes sized, configured, stimulated and positioned, as described herein, for achieving the desired neuromodulation effect. In some embodiments, the two or more electrodes within one assembly may include two or more electrode areas, such that the two or more electrode areas may be differentially stimulated to achieve different neuromodulation outcomes with one assembly, as described above. Alternatively, in some embodiments, the system comprises two or more assemblies, each containing at least one electrode for achieving the desired neuromodulation effect. The user may position the adhesive component on the first surface of the multi-electrode assembly, and press, stick, or otherwise secure the adhesive component to a body portion. In some embodiments, a user may remove a protective layer from the adhesive component before securing the adhesive component to a body portion of the user.

In some embodiments, the multi-electrode assembly may include sensors or other detectors that may detect a location or position of the multi-electrode assembly on the user. The multi-electrode assembly may begin delivering stimulation waveforms as soon as it is positioned in the correct location or position. Alternatively, the multi-electrode assembly may prevent a user from positioning the multi-electrode assembly in an inappropriate or incorrect location, such that the multi-electrode assembly may not deliver stimulation waveforms until it is repositioned or relocated.

Neuromodulation using a multi-electrode assembly may include coupling a controller to the at least two electrodes of the multi-electrode assembly through one or more connectors. The neurostimulator may be coupled to the multi-electrode assembly through a coupling element that couples the neurostimulator to the connectors on the electrode apparatus, as described above. Alternatively, the neurostimulator may be embedded in the flexible substrate (i.e. circuit components such as resistors, capacitors, current sources, microcontroller, switches, etc.) and electrically coupled to the electrodes in the electrode apparatus, such that all components are self-contained in the flexible substrate.

Neuromodulation using an electrode assembly may include electrically stimulating the at least two electrodes with the neurostimulator, such that the neurostimulator delivers stimulation waveforms to the at least two electrodes for transdermal/transcranial electrical stimulation. This may deliver stimulation waveforms to the electrode apparatus from the neurostimulator. Stimulation waveforms may include one or more waveforms selected from the group including: constant direct current; pulsed direct current stimulation (also referred to as pulsed monophasic alternating current stimulation); pulsed direct current stimulation with a constant direct current offset; alternating current stimulation (also referred to as biphasic alternating current stimulation); pulsed biphasic stimulation; or combined direct current stimulation and alternating current stimulation (also referred to as biased alternating current stimulation).

In some variations, any waveform described above can be combined in series or in parallel (i.e. concurrently) to create a hybrid waveform, or ensemble waveform. In embodiments, any waveform described above can be added, subtracted, convolved, or otherwise amplitude modulated. Moreover, in embodiments, any waveform above can have its amplitude ramped using linear, exponential, or another ramp shape including by one or more controllers that the user may manually adjust during stimulation.

The stimulation waveforms may include constant direct current stimulation above 3 mA maximum intensity. Alternatively, a constant direct current stimulation may be of any suitable maximum intensity such that a cognitive effect is induced. The stimulation waveforms may include a pulsed direct current stimulation above 5 mA (e.g., above 7 mA, etc.). Alternatively, a pulsed biphasic stimulation may be of any suitable magnitude such that a cognitive effect is induced. The stimulation waveforms may include an alternating current stimulation above 2 mA maximum intensity. Alternatively, an alternating current stimulation may be of any suitable maximum intensity such that a cognitive effect is induced. The stimulation waveforms may include a biased alternating current stimulation with a direct current offset less than 1.5 mA and maximum alternating current amplitude above 3 mA. Alternatively, the direct current offset and the maximum alternating current amplitude may be of any suitable magnitude such that a cognitive effect is induced. The values of the direct current offset and the maximum alternating current amplitude for the biased alternating current stimulation may be in any combination to achieve the desired stimulation waveform.

In some embodiments, using alternating current stimulation or pulsed direct current stimulation, pulses can comprise square waves, sine waves, saw tooth waves, triangular waves, rectified (unimodal) waves, pulse-width modulated, amplitude-modulated, frequency-modulated, or other pattern of alternating current waveform. For preferred embodiments using alternating current stimulation or pulsed biphasic or unimodal stimulation, a primary frequency of stimulation is between 0.5 Hz and 1 MHz; optionally between 650 Hz and 50 kHz; optionally between 650 Hz and 20 kHz; and optionally between 750 Hz and 20 kHz. Alternatively, the primary frequency stimulation may be in any suitable range such that a cognitive effect is induced.

In some embodiments, for pulsed biphasic stimulation and alternating current stimulation, the maximum intensity delivered to a subject transcranially is generally greater than 3.0 mA; optionally greater than 3.5 mA; optionally greater than 4 mA; optionally greater than 5 mA; optionally greater than 7.5 mA; optionally greater than 10 mA; optionally greater than 15 mA; and optionally greater than 20 mA. Alternatively, the maximum intensity may be of any suitable maximum intensity such that a cognitive effect is induced. In preferred embodiments using pulsed direct current stimulation and/or alternating current stimulation, efficacious peak current intensities are generally between about 3 mA and about 25 mA.

In some embodiments, for constant direct current stimulation, the maximum intensity delivered to a subject transcranially is greater than 3.0 mA; optionally greater than 3.5 mA; optionally greater than 4 mA; optionally greater than 5 mA; optionally greater than 7.5 mA; and optionally greater than 10 mA. Alternatively, the maximum intensity may be of any suitable maximum intensity such that a cognitive effect is induced.

In use, a user may interact with a controller (e.g., a smartphone controlled by application software/firmware) that pairs with the neurostimulator (e.g. by Bluetooth). The user may operate the controller to select the operational mode, e.g., the type of cognitive effect to be induced, such as an energy mode or calm mode, and/or the device could automatically detect based on the configuration of an electrode to which the apparatus is attached. The user may select, for example, from a set of ensemble waveforms which ensemble waveform to execute. There may be separate waveforms to evoke a desired experience/effect (e.g., "calm" or "energy" ensemble waveforms). An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, i.e. current amplitude, frequency, duty cycle, charge imbalance, shorting/capacitive discharge, etc., and these parameters may change at prespecified times as they change to new segments; a transition period may be included to switch between block properties. Once the user selects an ensemble waveform, they can start the neurostimulation and the user can control or change the perceived intensity (e.g., by dialing the perceived intensity up or down), pause, or stop the session using the phone (app). In general, the perceived intensity can be scaled by the user between 0-100% of a target perceived intensity (e.g., a target current, frequency, duty cycle, charge imbalance, and/or shorting/capacitive discharge), using a control such as one or more buttons, sliders, dials, toggles, etc., that may be present on the controller (e.g., smartphone) in communication with the neurostimulator. The controller may also allow a user to activate ("on demand") a waveform configuration that is designed to evoke a predetermined response. For example, the control device could be adapted to display one or more icons to trigger phosphenes or an intensification of the perceived cognitive effect of skin sensation intensity. In addition, the controller may be configured to allow the user to press an icon to help in applying the electrode apparatus and/or neurostimulator. For example, activating this control may cause the smartphone to activate a front-facing camera on the phone to help the user to attach the apparatus to the head. During or after a session, a user can access help screens, a profile page, social sharing interfaces (i.e. tweet your experience), feedback about a session, and analysis and history of previous use. In general, the system may also be configured to pass data to and from the controller and/or the neurostimulator and to/from a remote server via the Internet. These data may include user information, waveform data, information about the function or state of the hardware device or electrode assembly, etc.

In addition, the integrated neurostimulator and electrode apparatus may fit under the temple portion of an eyeglass frame for users wearing glasses; thus the portion of the combined assembly should ideally be thin enough to fit between glasses and the temple region. However, it may also be beneficial to have some portions of the system be sufficiently thick to allow the apparatus to contain a sufficient battery (or other power portion) so that the unit can be used for a reasonable amount of time between charges (e.g. at least 20 minutes of electrical stimulation, at least 30 minutes of electrical stimulation, at least 40 minutes of electrical stimulation, at least 50 minutes of electrical stimulation, at least 60 minutes of electrical stimulation, at least 120 minutes of electrical stimulation, etc.). Thus one portion of the apparatus may be thick enough to allow a standard battery and/or circuitry at one end region (e.g., an end that is worn higher up on the face).

In general, a user may wear a neuromodulation device and apply one or more waveforms (e.g., waveform ensembles) using the neuromodulation device to induce a cognitive effect. The apparatuses described herein may be configured to provide one or more cognitive effects. In general, a cognitive effect may include any induced cognitive effect that is perceived subjectively by the recipient as a sensory perception, movement, concept, instruction, other symbolic communication, or modifies the recipient's cognitive, emotional, physiological, attentional, or other cognitive state. For example, an effect of electrical stimulation is one or more of inhibition, excitation, or modulation of neuronal activity. Specific examples of cognitive effects may include relaxation, enhanced attention, mood elevation, increased energy (e.g., physiological arousal, increased subjective feelings of energy), or the like. Cognitive effects may be stereotypical across a population (though with individual variation and degree) and may be demonstrated by any appropriate means, including by subject reporting, objective testing, imaging, physiological recording, etc. Particular cognitive effects evoked may depend upon the position of the electrodes of the apparatus with respect to the subject, and/or the stimulation parameters described herein. The apparatuses described herein may be optimized to achieve a specific cognitive effect.

A cognitive effect of neuromodulation may cause a change in a user's level of energy, fatigue, sleepiness, alertness, wakefulness, anxiety, stress, sensory experience, motor performance, formation of ideas and thoughts, sexual arousal, creativity, relaxation, empathy, and/or connectedness that is detectable by an objective measurement (e.g. behavioral assay) and/or subjective report by the user.

For example, a cognitive effect of neuromodulation may cause a change in an emotional state of the user where the change is detectable by an objective measurement (e.g. behavioral assay) and/or subjective report by the user and an emotion affected is selected from the list including but not limited to: affection, anger, angst, anguish, annoyance, anxiety, apathy, arousal, awe, boredom, confidence, contempt, contentment, courage, curiosity, depression, desire, despair, disappointment, disgust, distrust, dread, ecstasy, embarrassment, envy, euphoria, excitement, fear, frustration, gratitude, grief, guilt, happiness, hatred, hope, horror, hostility, hurt, hysteria, indifference, interest, jealousy, joy, loathing, loneliness, love, lust, outrage, panic, passion, pity, pleasure, pride, rage, regret, relief, remorse, sadness, satisfaction, self-confidence, shame, shock, shyness, sorrow, suffering, surprise, terror, trust, wonder, worry, zeal, and zest.

In some variations, the cognitive effects evoked by the apparatuses described herein may be positive cognitive effects; positive cognitive effects may refer to cognitive effects resulting in an increase in alertness, an increase in relaxation, a decrease in fatigue, and a decrease in anxiety, an enhancement in motor performance, an increase in recall, and an increase in empathy.

A cognitive effect of neuromodulation may cause a change in brain activity measured by one or a plurality of: electroencephalography (EEG), magnetoencephalography (MEG), functional magnetic resonance imaging (fMRI), functional near-infrared spectroscopy (fNIRS), positron emission tomography (PET), single-photon emission computed tomography (SPECT), computed tomography (CT), functional tissue pulsatility imaging (fTPI), xenon 133 imaging, or other techniques for measuring brain activity known to one skilled in the art.

A cognitive effect of neuromodulation may be detectable by a physiological measurement of a subject, including but not limited to measurements of the following: brain activity, body temperature, electromyogram (EMG), galvanic skin conductance (GSC), heart rate, blood pressure, respiration rate, pulse oximetry, pupil dilation, eye movement, gaze direction, measurement of circulating hormone (e.g. cortisol or testosterone), protein (e.g. amylase), or gene transcript (i.e., mRNA); functional infrared thermography (e.g. of facial temperature); and other physiological measurement. A cognitive effect of neuromodulation may be detectable by a cognitive assessment that takes the form of one or more of: a test of motor control, a test of cognitive state, a test of cognitive ability, a sensory processing task, an event related potential assessment, a reaction time task, a motor coordination task, a language assessment, a test of attention, a test of emotional state, a behavioral assessment, an assessment of emotional state, an assessment of obsessive compulsive behavior, a test of social behavior, an assessment of risk-taking behavior, an assessment of addictive behavior, a standardized cognitive task, an assessment of "cognitive flexibility" such as the Stroop task, a working memory task (such as the n-back task), tests that measure learning rate, or a customized cognitive task.

In general, subjects treated with TES with appropriate electrode configurations (positions) and TES waveforms (waveform ensembles) may experience neuromodulation with cognitive effects including, but not limited to: enhanced focus and attention; enhanced alertness; increased focus and/or attention; enhanced wakefulness; increased subjective feeling of energy; increased objective (i.e. physiological) energy levels; higher levels of motivation (e.g. to work, exercise, complete chores, etc.); increased energy (e.g., physiological arousal, increased subjective feelings of energy); and a physical sensation of warmth in the chest.

In general, subjects treated with TES with appropriate electrode configurations (positions) and TES waveforms experience neuromodulation with cognitive effects including, but not limited to: a state of calm, including states of calm that can be rapidly induced (i.e. within about 5 minutes of starting a TES session); a care-free state of mind; a mental state free of worry; induction of sleep; a slowing of the passage of time; enhanced physiological, emotional, or and/or muscular relaxation; enhanced concentration; inhibition of distractions; increased cognitive and/or sensory clarity; a dissociated state; a state akin to mild intoxication by a psychoactive compound (i.e. alcohol); a state akin to mild euphoria induced by a psychoactive compound (i.e. a morphine); the induction of a state of mind described as relaxed and pleasurable; enhanced enjoyment of auditory and visual experiences (i.e. multimedia); reduced physiological arousal; increased capacity to handle emotional or other stressors; a reduction in psychophysiological arousal as associated with changes in the activity of the hypothalamic-pituitary-adrenal axis (HPA axis) generally associated with a reduction in biomarkers of stress, anxiety, and mental dysfunction; anxiolysis; a state of high mental clarity; enhanced physical performance; promotion of resilience to the deleterious consequences of stress; a physical sensation of relaxation in the periphery (i.e. arms and/or legs); and a physical sensation of being able to hear your heart beating.

Any of the apparatuses described herein may include a detection circuit to detect a connection between the strip electrode (including an electrode with integrated TES circuitry) another apparatus, such as a TES cable neurostimulator. The detection circuit may be included on a neurostimulator (e.g. cable neurostimulator) to detect some variations of the electrode apparatuses described herein. FIG. 123 illustrates one example of such a circuit.

Instead of or in addition to the detection capacitor described above, any of the variations described herein may also include one or more sensors. These sensors may be read by the neurostimulator, which may analyze, store, and/or transmit the sensed information to the controller and/or a third party platform. For example, any of the electrode apparatuses described herein may include one or more sensors that may provide information useful to determine when the electrode apparatus has degraded, and/or requires replacement, refurbishing, or removal. Although in many of the examples provided herein the electrode apparatus is configured to be single use, and disposable, in any of the examples described herein the electrode apparatus may be durable or multi-use.

For example, the apparatuses (including devices and systems) and methods described herein may be configured to determine when (or if) the electrode apparatus for TES neuromodulation has degraded and requires replacement, refurbishing, or removal. Using only electrode apparatuses that meet quality criteria is beneficial so that TES neuromodulation is comfortable for a subject and reliably induces a desired cognitive effect.

For example, a TES apparatus may incorporate an electrode apparatus or a set of electrode apparatuses. Disposability and replaceability may be important features for components of the system that contain electrodes, because electrodes typically degrade in important ways that affect comfort, efficacy, and usability.

As used herein, a disposable element may refer to a limited-use item (e.g., single-use or limited multiple-use, including 2-3 uses, 2-5 uses, 2-7 uses, 2-10 uses, or less than 5 uses, less than 10 uses, etc.). A disposable element may be used once (or 2-3 times, etc.) and then removed from the apparatus and replaced with a new element. In particular, the electrode apparatuses described herein may be disposable elements that include a conductive material (e.g., conductive gel, conductive adhesive, etc.) and/or adhesive that is only reliably useful a limited number of times before needing to be replaced or refurbished.

Beneficial features of transdermal electrodes that degrade over time and over use include adherence, pH buffering, and uniform distribution of current across the face of the electrode. In general, an electrode apparatus may define use cases for which properties (e.g., adhesion, pH buffering, uniform distribution of charge) are within acceptable ranges. Methods for determining when an electrode apparatus requires replacement or refurbishing may use one or more product specification, compare that value to one expected after a detected amount and type of electrode apparatus use, determine whether or not the electrode apparatus quality is outside a specified range, and then either inform a user that the electrode apparatus requires replacement or refurbishment or automatically stop a neurostimulation (or lock out the neurostimulator so that a waveform ensemble cannot be started).

Adherence is a first beneficial property of electrode apparatuses that degrades over time. In general, apparatuses and methods for maintaining adhesive properties over time and use may include a way to determine or estimate when the adhesive properties of an electrode apparatus have degraded such that the electrode requires replacement or refurbishment. The quality of an adherent active region of the electrode apparatus may be reduced each cycle of adherence to a subject and removal from the subject. For instance, a hydrocolloid adhesive component of an electrode apparatus on the dermal-facing portion of a disposable electrode apparatus may degrade when it is used or if it gets wet (e.g. due to rain, sweat, or a liquid spill). An adherent electrode apparatus will also generally require a storage device such as wax paper or plastic between uses to protect the adhesive for subsequent adherences of the unit on the subject's skin. The act of placing an adherent electrode apparatus onto a protective covering (or equivalently placing a protective covering on the electrode) may also somewhat degrade the adhesive properties of the electrode apparatus despite the composition of the covering being selected so as to minimally affect the adhesive. Transdermal electrode components of the system that become less adherent are less than ideal for any number of reasons, including that an electrode apparatus may partially or completely separate from a user's skin (e.g. fall off); or the impedance of electrical connection between an active region and a user's skin may increase because the physical connection is not uniform across the electrically conductive portion of the electrode apparatus.

Adhesive materials of an adhesive electrode apparatus may include a portion of the active region intended for delivering electrical stimulation (i.e. adhesive and conductive) and/or a portion of the electrode apparatus that is not intended for delivering electrical stimulation that is configured to cause an active region/portion of the electrode to be in close physical contact (i.e., low impedance) contact with a user's skin.

Buffering pH is a second beneficial property of electrode apparatuses that degrades over time. Causing current to be distributed evenly across the transdermal face of an electrode is a third beneficial property of electrode apparatuses that degrades over time. Uniform current distribution and pH buffering can be improved by features of electrode apparatuses, including the water composition of a hydrogel component of an electrode apparatus for TES and the amount of Ag and Ag/AgCl contained in a component that couples an electric current through the active region to the skin. Water in a hydrogel component of an electrode apparatus (or other water-containing conductive material) is consumed as net charge is transferred into a subject's body. Ag/AgCl components of an electrode (including components coated with Ag/AgCl and Ag/AgCl ink) improve the efficiency of charge transfer to tissue (essentially a salt solution) and are also consumed during electrical stimulation.

Charge imbalanced TES waveforms are often necessary for inducing cognitive effects, but these waveforms can consume Ag, Ag/AgCl, and water, causing the degradation of transdermal electrodes and limiting their effective use.

If too much water in an active region is consumed, the efficiency of redox reactions is reduced leading to pH changes that may cause skin irritation, pain, and/or tissue damage. Thus, in some variations a pH sensor may be sufficiently sensitive such that a user (or the neurostimulator and/or controller, for automated systems) can stop or turn down the net charge of stimulation or replace an electrode apparatus before irritation, pain, or tissue damage occurs. A pH-sensitive material may be incorporated in a visible portion of an electrode apparatus so that a user (or third party) can determine if pH changes are occurring. Alternatively, a pH sensor may be configured to detect pH changes and transmit this information to a visible part of an electrode apparatus, to a durable portion of a neurostimulator/controller, or to a computing device connected to a durable portion of a neurostimulator/controller in a wired or wireless fashion.

A TES system can automatically or by user input keep track of parameters of use that affect electrode quality, including but not limited to: number of adherence and removal cycles from the skin; number of TES sessions; duration of stimulation; cumulative net charge delivered; cumulative absolute charge delivered; peak current delivered; and the like. A Coulomb counter may be included in the electronic circuitry of a neurostimulator system to determine the amount of charge transferred to a subject during a stimulation session.

In some variations, a sensor contained in an electrode apparatus can be used to determine when the electrode apparatus has been placed on a user. This may be advantageous, because it does not require a self-report by a user each time an electrode apparatus is adhered or removed from the skin. Effective sensors for determining whether an electrode apparatus has been adhered to or removed from a subject's skin include, but are not limited to: an accelerometer, a capacitive sensor, an EMG sensor, an optical sensor (e.g. a light-emitting diode or other light source and a diode, CMOS, or other detector to measure reflectivity), a microphone, or another sensor effective for determining whether an electrode apparatus is adhered to or removed from a user's skin. For example, one or more accelerometers may be contained within an electrode assembly; in a durable assembly coupled to the electrode apparatus; or both.

In general, an appropriate signal processing and algorithm workflow may be applied to data from the one or more sensors in the above list to determine whether an electrode apparatus has been adhered to or removed from a user. Determining whether an electrode apparatus has been placed (adhered) onto a subject's body (generally, a subject's skin) may be achieved by a non-transitory computer-readable storage medium storing a set of instructions capable of being executed by a remote processor (including a smartphone, smartwatch, tablet computer, or the like), that when executed by the computing device containing the remote processor causes sampling of at least one sensor (e.g. a single-axis or multi-axis accelerometer) over time, and applies appropriate signal processing and signal detection algorithms to identify when an electrode is adhered to a subject or removed from a subject.

For example, with an accelerometer sensor, adherence of an electrode apparatus to a subject could be determined or estimated based on a sequence of accelerometer signals corresponding to a subject holding the electrode apparatus in their hand; followed by the user slowly placing the electrode apparatus onto his/her skin; followed by a period of time when accelerometer signals that are consistent with the biomechanics of the part of the body to which the electrode was adhered are detected (which can be known by the type of electrode apparatus and thus appropriate body positioning thereof; or by other means such as an image taken by a smartphone camera). One skilled in the art of wearable sensors and signal processing will recognize that signals from each of the sensors listed above can be used to define an algorithm that determines electrode-dermal connections with an appropriate reliability and sensitivity.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected," "attached" or "coupled" to another feature or element, it can be directly connected, attached or coupled to the other feature or element or intervening features or elements may be present. In contrast, when a feature or element is referred to as being "directly connected," "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise," and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A transdermal electrical stimulation (TES) device, the device comprising:
   a housing having a first surface;
   a first connector and a second connector, wherein the first connector is configured to electrically connect with a first electrode and the second connector is configured to electrically connect with a second electrode; and
   a TES controller at least partially within the housing, the controller comprising:
     a waveform generator configured to deliver a pulsed, asymmetric, biphasic electrical stimulation signal between the first and second connectors, and
     a capacitive discharge circuit triggered by the controller and connected to one or both of the first and second connectors and configured to deliver a capacitive discharging pulse between a positive pulse and a negative pulse of the biphasic electrical stimulation signal to discharge a capacitive charge on either or both the first electrode and the second electrode.

2. The device of claim 1, wherein the capacitive discharge circuit includes a double H-Bridge circuit configured to generate the capacitive discharging pulse.

3. The device of claim 1, wherein the first connector and a second connector are on the first surface.

4. The device of claim 1, wherein the controller is configured to trigger the capacitive discharge circuit multiple times within each cycle of the pulsed, asymmetric, biphasic electrical stimulation signal.

5. The device of claim 1, wherein the capacitive discharge circuit is configured to generate the capacitive discharging pulse so that it lasts between about 1 microsecond and 1 millisecond (ms).

6. The device of claim 1, further comprising a wireless communication module within the housing and connected to the controller.

7. The device of claim 1, further comprising a first electrode connected to the first connector and a second electrode connected to the second connector.

8. The device of claim 1, further wherein the controller is configured to trigger the capacitive discharge circuit to deliver the capacitive discharging pulse at a start or an end of a positive-going portion of the biphasic electrical signal.

9. The device of claim 1, further wherein the controller is configured to activate the capacitive discharge circuit to deliver the capacitive discharging pulse at a start or an end of a negative-going portion of the biphasic electrical signal.

10. The device of claim 1, wherein the controller includes a switch configured to turn off the current source for delivering the electrical stimulation signal when the capacitive discharge circuit is triggered.

11. The device of claim 1, wherein the controller is configured to trigger the capacitive discharging pulse after the positive pulse or the negative pulse.

12. A transdermal electrical stimulation (TES) device, the device comprising:
    a housing;
    a first surface on the housing;
    a first connector and a second connector on the first surface and separated by between 0.5 inches and 1.5 inches, wherein the first connector is configured to electrically connect with a first electrode of an electrode apparatus and the second connector is configured to electrically connect with a second electrode; and
    a TES controller at least partially within the housing, the controller comprising:
      a waveform generator configured to deliver a pulsed, asymmetric, biphasic electrical stimulation signal between the first and second connectors, and
      a capacitive discharge circuit triggered by the controller and connected to one or both of the first and second connectors and configured to deliver a gradual capacitive discharging pulse between a positive pulse and a negative pulse of the biphasic electrical stimulation signal, the capacitive discharging pulse delivering either or both: a first charge to counter a first capacitive charge on the first electrode, and a second charge to counter a second capacitive charge on the second electrode.

13. A method of applying transdermal electrical stimulation to a back of a subject's neck with a transdermal electrical stimulation (TES) device, the method comprising:
    delivering a pulsed, asymmetric, biphasic electrical stimulation signal between a pair of electrodes of a TES device attached to the back of the subject's neck, wherein the TES device comprises a first connector configured to electrically connect with a first electrode of the pair of electrodes and a second connector configured to electrically connect with a second electrode of the pair of electrodes, and a housing at least partially enclosing a controller having a waveform generator and a capacitive discharge circuit; and applying a capacitive discharging pulse between a positive pulse and a negative pulse of the biphasic electrical stimulation signal, the capacitive discharging pulse delivering either or both: a first charge that counters a first capacitive charge on the first electrode, and a second charge that counters a second capacitive charge on the second electrode.

14. The method of claim 13, wherein the capacitive discharging pulse is triggered after the positive pulse or the negative pulse.

15. A transdermal electrical stimulation (TES) device, the device comprising:

a housing having a first surface;

a first electrode and a second electrode; and a TES controller at least partially within the housing, the controller comprising:

a waveform generator configured to deliver a pulsed, asymmetric, biphasic electrical stimulation signal between the first and second electrodes, the biphasic pulse including a positive pulse and a negative pulse, and a capacitive discharge circuit triggered by the controller and connected to one or both of the first and second electrodes and configured to deliver a capacitive discharging pulse that begins at a falling edge of the positive pulse or a rising edge of the negative pulse of the biphasic electrical stimulation signal to discharge a capacitive charge on either or both of the first electrode and the second electrode.

* * * * *